US009598423B2

(12) United States Patent
Velaparthi et al.

(10) Patent No.: US 9,598,423 B2
(45) Date of Patent: Mar. 21, 2017

(54) SUBSTITUTED 4,5,6,7-TETRAHYDROPYRAZOLO[1,5-A]PYRAZINE DERIVATIVES AS CASEIN KINASE 1 D/E INHIBITORS

(71) Applicant: BRISTOL-MYERS SQUIBB COMPANY, Princeton, NJ (US)

(72) Inventors: Upender Velaparthi, Cheshire, CT (US); Chetan Padmakar Darne, Orange, CT (US); Peiying Liu, Madison, CT (US); Mark D. Wittman, Wallingford, CT (US); Bradley C. Pearce, East Hampton, CT (US); Erika M. V. Araujo, Woodbridge, CT (US); Bireshwar Dasgupta, East Hampton, CT (US); Jalathi Surendran Nair, Bangalore (IN); Sakthi Kumaran Janakiraman, Bangalore (IN); Chandrasekhar Reddy Rachamreddy, Bangalore (IN); Mallikarjuna Rao Mettu, Bangalore (IN); Arul Mozhi Selvan Subbiah Karuppiah, Bangalore (IN); Bandreddy Subba Reddy, Bangalore (IN); Pulicharla Nagalakshmi, Bangalore (IN); Rajesh Onkardas Bora, Bangalore (IN); Shilpa Holehatti Maheshwarappa, Davanagere District (IN); Selvakumar Kumaravel, Bangalore (IN); Dibakar Mullick, Howrah District (IN); Ramesh Sistla, Bangalore (IN)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 15/034,217

(22) PCT Filed: Nov. 14, 2014

(86) PCT No.: PCT/US2014/065599
§ 371 (c)(1),
(2) Date: May 4, 2016

(87) PCT Pub. No.: WO2015/073767
PCT Pub. Date: May 21, 2015

(65) Prior Publication Data
US 2016/0311824 A1    Oct. 27, 2016

Related U.S. Application Data

(60) Provisional application No. 61/904,116, filed on Nov. 14, 2013.

(51) Int. Cl.
*A61K 31/498* (2006.01)
*C07D 487/04* (2006.01)
*C07D 491/147* (2006.01)
*C07D 487/10* (2006.01)
*C07D 491/20* (2006.01)
*C07D 487/20* (2006.01)
*C07D 519/00* (2006.01)

(52) U.S. Cl.
CPC .......... *C07D 487/04* (2013.01); *C07D 487/10* (2013.01); *C07D 487/20* (2013.01); *C07D 491/147* (2013.01); *C07D 491/20* (2013.01); *C07D 519/00* (2013.01)

(58) Field of Classification Search
USPC .................................. 514/210.18, 221, 249
See application file for complete search history.

(56) References Cited

U.S. PATENT DOCUMENTS

| 9,273,058 B2 | 3/2016 | Velaparthi et al. |
| 2005/0222171 A1 | 10/2005 | Bold et al. |
| 2013/0090340 A1* | 4/2013 | Cote-Des-Combes C07D 487/04 514/249 |

FOREIGN PATENT DOCUMENTS

FR    2 960 876    12/2011

OTHER PUBLICATIONS

Zhang et al., Bioorganic & Medicinal Chemistry, vol. 16, No. 24, pp. 10165-10171 (2008).
Liu, et al., European Journal of Medicinal Chemistry, vol. 46, No. 6, pp. 2359-2367 (2011).

* cited by examiner

*Primary Examiner* — Pancham Bakshi
(74) *Attorney, Agent, or Firm* — Elliott Korsen; Hong Liu

(57) ABSTRACT

The invention provides compounds of Formula (I):

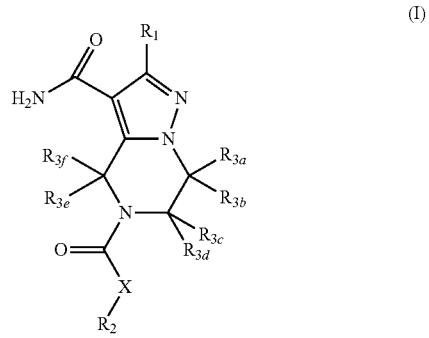

and pharmaceutically acceptable salts thereof. The compounds of Formula (I) inhibit protein kinase activity thereby making them useful as anticancer agents.

13 Claims, No Drawings

SUBSTITUTED 4,5,6,7-TETRAHYDROPYRAZOLO[1,5-A] PYRAZINE DERIVATIVES AS CASEIN KINASE 1 D/E INHIBITORS

CROSS REFERENCE TO RELATED APPLICATIONS

This application is a 371 application of PCT/US2014/065599 filed Nov. 14, 2014, which is entitled to priority pursuant to 35 U.S.C. §119(e) to U.S. provisional patent application No. 61/904,116, filed on Nov. 14, 2013, each of which is fully incorporated herein in its entirety.

FIELD OF THE INVENTION

The invention relates to novel substituted pyrazoles useful as protein kinase inhibitors. This invention also relates to methods of using the compounds in the treatment of proliferative and other types of diseases and to pharmaceutical compositions containing the compounds.

BACKGROUND OF THE INVENTION

The invention relates to substituted pyrazole compounds which inhibit protein kinase enzymes, compositions which contain protein kinase inhibiting compounds and methods of using inhibitors of protein kinase enzymes to treat diseases which are characterized by an overexpression or upregulation of protein kinases. Protein kinases mediate intracellular signal transduction by affecting a phosphoryl transfer from a nucleoside triphosphate to a protein acceptor that is involved in a signaling pathway. There are a number of kinases and pathways through which extracellular and other stimuli cause a variety of cellular responses to occur inside the cell. An extracellular stimulus may affect one or more cellular responses related to cell growth, migration, differentiation, secretion of hormones, activation of transcription factors, muscle contraction, glucose metabolism, control of protein synthesis and regulation of cell cycle.

Many diseases are associated with abnormal cellular responses triggered by protein kinase-mediated events. These diseases include autoimmune diseases, inflammatory diseases, neurological and neurodegenerative diseases, cancer, cardiovascular diseases, allergies and asthma, Alzheimer's disease or hormone-related diseases. Accordingly, there has been a substantial effort in medicinal chemistry to find protein kinase inhibitors that are effective as therapeutic agents.

Serine/threonine kinases are a class of protein kinases that are among the most promising drug targets for future small molecule inhibitors. Inhibition of serine/threonine kinases is likely to have relevance to the treatment of cancer, diabetes and a variety of inflammatory disorders. The successful development of GLEEVEC® as a Bcr/Abl protein kinase inhibitor has provided further evidence that protein kinases are valid drug targets for potential cancer therapies.

Casein kinase 1 (CK1) belongs to the serine/threonine kinase family. In mammals, the enzyme exists in seven isozymic forms: $\alpha$, $\beta$, $\gamma 1$, $\gamma 2$, $\gamma 3$, $\delta$, and $\epsilon$. By phosphorylating different substrate proteins, these isoforms are able to activate, inactivate, stabilize, or destabilize the functions of the proteins, regulating the functions of various types of different organisms. For example, a tumor suppressor factor p53 and an oncogene mdm2, which are both important proteins for controlling abnormal cell growth, are substrates of casein kinase 1.

Mammalian casein kinase 1$\delta$ and casein kinase 1$\epsilon$ are key regulators of diverse cellular growth and survival processes including Wnt signaling, DNA repair and circadian rhythms. They have a kinase domain that is similar to those of other isoforms. However, the N-terminal and C-terminal domains thereof are different from those of other isoforms. The C-terminal domain has a plurality of autophosphorylation sites, and it is considered to be involved in regulation of autoenzyme activity. Phosphorylation of p53 by casein kinase 1$\delta$ or casein kinase 1$\epsilon$ leads to a consequent change in the interaction between p53 and mdm2. It has also been known that casein kinase 1$\epsilon$ or casein kinase 1$\delta$ is involved in a regulatory protein associated with the formation of a spindle as a central body during cell division, and that the casein kinase 1$\delta$ or casein kinase 1$\epsilon$ is involved in apoptosis mediated by TRAIL (tumor necrosis factor-related apoptosis inducing factor) and Fas. It has been further reported that inhibition of casein kinase 1$\epsilon$ or casein kinase 1$\delta$ by a nonselective casein kinase 1 inhibitory compound IC261 reduces pancreatic tumor cell growth in vitro and in vivo (Brockschmidt et al., *Gut*, 57(6):799-806 (2008)). Hence, a medicament inhibiting the function of casein kinase 1$\delta$ or casein kinase 1$\epsilon$ would be expected to exert important phenotypic and therapeutic effects broadly in development and disease, especially cancer.

The present invention relates to a new class substituted pyrazoles found to be effective in inhibiting casein kinase 1$\delta$ or casein kinase 1$\epsilon$. These novel compounds are provided to be useful as pharmaceuticals with desirable stability, bioavailability, therapeutic index and toxicity values that are important to their drugability.

SUMMARY OF THE INVENTION

The invention is directed to substituted pyrazole compounds of Formulae (I)-(V) or stereoisomers, tautomers, pharmaceutically acceptable salts, solvates or prodrugs thereof, which inhibit protein kinase enzymes, especially protein kinase CK1 for the treatment of cancer.

The present invention also provides processes and intermediates for making the compounds of the present invention or stereoisomers, tautomers, pharmaceutically acceptable salts, solvates, or prodrugs thereof.

The present invention also provides pharmaceutical compositions comprising a pharmaceutically acceptable carrier and at least one of the compounds of the present invention or stereoisomers, tautomers, pharmaceutically acceptable salts, solvates, or prodrugs thereof.

The present invention also provides methods for inhibiting the activity of protein kinase CK1 comprising administering to a host in need of such treatment a therapeutically effective amount of at least one of the compounds of the present invention or stereoisomers, tautomers, pharmaceutically acceptable salts, solvates, or prodrugs thereof.

The present invention also provides methods for treating cancers comprising administering to a host in need of such treatment a therapeutically effective amount of at least one of the compounds of the present invention or stereoisomers, tautomers, pharmaceutically acceptable salts, solvates, or prodrugs thereof.

The present invention also provides the compounds of the present invention or stereoisomers, tautomers, pharmaceutically acceptable salts, solvates, or prodrugs thereof, for use in therapy.

The present invention also provides the use of the compounds of the present invention or stereoisomers, tautomers, pharmaceutically acceptable salts, solvates, or prodrugs thereof, in preparing a medicament for the treatment of cancer in a human patient, particularly a cancer receptive to treatment via inhibition of the CK1 enzyme.

These and other features of the invention will be set forth in the expanded form as the disclosure continues.

DETAILED DESCRIPTION OF THE INVENTION

The invention provides for novel substituted pyrazole compounds useful as therapeutic agents, pharmaceutical compositions employing such novel compounds and for methods of using such compounds.

In accordance with the invention, there are disclosed compounds of Formula (I) including enantiomers, diastereomers, tautomers, pharmaceutically-acceptable salts, prodrugs, hydrates, or solvates thereof,

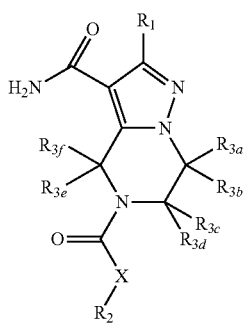

(I)

wherein:

X is independently selected from O and NH;

$R_1$ is independently selected from carbocyclyl substituted with 1-5 $R_5$, and heterocyclyl comprising carbon atoms and 1 to 3 heteroatoms selected from N, $NR_4$, O, S, and substituted with 1-5 $R_5$;

$R_2$ is independently selected from aryl substituted with 1-8 $R_7$ and heteroaryl comprising carbon atoms and 1 to 4 heteroatoms selected from N, $NR_6$, O, S, and substituted with 1-8 $R_7$;

$R_{3a}$, $R_{3b}$, $R_{3c}$, $R_{3d}$, $R_{3e}$ and $R_{3f}$ are independently selected from H, CN, $C_{1-4}$alkyl substituted with 1-3 $R_8$, —C(=O) $OR_b$, —C(=O)$NR_aR_a$, —C(=O)$R_b$, —$NR_aC$(=O)$R_b$, —$NR_aC$(=O)$OR_b$, —$(CH_2)_r$-carbocyclyl substituted with 1-3 $R_8$, and —$(CH_2)_r$-heterocyclyl substituted with 1-3 $R_8$;

alternatively, $R_{3a}$ and $R_{3b}$, or $R_{3e}$ and $R_{3d}$, or $R_{3e}$ and $R_{3f}$, together with the carbon atom to which they are both attached form a spiral carbocyclic or heterocyclic ring comprising carbon atoms and 1 to 4 heteroatoms selected from N, O, S, each substituted with 1-5 $R_8$;

alternatively, $R_{3a}$ and $R_{3c}$ or $R_{3b}$ and $R_{3d}$ together form a heterocyclic ring comprising carbon atoms and 1 to 4 heteroatoms selected from N, O, S, and substituted with 1-5 $R_8$;

$R_4$ is independently selected from H, $C_{1-4}$ alkyl substituted with 0-3 $R_e$, —$(CH_2)_rCN$, —$(CH_2)_rOR_b$, $(CH_2)_rS(O)_pR_c$, —$(CH_2)_rC$(=O)$R_b$, —$(CH_2)_rNR_aR_a$, —$(CH_2)_rC$(=O)$NR_aR_a$, —$(CH_2)_rNR_aC$(=O)$R_b$, —$(CH_2)_rNR_aC$(=O)$OR_b$, —$(CH_2)_aOC$(=O)$NR_aR_a$, —$(CH_2)_aNR_aC$(=O)$NR_aR_a$, —$(CH_2)_aC$(=O)$OR_b$, —$(CH_2)_rS(O)_2NR_aR_a$, —$(CH_2)_rNR_aS(O)_2NR_aR_a$, —$(CH_2)_rNR_aS(O)_2R_c$, $(CH_2)_r$-carbocyclyl substituted with 0-3 $R_e$, and —$(CH_2)_r$-heterocyclyl substituted with 0-3 $R_e$;

$R_5$, at each occurrence, is independently selected from H, $C_{1-4}$ alkyl substituted with 0-3 $R_e$, F, Cl, Br, =O, CN, $NO_2$, —$OR_b$, —$(CH_2)_rCN$, —$(CH_2)_rOR_b$, $(CH_2)_rS(O)_pR_c$, —$(CH_2)_rC$(=O)$R_b$, —$(CH_2)_rNR_aR_a$, —$(CH_2)_rC$(=O)$NR_aR_a$, —$(CH_2)_rNR_aC$(=O)$R_b$, —$(CH_2)_rNR_aC$(=O)$OR_b$, —$(CH_2)_rOC$(=O)$NR_aR_a$, —$(CH_2)_rNR_aC$(=O)$NR_aR_a$, —$(CH_2)_rC$(=O)$OR_b$, —$(CH_2)_rS(O)_2NR_aR_a$, —$(CH_2)_rNR_aS(O)_2NR_aR_a$, —$(CH_2)_rNR_aS(O)_2R_c$, $(CH_2)_r$-carbocyclyl substituted with 0-3 $R_e$, and —$(CH_2)_r$-heterocyclyl substituted with 0-3 $R_e$;

$R_6$ is independently selected from H, —C(=O)$R_b$, —CO(=O)$R_b$, —S(O)$_pR_c$, $C_{1-6}$ alkyl substituted with 0-5 $R_e$, —$(CH_2)_r$—$C_{3-6}$carbocyclyl substituted with 0-5 $R_e$, and —$(CH_2)_r$-heterocyclyl substituted with 0-5 $R_e$;

$R_7$, at each occurrence, is independently selected from H, F, Cl, Br, —$(CR_dR_d)_rCN$, $NO_2$, —$(CR_dR_d)_rOR_b$, —$S(O)_pR_c$, —C(=O)$R_b$, —$(CR_dR_d)_rNR_aR_a$, —$(CR_dR_d)_rC$(=O)$NR_aR_a$, —$NR_aC$(=O)$R_b$, —$NR_aC$(=O)$OR_b$, —OC(=O)$NR_aR_a$, —$NR_aC$(=O)$NR_aR_a$, —$(CR_dR_d)_rC$(=O)$OR_b$, —S(O)$_2NR_aR_a$, —$NR_aS(O)_2NR_aR_a$, —$NR_aS(O)_2R_c$, $C_{1-6}$ alkyl substituted with 0-5 $R_e$, —$(CR_dR_d)_r$—$C_{3-6}$carbocyclyl substituted with 0-5 $R_e$, and —$(CR_dR_d)_r$-heterocyclyl substituted with 0-5 $R_e$;

$R_8$, at each occurrence, is independently selected from H, F, Cl, Br, CN, $C_{1-6}$ alkyl substituted with 0-5 $R_e$, $C_{2-6}$ alkenyl, $C_{2-6}$ alkynyl, —$(CH_2)_r$—$C_{3-6}$ cycloalkyl substituted with 0-5 $R_e$, —$(CH_2)_r$-aryl substituted with 0-5 $R_e$, —$(CH_2)_r$-heterocyclyl substituted with 0-5 $R_e$, $CO_2H$, —$(CH_2)_rOR_b$, and —$(CH_2)_rNR_aR_a$;

$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_d$, at each occurrence, is independently selected from H and $C_{1-4}$alkyl substituted with 0-5 $R_e$;

$R_e$, at each occurrence, is independently selected from F, Cl, Br, CN, $NO_2$, =O, $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, —$(CH_2)_r$-aryl, —$(CH_2)_r$-heterocyclyl, $CO_2H$, —$(CH_2)_rOR_f$, $SR_f$, and —$(CH_2)_rNR_fR_f$;

$R_f$, at each occurrence, is independently selected from H, $C_{1-5}$ alkyl optionally substituted with F, Cl, Br, $C_{3-6}$ cycloalkyl, and phenyl, or $R_f$ and $R_f$ together with the nitrogen atom to which they are both attached form a heterocyclic ring optionally substituted with $C_{1-4}$alkyl;

p, at each occurrence, is independently selected from zero, 1, and 2; and r, at each occurrence, is independently selected from zero, 1, 2, 3, and 4.

In another aspect, there are disclosed compounds of Formula (II) including enantiomers, diastereomers, tautomers, pharmaceutically acceptable salts, prodrugs, hydrates, or solvates thereof,

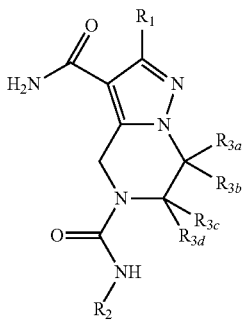

(II)

wherein:
R$_1$ is independently selected from aryl substituted with 1-4 R$_5$, and 5- to 12-membered heteroaryl comprising carbon atoms and 1 to 3 heteroatoms selected from N, NR$_4$, O, S, and substituted with 1-4 R$_5$;
R$_2$ is independently selected from aryl substituted with 1-8 R$_7$ and heteroaryl comprising carbon atoms and 1 to 4 heteroatoms selected from N, NR$_6$, O, S, and substituted with 1-8 R$_7$;
R$_{3a}$, R$_{3b}$, R$_{3c}$, and R$_{3d}$ are independently selected from H, CN, C$_{1-4}$alkyl substituted with 1-3 R$_8$, —C(=O)OR$_b$, —C(=O)NR$_a$R$_a$, —C(=O)R$_b$, —NR$_a$C(=O)R$_b$, —NR$_a$C(=O)OR$_b$, —(CH$_2$)$_r$-carbocyclyl substituted with 1-3 R$_8$, and —(CH$_2$)$_r$-heterocyclyl substituted with 1-3 R$_8$;
  alternatively, R$_{3a}$ and R$_{3b}$, or R$_{3c}$ and R$_{3d}$, or R$_{3e}$ and R$_{3f}$ together with the carbon atom to which they are both attached form a spiral carbocyclic or heterocyclic ring comprising carbon atoms and 1 to 4 heteroatoms selected from N, O, S, each substituted with 0-5 R$_e$;
alternatively, R$_{3a}$ and R$_{3c}$ or R$_{3b}$ and R$_{3d}$ together form a heterocyclic ring comprising carbon atoms and 1 to 4 heteroatoms selected from N, O, S, and substituted with 0-5 R$_e$;
R$_4$ is independently selected from H and C$_{1-4}$ alkyl substituted with 0-3 R$_e$;
R$_5$, at each occurrence, is independently selected from H, C$_{1-4}$ alkyl substituted with 0-3 R$_e$, F, Cl, Br, =O, CN, NO$_2$, —OR$_b$, —(CH$_2$)$_r$CN, —(CH$_2$)$_r$OR$_b$, (CH$_2$)$_r$S(O)$_p$R$_c$, —(CH$_2$)$_r$C(=O)R$_b$, —(CH$_2$)$_r$NR$_a$R$_a$, —(CH$_2$)$_r$C(=O)NR$_a$R$_a$, —(CH$_2$)$_r$NR$_a$C(=O)R$_b$, —(CH$_2$)$_r$NR$_a$C(=O)OR$_b$, —(CH$_2$)$_r$OC(=O)NR$_a$R$_a$, —(CH$_2$)$_r$NR$_a$C(=O)NR$_a$R$_a$, —(CH$_2$)$_r$C(=O)OR$_b$, —(CH$_2$)$_r$S(O)$_2$NR$_a$R$_a$, —(CH$_2$)$_r$NR$_a$S(O)$_2$NR$_a$R$_a$, —(CH$_2$)$_r$NR$_a$S(O)$_2$R$_c$, (CH$_2$)$_r$-carbocyclyl substituted with 0-3 R$_e$, and —(CH$_2$)$_r$-heterocyclyl substituted with 0-3 R$_e$;
R$_6$ is independently selected from H, —C(=O)R$_b$, —CO(=O)R$_b$, —S(O)$_p$R$_c$, C$_{1-6}$ alkyl substituted with 0-5 R$_e$, —(CH$_2$)$_r$—C$_{3-6}$carbocyclyl substituted with 0-5 R$_e$, and —(CH$_2$)$_r$-heterocyclyl substituted with 0-5 R$_e$;
R$_7$, at each occurrence, is independently selected from H, F, Cl, Br, —(CR$_d$R$_d$)$_r$CN, NO$_2$, —(CR$_d$R$_d$)$_r$OR$_b$, —S(O)$_p$R$_c$, —C(=O)R$_b$, —(CR$_d$R$_d$)$_r$NR$_a$R$_a$, —(CR$_d$R$_d$)$_r$C(=O)NR$_a$R$_a$, —NR$_a$C(=O)R$_b$, —NR$_a$C(=O)OR$_b$, —OC(=O)NR$_a$R$_a$, —NR$_a$C(=O)NR$_a$R$_a$, —(CR$_d$R$_d$)$_r$C(=O)OR$_b$, —S(O)$_2$NR$_a$R$_a$, —NR$_a$S(O)$_2$NR$_a$R$_a$, —NR$_a$S(O)$_2$R$_c$, C$_{1-6}$ alkyl substituted with 0-5 R$_e$, —(CR$_d$R$_d$)$_r$—C$_{3-6}$carbocyclyl substituted with 0-5 R$_e$, and —(CR$_d$R$_d$)$_r$-heterocyclyl substituted with 0-5 R$_e$;
R$_8$, at each occurrence, is independently selected from H, F, Cl, Br, CN, C$_{1-6}$ alkyl substituted with 0-5 R$_e$, C$_{2-6}$ alkenyl, C$_{2-6}$ alkynyl, —(CH$_2$)$_r$—C$_{3-6}$ cycloalkyl substituted with 0-5 R$_e$, —(CH$_2$)$_r$-aryl substituted with 0-5 R$_e$, —(CH$_2$)$_r$-heterocyclyl substituted with 0-5 R$_e$, CO$_2$H, —(CH$_2$)$_r$OR$_b$, and —(CH$_2$)$_r$NR$_a$R$_a$;
R$_a$, at each occurrence, is independently selected from H, CN, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;
R$_b$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$;
R$_c$, at each occurrence, is independently selected from C$_{1-6}$ alkyl substituted with 0-5 R$_e$, C$_{2-6}$alkenyl substituted with 0-5 R$_e$, C$_{2-6}$alkynyl substituted with 0-5 R$_e$, C$_{3-6}$carbocyclyl, and heterocyclyl;
R$_d$, at each occurrence, is independently selected from H and C$_{1-4}$alkyl substituted with 0-5 R$_e$;
R$_e$, at each occurrence, is independently selected from F, Cl, Br, CN, NO$_2$, =O, C$_{1-6}$ alkyl substituted with 0-5 R$_f$, C$_{2-6}$ alkenyl, C$_{2-6}$ alkynyl, —(CH$_2$)$_r$—C$_{3-6}$ cycloalkyl, CO$_2$H, —(CH$_2$)$_r$OR$_f$, SR$_f$, and —(CH$_2$)$_r$NR$_f$R$_f$;
R$_f$, at each occurrence, is independently selected from H, C$_{1-5}$ alkyl, C$_{3-6}$ cycloalkyl, and phenyl, or R$_f$ and R$_f$ together with the nitrogen atom to which they are both attached form a heterocyclic ring optionally substituted with C$_{1-4}$alkyl;
p, at each occurrence, is independently selected from zero, 1, and 2; and
r, at each occurrence, is independently selected from zero, 1, 2, 3, and 4.

In another embodiment, there are disclosed compounds of Formula (II) including enantiomers, diastereomers, tautomers, pharmaceutically-acceptable salts, prodrugs, hydrates, or solvates thereof, wherein:
R$_1$ is independently selected from aryl, pyridyl, pyrimidinyl, pyrazinyl, pyridazinyl, triazinyl, furyl, thienyl, imidazolyl, thiazolyl, indolyl, oxazolyl, isoxazolyl, pyrazolyl, triazolyl, tetrazolyl, indazolyl, 1,2,4-thiadiazolyl, isothiazolyl, quinolinyl, isoquinolinyl, each substituted with 1-4 R$_4$ and R$_5$;
R$_4$, at each occurrence, is independently selected from H and C$_{1-4}$ alkyl substituted with 0-3 R$_e$;
R$_5$, at each occurrence, is independently selected from H, C$_{1-4}$ alkyl substituted with 0-3 R$_e$, F, Cl, Br, =O, CN, NO$_2$, —OR$_b$, —S(O)$_p$R$_c$, —CN, —OR$_b$, —(CH$_2$)$_r$C(=O)R$_b$, —(CH$_2$)$_r$NR$_a$R$_a$, —(CH$_2$)$_r$C(=O)NR$_a$R$_a$, —(CH$_2$)$_r$NHC(=O)R$_b$, —(CH$_2$)$_r$NHC(=O)OR$_b$, —(CH$_2$)$_r$OC(=O)NR$_a$R$_a$, —(CH$_2$)$_r$NHC(=O)NR$_a$R$_a$, —(CH$_2$)$_r$C(=O)OR$_b$, —(CH$_2$)$_r$S(O)$_2$NR$_a$R$_a$, —(CH$_2$)$_r$NHS(O)$_2$NR$_a$R$_a$, —(CH$_2$)$_r$NHS(O)$_2$R$_c$, (CH$_2$)$_r$-carbocyclyl substituted with 0-3 R$_e$, and —(CH$_2$)$_r$-heterocyclyl substituted with 0-3 R$_e$;
R$_a$, at each occurrence, is independently selected from H, CN, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_e$, at each occurrence, is independently selected from F, Cl, Br, CN, $NO_2$, =O, $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, $CO_2H$, —$(CH_2)_rOR_f$, $SR_f$, and —$(CH_2)_rNR_fR_f$;

$R_f$, at each occurrence, is independently selected from H, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

p, at each occurrence, is independently selected from zero, 1, and 2; and r, at each occurrence, is independently selected from zero, 1, 2, 3, and 4;

and other variables are as defined in Formula (II) above.

In another embodiment, there are disclosed compounds of Formula (II) including enantiomers, diastereomers, tautomers, pharmaceutically-acceptable salts, prodrugs, hydrates, or solvates thereof, wherein:

$R_1$ is independently selected from

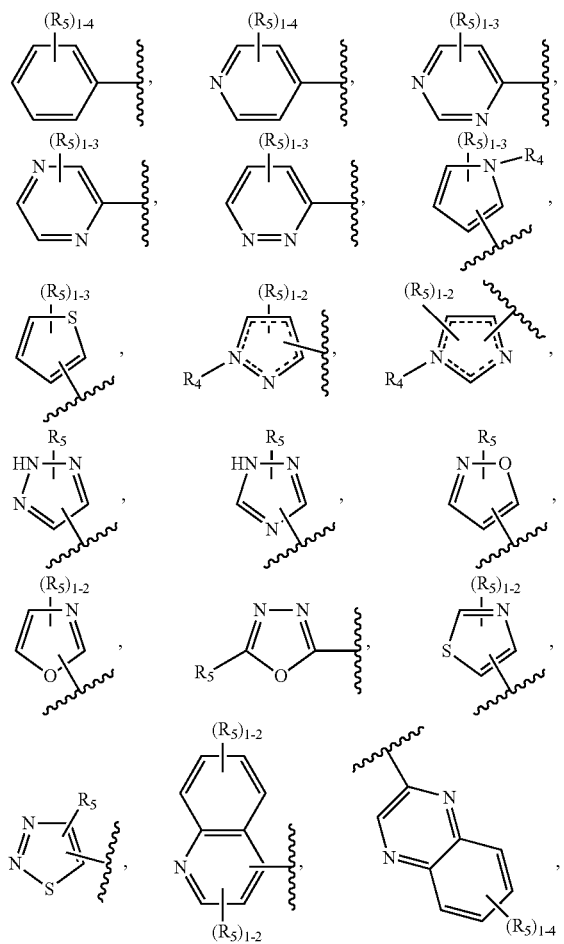

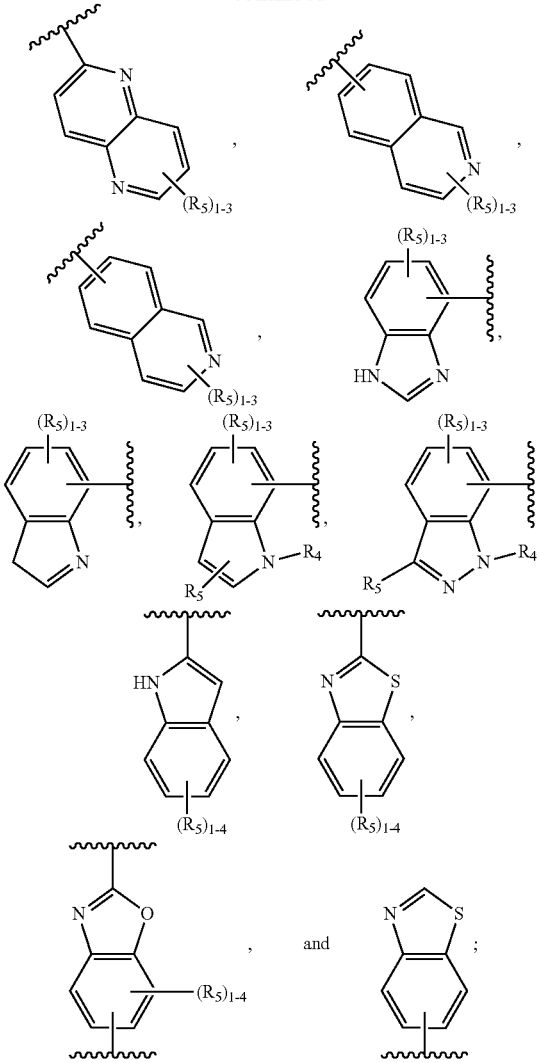

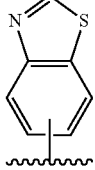

$R_4$, at each occurrence, is independently selected from H, $C_{1-4}$ alkyl substituted with 0-3 $R_e$;

$R_5$, at each occurrence, is independently selected from H, $C_{1-4}$ alkyl substituted with 0-3 $R_e$, F, Cl, Br, =O, CN, $NO_2$, —$OR_b$, —$S(O)_pR_c$, —CN, —$OR_b$, —$(CH_2)_rC(=O)R_b$, —$(CH_2)_rNR_aR_a$, —$(CH_2)_rC(=O)NR_aR_a$, —$(CH_2)_rNHC(=O)R_b$, —$(CH_2)_rNHC(=O)OR_b$, —$(CH_2)_rOC(=O)NR_aR_a$, —$(CH_2)_rNHC(=O)NR_aR_a$, —$(CH_2)_rC(=O)OR_b$, —$(CH_2)_rS(O)_2NR_aR_a$, —$(CH_2)_rNHS(O)_2NR_aR_a$, —$(CH_2)_rNHS(O)_2R_c$, —$(CH_2)_r$—$C_{3-6}$cycloalkyl, —$(CH_2)_r$-aryl substituted with 0-3 $R_e$, and —$(CH_2)_r$-heterocyclyl substituted with 0-3 $R_e$;

$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_e$, at each occurrence, is independently selected from F, Cl, Br, CN, $NO_2$, =O, $C_{1-6}$ alkyl, $C_{2-6}$ alkenyl, $C_{2-6}$ alkynyl, —$(CH_2)_r$—$C_{3-6}$ cycloalkyl, and $CO_2H$;

p, at each occurrence, is independently selected from zero, 1, and 2; and r, at each occurrence, is independently selected from zero, 1, 2, 3, and 4;

and other variables are as defined in Formula (II) above.

In another aspect, there are disclosed compounds of Formula (III) including enantiomers, diastereomers, tautomers, pharmaceutically-acceptable salts, prodrugs, hydrates, or solvates thereof,

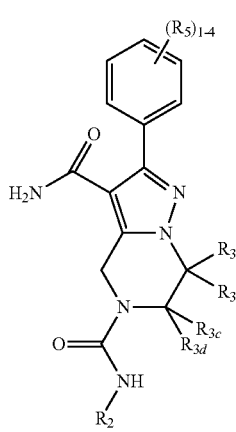

(III)

wherein:

$R_2$ is independently selected from aryl substituted with 1-8 $R_7$ and heteroaryl comprising carbon atoms and 1 to 4 heteroatoms selected from N, $NR_6$, O, S, and substituted with 1-8 $R_7$;

$R_{3a}$, $R_{3b}$, $R_{3c}$, and $R_{3d}$ are independently selected from H, CN, $C_{1-4}$alkyl substituted with 1-3 $R_8$, —C(=O)$OR_b$, —C(=O)$NR_aR_a$, —C(=O)$R_b$, —$NR_aC$(=O)$R_b$, —$NR_aC$(=O)$OR_b$, —$(CH_2)_r$-carbocyclyl substituted with 1-3 $R_8$, and —$(CH_2)_r$-heterocyclyl substituted with 1-3 $R_8$;

alternatively, $R_{3a}$ and $R_{3b}$, together with the carbon atom to which they are both attached form a spiral carbocyclic or heterocyclic ring comprising carbon atoms and 1 to 4 heteroatoms selected from N, O, S, each substituted with 1-5 $R_8$;

alternatively, $R_{3a}$ and $R_{3c}$ or $R_{3b}$ and $R_{3d}$ together form a heterocyclic ring comprising carbon atoms and 1 to 4 heteroatoms selected from N, O, S, and substituted with 1-5 $R_8$;

$R_5$, at each occurrence, is independently selected from H, $C_{1-4}$alkyl substituted with 0-3 $R_e$, F, Cl, Br, —S(O)$_pR_c$, —CN, —$OR_b$, $NR_aR_a$, $C_{3-6}$cycloalkyl, aryl substituted with 0-3 $R_e$, and heterocyclyl substituted with 0-3 $R_e$;

$R_6$ is independently selected from H, —C(=O)$R_b$, —CO(=O)$R_b$, —S(O)$_pR_c$, $C_{1-6}$ alkyl substituted with 0-5 $R_e$, —$(CH_2)_r$—$C_{3-6}$carbocyclyl substituted with 0-5 $R_e$, and —$(CH_2)_r$-heterocyclyl substituted with 0-5 $R_e$;

$R_7$, at each occurrence, is independently selected from H, F, Cl, Br, —$(CR_dR_d)_rCN$, $NO_2$, —$(CR_dR_d)_rOR_b$, —S(O)$_p$ $R_c$, —C(=O)$R_b$, —$(CR_dR_d)_rNR_aR_a$, —$(CR_dR_d)_rC$(=O) $NR_aR_a$, —$NR_aC$(=O)$R_b$, —$NR_aC$(=O)$OR_b$, —OC(=O)$NR_aR_a$, —$NR_aC$(=O)$NR_aR_a$, —$(CR_dR_d)_rC$(=O) $OR_b$, —S(O)$_2NR_aR_a$, —$NR_aS$(O)$_2NR_aR_a$, —$NR_aS$(O)$_2$ $R_c$, $C_{1-6}$ alkyl substituted with 0-5 $R_e$, —$(CR_dR_d)_r$—$C_{3-6}$ carbocyclyl substituted with 0-5 $R_e$, and —$(CR_dR_d)_r$-heterocyclyl substituted with 0-5 $R_e$;

$R_8$, at each occurrence, is independently selected from H, F, Cl, Br, CN, $C_{1-6}$alkyl substituted with 0-5 $R_e$, $C_{2-6}$ alkenyl, $C_{2-6}$ alkynyl, —$(CH_2)_r$—$C_{3-6}$ cycloalkyl substituted with 0-5 $R_e$, —$(CH_2)_r$-aryl substituted with 0-5 $R_e$, —$(CH_2)_r$-heterocyclyl substituted with 0-5 $R_e$, $CO_2H$, —$(CH_2)_rOR_b$, and —$(CH_2)_rNR_aR_a$;

$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_d$, at each occurrence, is independently selected from H and $C_{1-4}$alkyl substituted with 0-5 $R_e$;

$R_e$, at each occurrence, is independently selected from F, Cl, Br, CN, $NO_2$, =O, $CO_2H$, $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, —$(CH_2)_rOR_f$, $SR_f$, and —$(CH_2)_rNR_fR_f$;

$R_f$, at each occurrence, is independently selected from H, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

p, at each occurrence, is independently selected from zero, 1, and 2; and r, at each occurrence, is independently selected from zero, 1, 2, 3, and 4.

In another embodiment, there are disclosed compounds of formula (III) including enantiomers, diastereomers, tautomers, pharmaceutically-acceptable salts, prodrugs, hydrates, or solvates thereof, wherein:

$R_2$ is

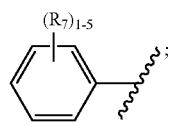

$R_{3a}$ and $R_{3b}$ are independently selected from H, $CH_2CH_3$, $CH_3$, $CH_2OH$, $CH_2CH_2OH$, $CH_2CH_2OC_{1-4}$alkyl, $CH_2F$, $CHF_2$, $CH_2CH_2F$, $CF_3$, $CH_2OCHF_2$, $CH_2CN$, $CH_2CH_2CN$, $CH_2OC_{1-4}$alkyl, $C(CH_3)_3$, $CH(CH_3)_2$, $C(CH_3)_2OH$, $C(CH_3)_2F$, $C(=O)NH$—$C_{3-6}$cycloalkyl, $C(=O)NH$-heterocyclyl, and —$CH_2$-heterocyclyl, wherein the heterocyclyl is independently selected from

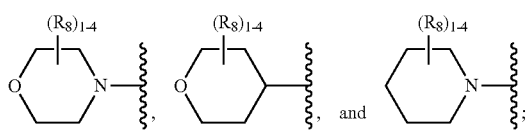

$R_{3c}$ and $R_{3d}$ are independently selected from H, $CH_3$, $CH(CH_3)_2$, $CF_3$, and $C_{3-6}$cycloalkyl;

$R_5$, at each occurrence, is independently selected from H, $C_{1-4}$ alkyl substituted with 0-3 $R_e$, F, Cl, Br, —S(O)$_p$R$_c$, —CN, —OR$_b$, NR$_a$R$_a$, $C_{3-6}$cycloalkyl, and aryl substituted with 0-3 $R_e$;

$R_7$, at each occurrence, is independently selected from H, F, Cl, Br, —(CH$_2$)$_r$CN, NO$_2$, —(CH$_2$)$_r$OR$_b$, —S(O)$_p$R$_c$, —C(=O)R$_b$, —NR$_a$R$_a$, —C(=O)NR$_a$R$_a$, —NHC(=O)R$_b$, —NHC(=O)OR$_b$, —OC(=O)NR$_a$R$_a$, —NHC(=O)NR$_a$R$_a$, —C(=O)OR$_b$, —S(O)$_2$NR$_a$R$_a$, —NHS(O)$_2$NR$_a$R$_a$, —NHS(O)$_2$R$_c$, $C_{1-6}$ alkyl substituted with 0-5 $R_e$, $C_{3-6}$cycloalkyl substituted with 0-5 $R_e$, aryl substituted with 0-5 $R_e$, and heterocyclyl substituted with 0-5 $R_e$;

$R_8$, at each occurrence, is independently selected from H, F, Cl, Br, CN, $C_{1-6}$ alkyl substituted with 0-5 $R_e$, —(CH$_2$)$_r$—C$_{3-6}$ cycloalkyl substituted with 0-5 $R_e$, —(CH$_2$)$_r$-aryl substituted with 0-5 $R_e$, —(CH$_2$)$_r$-heterocyclyl substituted with 0-5 $R_e$, CO$_2$H, —(CH$_2$)$_r$OR$_b$, and —(CH$_2$)$_r$NR$_a$R$_a$;

$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —(CH$_2$)$_r$—C$_{3-10}$carbocyclyl substituted with 0-5 $R_e$, and —(CH$_2$)$_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, aryl substituted with 0-5 $R_e$, and heterocyclyl substituted with 0-5 $R_e$;

$R_c$, at each occurrence, is independently selected from $C_{1-6}$ alkyl substituted with 0-5 $R_e$, $C_{3-6}$carbocyclyl, and heterocyclyl;

$R_e$, at each occurrence, is independently selected from F, Cl, Br, CN, NO$_2$, =O, CO$_2$H, $C_{1-6}$ alkyl, $C_{2-6}$ alkenyl, $C_{2-6}$ alkynyl, and —(CH$_2$)$_r$—C$_{3-6}$ cycloalkyl;

p, at each occurrence, is independently selected from zero, 1, and 2; and r, at each occurrence, is independently selected from zero, 1, 2, 3, and 4;

and other variables are as defined in Formula (III) above.

In another embodiment, there are disclosed compounds of formula (III) including enantiomers, diastereomers, tautomers, pharmaceutically-acceptable salts, prodrugs, hydrates, or solvates thereof, wherein:

$R_2$ is

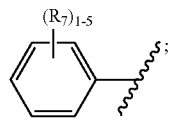

$R_7$, at each occurrence, is independently selected from H, F, Cl, Br, CN, —OC$_{1-4}$alkyl substituted with 0-5 $R_e$, —S(O)$_2$ C$_{1-4}$alkyl, —C(=O)R$_b$, —NR$_a$R$_a$, —C(=O)

NR$_a$R$_a$, $C_{1-4}$ alkyl substituted with 0-5 $R_e$, $C_{3-6}$cycloalkyl substituted with 0-5 $R_e$, aryl substituted with 0-5 $R_e$, and heterocyclyl substituted with 0-5 $R_e$;

$R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —(CH$_2$)$_r$—C$_{3-10}$carbocyclyl substituted with 0-5 $R_e$, and —(CH$_2$)$_r$-heterocyclyl substituted with 0-5 $R_e$; or $R_a$ and $R_a$ together with the nitrogen atom to which they are both attached form a heterocyclic ring substituted with 0-5 $R_e$; wherein the heterocyclic ring is independently selected from

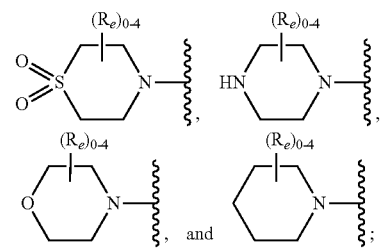

and $R_e$, at each occurrence, is independently selected from F, Cl, Br, CN, NO$_2$, =O, CO$_2$H, $C_{1-6}$ alkyl, $C_{2-6}$ alkenyl, $C_{2-6}$ alkynyl, and —(CH$_2$)$_r$—C$_{3-6}$ cycloalkyl;

and other variables are as defined in Formula (III) above.

In another embodiment, there are disclosed compounds of Formula (III) including enantiomers, diastereomers, tautomers, pharmaceutically-acceptable salts, prodrugs, hydrates, or solvates thereof, wherein:

$R_2$ is independently selected from

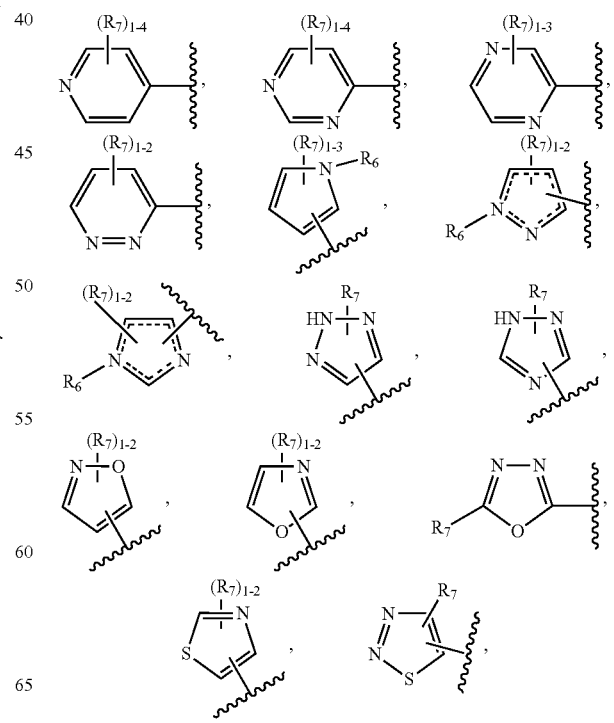

-continued

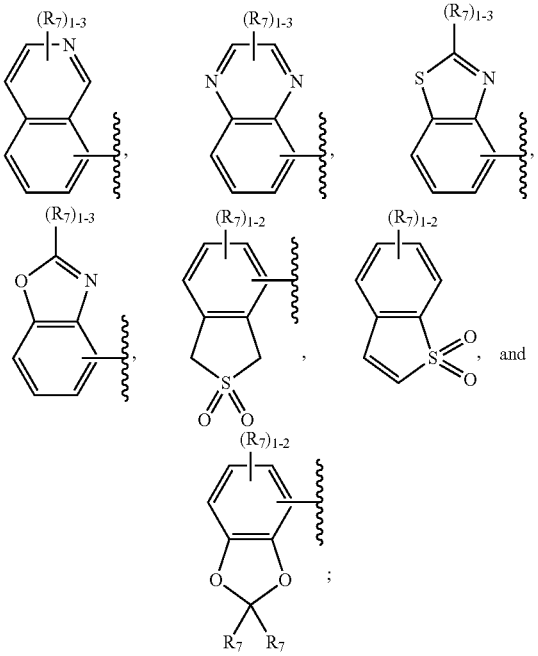

$R_{3a}$ and $R_{3b}$ are independently selected from H, CH$_2$CH$_3$, CH$_3$, CH$_2$OH, CH$_2$CH$_2$OH, CH$_2$CH$_2$OC$_{1-4}$alkyl, CH$_2$F, CHF$_2$, CH$_2$CH$_2$F, CF$_3$, CH$_2$OCHF$_2$, CH$_2$CN, CH$_2$CH$_2$CN, CH$_2$OC$_{1-4}$alkyl, C(CH$_3$)$_3$, CH(CH$_3$)$_2$, C(CH$_3$)$_2$OH, C(CH$_3$)$_2$F, C(=O)NH—C$_{3-6}$cycloalkyl, C(=O)NH-heterocyclyl, and —CH$_2$-heterocyclyl, wherein the heterocyclyl is independently selected from

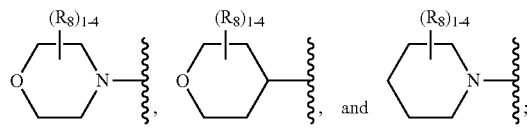

$R_{3c}$ and $R_{3d}$ are independently selected from H, CH$_3$, CH(CH$_3$)$_2$, CF$_3$, and C$_{3-6}$ cycloalkyl;

$R_5$, at each occurrence, is independently selected from H, C$_{1-4}$ alkyl substituted with 0-3 $R_e$, F, Cl, Br, —S(O)$_p$R$_c$, —CN, —OR$_b$, NR$_a$R$_a$, C$_{3-6}$cycloalkyl, and aryl substituted with 0-3 $R_e$;

$R_6$, at each occurrence, is independently selected from H, C$_{1-4}$ alkyl substituted with 0-3 $R_e$;

$R_7$, at each occurrence, is independently selected from H, F, Cl, Br, —(CH$_2$)$_r$CN, NO$_2$, —(CH$_2$)$_r$OR$_b$, —S(O)$_p$R$_c$, —C(=O)R$_b$, —NR$_a$R$_a$, —C(=O)NR$_a$R$_a$, —NHC(=O)R$_b$, —NHC(=O)OR$_b$, —OC(=O)NR$_a$R$_a$, —NHC(=O)NR$_a$R$_a$, —C(=O)OR$_b$, —S(O)$_2$NR$_a$R$_a$, —NHS(O)$_2$NR$_a$R$_a$, —NHS(O)$_2$R$_c$, C$_{1-6}$ alkyl substituted with 0-5 $R_e$, C$_{3-6}$cycloalkyl substituted with 0-5 $R_e$, aryl substituted with 0-5 $R_e$, and heterocyclyl substituted with 0-5 $R_e$;

$R_8$, at each occurrence, is independently selected from H, F, Cl, Br, CN, C$_{1-6}$ alkyl substituted with 0-5 $R_e$, —(CH$_2$)$_r$—C$_{3-6}$ cycloalkyl substituted with 0-5 $R_e$, —(CH$_2$)$_r$-aryl substituted with 0-5 $R_e$, —(CH$_2$)$_r$-heterocyclyl substituted with 0-5 $R_e$, CO$_2$H, —(CH$_2$)$_r$OR$_b$, and —(CH$_2$)$_r$NR$_a$R$_a$;

$R_a$, at each occurrence, is independently selected from H, CN, C$_{1-6}$ alkyl substituted with 0-5 $R_e$, C$_{2-6}$ alkenyl substituted with 0-5 $R_e$, C$_{2-6}$ alkynyl substituted with 0-5 $R_e$, —(CH$_2$)$_r$—C$_{3-10}$carbocyclyl substituted with 0-5 $R_e$, and —(CH$_2$)$_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, C$_{1-6}$ alkyl substituted with 0-5 $R_e$, C$_{2-6}$ alkenyl substituted with 0-5 $R_e$, C$_{2-6}$ alkynyl substituted with 0-5 $R_e$, aryl substituted with 0-5 $R_e$, and heterocyclyl substituted with 0-5 $R_e$;

$R_c$, at each occurrence, is independently selected from C$_{1-6}$ alkyl substituted with 0-5 $R_e$, C$_{3-6}$carbocyclyl, and heterocyclyl;

$R_e$, at each occurrence, is independently selected from F, Cl, Br, CN, NO$_2$, =O, CO$_2$HC$_{1-6}$ alkyl, C$_{2-6}$alkenyl, C$_{2-6}$ alkynyl, and —(CH$_2$)$_r$—C$_{3-6}$ cycloalkyl;

p, at each occurrence, is independently selected from zero, 1, and 2; and r, at each occurrence, is independently selected from zero, 1, 2, 3, and 4;

and other variables are as defined in Formula (III) above.

In another embodiment, there are disclosed compounds of Formula (III) including enantiomers, diastereomers, tautomers, pharmaceutically-acceptable salts, prodrugs, hydrates, or solvates thereof, wherein:

$R_{3a}$ and $R_{3b}$, or $R_{3c}$ and $R_{3d}$, together with the carbon atom to which they are both attached form a spiral carbocyclic or heterocyclic ring comprising carbon atoms and 1 to 4 heteroatoms selected from N, O, S, each substituted with 1-5 $R_8$;

alternatively, $R_{3c}$ and $R_{3d}$, together with the carbon atom to which they are both attached form a spiral carbocyclic ring comprising carbon atoms and 1 to 4 heteroatoms selected from N, O, S, each substituted with 1-5 $R_8$;

and other variables are as defined in Formula (III) above.

In another aspect, there are disclosed compounds of Formula (IV) including enantiomers, diastereomers, tautomers, pharmaceutically-acceptable salts, prodrugs, hydrates, or solvates thereof,

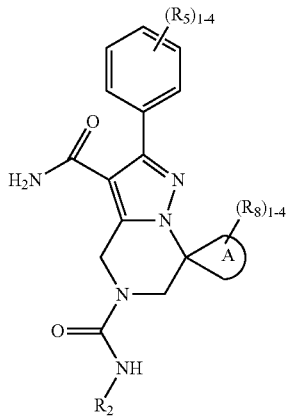

(IV)

wherein:

Ring A is C$_{3-6}$cycloalkyl or heterocyclyl;

$R_2$ is independently selected from aryl substituted with 1-8 $R_7$ and heteroaryl comprising carbon atoms and 1 to 4 heteroatoms selected from N, O, S, and substituted with 1-8 $R_7$;

R$_5$, at each occurrence, is independently selected from H, C$_{1-4}$ alkyl substituted with 0-3 R$_e$, F, Cl, Br, —S(O)$_p$R$_c$, —CN, —OR$_b$, NR$_a$R$_a$, C$_{3-6}$cycloalkyl, aryl substituted with 0-3 R$_e$, and heterocyclyl substituted with 0-3 R$_e$;

R$_7$, at each occurrence, is independently selected from H, F, Cl, Br, CN, NO$_2$, —OR$_b$, —S(O)$_p$R$_c$, —C(=O)R$_b$, —NR$_a$R$_a$, —C(=O)NR$_a$R$_a$, —NHC(=O)R$_b$, —NHC(=O)OR$_b$, —OC(=O)NR$_a$R$_a$, —NHC(=O)NR$_a$R$_a$, —C(=O)OR$_b$, —S(O)$_2$NR$_a$R$_a$, C$_{1-6}$ alkyl substituted with 0-5 R$_e$, aryl substituted with 0-5 R$_e$, and heterocyclyl substituted with 0-5 R$_e$;

R$_8$, at each occurrence, is independently selected from H, F, Cl, Br, CN, C$_{1-6}$ alkyl substituted with 0-5 R$_e$, C$_{2-6}$ alkenyl, C$_{2-6}$ alkynyl, —(CH$_2$)$_r$—C$_{3-6}$ cycloalkyl substituted with 0-5 R$_e$, —(CH$_2$)$_r$-aryl substituted with 0-5 R$_e$, —(CH$_2$)$_r$-heterocyclyl substituted with 0-5 R$_e$, CO$_2$H, —(CH$_2$)$_r$OR$_b$, and —(CH$_2$)$_r$NR$_a$R$_a$;

R$_a$, at each occurrence, is independently selected from H, CN, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;

R$_b$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, aryl substituted with 0-5 R$_e$, and heterocyclyl substituted with 0-5 R$_e$;

R$_c$, at each occurrence, is independently selected from C$_{1-6}$ alkyl substituted with 0-5 R$_e$, C$_{3-6}$carbocyclyl, and heterocyclyl;

R$_e$, at each occurrence, is independently selected from F, Cl, Br, CN, NO$_2$, =O, and CO$_2$H, C$_{1-6}$ alkyl, C$_{2-6}$ alkenyl, C$_{2-6}$ alkynyl, and —(CH$_2$)$_r$—C$_{3-6}$ cycloalkyl;

p, at each occurrence, is independently selected from zero, 1, and 2; and r, at each occurrence, is independently selected from zero, 1, 2, 3, and 4.

In another embodiment, there are disclosed compounds of Formula (III) including enantiomers, diastereomers, tautomers, pharmaceutically-acceptable salts, prodrugs, hydrates, or solvates thereof, wherein:

R$_{3a}$ and R$_{3c}$ together form a carbocyclic or heterocyclic ring comprising carbon atoms and 1 to 4 heteroatoms selected from N, O, S, wherein the carbocyclic or heterocyclic ring is substituted with 1-5 R$_8$; and R$_{3b}$ and R$_{3d}$ are independently selected from H and C$_{1-4}$alkyl;

and other variables are as defined in Formula (III) above.

In another aspect, there are disclosed compounds of Formula (V) including enantiomers, diastereomers, tautomers, pharmaceutically-acceptable salts, prodrugs, hydrates, or solvates thereof,

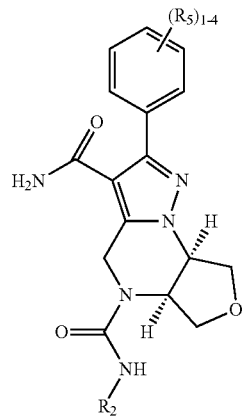

wherein:

R$_2$ is independently selected from aryl substituted with 1-8 R$_7$ and heteroaryl comprising carbon atoms and 1 to 4 heteroatoms selected from N, O, S, and substituted with 1-8 R$_7$;

R$_5$, at each occurrence, is independently selected from H, C$_{1-4}$ alkyl substituted with 0-3 R$_e$, F, Cl, Br, —S(O)$_p$R$_c$, —CN, —OR$_b$, NR$_a$R$_a$, C$_{3-6}$cycloalkyl, aryl substituted with 0-3 R$_e$, and heterocyclyl substituted with 0-3 R$_e$;

R$_7$, at each occurrence, is independently selected from H, F, Cl, Br, CN, NO$_2$, —OR$_b$, —S(O)$_p$R$_c$, —C(=O)R$_b$, —NR$_a$R$_a$, —C(=O)NR$_a$R$_a$, —NHC(=O)R$_b$, —NHC(=O)OR$_b$, —OC(=O)NR$_a$R$_a$, —NHC(=O)NR$_a$R$_a$, —C(=O)OR$_b$, —S(O)$_2$NR$_a$R$_a$, C$_{1-6}$ alkyl substituted with 0-5 R$_e$, aryl substituted with 0-5 R$_e$, and heterocyclyl substituted with 0-5 R$_e$;

R$_a$, at each occurrence, is independently selected from H, CN, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;

R$_b$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, aryl substituted with 0-5 R$_e$, and heterocyclyl substituted with 0-5 R$_e$;

R$_c$, at each occurrence, is independently selected from C$_{1-6}$ alkyl substituted with 0-5 R$_e$, C$_{3-6}$carbocyclyl, and heterocyclyl;

R$_e$, at each occurrence, is independently selected from F, Cl, Br, CN, NO$_2$, =O, CO$_2$H, C$_{1-6}$ alkyl, C$_{2-6}$ alkenyl, C$_{2-6}$ alkynyl, and —(CH$_2$)$_r$—C$_{3-6}$ cycloalkyl;

p, at each occurrence, is independently selected from zero, 1, and 2; and r, at each occurrence, is independently selected from zero, 1, 2, 3, and 4.

All aspects of the compounds, including individual variable definitions, may be combined with other aspects to form additional compounds. For example, in one embodiment of Formula (I), R$_1$ is phenyl, R$_2$ is substituted aryl, and R$_3$ is hydrogen. In another embodiment, R$_1$ is heteroaryl, R$_2$ is heteroaryl, and R$_3$ is substituted alkyl.

In certain embodiments, the present invention includes compounds of Formula (III), or stereoisomers, tautomers, pharmaceutically acceptable salts, solvates, or prodrugs thereof, wherein:

R₁ is phenyl substituted with 1-4 R₅;
R₂ is aryl substituted with 1-5 R₇;
R₃ₐ and R₃ᵦ are independently selected from H, CH₂CH₃, CH₃, CH₂OH, CH₂CH₂OH, CH₂CH₂OC₁₋₄alkyl, CH₂F, CHF₂, CH₂CH₂F, CF₃, CH₂OCHF₂, CH₂CN, CH₂CH₂CN, CH₂OC₁₋₄alkyl, C(CH₃)₃, CH(CH₃)₂, C(CH₃)₂OH, and C(CH₃)₂F;
R₃c and R₃d are independently selected from H, CH₃, CH(CH₃)₂, CF₃, and C₃₋₆ cycloalkyl;
R₅, at each occurrence, is independently selected from H, C₁₋₄ alkyl substituted with 0-3 Rₑ, F, Cl, Br, =O, CN, NO₂, —ORᵦ, —(CH₂)ᵣCN, —(CH₂)ᵣORᵦ, (CH₂)ᵣS(O)ₚRc, —(CH₂)ᵣC(=O)Rᵦ, —(CH₂)ᵣNRₐRₐ, —(CH₂)ᵣC(=O)NRₐRₐ, —(CH₂)ᵣNRₐC(=O)Rᵦ, —(CH₂)ᵣNRₐC(=O)ORᵦ, —(CH₂)ᵣOC(=O)NRₐRₐ, —(CH₂)ᵣNRₐC(=O)NRₐRₐ, —(CH₂)ᵣC(=O)ORᵦ, —(CH₂)ᵣS(O)₂NRₐRₐ, —(CH₂)ᵣNRₐS(O)₂NRₐRₐ, —(CH₂)ᵣNRₐS(O)₂Rc, (CH₂)ᵣ-carbocyclyl substituted with 0-3 Rₑ, and —(CH₂)ᵣ-heterocyclyl substituted with 0-3 Rₑ;
R₇, at each occurrence, is independently selected from H, F, Cl, Br, CN, NO₂, —ORᵦ, —S(O)ₚRc, —C(=O)Rᵦ, —(CRdRd)ᵣNRₐRₐ, —(CRd)ᵣC(=O)NRₐRₐ, —NRₐC(=O)Rᵦ, —NRₐC(=O)ORᵦ, —OC(=O)NRₐRₐ, —NRₐC(=O)NRₐRₐ, —(CRdRd)ᵣC(=O)ORᵦ, —S(O)₂NRₐRₐ, —NRₐS(O)₂NRₐRₐ, —NRₐS(O)₂Rc, C₁₋₆ alkyl substituted with 0-5 Rₑ, —(CRdRd)ᵣ—C₃₋₆carbocyclyl substituted with 0-5 Rₑ, and —(CRdRd)ᵣ-heterocyclyl substituted with 0-5 Rₑ;
Rₐ, at each occurrence, is independently selected from H, CN, C₁₋₆ alkyl substituted with 0-5 Rₑ, C₂₋₆ alkenyl substituted with 0-5 Rₑ, C₂₋₆ alkynyl substituted with 0-5 Rₑ, —(CH₂)ᵣ—C₃₋₁₀carbocyclyl substituted with 0-5 Rₑ, and —(CH₂)ᵣ-heterocyclyl substituted with 0-5 Rₑ; or Rₐ and Rₐ together with the nitrogen atom to which they are both attached form a heterocyclic ring substituted with 0-5 Rₑ;
Rᵦ, at each occurrence, is independently selected from H, C₁₋₆ alkyl substituted with 0-5 Rₑ, C₂₋₆ alkenyl substituted with 0-5 Rₑ, C₂₋₆ alkynyl substituted with 0-5 Rₑ, —(CH₂)ᵣ—C₃₋₁₀carbocyclyl substituted with 0-5 Rₑ, and —(CH₂)ᵣ-heterocyclyl substituted with 0-5 Rₑ;
Rc, at each occurrence, is independently selected from C₁₋₆ alkyl substituted with 0-5 Rₑ, C₂₋₆alkenyl substituted with 0-5 Rₑ, C₂₋₆alkynyl substituted with 0-5 Rₑ, C₃₋₆carbocyclyl, and heterocyclyl;
Rₑ, at each occurrence, is independently selected from F, Cl, Br, CN, NO₂, =O, CO₂H, C₁₋₆ alkyl substituted with 0-5 Rf, C₂₋₆ alkenyl, C₂₋₆ alkynyl, —(CH₂)ᵣ—C₃₋₆ cycloalkyl, —(CH₂)ᵣORf, SRf, and —(CH₂)ᵣNRfRf;
Rf, at each occurrence, is independently selected from H, C₁₋₅ alkyl, C₃₋₆ cycloalkyl, and phenyl, or Rf and Rf together with the nitrogen atom to which they are both attached form a heterocyclic ring optionally substituted with C₁₋₄alkyl;
p, at each occurrence, is independently selected from zero, 1, and 2; and
r, at each occurrence, is independently selected from zero, 1, 2, 3, and 4.

In certain embodiments, the present invention includes compounds of Formula (III), or stereoisomers, tautomers, pharmaceutically acceptable salts, solvates, or prodrugs thereof, wherein:
R₁ is phenyl substituted with 1-4 R₅;
R₂ is aryl substituted with 1-5 R₇;
R₃ₐ and R₃ᵦ are independently selected from H, CH₂CH₃, CH₃, CH₂OH, CH₂CH₂OH, CH₂CH₂OC₁₋₄alkyl, CH₂F, CHF₂, CH₂CH₂F, CF₃, CH₂OCHF₂, CH₂CN, CH₂CH₂CN, CH₂OC₁₋₄alkyl, C(CH₃)₃, CH(CH₃)₂, C(CH₃)₂OH, and C(CH₃)₂F;
R₃c and R₃d are independently selected from H, CH₃, CH(CH₃)₂, CF₃, and C₃₋₆ cycloalkyl;
R₅, at each occurrence, is independently selected from H, C₁₋₄ alkyl substituted with 0-3 Rₑ, F, Cl, Br, =O, CN, NO₂, —ORᵦ, —(CH₂)ᵣCN, —(CH₂)ᵣORᵦ, (CH₂)ᵣS(O)ₚRc, —(CH₂)ᵣC(=O)Rᵦ, —(CH₂)ᵣNRₐRₐ, —(CH₂)ᵣC(=O)NRₐRₐ, —(CH₂)ᵣNRₐC(=O)Rᵦ, (CH₂)ᵣ-carbocyclyl substituted with 0-3 Rₑ, and —(CH₂)ᵣ-heterocyclyl substituted with 0-3 Rₑ;
R₇, at each occurrence, is independently selected from H, F, Cl, Br, CN, —OC₁₋₄alkyl substituted with 0-5 Rₑ, —S(O)₂ C₁₋₄alkyl, —C(=O)Rᵦ, —NRₐRₐ, —C(=O)NRₐRₐ, C₁₋₄ alkyl substituted with 0-5 Rₑ, C₃₋₆cycloalkyl substituted with 0-5 Rₑ, aryl substituted with 0-5 Rₑ, and heterocyclyl substituted with 0-5 Rₑ;
Rₐ, at each occurrence, is independently selected from H, C₁₋₆ alkyl substituted with 0-5 Rₑ, C₂₋₆ alkenyl substituted with 0-5 Rₑ, C₂₋₆ alkynyl substituted with 0-5 Rₑ, —(CH₂)ᵣ—C₃₋₁₀carbocyclyl substituted with 0-5 Rₑ, and —(CH₂)ᵣ-heterocyclyl substituted with 0-5 Rₑ; or Rₐ and Rₐ together with the nitrogen atom to which they are both attached form a heterocyclic ring substituted with 0-5 Rₑ; wherein the heterocyclic ring is independently selected from

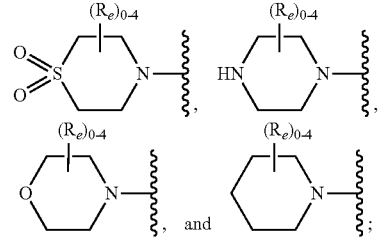

and
Rᵦ, at each occurrence, is independently selected from H, C₁₋₆ alkyl substituted with 0-5 Rₑ, C₂₋₆ alkenyl substituted with 0-5 Rₑ, C₂₋₆ alkynyl substituted with 0-5 Rₑ, —(CH₂)ᵣ—C₃₋₁₀carbocyclyl substituted with 0-5 Rₑ, and —(CH₂)ᵣ-heterocyclyl substituted with 0-5 Rₑ;
Rc, at each occurrence, is independently selected from C₁₋₆ alkyl substituted with 0-5 Rₑ, C₂₋₆alkenyl substituted with 0-5 Rₑ, C₂₋₆alkynyl substituted with 0-5 Rₑ, C₃₋₆carbocyclyl, and heterocyclyl;
Rₑ, at each occurrence, is independently selected from F, Cl, Br, CN, NO₂, =O, CO₂H, C₁₋₆ alkyl substituted with 0-5 Rf, C₂₋₆ alkenyl, C₂₋₆ alkynyl, —(CH₂)ᵣ—C₃₋₆ cycloalkyl, —(CH₂)ᵣORf, SRf, and —(CH₂)ᵣNRfRf;
Rf, at each occurrence, is independently selected from H, C₁₋₅ alkyl, C₃₋₆ cycloalkyl, and phenyl, or Rf and Rf together with the nitrogen atom to which they are both attached form a heterocyclic ring optionally substituted with C₁₋₄alkyl;
p, at each occurrence, is independently selected from zero, 1, and 2; and
r, at each occurrence, is independently selected from zero, 1, 2, 3, and 4.

In certain embodiments, the present invention includes compounds of Formula (III), or stereoisomers, tautomers, pharmaceutically acceptable salts, solvates, or prodrugs thereof, wherein:

$R_1$ is phenyl substituted with 1-4 $R_5$;

$R_2$ is heteroaryl substituted with 1-5 $R_7$;

$R_{3a}$ and $R_{3b}$ are independently selected from H, $CH_2CH_3$, $CH_3$, $CH_2OH$, $CH_2CH_2OH$, $CH_2CH_2OC_{1-4}alkyl$, $CH_2F$, $CHF_2$, $CH_2CH_2F$, $CF_3$, $CH_2OCHF_2$, $CH_2CN$, $CH_2CH_2CN$, $CH_2OC_{1-4}alkyl$, $C(CH_3)_3$, $CH(CH_3)_2$, $C(CH_3)_2OH$, and $C(CH_3)_2F$;

$R_{3c}$ and $R_{3d}$ are independently selected from H, $CH_3$, $CH(CH_3)_2$, $CF_3$, and $C_{3-6}$ cycloalkyl;

$R_5$, at each occurrence, is independently selected from H, $C_{1-4}$ alkyl substituted with 0-3 $R_e$, F, Cl, Br, =O, CN, $NO_2$, —$OR_b$, —$(CH_2)_rCN$, —$(CH_2)_rOR_b$, $(CH_2)_rS(O)_pR_c$, —$(CH_2)_rC(=O)R_b$, —$(CH_2)_rNR_aR_a$, —$(CH_2)_rC(=O)NR_aR_a$, —$(CH_2)_rNR_aC(=O)R_b$, —$(CH_2)_rNR_aC(=O)OR_b$, —$(CH_2)_rOC(=O)NR_aR_a$, —$(CH_2)_rNR_aC(=O)NR_aR_a$, —$(CH_2)_rC(=O)OR_b$, —$(CH_2)_rS(O)_2NR_aR_a$, —$(CH_2)_rNR_aS(O)_2NR_aR_a$, —$(CH_2)_rNR_aS(O)_2R_c$, $(CH_2)_r$-carbocyclyl substituted with 0-3 $R_e$, and —$(CH_2)_r$-heterocyclyl substituted with 0-3 $R_e$;

$R_7$, at each occurrence, is independently selected from H, F, Cl, Br, =O, CN, $NO_2$, —$OR_b$, —$S(O)_pR_c$, —$C(=O)R_b$, —$(CR_dR_d)_rNR_aR_a$, —$(CR_dR_d)_rC(=O)NR_aR_a$, —$NR_aC(=O)R_b$, —$NR_aC(=O)OR_b$, —$OC(=O)NR_aR_a$, —$NR_aC(=O)NR_aR_a$, —$(CR_dR_d)_rC(=O)OR_b$, —$S(O)_2NR_aR_a$, —$NR_aS(O)_2NR_aR_a$, —$NR_aS(O)_2R_c$, $C_{1-6}$ alkyl substituted with 0-5 $R_e$, —$(CR_dR_d)_r$—$C_{3-6}$carbocyclyl substituted with 0-5 $R_e$, and —$(CR_dR_d)_r$-heterocyclyl substituted with 0-5 $R_e$;

$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_d$, at each occurrence, is independently selected from H and $C_{1-4}$alkyl substituted with 0-5 $R_e$;

$R_e$, at each occurrence, is independently selected from F, Cl, Br, CN, $NO_2$, =O, $CO_2H$, $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, —$(CH_2)_rOR_f$, $SR_f$, and —$(CH_2)_rNR_fR_f$;

$R_f$, at each occurrence, is independently selected from H, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

p, at each occurrence, is independently selected from zero, 1, and 2; and r, at each occurrence, is independently selected from zero, 1, 2, 3, and 4.

In certain embodiments, the present invention includes compounds of Formula (III), or stereoisomers, tautomers, pharmaceutically acceptable salts, solvates, or prodrugs thereof, wherein:

$R_1$ is phenyl substituted with 1-4 $R_5$;

$R_2$ is independently selected from aryl substituted with 1-8 $R_7$ and heteroaryl comprising carbon atoms and 1 to 4 heteroatoms selected from N, O, S, and substituted with 1-8 $R_7$;

$R_{3a}$ and $R_{3b}$, or $R_{3c}$ and $R_d$, together with the carbon atom to which they are both attached form a spiral carbocyclic or heterocyclic ring comprising carbon atoms and 1 to 4 heteroatoms selected from N, O, S, each substituted with 1-5 $R_8$;

$R_4$ is independently selected from H and $C_{1-4}$ alkyl substituted with 0-3 $R_e$;

$R_5$, at each occurrence, is independently selected from H, $C_{1-4}$ alkyl substituted with 0-3 $R_e$, F, Cl, Br, =O, CN, $NO_2$, —$OR_b$, —$(CH_2)_rCN$, —$(CH_2)_rOR_b$, $(CH_2)_rS(O)_pR_c$, —$(CH_2)_rC(=O)R_b$, —$(CH_2)_rNR_aR_a$, —$(CH_2)_rC(=O)NR_aR_a$, —$(CH_2)_rNR_aC(=O)R_b$, —$(CH_2)_rNR_aC(=O)OR_b$, —$(CH_2)_rOC(=O)NR_aR_a$, —$(CH_2)_rNR_aC(=O)NR_aR_a$, —$(CH_2)_rC(=O)OR_b$, —$(CH_2)_rS(O)_2NR_aR_a$, —$(CH_2)_rNR_aS(O)_2NR_aR_a$, —$(CH_2)_rNR_aS(O)_2R_c$, $(CH_2)_r$-carbocyclyl substituted with 0-3 $R_e$, and —$(CH_2)_r$-heterocyclyl substituted with 0-3 $R_e$;

$R_7$, at each occurrence, is independently selected from H, F, Cl, Br, —$(CR_dR_d)_rCN$, $NO_2$, —$(CR_dR_d)_rOR_b$, —$S(O)_pR_c$, —$C(=O)R_b$, —$(CR_dR_d)_rNR_aR_a$, —$(CR_dR_d)_rC(=O)NR_aR_a$, —$NR_aC(=O)R_b$, —$NR_aC(=O)OR_b$, —$OC(=O)NR_aR_a$, —$NR_aC(=O)NR_aR_a$, —$(CR_dR_d)_rC(=O)OR_b$, —$S(O)_2NR_aR_a$, —$NR_aS(O)_2NR_aR_a$, —$NR_aS(O)_2R_c$, $C_{1-6}$ alkyl substituted with 0-5 $R_e$, —$(CR_dR_d)_r$—$C_{3-6}$ carbocyclyl substituted with 0-5 $R_e$, and —$(CR_dR_d)_r$-heterocyclyl substituted with 0-5 $R_e$;

$R_8$, at each occurrence, is independently selected from H, F, Cl, Br, CN, $C_{1-6}$ alkyl substituted with 0-5 $R_e$, $C_{2-6}$ alkenyl, $C_{2-6}$ alkynyl, —$(CH_2)_r$—$C_{3-6}$ cycloalkyl substituted with 0-5 $R_e$, —$(CH_2)_r$-aryl substituted with 0-5 $R_e$, —$(CH_2)_r$-heterocyclyl substituted with 0-5 $R_e$, $CO_2H$, —$(CH_2)_rOR_b$, and —$(CH_2)_rNR_aR_a$;

$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_d$, at each occurrence, is independently selected from H and $C_{1-4}$alkyl substituted with 0-5 $R_e$;

$R_e$, at each occurrence, is independently selected from F, Cl, Br, CN, $NO_2$, =O, $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, $CO_2H$, —$(CH_2)_rOR_f$, $SR_f$, and —$(CH_2)_rNR_fR_f$;

$R_f$, at each occurrence, is independently selected from H, $C_{1-5}$alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

p, at each occurrence, is independently selected from zero, 1, and 2; and r, at each occurrence, is independently selected from zero, 1, 2, 3, and 4.

In certain embodiments, the present invention includes compounds of Formula (II), or stereoisomers, tautomers, pharmaceutically acceptable salts, solvates, or prodrugs thereof, wherein:

$R_1$ is heteroaryl comprising carbon atoms and 1 to 3 heteroatoms selected from N, $NR_4$, O, S, wherein the heteroaryl is substituted with 1-5 $R_5$ and selected from thiazolyl, oxazolyl, pyrazolyl, triazolyl, tetrazolyl, thiadiazolyl, isoxazolyl, imidazolyl, pyridyl, pyrimidinyl, pyrazinyl, pyridazinyl, indolyl, indazolyl, isoindolyl, indolinyl, isoindolinyl, benzimidazolyl, benzothiazolyl, benzotriazolyl, quinolinyl, and isoquinolinyl;

$R_2$ is independently selected from aryl substituted with 1-8 $R_7$ and heteroaryl comprising carbon atoms and 1 to 4 heteroatoms selected from N, $NR_6$, O, S, and substituted with 1-8 $R_7$;

$R_{3a}$, $R_{3b}$, $R_{3c}$, $R_{3d}$, $R_{3e}$ and $R_{3f}$ are independently selected from H, CN, $C_{1-4}$alkyl substituted with 1-3 $R_8$, —C(=O)$OR_b$, —C(=O)$NR_aR_a$, —C(=O)$R_b$, —$NR_aC$(=O)$R_b$, —$NR_aC$(=O)$OR_b$, —$(CH_2)_r$-carbocyclyl substituted with 1-3 $R_8$, and —$(CH_2)_r$-heterocyclyl substituted with 1-3 $R_8$;

alternatively, $R_{3a}$ and $R_{3b}$, or $R_{3c}$ and $R_{3d}$, or $R_{3e}$ and $R_{3f}$ together with the carbon atom to which they are both attached form a spiral carbocyclic or heterocyclic ring comprising carbon atoms and 1 to 4 heteroatoms selected from N, O, S, each substituted with 1-5 $R_8$;

alternatively, $R_{3a}$ and $R_{3c}$ or $R_{3b}$ and $R_{3d}$ together form a heterocyclic ring comprising carbon atoms and 1 to 4 heteroatoms selected from N, O, S, and substituted with 1-5 $R_8$;

$R_4$ is independently selected from H and $C_{1-4}$ alkyl substituted with 0-3 $R_e$;

$R_5$, at each occurrence, is independently selected from H, $C_{1-4}$ alkyl substituted with 0-3 $R_e$, F, Cl, Br, =O, CN, $NO_2$, —$OR_b$, —$(CH_2)_r$CN, —$(CH_2)_rOR_b$, $(CH_2)_rS(O)_pR_c$, —$(CH_2)_rC$(=O)$R_b$, —$(CH_2)_rNR_aR_a$, —$(CH_2)_rC$(=O)$NR_aR_a$, —$(CH_2)_rNR_aC$(=O)$R_b$, —$(CH_2)_rNR_aC$(=O)$OR_b$, —$(CH_2)_rOC$(=O)$NR_aR_a$, —$(CH_2)_rNR_aC$(=O)$NR_aR_a$, —$(CH_2)_rC$(=O)$OR_b$, —$(CH_2)_rS(O)_2NR_aR_a$, —$(CH_2)_rNR_aS(O)_2NR_aR_a$, —$(CH_2)_rNR_aS(O)_2R_c$, $(CH_2)_r$-carbocyclyl substituted with 0-3 $R_e$, and —$(CH_2)_r$-heterocyclyl substituted with 0-3 $R_e$;

$R_7$, at each occurrence, is independently selected from H, F, Cl, Br, CN, $NO_2$, —$OR_b$, —$S(O)_pR_c$, —$C(=O)R_b$, —$(CR_dR_d)_rNR_aR_a$, —$(CR_dR_d)_rC$(=O)$NR_aR_a$, —$NR_aC$(=O)$R_b$, —$NR_aC$(=O)$OR_b$, —$OC(=O)NR_aR_a$, —$NR_aC$(=O)$NR_aR_a$, —$(CR_dR_d)_rC$(=O)$OR_b$, —$S(O)_2NR_aR_a$, —$NR_aS(O)_2NR_aR_a$, —$NR_aS(O)_2R_c$, $C_{1-6}$ alkyl substituted with 0-5 $R_e$, —$(CR_dR_d)_rC_{3-6}$carbocyclyl substituted with 0-5 $R_e$, and —$(CR_dR_d)_r$-heterocyclyl substituted with 0-5 $R_e$;

$R_8$, at each occurrence, is independently selected from H, F, Cl, Br, CN, $C_{1-6}$ alkyl substituted with 0-5 $R_e$, $C_{2-6}$ alkenyl, $C_{2-6}$ alkynyl, —$(CH_2)_r$—$C_{3-6}$ cycloalkyl substituted with 0-5 $R_e$, —$(CH_2)_r$-aryl substituted with 0-5 $R_e$, —$(CH_2)_r$-heterocyclyl substituted with 0-5 $R_e$, $CO_2H$, —$(CH_2)_rOR_b$, and —$(CH_2)_rNR_aR_a$;

$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_e$, at each occurrence, is independently selected from F, Cl, Br, CN, $NO_2$, =O, $CO_2H$, $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, —$(CH_2)_rOR_f$, $SR_f$, and —$(CH_2)_rNR_fR_f$;

$R_f$, at each occurrence, is independently selected from H, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

p, at each occurrence, is independently selected from zero, 1, and 2; and r, at each occurrence, is independently selected from zero, 1, 2, 3, and 4.

In certain embodiments, the present invention includes compounds of Formula (II), or stereoisomers, tautomers, pharmaceutically acceptable salts, solvates, or prodrugs thereof, wherein:

$R_1$ is heteroaryl comprising carbon atoms and 1 to 3 heteroatoms selected from N, $NR_4$, O, S, wherein the heteroaryl is substituted with 1-5 $R_5$ and selected from thiazolyl, oxazolyl, pyrazolyl, triazolyl, tetrazolyl, thiadiazolyl, isoxazolyl, imidazolyl, pyridyl, pyrimidinyl, pyrazinyl, pyridazinyl, indolyl, indazolyl, isoindolyl, indolinyl, isoindolinyl, benzimidazolyl, benzothiazolyl, benzotriazolyl, quinolinyl, and isoquinolinyl;

$R_2$ is aryl substituted with 1-5 $R_7$;

$R_{3a}$, $R_{3b}$, $R_{3c}$, $R_{3d}$, $R_{3e}$ and $R_{3f}$ are independently selected from H, CN, $C_{1-4}$alkyl substituted with 1-3 $R_8$, —C(=O)$OR_b$, —C(=O)$NR_aR_a$, —C(=O)$R_b$, —$NR_aC$(=O)$R_b$, —$NR_aC$(=O)$OR_b$, —$(CH_2)_r$-carbocyclyl substituted with 1-3 $R_8$, and —$(CH_2)_r$-heterocyclyl substituted with 1-3 $R_8$;

alternatively, $R_{3a}$ and $R_{3b}$, or $R_{3c}$ and $R_{3d}$, or $R_{3e}$ and $R_{3f}$ together with the carbon atom to which they are both attached form a spiral carbocyclic or heterocyclic ring comprising carbon atoms and 1 to 4 heteroatoms selected from N, O, S, each substituted with 1-5 $R_8$;

alternatively, $R_{3a}$ and $R_{3c}$ or $R_{3b}$ and $R_{3d}$ together form a heterocyclic ring comprising carbon atoms and 1 to 4 heteroatoms selected from N, O, S, and substituted with 1-5 $R_8$;

$R_4$ is independently selected from H and $C_{1-4}$ alkyl substituted with 0-3 $R_e$;

$R_5$, at each occurrence, is independently selected from H, $C_{1-4}$ alkyl substituted with 0-3 $R_e$, F, Cl, Br, =O, CN, $NO_2$, —$OR_b$, —$(CH_2)_r$CN, —$(CH_2)_rOR_b$, $(CH_2)_rS(O)_pR_c$, —$(CH_2)_rC$(=O)$R_b$, —$(CH_2)_rNR_aR_a$, —$(CH_2)_rC$(=O)$NR_aR_a$, —$(CH_2)_rNR_aC$(=O)$R_b$, —$(CH_2)_rNR_aC$(=O)$OR_b$, —$(CH_2)_rOC$(=O)$NR_aR_a$, —$(CH_2)_rNR_aC$(=O)$NR_aR_a$, —$(CH_2)_rC$(=O)$OR_b$, —$(CH_2)_rS(O)_2NR_aR_a$, —$(CH_2)_rNR_aS(O)_2NR_aR_a$, —$(CH_2)_rNR_aS(O)_2R_c$, $(CH_2)_r$-carbocyclyl substituted with 0-3 $R_e$, and —$(CH_2)_r$-heterocyclyl substituted with 0-3 $R_e$;

$R_7$, at each occurrence, is independently selected from H, F, Cl, Br, CN, $NO_2$, —$OR_b$, —$S(O)_pR_c$, —$C(=O)R_b$, —$(CR_dR_d)_rNR_aR_a$, —$(CR_dR_d)_rC(=O)NR_aR_a$, —$NR_aC(=O)R_b$, —$NR_aC(=O)OR_b$, —$OC(=O)NR_aR_a$, —$NR_aC(=O)NR_aR_a$, —$(CR_dR_d)_rC(=O)OR_b$, —$S(O)_2NR_aR_a$, —$NR_aS(O)_2NR_aR_a$, —$NR_aS(O)_2R_c$, $C_{1-6}$ alkyl substituted with 0-5 $R_e$, —$(CR_dR_d)_r$—$C_{3-6}$carbocyclyl substituted with 0-5 $R_e$, and —$(CR_dR_d)_r$-heterocyclyl substituted with 0-5 $R_e$;

$R_8$, at each occurrence, is independently selected from H, F, Cl, Br, CN, $C_{1-6}$ alkyl substituted with 0-5 $R_e$, $C_{2-6}$ alkenyl, $C_{2-6}$ alkynyl, —$(CH_2)_r$—$C_{3-6}$ cycloalkyl substituted with 0-5 $R_e$, —$(CH_2)_r$-aryl substituted with 0-5 $R_e$, —$(CH_2)_r$-heterocyclyl substituted with 0-5 $R_e$, $CO_2H$, —$(CH_2)_rOR_b$, and —$(CH_2)_rNR_aR_a$;

$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_d$, at each occurrence, is independently selected from H and $C_{1-4}$alkyl substituted with 0-5 $R_e$;

$R_e$, at each occurrence, is independently selected from F, Cl, Br, CN, $NO_2$, =O, $CO_2H$, $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, —$(CH_2)_rOR_f$, $SR_f$, and —$(CH_2)_rNR_fR_f$;

$R_f$, at each occurrence, is independently selected from H, $C_{1-5}$alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

p, at each occurrence, is independently selected from zero, 1, and 2; and r, at each occurrence, is independently selected from zero, 1, 2, 3, and 4.

In certain embodiments, the present invention includes compounds of Formula (II), or stereoisomers, tautomers, pharmaceutically acceptable salts, solvates, or prodrugs thereof, wherein:

$R_1$ is heteroaryl comprising carbon atoms and 1 to 3 heteroatoms selected from N, $NR_4$, O, S, wherein the heteroaryl is substituted with 1-5 $R_5$ and selected from thiazolyl, oxazolyl, pyrazolyl, triazolyl, tetrazolyl, thiadiazolyl, isoxazolyl, imidazolyl, pyridyl, pyrimidinyl, pyrazinyl, pyridazinyl, indolyl, indazolyl, isoindolyl, indolinyl, isoindolinyl, benzimidazolyl, benzothiazolyl, benzotriazolyl, quinolinyl, and isoquinolinyl;

$R_2$ is heteroaryl comprising carbon atoms and 1 to 4 heteroatoms selected from N, O, S, and substituted with 1-8 $R_7$;

$R_{3a}$, $R_{3b}$, $R_{3c}$, $R_{3d}$, $R_{3e}$ and $R_{3f}$ are independently selected from H, CN, $C_{1-4}$alkyl substituted with 1-3 $R_8$, —$C(=O)OR_b$, —$C(=O)NR_aR_a$, —$C(=O)R_b$, —$NR_aC(=O)R_b$, —$NR_aC(=O)OR_b$, —$(CH_2)_r$-carbocyclyl substituted with 1-3 $R_8$, and —$(CH_2)_r$-heterocyclyl substituted with 1-3 $R_8$;

alternatively, $R_{3a}$ and $R_{3b}$, or $R_{3c}$ and $R_{3d}$, or $R_{3e}$ and $R_{3f}$ together with the carbon atom to which they are both attached form a spiral carbocyclic or heterocyclic ring comprising carbon atoms and 1 to 4 heteroatoms selected from N, O, S, each substituted with 1-5 $R_8$;

alternatively, $R_{3a}$ and $R_{3c}$ or $R_{3b}$ and $R_{3d}$ together form a heterocyclic ring comprising carbon atoms and 1 to 4 heteroatoms selected from N, O, S, and substituted with 1-5 $R_8$;

$R_4$ is independently selected from H and $C_{1-4}$ alkyl substituted with 0-3 $R_e$;

$R_5$, at each occurrence, is independently selected from H, $C_{1-4}$ alkyl substituted with 0-3 $R_e$, F, Cl, Br, =O, CN, $NO_2$, —$OR_b$, —$(CH_2)_rCN$, —$(CH_2)_rOR_b$, $(CH_2)_rS(O)_pR_c$, —$(CH_2)_rC(=O)R_b$, —$(CH_2)_rNR_aR_a$, —$(CH_2)_rC(=O)NR_aR_a$, —$(CH_2)_rNR_aC(=O)R_b$, —$(CH_2)_rNR_aC(=O)OR_b$, —$(CH_2)_rOC(=O)NR_aR_a$, —$(CH_2)_rNR_aC(=O)NR_aR_a$, —$(CH_2)_rC(=O)OR_b$, —$(CH_2)_rS(O)_2NR_aR_a$, —$(CH_2)_rNR_aS(O)_2NR_aR_a$, —$(CH_2)_rNR_aS(O)_2R_c$, $(CH_2)_r$-carbocyclyl substituted with 0-3 $R_e$, and —$(CH_2)_r$-heterocyclyl substituted with 0-3 $R_e$;

$R_6$ is independently selected from H, —$C(=O)R_b$, —$CO(=O)R_b$, —$S(O)_pR_c$, $C_{1-6}$ alkyl substituted with 0-5 $R_e$, —$(CH_2)_r$—$C_{3-6}$carbocyclyl substituted with 0-5 $R_e$, and —$(CH_2)_r$-heterocyclyl substituted with 0-5 $R_e$;

$R_7$, at each occurrence, is independently selected from H, F, Cl, Br, =O, CN, $NO_2$, —$OR_b$, —$S(O)_pR_c$, —$C(=O)R_b$, —$(CR_dR_d)_rNR_aR_a$, —$(CR_dR_d)_rC(=O)NR_aR_a$, —$NR_aC(=O)R_b$, —$NR_aC(=O)OR_b$, —$OC(=O)NR_aR_a$, —$NR_aC(=O)NR_aR_a$, —$(CR_dR_d)_rC(=O)OR_b$, —$S(O)_2NR_aR_a$, —$NR_aS(O)_2NR_aR_a$, —$NR_aS(O)_2R_c$, $C_{1-6}$ alkyl substituted with 0-5 $R_e$, —$(CR_dR_d)_rC_{3-6}$carbocyclyl substituted with 0-5 $R_e$, and —$(CR_dR_d)_r$-heterocyclyl substituted with 0-5 $R_e$;

$R_8$, at each occurrence, is independently selected from H, F, Cl, Br, CN, $C_{1-6}$ alkyl substituted with 0-5 $R_e$, $C_{2-6}$ alkenyl, $C_{2-6}$ alkynyl, —$(CH_2)_r$—$C_{3-6}$ cycloalkyl substituted with 0-5 $R_e$, —$(CH_2)_r$-aryl substituted with 0-5 $R_e$, —$(CH_2)_r$-heterocyclyl substituted with 0-5 $R_e$, $CO_2H$, —$(CH_2)_rOR_b$, and —$(CH_2)_rNR_aR_a$;

$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_d$, at each occurrence, is independently selected from H and $C_{1-4}$alkyl substituted with 0-5 $R_e$;

$R_e$, at each occurrence, is independently selected from F, Cl, Br, CN, $NO_2$, =O, $CO_2H$, $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, —$(CH_2)_rOR_f$, $SR_f$, and —$(CH_2)_rNR_fR_f$;

$R_f$, at each occurrence, is independently selected from H, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

p, at each occurrence, is independently selected from zero, 1, and 2; and r, at each occurrence, is independently selected from zero, 1, 2, 3, and 4.

It should further be understood that solvates (e.g., hydrates) of the compounds of Formulae (I)-(V) are also within the scope of the invention. Methods of solvation are generally known in the art. The inventive compounds may either be in the free or hydrate form.

Compounds of this invention may have one or more asymmetric centers. Unless otherwise indicated, all chiral (enantiomeric and diastereomeric) and racemic forms of compounds of the present invention are included in the present invention. Many geometric isomers of olefins, C=N double bonds, and the like can also be present in the compounds, and all such stable isomers are contemplated in the present invention. Cis- and trans-geometric isomers of the compounds of the present invention are described and may be isolated as a mixture of isomers or as separated isomeric forms. The present compounds can be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated. When no specific mention is made of the configuration (cis, trans or R or S) of a compound (or of an asymmetric carbon), then any one of the isomers or a mixture of more than one isomer is intended. The processes for preparation can use racemates, enantiomers, or diastereomers as starting materials. All processes used to prepare compounds of the present invention and intermediates made therein are considered to be part of the present invention. When enantiomeric or diastereomeric products are prepared, they can be separated by conventional methods, for example, by chromatography or fractional crystallization. Compounds of the present invention, and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

DEFINITIONS

The following are definitions of terms used in this specification and appended claims. The initial definition provided for a group or term herein applies to that group or term throughout the specification and claims, individually or as part of another group, unless otherwise indicated.

In accordance with a convention used in the art,

is used in structural formulas herein to depict the bond that is the point of attachment of the moiety or substituent to the core or backbone structure.

A dash "—" that is not between two letters or symbols is used to indicate a point of attachment for a substituent. For example, —CONH$_2$ is attached through the carbon atom.

As used herein, the term "alkyl" or "alkylene" is intended to include both branched and straight-chain saturated aliphatic hydrocarbon groups having the specified number of carbon atoms. For example, "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$-$C_6$ alkyl" denotes alkyl having 1 to 6 carbon atoms. Alkyl groups can be unsubstituted or substituted so that one or more of its hydrogens are replaced by another chemical group. Example alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like.

"Haloalkyl" is intended to include both branched and straight-chain saturated aliphatic hydrocarbon groups having the specified number of carbon atoms, substituted with 1 or more halogen. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" which is intended to include both branched and straight-chain saturated aliphatic hydrocarbon groups having the specified number of carbon atoms, substituted with 1 or more fluorine atoms.

The term "halogen" or "halo" refers to fluorine (F), chlorine (Cl), bromine (Br) and iodine.

"Haloalkoxy" or "haloalkyloxy" represents a haloalkyl group as defined above with the indicated number of carbon atoms attached through an oxygen bridge. For example, "$C_{1-6}$ haloalkoxy" is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, pentafluorothoxy, and the like. Similarly, "haloalkylthio" or "thiohaloalkoxy" represents a haloalkyl group as defined above with the indicated number of carbon atoms attached through a sulphur bridge; for example trifluoromethyl-S—, pentafluoroethyl-S—, and the like.

As used herein, "carbocycle", "carbocyclic residue", or "carbocyclyl" is intended to mean any stable 3-, 4-, 5-, 6-, or 7-membered monocyclic or bicyclic or 7-, 8-, 9-, 10-, 11-, 12-, or 13-membered bicyclic or tricyclic hydrocarbon ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, and indanyl. When the term "carbocycle", "carbocyclic residue", or "carbocyclyl" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

The term "aryl" refers to monocyclic, bicyclic, tricyclic aromatic hydrocarbon groups having 6 to 15 carbon atoms in the ring portion, such as phenyl, naphthyl, biphenyl and diphenyl groups, each of which may be substituted. Aryl groups which are bicyclic or tricyclic must include at least one fully aromatic ring but the other fused ring or rings may be aromatic or non-aromatic. When an aryl is substituted with a further heterocyclic ring, said ring may be attached to the aryl through a carbon atom or a heteroatom and said ring in turn is optionally substituted with one to two substituents as valence allows.

The terms "aryloxy", "arylamino", "arylalkylamino", "arylthio", "arylalkanoylamino", "arylsulfonyl", "arylalkoxy", "arylsulfinyl", "arylheteroaryl", "arylalkylthio", "arylcarbonyl", "arylalkenyl", or "arylalkylsulfonyl" refer to an aryl or substituted aryl bonded to an oxygen; an amino; an alkylamino; a thio; an alkanoylamino; a sulfonyl; an alkoxy; a sulfinyl; a heteroaryl or substituted heteroaryl; an alkylthio; a carbonyl; an alkenyl; or an alkylsulfonyl, respectively.

The term "alkenyl" refers to straight or branched chain hydrocarbon groups of 2 to 20 carbon atoms, preferably 2 to 15 carbon atoms, and most preferably 2 to 8 carbon atoms, having one to four double bonds.

The term "alkynyl" refers to straight or branched chain hydrocarbon groups of 2 to 20 carbon atoms, preferably 2 to 15 carbon atoms, and most preferably 2 to 8 carbon atoms, having one to four triple bonds.

The term "cycloalkyl" refers to an optionally substituted, saturated cyclic hydrocarbon ring systems, preferably containing 1 to 3 rings and 3 to 7 carbons per ring. Exemplary groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, or one or more groups described above as alkyl substituents. Accordingly, in compounds of formula I, the term "cycloalkyl" includes cyclopropyl, cyclobutyl, cyclopentyl, cyclohexyl, cycloheptyl, bicyclooctyl, etc., as well as the following ring systems,

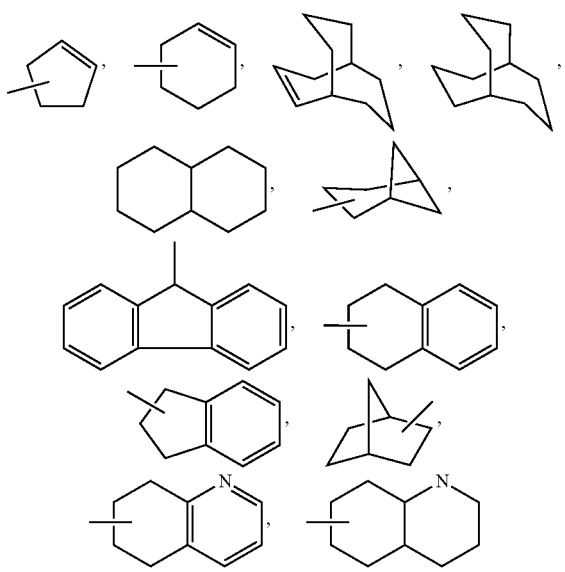

and the like, which optionally may be substituted at any available atoms of the ring(s). Preferred cycloalkyl groups include cyclopropyl, cyclopentyl, cyclohexyl,

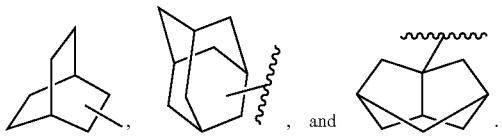

As used herein, the term "heterocycle", "heterocyclyl", "heterocyclic ring" or "heterocyclic group" is intended to mean a stable 4-, 5-, 6-, or 7-membered monocyclic or bicyclic or 7-, 8-, 9-, 10-, 11-, 12-, 13-, or 14-membered bicyclic heterocyclic ring which is saturated, partially unsaturated or fully unsaturated or aromatic, and which consists of carbon atoms and 1, 2, 3 or 4 heteroatoms independently selected from N, O and S; and including any bicyclic group in which any of the above-defined heterocyclic rings is fused to a benzene ring. The nitrogen and sulfur heteroatoms may optionally be oxidized (i.e., N→O and $S(O)_p$). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on a carbon atom or on a nitrogen atom if the resulting compound is stable. A nitrogen atom in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle", "heterocyclyl", "heterocyclic ring" or "heterocyclic group" is used, it is intended to include heteroaryl.

Examples of heterocycles include, but are not limited to, acridinyl, azocinyl, benzimidazolyl, benzofuranyl, benzothiofuranyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Preferred 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Preferred 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

Bridged rings are also included in the definition of heterocycle. A bridged ring occurs when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "heteroaryl" refers to substituted and unsubstituted aromatic 5- or 6-membered monocyclic groups, 9- or 10-membered bicyclic groups, and 11- to 14-membered tricyclic groups which have at least one heteroatom (O, S or N) in at least one of the rings, said heteroatom-containing ring preferably having 1, 2, or 3 heteroatoms selected from O, S, and N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. Heteroaryl groups can be substituted or unsubstituted. The nitrogen atom may be substituted or unsubstituted (i.e., N or NR wherein R is H or another substituent, if defined). The nitrogen and sulfur heteroatoms may optionally be oxidized (i.e., N→O and $S(O)_p$) and the nitrogen atoms may optionally be quaternized.

Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero, one, two or three substituents.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxazolyl, benzothienyl, quinolinyl, dihydroisoquinolinyl, tetrahydroquinolinyl, isoquinolinyl, benzimidazolyl, benzopyranyl, benzoxazinyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, and the like.

Exemplary tricyclic heteroaryl groups include carbazolyl, benzidolyl, phenanthrollinyl, acridinyl, phenanthridinyl, xanthenyl and the like.

The term "heteroatoms" shall include oxygen, sulfur and nitrogen.

As referred to herein, the term "substituted" means that one or more hydrogen atoms is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

When any variable occurs more than one time in any constituent or formula for a compound, its definition at each occurrence is independent of its definition at every other occurrence. Thus, for example, if a group is shown to be substituted with 0-3 $R_e$, then said group may optionally be substituted with up to three $R_e$ groups and $R_e$ at each occurrence is selected independently from the definition of $R_e$. Also, combinations of substituents and/or variables are permissible only if such combinations result in stable compounds.

Utility

The compounds of the invention may be used to modulate kinase activities.

Applicants have discovered that compounds of Formulae (I)-(V) have particular utility in treating proliferative conditions associated with the modulation of kinase activity, and particularly the inhibition of serine/threonine kinase activities. The compounds of the present invention can be used to treat proliferative disorders associated with abnormal kinase activity. As used herein, the terms "treating" and "treatment" encompass either or both responsive and prophylaxis measures, e.g., measures designed to inhibit or delay the onset of the disease or disorder, achieve a full or partial reduction of the symptoms or disease state, and/or to alleviate, ameliorate, lessen, or cure the disease or disorder and/or its symptoms.

Accordingly, one aspect of the invention is the use of a compound of the Formulae (I)-(V), or a pharmaceutically acceptable salt thereof in the manufacture of a medicament for use in the production of an antiproliferative effect in a warm-blooded animal such as a human being.

According to a further feature of the invention there is provided a method for producing an antiproliferative effect in a warm-blooded animal, such as a human being, in need of such treatment which comprises administering to said animal an effective amount of a compound of Formulae (I)-(V) or a pharmaceutically acceptable salt thereof as defined herein before.

The anti-proliferative treatment defined herein before may be applied as a sole therapy or may involve, in addition to a compound of the invention, one or more other substances and/or treatments. Such treatment may be achieved by way of the simultaneous, sequential or separate administration of the individual components of the treatment. The compounds of this invention may also be useful in combination with known anti-cancer and cytotoxic agents and treatments, including radiation. Compounds of Formulae (I)-(V) may be used sequentially with known anticancer or cytotoxic agents and treatment, including radiation when a combination formulation is inappropriate.

The term "anti-cancer" agent includes any known agent that is useful for the treatment of cancer including the following: 17α-ethinylestradiol, diethylstilbestrol, testosterone, prednisone, fluoxymesterone, dromostanolone propionate, testolactone, megestrolacetate, methylprednisolone, methyl-testosterone, prednisolone, triamcinolone, chlorotrianisene, hydroxyprogesterone, aminoglutethimide, estramustine, medroxyprogesteroneacetate, leuprolide, flutamide, toremifene, ZOLADEX®; matrix metalloproteinase inhibitors; VEGF inhibitors, such as anti-VEGF antibodies (AVASTIN®) and small molecules such as ZD6474 and SU6668; Vatalanib, BAY-43-9006, SU11248, CP-547632, and CEP-7055; HER 1 and HER 2 inhibitors including anti-HER2 antibodies (HERCEPTIN); EGFR inhibitors including gefitinib, erlotinib, ABX-EGF, EMD72000, 11F8, and cetuximab; Eg5 inhibitors, such as SB-715992, SB-743921, and MKI-833; pan Her inhibitors, such as canertinib, EKB-569, CI-1033, AEE-788, XL-647, mAb 2C4, and GW-572016; Src inhibitors, e.g., GLEEVEC® and dasatinib; CASODEX® (bicalutamide, Astra Zeneca), Tamoxifen; MEK-1 kinase inhibitors, MAPK kinase inhibitors, PI3 kinase inhibitors; PDGF inhibitors, such as imatinib; antiangiogenic and antivascular agents which, by interrupting blood flow to solid tumors, render cancer cells quiescent by depriving them of nutrition; castration, which renders androgen dependent carcinomas non-proliferative; inhibitors of non-receptor and receptor tyrosine kinases; inhibitors of integrin signaling; tubulin acting agents such as vinblastine, vincristine, vinorelbine, vinflunine, paclitaxel, docetaxel, 7-O-methylthiomethylpaclitaxel, 4-desacetyl-4-methylcarbonatepaclitaxel, 3'-tert-butyl-3'-N-tert-butyloxycarbonyl-4-deacetyl-3'-dephenyl-3'-N-debenzoyl-4-O-methoxycarbonyl-paclitaxel, C-4 methyl carbonate paclitaxel, epothilone A, epothilone B, epothilone C, epothilone D, [1S-[1R*,3R*(E),7R*,10S*,11R*,12R*,16S*]]-7-11-dihydroxy-8,8,10,12,16-pentamethyl-3-[1-methyl-2-(2-methyl-4-thiazolyl)ethenyl]-4-aza-17 oxabicyclo[14.1.0] heptadecane-5,9-dione (ixabepilone), [1S-[1R*,3R*(E),7R*,10S*,11R*,12R*,16S*]]-3-[2-[2-(aminomethyl)-4-thiazolyl]-1-methylethenyl]-7,11-dihydroxy-8,8,10,12,16-pentamethyl-4-17-dioxabicyclo[14.1.0]-heptadecane-5,9-dione, and derivatives thereof; other CDK inhibitors, antiproliferative cell cycle inhibitors, epidophyllotoxin, etoposide, VM-26; antineoplastic enzymes, e.g., topoisomerase I inhibitors, camptothecin, topotecan, SN-38; procarbazine; mitoxantrone; platinum coordination complexes such as cisplatin, carboplatin and oxaliplatin; biological response modifiers; growth inhibitors; antihormonal therapeutic agents; leucovorin; tegafur; antimetabolites such as purine antagonists (e.g., 6-thioguanine and 6-mercaptopurine; glutamine antagonists, e.g., DON (AT-125; d-oxonorleucine); ribonucleotide reductase inhibitors; mTOR inhibitors; and haematopoietic growth factors.

Additional cytotoxic agents include, cyclophosphamide, doxorubicin, daunorubicin, mitoxanthrone, melphalan, hexamethyl melamine, thiotepa, cytarabin, idatrexate, trimetrexate, dacarbazine, L-asparaginase, bicalutamide, leuprolide, pyridobenzoindole derivatives, interferons, and interleukins.

In the field of medical oncology it is normal practice to use a combination of different forms of treatment to treat each patient with cancer. In medical oncology the other component(s) of such treatment in addition to the antiproliferative treatment defined herein may be surgery, radiotherapy or chemotherapy. Such chemotherapy may cover three main categories of therapeutic agent:

(i) antiangiogenic agents that work by different mechanisms from those defined herein before (for example, linomide, inhibitors of integrin αvβ3 function, angiostatin, razoxane);

(ii) cytostatic agents such as antiestrogens (for example, tamoxifen, toremifene, raloxifene, droloxifene, iodoxifene), progestogens (for example, megestrol acetate), aromatase inhibitors (for example, anastrozole, letrozole, borazole, exemestane), antihormones, antiprogestogens, antiandrogens (for example, flutamide, nilutamide, bicalutamide, cyproterone acetate), LHRH agonists and antagonists (for example, goserelin acetate, leuprolide), inhibitors of testosterone 5α-dihydroreductase (for example, finasteride), farnesyltransferase inhibitors, anti-invasion agents (for example, metalloproteinase inhibitors such as marimastat and inhibitors of urokinase plasminogen activator receptor function) and inhibitors of growth factor function, (such growth factors include for example, EGF, FGF, platelet derived growth factor and hepatocyte growth factor, such inhibitors include growth factor antibodies, growth factor receptor antibodies such as AVASTIN® (bevacizumab) and ERBITUX® (cetuximab); tyrosine kinase inhibitors and serine/threonine kinase inhibitors); and (iii) antiproliferative/antineoplastic drugs and combinations thereof, as used in medical oncology, such as antimetabolites (for example, antifolates such as methotrexate, fluoropyrimidines such as 5-fluorouracil, purine and adenosine analogues, cytosine arabinoside); intercalating antitumor antibiotics (for example, anthracyclines such as doxorubicin, daunomycin, epirubicin and idarubicin, mitomycin-C, dactinomycin, mithramycin); platinum derivatives (for example, cisplatin, carboplatin); alkylating agents (for example, nitrogen mustard, melphalan, chlorambucil, busulphan, cyclophosphamide, ifosfamide, nitrosoureas, thiotepa; antimitotic agents (for example, vinca alkaloids like vincristine, vinorelbine, vinblastine and vinflunine) and taxoids such as TAXOL® (paclitaxel), Taxotere (docetaxel) and newer microbtubule agents such as epothilone analogs (ixabepilone), discodermolide analogs, and eleutherobin analogs; topoisomerase inhibitors (for example, epipodophyllotoxins such as etoposide and teniposide, amsacrine, topotecan, irinotecan); cell cycle inhibitors (for example, flavopyridols); biological response modifiers and proteasome inhibitors such as VELCADE® (bortezomib).

As stated above, the Formulae (I)-(V) compounds of the invention are of interest for their antiproliferative effects. Such compounds of the invention are expected to be useful in a wide range of disease states including cancer, psoriasis, and rheumatoid arthritis.

More specifically, the compounds of Formulae (I)-(V) are useful in the treatment of a variety of cancers, including (but not limited to) the following:

carcinoma, including that of the prostate, pancreatic ductal adenocarcinoma, breast, colon, lung, ovary, pancreas, and thyroid;

tumors of the central and peripheral nervous system, including neuroblastoma, glioblastoma, and medulloblastoma; and other tumors, including melanoma and multiple myeloma.

Due to the key role of kinases in the regulation of cellular proliferation in general, inhibitors could act as reversible cytostatic agents which may be useful in the treatment of any disease process which features abnormal cellular proliferation, e.g., benign prostate hyperplasia, familial adenomatosis polyposis, neurofibromatosis, pulmonary fibrosis, arthritis, psoriasis, glomerulonephritis, restenosis following angioplasty or vascular surgery, hypertrophic scar formation and inflammatory bowel disease.

The compounds of Formulae (I)-(V) are especially useful in treatment of tumors having a high incidence of serine/threonine kinase activity, such as prostate, colon, lung, brain, thyroid and pancreatic tumors. Additionally, the compounds of the invention may be useful in treatment of sarcomas and pediatric sarcomas. By the administration of a composition (or a combination) of the compounds of this invention, development of tumors in a mammalian host is reduced.

Compounds of Formulae (I)-(V) may also be useful in the treatment of other cancerous diseases (such as acute myelogenous leukemia) that may be associated with signal transduction pathways operating through kinases such as DYRK1a, CDK, and GSK3β. The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Accordingly, the present invention further includes compositions comprising one or more compounds of Formulae (I)-(V) and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences*, 17th Edition (1985), which is incorporated herein by reference in its entirety.

The pharmaceutical compositions of the invention containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

The pharmaceutical compositions may be in the form of sterile injectable aqueous solutions. Among the acceptable vehicles and solvents that may be employed are water, Ringer's solution and isotonic sodium chloride solution. The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS® Model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above.

The compounds of Formulae (I)-(V) may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; buccally; parenterally, such as by subcutaneous, intravenous, intramuscular or intrasternal injection or infusion techniques (e.g., as sterile injectable aq. or non-aq. solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as Plastibase (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., Gantrez); and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

When a compound according to this invention is administered into a human subject, the daily dosage will normally be determined by the prescribing physician with the dosage generally varying according to the age, weight, sex and response of the individual patient, as well as the severity of the patient's symptoms. Exemplary dosage amounts for a mammal may include from about 0.05 to 1000 mg/kg; 1-1000 mg/kg; 1-50 mg/kg; 5-250 mg/kg; 250-1000 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species, that are affected by mediation of protein kinase enzyme levels.

If formulated as a fixed dose, a combination product can, for example, utilize a dosage of the compound of Formulae (I)-(V) within the dosage range described above and the dosage of another anti-cancer agent/treatment within the approved dosage range for such known anti-cancer agent/treatment. If a combination product is inappropriate, the compounds of Formulae (I)-(V) and the other anti-cancer agent/treatment can, for example, be administered simultaneously or sequentially. If administered sequentially, the present invention is not limited to any particular sequence of administration. For example, compounds of Formulae (I)-(V) can be administered either prior to, or after, administration of the known anti-cancer agent or treatment.

Biological Assays

CK1ε and CK1δ Kinase Assays

The kinase assay was performed in V-bottom 384-well plates. The final assay volume was 30 µl prepared from 15 µl additions of enzyme, substrates (fluoresceinated peptide FL-AHA-KRRRAL-PSER-VASLPGL-OH and ATP) and test compounds in assay buffer (20 mM HEPES pH 7.4, 30 mM $MgCl_2$, 0.015% Brij35 and 4 mM DTT). The reaction was incubated at room temperature for 22 hours and terminated by adding 45 µl of 35 mM EDTA to each sample. The reaction mixture was analyzed on the Caliper LABCHIP®3000 (Caliper, Hopkinton, Mass.) by electrophoretic separation of the unphosphorylated substrate and phosphorylated product. Inhibition data were calculated by comparison of the no enzyme control reactions for 100% inhibition and vehicle-only reactions for 0% inhibition. The final concentration of reagents in the assay were 200 pM CK1ε or CK1δ, 50 µM ATP, 1.5 µM FL-AHA-KRRRAL-PSER-VASLPGL-OH, and 1.6% DMSO. Dose response curves were generated to determine the concentration required to inhibit 50% of the kinase activity ($IC_{50}$). Compounds were dissolved at 10 mM in dimethylsulfoxide (DMSO) and evaluated at eleven concentrations. $IC_{50}$ values were derived by non-linear regression analysis.

The following Compounds were found to have the $IC_{50}$ described in Table A when measured in the assays described above. $IC_{50}$ ranges against CK1ε and CK1δ are as follows: A=0.01-10 nM; B=10.01-100 nM; C=100.01-2000 nM.

TABLE A

| Example No. | CK1ε ($IC_{50}$, nM) | CK1δ ($IC_{50}$, nM) |
|---|---|---|
| 1 | B | B |
| 2 | B | B |
| 3 | B | A |
| 4 | B | B |
| 5 | B | B |
| 6 | A | A |
| 7 | B | B |
| 8 | B | B |
| 9 | A | A |
| 10 | A | A |
| 11 | B | B |
| 12 | C | B |
| 13 | B | A |
| 14 | B | B |
| 15 | C | B |
| 16 | A | A |
| 17 | B | A |
| 18 | C | B |
| 19 | A | A |
| 20 | B | B |
| 21 | A | A |
| 22 | A | A |
| 23 | A | |
| 24 | B | B |
| 25 | B | A |
| 26 | B | B |
| 27 | B | B |
| 28 | B | B |
| 29 | B | A |
| 30 | B | B |
| 31 | A | A |
| 32 | B | B |
| 33 | B | A |
| 34 | B | A |

TABLE A-continued

| Example No. | CK1ε (IC$_{50}$, nM) | CK1δ (IC$_{50}$, nM) |
| --- | --- | --- |
| 35 | A | A |
| 36 | B | A |
| 37 | A | A |
| 38 | A | A |
| 39 | B | A |
| 40 | C | B |
| 41 | A | A |
| 42 | C | B |
| 43 | B | B |
| 44 | B | A |
| 45 | A | A |
| 46 | B | A |
| 47 | C | B |
| 48 | C | B |
| 49 | A | A |
| 50 | A | A |
| 51 | A | A |
| 52 | B | B |
| 53 | A | A |
| 54 | A | A |
| 55 | A | A |
| 56 | A | A |
| 57 | C | B |
| 58 | A | A |
| 59 | A | A |
| 60 | A | A |
| 61 | A | A |
| 62 | A | A |
| 63 | A | A |
| 64 | B | B |
| 65 | C | C |
| 66 | B | A |
| 67 | A | A |
| 68 | B | A |
| 69 | A | A |
| 70 | A | A |
| 71 | A | A |
| 72 | A | A |
| 73 | A | A |
| 74 | A | A |
| 75 | B | B |
| 76 | A | A |
| 77 | A | A |
| 78 | A | A |
| 79 | A | A |
| 80 | A | A |
| 81 | A | A |
| 82 | A | A |
| 83 | B | C |
| 84 | B | A |
| 85 | A | A |
| 86 | B | A |
| 87 | B | A |
| 88 | B | B |
| 89 | B | A |
| 90 | B | A |
| 91 | C | B |
| 92 | C | C |
| 93 | A | A |
| 94 | A | A |
| 95 | A | A |
| 96 | B | B |
| 97 | B | A |
| 98 | A | A |
| 99 | A | A |
| 100 | A | A |
| 101 | A | A |
| 102 | B | A |
| 103 | B | A |
| 104 | A | A |
| 105 | B | A |
| 106 | B | A |
| 107 | C | B |
| 108 | A | A |
| 109 | A | A |
| 110 | C | B |
| 111 | C | C |
| 112 | C | B |
| 113 | C | B |
| 114 | B | B |
| 115 | C | B |
| 116 | B | B |
| 117 | A | A |
| 118 | C | C |
| 119 | A | A |
| 120 | C | B |
| 121 | C | B |
| 122 | C | C |
| 123 | C | B |
| 124 | C | C |
| 125 | C | C |
| 126 | C | C |
| 127 | C | C |
| 128 | A | B |
| 129 | A | A |
| 130 | B | B |
| 131 | C | C |
| 132 | C | C |
| 133 | C | C |
| 134 | C | C |
| 135 | C | C |
| 136 | C | C |
| 137 | B | A |
| 138 | C | C |
| 139 | C | B |
| 140 | C | C |
| 141 | C | C |
| 142 | C | C |
| 143 | B | A |
| 144 | C | C |
| 145 | C | C |
| 146 | C | C |
| 147 | C | C |
| 148 | A | A |
| 149 | C | B |
| 150 | B | A |
| 151 | C | C |
| 152 | A | A |
| 153 | C | C |
| 154 | B | B |
| 155 | C | C |
| 156 | A | A |
| 157 | A | A |
| 158 | A | A |
| 159 | A | A |
| 160 | A | A |
| 161 | A | A |
| 162 | A | A |
| 163 | A | A |
| 164 | A | A |
| 165 | A | A |
| 166 | A | A |
| 167 | A | A |
| 168 | A | A |
| 169 | A | A |
| 170 | A | A |
| 171 | A | A |
| 172 | A | A |
| 173 | A | A |
| 174 | A | A |
| 175 | A | A |
| 176 | A | A |
| 177 | A | A |
| 178 | | |
| 179 | A | A |
| 180 | A | A |
| 181 | A | A |
| 182 | A | A |
| 183 | A | A |
| 184 | A | A |
| 185 | A | A |
| 186 | A | A |
| 187 | A | A |
| 188 | A | A |

TABLE A-continued

| Example No. | CK1ε (IC$_{50}$, nM) | CK1δ (IC$_{50}$, nM) |
|---|---|---|
| 189 | A | A |
| 190 | A | A |
| 191 | A | A |
| 192 | A | A |
| 193 | A | A |
| 194 | A | A |
| 195 | A | A |
| 196 | A | A |
| 197 | A | A |
| 198 | A | A |
| 199 | A | A |
| 200 | A | A |
| 201 | A | A |
| 202 | A | A |
| 203 | A | A |
| 204 | A | A |
| 205 | A | A |
| 206 | A | A |
| 207 | A | A |
| 208 | A | A |
| 209 | A | A |
| 210 | A | A |
| 211 | A | A |
| 212 | A | A |
| 213 | A | A |
| 214 | A | A |
| 215 | A | A |
| 216 | A | A |
| 217 | A | A |
| 218 | A | B |
| 219 | A | A |
| 220 | A | A |
| 221 | A | A |
| 222 | A | A |
| 223 | A | A |
| 224 | A | A |
| 225 | A | A |
| 226 | | |
| 227 | A | A |
| 228 | A | A |
| 229 | A | A |
| 230 | A | A |
| 231 | A | A |
| 232 | A | A |
| 233 | A | A |
| 234 | A | A |
| 235 | A | A |
| 236 | A | A |
| 237 | A | A |
| 238 | A | A |
| 239 | A | |
| 240 | A | A |
| 241 | A | A |
| 242 | A | A |
| 243 | A | A |
| 244 | A | A |
| 245 | A | A |
| 246 | A | A |
| 247 | A | A |
| 248 | A | A |
| 249 | A | A |
| 250 | A | A |
| 251 | A | A |
| 252 | A | A |
| 253 | A | A |
| 254 | A | A |
| 255 | A | A |
| 256 | A | A |
| 257 | A | A |
| 258 | A | A |
| 259 | A | A |
| 260 | A | A |
| 261 | A | A |
| 262 | A | A |
| 263 | A | A |
| 264 | A | A |
| 265 | A | |
| 266 | A | A |
| 267 | A | |
| 268 | A | |
| 269 | A | |
| 270 | A | A |
| 271 | A | A |
| 272 | A | A |
| 273 | A | A |
| 274 | C | C |
| 275 | A | A |
| 276 | A | A |
| 277 | A | B |
| 278 | B | B |
| 279 | A | A |
| 280 | A | A |
| 281 | A | A |
| 282 | A | A |
| 283 | C | C |
| 284 | B | B |
| 285 | A | A |
| 286 | C | C |
| 287 | A | B |
| 288 | C | C |
| 289 | A | A |
| 290 | C | C |
| 291 | A | A |
| 292 | A | |
| 293 | A | A |
| 294 | A | A |
| 295 | A | |
| 296 | A | |
| 297 | A | A |
| 298 | | |
| 299 | A | A |
| 300 | A | A |
| 301 | A | A |
| 302 | A | A |
| 303 | A | A |
| 304 | | |
| 305 | | |
| 306 | | |
| 307 | | |
| 308 | A | A |
| 309 | A | A |
| 310 | A | A |
| 311 | A | A |
| 312 | A | A |
| 313 | A | A |
| 314 | A | A |
| 315 | A | A |
| 316 | A | A |
| 317 | A | A |
| 318 | A | A |
| 319 | A | A |
| 320 | A | A |
| 321 | A | A |
| 322 | A | A |
| 323 | A | B |
| 324 | A | A |
| 325 | A | A |
| 326 | A | A |
| 327 | A | A |
| 328 | B | B |
| 329 | A | A |
| 330 | A | A |
| 331 | A | A |
| 332 | A | A |
| 333 | A | A |
| 334 | A | A |
| 335 | C | C |
| 336 | A | A |
| 337 | | |
| 338 | | |
| 339 | | |
| 340 | | |
| 341 | C | C |
| 342 | A | A |

TABLE A-continued

| Example No. | CK1ε (IC$_{50}$, nM) | CK1δ (IC$_{50}$, nM) |
| --- | --- | --- |
| 343 | B | B |
| 344 | A | A |
| 345 | B | B |
| 346 | A | A |
| 347 | A | A |
| 348 | A | A |
| 349 | A | A |
| A1 | A | A |
| A2 | A | A |
| A3 | A | A |
| A4 | A | A |
| A5 | A | A |
| A6 | | A |
| A7 | | A |
| A8 | A | A |
| A9 | A | A |
| A10 | A | A |
| A11 | A | A |
| A12 | A | A |
| A13 | A | A |
| A14 | | |
| A15 | A | A |
| A16 | A | A |
| A17 | A | A |
| A18 | | A |
| A19 | | A |
| A20 | A | A |
| A21 | A | A |
| A22 | A | A |
| A23 | | A |
| A24 | A | A |
| A25 | A | A |
| A26 | A | A |
| A27 | A | A |
| A28 | B | B |
| A29 | B | B |
| A30 | A | A |
| A31 | A | A |
| A32 | A | A |
| A33 | A | A |
| A34 | A | A |
| A35 | A | A |
| A36 | A | A |
| A37 | A | A |
| A38 | A | A |
| A39 | A | A |
| A40 | A | A |
| A41 | A | A |
| A42 | A | A |
| A43 | A | A |
| A44 | A | A |
| A45 | A | A |
| A46 | A | A |
| A47 | A | A |
| A48 | A | A |
| A49 | A | A |
| A50 | A | A |
| A51 | A | A |
| A52 | A | |
| A53 | A | |
| A54 | A | |
| A55 | A | A |
| A56 | A | A |
| A57 | A | A |
| A58 | A | A |
| A59 | A | A |
| A60 | A | A |
| A61 | A | A |
| A62 | A | A |
| A63 | A | A |
| A64 | C | C |
| A65 | C | C |
| A66 | | A |
| A67 | | A |
| A68 | A | A |
| A69 | A | A |
| A70 | A | A |
| A71 | A | A |
| A72 | A | A |
| A73 | A | A |
| A74 | A | A |
| A75 | A | A |
| A76 | B | B |
| A77 | A | A |
| A78 | A | A |
| A79 | C | C |
| A80 | A | A |
| A81 | B | A |
| A82 | | |
| A83 | | |
| A84 | B | B |
| A85 | A | A |
| A86 | A | A |
| A87 | A | A |
| A88 | A | A |
| A89 | A | A |

Methods of Preparation

The compounds of the present invention may be prepared by methods such as those illustrated in the following schemes. Solvents, temperatures, pressures, and other reaction conditions may readily be selected by one of ordinary skill in the art. Starting materials are commercially available or readily prepared by one of ordinary skill in the art. These schemes are illustrative and are not meant to limit the possible techniques one skilled in the art may use to manufacture compounds disclosed herein. Different methods may be evident to those skilled in the art. Additionally, the various steps in the synthesis may be performed in an alternate sequence or order to give the desired compound(s). All documents cited herein are incorporated herein by reference in their entirety.

In general, the time taken to complete a reaction procedure will be judged by the person performing the procedure, preferably with the aid of information obtained by monitoring the reaction by methods such as HPLC or TLC. A reaction does not have to go to completion to be useful to this invention. The methods for the preparation of various heterocycles used to this invention can be found in standard organic reference books, for example, Katritzky, A. R. et al., eds., *Comprehensive Heterocyclic Chemistry, The Structure, Reactions, Synthesis and Uses, of Heterocyclic Compounds*, First Edition, Pergamon Press, New York (1984), and Katritzky, A. R. et al., eds., *Comprehensive Heterocyclic Chemistry II, A Review of the Literature* 1982-1995: *The Structure, Reactions, Synthesis and Uses, of Heterocyclic Compounds*, Pergamon Press, New York (1996).

Unless otherwise specified, the various substituents of the compounds are:

HPLC Methods: The analytical HPLC/LC-MS retention time reported for each example and intermediate uses one of the following general analytical HPLC/LC-MS methods:

Method A: SunFire C18 (4.6×150) mm, 3.5μ column; flow rate 1 mL/min; gradient time 15 min; 10% Solvent B to 100% Solvent B; monitoring at 254 nm and 220 nm (Solvent A: 5% Acetonitrile, 95% water, 0.05% TFA; Solvent B: 95% Acetonitrile, 5% water, 0.05% TFA).

Method B: XBridge Phenyl (4.6×150) mm, 3.5 column; flow rate 1 mL/min; gradient time 15 min; 10% Solvent B to 100% Solvent B; monitoring at 254 nm and 220 nm (Solvent A: 5% Acetonitrile, 95% water, 0.05% TFA; Solvent B: 95% Acetonitrile, 5% water, 0.05% TFA).

Method C: SunFire C18 (4.6×150) mm, 3.5 g column; flow rate 1 mL/min; gradient time 23 min; 100% Solvent A to 100% Solvent B and holding 100% Solvent B for 5 min; monitoring at 254 nm and 220 nm (Solvent A: 5% Acetonitrile, 95% water, 0.05% TFA; Solvent B: 95% Acetonitrile, 5% water, 0.05% TFA).

Method D: XBridge Phenyl (4.6×150) mm, 3.5 column; flow rate 1 mL/min; gradient time 23 min; 100% Mobile Phase A to 100% Mobile Phase B and holding 100% Solvent B for 5 min; monitoring at 254 nm and 220 nm (Solvent A: 5% Acetonitrile, 95% water, 0.05% TFA; Solvent B: 95% Acetonitrile, 5% water, 0.05% TFA).

Method E: Column: Ascentis Express C18 (50×2.1) mm, 2.7 μm; flow rate 1.1 mL/min; gradient time 3 min; Temperature: 50° C., 0% Solvent B to 100% Solvent B; monitoring at 220 nm (Solvent A: 95% Water: 5% Acetonitrile; 10 mM $NH_4OAc$; Solvent B: 5% Water: 95% Acetonitrile; 10 mM $NH_4OAc$).

Method F: SunFire C18 (4.6×150) mm, 3.5 g column; flow rate 1 mL/min; gradient time 23 min; 10% Solvent B to 100% Solvent B; monitoring at 254 nm to 220 nm (Solvent A: 5% Acetonitrile, 95% Water, 0.05% TFA; Solvent B: 95% Acetonitrile, 5% Water, 0.05% TFA).

Method G: XBridge Phenyl (4.6×150) mm, 3.5 g column, flow rate 1 mL/min; gradient time 23 min; 10% Solvent B to 100% Solvent B; monitoring at 254 nm to 220 nm (Solvent A: 5% Acetonitrile, 95% Water, 0.05% TFA; Solvent B: 95% Acetonitrile, 5% Water, 0.05% TFA).

Method H: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min.

Method I: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow rate: 0.5 mL/min.

Method J: Column: Ascentis Express C18 (50×4.6) mm, 2.7 μm, flow rate 4 mL/min; gradient: 0 to 100% Solvent B over 4 min; Temperature: 50° C. Monitoring at 220 nm (Solvent A: 95:05 water: $CH_3CN$ with 10 mM $NH_4OAc$ and Solvent B: 05:95 water: $CH_3CN$ with 10 mM $NH_4OAc$).

Method K: Column: Ascentis Express C18 (50×4.6) mm, 2.7 μm, flow rate 4 mL/min; gradient: 0 to 100% Solvent B over 4 min; Temperature: 50° C.; monitoring at 220 nm (Solvent A: 95:05 water: $CH_3CN$ with 0.1% TFA and Solvent B: 05:95 water: $CH_3CN$ with 0.1% TFA).

Method L: Column: Ascentis Express C18 (50×2.1) mm, 2.7 μm, flow rate 1.1 mL/min; gradient: 0 to 100% Solvent B over 3 min; Temperature: 50° C.; monitoring at 220 nm (Solvent A: 95:05 water: $CH_3CN$ with 0.1% TFA and Solvent B: 05:95 water: $CH_3CN$ with 0.1% TFA).

Method M: SunFire C18 (4.6×150) mm, 5 g column; flow rate 1 mL/min; gradient time 15 min; 10% Solvent B to 100% Solvent B; monitoring at 254 nm and 220 nm (Solvent A: 5% Acetonitrile, 95% water, 0.05% TFA; Solvent B: 95% Acetonitrile, 5% water, 0.05% TFA).

ABBREVIATIONS

The following abbreviations are used in the example section below and elsewhere herein:

Ac Acetyl
AcOH Acetic acid
Aq. Aqueous
$B_2Pin_2$ Bis(pinacolato)diboron
BAIB bis(acetoxy)iodobenzene
BMS Borane dimethylsulfide
$BH_3$.THF Borane in tetrahydrofuran
Bn Benzyl
$Boc_2O$ Di-tert-butyl dicarbonate
n-BuLi n-Butyl lithium
t-BuNCO 2-Isocyanato-2-methylpropane
CAN Ceric ammonium nitrate
CDI 1,1'-Carbonyldiimidazole
DAST Diethylaminosulfur trifluoride
dba Dibenzylideneacetone
DBU 1,8-Diazabicyclo[5.4.0]undec-7-ene
DCM Dichloromethane
DCE 1,2-Dichloroethene
DEAD Diethyl azodicarboxylate
DEOXO-FLUOR® bis(2-methoxyethyl)aminosulfur trifluoride
DIAD Diisopropyl azodicarboxylate
DIBAD Di-tert-butylazodicarboxylate
diglyme 1-Methoxy-2-(2-methoxyethoxy)ethane
DIPEA Diisopropylethylamine
DMAP 4-Dimethylaminopyridine
DMF Dimethyl formamide
DMSO Dimethylsulfoxide
DPPA Diphenylphosphoryl azide
dppf 1,1'-Bis(diphenylphosphino)ferrocene
EtOAc Ethyl acetate
EtOH Ethanol
EtI Iodoethane
HATU (O-(7-azabenzotriazol-1-yl)-N,N,N',N-tetramethyluronium hexafluorophosphate)
HPLC High-performance liquid chromatography
IPA Isopropyl alcohol
KHDMS Potassium bis(trimethylsilyl)amide
LAH lithium diisopropylamide
LDA Lithium aluminiumhydride
LHMDS Lithium bis(trimethylsilyl)amide
MeOH Methanol
MeI Iodomethane
Ms Methanesulfonyl
NBS N-Bromosuccinimide
NIS N-Iodosuccinimide
NMP N-Methyl-2-pyrrolidone
$PPh_3$ or TPP Triphenylphosphine
$Pd(PPh_3)_4$ Tetrakis(triphenylphosphine)palladium(0)
$Pd_2(dba)_3$ Tris(dibenzylideneacetone)dipalladium(0)
$PdCl_2(dppf)$ [1,1'-Bis(diphenylphosphino)ferrocene]dichloropalladium(II)
$PdCl_2(PPh_3)_2$ Bis(triphenylphosphine)palladium(II) dichloride
PTSA p-Toluenesulfonic acid
Py Pyridine
RT Room Temperature
SFC Supercritical fluid chromatography
TBAF Tetrabutylammonium fluoride
TLC Thin layer chromatography
TEMPO 2,2,6,6-Tetramethylpiperidinyloxy
TEA or $Et_3N$ Triethylamine
TFA Trifluoroacetic acid
$Tf_2O$ Trifluoromethanesulfonic anhydride
THF Tetrahydrofuran
TBSCl or TBDMS-Cl tert-Butyldimethylsilyl chloride Scheme 1
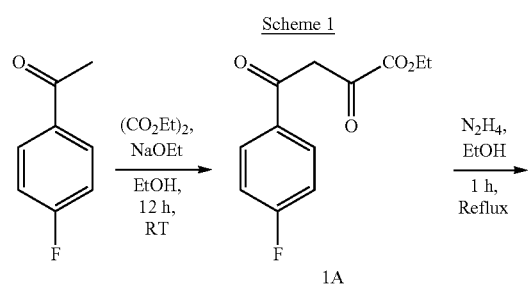
1A
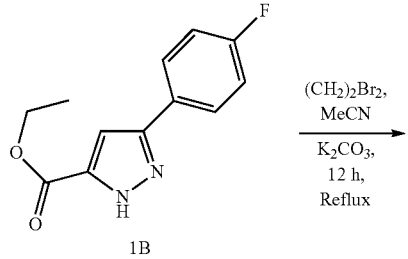
1B
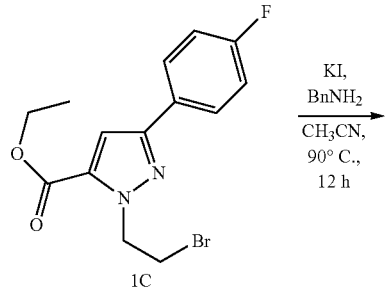
1C
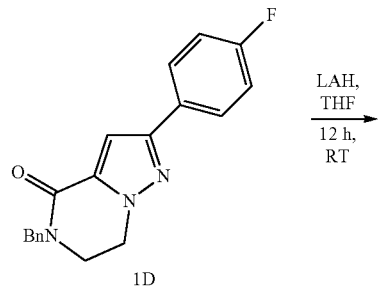
1D
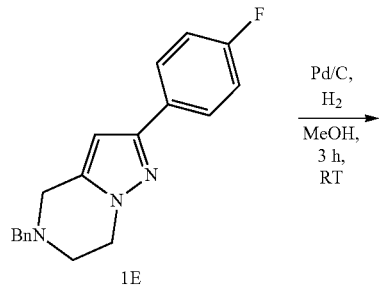
1E
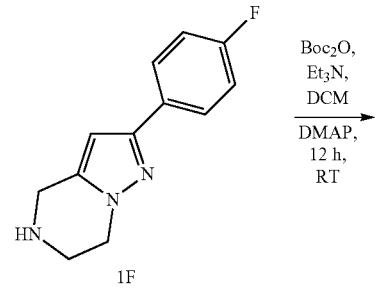
1F
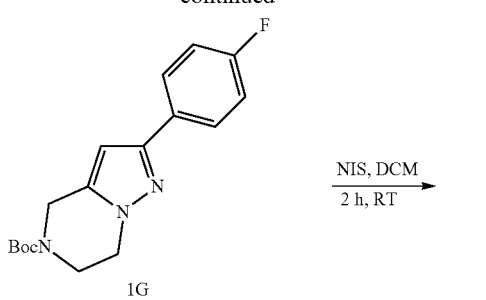
1G
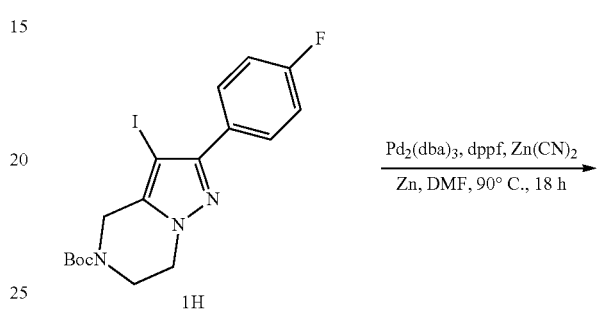
1H
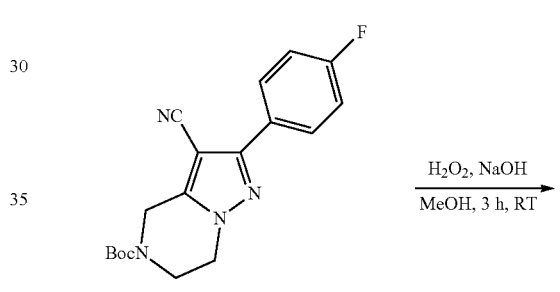
1I
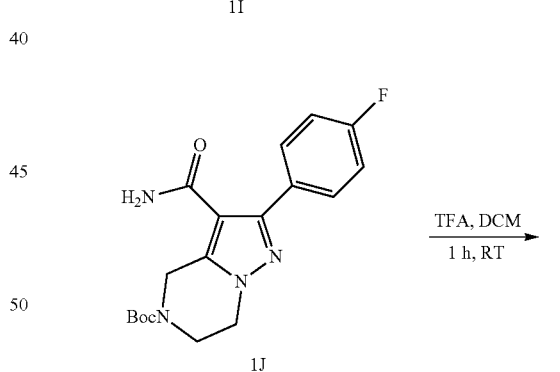
1J
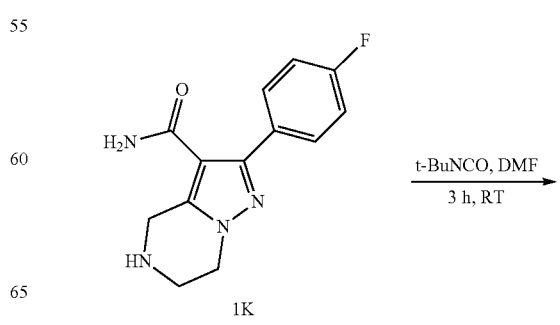
1K -continued

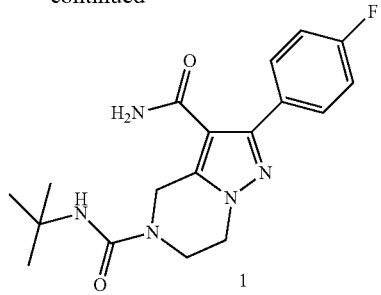

1

Intermediate 1A: Ethyl 4-(4-fluorophenyl)-2,4-dioxobutanoate

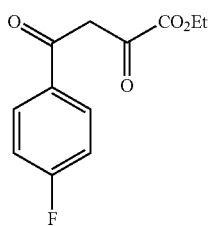 [SMILES: CCOC(=O)C(=O)CC(=O)c1ccc(F)cc1]

To a solution of sodium ethoxide (351 mL, 21% in ethanol, 1629 mmol) was added 1-(4-fluorophenyl) ethanone (150 g, 1086 mmol) in ethanol (100 mL) at 0° C. under a nitrogen atmosphere and the resulting reaction mixture was stirred at RT for 10 min. Diethyl oxalate (156 mL, 1140 mmol) in ethanol (100 mL) was added and the reaction was allowed to stir at RT for 12 h. The reaction mixture was cooled to 0° C. and acidified with 1.5 N HCl and the solid was filtered and the filtrate was diluted with water and extracted with DCM (3×750 mL). The combined organic layer was washed with brine, dried over $Na_2SO_4$, filtered and concentrated to afford Intermediate 1A (180 g, 70%) which was taken to next step without further purification. MS(ES): m/z=237 [M−H]$^+$; $^1$H NMR (300 MHz, CDCl$_3$) δ ppm 15.2 (bs, 1H), 8.00-8.09 (m, 2H), 7.15-7.25 (m, 2H), 7.05 (s, 1H), 4.42 (q, J=7.15 Hz, 2H), 1.43 (t, J=7.15 Hz, 3H).

Intermediate 1B: Ethyl 3-(4-fluorophenyl)-1H-pyrazole-5-carboxylate

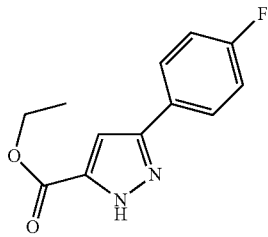 [SMILES: CCOC(=O)c1cc(-c2ccc(F)cc2)n[nH]1]

To a solution of Intermediate 1A (120 g, 504 mmol) in ethanol (1200 mL) was added hydrazine monohydrate (25.7 mL, 529 mmol) slowly and the resulting reaction mixture was refluxed for 1 h. The reaction mixture was cooled to RT, poured into ice-cold water, and the resultant solid dried under vacuum to afford Intermediate 1B (80 g, 67%). MS(ES): m/z=235 [M+H]$^+$; $^1$H NMR (300 MHz, CDCl$_3$) δ ppm 7.75 (m, 2H), 7.12 (m, 2H), 7.07 (s, 1H), 4.42 (q, J=7.2 Hz, 2H), 1.42 (t, J=7.2 Hz, 3H).

Intermediate 1C: Ethyl 1-(2-bromoethyl)-3-(4-fluorophenyl)-1H-pyrazole-5-carboxylate

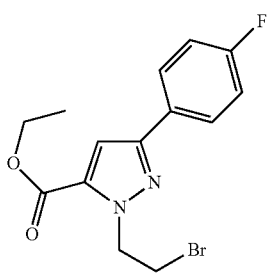 [SMILES: CCOC(=O)c1cc(-c2ccc(F)cc2)nn1CCBr]

To a solution of Intermediate 1B (135 g, 576 mmol) and potassium carbonate (159 g, 1153 mmol) in acetonitrile (1400 mL) was added 1,2-dibromoethane (59.6 mL, 692 mmol) and the resulting reaction mixture was refluxed for 4 h. Acetonitrile was removed under reduced pressure and the residue was diluted with water. The aqueous layer was extracted with DCM (2×500 mL). The combined organic layer was washed with brine, dried over $Na_2SO_4$, filtered and concentrated. The residue was purified by ISCO using 880 g REDISEP® column and 1% methanol in chloroform as eluent. Combined fractions were concentrated to afford Intermediate 1C (90 g, 45%). MS(ES): m/z=343 [M+H]$^+$; $^1$H NMR (400 MHz, DMSO-d$_6$) δ ppm 7.91-7.97 (m, 2H), 7.41 (s, 1H), 7.24-7.30 (m, 2H), 4.96 (t, J=6.34 Hz, 2H), 4.36 (q, J=7.11 Hz, 2H), 3.90 (t, J=6.34 Hz, 2H), 1.35 (t, J=7.12 Hz, 3H).

Intermediate 1D: 5-Benzyl-2-(4-fluorophenyl)-6,7-dihydropyrazolo[1,5-a]pyrazin-4(5H)-one

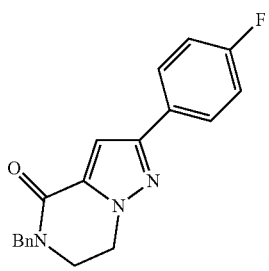 [SMILES: O=C1c2cc(-c3ccc(F)cc3)nn2CCN1Cc1ccccc1]

To a solution of Intermediate 1C (80 g, 234 mmol) and potassium iodide (78 g, 469 mmol) in acetonitrile (800 mL) was added benzyl amine (28.2 mL, 258 mmol) and the reaction mixture was stirred at 90° C. for 12 h. Acetonitrile was removed under reduced pressure, crude was diluted with water and the aqueous layer was extracted with DCM (3×500 mL). The combined organic layer washed with brine, dried over $Na_2SO_4$, filtered and concentrated. The residue was purified by silica gel chromatography (120 g REDISEP® column, eluting with 1-2% methanol in chloroform). Collected fractions were concentrated together to afford Intermediate 1D (35 g, 46%). MS(ES): m/z=322

[M+H]+; 1H NMR (400 MHz, CDCl3) δ ppm 7.71-7.83 (m, 2H), 7.29-7.42 (m, 5H), 7.14 (s, 1H), 7.06-7.12 (m, 2H), 4.78 (s, 2H), 4.32-4.40 (m, 2H), 3.63-3.75 (m, 2H).

Intermediate 1E: 5-Benzyl-2-(4-fluorophenyl)-4,5,6,7-tetrahydropyrazolo[1,5-a]pyrazine

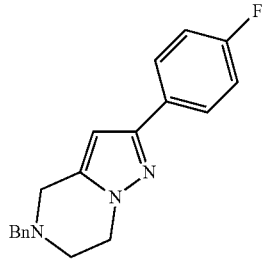 [SMILES: Fc1ccc(-c2cc3n(n2)CCN(Cc2ccccc2)C3)cc1]

To a solution of Intermediate 1D (23.00 g, 71.6 mmol) in THF (230 mL) under N2 at −10° C. was added LAH (59.6 mL, 2.4 M solution in THF, 143 mmol). The reaction mixture was allowed to stir at room temperature for 12 h. The reaction mixture was quenched with ice-cold water and filtered through CELITE® pad and the filtrate was extracted with chloroform (3×150 mL). The combined organic layer was washed with brine, dried over Na2SO4, filtered and concentrated. The residue was triturated with diethyl ether (2×150 mL) and the resulting solid was filtered, rinsed with diethyl ether and dried to afford Intermediate 1E (17 g, 77%). MS(ES): m/z=308 [M+H]+; 1H NMR (300 MHz, CDCl3) δ ppm 7.67-7.82 (m, 2H), 7.31-7.47 (m, 5H), 7.01-7.14 (m, 2H), 6.19 (s, 1H), 4.22 (t, J=4.2 Hz, 2H), 3.73 (s, 2H), 3.70 (s, 2H), 2.97 (t, J=5.6 Hz, 2H).

Intermediate 1F: 2-(4-Fluorophenyl)-4,5,6,7-tetrahydropyrazolo[1,5-a]pyrazine

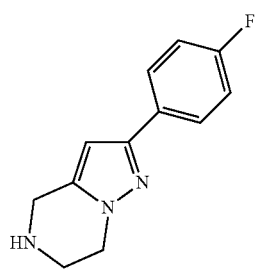 [SMILES: Fc1ccc(-c2cc3n(n2)CCNC3)cc1]

To a degassed solution of Intermediate 1E (17 g, 55.3 mmol) in methanol (170 mL) was added 10% palladium on carbon (2.94 g, 2.77 mmol) and stirred under H2 atmospheric pressure for 3 h. The reaction mixture was filtered through CELITE® pad, washed with methanol (500 mL) and concentrated. The residue was triturated with diethyl ether (2×100 mL) and the resulting solid was filtered, rinsed with diethyl ether and dried under vacuum to afford Intermediate 1F (9 g, 75%). MS(ES): m/z=218 [M+H]+; 1H NMR (300 MHz, DMSO-d6) δ ppm 7.73-7.87 (m, 2H), 7.13-7.28 (m, 2H), 6.43 (s, 1H), 4.02 (t, J=5.57 Hz, 2H), 3.94 (s, 2H), 3.16 (t, J=5.57 Hz, 2H).

Intermediate 1G: tert-Butyl 2-(4-fluorophenyl)-6,7-dihydropyrazolo[1,5-a]pyrazine-5(4H)-carboxylate

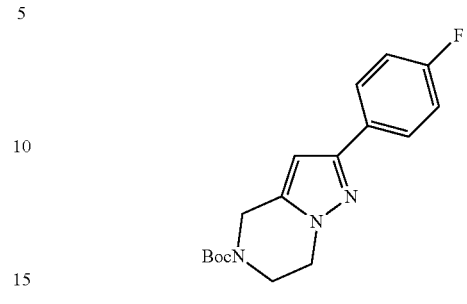

To a stirred solution of Intermediate 1F (9.50 g, 43.7 mmol) and triethylamine (18.29 mL, 131 mmol) in DCM (80 mL) was added Boc2O (19.09 g, 87 mmol) and DMAP (0.534 g, 4.37 mmol) and the reaction mixture was stirred at RT for 12 h. DCM was removed under reduced pressure and the residue was purified by ISCO using 120 g REDISEP® column and 1-2% methanol in chloroform as eluent. Collected fractions were concentrated together to afford Intermediate 1G (11 g, 79%). MS(ES): m/z=318 [M+H]+; 1H NMR (400 MHz, CDCl3) δ ppm 7.70-7.75 (m, 2H), 7.02-7.12 (m, 2H), 6.31 (s, 1H), 4.68 (s, 2H), 4.21 (t, J=5.4 Hz, 2H), 3.92 (t, J=5.7 Hz, 2H), 1.50 (s, 9H).

Intermediate 1H: tert-Butyl 2-(3-fluorophenyl)-3-iodo-6,7-dihydropyrazolo[1,5-a]pyrazine-5(4H)-carboxylate

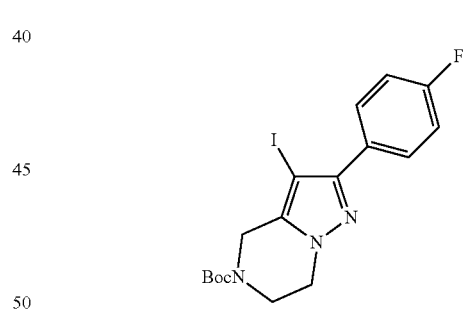

To a solution of Intermediate 1G (5.0 g, 15.76 mmol) in dichloromethane (25 mL) was added NIS (5.32 g, 23.63 mmol) and stirred at room temperature for 1 h. The reaction mixture was diluted with DCM and washed with water. The organic layer was dried over Na2SO4 and concentrated. The crude product was purified by ISCO using 40 g silica column using 1-2% methanol in chloroform as solvent. Collected fractions were concentrated together to afford Intermediate 1H (6 g, 86%) as white solid. MS(ES): m/z=444 [M+H]+; 1H NMR (400 MHz, CDCl3) δ ppm 7.79 (m, 2H), 7.11 (m, 2H), 4.55 (s, 2H), 4.20 (t, J=5.36 Hz, 2H), 3.92 (t, J=5.30 Hz, 2H), 1.52 (s, 9H).

Intermediate 1I: tert-Butyl 3-cyano-2-(3-fluorophenyl)-6,7-dihydropyrazolo[1,5-a]pyrazine-5(4H)-carboxylate

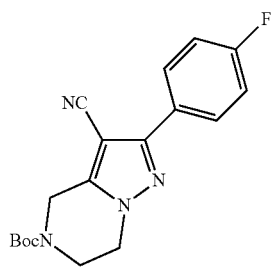 [SMILES: CC(C)(C)OC(=O)N1CCn2nc(-c3ccc(F)cc3)c(C#N)c2C1]

To a solution of Intermediate 1H (6.0 g, 13.54 mmol) in DMF (10 mL) was added zinc cyanide (2.066 g, 17.60 mmol) and zinc (0.265 g, 4.06 mmol) to give a brown suspension. The reaction mixture was degassed under nitrogen for 15 min, added Pd$_2$(dba)$_3$ (0.620 g, 0.677 mmol), dppf (0.750 g, 1.354 mmol), and stirred at 90° C. for 18 h. The reaction mixture was quenched with water and the aqueous layer was extracted with ethyl acetate (3×50 mL). Combined organic layer was washed with aqueous ammonia (2×50 mL), water, dried over Na$_2$SO$_4$, filtered and concentrated to afford crude Intermediate 1I as a brown gummy solid. The residue was purified by ISCO using 40 g REDISEP® silica gel column eluting with 3% MeOH in chloroform. The collected fractions were concentrated together to afford Intermediate 1I (3 g, 64%) as white solid. MS(ES): m/z=343 [M+H]$^+$; $^1$H NMR (300 MHz, DMSO-d$_6$) δ ppm 7.84-7.94 (m, 2H), 7.34-7.44 (m, 2H), 4.78 (s, 2H), 4.23 (t, J=5.36 Hz, 2H), 3.87 (t, J=5.45 Hz, 2H), 1.46 (s, 9H).

Intermediate 1J: tert-Butyl 3-carbamoyl-2-(3-fluorophenyl)-6,7-dihydropyrazolo[1,5-a]pyrazine-5(4H)-carboxylate

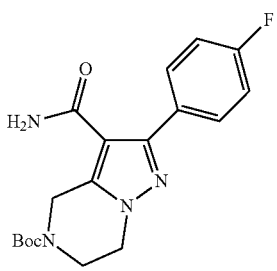 [SMILES: CC(C)(C)OC(=O)N1CCn2nc(-c3ccc(F)cc3)c(C(N)=O)c2C1]

To a solution of Intermediate 1I (3.0 g, 8.76 mmol) in MeOH (10 mL) was added NaOH (10 mL, 10% NaOH solution, 25 mmol) and H$_2$O$_2$ (2.5 mL, 30% w/v in H$_2$O, 22 mmol). The reaction mixture was stirred at room temperature for 3 h. Methanol was removed from the reaction mixture and the residue was diluted with 10 mL of water and extracted with ethyl acetate (3×15 mL). The combined organic layer was washed with water (15 mL), brine, dried over Na$_2$SO$_4$, filtered and concentrated to afford crude Intermediate 1J (3 g, 95%) as an off-white solid, which was taken to the next step without further purification. MS(ES): m/z=361 [M+H]$^+$; $^1$H NMR (400 MHz, DMSO-d$_6$) δ ppm 7.66-7.71 (m, 2H), 7.22-7.30 (m, 2H), 6.94 (bs, 1H), 4.75 (s, 2H), 4.16 (t, J=5.40 Hz, 2H), 3.85 (t, J=5.36 Hz, 2H), 1.46 (s, 9H).

Intermediate 1K: 2-(3-Fluorophenyl)-4,5,6,7-tetrahydropyrazolo[1,5-a]pyrazine-3-carboxamide

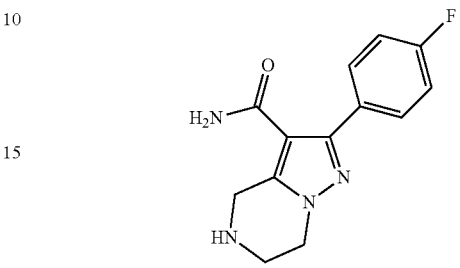

To a solution of Intermediate 1J (3.0 g, 8.32 mmol) in dichloromethane (20 mL) was added TFA (10.26 mL, 133 mmol) dropwise at 0° C. and stirred at room temperature for 3 h. Volatiles were removed, and the residue was quenched with 10% NaHCO$_3$ solution. The off-white solid product 1K (2 g, 92%) was filtered and dried under vacuum and was used in the next step without further purification. MS(ES): m/z=261 [M+H]$^+$; $^1$H NMR (400 MHz, DMSO-d$_6$) δ ppm 7.66-7.73 (m, 2H), 7.22-7.25 (m, 2H), 7.21 (bs, 1H), 7.20 (bs, 1H), 3.98-4.05 (m, 4H), 3.13 (bs, 2H), 2.63 (s, 1H).

Compound 1: N$^5$-(tert-Butyl)-2-(3-fluorophenyl)-6,7-dihydropyrazolo[1,5-a]pyrazine-3,5(4H)-dicarboxamide

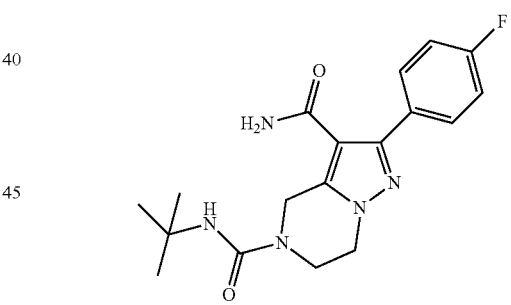

To a solution of Intermediate 1K (30 mg, 0.115 mmol) in DMF (1 mL) was added tert-butylisocyanate (28.6 mg, 0.288 mmol) at 0° C. The reaction mixture was stirred at room temperature for 3 h. The reaction mixture was quenched with water and extracted with ethyl acetate (3×5 mL). The combined organic layer was washed with water (2×5 mL), brine, dried over Na$_2$SO$_4$ and concentrated to afford the crude product as brown semi-solid. The residue was dissolved in a mixture of acetonitrile and methanol and was purified via preparative HPLC. Fractions containing the desired product (0.01 g, 24%) were combined and dried under vacuum. MS(ES): m/z=360 [M+H]$^+$; HPLC Ret. Time 6.66 min. and 6.14 min. (HPLC Methods A and B); $^1$H NMR (400 MHz, DMSO-d$_6$) δ ppm 7.69 (m, 2H), 7.25 (m, 2H), 7.25 (bs, 1H), 6.98 (bs, 1H), 6.26 (s, 1H), 4.69 (s, 2H), 4.11 (t, J=5.7 Hz, 2H), 3.80 (t, J=5.7 Hz, 2H), 1.29 (s, 9H).

The Compounds shown in Table 1 have been prepared similar to 1 using Intermediate 1K and various isocyanate.
TABLE 1
| Ex. No. | Structure | Name | [M + H]+ | Ret Time (min.) | HPLC Method |
|---|---|---|---|---|---|
| 2 | 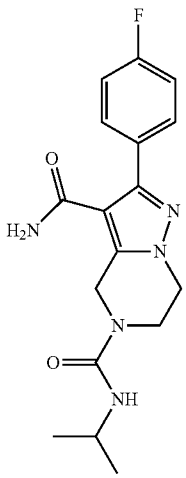 [SMILES: CC(C)NC(=O)N1CCn2nc(-c3ccc(F)cc3)c(C(N)=O)c2C1] | 2-(4-Fluorophenyl)-N5-isopropyl-6,7-dihydropyrazolo[1,5-a]pyrazine-3,5(4H)-dicarboxamide | 345 | 6.606<br>6.184 | A<br>B |
| 3 | 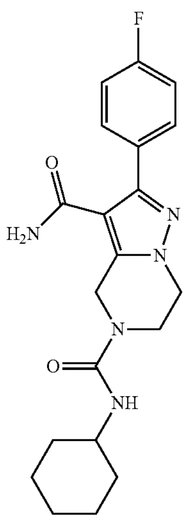 [SMILES: NC(=O)c1c(-c2ccc(F)cc2)nn2c1CN(C(=O)NC1CCCCC1)CC2] | N5-Cyclohexyl-2-(4-fluorophenyl)-6,7-dihydropyrazolo[1,5-a]pyrazine-3,5(4H)-dicarboxamide | 386 | 7.948<br>7.838 | A<br>B |
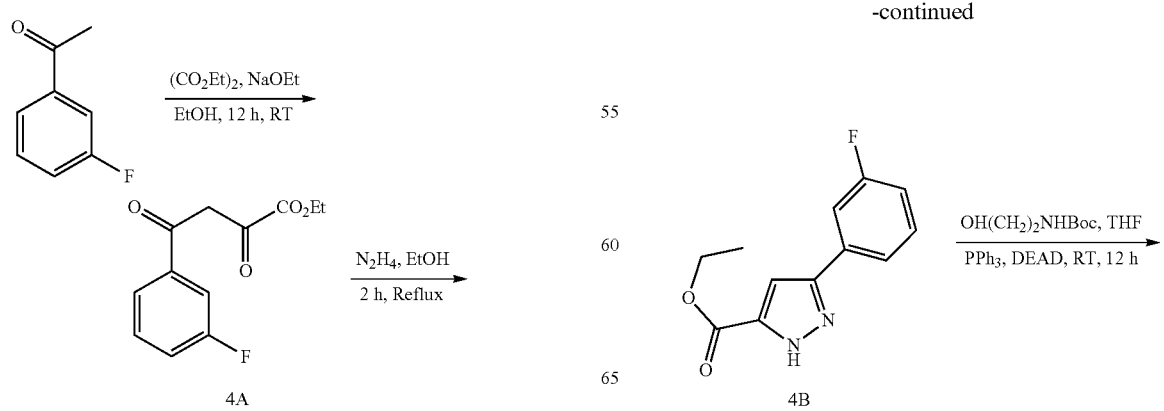
Scheme 2

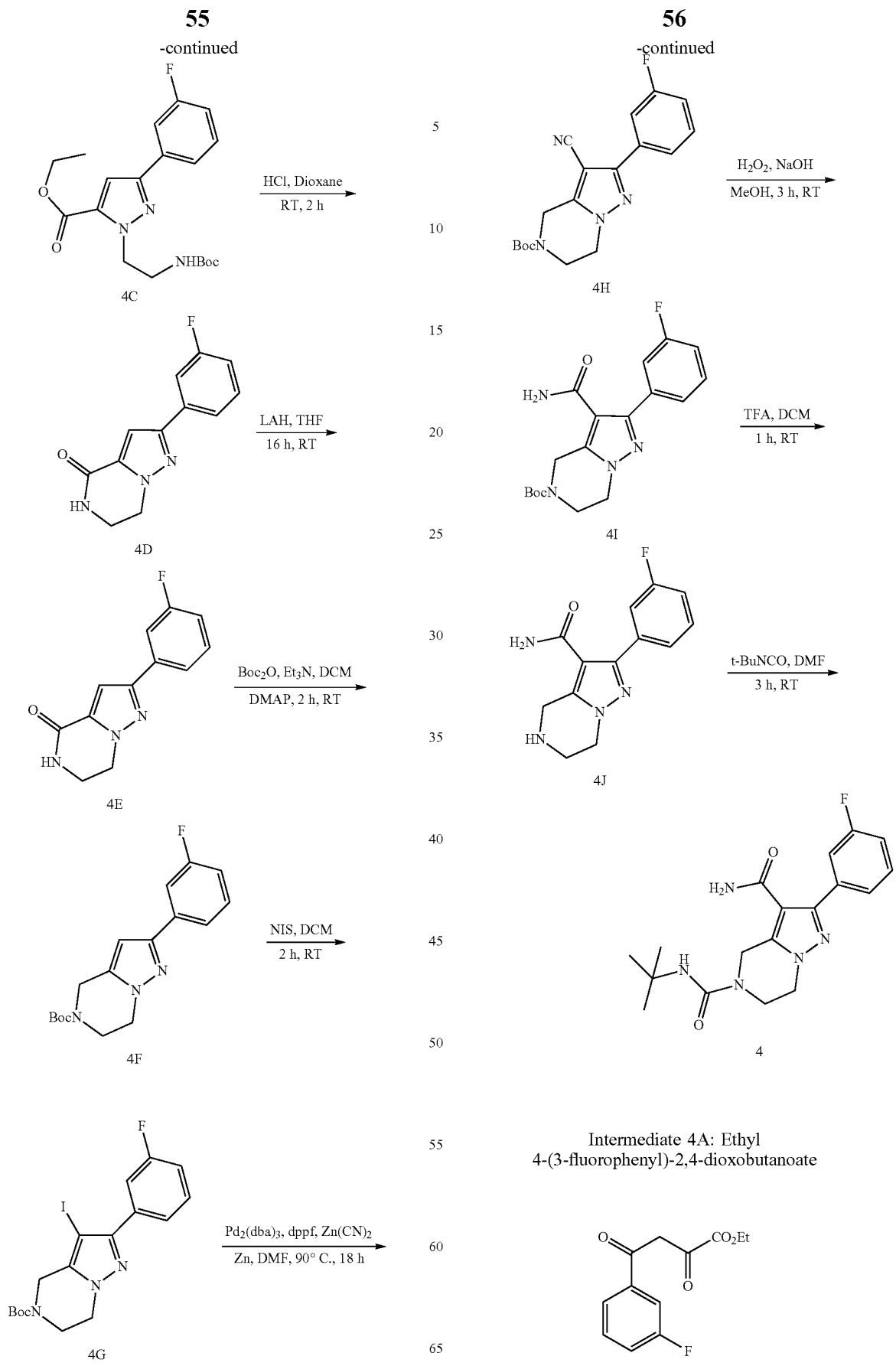
Intermediate 4A: Ethyl 4-(3-fluorophenyl)-2,4-dioxobutanoate

To a solution of sodium ethoxide (123 g, 362 mmol) in ethanol (300 mL) at 0° C. was added a solution of diethyl oxalate (49.4 mL, 362 mmol) in ethanol (25 mL) and the resulting solution was stirred for 10 min. 1-(3-Fluorophenyl) ethanone (50 g, 362 mmol) in ethanol (25 mL) was added and the reaction mixture was stirred at room temperature for 16 h. Ethanol was distilled off under reduced pressure and the residue obtained was quenched with ice-cold water and the brown product was filtered. This crude product was purified by ISCO using 220 g silica gel column and 20% ethyl acetate in hexane as eluent. The combined fractions were concentrated to afford Intermediate 4A (62.5 g, 73%). MS(ES): m/z=239 [M+H]$^+$; $^1$H NMR (400 MHz, CDCl$_3$) δ ppm 15.13 (bs, 1H), 7.77-7.83 (m, 1H), 7.67-7.73 (m, 1H), 7.51 (td, J=8.03, 5.48 Hz, 1H), 7.29-7.37 (m, 1H), 7.28 (s, 1H), 4.43 (q, J=7.18 Hz, 2H), 1.40-1.47 (m, 3H).

Intermediate 4B: Ethyl 3-(3-fluorophenyl)-1H-pyrazole-5-carboxylate

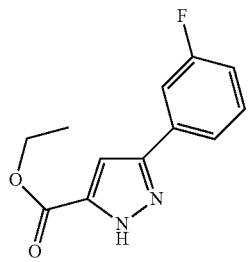 [SMILES: CCOC(=O)c1cc(-c2cccc(F)c2)n[nH]1]

To a solution of Intermediate 4A (100 g, 420 mmol) in ethanol (250 mL) was added hydrazine (13.83 mL, 441 mmol) in ethanol (250 mL) to give a brown solution. The reaction mixture was stirred at 80° C. for 2 h. Ethanol was removed under reduced pressure and the residue was diluted with water and extracted with ethyl acetate (3×100 mL). The combined organic layer was washed with water (2×100 mL), brine, dried over Na$_2$SO$_4$, filtered and concentrated under reduced pressure. The brown solid thus obtained was purified by ISCO using 20% ethyl acetate in hexane as eluent. The combined fractions were concentrated to afford Intermediate 4B (85 g, 86%) MS(ES): m/z=233 [M+H]$^+$; $^1$H NMR (400 MHz, DMSO-d$_6$) δ ppm 14.06 (bs, 1H), 7.68-7.75 (m, 2H), 7.45-7.55 (m, 1H), 7.36 (s, 1H), 7.20 (t, J=7.53 Hz, 1H), 4.34 (q, J=7.03 Hz, 2H), 1.34 (t, J=7.03 Hz, 3H).

Intermediate 4C: Ethyl 1-(2-((Tert-butoxycarbonyl) amino)ethyl)-3-(3-fluorophenyl)-1H-pyrazole-5-carboxylate

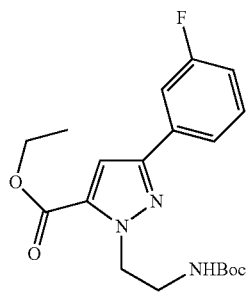 [SMILES: CCOC(=O)c1cc(-c2cccc(F)c2)nn1CCNC(=O)OC(C)(C)C]

A solution of 4B (12 g, 51.2 mmol) and PPh$_3$ (20.16 g, 77 mmol) in THF (10 mL) at 0° C. was added DIAD (14.94 mL, 77 mmol) in THF (10 mL) and the resulting reaction mixture was stirred at the same temperature for 30 min. tert-Butyl (2-hydroxyethyl) carbamate (9.91 g, 61.5 mmol) was then added and the reaction mixture was stirred at room temperature for 2 h. The volatiles were evaporated from the reaction mixture under reduced pressure and the resultant residue was quenched with ice. The aqueous layer was extracted with ethyl acetate (3×1000 mL). The combined organic layer was washed with 1.5 N HCl (2×100 mL), brine, dried over Na$_2$SO$_4$, filtered and concentrated to afford the crude product, which was purified by ISCO (5:1 Hex/EtOAc; 120 g column). Collected fractions were concentrated together to afford pale yellow solid 4C (16 g, 83%). MS(ES): m/z=378 [M+H]$^+$; $^1$H NMR (400 MHz, CDCl$_3$) δ ppm 7.54-7.59 (m, 1H), 7.48-7.54 (m, 1H), 7.36 (td, J=8.03, 6.02 Hz, 1H), 7.13 (s, 1H), 6.98-7.05 (m, 1H), 6.32 (bs, 1H), 4.98 (quin, J=6.27 Hz, 2H), 4.37 (q, J=7.19 Hz, 2H), 3.64 (d, J=5.02 Hz, 2H), 1.39-1.41 (m, 3H), 1.27 (s, 9H).

Intermediate 4D: 2-(3-Fluorophenyl)-6,7-dihydropyrazolo[1,5-a]pyrazin-4(5H)-one

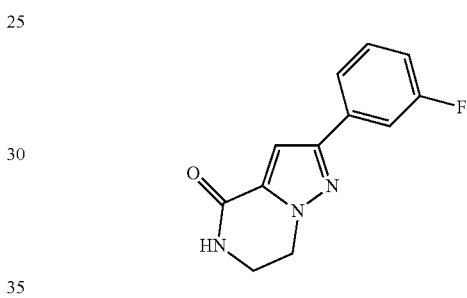

A 250 mL round-bottomed flask was charged with 4C (14 g, 37.1 mmol) and HCl in 1,4-dioxane (185 mL, 185 mmol) to give a yellow solution. The reaction mixture was stirred at room temperature for 2 h. The reaction mixture was concentrated under reduced pressure and to this residue was added 10% NaHCO$_3$ slowly until pH became 8.0. The aqueous layer was extracted with ethyl acetate (3×100 mL) and the combined organic layer was washed with water (2×100 mL), brine, dried over Na$_2$SO$_4$, filtered and concentrated to give the desired product 4D as an off-white solid, which was used in the next step without purification. MS(ES): m/z=231 [M+H]$^+$; $^1$H NMR (400 MHz, DMSO-d$_6$) δ ppm 8.26 (bs, 1H), 7.70-7.75 (m, 1H), 7.63-7.69 (m, 1H), 7.47 (td, J=8.03, 6.53 Hz, 1H), 7.11-7.20 (m, 1H), 4.32-4.40 (m, 2H), 3.65 (tt, J=4.64, 3.14 Hz, 2H).

Intermediate 4E: 2-(3-Fluorophenyl)-4,5,6,7-tetrahydropyrazolo[1,5-a]pyrazine

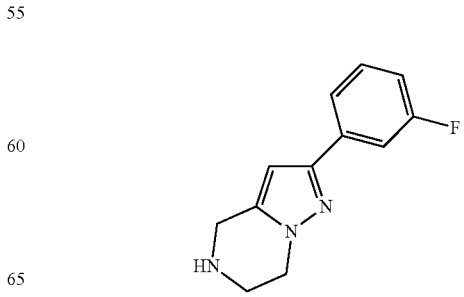

To a solution of Intermediate 4D (4.5 g, 19.46 mmol) in THF (100 mL) at −10° C. was added LAH (16.22 mL, 2.4 M in THF, 38.9 mmol) dropwise. The reaction mixture was stirred at room temperature for 16 h, was quenched with saturated NH$_4$Cl at 0° C. and the aqueous layer was extracted with ethyl acetate (3×50 mL). The combined organic layer was washed with water (2×50 mL), brine, filtered through CELITE®, dried over Na$_2$SO$_4$ and concentrated to afford crude Compound 4E as an off-white solid (4 g, 90%), which was used in the next step without purification. MS(ES): m/z=218 [M+H]$^+$; $^1$H NMR (400 MHz, CDCl$_3$) δ ppm 7.53-7.59 (m, 1H), 7.50 (ddd, J=10.29, 2.55, 1.51 Hz, 1H), 7.35 (td, J=7.93, 6.04 Hz, 1H), 6.99 (tdd, J=8.40, 8.40, 2.64, 0.94 Hz, 1H), 6.29 (s, 1H), 4.19 (t, J=5.67 Hz, 2H), 4.12 (s, 2H), 3.33-3.40 (m, 2H).

Intermediate 4F: tert-Butyl 2-(3-fluorophenyl)-6,7-dihydropyrazolo[1,5-a]pyrazine-5(4H)-carboxylate

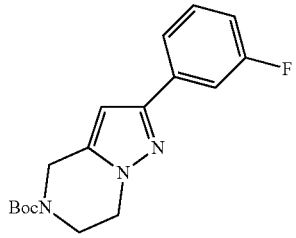 [SMILES: CC(C)(C)OC(=O)N1CCn2nc(-c3cccc(F)c3)cc2C1]

To a solution of Intermediate 4E (4.0 g, 20.71 mmol) in dichloromethane (150 mL) was added triethylamine (7.70 mL, 55.2 mmol), and DMAP (0.225 g, 1.841 mmol) to give a colorless solution. The reaction was cooled to 0° C. and Boc$_2$O (4.82 g, 22.10 mmol) was then added and the reaction mixture was stirred at room temperature for 2 h. The reaction mixture was diluted with dichloromethane (100 mL), washed with water (2×100 mL), dried over Na$_2$SO$_4$, filtered and concentrated to afford the crude compound as an off-white solid. The crude product was purified by silica gel chromatography (24 g REDISEP® column, eluting with 30% ethyl acetate in hexane). Collected fractions were concentrated together to afford Intermediate 4F (5 g, 86%) as white solid. MS(ES): m/z=318 [M+H]$^+$; $^1$H NMR (400 MHz, CDCl$_3$) δ ppm 7.53 (dt, J=7.53, 1.25 Hz, 1H), 7.47 (ddd, J=10.54, 2.51, 1.51 Hz, 1H), 7.31-7.38 (m, 1H), 6.95-7.03 (m, 1H), 6.35 (s, 1H), 4.69 (s, 2H), 4.22 (t, J=5.27 Hz, 2H), 3.92 (t, J=5.52 Hz, 2H), 1.51 (s, 9H).

Intermediate 4G: tert-Butyl 2-(3-fluorophenyl)-3-iodo-6,7-dihydropyrazolo[1,5-a]pyrazine-5(4H)-carboxylate

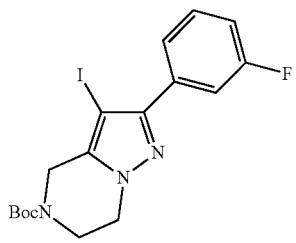 [SMILES: CC(C)(C)OC(=O)N1CCn2nc(-c3cccc(F)c3)c(I)c2C1]

To a solution of Intermediate 4F (5.0 g, 15.76 mmol) in dichloromethane (25 mL) was added NIS (5.32 g, 23.63 mmol) and stirred at room temperature for 2 h. The reaction mixture was diluted with DCM and washed with water. The organic layer was dried over Na$_2$SO$_4$ and concentrated to afford Intermediate 4G (6 g, 86%) as a colorless semi-solid which was used in the next step without any purification. MS(ES): m/z=444 [M+H]$^+$; $^1$H NMR (400 MHz, CDCl$_3$) δ ppm 7.61-7.66 (m, 1H), 7.56 (ddd, J=10.04, 2.51, 1.51 Hz, 1H), 7.39 (td, J=8.03, 6.02 Hz, 1H), 7.04-7.10 (m, 1H), 4.56 (bs, 2H), 4.22 (t, J=5.52 Hz, 2H), 3.92 (t, J=5.52 Hz, 2H), 1.52 (s, 9H).

Intermediate 4H: tert-Butyl 3-cyano-2-(3-fluorophenyl)-6,7-dihydropyrazolo[1,5-a]pyrazine-5(4H)-carboxylate

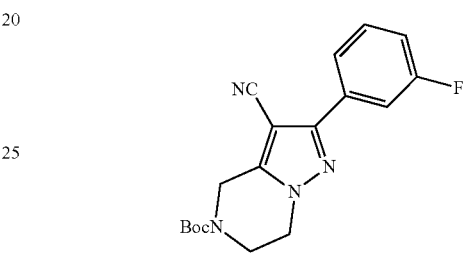

To a solution of Intermediate 4G (5.0 g, 11.28 mmol) in DMF (50 mL) was added zinc cyanide (1.722 g, 14.66 mmol) and zinc (0.221 g, 3.38 mmol) to give a brown suspension. The reaction mixture was degassed under nitrogen for 15 min and added Pd$_2$(dba)$_3$ (0.516 g, 0.564 mmol) and dppf (0.625 g, 1.128 mmol). The reaction mixture was stirred at 90° C. for 18 h. The reaction mixture was quenched with water and the aqueous layer was extracted with ethyl acetate (3×50 mL). The combined organic layer was washed with aqueous ammonia (2×50 mL), water, dried over Na$_2$SO$_4$, filtered and concentrated to afford the crude product as brown semi-solid. The crude was purified by silica gel chromatography (40 g REDISEP® column, eluting with 50% EtOAc in hexane). Collected fractions concentrated together to afford Intermediate 4H (3 g, 78%) as white solid. MS(ES): m/z=343 [M+H]$^+$; $^1$H NMR (400 MHz, CDCl$_3$) δ ppm 7.73-7.78 (m, 1H), 7.62-7.68 (m, 1H), 7.43 (td, J=8.03, 5.52 Hz, 1H), 7.08-7.15 (m, 1H), 4.82 (s, 2H), 4.24 (t, J=5.52 Hz, 2H), 3.96 (t, J=5.27 Hz, 2H), 1.52 (s, 9H).

Intermediate 4I: tert-Butyl 3-carbamoyl-2-(3-fluorophenyl)-6,7-dihydropyrazolo[1,5-a]pyrazine-5(4H)-carboxylate

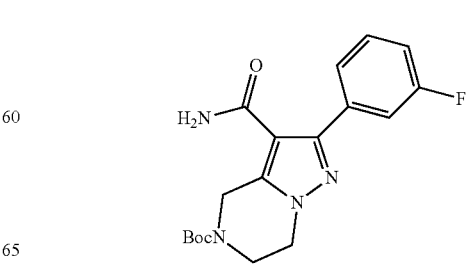

To a solution of Intermediate 4H (3.0 g, 8.76 mmol) in MeOH (10 mL) was added NaOH (10 ml, 10% NaOH solution, 25 mmol) and $H_2O_2$ (2.5 mL, 30% w/v in $H_2O$, 22 mmol). The reaction mixture was stirred at room temperature for 3 h. Methanol was removed from the reaction mixture and the residue was diluted with 10 mL of water and extracted with ethyl acetate (3×15 mL). The combined organic layer was washed with water (15 mL), brine, dried over $Na_2SO_4$, filtered and concentrated to afford crude Intermediate 4I (3 g, 95%) as an off-white solid, which was used in the next step without further purification. MS(ES): m/z=361 [M+H]$^+$; $^1$H NMR (300 MHz, DMSO-d$_6$) δ ppm 7.53 (d, J=1.51 Hz, 1H), 7.43-7.50 (m, 2H), 7.32 (bs, 1H), 7.18-7.24 (m, 1H), 7.14 (bs, 1H), 4.75 (s, 2H), 4.17 (t, J=5.27 Hz, 2H), 3.85 (t, J=5.52 Hz, 2H), 1.41-1.49 (m, 8H).

Intermediate 4J: 2-(3-Fluorophenyl)-4,5,6,7-tetrahydropyrazolo[1,5-a]pyrazine-3-carboxamide

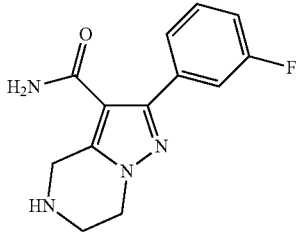 [SMILES: NC(=O)c1c(-c2cccc(F)c2)nn2c1CNCC2]

To a solution of Intermediate 4I (3.0 g, 8.32 mmol) in dichloromethane (20 mL) at 0° C. was added TFA (10.26 mL, 133 mmol) dropwise and stirred at room temperature for 1 h. TFA was removed from the reaction mixture and the residue was quenched with 10% NaHCO$_3$ solution. The solid was filtered to obtain Intermediate 4J (2 g, 92%) as an off-white solid, which was used in the next step without purification. MS(ES): m/z=261 [M+H]$^+$; $^1$H NMR (400 MHz, DMSO-d$_6$) δ ppm 7.52-7.57 (m, 1H), 7.46-7.52 (m, 1H), 7.40-7.46 (m, 1H), 7.14-7.27 (m, 2H), 7.08 (bs, 1H), 4.03 (d, J=5.02 Hz, 4H), 3.13 (d, J=5.02 Hz, 2H), 2.64 (d, J=6.02 Hz, 1H).

Compound 4: N$^5$-(tert-Butyl)-2-(3-fluorophenyl)-6,7-dihydropyrazolo[1,5-a]pyrazine-3,5(4H)-dicarboxamide

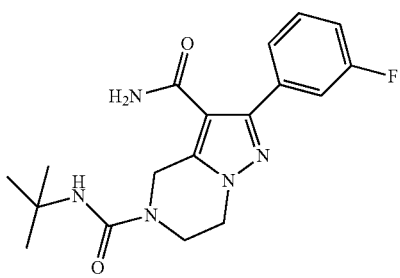 [SMILES: CC(C)(C)NC(=O)N1CCn2nc(-c3cccc(F)c3)c(C(N)=O)c2C1]

To a solution of Intermediate 4J (50 mg, 0.192 mmol) in DMF (2 mL) at 0° C. was added tert-butylisocyanate (38 mg, 0.384 mmol). The reaction mixture was stirred at room temperature for 12 h, quenched with water and extracted with ethyl acetate (3×5 mL). The combined organic layer was washed with water (2×5 mL), brine, dried over Na$_2$SO$_4$, filtered and concentrated to afford the crude product as brown semi-solid. The residue was further purified by preparative HPLC to afford pure product 4 as white powder (40 mg, 57%). MS(ES): m/z=360 [M+H]$^+$; HPLC Ret. Time 7.35 min. and 7.33 min. (HPLC Methods A and B); $^1$H NMR (400 MHz, DMSO-d$_6$) δ ppm 7.51-7.54 (m, 1H), 7.47-7.50 (m, 1H), 7.44-7.46 (m, 1H), 7.18-7.24 (m, 1H), 4.74 (s, 2H), 4.17 (t, J=5.52 Hz, 2H), 3.85 (t, J=5.52 Hz, 2H), 1.45-1.48 (s, 9H).

General Methods to Synthesize Ureas:

Method A:

To a solution of Intermediate 4J (30 mg, 0.115 mmol) in DMF (1 mL) was added the corresponding isocyanate (0.288 mmol) at 0° C. and the reaction mixture was stirred at room temperature for 3 h. The reaction mixture was quenched with water and extracted with ethyl acetate (3×5 mL). The combined organic layer was washed with water (2×5 mL), brine, dried over Na$_2$SO$_4$, filtered and concentrated to afford the crude product. The crude product was further purified by preparative HPLC.

Method B:

To a solution of primary amine (0.192 mmol) and triethylamine (0.480 mmol) in tetrahydrofuran (3 mL) at 0° C. was added triphosgene (0.096 mmol) and the reaction mixture stirred for 30 min. at the same temperature. Intermediate 4J (25 mg, 0.096 mmol) in THF was added and the solution was stirred at room temperature for 2 h. Reaction progress was monitored by TLC. The reaction mixture was quenched with water and extracted with ethyl acetate (3×5 mL). The combined organic layer was washed with 10% NaHCO$_3$ (2×5 mL), water, dried over Na$_2$SO$_4$ and concentrated to afford the crude product as an off-white solid. The crude product was further purified by preparative HPLC.

Method C:

To a solution of acid (0.192 mmol) and TEA (0.288 mmol) in toluene (3 mL) was added diphenylphosphoryl azide (0.192 mmol) to give a colorless solution. The reaction mixture was stirred at 90° C. for 1.5 h and cooled to RT. Intermediate 4J (25 mg, 0.096 mmol) in THF was added and the reaction mixture was stirred at 60° C. for 4 h. Reaction progress was monitored by TLC. The reaction mixture was quenched with water and extracted with ethyl acetate (3×5 mL). The combined organic layer was washed with 10% NaHCO$_3$ (2×5 mL), water, dried over Na$_2$SO$_4$ and concentrated to afford the crude product as an off-white solid. The crude product was further purified by preparative HPLC.

Method D:

To a solution of primary amine (0.192 mmol) and triethylamine (0.480 mmol) in tetrahydrofuran (3 mL) at 0° C. were added phenyl chloroformate (0.096 mmol) and the reaction mixture stirred for 60 min. at RT. The reaction mixture was quenched with water and the phenyl carbamate formed was extracted and the Intermediate 4J (25 mg, 0.096 mmol) in THF was added to the extract and the resulting solution was stirred at room temperature for 2 h. Reaction progress was monitored by TLC. The reaction mixture was quenched with water and extracted with ethyl acetate (3×5 mL). The combined organic layer was washed with 10% NaHCO$_3$ (2×5 mL), water, dried over Na$_2$SO$_4$ and concentrated to afford the crude product as an off-white solid. The crude product was further purified by preparative HPLC.

The Compounds described in Table 2 were synthesized analogous to Compound 4 by reacting Compound 4J with corresponding reagents.

TABLE 2

| Ex. No. | Structure | Name | Synthetic Method | [M + H]⁺ | Ret Time (min.) | HPLC Method |
|---|---|---|---|---|---|---|
| 5 | 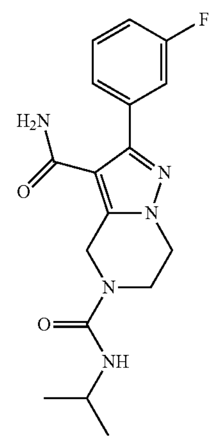 [SMILES: CC(C)NC(=O)N1CCn2nc(-c3cccc(F)c3)c(C(N)=O)c2C1] | 2-(3-Fluorophenyl)-N⁵-isopropyl-6,7-dihydropyrazolo[1,5-a]pyrazine-3,5(4H)-dicarboxamide | A | 346 | 6.41<br>5.79 | A<br>B |
| 6 | 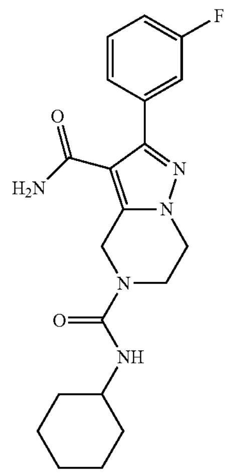 [SMILES: NC(=O)c1c(-c2cccc(F)c2)nn2c1CN(C(=O)NC1CCCCC1)CC2] | N⁵-Cyclohexyl-2-(3-fluorophenyl)-6,7-dihydropyrazolo[1,5-a]pyrazine-3,5(4H)-dicarboxamide | A | 386 | 14.34<br>13.57 | C<br>D |
| 7 | 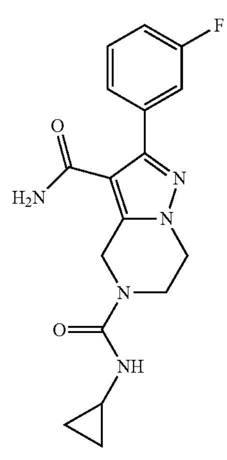 [SMILES: NC(=O)c1c(-c2cccc(F)c2)nn2c1CN(C(=O)NC1CC1)CC2] | N⁵-Cyclopropyl-2-(3-fluorophenyl)-6,7-dihydropyrazolo[1,5-a]pyrazine-3,5(4H)-dicarboxamide | B | 344 | 6.06<br>5.39 | A<br>B |

TABLE 2-continued

| Ex. No. | Structure | Name | Synthetic Method | [M + H]+ | Ret Time (min.) | HPLC Method |
|---|---|---|---|---|---|---|
| 8 | 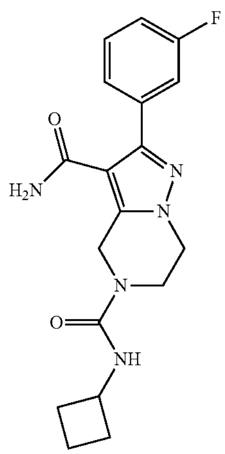 [SMILES: NC(=O)c1c(-c2cccc(F)c2)nn2c1CN(C(=O)NC1CCC1)CC2] | N5-Cyclobutyl-2-(3-fluorophenyl)-6,7-dihydropyrazolo[1,5-a]pyrazine-3,5(4H)-dicarboxamide | B | 358 | 6.89<br>6.48 | A<br>B |
| 9 | 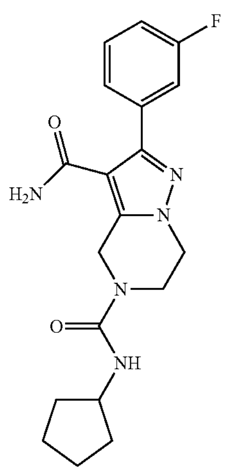 [SMILES: NC(=O)c1c(-c2cccc(F)c2)nn2c1CN(C(=O)NC1CCCC1)CC2] | N5-Cyclopentyl-2-(3-fluorophenyl)-6,7-dihydropyrazolo[1,5-a]pyrazine-3,5(4H)-dicarboxamide | B | 372 | 7.43<br>6.95 | A<br>B |
| 10 | 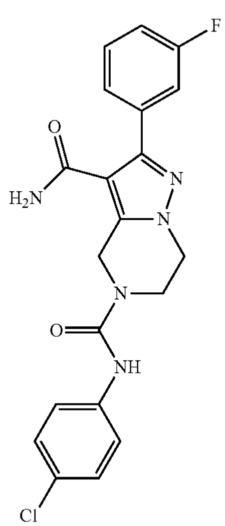 [SMILES: NC(=O)c1c(-c2cccc(F)c2)nn2c1CN(C(=O)Nc1ccc(Cl)cc1)CC2] | N5-(4-Chlorophenyl)-2-(3-fluorophenyl)-6,7-dihydropyrazolo[1,5-a]pyrazine-3,5(4H)-dicarboxamide | A | 414 | 8.87<br>8.36 | A<br>B |

TABLE 2-continued

| Ex. No. | Structure | Name | Synthetic Method | [M + H]+ | Ret Time (min.) | HPLC Method |
|---|---|---|---|---|---|---|
| 11 | 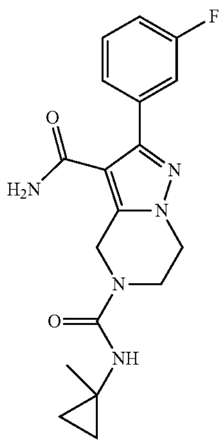 [SMILES: CC1(NC(=O)N2CCn3nc(-c4cccc(F)c4)c(C(N)=O)c3C2)CC1] | 2-(3-Fluorophenyl)-N5-(1-methylcyclopropyl)-6,7-dihydropyrazolo[1,5-a]pyrazine-3,5(4H)-dicarboxamide | C | 358 | 6.46<br>6.06 | A<br>B |
| 12 | 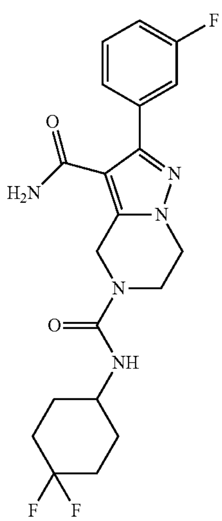 [SMILES: NC(=O)c1c(-c2cccc(F)c2)nn2c1CN(C(=O)NC1CCC(F)(F)CC1)CC2] | N5-(4,4-Difluorocyclohexyl)-2-(3-fluorophenyl)-6,7-dihydropyrazolo[1,5-a]pyrazine-3,5(4H)-dicarboxamide | B | 422 | 7.42<br>6.63 | A<br>B |
| 13 | 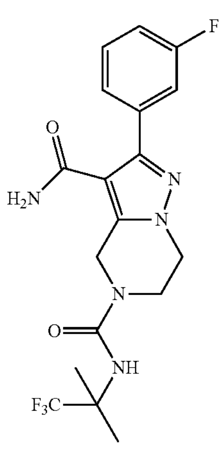 [SMILES: CC(C)(NC(=O)N1CCn2nc(-c3cccc(F)c3)c(C(N)=O)c2C1)C(F)(F)F] | 2-(3-Fluorophenyl)-N5-(1,1,1-trifluoro-2-methylpropan-2-yl)-6,7-dihydropyrazolo[1,5-a]pyrazine-3,5(4H)-dicarboxamide | B | 414 | 7.96<br>7.52 | A<br>B |

TABLE 2-continued

| Ex. No. | Structure | Name | Synthetic Method | [M + H]+ | Ret Time (min.) | HPLC Method |
|---|---|---|---|---|---|---|
| 14 | 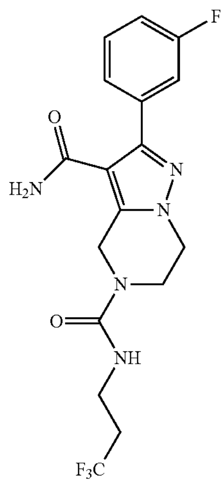 [SMILES: NC(=O)c1c(-c2cccc(F)c2)nn2c1CN(C(=O)NCCC(F)(F)F)CC2] | 2-(3-Fluorophenyl)-$N^5$-(3,3,3-trifluoropropyl)-6,7-dihydropyrazolo[1,5-a]pyrazine-3,5(4H)-dicarboxamide | C | 400 | 7.19<br>6.79 | A<br>B |
| 15 | 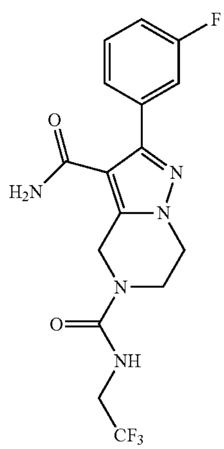 [SMILES: NC(=O)c1c(-c2cccc(F)c2)nn2c1CN(C(=O)NCC(F)(F)F)CC2] | 2-(3-Fluorophenyl)-$N^5$-(2,2,2-trifluoroethyl)-6,7-dihydropyrazolo[1,5-a]pyrazine-3,5(4H)-dicarboxamide | C | 386 | 7.00<br>6.58 | A<br>B |
| 16 | 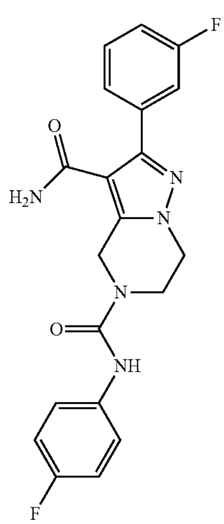 [SMILES: NC(=O)c1c(-c2cccc(F)c2)nn2c1CN(C(=O)Nc1ccc(F)cc1)CC2] | 2-(3-Fluorophenyl)-$N^5$-(4-fluorophenyl)-6,7-dihydropyrazolo[1,5-a]pyrazine-3,5(4H)-dicarboxamide | B | 398 | 7.99<br>7.62 | A<br>B |

TABLE 2-continued

| Ex. No. | Structure | Name | Synthetic Method | [M + H]+ | Ret Time (min.) | HPLC Method |
|---|---|---|---|---|---|---|
| 17 | 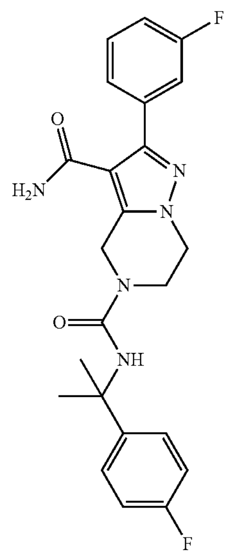 [SMILES: CC(C)(NC(=O)N1CCn2nc(-c3cccc(F)c3)c(C(N)=O)c2C1)c1ccc(F)cc1] | 2-(3-Fluorophenyl)-N5-(2-(4-fluorophenyl)propan-2-yl)-6,7-dihydropyrazolo[1,5-a]pyrazine-3,5(4H)-dicarboxamide | B | 440 | 8.82 8.34 | A B |
| 18 | 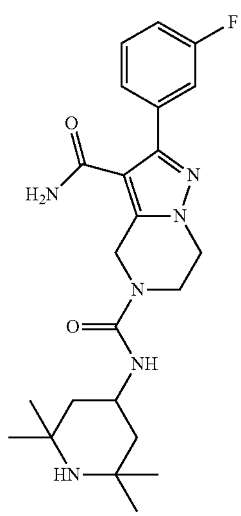 [SMILES: CC1(C)CC(NC(=O)N2CCn3nc(-c4cccc(F)c4)c(C(N)=O)c3C2)CC(C)(C)N1] | 2-(3-Fluorophenyl)-N5-(2,2,6,6-tetramethylpiperidin-4-yl)-6,7-dihydropyrazolo[1,5-a]pyrazine-3,5(4H)-dicarboxamide | B | 443 | 9.09 10.11 | C D |
| 19 | 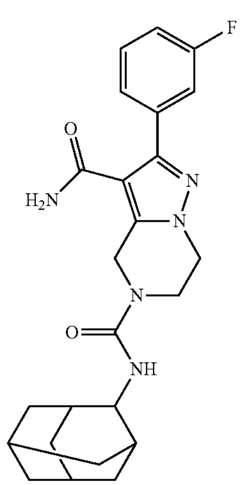 [SMILES: NC(=O)c1c(-c2cccc(F)c2)nn2c1CN(C(=O)NC1C3CC4CC(C3)CC1C4)CC2] | N5-(Adamantan-2-yl)-2-(3-fluorophenyl)-6,7-dihydropyrazolo[1,5-a]pyrazine-3,5(4H)-dicarboxamide | B | 348 | 9.70 8.89 | A B |

TABLE 2-continued

| Ex. No. | Structure | Name | Synthetic Method | [M + H]+ | Ret Time (min.) | HPLC Method |
|---|---|---|---|---|---|---|
| 20 | 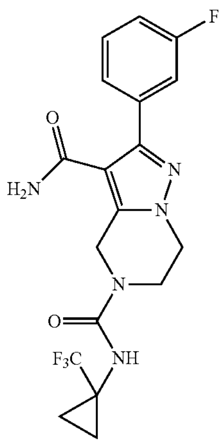 [SMILES: NC(=O)c1c(-c2cccc(F)c2)nn2c1CN(C(=O)NC1(C(F)(F)F)CC1)CC2] | 2-(3-Fluorophenyl)-N5-(1-(trifluoromethyl)cyclopropyl)-6,7-dihydropyrazolo[1,5-a]pyrazine-3,5(4H-dicarboxamide | B | 412 | 7.25<br>6.77 | A<br>B |
| 21 | 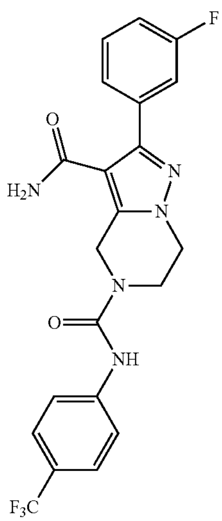 [SMILES: NC(=O)c1c(-c2cccc(F)c2)nn2c1CN(C(=O)Nc1ccc(C(F)(F)F)cc1)CC2] | 2-(3-Fluorophenyl)-N5-(4-(trifluoromethyl)phenyl)-6,7-dihydropyrazolo[1,5-a]pyrazine-3,5(4H)-dicarboxamide | B | 448 | 9.55<br>8.88 | A<br>B |
| 22 | 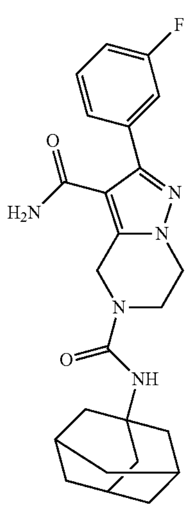 [SMILES: NC(=O)c1c(-c2cccc(F)c2)nn2c1CN(C(=O)NC13CC4CC(CC(C4)C1)C3)CC2] | N5-(Adamantan-1-yl)-2-(3-fluorophenyl)-6,7-dihydropyrazolo[1,5-a]pyrazine-3,5(4H)-dicarboxamide | A | 438 | 9.93<br>9.17 | A<br>B |

TABLE 2-continued

| Ex. No. | Structure | Name | Synthetic Method | [M + H]+ | Ret Time (min.) | HPLC Method |
|---|---|---|---|---|---|---|
| 23 | 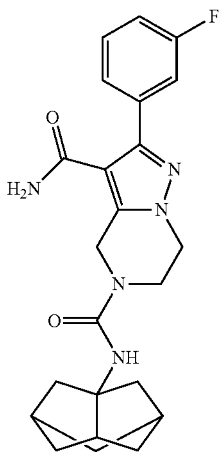 [SMILES: NC(=O)c1c(-c2cccc(F)c2)nn2c1CN(C(=O)NC13CC4CC(CC1C4)C3)CC2] | 2-(3-Fluorophenyl)-N5-((2R,5S)-octahydro-2,5-methanopentalen-6a-yl)-6,7-dihydropyrazolo[1,5-a]pyrazine-3,5(4H)-dicarboxamide | C | 424 | 9.30<br>8.62 | A<br>B |
| 24 | 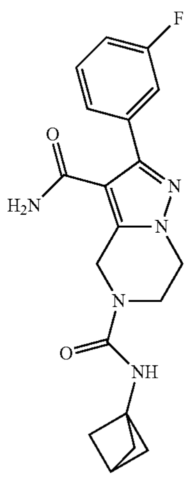 [SMILES: NC(=O)c1c(-c2cccc(F)c2)nn2c1CN(C(=O)NC13CC(C1)C3)CC2] | N5-(Bicyclo[1.1.1]pentan-1-yl)-2-(3-fluorophenyl)-6,7-dihydropyrazolo[1,5-a]pyrazine-3,5(4H)-dicarboxamide | B | 370 | 7.16<br>6.91 | A<br>B |
| 25 | 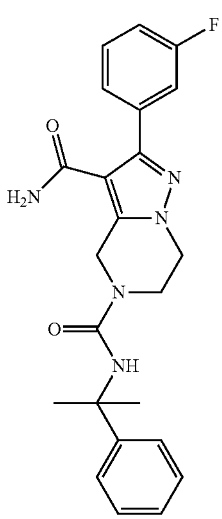 [SMILES: CC(C)(NC(=O)N1CCn2nc(-c3cccc(F)c3)c(C(N)=O)c2C1)c1ccccc1] | 2-(3-Fluorophenyl)-N5-(2-phenylpropan-2-yl)-6,7-dihydropyrazolo[1,5-a]pyrazine-3,5(4H)-dicarboxamide | B | 422 | 8.53<br>8.10 | A<br>B |

TABLE 2-continued

| Ex. No. | Structure | Name | Synthetic Method | [M + H]+ | Ret Time (min.) | HPLC Method |
|---|---|---|---|---|---|---|
| 26 | 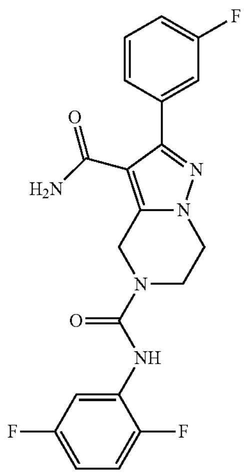 [SMILES: NC(=O)c1c(-c2cccc(F)c2)nn2c1CN(C(=O)Nc1cc(F)ccc1F)CC2] | N5-(2,5-Difluorophenyl)-2-(3-fluorophenyl)-6,7-dihydropyrazolo[1,5-a]pyrazine-3,5(4H)-dicarboxamide | B | 416 | 8.21<br>7.87 | A<br>B |
| 27 | 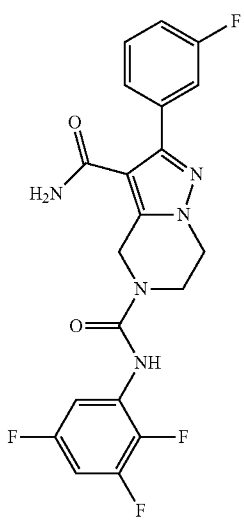 [SMILES: NC(=O)c1c(-c2cccc(F)c2)nn2c1CN(C(=O)Nc1cc(F)cc(F)c1F)CC2] | 2-(3-Fluorophenyl)-N5-(2,3,5-trifluorophenyl)-6,7-dihydropyrazolo[1,5-a]pyrazine-3,5(4H)-dicarboxamide | B | 434 | 9.69<br>9.03 | A<br>B |
| 28 | 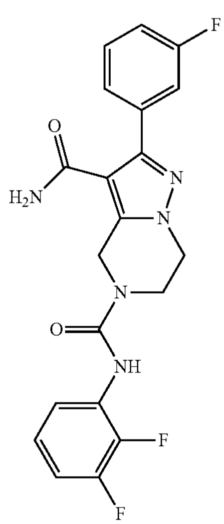 [SMILES: NC(=O)c1c(-c2cccc(F)c2)nn2c1CN(C(=O)Nc1cccc(F)c1F)CC2] | N5-(2,3-Difluorophenyl)-2-(3-fluorophenyl)-6,7-dihydropyrazolo[1,5-a]pyrazine-3,5(4H)-dicarboxamide | B | 416 | 8.05<br>7.76 | A<br>B |

TABLE 2-continued

| Ex. No. | Structure | Name | Synthetic Method | [M + H]+ | Ret Time (min.) | HPLC Method |
|---|---|---|---|---|---|---|
| 29 | 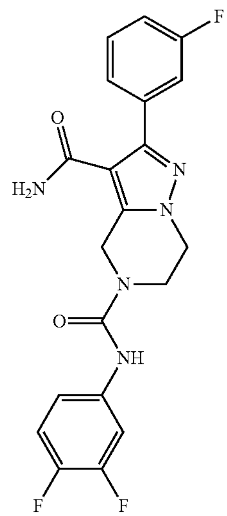 [SMILES: NC(=O)c1c(-c2cccc(F)c2)nn2c1CN(C(=O)Nc1ccc(F)c(F)c1)CC2] | N5-(3,4-Difluorophenyl)-2-(3-fluorophenyl)-6,7-dihydropyrazolo[1,5-a]pyrazine-3,5(4H)-dicarboxamide | B | 416 | 8.72<br>8.25 | A<br>B |
| 30 | 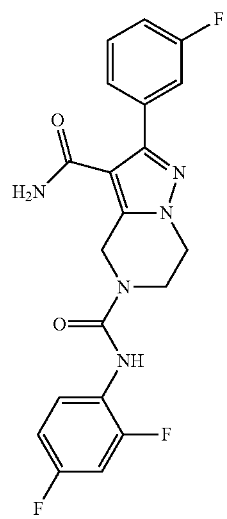 [SMILES: NC(=O)c1c(-c2cccc(F)c2)nn2c1CN(C(=O)Nc1ccc(F)cc1F)CC2] | N5-(2,4-Difluorophenyl)-2-(3-fluorophenyl)-6,7-dihydropyrazolo[1,5-a]pyrazine-3,5(4H)-dicarboxamide | B | 416 | 7.88<br>7.55 | A<br>B |
| 31 | 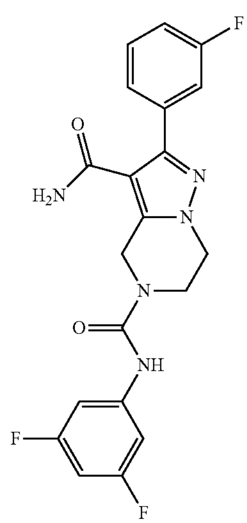 [SMILES: NC(=O)c1c(-c2cccc(F)c2)nn2c1CN(C(=O)Nc1cc(F)cc(F)c1)CC2] | N5-(3,5-Difluorophenyl)-2-(3-fluorophenyl)-6,7-dihydropyrazolo[1,5-a]pyrazine-3,5(4H)-dicarboxamide | B | 416 | 9.04<br>8.54 | A<br>B |

TABLE 2-continued

| Ex. No. | Structure | Name | Synthetic Method | [M + H]+ | Ret Time (min.) | HPLC Method |
|---|---|---|---|---|---|---|
| 32 | 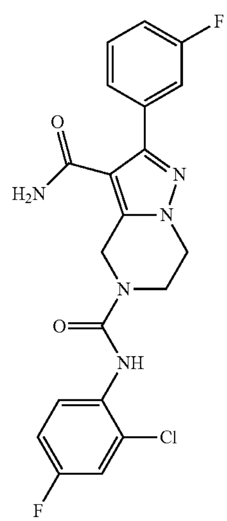 [SMILES: NC(=O)c1c(-c2cccc(F)c2)nn2c1CN(C(=O)Nc1ccc(F)cc1Cl)CC2] | N5-(2-Chloro-4-fluorophenyl)-2-(3-fluorophenyl)-6,7-dihydropyrazolo[1,5-a]pyrazine-3,5(4H)-dicarboxamide | B | 432 | 8.29<br>7.96 | A<br>B |
| 33 | 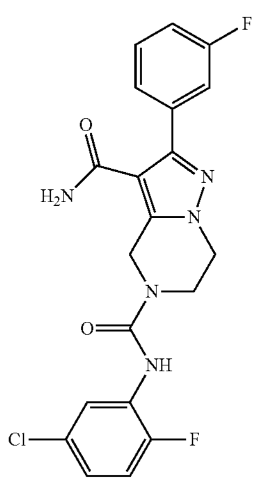 [SMILES: NC(=O)c1c(-c2cccc(F)c2)nn2c1CN(C(=O)Nc1cc(Cl)ccc1F)CC2] | N5-(5-Chloro-2-fluorophenyl)-2-(3-fluorophenyl)-6,7-dihydropyrazolo[1,5-a]pyrazine-3,5(4H)-dicarboxamide | B | 432 | 8.79<br>8.41 | A<br>B |
| 34 | 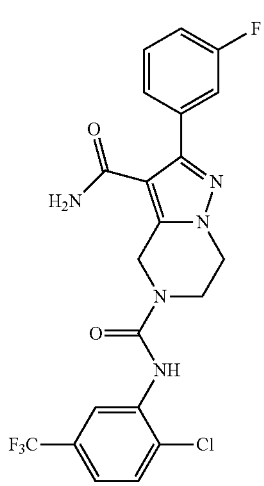 | N5-(2-Chloro-5-(trifluoromethyl)phenyl)-2-(3-fluorophenyl)-6,7-dihydropyrazolo[1,5-a]pyrazine-3,5(4H)-dicarboxamide | B | 482 | 9.25<br>9.83 | B<br>A |

TABLE 2-continued

| Ex. No. | Structure | Name | Synthetic Method | [M + H]+ | Ret Time (min.) | HPLC Method |
|---|---|---|---|---|---|---|
| 35 | 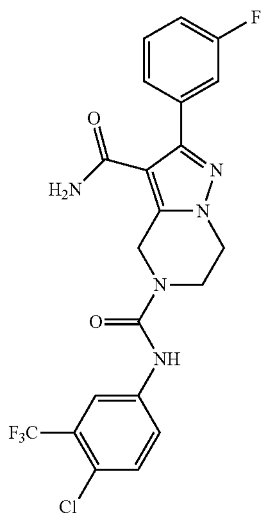 [SMILES: NC(=O)c1c(-c2cccc(F)c2)nn2c1CN(C(=O)Nc1ccc(Cl)c(C(F)(F)F)c1)CC2] | $N^5$-(4-Chloro-3-(trifluoromethyl)phenyl)-2-(3-fluorophenyl)-6,7-dihydropyrazolo[1,5-a]pyrazine-3,5(4H)-dicarboxamide | B | 482 | 9.64 10.37 | B A |
| 36 | 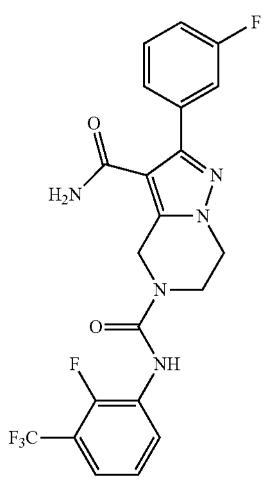 | $N^5$-(2-Fluoro-3-(trifluoromethyl)phenyl)-2-(3-fluorophenyl)-6,7-dihydropyrazolo[1,5-a]pyrazine-3,5(4H)-dicarboxamide | B | 466 | 8.79 9.26 | B A |
| 37 | 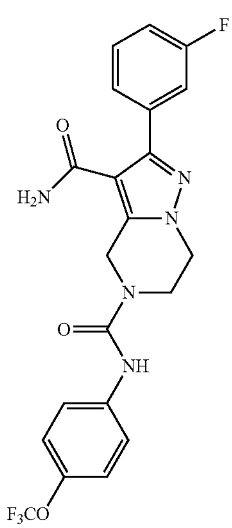 [SMILES: NC(=O)c1c(-c2cccc(F)c2)nn2c1CN(C(=O)Nc1ccc(OC(F)(F)F)cc1)CC2] | 2-(3-Fluorophenyl)-$N^5$-(4-(trifluoromethoxy)phenyl)-6,7-dihydropyrazolo[1,5-a]pyrazine-3,5(4H)-dicarboxamide | B | 464 | 9.93 9.67 | B A |

TABLE 2-continued

| Ex. No. | Structure | Name | Synthetic Method | [M + H]+ | Ret Time (min.) | HPLC Method |
|---|---|---|---|---|---|---|
| 38 | 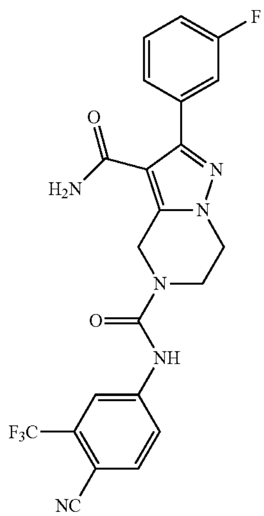 [SMILES: N#Cc1ccc(NC(=O)N2CCn3nc(-c4cccc(F)c4)c(C(N)=O)c3C2)cc1C(F)(F)F] | N5-(4-Cyano-3-(trifluoromethyl)phenyl)-2-(3-fluorophenyl)-6,7-dihydropyrazolo[1,5-a]pyrazine-3,5(4H)-dicarboxamide | B | 473 | 9.03<br>9.49 | B<br>A |
| 39 | 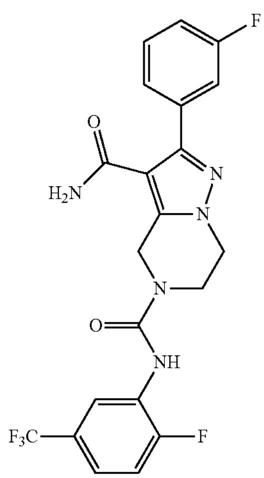 | N5-(2-Fluoro-5-(trifluoromethyl)phenyl)-2-(3-fluorophenyl)-6,7-dihydropyrazolo[1,5-a]pyrazine-3,5(4H)-dicarboxamide | B | 466 | 9.71<br>9.32 | B<br>A |
| 40 | 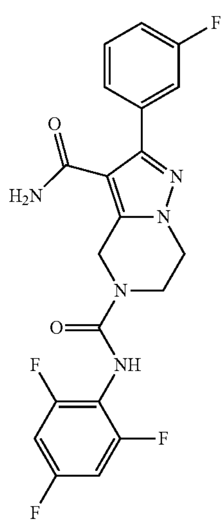 [SMILES: NC(=O)c1c(-c2cccc(F)c2)nn2c1CN(C(=O)Nc1c(F)cc(F)cc1F)CC2] | 2-(3-Fluorophenyl)-N5-(2,4,6-trifluorophenyl)-6,7-dihydropyrazolo[1,5-a]pyrazine-3,5(4H)-dicarboxamide | B | 434 | 8.39<br>7.76 | B<br>A |

TABLE 2-continued

| Ex. No. | Structure | Name | Synthetic Method | [M + H]+ | Ret Time (min.) | HPLC Method |
|---|---|---|---|---|---|---|
| 41 | 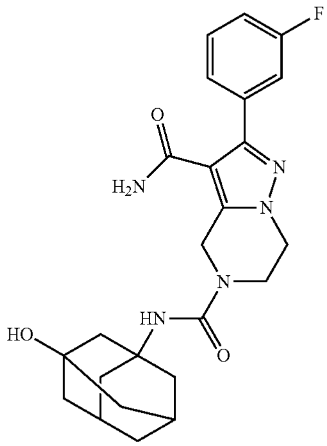 [SMILES: NC(=O)c1c(-c2cccc(F)c2)nn2c1CN(C(=O)NC13CC4CC(CC(O)(C4)C1)C3)CC2] | 2-(3-Fluorophenyl)-N5-(3-hydroxyadamantan-1-yl)-6,7-dihydropyrazolo[1,5-a]pyrazine-3,5(4H)-dicarboxamide | B | 454 | 7.22 6.70 | B A |
| 42 | 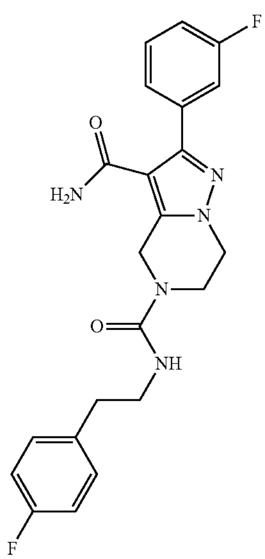 [SMILES: NC(=O)c1c(-c2cccc(F)c2)nn2c1CN(C(=O)NCCc1ccc(F)cc1)CC2] | N5-(4-Fluorophenethyl)-2-(3-fluorophenyl)-6,7-dihydropyrazolo[1,5-a]pyrazine-3,5(4H)-dicarboxamide | A | 426 | 1.276 | E |
| 43 | 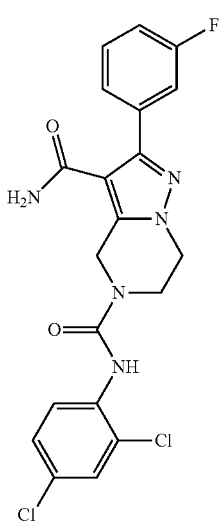 [SMILES: NC(=O)c1c(-c2cccc(F)c2)nn2c1CN(C(=O)Nc1ccc(Cl)cc1Cl)CC2] | N5-(2,4-Dichlorophenyl)-2-(3-fluorophenyl)-6,7-dihydropyrazolo[1,5-a]pyrazine-3,5(4H)-dicarboxamide | A | 449 | 1.441 | E |

TABLE 2-continued
| Ex. No. | Structure | Name | Synthetic Method | [M + H]⁺ | Ret Time (min.) | HPLC Method |
|---|---|---|---|---|---|---|
| 44 | 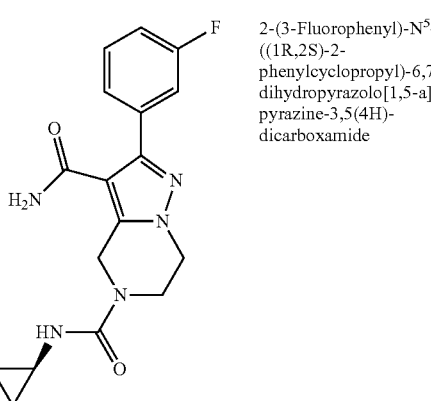 | 2-(3-Fluorophenyl)-N⁵-((1R,2S)-2-phenylcyclopropyl)-6,7-dihydropyrazolo[1,5-a]pyrazine-3,5(4H)-dicarboxamide | A | 420 | 1.325 | E |
| 45 | 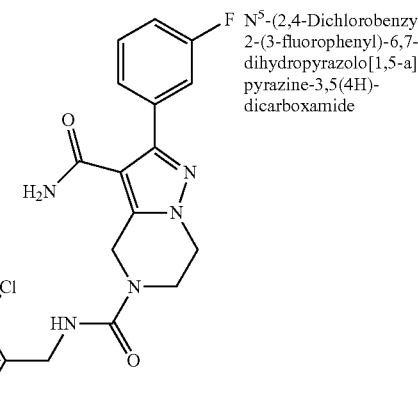 | N⁵-(2,4-Dichlorobenzyl)-2-(3-fluorophenyl)-6,7-dihydropyrazolo[1,5-a]pyrazine-3,5(4H)-dicarboxamide | A | 464 | 1.483 | E |
| 46 | 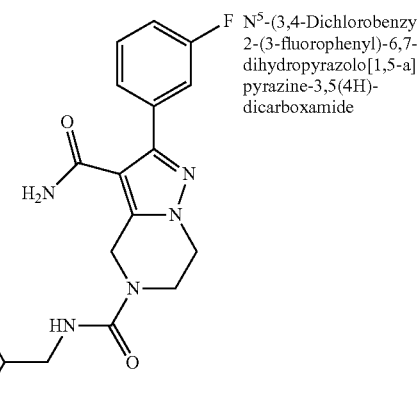 | N⁵-(3,4-Dichlorobenzyl)-2-(3-fluorophenyl)-6,7-dihydropyrazolo[1,5-a]pyrazine-3,5(4H)-dicarboxamide | A | 463 | 1.484 | E |

TABLE 2-continued
| Ex. No. | Structure | Name | Synthetic Method | [M + H]+ | Ret Time (min.) | HPLC Method |
|---|---|---|---|---|---|---|
| 47 | 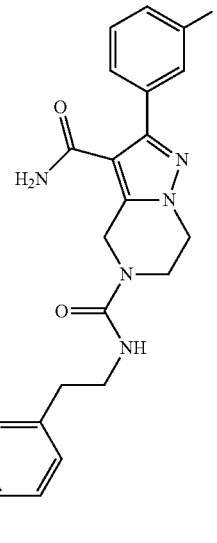 | 2-(3-Fluorophenyl)-N$^5$-(4-methoxyphenethyl)-6,7-dihydropyrazolo[1,5-a]pyrazine-3,5(4H)-dicarboxamide | A | 438 | 1.230 | E |
| 48 | 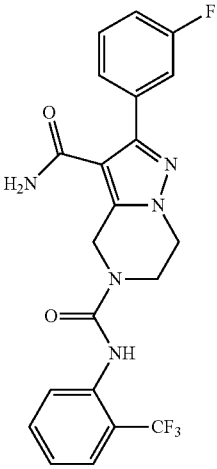 [SMILES: NC(=O)c1c(-c2cccc(F)c2)nn2c1CN(C(=O)Nc1ccccc1C(F)(F)F)CC2] | 2-(3-Fluorophenyl)-N$^5$-(2-(trifluoromethyl)phenyl)-6,7-dihydropyrazolo[1,5-a]pyrazine-3,5(4H)-dicarboxamide | A | 448 | 1.269 | E |
| 49 | 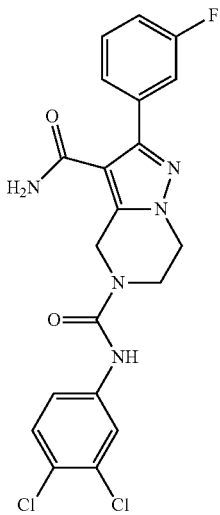 [SMILES: NC(=O)c1c(-c2cccc(F)c2)nn2c1CN(C(=O)Nc1ccc(Cl)c(Cl)c1)CC2] | N$^5$-(3,4-Dichlorophenyl)-2-(3-fluorophenyl)-6,7-dihydropyrazolo[1,5-a]pyrazine-3,5(4H)-dicarboxamide | A | 448 | 1.572 | E |

TABLE 2-continued

| Ex. No. | Structure | Name | Synthetic Method | [M + H]+ | Ret Time (min.) | HPLC Method |
|---|---|---|---|---|---|---|
| 50 | 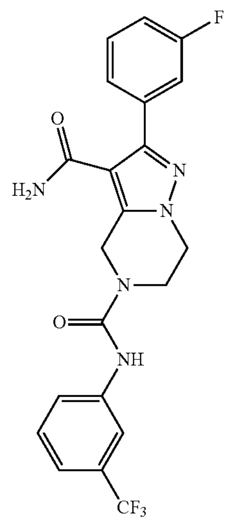 [SMILES: NC(=O)c1c(-c2cccc(F)c2)nn2c1CN(C(=O)Nc1cccc(C(F)(F)F)c1)CC2] | 2-(3-Fluorophenyl)-N5-(3-(trifluoromethyl)phenyl)-6,7-dihydropyrazolo[1,5-a]pyrazine-3,5(4H)-dicarboxamide | A | 448 | 1.516 | E |
| 51 | 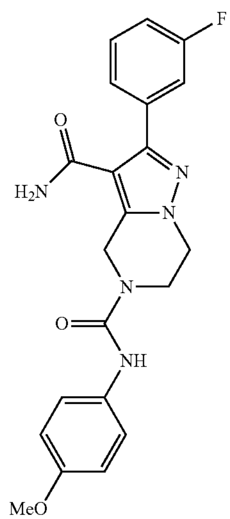 [SMILES: COc1ccc(NC(=O)N2CCn3nc(-c4cccc(F)c4)c(C(N)=O)c3C2)cc1] | 2-(3-Fluorophenyl)-N5-(4-methoxyphenyl)-6,7-dihydropyrazolo[1,5-a]pyrazine-3,5(4H)-dicarboxamide | A | 410 | 1.134 | E |
| 52 | 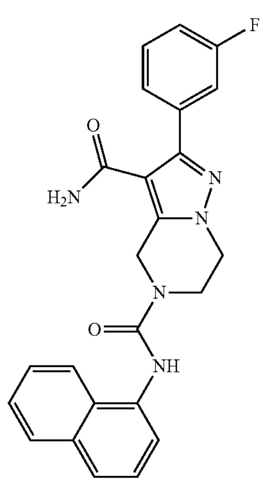 [SMILES: NC(=O)c1c(-c2cccc(F)c2)nn2c1CN(C(=O)Nc1cccc3ccccc13)CC2] | 2-(3-Fluorophenyl)-N5-(naphthalen-1-yl)-6,7-dihydropyrazolo[1,5-a]pyrazine-3,5(4H)-dicarboxamide | A | 430 | 1.303 | E |

TABLE 2-continued

| Ex. No. | Structure | Name | Synthetic Method | [M + H]+ | Ret Time (min.) | HPLC Method |
|---|---|---|---|---|---|---|
| 53 | 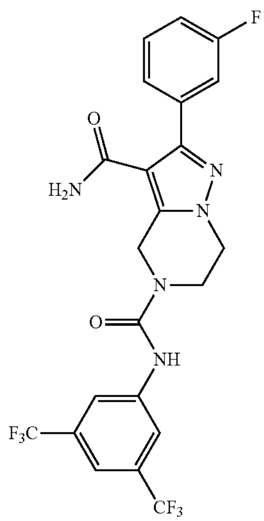 [SMILES: NC(=O)c1c(-c2cccc(F)c2)nn2c1CN(C(=O)Nc1cc(C(F)(F)F)cc(C(F)(F)F)c1)CC2] | N5-(3,5-Bis(trifluoromethyl)phenyl)-2-(3-fluorophenyl)-6,7-dihydropyrazolo[1,5-a]pyrazine-3,5(4H)-dicarboxamide | A | 516 | 1.837 | E |
| 54 | 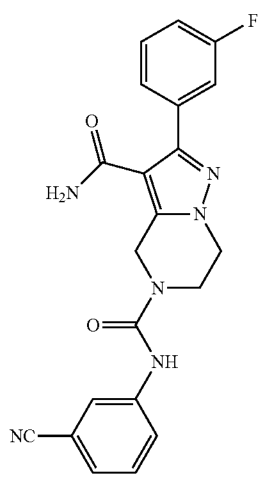 [SMILES: N#Cc1cccc(NC(=O)N2CCn3nc(-c4cccc(F)c4)c(C(N)=O)c3C2)c1] | N5-(3-Cyanophenyl)-2-(3-fluorophenyl)-6,7-dihydropyrazolo[1,5-a]pyrazine-3,5(4H)-dicarboxamide | A | 405 | 1.190 | E |
| 55 | 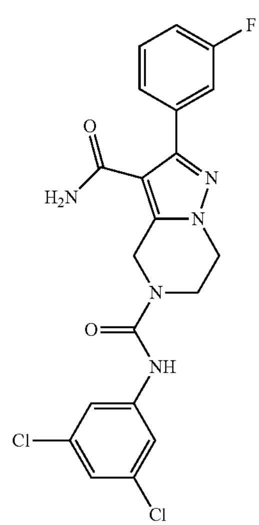 [SMILES: NC(=O)c1c(-c2cccc(F)c2)nn2c1CN(C(=O)Nc1cc(Cl)cc(Cl)c1)CC2] | N5-(3,5-Dichlorophenyl)-2-(3-fluorophenyl)-6,7-dihydropyrazolo[1,5-a]pyrazine-3,5(4H)-dicarboxamide | A | 449 | 1.64 | E |

TABLE 2-continued

| Ex. No. | Structure | Name | Synthetic Method | [M + H]+ | Ret Time (min.) | HPLC Method |
|---|---|---|---|---|---|---|
| 56 | 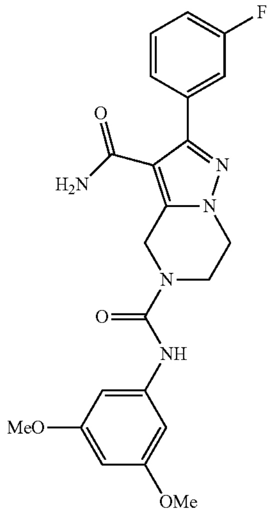 [SMILES: COc1cc(NC(=O)N2CCn3nc(-c4cccc(F)c4)c(C(N)=O)c3C2)cc(OC)c1] | N5-(3,5-Dimethoxyphenyl)-2-(3-fluorophenyl)-6,7-dihydropyrazolo[1,5-a]pyrazine-3,5(4H)-dicarboxamide | A | 440 | 1.248 | E |
| 57 | 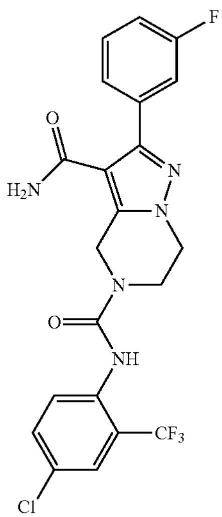 [SMILES: NC(=O)c1c(-c2cccc(F)c2)nn2c1CN(C(=O)Nc1ccc(Cl)cc1C(F)(F)F)CC2] | N5-(4-Chloro-2-(trifluoromethyl)phenyl)-2-(3-fluorophenyl)-6,7-dihydropyrazolo[1,5-a]pyrazine-3,5(4H)-dicarboxamide | A | 482 | 1.466 | E |
| 58 | 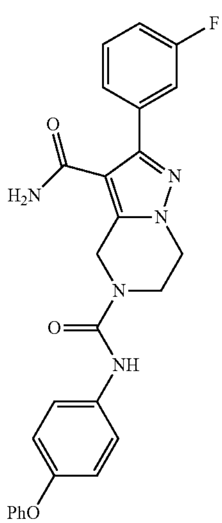 | 2-(3-Fluorophenyl)-N5-(4-phenoxyphenyl)-6,7-dihydropyrazolo[1,5-a]pyrazine-3,5(4H)-dicarboxamide | A | 472 | 1.613 | E |

TABLE 2-continued

| Ex. No. | Structure | Name | Synthetic Method | [M + H]+ | Ret Time (min.) | HPLC Method |
|---|---|---|---|---|---|---|
| 59 | 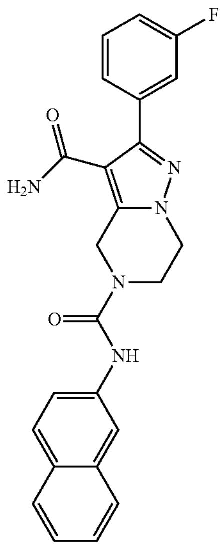 [SMILES: NC(=O)c1c(-c2cccc(F)c2)nn2c1CN(C(=O)Nc1ccc3ccccc3c1)CC2] | 2-(3-Fluorophenyl)-N5-(naphthalen-2-yl)-6,7-dihydropyrazolo[1,5-a]pyrazine-3,5(4H)-dicarboxamide | A | 430 | 1.459 | E |
| 60 | 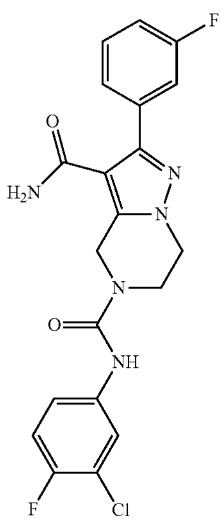 [SMILES: NC(=O)c1c(-c2cccc(F)c2)nn2c1CN(C(=O)Nc1ccc(F)c(Cl)c1)CC2] | N5-(3-Chloro-4-fluorophenyl)-2-(3-fluorophenyl)-6,7-dihydropyrazolo[1,5-a]pyrazine-3,5(4H)-dicarboxamide | A | 432 | 1.424 | E |
| 61 | 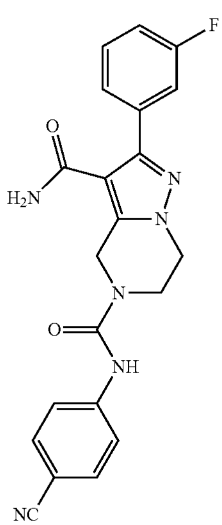 [SMILES: N#Cc1ccc(NC(=O)N2CCn3nc(-c4cccc(F)c4)c(C(N)=O)c3C2)cc1] | N5-(4-Cyanophenyl)-2-(3-fluorophenyl)-6,7-dihydropyrazolo[1,5-a]pyrazine-3,5(4H)-dicarboxamide | A | 405 | 1.186 | E |

TABLE 2-continued

| Ex. No. | Structure | Name | Synthetic Method | [M + H]+ | Ret Time (min.) | HPLC Method |
|---|---|---|---|---|---|---|
| 62 | 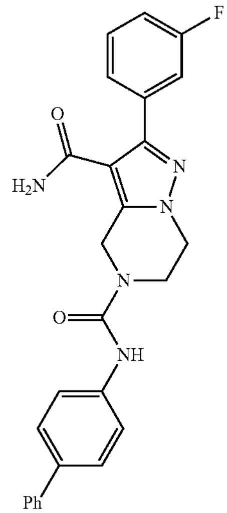 [SMILES: NC(=O)c1c(-c2cccc(F)c2)nn2c1CN(C(=O)Nc1ccc(-c3ccccc3)cc1)CC2] | N5-([1,1'-Biphenyl]-4-yl)-2-(3-fluorophenyl)-6,7-dihydropyrazolo[1,5-a]pyrazine-3,5(4H)-dicarboxamide | A | 456 | 1.621 | E |
| 63 | 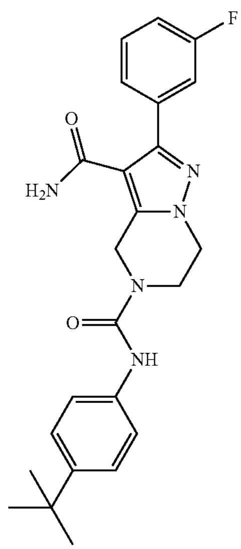 [SMILES: CC(C)(C)c1ccc(NC(=O)N2CCn3nc(-c4cccc(F)c4)c(C(N)=O)c3C2)cc1] | N5-(4-(tert-Butyl)phenyl)-2-(3-fluorophenyl)-6,7-dihydropyrazolo[1,5-a]pyrazine-3,5(4H)-dicarboxamide | A | 436 | 1.657 | E |
| 64 | 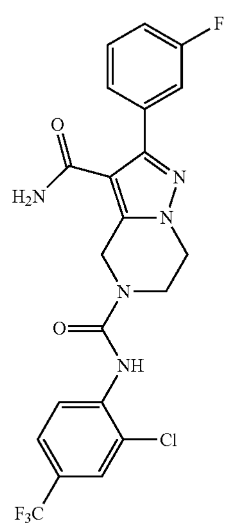 [SMILES: NC(=O)c1c(-c2cccc(F)c2)nn2c1CN(C(=O)Nc1ccc(C(F)(F)F)cc1Cl)CC2] | N5-(2-Chloro-4-(trifluoromethyl)phenyl)-2-(3-fluorophenyl)-6,7-dihydropyrazolo[1,5-a]pyrazine-3,5(4H)-dicarboxamide | A | 482 | 1.610 | E |

TABLE 2-continued

| Ex. No. | Structure | Name | Synthetic Method | [M + H]+ | Ret Time (min.) | HPLC Method |
|---|---|---|---|---|---|---|
| 65 | 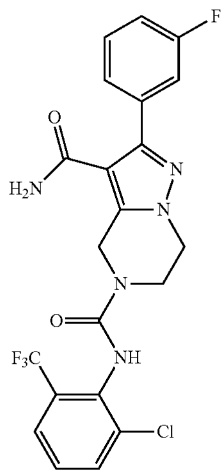 [SMILES: NC(=O)c1c(-c2cccc(F)c2)nn2c1CN(C(=O)Nc1c(Cl)cccc1C(F)(F)F)CC2] | N5-(2-Chloro-6-(trifluoromethyl)phenyl)-2-(3-fluorophenyl)-6,7-dihydropyrazolo[1,5-a]pyrazine-3,5(4H)-dicarboxamide | A | 482 | 1.259 | E |
| 66 | 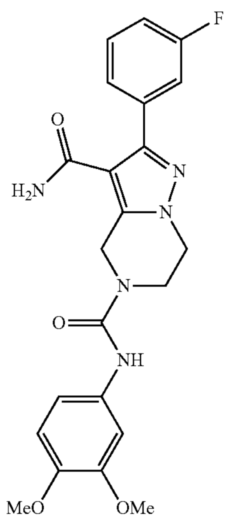 [SMILES: COc1ccc(NC(=O)N2CCn3nc(-c4cccc(F)c4)c(C(N)=O)c3C2)cc1OC] | N5-(3,4-Dimethoxyphenyl)-2-(3-fluorophenyl)-6,7-dihydropyrazolo[1,5-a]pyrazine-3,5(4H)-dicarboxamide | A | 440 | 1.066 | E |
| 67 | 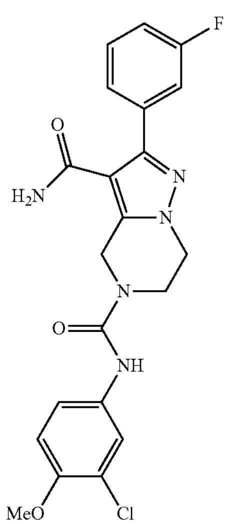 [SMILES: COc1ccc(NC(=O)N2CCn3nc(-c4cccc(F)c4)c(C(N)=O)c3C2)cc1Cl] | N5-(3-Chloro-4-methoxyphenyl)-2-(3-fluorophenyl)-6,7-dihydropyrazolo[1,5-a]pyrazine-3,5(4H)-dicarboxamide | A | 444 | 1.310 | E |

TABLE 2-continued

| Ex. No. | Structure | Name | Synthetic Method | [M + H]+ | Ret Time (min.) | HPLC Method |
|---|---|---|---|---|---|---|
| 68 | 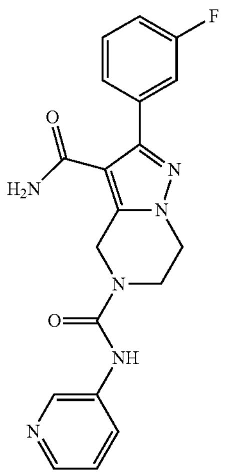 [SMILES: NC(=O)c1c(-c2cccc(F)c2)nn2c1CN(C(=O)Nc1cccnc1)CC2] | 2-(3-Fluorophenyl)-N5-(pyridin-3-yl)-6,7-dihydropyrazolo[1,5-a]pyrazine-3,5(4H)-dicarboxamide | A | 381 | 0.886 | E |
| 69 | 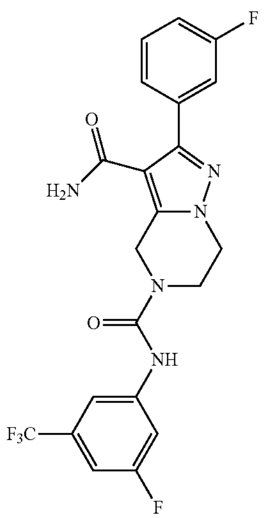 [SMILES: NC(=O)c1c(-c2cccc(F)c2)nn2c1CN(C(=O)Nc1cc(F)cc(C(F)(F)F)c1)CC2] | N5-(3-Fluoro-5-(trifluoromethyl)phenyl)-2-(3-fluorophenyl)-6,7-dihydropyrazolo[1,5-a]pyrazine-3,5(4H)-dicarboxamide | A | 466 | 1.631 | E |
| 70 | 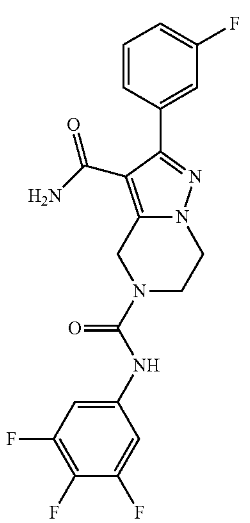 [SMILES: NC(=O)c1c(-c2cccc(F)c2)nn2c1CN(C(=O)Nc1cc(F)c(F)c(F)c1)CC2] | 2-(3-Fluorophenyl)-N5-(3,4,5-trifluorophenyl)-6,7-dihydropyrazolo[1,5-a]pyrazine-3,5(4H)-dicarboxamide | B | 434 | 14.7<br>13.49 | F<br>G |

TABLE 2-continued

| Ex. No. | Structure | Name | Synthetic Method | [M + H]+ | Ret Time (min.) | HPLC Method |
|---|---|---|---|---|---|---|
| 71 | 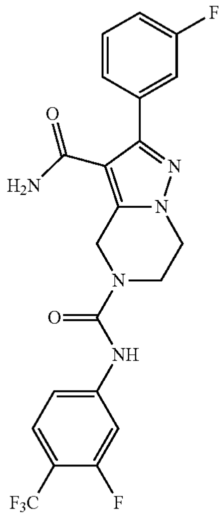 [SMILES: NC(=O)c1c(-c2cccc(F)c2)nn2c1CN(C(=O)Nc1ccc(C(F)(F)F)c(F)c1)CC2] | N5-(3-Fluoro-4-(trifluoromethyl)phenyl)-2-(3-fluorophenyl)-6,7-dihydropyrazolo[1,5-a]pyrazine-3,5(4H)-dicarboxamide | B | 466 | 16.11<br>14.73 | F<br>G |
| 72 | 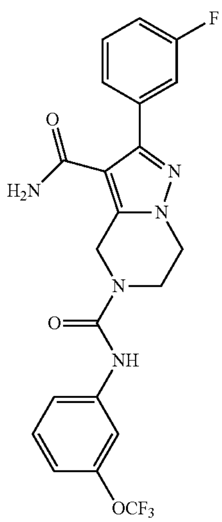 [SMILES: NC(=O)c1c(-c2cccc(F)c2)nn2c1CN(C(=O)Nc1cccc(OC(F)(F)F)c1)CC2] | 2-(3-Fluorophenyl)-N5-(3-(trifluoromethoxy)phenyl)-6,7-dihydropyrazolo[1,5-a]pyrazine-3,5(4H)-dicarboxamide | B | 464 | 15.59<br>14.07 | F<br>G |
| 73 | 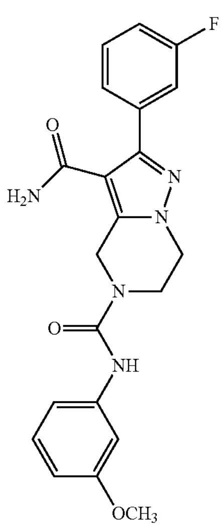 [SMILES: COc1cccc(NC(=O)N2CCn3nc(-c4cccc(F)c4)c(C(N)=O)c3C2)c1] | 2-(3-Fluorophenyl)-N5-(3-methoxyphenyl)-6,7-dihydropyrazolo[1,5-a]pyrazine-3,5(4H)-dicarboxamide | B | 410 | 11.76<br>11.05 | F<br>G |

TABLE 2-continued

| Ex. No. | Structure | Name | Synthetic Method | [M + H]+ | Ret Time (min.) | HPLC Method |
|---|---|---|---|---|---|---|
| 74 | 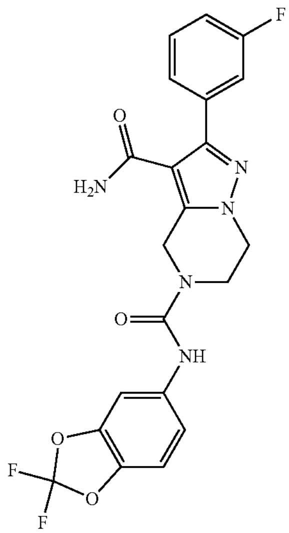 [SMILES: NC(=O)c1c(-c2cccc(F)c2)nn2c1CN(C(=O)Nc1ccc3c(c1)OC(F)(F)O3)CC2] | N5-(2,2-Difluorobenzo[d][1,3]dioxol-5-yl)-2-(3-fluorophenyl)-6,7-dihydropyrazolo[1,5-a]pyrazine-3,5(4H)-dicarboxamide | B | 460 | 14.82<br>13.56 | F<br>G |
| 75 | 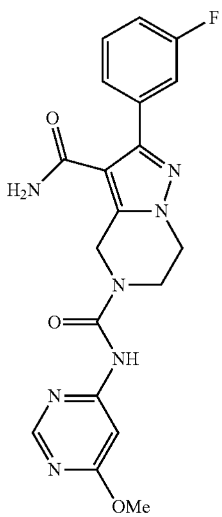 [SMILES: COc1cc(NC(=O)N2CCn3nc(-c4cccc(F)c4)c(C(N)=O)c3C2)ncn1] | 2-(3-Fluorophenyl)-N5-(6-methoxypyrimidin-4-yl)-6,7-dihydropyrazolo[1,5-a]pyrazine-3,5(4H)-dicarboxamide | B | 412 | 12.78<br>12.18 | C<br>D |
| 76 | 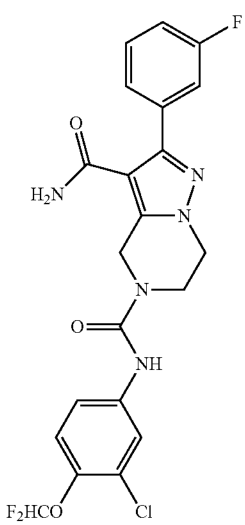 [SMILES: NC(=O)c1c(-c2cccc(F)c2)nn2c1CN(C(=O)Nc1ccc(OC(F)F)c(Cl)c1)CC2] | N5-(3-Chloro-4-(difluoromethoxy)phenyl)-2-(3-fluorophenyl)-6,7-dihydropyrazolo[1,5-a]pyrazine-3,5(4H)-dicarboxamide | B | 480 | 9.16<br>9.59 | B<br>A |

TABLE 2-continued

| Ex. No. | Structure | Name | Synthetic Method | [M + H]+ | Ret Time (min.) | HPLC Method |
|---|---|---|---|---|---|---|
| 77 | 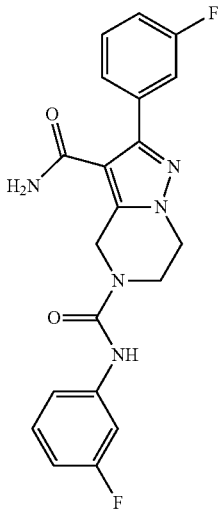 [SMILES: NC(=O)c1c(-c2cccc(F)c2)nn2c1CN(C(=O)Nc1cccc(F)c1)CC2] | $N^5$,2-Bis(3-fluorophenyl)-6,7-dihydropyrazolo[1,5-a]pyrazine-3,5(4H)-dicarboxamide | B | 398 | 16.34<br>15.21 | C<br>D |
| 78 | 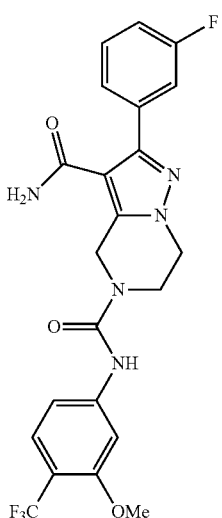 | 2-(3-Fluorophenyl)-$N^5$-(3-methoxy-4-(trifluoromethyl)phenyl)-6,7-dihydropyrazolo[1,5-a]pyrazine-3,5(4H)-dicarboxamide | B | 478 | 14.53<br>13.53 | F<br>G |
| 79 | 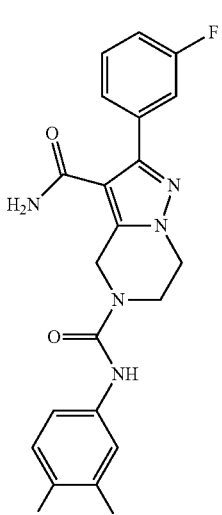 | $N^5$-(3-Chloro-4-(trifluoromethyl)phenyl)-2-(3-fluorophenyl)-6,7-dihydropyrazolo[1,5-a]pyrazine-3,5(4H)-dicarboxamide | B | 482 | 15.22<br>16.90 | G<br>F |

TABLE 2-continued

| Ex. No. | Structure | Name | Synthetic Method | [M + H]+ | Ret Time (min.) | HPLC Method |
|---|---|---|---|---|---|---|
| 80 | 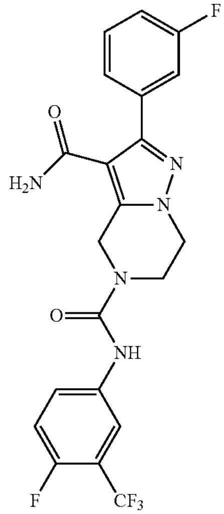 [SMILES: NC(=O)c1c(-c2cccc(F)c2)nn2c1CN(C(=O)Nc1ccc(F)c(C(F)(F)F)c1)CC2] | $N^5$-(4-Fluoro-3-(trifluoromethyl)phenyl)-2-(3-fluorophenyl)-6,7-dihydropyrazolo[1,5-a]pyrazine-3,5(4H)-dicarboxamide | B | 466 | 15.43<br>13.97 | F<br>G |
| 81 | 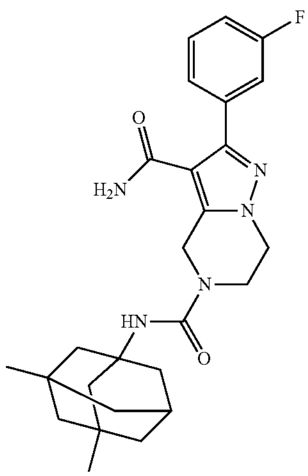 [SMILES: CC12CC3CC(C)(C1)CC(NC(=O)N1CCn4nc(-c5cccc(F)c5)c(C(N)=O)c4C1)(C3)C2] | $N^5$-(3,5-Dimethyladamantan-1-yl)-2-(3-fluorophenyl)-6,7-dihydropyrazolo[1,5-a]pyrazine-3,5(4H)-dicarboxamide | C | 466 | 18.48<br>16.03 | C<br>D |
| 82 | 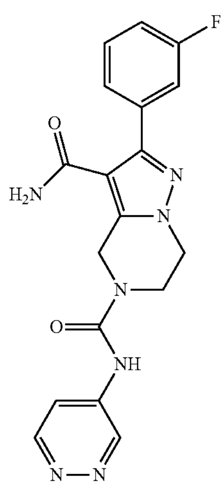 [SMILES: NC(=O)c1c(-c2cccc(F)c2)nn2c1CN(C(=O)Nc1ccnnc1)CC2] | 2-(3-Fluorophenyl)-$N^5$-(pyridazin-4-yl)-6,7-dihydropyrazolo[1,5-a]pyrazine-3,5(4H)-dicarboxamide | D | 382 | 9.58<br>8.68 | D<br>C |

TABLE 2-continued

| Ex. No. | Structure | Name | Synthetic Method | [M + H]+ | Ret Time (min.) | HPLC Method |
|---|---|---|---|---|---|---|
| 83 | 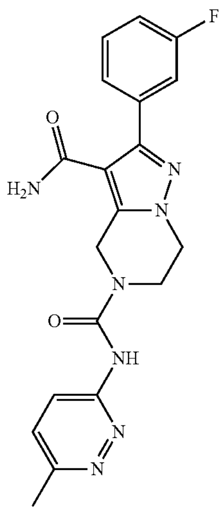 [SMILES: Cc1ccc(NC(=O)N2CCn3nc(-c4cccc(F)c4)c(C(N)=O)c3C2)nn1] | 2-(3-Fluorophenyl)-$N^5$-(6-methylpyridazin-3-yl)-6,7-dihydropyrazolo[1,5-a]pyrazine-3,5(4H)-dicarboxamide | D | 396 | 9.79<br>9.27 | D<br>C |
| 84 | 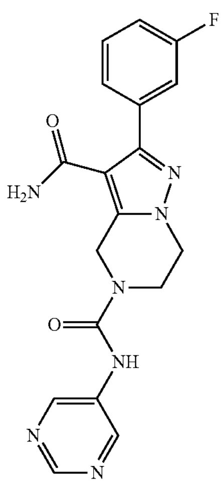 [SMILES: NC(=O)c1c(-c2cccc(F)c2)nn2c1CN(C(=O)Nc1cncnc1)CC2] | 2-(3-Fluorophenyl)-$N^5$-(pyrimidin-5-yl)-6,7-dihydropyrazolo[1,5-a]pyrazine-3,5(4H)-dicarboxamide | B | 382 | 10.43<br>10.80 | D<br>C |
| 85 | 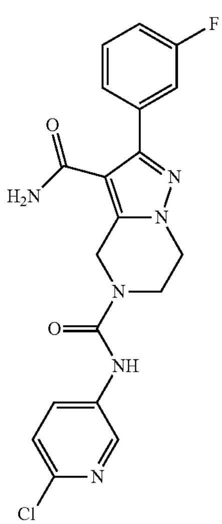 [SMILES: NC(=O)c1c(-c2cccc(F)c2)nn2c1CN(C(=O)Nc1ccc(Cl)nc1)CC2] | $N^5$-(6-Chloropyridin-3-yl)-2-(3-fluorophenyl)-6,7-dihydropyrazolo[1,5-a]pyrazine-3,5(4H)-dicarboxamide | D | 415 | 7.21<br>7.31 | B<br>A |

TABLE 2-continued

| Ex. No. | Structure | Name | Synthetic Method | [M + H]+ | Ret Time (min.) | HPLC Method |
|---|---|---|---|---|---|---|
| 86 | 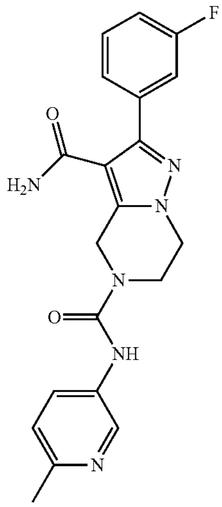 [SMILES: Cc1ccc(NC(=O)N2CCn3nc(-c4cccc(F)c4)c(C(N)=O)c3C2)cn1] | 2-(3-Fluorophenyl)-N$^5$-(6-methylpyridin-3-yl)-6,7-dihydropyrazolo[1,5-a]pyrazine-3,5(4H)-dicarboxamide | D | 395 | 8.46<br>9.74 | C<br>D |
| 87 | 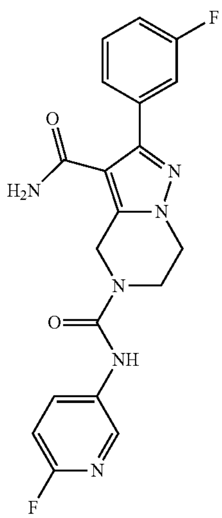 [SMILES: NC(=O)c1c(-c2cccc(F)c2)nn2c1CN(C(=O)Nc1ccc(F)nc1)CC2] | 2-(3-Fluorophenyl)-N$^5$-(6-fluoropyridin-3-yl)-6,7-dihydropyrazolo[1,5-a]pyrazine-3,5(4H)-dicarboxamide | D | 399 | 6.79<br>6.71 | A<br>B |
| 88 | 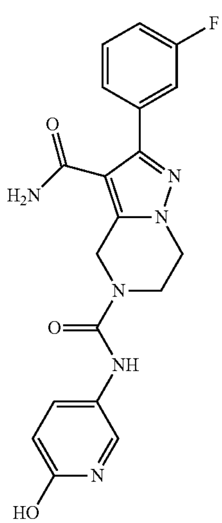 [SMILES: NC(=O)c1c(-c2cccc(F)c2)nn2c1CN(C(=O)Nc1ccc(O)nc1)CC2] | 2-(3-Fluorophenyl)-N$^5$-(6-hydroxypyridin-3-yl)-6,7-dihydropyrazolo[1,5-a]pyrazine-3,5(4H)-dicarboxamide | D | 397 | 9.57<br>9.86 | D<br>C |

TABLE 2-continued

| Ex. No. | Structure | Name | Synthetic Method | [M + H]+ | Ret Time (min.) | HPLC Method |
|---|---|---|---|---|---|---|
| 89 | 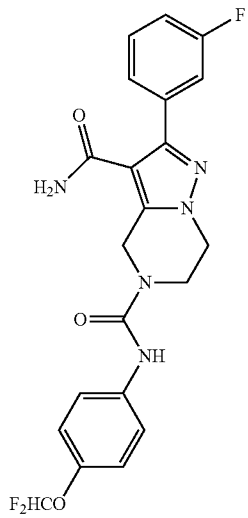 [SMILES: NC(=O)c1c(-c2cccc(F)c2)nn2c1CN(C(=O)Nc1ccc(OC(F)F)cc1)CC2] | $N^5$-(4-(Difluoromethoxy)phenyl)-2-(3-fluorophenyl)-6,7-dihydropyrazolo[1,5-a]pyrazine-3,5(4H)-dicarboxamide | B | 446 | 8.53<br>8.82 | B<br>A |
| 90 | 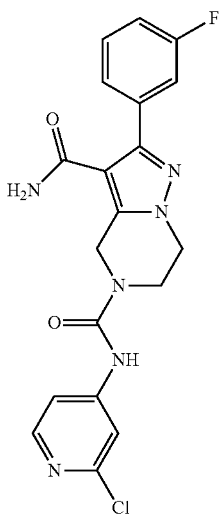 [SMILES: NC(=O)c1c(-c2cccc(F)c2)nn2c1CN(C(=O)Nc1ccnc(Cl)c1)CC2] | $N^5$-(2-Chloropyridin-4-yl)-2-(3-fluorophenyl)-6,7-dihydropyrazolo[1,5-a]pyrazine-3,5(4H)-dicarboxamide | D | 415 | 7.22<br>7.10 | A<br>B |
| 91 | 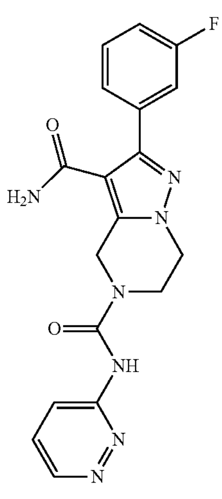 [SMILES: NC(=O)c1c(-c2cccc(F)c2)nn2c1CN(C(=O)Nc1cccnn1)CC2] | 2-(3-Fluorophenyl)-$N^5$-(pyridazin-3-yl)-6,7-dihydropyrazolo[1,5-a]pyrazine-3,5(4H)-dicarboxamide | B | 382 | 10.07<br>9.86 | D<br>C |

TABLE 2-continued

| Ex. No. | Structure | Name | Synthetic Method | [M + H]+ | Ret Time (min.) | HPLC Method |
|---|---|---|---|---|---|---|
| 92 | 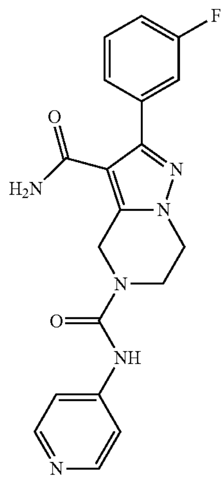 [SMILES: NC(=O)c1c(-c2cccc(F)c2)nn2c1CN(C(=O)Nc1ccncc1)CC2] | 2-(3-Fluorophenyl)-N5-(pyridin-4-yl)-6,7-dihydropyrazolo[1,5-a]pyrazine-3,5(4H)-dicarboxamide | D | 381 | 8.81<br>8.49 | A<br>B |
| 93 | 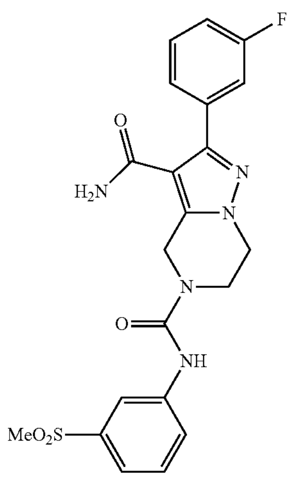 [SMILES: CS(=O)(=O)c1cccc(NC(=O)N2CCn3nc(-c4cccc(F)c4)c(C(N)=O)c3C2)c1] | 2-(3-Fluorophenyl)-N5-(3-(methylsulfonyl)phenyl)-6,7-dihydropyrazolo[1,5-a]pyrazine-3,5(4H)-dicarboxamide | A | 458 | 13.71<br>13.43 | C<br>D |
| 94 | 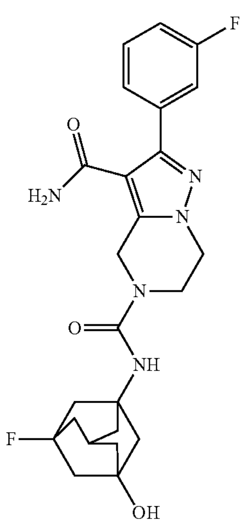 [SMILES: NC(=O)c1c(-c2cccc(F)c2)nn2c1CN(C(=O)NC13CC4CC(O)(CC(F)(C4)C1)C3)CC2] | N5-(3-Fluoro-5-hydroxyadamantan-1-yl)-2-(3-fluorophenyl)-6,7-dihydropyrazolo[1,5-a]pyrazine-3,5(4H)-dicarboxamide | C | 472 | 13.06<br>12.08 | C<br>D |

TABLE 2-continued
| Ex. No. | Structure | Name | Synthetic Method | [M + H]+ | Ret Time (min.) | HPLC Method |
|---|---|---|---|---|---|---|
| 95 | 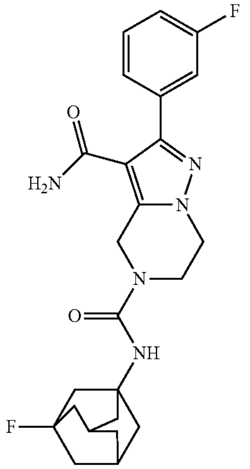 [SMILES: NC(=O)c1c(-c2cccc(F)c2)nn2c1CN(C(=O)NC13CC4CC(CC(F)(C4)C1)C3)CC2] | $N^5$-(3-Fluoroadamantan-1-yl)-2-(3-fluorophenyl)-6,7-dihydropyrazolo[1,5-a]pyrazine-3,5(4H)-dicarboxamide | C | 456 | 8.32<br>9.03 | B<br>A |
| 96 | 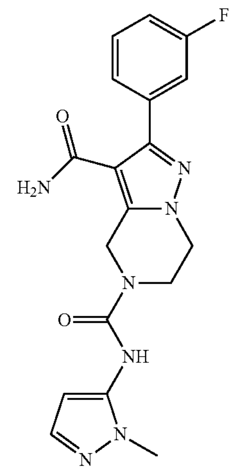 [SMILES: Cn1nccc1NC(=O)N1CCn2nc(-c3cccc(F)c3)c(C(N)=O)c2C1] | 2-(3-Fluorophenyl)-$N^5$-(1-methyl-1H-pyrazol-5-yl)-6,7-dihydropyrazolo[1,5-a]pyrazine-3,5(4H)-dicarboxamide | B | 384 | 10.41<br>10.56 | D<br>C |
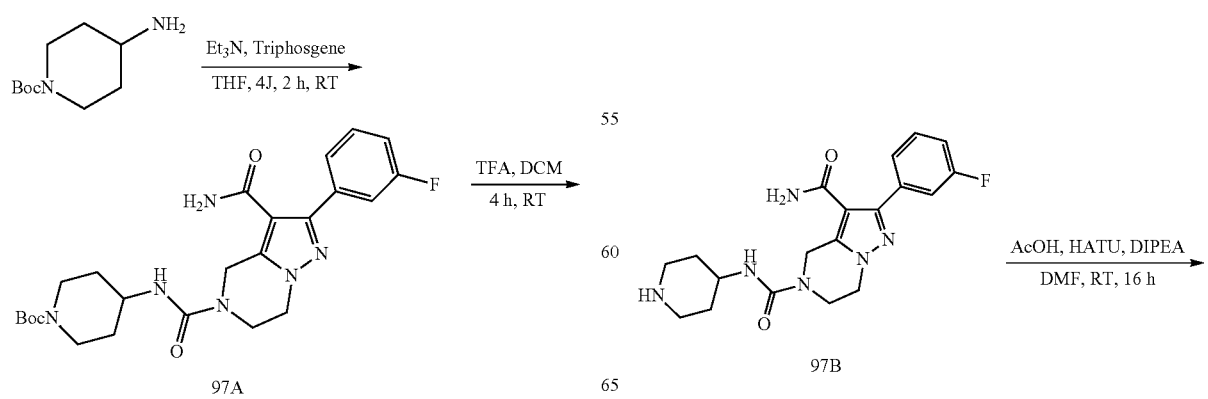

-continued

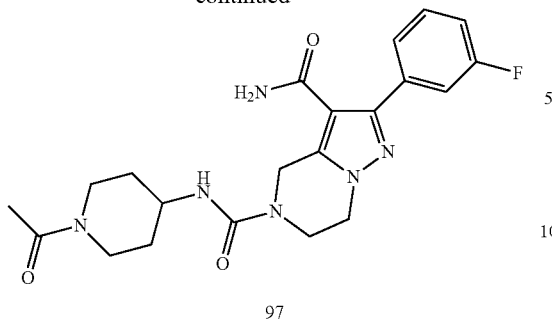

97

Intermediate 97A: tert-Butyl 4-(3-carbamoyl-2-(3-fluorophenyl)-4,5,6,7-tetrahydropyrazolo[1,5-a]pyrazine-5-carboxamido)piperidine-1-carboxylate

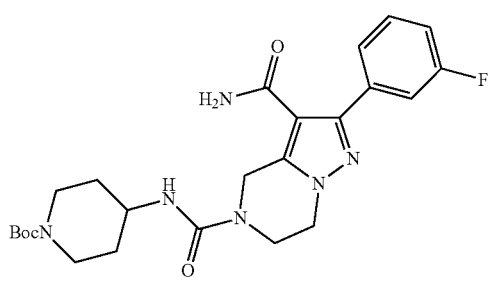 [SMILES: CC(C)(C)OC(=O)N1CCC(NC(=O)N2CCn3nc(-c4cccc(F)c4)c(C(N)=O)c3C2)CC1]

To a solution of tert-butyl 4-aminopiperidine-1-carboxylate (308 mg, 1.537 mmol) and TEA (0.536 mL, 3.84 mmol) in THF (3 mL) was added triphosgene (228 mg, 0.768 mmol) at 0° C. and stirred for 30 min. at the same temperature. A solution of Intermediate 4J (200 mg, 0.768 mmol) in THF was added and the reaction mixture was stirred at room temperature for 2 h. The reaction mixture was quenched with water and the aqueous layer was extracted with ethyl acetate (3×5 mL). The combined organic layer was washed with 10% NaHCO$_3$ (2×5 mL), water, dried over Na$_2$SO$_4$, filtered and concentrated. The crude product was purified using reverse phase HPLC method to afford Intermediate 97A (300 mg, 80%) as a white solid. MS(ES): m/z=487 [M+H]$^+$; $^1$H NMR (400 MHz, DMSO-d$_6$) δ ppm 7.51-7.55 (m, 1H), 7.42-7.51 (m, 2H), 7.35 (bs, 1H), 7.22 (m, 1H), 7.15 (bs, 1H), 6.70 (d, J=7.53 Hz, 1H), 4.72 (s, 2H), 4.14 (t, J=4.8 Hz, 2H), 3.89 (m, 2H), 3.84 (t, J=4.4 Hz, 2H), 3.65 (m, 1H), 2.85-2.78 (m, 2H), 1.75 (m, 2H), 1.41 (s, 9H), 1.32 (m, 2H).

Intermediate 97B: 2-(3-Fluorophenyl)-N$^5$-(piperidin-4-yl)-6,7-dihydropyrazolo[1,5-a]pyrazine-3,5(4H)-dicarboxamide

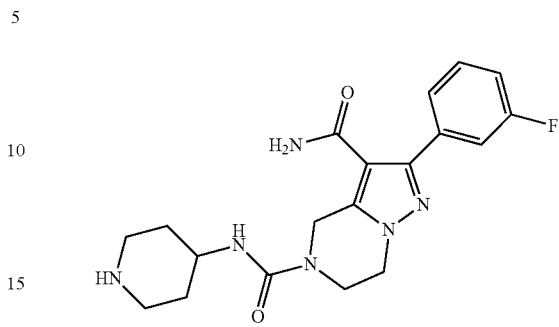

To a solution of Intermediate 97A (300 mg, 0.617 mmol) in DCM (3 mL) was added TFA (0.238 mL, 3.08 mmol) at 0° C. and the reaction mixture was stirred at room temperature for 4 h. The reaction mixture was concentrated and the resultant residue was basified to pH ~8.0 with 10% NaHCO$_3$ solution. The aqueous layer was extracted with DCM (3×5 mL) and the combined organic layer was washed with water (2×5 mL), brine, dried over Na$_2$SO$_4$, filtered and concentrated to afford Intermediate 97B (200 mg, 80%) as white solid. MS(ES): m/z=387 [M+H]$^+$; $^1$H NMR (400 MHz, DMSO-d$_6$) ppm 8.50 (bs, 1H), 7.46 (m, 3H), 7.32 (bs, 1H), 7.21 (m, 1H), 7.11 (bs, 1H), 6.86 (d, J=7.03 Hz, 1H), 4.74 (s, 2H), 4.15 (t, J=5.27 Hz, 2H), 3.86 (t, J=5.27 Hz, 2H), 3.72 (m, 1H), 3.27 (s, 2H), 2.96 (m, 2H), 1.93 (m, 2H), 1.54 (m, 2H).

Example 97

Method A

Amides

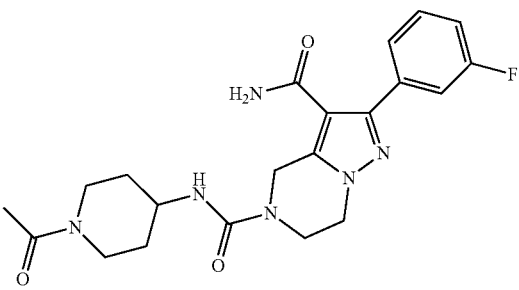 [SMILES: CC(=O)N1CCC(NC(=O)N2CCn3nc(-c4cccc(F)c4)c(C(N)=O)c3C2)CC1]

To a solution of Intermediate 97B (0.025 g, 0.065 mmol) in dry DMF (0.8 mL) was added HATU (0.049 g, 0.129 mmol) and DIPEA (0.034 mL, 0.194 mmol). To this was added acetic acid (7 µL, 0.129 mmol) and the reaction was stirred at RT for 16 h. The reaction was monitored by TLC, which showed the completion of the reaction. The DMF was removed under high vacuum. The reaction mixture was quenched with 10% sodium bicarbonate solution and extracted with DCM (3×30 mL). The combined organic layer was washed with sodium bicarbonate solution, water, and brine, dried over Na$_2$SO$_4$, filtered and concentrated to give the crude product. The crude product was further purified by preparative HPLC purification to afford the pure product 97 as a white solid (9 mg, 32%). MS(ES): m/z=429 [M+H]+; HPLC Ret. Time 10.76 min. and 10.46 min. (HPLC Methods C and D); $^1$H NMR (400 MHz, DMSO-$d_6$) δ ppm 7.51-7.56 (m, 1H), 7.42-7.51 (m, 2H), 7.34 (br. s., 1H), 7.17-7.23 (m, 1H), 7.14 (br. s., 1H), 6.67-6.75 (m, 1H), 4.73 (s, 2H), 4.30 (d, J=13.05 Hz, 1H), 4.14 (t, J=5.27 Hz, 2H), 3.84 (t, J=5.27 Hz, 2H), 3.79 (d, J=14.56 Hz, 1H), 3.66-3.75 (m, 1H), 3.08 (t, J=11.29 Hz, 1H), 2.57-2.67 (m, 1H), 2.00 (s, 3H), 1.72-1.86 (m, 2H), 1.35-1.44 (m, 1H), 1.27-1.34 (m, 1H).

Method B

Sulfonamides

To a solution of Intermediate 97B (0.025 g, 0.065 mmol) and DIPEA (0.034 mL, 0.194 mmol) in dry DCM (0.8 mL) was added cyclopropanesulfonyl chloride (0.018 g, 0.129 mmol) and the reaction was stirred at RT for 16 hours. The reaction mixture was quenched with 10% sodium bicarbonate solution and extracted with DCM (3×30 ml). The combined organic layer was washed with sodium bicarbonate solution, water, and brine, dried over $Na_2SO_4$, filtered and concentrated to furnish the crude product. The crude product was further purified by preparative HPLC purification Method C Reductive Amination To a solution of Intermediate 97B (0.025 g, 0.065 mmol) in dry DCM (0.5 mL) and methanol (0.5 mL) was added 3,3,3-trifluoropropanal (0.014 g, 0.129 mmol) and stirred at RT for 30 minutes. To this mixture, sodium cyanoborohydride (8.13 mg, 0.129 mmol) was added, the reaction mixture was stirred at RT for 3 h and the solvent was removed under reduced pressure. The residue was partitioned between ethyl acetate and water, layers separated, and the aqueous layer was extracted with EtOAc (3×10 mL). The combined organic layer was washed with water, brine, dried over $Na_2SO_4$ and concentrated under reduced pressure to afford the crude product, which was further purified by preparative HPLC purification.

Method D

Carbamates

Step 1: Pyridin-2-yl(1,1,1-trifluoro-2-methylpropan-2-yl) carbonate: To a solution of di(pyridin-2-yl) carbonate (250 mg, 1.156 mmol) in DCM (5 mL) was added DMAP (706 mg, 5.78 mmol) followed by DIPEA (0.202 mL, 1.156 mmol) and 1,1,1-trifluoro-2-methylpropan-2-ol (148 mg, 1.156 mmol). The reaction mixture was stirred at RT overnight, concentrated and the crude was taken to the next step without further purification.

Step 2: To a stirred solution of 97B (0.015 g, 0.039 mmol) in DCM (1.500 mL) was added DIPEA (0.020 mL, 0.116 mmol) and pyridin-2-yl(1,1,1-trifluoro-2-methylpropan-2-yl)carbonate (9.67 mg, 0.039 mmol) and resulting mixture was stirred at 25° C. overnight. The reaction mixture was concentrated and the crude obtained was purified by preparative HPLC purification.

The Compounds described in Table 3 were synthesized analogous to Compound 97 by reacting Compound 97B with corresponding acids, sulfonyl chlorides and aldehydes.

TABLE 3

| Ex. No. | Structure | Name | Synthetic Method | [M + H]+ | Ret. Time (min.) | HPLC Method |
|---|---|---|---|---|---|---|
| 98 | 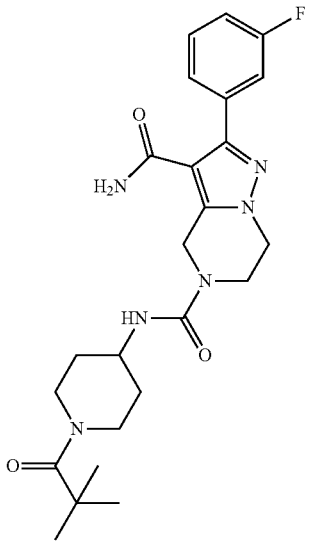 [SMILES: CC(C)(C)C(=O)N1CCC(NC(=O)N2CCn3nc(-c4cccc(F)c4)c(C(N)=O)c3C2)CC1] | 2-(3-Fluorophenyl)-N$^5$-(1-pivaloylpiperidin-4-yl)-6,7-dihydropyrazolo[1,5-a]pyrazine-3,5(4H)-dicarboxamide | A | 471 | 13.96 13.29 | A B |

TABLE 3-continued

| Ex. No. | Structure | Name | Synthetic Method | [M + H]+ | Ret. Time (min.) | HPLC Method |
|---|---|---|---|---|---|---|
| 99 | 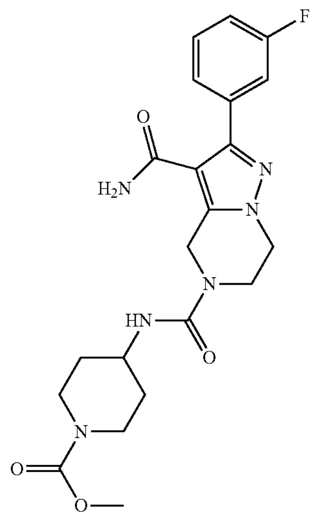 [SMILES: COC(=O)N1CCC(NC(=O)N2CCn3nc(-c4cccc(F)c4)c(C(N)=O)c3C2)CC1] | Methyl 4-(3-carbamoyl-2-(3-fluorophenyl)-4,5,6,7-tetrahydropyrazolo[1,5-a]pyrazine-5-carboxamido)piperidine-1-carboxylate | B | 445 | 6.88<br>6.39 | A<br>B |
| 100 | 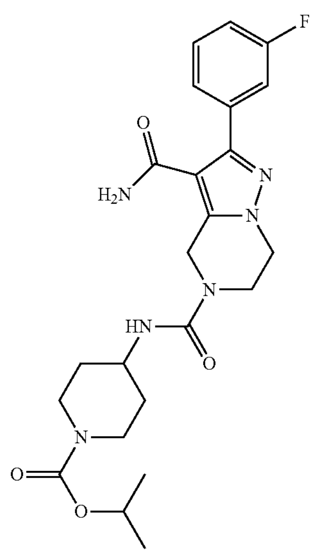 [SMILES: CC(C)OC(=O)N1CCC(NC(=O)N2CCn3nc(-c4cccc(F)c4)c(C(N)=O)c3C2)CC1] | Isopropyl 4-(3-carbamoyl-2-(3-fluorophenyl)-4,5,6,7-tetrahydropyrazolo[1,5-a]pyrazine-5-carboxamido)piperidine-1-carboxylate | B | 473 | 8.01<br>7.40 | A<br>B |

TABLE 3-continued

| Ex. No. | Structure | Name | Synthetic Method | [M + H]+ | Ret. Time (min.) | HPLC Method |
|---|---|---|---|---|---|---|
| 101 | 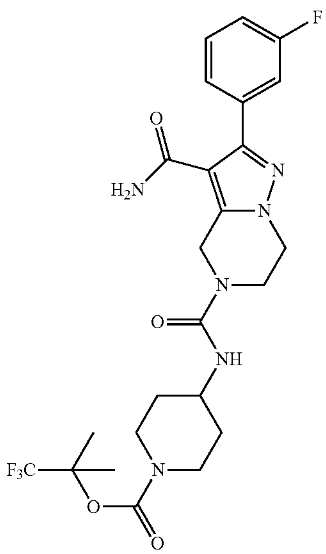 [SMILES: CC(C)(OC(=O)N1CCC(NC(=O)N2CCn3nc(-c4cccc(F)c4)c(C(N)=O)c3C2)CC1)C(F)(F)F] | 1,1,1-Trifluoro-2-methylpropan-2-yl 4-(3-carbamoyl-2-(3-fluorophenyl)-4,5,6,7-tetrahydropyrazolo[1,5-a]pyrazine-5-carboxamido)piperidine-1-carboxylate | D | 541 | 9.026<br>8.726 | A<br>B |
| 102 | 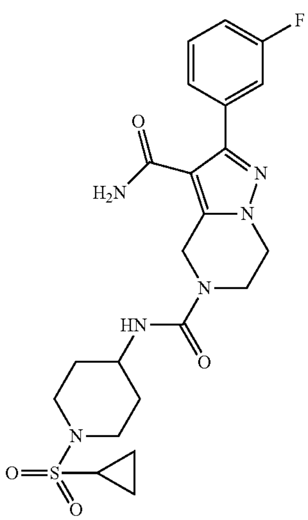 [SMILES: NC(=O)c1c(-c2cccc(F)c2)nn2c1CN(C(=O)NC1CCN(S(=O)(=O)C3CC3)CC1)CC2] | $N^5$-(1-(Cyclopropylsulfonyl)piperidin-4-yl)-2-(3-fluorophenyl)-6,7-dihydropyrazolo[1,5-a]pyrazine-3,5(4H)-dicarboxamide | B | 491 | 7.38<br>6.96 | A<br>B |
| 103 | 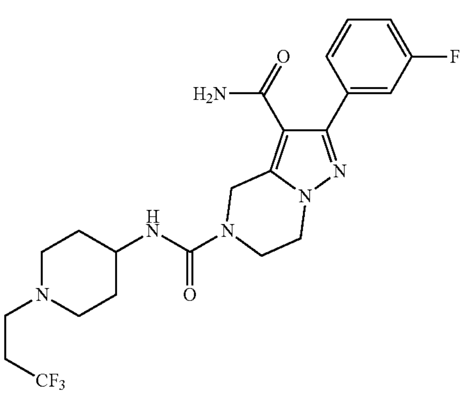 [SMILES: NC(=O)c1c(-c2cccc(F)c2)nn2c1CN(C(=O)NC1CCN(CCC(F)(F)F)CC1)CC2] | 2-(3-Fluorophenyl)-$N^5$-(1-(3,3,3-trifluoropropyl)piperidin-4-yl)-6,7-dihydropyrazolo[1,5-a]pyrazine-3,5(4H)-dicarboxamide | C | 483 | 9.28<br>10.56 | C<br>D |

Scheme 4
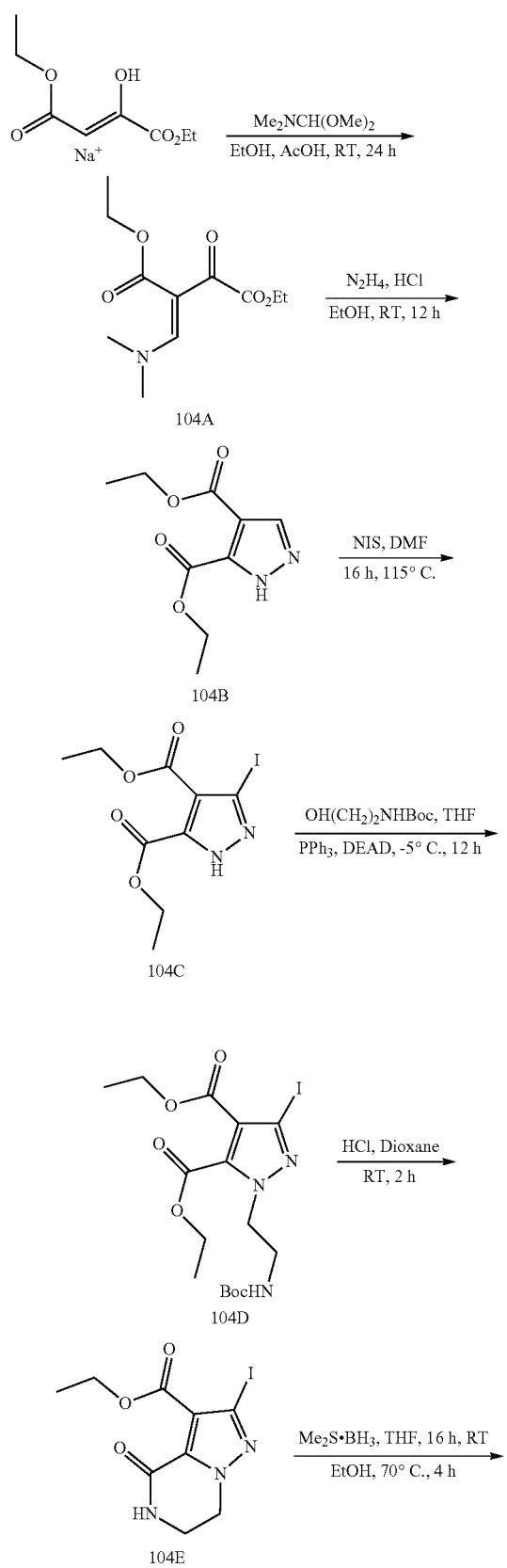
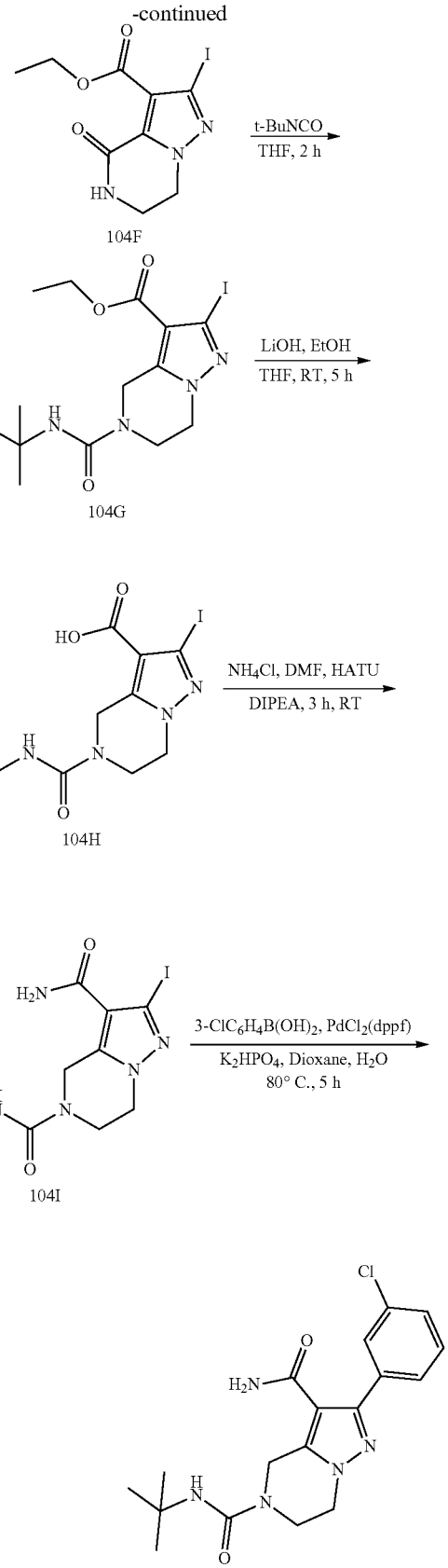

Intermediate 104A: Diethyl 2-((dimethylamino)methylene)-3-oxosuccinate

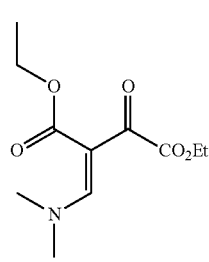 [SMILES: CCOC(=O)C(=O)/C(=C/N(C)C)C(=O)OCC]

To a solution of diethyl oxalacetate sodium salt (100 g, 476 mmol) in ethanol (250.00 mL) was added 1,1-dimethoxy-N,N-dimethylmethanamine (113 g, 952 mmol) and the reaction was stirred at room temperature for 30 min. Acetic acid (54.5 mL, 952 mmol) was added slowly over a period of 3 h and stirred at room temperature for 24 h. The volatile components were evaporated under reduced pressure and the oily residue was purified by silica gel chromatography (750 g REDISEP® column, eluting with 30% EtOAc in hexane). Fractions containing the product were combined and evaporated to afford Intermediate 104A (43 g, 30.8%). MS(ES): m/z=244 [M+H]$^+$; $^1$H NMR (400 MHz, CDCl$_3$) δ ppm 7.84 (s, 1H), 4.31 (q, J=7.2 Hz, 2H), 4.18 (q, J=5.4 Hz, 2H), 3.35 (s, 3H), 3.04 (s, 3H), 1.36 (t, J=7.2 Hz, 3H), 1.26 (t, J=7.2 Hz, 3H).

Intermediate 104B: Diethyl 1H-pyrazole-4,5-dicarboxylate

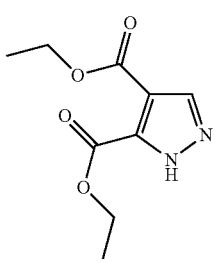

To a stirred solution of 104A (45 g, 185 mmol) in ethanol (150 mL) was added N$_2$H$_4$.HCl (12.67 g, 185 mmol) and the reaction mixture was stirred at RT overnight. The volatiles were evaporated under vacuum and the crude residue was dissolved in water and was extracted with EtOAc (3×50 mL). The combined organic layer was dried over Na$_2$SO$_4$, filtered and evaporated under vacuum. The resulting crude product obtained was purified by ISCO using EtOAc and hexane to afford 104B (21.00 g, 97 mmol, 52.4%). MS(ES): m/z=211 [M−H]$^+$; $^1$H NMR (300 MHz, CDCl$_3$) δ ppm 8.22 (s, 1H) 4.48 (q, J=7.11 Hz, 2H) 4.36 (q, J=7.18 Hz, 2H) 1.33-1.49 (m, 6H).

Intermediate 104C: Diethyl 3-iodo-1H-pyrazole-4,5-dicarboxylate

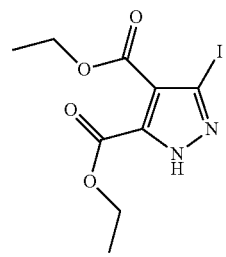 [SMILES: CCOC(=O)c1[nH]nc(I)c1C(=O)OCC]

To a stirred solution of 104B (19 g, 90 mmol) in DMF (50 mL) was added NIS (30.2 g, 134 mmol) and the reaction mixture was stirred for 16 h at 115° C. LCMS indicated the completion of the reaction. DMF was evaporated, the crude was dissolved in EtOAc, washed with water, sodium thiosulfate solution, dried, filtered and evaporated under vacuum to furnish crude product, which was purified by ISCO using EtOAc and hexane system. Fractions collected at 18-20% EtOAc in hexane were evaporated to get 104C (12.5 g, 37.0 mmol, 41.3% yield). MS(ES): m/z=338 [M+H]$^+$; $^1$H NMR (400 MHz, DMSO-d$_6$) δ ppm 14.25 (bs, 1H), 4.27 (m, 4H), 1.26 (m, 6H).

Intermediate 104D: Diethyl 1-(2-((Tert-butoxycarbonyl)amino)ethyl)-3-iodo-1H-pyrazole-4,5-dicarboxylate

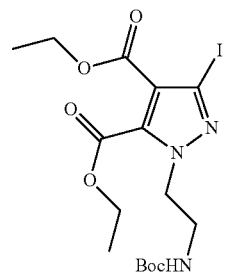 [SMILES: CCOC(=O)c1c(I)nn(CCNC(=O)OC(C)(C)C)c1C(=O)OCC]

To a stirred solution of Intermediate 104C (10.000 g, 29.6 mmol) in THF (100 mL) cooled at −5° C. was added triphenylphosphine (11.64 g, 44.4 mmol) and DIAD (8.63 mL, 44.4 mmol) dropwise and stirred for 30 min. at the same temperature. Solution of tert-butyl(2-hydroxyethyl) carbamate (7.15 g, 44.4 mmol) in THF (10 mL) was added at −5° C. and the stirring was continued for additional 1.5 h. The volatiles were evaporated under vacuum and crude was purified by silica gel chromatography (120 g REDISEP® column, eluting with 18% EtOAc in hexane). Fractions containing the product were combined and evaporated to afford the Intermediate 104D (8.2 g, 57%). MS(ES): m/z=482 [M+H]$^+$; $^1$H NMR (400 MHz, CDCl$_3$) δ ppm 4.79 (bs, 1H), 4.28-4.48 (m, 6H), 3.58 (d, J=5.02 Hz, 2H), 1.43 (s, 9H), 1.33-1.40 (m, 6H).

Intermediate 104E: Ethyl 2-iodo-4-oxo-4,5,6,7-tetrahydropyrazolo[1,5-a]pyrazine-3-carboxylate

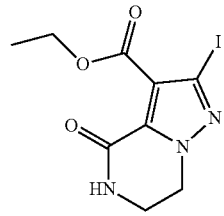 [SMILES: CCOC(=O)c1c(I)nn2c1C(=O)NCC2]

The Intermediate 104D (7 g, 14.54 mmol) was dissolved in HCl in dioxane (2.210 mL, 4M solution, 72.7 mmol) and the reaction mixture was stirred at RT for 3 h. Volatiles were evaporated from the reaction mixture and the residue was dissolved in cold water and basified by adding solid NaHCO₃ (pH=8-9). The aqueous layer was extracted with DCM (4×25 mL) and the combined organic layer was dried, filtered and evaporated under vacuum at 60° C. for 2 h to give 104E (4.750 g, 14.17 mmol, 97%). MS(ES): m/z=336 [M+H]$^+$; $^1$H NMR (400 MHz, DMSO-d$_6$) δ ppm 8.43 (bs, 1H), 4.31-4.37 (m, 2H), 4.24 (q, J=7.11 Hz, 2H), 3.56-3.62 (m, 2H), 1.27 (t, J=7.09 Hz, 3H).

Intermediate 104F: Ethyl 2-iodo-4,5,6,7-tetrahydropyrazolo[1,5-a]pyrazine-3-carboxylate

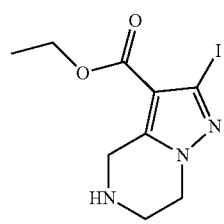

To a stirred solution of Intermediate 104E (5 g, 14.92 mmol) in THF (200 mL) was added dropwise borane dimethyl sulfide complex (15 mL, 158 mmol) at RT. The resulting mixture was stirred at RT for 18 h. The reaction mixture was quenched with ethanol (100 mL) slowly and stirred at 70 OC for 4 h. Volatiles were evaporated under vacuum and the crude was purified by ISCO using methanol (2%) in chloroform as eluent to furnish 104F (2.9 g, 60%). MS(ES): m/z=321 [M+H]$^+$; $^1$H NMR (400 MHz, CD₃OD) δ ppm 4.25-4.34 (m, 2H), 4.22 (s, 2H), 4.12 (t, J=5.46 Hz, 2H), 3.20-3.28 (m, 2H), 1.38 (td, J=7.12, 1.69 Hz, 3H).

Intermediate 104G: Ethyl 5-(tert-butylcarbamoyl)-2-iodo-4,5,6,7-tetrahydropyrazolo[1,5-a]pyrazine-3-carboxylate

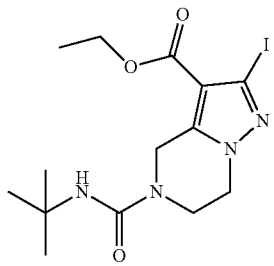 [SMILES: CCOC(=O)c1c(I)nn2c1CN(C(=O)NC(C)(C)C)CC2]

To a stirred solution of Intermediate 104F (2.4 g, 7.47 mmol) in THF (20 mL) was added 2-isocyanato-2-methylpropane (0.741 g, 7.47 mmol) and the reaction mixture was stirred for 1.5 h. The volatiles were evaporated under reduced pressure. The crude was purified by silica gel chromatography (120 g REDISEP® column, eluting with 28% EtOAc in hexane). Fractions containing the product were combined and evaporated to afford Intermediate 104G (2.2 g, 70%). MS(ES): m/z=421 [M+H]$^+$; $^1$H NMR (400 MHz, DMSO-d$_6$) δ ppm 6.25 (s, 1H), 4.72 (s, 2H), 4.25 (q, J=6.8 Hz, 2H), 4.10 (t, J=5.24 Hz, 2H), 3.75 (m, 2H), 1.30 (t, J=7.2 Hz, 3H) 1.28 (s, 9H).

Intermediate 104H: 5-(tert-Butylcarbamoyl)-2-iodo-4,5,6,7-tetrahydropyrazolo[1,5-a]pyrazine-3-carboxylic acid

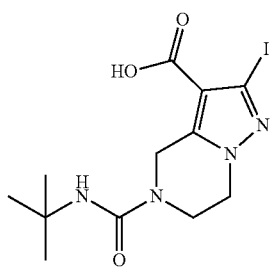 [SMILES: CC(C)(C)NC(=O)N1CCn2nc(I)c(C(=O)O)c2C1]

To a stirred solution of Intermediate 104G (2.1 g, 5.00 mmol) in EtOH (10 mL) and THF (5 mL) was added a solution of lithium hydroxide (0.718 g, 30.0 mmol) in water (1 mL) and stirred at RT for 5 h. Solvent was evaporated under reduced pressure and the crude was dissolved in water and acidified with 1.5 N HCl at 0° C. The resultant precipitate was filtered and dried under vacuum to afford Intermediate 104H (1.8 g, 81%). MS(ES): m/z=393 [M+H]$^+$; $^1$H NMR (300 MHz, DMSO-d$_6$) δ ppm 12.61 (s, 1H), 6.27 (s, 1H), 4.69 (s, 2H), 4.09 (t, J=5.26 Hz, 2H), 3.74 (t, J=5.26, 2H), 1.28 (s, 9H).

139
Intermediate 4I: N⁵-(tert-Butyl)-2-iodo-6,7-dihydro-pyrazolo[1,5-a]pyrazine-3,5(4H)-dicarboxamide

140
Compound 104: N⁵-(tert-Butyl)-2-(3-chlorophenyl)-6,7-dihydropyrazolo[1,5-a]pyrazine-3,5(4H)-dicarboxamide


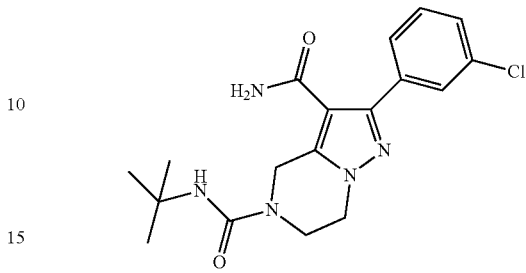

To a stirred solution of Intermediate 104H (1.800 g, 4.59 mmol) in DMF (20 mL) was added ammonium chloride (1.473 g, 27.5 mmol), HATU (3.49 g, 9.18 mmol) and DIPEA (3.21 mL, 18.36 mmol) and the resulting reaction mixture was stirred for 3 h at RT. DMF was evaporated from the reaction mixture, water was added and extracted with EtOAc. The combined organic layer was washed with cold water, dried over Na₂SO₄ and concentrated under vacuum to give the crude product, which was purified by ISCO using 70% ethyl acetate in hexane as eluent. The fractions containing the desired product were combined and evaporated to afford Intermediate 1041 (1.5 g, 85%). MS(ES): m/z=392 [M+H]⁺; ¹H NMR (300 MHz, DMSO-d₆) δ ppm 7.37 (bs, 1H), 6.86 (bs, 1H), 6.24 (s, 1H), 4.67 (s, 2H), 4.07 (t, J=5.31 Hz, 2H), 3.73 (t, J=5.31 Hz, 2H), 1.20 (s, 9H).

To a stirred solution of 1041 (200 mg, 0.511 mmol) and (3-chlorophenyl)boronic acid (160 mg, 1.022 mmol) in 1,4-dioxane (2 mL) and water (0.20 mL) was added potassium phosphate dibasic (267 mg, 1.534 mmol). The reaction mixture was degassed for 5 min. with nitrogen, PdCl₂(dppf)-CH₂Cl₂ (29.2 mg, 0.036 mmol) was added and stirred at 80° C. for 5 h. Reaction progress was monitored by LCMS. The reaction mixture was diluted with water (15 mL) and the aqueous layer was back extracted with ethyl acetate (3×15 mL). The combined organic layer washed with brine (2×25 mL), dried over Na₂SO₄, filtered and concentrated. The crude product was purified by reverse phase preparative HPLC to afford Compound 104 (0.125 g, 65%). MS(ES): m/z=376 [M+H]⁺; HPLC Ret. Time 8.11 min. and 8.47 min. (HPLC Methods A and B); ¹H NMR (400 MHz, DMSO-d₆) δ ppm 7.72 (dd, J=3.45, 0.69 Hz, 1H), 7.65 (dt, J=6.71, 1.88 Hz, 1H), 7.43 (m, 2H), 7.28 (m, 2H), 6.28 (s, 1H), 4.69 (s, 2H), 4.13 (t, J=5.30 Hz, 2H), 3.81 (t, J=5.33 Hz, 2H), 1.28 (s, 9H).

The Compounds described in Table 4 were synthesized analogous to Compound 104 by reacting Compound 1041 with corresponding boronic acids.

TABLE 4

| Ex. No. | Structure | Name | [M + H]⁺ | Ret Time (min.) | HPLC Method |
|---|---|---|---|---|---|
| 105 | (structure shown) | N⁵-(tert-Butyl)-2-(3,5-difluorophenyl)-6,7-dihydropyrazolo[1,5-a]pyrazine-3,5(4H)-dicarboxamide | 378 | 7.929<br>8.331 | A<br>B |

TABLE 4-continued

| Ex. No. | Structure | Name | [M + H]+ | Ret Time (min.) | HPLC Method |
|---|---|---|---|---|---|
| 106 | 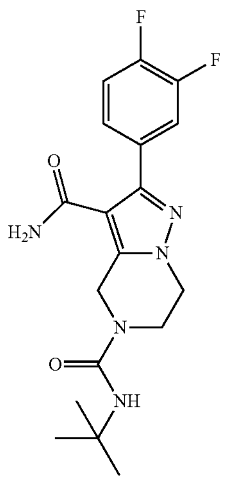 [SMILES: CC(C)(C)NC(=O)N1CCn2nc(-c3ccc(F)c(F)c3)c(C(N)=O)c2C1] | N5-(tert-Butyl)-2-(3,4-difluorophenyl)-6,7-dihydropyrazolo[1,5-a]pyrazine-3,5(4H)-dicarboxamide | 378 | 7.811<br>8.249 | A<br>B |
| 107 | 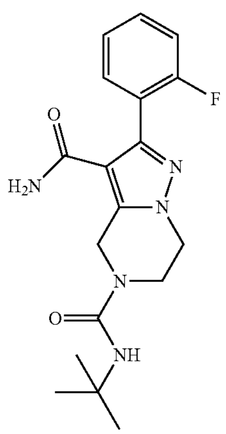 [SMILES: CC(C)(C)NC(=O)N1CCn2nc(-c3ccccc3F)c(C(N)=O)c2C1] | N5-(tert-Butyl)-2-(2-fluorophenyl)-6,7-dihydropyrazolo[1,5-a]pyrazine-3,5(4H)-dicarboxamide | 360 | 7.23<br>7.50 | A<br>B |
| 108 | 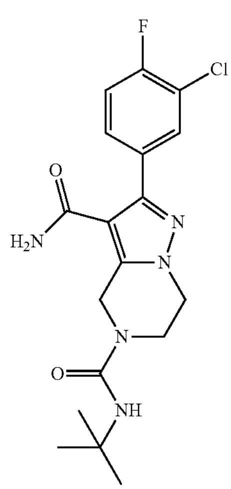 [SMILES: CC(C)(C)NC(=O)N1CCn2nc(-c3ccc(F)c(Cl)c3)c(C(N)=O)c2C1] | N5-(tert-Butyl)-2-(3-chloro-4-fluorophenyl)-6,7-dihydropyrazolo[1,5-a]pyrazine-3,5(4H)-dicarboxamide | 394 | 8.388<br>8.800 | A<br>B |

TABLE 4-continued
| Ex. No. | Structure | Name | [M + H]+ | Ret Time (min.) | HPLC Method |
|---|---|---|---|---|---|
| 109 | 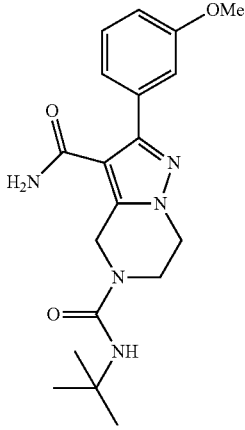 [SMILES: COc1cccc(-c2nn3c(c2C(N)=O)CN(C(=O)NC(C)(C)C)CC3)c1] | N5-(tert-Butyl)-2-(3-methoxyphenyl)-6,7-dihydropyrazolo[1,5-a]pyrazine-3,5(4H)-dicarboxamide | 372 | 13.92<br>13.02 | C<br>D |
| 110 | 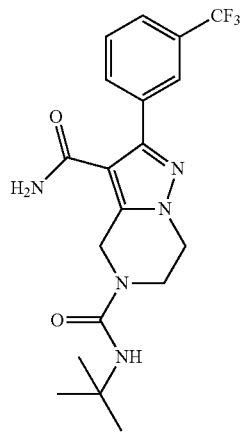 | N5-(tert-Butyl)-2-(3-(trifluoromethyl)phenyl)-6,7-dihydropyrazolo[1,5-a]pyrazine-3,5(4H)-dicarboxamide | 410 | 8.778<br>8.210 | A<br>B |
| 111 | 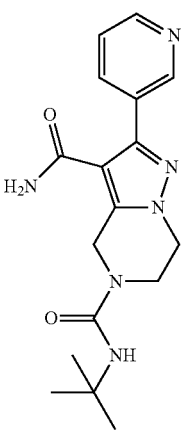 [SMILES: CC(C)(C)NC(=O)N1CCn2nc(-c3cccnc3)c(C(N)=O)c2C1] | N5-(tert-Butyl)-2-(pyridin-3-yl)-6,7-dihydropyrazolo[1,5-a]pyrazine-3,5(4H)-dicarboxamide | 343 | 7.373<br>7.996 | C<br>D |

TABLE 4-continued

| Ex. No. | Structure | Name | [M + H]+ | Ret Time (min.) | HPLC Method |
|---|---|---|---|---|---|
| 112 | 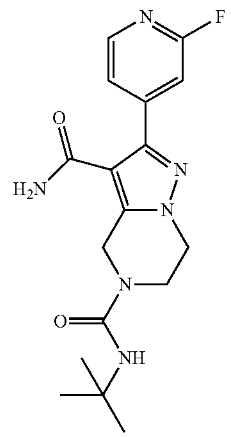 [SMILES: CC(C)(C)NC(=O)N1CCn2nc(-c3ccnc(F)c3)c(C(N)=O)c2C1] | N5-(tert-Butyl)-2-(2-fluoropyridin-4-yl)-6,7-dihydropyrazolo[1,5-a]pyrazine-3,5(4H)-dicarboxamide | 361 | 10.988 | D |
| 113 | 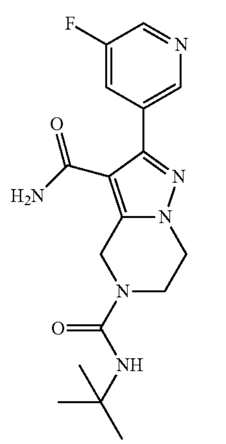 [SMILES: CC(C)(C)NC(=O)N1CCn2nc(-c3cncc(F)c3)c(C(N)=O)c2C1] | N5-(tert-Butyl)-2-(5-fluoropyridin-3-yl)-6,7-dihydropyrazolo[1,5-a]pyrazine-3,5(4H)-dicarboxamide | 361 | 10.918 10.306 | C D |
| 114 | 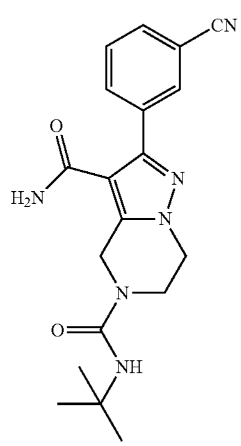 [SMILES: CC(C)(C)NC(=O)N1CCn2nc(-c3cccc(C#N)c3)c(C(N)=O)c2C1] | N5-(tert-Butyl)-2-(3-cyanophenyl)-6,7-dihydropyrazolo[1,5-a]pyrazine-3,5(4H)-dicarboxamide | 367 | 13.465 12.598 | C D |

TABLE 4-continued

| Ex. No. | Structure | Name | [M + H]+ | Ret Time (min.) | HPLC Method |
|---|---|---|---|---|---|
| 115 | 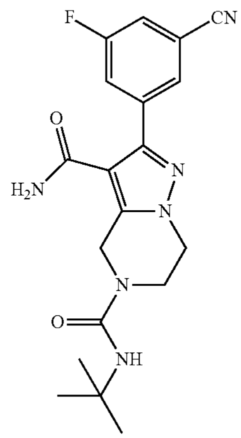 [SMILES: CC(C)(C)NC(=O)N1CCn2nc(-c3cc(F)cc(C#N)c3)c(C(N)=O)c2C1] | N5-(tert-Butyl)-2-(3-cyano-5-fluorophenyl)-6,7-dihydropyrazolo[1,5-a]pyrazine-3,5(4H)-dicarboxamide | | 7.747<br>7.337 | A<br>B |
| 116 | 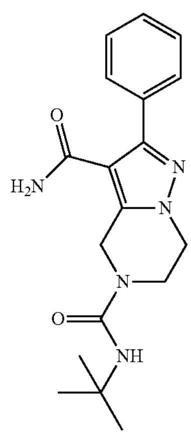 | N5-(tert-Butyl)-2-phenyl-6,7-dihydropyrazolo[1,5-a]pyrazine-3,5(4H)-dicarboxamide | 342 | 1.027 | E |
| 117 | 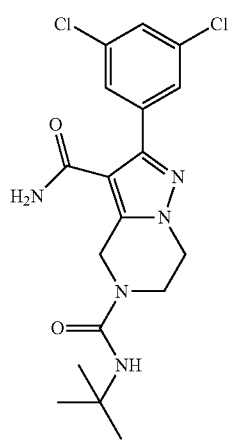 [SMILES: CC(C)(C)NC(=O)N1CCn2nc(-c3cc(Cl)cc(Cl)c3)c(C(N)=O)c2C1] | N5-(tert-Butyl)-2-(3,5-dichlorophenyl)-6,7-dihydropyrazolo[1,5-a]pyrazine-3,5(4H)-dicarboxamide | 410 | 1.47 | E |

TABLE 4-continued

| Ex. No. | Structure | Name | [M + H]+ | Ret Time (min.) | HPLC Method |
|---|---|---|---|---|---|
| 118 | 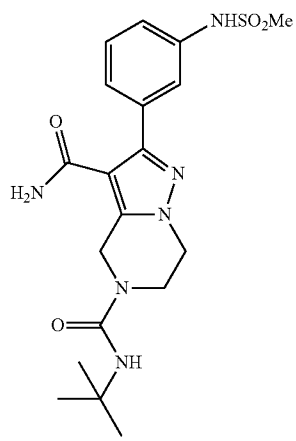 | $N^5$-(tert-Butyl)-2-(3-(methylsulfonamido)phenyl)-6,7-dihydropyrazolo[1,5-a]pyrazine-3,5(4H)-dicarboxamide | 435 | 0.929 | E |
| 119 | 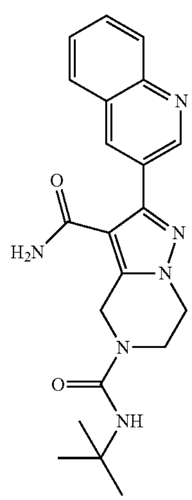 [SMILES: CC(C)(C)NC(=O)N1CCn2nc(-c3cnc4ccccc4c3)c(C(N)=O)c2C1] | $N^5$-(tert-Butyl)-2-(quinolin-3-yl)-6,7-dihydropyrazolo[1,5-a]pyrazine-3,5(4H)-dicarboxamide | 393 | 1.051 | E |
| 120 | 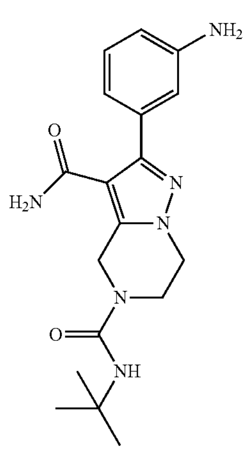 [SMILES: CC(C)(C)NC(=O)N1CCn2nc(-c3cccc(N)c3)c(C(N)=O)c2C1] | 2-(3-Aminophenyl)-$N^5$-(tert-butyl)-6,7-dihydropyrazolo[1,5-a]pyrazine-3,5(4H)-dicarboxamide | 357 | 0.856 | E |

TABLE 4-continued

| Ex. No. | Structure | Name | [M + H]+ | Ret Time (min.) | HPLC Method |
|---|---|---|---|---|---|
| 121 | 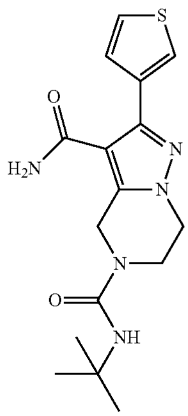 [SMILES: CC(C)(C)NC(=O)N1CCn2nc(-c3ccsc3)c(C(N)=O)c2C1] | N5-(tert-Butyl)-2-(thiophen-3-yl)-6,7-dihydropyrazolo[1,5-a]pyrazine-3,5(4H)-dicarboxamide | 348 | 0.972 | E |
| 122 | 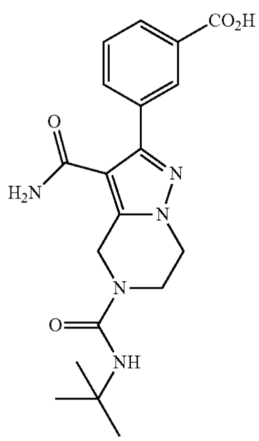 [SMILES: CC(C)(C)NC(=O)N1CCn2nc(-c3cccc(C(=O)O)c3)c(C(N)=O)c2C1] | 3-(5-(tert-Butylcarbamoyl)-3-carbamoyl-4,5,6,7-tetrahydropyrazolo[1,5-a]pyrazin-2-yl)benzoic acid | 386 | 0.614 | E |
| 123 | 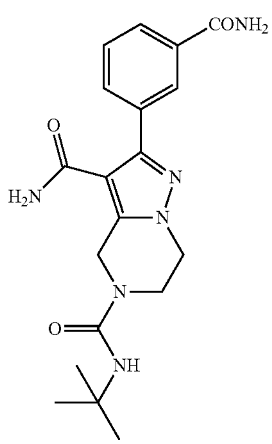 [SMILES: CC(C)(C)NC(=O)N1CCn2nc(-c3cccc(C(N)=O)c3)c(C(N)=O)c2C1] | N5-(tert-Butyl)-2-(3-carbamoylphenyl)-6,7-dihydropyrazolo[1,5-a]pyrazine-3,5(4H)-dicarboxamide | 385 | 0.776 | E |

TABLE 4-continued
| Ex. No. | Structure | Name | [M + H]+ | Ret Time (min.) | HPLC Method |
|---|---|---|---|---|---|
| 124 | 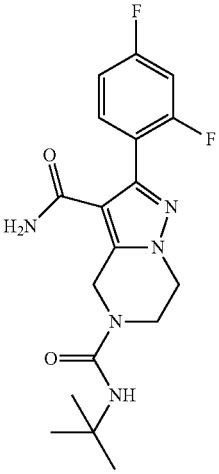 [SMILES: CC(C)(C)NC(=O)N1CCn2nc(-c3ccc(F)cc3F)c(C(N)=O)c2C1] | N5-(tert-Butyl)-2-(2,4-difluorophenyl)-6,7-dihydropyrazolo[1,5-a]pyrazine-3,5(4H)-dicarboxamide | 378 | 1.091 | E |
| 125 | 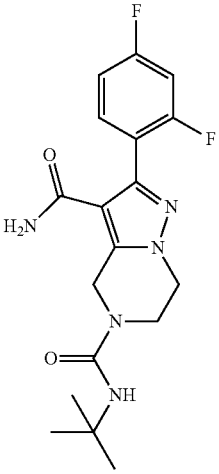 [SMILES: CC(C)(C)NC(=O)N1CCn2nc(-c3ccc(F)cc3F)c(C(N)=O)c2C1] | N5-(tert-Butyl)-2-(2,6-difluoropyridin-3-yl)-6,7-dihydropyrazolo[1,5-a]pyrazine-3,5(4H)-dicarboxamide | 379 | 0.986 | E |
| 126 | 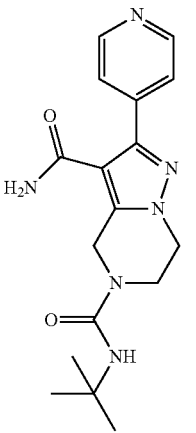 [SMILES: CC(C)(C)NC(=O)N1CCn2nc(-c3ccncc3)c(C(N)=O)c2C1] | N5-(tert-Butyl)-2-(pyridin-4-yl)-6,7-dihydropyrazolo[1,5-a]pyrazine-3,5(4H)-dicarboxamide | 343 | 7.548<br>7.983 | C<br>D |

TABLE 4-continued

| Ex. No. | Structure | Name | [M + H]+ | Ret Time (min.) | HPLC Method |
|---|---|---|---|---|---|
| 127 | 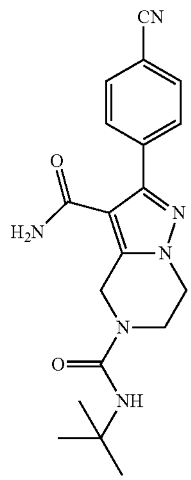 [SMILES: CC(C)(C)NC(=O)N1CCn2nc(-c3ccc(C#N)cc3)c(C(N)=O)c2C1] | N5-(tert-Butyl)-2-(4-cyanophenyl)-6,7-dihydropyrazolo[1,5-a]pyrazine-3,5(4H)-dicarboxamide | 376 | 13.058<br>12.571 | C<br>D |
| 128 | 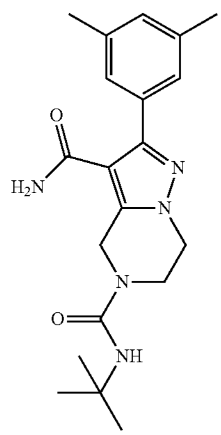 [SMILES: Cc1cc(C)cc(-c2nn3c(c2C(N)=O)CN(C(=O)NC(C)(C)C)CC3)c1] | N5-(tert-Butyl)-2-(3,5-dimethylphenyl)-6,7-dihydropyrazolo[1,5-a]pyrazine-3,5(4H)-dicarboxamide | 370 | 1.307 | E |
| 129 | 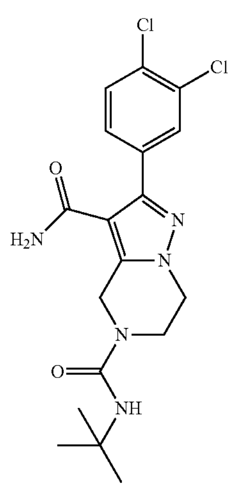 [SMILES: CC(C)(C)NC(=O)N1CCn2nc(-c3ccc(Cl)c(Cl)c3)c(C(N)=O)c2C1] | N5-(tert-Butyl)-2-(3,4-dichlorophenyl)-6,7-dihydropyrazolo[1,5-a]pyrazine-3,5(4H)-dicarboxamide | 410 | 1.423 | E |

TABLE 4-continued

| Ex. No. | Structure | Name | [M + H]+ | Ret Time (min.) | HPLC Method |
|---|---|---|---|---|---|
| 130 | 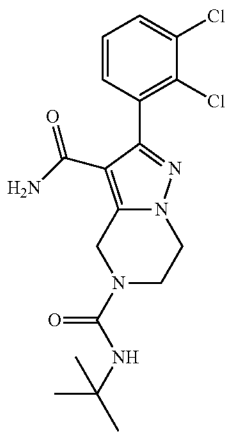 [SMILES: CC(C)(C)NC(=O)N1CCn2nc(-c3cccc(Cl)c3Cl)c(C(N)=O)c2C1] | $N^5$-(tert-Butyl)-2-(2,3-dichlorophenyl)-6,7-dihydropyrazolo[1,5-a]pyrazine-3,5(4H)-dicarboxamide | 410 | 1.266 | E |
| 131 | 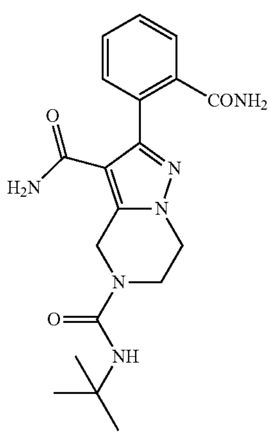 [SMILES: CC(C)(C)NC(=O)N1CCn2nc(-c3ccccc3C(N)=O)c(C(N)=O)c2C1] | $N^5$-(tert-Butyl)-2-(2-carbamoylphenyl)-6,7-dihydropyrazolo[1,5-a]pyrazine-3,5(4H)-dicarboxamide | 385 | 0.733 | E |
| 132 | 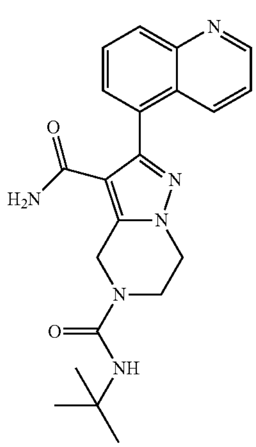 [SMILES: CC(C)(C)NC(=O)N1CCn2nc(-c3cccc4ncccc34)c(C(N)=O)c2C1] | $N^5$-(tert-Butyl)-2-(quinolin-5-yl)-6,7-dihydropyrazolo[1,5-a]pyrazine-3,5(4H)-dicarboxamide | 393 | 0.918 | E |

TABLE 4-continued

| Ex. No. | Structure | Name | [M + H]+ | Ret Time (min.) | HPLC Method |
|---|---|---|---|---|---|
| 133 | 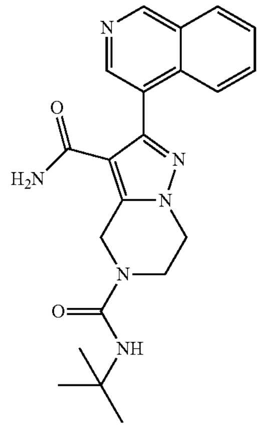 [SMILES: CC(C)(C)NC(=O)N1CCn2nc(-c3cncc4ccccc34)c(C(N)=O)c2C1] | $N^5$-(tert-Butyl)-2-(isoquinolin-4-yl)-6,7-dihydropyrazolo[1,5-a]pyrazine-3,5(4H)-dicarboxamide | 393 | 0.979 | E |
| 134 | 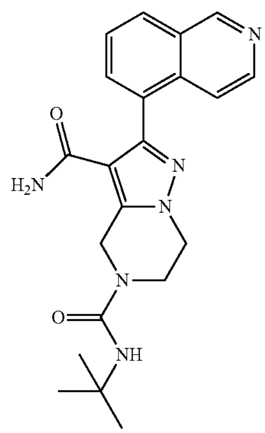 [SMILES: CC(C)(C)NC(=O)N1CCn2nc(-c3cccc4cnccc34)c(C(N)=O)c2C1] | $N^5$-(tert-Butyl)-2-(isoquinolin-5-yl)-6,7-dihydropyrazolo[1,5-a]pyrazine-3,5(4H)-dicarboxamide | 393 | 0.916 | E |
| 135 | 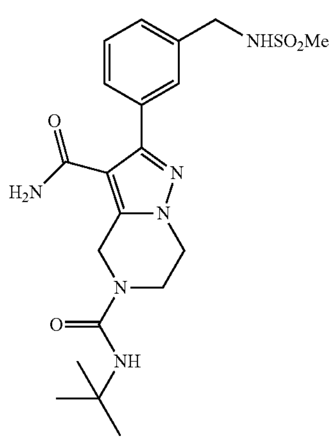 | $N^5$-(tert-Butyl)-2-(3-(methylsulfonamidomethyl)phenyl)-6,7-dihydropyrazolo[1,5-a]pyrazine-3,5(4H)-dicarboxamide | 449 | 0.922 | E |

TABLE 4-continued

| Ex. No. | Structure | Name | [M + H]⁺ | Ret Time (min.) | HPLC Method |
|---|---|---|---|---|---|
| 136 | 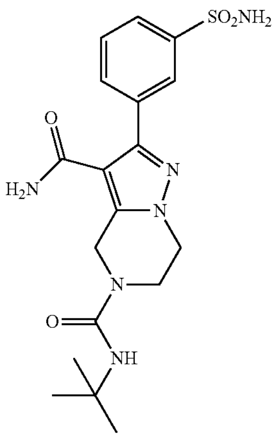 [SMILES: CC(C)(C)NC(=O)N1CCn2nc(-c3cccc(S(N)(=O)=O)c3)c(C(N)=O)c2C1] | $N^5$-(tert-Butyl)-2-(3-sulfamoylphenyl)-6,7-dihydropyrazolo[1,5-a]pyrazine-3,5(4H)-dicarboxamide | 421 | 0.822 | E |
| 137 | 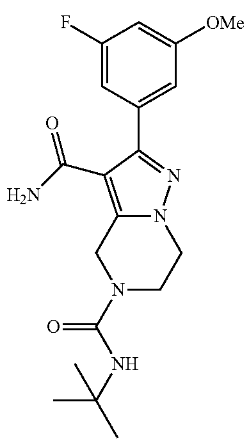 [SMILES: COc1cc(F)cc(-c2nn3c(c2C(N)=O)CN(C(=O)NC(C)(C)C)CC3)c1] | $N^5$-(tert-Butyl)-2-(3-fluoro-5-methoxyphenyl)-6,7-dihydropyrazolo[1,5-a]pyrazine-3,5(4H)-dicarboxamide | 390 | 1.18 | E |
| 138 | 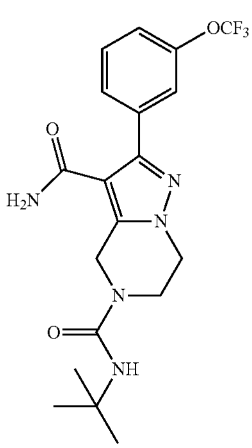 [SMILES: CC(C)(C)NC(=O)N1CCn2nc(-c3cccc(OC(F)(F)F)c3)c(C(N)=O)c2C1] | $N^5$-(tert-Butyl)-2-(3-(trifluoromethoxy)phenyl)-6,7-dihydropyrazolo[1,5-a]pyrazine-3,5(4H)-dicarboxamide | 426 | 1.416 | E |

TABLE 4-continued

| Ex. No. | Structure | Name | [M + H]+ | Ret Time (min.) | HPLC Method |
|---|---|---|---|---|---|
| 139 | 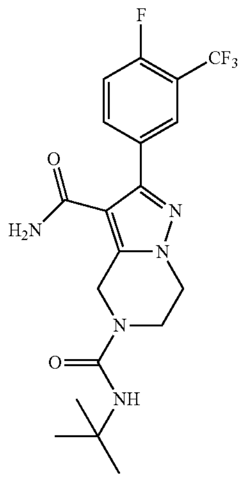 [SMILES: CC(C)(C)NC(=O)N1CCn2nc(-c3ccc(F)c(C(F)(F)F)c3)c(C(N)=O)c2C1] | $N^5$-(tert-Butyl)-2-(4-fluoro-3-(trifluoromethyl)phenyl)-6,7-dihydropyrazolo[1,5-a]pyrazine-3,5(4H)-dicarboxamide | 428 | 1.424 | E |
| 140 | 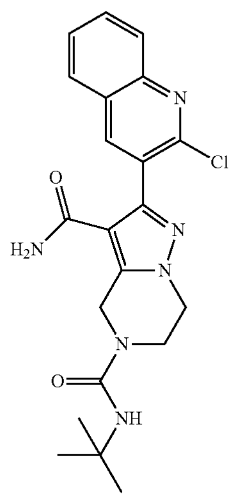 [SMILES: CC(C)(C)NC(=O)N1CCn2nc(-c3cc4ccccc4nc3Cl)c(C(N)=O)c2C1] | $N^5$-(tert-Butyl)-2-(2-chloroquinolin-3-yl)-6,7-dihydropyrazolo[1,5-a]pyrazine-3,5(4H)-dicarboxamide | 427 | 1.150 | E |
| 141 | 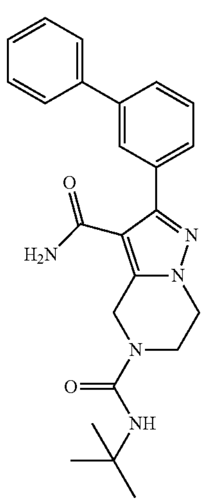 [SMILES: CC(C)(C)NC(=O)N1CCn2nc(-c3cccc(-c4ccccc4)c3)c(C(N)=O)c2C1] | 2-([1,1'-Biphenyl]-3-yl)-$N^5$-(tert-butyl)-6,7-dihydropyrazolo[1,5-a]pyrazine-3,5(4H)-dicarboxamide | 418 | 9.383 8.932 | A B |

TABLE 4-continued

| Ex. No. | Structure | Name | [M + H]+ | Ret Time (min.) | HPLC Method |
|---|---|---|---|---|---|
| 142 | 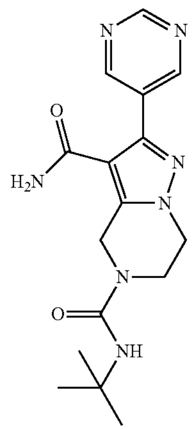 [SMILES: CC(C)(C)NC(=O)N1CCn2nc(-c3cncnc3)c(C(N)=O)c2C1] | N5-(tert-Butyl)-2-(pyrimidin-5-yl)-6,7-dihydropyrazolo[1,5-a]pyrazine-3,5(4H)-dicarboxamide | 344 | 9.416<br>8.804 | C<br>D |
| 143 | 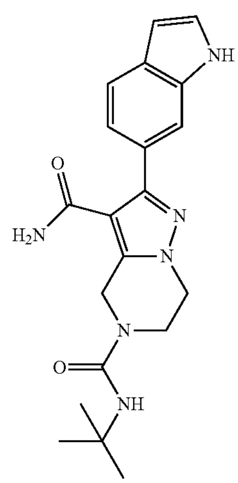 [SMILES: CC(C)(C)NC(=O)N1CCn2nc(-c3ccc4cc[nH]c4c3)c(C(N)=O)c2C1] | N5-(tert-Butyl)-2-(1H-indol-6-yl)-6,7-dihydropyrazolo[1,5-a]pyrazine-3,5(4H)-dicarboxamide | 381 | 7.368<br>7.150 | A<br>B |
| 144 | 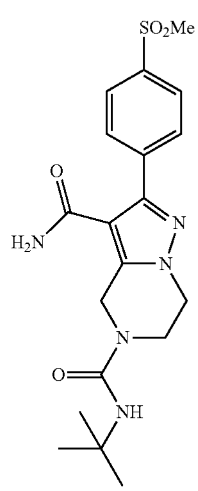 [SMILES: CC(C)(C)NC(=O)N1CCn2nc(-c3ccc(S(C)(=O)=O)cc3)c(C(N)=O)c2C1] | N5-(tert-Butyl)-2-(4-(methylsulfonyl)phenyl)-6,7-dihydropyrazolo[1,5-a]pyrazine-3,5(4H)-dicarboxamide | 420 | 6.356<br>6.183 | A<br>B |

TABLE 4-continued

| Ex. No. | Structure | Name | [M + H]$^+$ | Ret Time (min.) | HPLC Method |
|---|---|---|---|---|---|
| 145 | 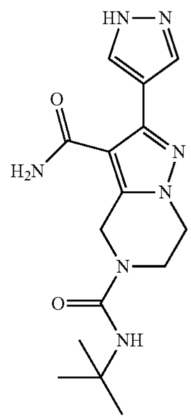 [SMILES: CC(C)(C)NC(=O)N1CCn2nc(-c3cn[nH]c3)c(C(N)=O)c2C1] | N$^5$-(tert-Butyl)-2-(1H-pyrazol-4-yl)-6,7-dihydropyrazolo[1,5-a]pyrazine-3,5(4H)-dicarboxamide | 332 | 9.380<br>8.760 | C<br>D |
| 146 | 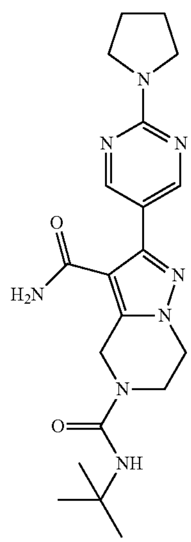 [SMILES: CC(C)(C)NC(=O)N1CCn2nc(-c3cnc(N4CCCC4)nc3)c(C(N)=O)c2C1] | N$^5$-(tert-Butyl)-2-(2-(pyrrolidin-1-yl)pyrimidin-5-yl)-6,7-dihydropyrazolo[1,5-a]pyrazine-3,5(4H)-dicarboxamide | 413 | 10.486<br>10.870 | C<br>D |
| 147 | 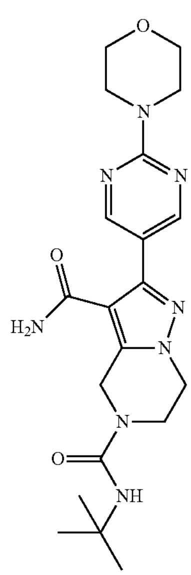 [SMILES: CC(C)(C)NC(=O)N1CCn2nc(-c3cnc(N4CCOCC4)nc3)c(C(N)=O)c2C1] | N$^5$-(tert-Butyl)-2-(2-morpholinopyrimidin-5-yl)-6,7-dihydropyrazolo[1,5-a]pyrazine-3,5(4H)-dicarboxamide | 429 | 11.715<br>11.137 | C<br>D |

TABLE 4-continued

| Ex. No. | Structure | Name | [M + H]+ | Ret Time (min.) | HPLC Method |
|---|---|---|---|---|---|
| 148 | 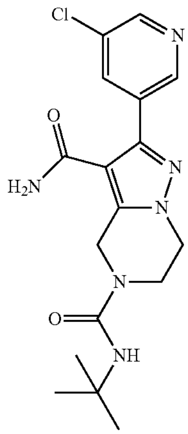 [SMILES: CC(C)(C)NC(=O)N1CCn2nc(-c3cncc(Cl)c3)c(C(N)=O)c2C1] | N5-(tert-Butyl)-2-(5-chloropyridin-3-yl)-6,7-dihydropyrazolo[1,5-a]pyrazine-3,5(4H)-dicarboxamide | 377 | 11.980<br>11.969 | C<br>D |
| 149 | 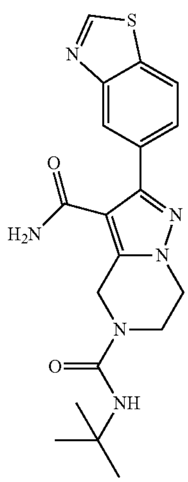 [SMILES: CC(C)(C)NC(=O)N1CCn2nc(-c3ccc4scnc4c3)c(C(N)=O)c2C1] | 2-(Benzo[d]thiazol-5-yl)-N5-(tert-Butyl)-6,7-dihydropyrazolo[1,5-a]pyrazine-3,5(4H)-dicarboxamide | 399 | 6.621<br>6.505 | A<br>B |
| 150 | 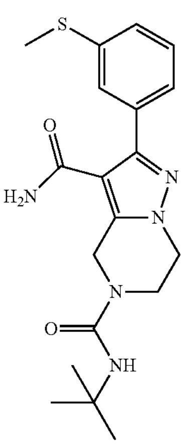 | N5-(tert-Butyl)-2-(3-(methylthio)phenyl)-6,7-dihydropyrazolo[1,5-a]pyrazine-3,5(4H)-dicarboxamide | 388 | 8.062<br>7.836 | A<br>B |

TABLE 4-continued

| Ex. No. | Structure | Name | [M + H]+ | Ret Time (min.) | HPLC Method |
|---|---|---|---|---|---|
| 151 | 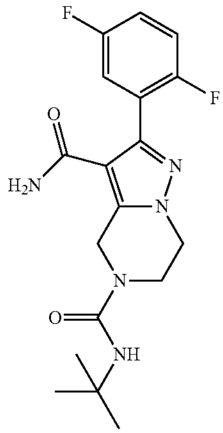 [SMILES: CC(C)(C)NC(=O)N1CCn2nc(-c3cc(F)ccc3F)c(C(N)=O)c2C1] | N5-(tert-Butyl)-2-(2,5-difluorophenyl)-6,7-dihydropyrazolo[1,5-a]pyrazine-3,5(4H)-dicarboxamide | 376 | 7.431<br>7.184 | A<br>B |
| 152 | 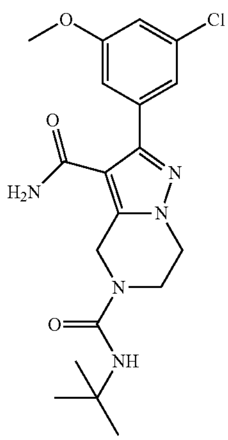 [SMILES: COc1cc(Cl)cc(-c2nn3c(c2C(N)=O)CN(C(=O)NC(C)(C)C)CC3)c1] | N5-(tert-Butyl)-2-(3-chloro-5-methoxyphenyl)-6,7-dihydropyrazolo[1,5-a]pyrazine-3,5(4H)-dicarboxamide | 406 | 8.476<br>8.041 | A<br>B |
| 153 | 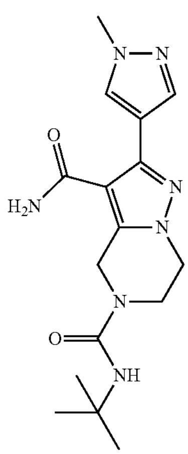 [SMILES: Cn1cc(-c2nn3c(c2C(N)=O)CN(C(=O)NC(C)(C)C)CC3)cn1] | N5-(tert-Butyl)-2-(1-methyl-1H-pyrazol-4-yl)-6,7-dihydropyrazolo[1,5-a]pyrazine-3,5(4H)-dicarboxamide | 346 | 9.716<br>9.562 | C<br>D |

TABLE 4-continued

| Ex. No. | Structure | Name | [M + H]+ | Ret Time (min.) | HPLC Method |
|---|---|---|---|---|---|
| 154 | 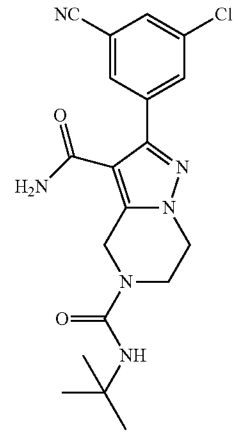 [SMILES: CC(C)(C)NC(=O)N1CCn2nc(-c3cc(Cl)cc(C#N)c3)c(C(N)=O)c2C1] | N5-(tert-Butyl)-2-(3-chloro-5-cyanophenyl)-6,7-dihydropyrazolo[1,5-a]pyrazine-3,5(4H)-dicarboxamide | 401 | 8.297<br>7.933 | A<br>B |
| 155 | 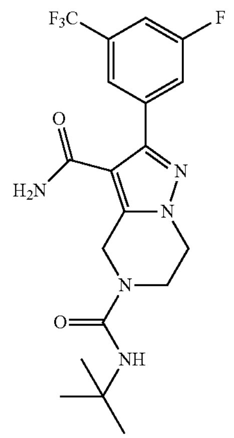 [SMILES: CC(C)(C)NC(=O)N1CCn2nc(-c3cc(F)cc(C(F)(F)F)c3)c(C(N)=O)c2C1] | N5-(tert-Butyl)-2-(3-fluoro-5-(trifluoromethyl)phenyl)-6,7-dihydropyrazolo[1,5-a]pyrazine-3,5(4H)-dicarboxamide | 428 | 9.239<br>8.335 | A<br>B |

Scheme 5

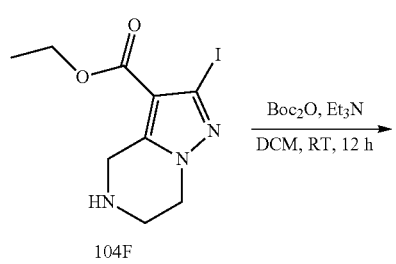

104F

Boc2O, Et3N
————————→
DCM, RT, 12 h

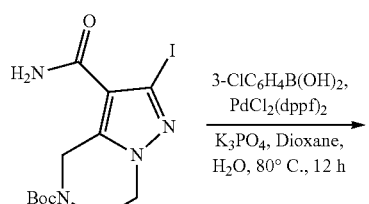

156A

NaOH, MeOH
————————→
H2O, RT, 6 h

156B

NH4Cl, HATU, DIPEA
————————→
DMF, RT, 15 h

-continued

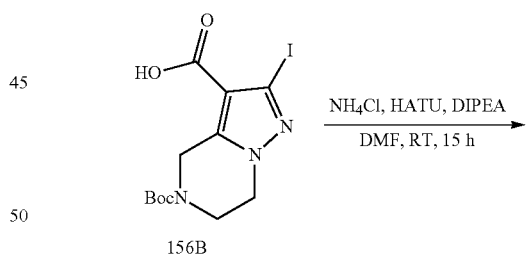

156C

3-ClC6H4B(OH)2,
PdCl2(dppf)2
————————→
K3PO4, Dioxane,
H2O, 80° C., 12 h

-continued

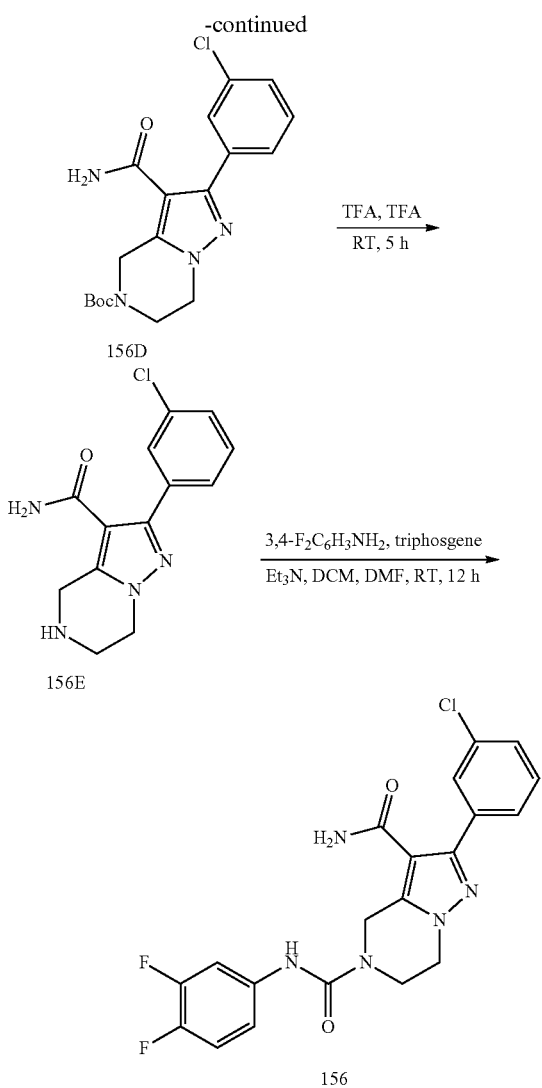

Intermediate 156A: 5-tert-Butyl 3-ethyl2-iodo-6,7-dihydropyrazolo[1,5-a]pyrazine-3,5(4H)-dicarboxylate

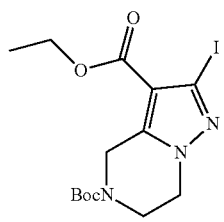 [SMILES: CCOC(=O)c1c(I)nn2c1CN(C(=O)OC(C)(C)C)CC2]

To a stirred solution of 104F (0.7 g, 2.180 mmol) in dichloromethane (10 mL) was added triethylamine (0.912 mL, 6.54 mmol) and Boc$_2$O (0.952 g, 4.36 mmol). The resulting reaction mixture was stirred at RT overnight and the reaction progress was monitored by LCMS. The reaction mixture was diluted with dichloromethane (20 mL), washed with water, brine, dried over Na$_2$SO$_4$, filtered and concentrated. The crude product obtained was purified by ISCO (24 g silica gel column) using petroleum ether and ethyl acetate (9:1) mixture as eluent. Fractions were collected and concentrated to afford Intermediate 156A (800 mg, 87%). MS(ES): m/z=422 [M+H]$^+$; $^1$H NMR (400 MHz, CDCl$_3$) δ ppm 4.86 (s, 2H), 4.32 (q, J=6.8 Hz, 2H), 4.20 (m, 2H), 3.87 (t, J=5.6 Hz, 2H), 1.50 (s, 9H), 1.38 (t, J=7.2 Hz, 3H).

Intermediate 156B: 5-(tert-Butoxycarbonyl)-2-iodo-4,5,6,7-tetrahydropyrazolo[1,5-a]pyrazine-3-carboxylic acid

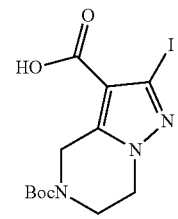 [SMILES: CC(C)(C)OC(=O)N1CCn2nc(I)c(C(=O)O)c2C1]

To a stirred solution of 156A (0.80 g, 1.899 mmol) in methanol (7 mL) was added sodium hydroxide (0.760 g, 1.899 mmol) in water (3 mL). The resulting reaction mixture was stirred at RT for 6 h. Methanol was removed under reduced pressure and the aqueous layer was acidified with 1.5 N HCl solution. The aqueous layer was back extracted with dichloromethane (3×25 mL). The combined organic layer was dried over Na$_2$SO$_4$, filtered and concentrated to give the desired Intermediate 156B (700 mg, 94%). MS(ES): m/z=394 [M+H]$^+$; $^1$H NMR (400 MHz, CDCl$_3$) δ ppm 4.89 (s, 2H), 4.22 (t, J=5.2 Hz, 2H), 3.88 (t, J=5.6 Hz, 2H), 1.51 (s, 9H).

Intermediate 156C: tert-Butyl 3-carbamoyl-2-iodo-6,7-dihydropyrazolo[1,5-a]pyrazine-5(4H)-carboxylate

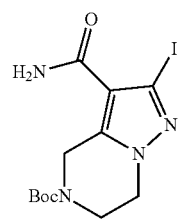

To a stirred solution of 156B (0.700 g, 1.780 mmol) and ammonium chloride (0.190 g, 3.56 mmol) in DMF (7 mL) were added HATU (1.354 g, 3.56 mmol) and DIPEA (0.933 mL, 5.34 mmol). The resulting reaction mixture was stirred at RT overnight. The reaction mixture was diluted with water (20 mL) and the aqueous layer was back extracted with ethyl acetate (2×30 mL). The combined organic layer was washed with brine, dried over Na$_2$SO$_4$, filtered and concentrated. The crude product was purified by ISCO (24 g silica gel column) using 2% methanol in chloroform as eluent to afford pure Intermediate 156C (670 mg, 96%). MS(ES): m/z=[M+H]$^+$; $^1$H NMR (400 MHz, DMSO-d$_6$) δ ppm 7.38 (bs, 1H), 6.86 (bs, 1H), 4.72 (s, 2H), 4.12 (t, J=5.2 Hz, 2H), 3.77 (t, J=5.7 Hz, 2H), 1.43 (s, 9H).

Intermediate 156D: tert-Butyl 3-carbamoyl-2-(3-chlorophenyl)-6,7-dihydropyrazolo[1,5-a]pyrazine-5(4H)-carboxylate

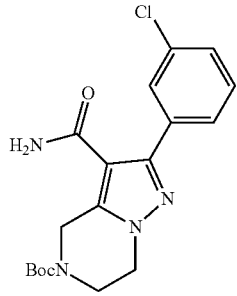 [SMILES: CC(C)(C)OC(=O)N1CCn2nc(-c3cccc(Cl)c3)c(C(N)=O)c2C1]

To a stirred solution of Intermediate 156C (500 mg, 1.275 mmol) and (3-chlorophenyl)boronic acid (399 mg, 2.55 mmol) in 1,4-dioxane (5 mL) and water (1 mL) was added and potassium phosphate tribasic (666 mg, 3.82 mmol). The reaction mixture was purged with nitrogen for 5 min. PdCl$_2$(dppf)-CH$_2$Cl$_2$ (52.1 mg, 0.064 mmol) was added and the reaction mixture was stirred at 80° C. for 12 h. The reaction mixture was diluted with water (20 mL) and extracted with ethyl acetate (3×25 mL). The combined organic layer was washed with brine, dried over Na$_2$SO$_4$ and concentrated. The crude was purified by ISCO (24 g silica column) using 2% methanol in chloroform. Fractions were collected and concentrated to afford Intermediate 156D (380 mg, 79%). MS(ES): m/z=377 [M+H]$^+$; $^1$H NMR (300 MHz, CDCl$_3$) δ ppm 7.60 (s, 1H), 7.46 (m, 3H), 5.32 (bs, 2H), 4.97 (s, 2H), 4.21 (t, J=5.1 Hz, 2H), 3.94 (t, J=5.7 Hz, 2H), 1.29 (s, 9H).

Intermediate 156E: 2-(3-Chlorophenyl)-4,5,6,7-tetrahydropyrazolo[1,5-a]pyrazine-3-carboxamide

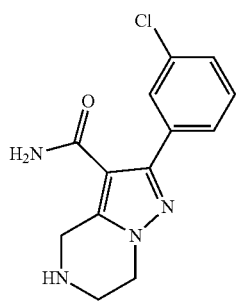 [SMILES: NC(=O)c1c(-c2cccc(Cl)c2)nn2c1CNCC2]

To a stirred solution of 156D (350 mg, 0.929 mmol) in DCM (10 mL) was added dropwise TFA (2 mL) at 0° C. and the reaction mixture was stirred at RT overnight. TFA and DCM were removed under reduced pressure, the crude was basified with saturated sodium hydroxide solution, the resultant solid was filtered, washed with water, dried under vacuum to afford 156E (250 mg, 97%). MS(ES): m/z=277 [M+H]$^+$; $^1$H NMR (400 MHz, DMSO-d$_6$) δ ppm 7.71-7.73 (m, 1H), 7.65 (dt, J=7.04, 1.72 Hz, 1H), 7.37-7.45 (m, 2H), 7.20 (bs, 1H), 7.10 (bs, 1H), 4.00-4.05 (m, 4H), 3.12 (d, J=4.83 Hz, 2H), 2.63 (s, 1H).

Compound 156: 2-(3-Chlorophenyl)-N$^5$-(3,4-difluorophenyl)-6,7-dihydropyrazolo[1,5-a]pyrazine-3,5(4H)-dicarboxamide

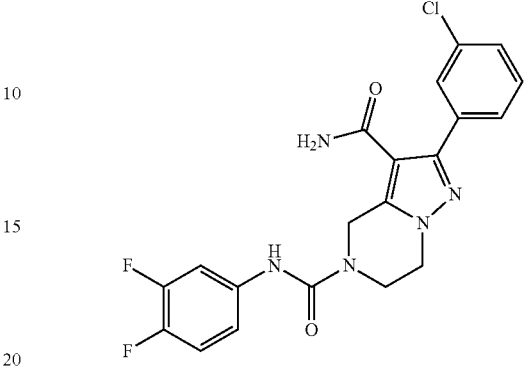

To a stirred solution of 3,4-difluoroaniline (23.33 mg, 0.181 mmol) in DCM (2 mL) under nitrogen was added triethylamine (0.025 mL, 0.181 mmol) and the reaction mixture was cooled to 0° C. and triphosgene (26.8 mg, 0.090 mmol) in DCM (1 mL) was added stirred at the same temperature for 10 min. A solution of 156E (25 mg, 0.090 mmol) in DMF (1 mL) was added dropwise and the resulting reaction mixture was stirred at RT overnight. It was diluted with water and the aqueous layer was back extracted with ethyl acetate (3×10 mL). The combined organic layer was washed with brine, dried over Na$_2$SO$_4$ and concentrated. The crude product obtained was purified by reverse phase preparative HPLC to afford pure product 156 as an off-white solid (10 mg, 25%). MS(ES): m/z=432 [M+H]$^+$; HPLC Ret. Time 9.92 min. and 8.82 min. (HPLC Methods A and B); $^1$H NMR (400 MHz, CD$_3$OD) δ ppm 7.68-7.71 (m, 1H), 7.60 (ddd, J=5.32, 3.47, 1.63 Hz, 1H), 7.48-7.53 (m, 1H), 7.44-7.48 (m, 2H), 7.16-7.20 (m, 2H), 5.01 (s, 2H), 4.31 (t, J=5.40 Hz, 2H), 4.08 (t, J=5.40 Hz, 2H).

General Methods for the Syntheses of Ureas:

Method A:

To a solution of Intermediate 156E (30 mg, 0.115 mmol) in DMF (1 mL) was added the corresponding isocyanate (0.288 mmol) at 0° C. The reaction mixture was stirred at room temperature for 3 h. The reaction mixture was quenched with water and extracted with ethyl acetate (3×5 mL). The combined organic layer was washed with water (2×5 mL), brine solution, dried over Na$_2$SO$_4$, filtered and concentrated to afford the crude product which was purified by preparative HPLC.

Method B:

To a solution of primary amine (0.192 mmol) and triethylamine (0.480 mmol) in tetrahydrofuran (3 mL) at 0° C. was added triphosgene (0.096 mmol) and the reaction mixture stirred for 30 min at the same temperature. Intermediate 156E (25 mg, 0.096 mmol) in DMF was added and the solution was stirred at RT for 2 h. The reaction mixture was quenched with water and extracted with ethyl acetate (3×5 mL). The combined organic layer was washed with 10% NaHCO$_3$ (2×5 mL), water, dried over Na$_2$SO$_4$ and concentrated to afford the crude product, which was further purified by preparative HPLC.

Method C:

To a solution of primary amine (0.192 mmol) and triethylamine (0.480 mmol) in tetrahydrofuran (3 mL) at 0° C. were added phenyl chloroformate (0.096 mmol) and the reaction mixture stirred for 60 min at RT. The reaction mixture was quenched with water and the phenyl carbamate formed was extracted and the Intermediate 156E (25 mg, 0.096 mmol) in THF was added to the extract and the resulting solution was stirred at room temperature for 2 h. The reaction mixture was quenched with water and extracted with ethyl acetate (3×5 mL). The combined organic layer was washed with 10% NaHCO$_3$ (2×5 mL), water, dried over Na$_2$SO$_4$ and concentrated to afford the crude product which was further purified by preparative HPLC.

The Compounds described in Table 5 were synthesized analogous to Compound 156 by reacting Compound 156E with corresponding reagents.

TABLE 5

| Ex. No. | Structure | Name | Synthetic Method | [M + H]$^+$ | Ret Time (min.) | HPLC Method |
|---|---|---|---|---|---|---|
| 157 | 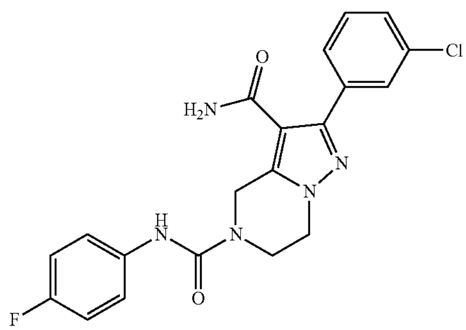 [SMILES: NC(=O)c1c(-c2cccc(Cl)c2)nn2c1CN(C(=O)Nc1ccc(F)cc1)CC2] | 2-(3-Chlorophenyl)-N$^5$-(4-fluorophenyl)-6,7-dihydropyrazolo[1,5-a]pyrazine-3,5(4H)-dicarboxamide | B | 414 | 8.789 8.522 | A B |
| 158 | 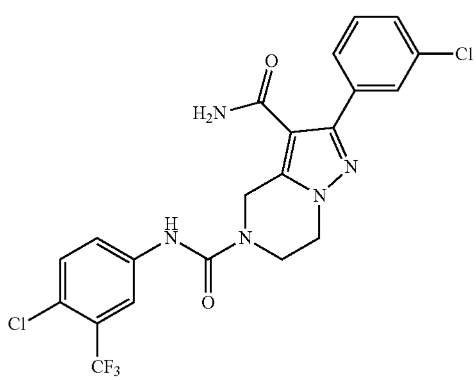 [SMILES: NC(=O)c1c(-c2cccc(Cl)c2)nn2c1CN(C(=O)Nc1ccc(Cl)c(C(F)(F)F)c1)CC2] | N$^5$-(4-Chloro-3-(trifluoromethyl)phenyl)-2-(3-chlorophenyl)-6,7-dihydropyrazolo[1,5-a]pyrazine-3,5(4H)-dicarboxamide | B | 498 | 10.821 10.044 | A B |
| 159 | 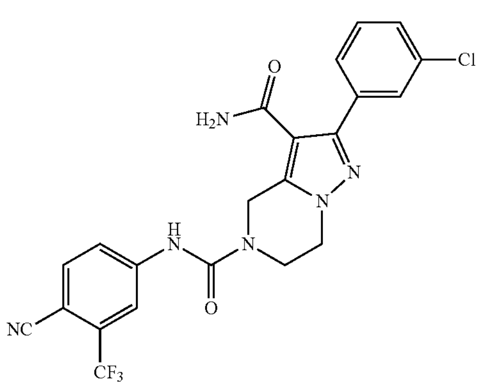 [SMILES: N#Cc1ccc(NC(=O)N2CCn3nc(-c4cccc(Cl)c4)c(C(N)=O)c3C2)cc1C(F)(F)F] | 2-(3-Chlorophenyl)-N$^5$-(4-cyano-3-(trifluoromethyl)phenyl)-6,7-dihydropyrazolo[1,5-a]pyrazine-3,5(4H)-dicarboxamide | B | 487 | 10.126 9.668 | A B |

TABLE 5-continued

| Ex. No. | Structure | Name | Synthetic Method | [M + H]+ | Ret Time (min.) | HPLC Method |
|---|---|---|---|---|---|---|
| 160 | 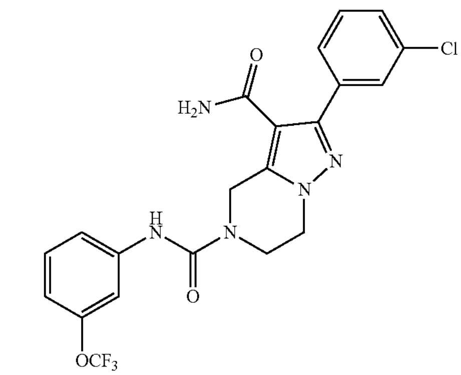 [SMILES: NC(=O)c1c(-c2cccc(Cl)c2)nn2c1CN(C(=O)Nc1cccc(OC(F)(F)F)c1)CC2] | 2-(3-Chlorophenyl)-N5-(3-(trifluoromethoxy)phenyl)-6,7-dihydropyrazolo[1,5-a]pyrazine-3,5(4H)-dicarboxamide | B | 480 | 10.292 9.665 | A B |
| 161 | 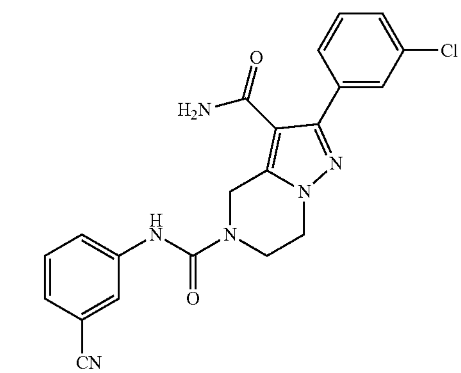 [SMILES: N#Cc1cccc(NC(=O)N2CCn3nc(-c4cccc(Cl)c4)c(C(N)=O)c3C2)c1] | 2-(3-Chlorophenyl)-N5-(3-cyanophenyl)-6,7-dihydropyrazolo[1,5-a]pyrazine-3,5(4H)-dicarboxamide | B | 421 | 8.541 8.323 | A B |
| 162 | 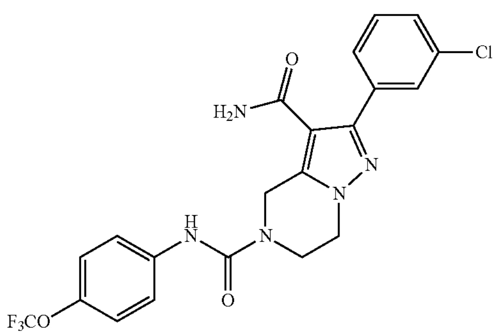 [SMILES: NC(=O)c1c(-c2cccc(Cl)c2)nn2c1CN(C(=O)Nc1ccc(OC(F)(F)F)cc1)CC2] | 2-(3-Chlorophenyl)-N5-(4-(trifluoromethoxy)phenyl)-6,7-dihydropyrazolo[1,5-a]pyrazine-3,5(4H)-dicarboxamide | B | 480 | 10.148 9.559 | A B |
| 163 | 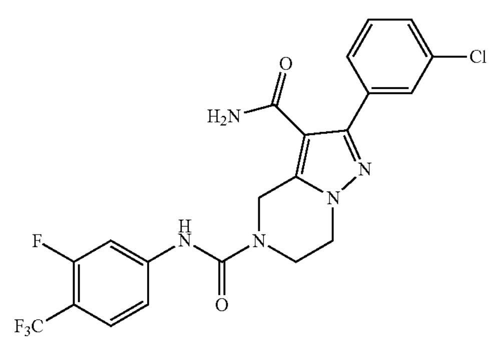 [SMILES: NC(=O)c1c(-c2cccc(Cl)c2)nn2c1CN(C(=O)Nc1ccc(C(F)(F)F)c(F)c1)CC2] | 2-(3-Chlorophenyl)-N5-(3-fluoro-4-(trifluoromethyl)phenyl)-6,7-dihydropyrazolo[1,5-a]pyrazine-3,5(4H)-dicarboxamide | B | 482 | 10.510 9.833 | A B |

TABLE 5-continued

| Ex. No. | Structure | Name | Synthetic Method | [M + H]+ | Ret Time (min.) | HPLC Method |
|---|---|---|---|---|---|---|
| 164 | 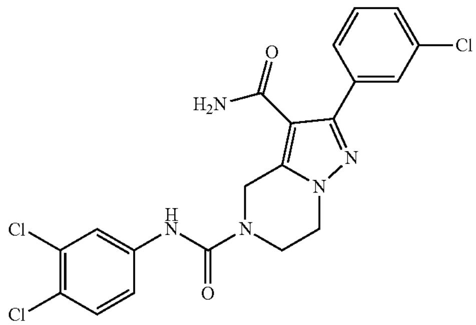 [SMILES: NC(=O)c1c(-c2cccc(Cl)c2)nn2c1CN(C(=O)Nc1ccc(Cl)c(Cl)c1)CC2] | 2-(3-Chlorophenyl)-N5-(3,4-dichlorophenyl)-6,7-dihydropyrazolo[1,5-a]pyrazine-3,5(4H)-dicarboxamide | A | 464 | 10.453 9.768 | A B |
| 165 | 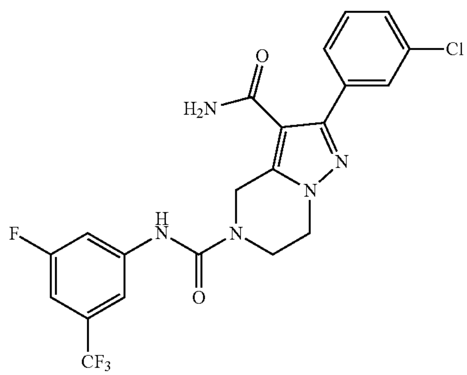 [SMILES: NC(=O)c1c(-c2cccc(Cl)c2)nn2c1CN(C(=O)Nc1cc(F)cc(C(F)(F)F)c1)CC2] | 2-(3-Chlorophenyl)-N5-(3-fluoro-5-(trifluoromethyl)phenyl)-6,7-dihydropyrazolo[1,5-a]pyrazine-3,5(4H)-dicarboxamide | A | 482 | 10.696 9.888 | A B |
| 166 | 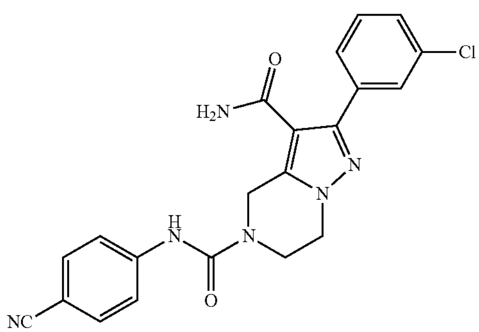 [SMILES: N#Cc1ccc(NC(=O)N2CCn3nc(-c4cccc(Cl)c4)c(C(N)=O)c3C2)cc1] | 2-(3-Chlorophenyl)-N5-(4-cyanophenyl)-6,7-dihydropyrazolo[1,5-a]pyrazine-3,5(4H)-dicarboxamide | A | 421 | 8.576 8.300 | A B |
| 167 | 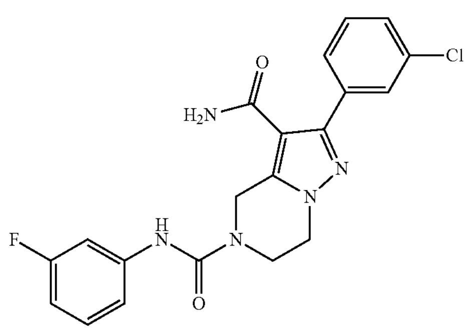 [SMILES: NC(=O)c1c(-c2cccc(Cl)c2)nn2c1CN(C(=O)Nc1cccc(F)c1)CC2] | 2-(3-Chlorophenyl)-N5-(3-fluorophenyl)-6,7-dihydropyrazolo[1,5-a]pyrazine-3,5(4H)-dicarboxamide | B | 414 | 8.971 8.618 | A B |

TABLE 5-continued

| Ex. No. | Structure | Name | Synthetic Method | [M + H]+ | Ret Time (min.) | HPLC Method |
|---|---|---|---|---|---|---|
| 168 | 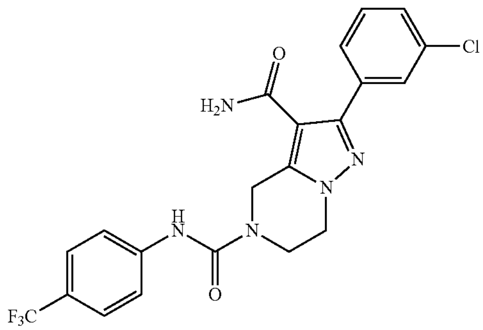 [SMILES: NC(=O)c1c(-c2cccc(Cl)c2)nn2c1CN(C(=O)Nc1ccc(C(F)(F)F)cc1)CC2] | 2-(3-Chlorophenyl)-N$^5$-(4-(trifluoromethyl)phenyl)-6,7-dihydropyrazolo[1,5-a]pyrazine-3,5(4H)-dicarboxamide | B | 464 | 10.253<br>9.605 | A<br>B |
| 169 | 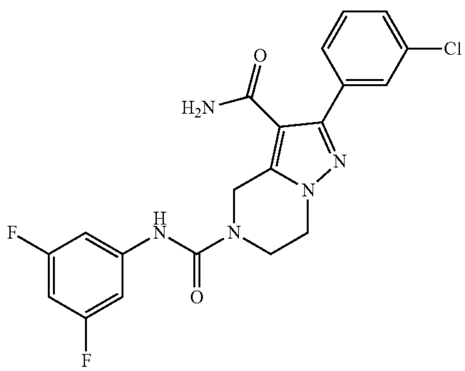 [SMILES: NC(=O)c1c(-c2cccc(Cl)c2)nn2c1CN(C(=O)Nc1cc(F)cc(F)c1)CC2] | 2-(3-Chlorophenyl)-N$^5$-(3,5-difluorophenyl)-6,7-dihydropyrazolo[1,5-a]pyrazine-3,5(4H)-dicarboxamide | B | 432 | 9.478<br>9.190 | A<br>B |
| 170 | 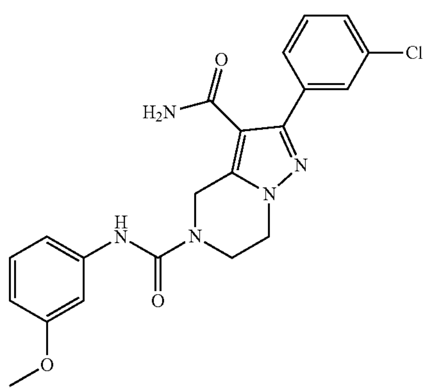 [SMILES: COc1cccc(NC(=O)N2CCn3nc(-c4cccc(Cl)c4)c(C(N)=O)c3C2)c1] | 2-(3-Chlorophenyl)-N$^5$-(3-methoxyphenyl)-6,7-dihydropyrazolo[1,5-a]pyrazine-3,5(4H)-dicarboxamide | B | 426 | 8.657<br>8.368 | A<br>B |
| 171 | 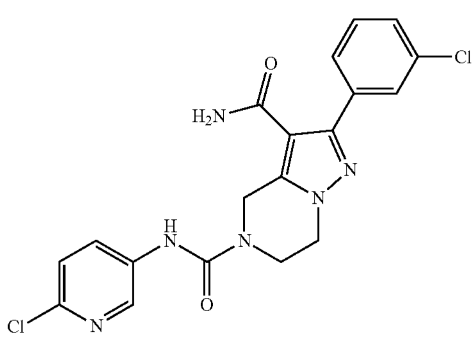 [SMILES: NC(=O)c1c(-c2cccc(Cl)c2)nn2c1CN(C(=O)Nc1ccc(Cl)nc1)CC2] | 2-(3-Chlorophenyl)-N$^5$-(6-chloropyridin-3-yl)-6,7-dihydropyrazolo[1,5-a]pyrazine-3,5(4H)-dicarboxamide | C | 431 | 8.037<br>7.886 | A<br>B |

Scheme 6

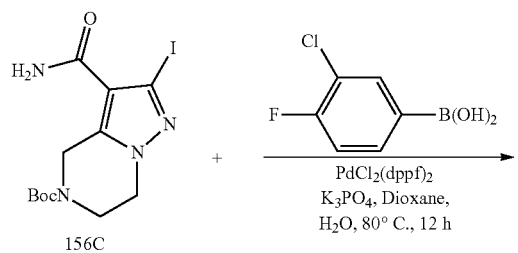

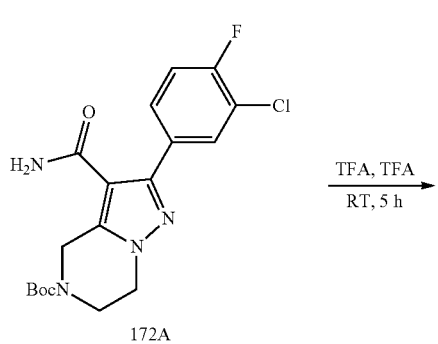

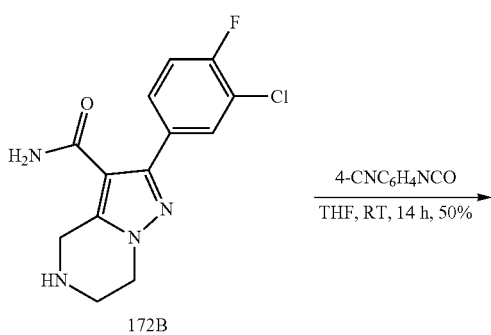

Intermediate 172A: tert-Butyl 3-carbamoyl-2-(3-chloro-4-fluorophenyl)-6,7-dihydropyrazolo[1,5-a]pyrazine-5(4H)-carboxylate

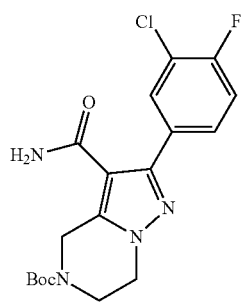 [SMILES: CC(C)(C)OC(=O)N1CCn2nc(-c3ccc(F)c(Cl)c3)c(C(N)=O)c2C1]

To a stirred solution of Intermediate 156C (5 g, 12.7 mmol), (3-chloro-4-fluorophenyl)boronic acid (3.33 g, 19.12 mmol) in 1,4-dioxane (75 mL) and water (7.5 mL) was added and $K_3PO_4$ (8.12 g, 38.2 mmol) and the reaction mixture was purged with nitrogen for 5 min. $PdCl_2(dppf)$-$CH_2Cl_2$ (0.521 g, 0.637 mmol) was added and the reaction mixture was stirred at 80° C. for 12 h. The reaction mixture was diluted with water (75 mL) and extracted with EtOAc (3×75 mL). The combined organic layer was washed with brine, dried over $Na_2SO_4$, filtered and the filtrate concentrated. The crude reaction mixture was purified by silica gel chromatography (24 g REDISEP® column, eluting with 2% MeOH in $CHCl_3$). Fractions were collected and concentrated to afford Intermediate 172A (4.2 g, 78%) as a white solid. MS(ES): m/z=395 [M+H]$^+$; $^1$H NMR (300 MHz, DMSO-$d_6$) δ ppm 7.81-7.87 (m, 1H), 7.63-7.72 (m, 1H), 7.47 (s, 1H), 7.15-7.37 (m, 2H), 4.74 (s, 2H), 4.16 (s, 2H), 3.80-3.88 (m, 2H), 1.45 (s, 9H).

Intermediate 172B: 2-(3-Chloro-4-fluorophenyl)-4,5,6,7-tetrahydropyrazolo[1,5-a]pyrazine-3-carboxamide

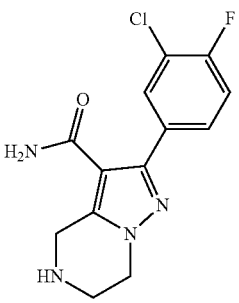 [SMILES: NC(=O)c1c(-c2ccc(F)c(Cl)c2)nn2c1CNCC2]

To a stirred solution of Intermediate 172A (4.2 g, 10.64 mmol) in DCM (15 mL) was added TFA (12.29 mL, 160 mmol) dropwise at 0° C. and the reaction mixture was stirred at RT for 12 h. The reaction mixture was concentrated under reduced pressure and the crude was basified with a saturated aq. NaOH solution and stirred for 10 min. The solid product separated was filtered, washed with water, and dried under vacuum to afford 172B as a white solid (2.8 g, 87%). MS(ES): m/z=295 [M+H]$^+$; $^1$H NMR (400 MHz, DMSO-d$_6$) δ ppm 7.86 (dd, J=7.53, 2.01 Hz, 1H), 7.69 (ddd, J=8.66, 4.89, 2.01 Hz, 1H), 7.44 (t, J=8.78 Hz, 1H), 7.11-7.20 (m, 2H), 3.99-4.04 (m, 4H), 3.12 (d, J=6.02 Hz, 2H), 2.62 (s, 1H).

Compound 172: 2-(3-Chloro-4-fluorophenyl)-N$^5$-(4-cyanophenyl)-6,7-dihydropyrazolo[1,5-a]pyrazine-3,5(4-dicarboxamide To a solution of Intermediate 172B (0.20 g, 0.679 mmol) in THF (5 mL) was added 4-isocyanatobenzonitrile (0.117 g, 0.814 mmol) and the reaction mixture was stirred at RT for 14 h. The reaction mixture was quenched with water and extracted with ethyl acetate (3×5 mL). The combined organic layer was washed with a 10% aqueous solution of NaHCO$_3$, brine, dried over Na$_2$SO$_4$, filtered and the filtrate concentrated. The crude product was purified by preparative HPLC to afford Compound 172 as an off-white solid (147 mg, 50%). HPLC retention times 8.99 min. and 8.73 min. (Methods A and B respectively). MS(ES): m/z=439 [M+H]$^+$; $^1$H NMR (400 MHz, DMSO-d$_6$) δ ppm 9.45 (br. s., 1H), 7.85 (m, 1H), 7.65-7.76 (m, 5H), 7.44-7.57 (m, 1H), 7.38 (br. s., 1H), 7.16 (br. s., 1H), 4.92 (s, 2H), 4.26 (t, J=5.27 Hz, 2H), 4.01 (t, J=5.52 Hz, 2H).

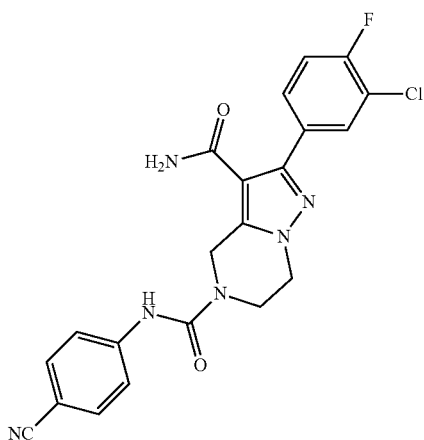 [SMILES: N#Cc1ccc(NC(=O)N2CCn3nc(-c4ccc(F)c(Cl)c4)c(C(N)=O)c3C2)cc1]

The Compounds shown in Table 6 have been prepared similar to Compound 172 by coupling of Intermediate 172B with various readily available isocyanates or in-situ generated from respective anilines.

TABLE 6

| Ex. No. | Structure | Name | [M + H]$^+$ | Ret Time (min.) | HPLC Methods |
|---|---|---|---|---|---|
| 173 | 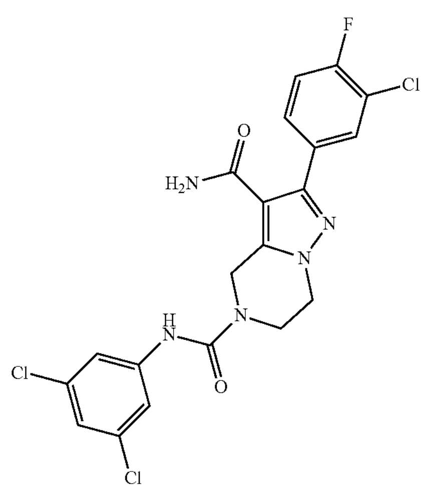 [SMILES: NC(=O)c1c(-c2ccc(F)c(Cl)c2)nn2c1CN(C(=O)Nc1cc(Cl)cc(Cl)c1)CC2] | 2-(3-Chloro-4-fluorophenyl)-N$^5$-(3,5-dichlorophenyl)-6,7-dihydropyrazolo[1,5-a]pyrazine-3,5(4H)-dicarboxamide | 484 | 10.296<br>11.179 | B<br>A |

TABLE 6-continued

| Ex. No. | Structure | Name | [M + H]⁺ | Ret Time (min.) | HPLC Methods |
|---|---|---|---|---|---|
| 174 | 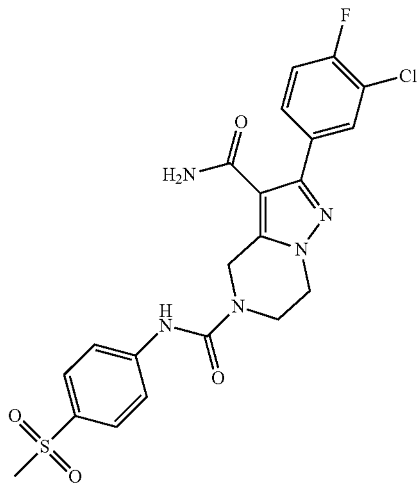 [SMILES: CS(=O)(=O)c1ccc(NC(=O)N2CCn3nc(-c4ccc(F)c(Cl)c4)c(C(N)=O)c3C2)cc1] | 2-(3-Chloro-4-fluorophenyl)-$N^5$-(4-(methylsulfonyl)phenyl)-6,7-dihydropyrazolo[1,5-a]pyrazine-3,5(4H)-dicarboxamide | 492 | 7.828<br>7.880 | B<br>A |
| 175 | 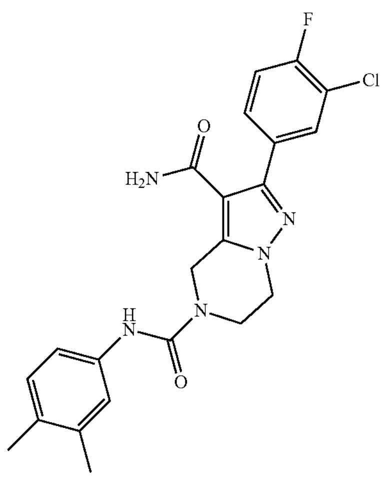 [SMILES: Cc1ccc(NC(=O)N2CCn3nc(-c4ccc(F)c(Cl)c4)c(C(N)=O)c3C2)cc1C] | 2-(3-Chloro-4-fluorophenyl)-$N^5$-(3,4-dimethylphenyl)-6,7-dihydropyrazolo[1,5-a]pyrazine-3,5(4H)-dicarboxamide | 442 | 9.712<br>8.891 | A<br>B |
| 176 | 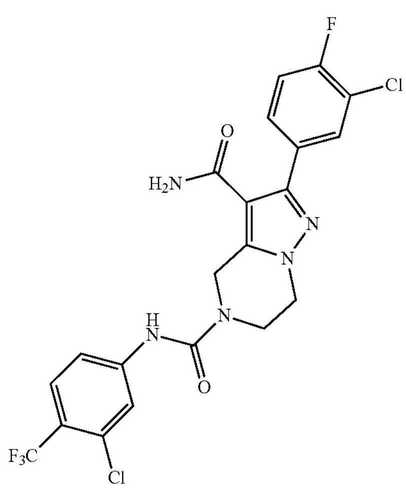 [SMILES: NC(=O)c1c(-c2ccc(F)c(Cl)c2)nn2c1CN(C(=O)Nc1ccc(C(F)(F)F)c(Cl)c1)CC2] | $N^5$-(3-Chloro-4-(trifluoromethyl)phenyl)-2-(3-chloro-4-fluorophenyl)-6,7-dihydropyrazolo[1,5-a]pyrazine-3,5(4H)-dicarboxamide | 518 | 11.240<br>10.294 | A<br>B |

TABLE 6-continued

| Ex. No. | Structure | Name | [M + H]⁺ | Ret Time (min.) | HPLC Methods |
|---|---|---|---|---|---|
| 177 | 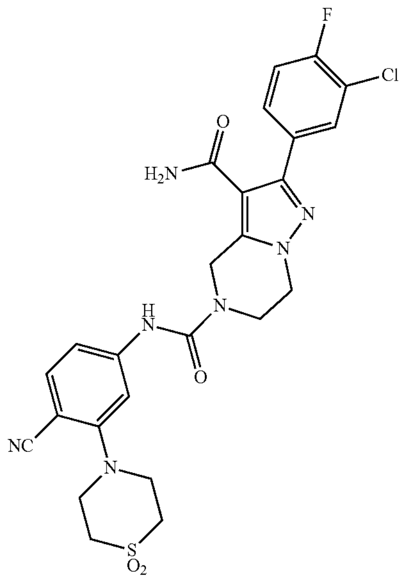 [SMILES: N#Cc1ccc(NC(=O)N2CCn3nc(-c4ccc(F)c(Cl)c4)c(C(N)=O)c3C2)cc1N1CCS(=O)(=O)CC1] | 2-(3-Chloro-4-fluorophenyl)-N⁵-(4-cyano-3-(1,1-dioxidothiomorpholino)phenyl)-6,7-dihydropyrazolo[1,5-a]pyrazine-3,5(4H)-dicarboxamide | 573 | 1.243<br>1.256 | J<br>L |
| 178 | 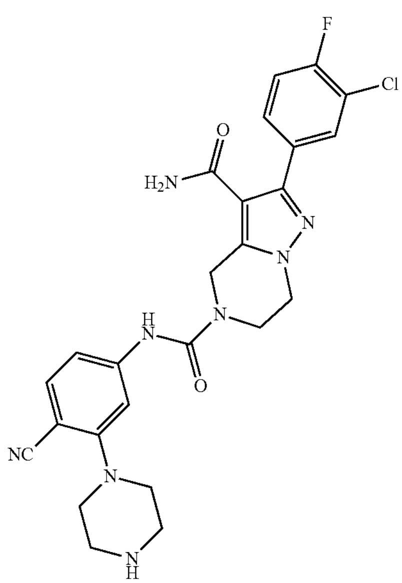 [SMILES: N#Cc1ccc(NC(=O)N2CCn3nc(-c4ccc(F)c(Cl)c4)c(C(N)=O)c3C2)cc1N1CCNCC1] | 2-(3-Chloro-4-fluorophenyl)-N⁵-(4-cyano-3-(piperazin-1-yl)phenyl)-6,7-dihydropyrazolo[1,5-a]pyrazine-3,5(4H)-dicarboxamide | 524 | 1.126<br>1.014 | E<br>L |

TABLE 6-continued

| Ex. No. | Structure | Name | [M + H]⁺ | Ret Time (min.) | HPLC Methods |
|---|---|---|---|---|---|
| 179 | 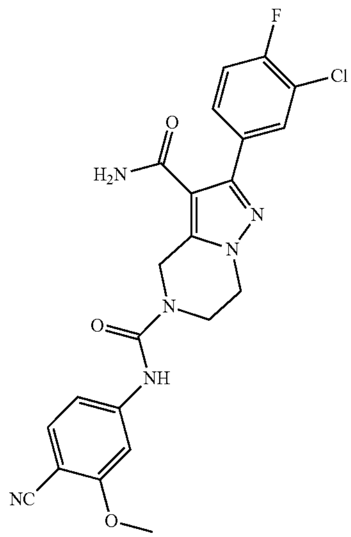 [SMILES: COc1cc(NC(=O)N2CCn3nc(-c4ccc(F)c(Cl)c4)c(C(N)=O)c3C2)ccc1C#N] | 2-(3-Chloro-4-fluorophenyl)-N⁵-(4-cyano-3-methoxyphenyl)-6,7-dihydropyrazolo[1,5-a]pyrazine-3,5(4H)-dicarboxamide | 467 | 9.02<br>8.76 | A<br>B |
| 180 | 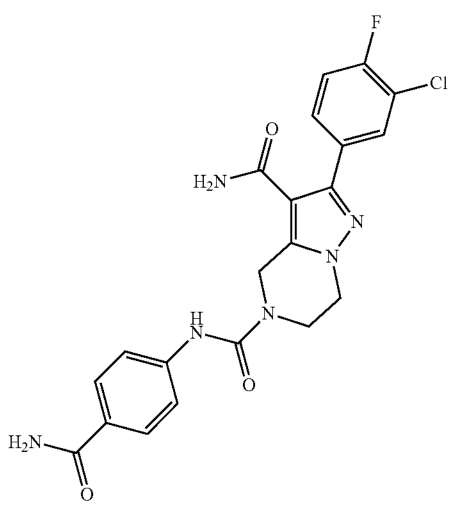 [SMILES: NC(=O)c1ccc(NC(=O)N2CCn3nc(-c4ccc(F)c(Cl)c4)c(C(N)=O)c3C2)cc1] | N⁵-(4-Carbamoylphenyl)-2-(3-chloro-4-fluorophenyl)-6,7-dihydropyrazolo[1,5-a]pyrazine-3,5(4H)-dicarboxamide | 457.2 | 6.95<br>7.07 | A<br>B |
| 181 | 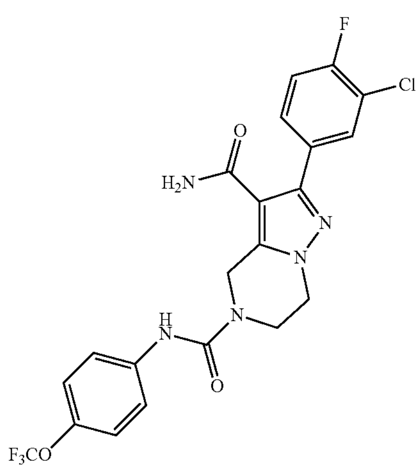 [SMILES: NC(=O)c1c(-c2ccc(F)c(Cl)c2)nn2c1CN(C(=O)Nc1ccc(OC(F)(F)F)cc1)CC2] | 2-(3-Chloro-4-fluorophenyl)-N⁵-(4-(trifluoromethoxy)phenyl)-6,7-dihydropyrazolo[1,5-a]pyrazine-3,5(4H)-dicarboxamide | 498.0 | 1.63<br>1.64 | E<br>L |

TABLE 6-continued

| Ex. No. | Structure | Name | [M + H]+ | Ret Time (min.) | HPLC Methods |
|---|---|---|---|---|---|
| 182 | 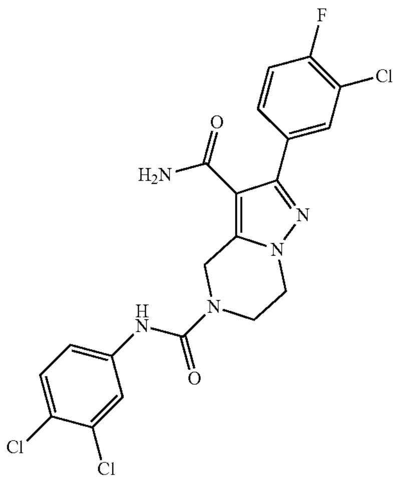 | 2-(3-Chloro-4-fluorophenyl)-$N^5$-(3,4-dichlorophenyl)-6,7-dihydropyrazolo[1,5-a]pyrazine-3,5(4H)-dicarboxamide | 482.0 | 10.53<br>9.98 | A<br>B |
| 183 | 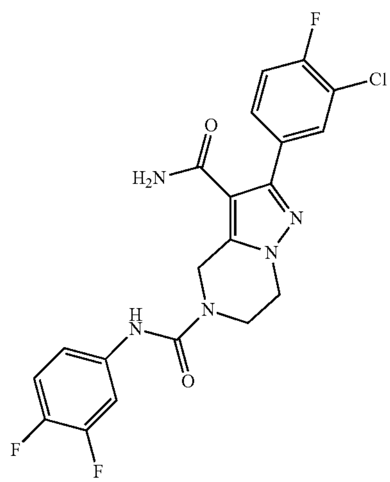 [SMILES: NC(=O)c1c(-c2ccc(F)c(Cl)c2)nn2c1CN(C(=O)Nc1ccc(F)c(F)c1)CC2] | 2-(3-Chloro-4-fluorophenyl)-$N^5$-(3,4-difluorophenyl)-6,7-dihydropyrazolo[1,5-a]pyrazine-3,5(4H)-dicarboxamide | 450 | 9.61<br>9.04 | A<br>B |
| 184 | 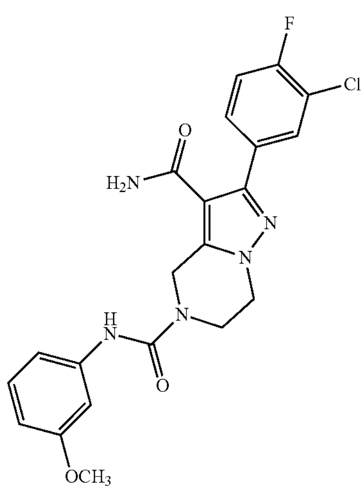 [SMILES: COc1cccc(NC(=O)N2CCn3nc(-c4ccc(F)c(Cl)c4)c(C(N)=O)c3C2)c1] | 2-(3-Chloro-4-fluorophenyl)-$N^5$-(3-(trifluoromethoxy)phenyl)-6,7-dihydropyrazolo[1,5-a]pyrazine-3,5(4H)-dicarboxamide | 498 | 10.39<br>9.83 | A<br>B |

TABLE 6-continued

| Ex. No. | Structure | Name | [M + H]$^+$ | Ret Time (min.) | HPLC Methods |
|---|---|---|---|---|---|
| 185 | 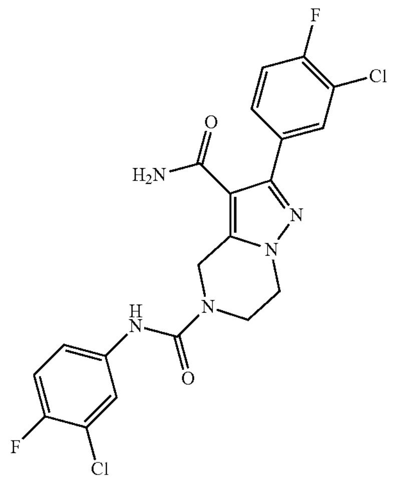 [SMILES: NC(=O)c1c(-c2ccc(F)c(Cl)c2)nn2c1CN(C(=O)Nc1ccc(F)c(Cl)c1)CC2] | $N^5$,2-Bis(3-chloro-4-fluorophenyl)-6,7-dihydropyrazolo[1,5-a]pyrazine-3,5(4H)-dicarboxamide | 466.0 | 9.83 9.56 | A B |
| 186 | 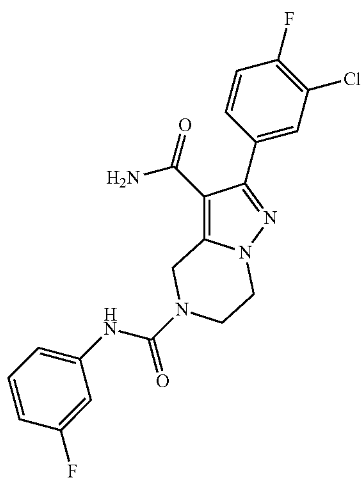 [SMILES: NC(=O)c1c(-c2ccc(F)c(Cl)c2)nn2c1CN(C(=O)Nc1cccc(F)c1)CC2] | 2-(3-Chloro-4-fluorophenyl)-$N^5$-(3-fluorophenyl)-6,7-dihydropyrazolo[1,5-a]pyrazine-3,5(4H)-dicarboxamide | 432 | 9.18 9.86 | A B |
| 187 | 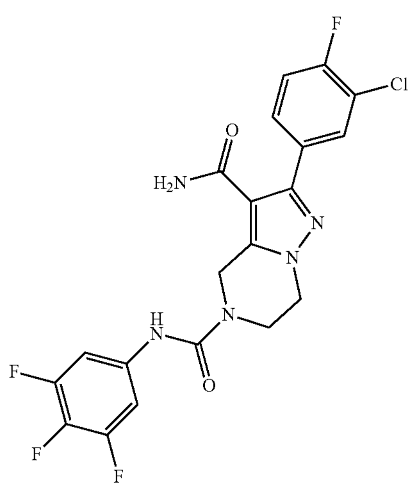 [SMILES: NC(=O)c1c(-c2ccc(F)c(Cl)c2)nn2c1CN(C(=O)Nc1cc(F)c(F)c(F)c1)CC2] | 2-(3-Chloro-4-fluorophenyl)-$N^5$-(3,4,5-trifluorophenyl)-6,7-dihydropyrazolo[1,5-a]pyrazine-3,5(4H)-dicarboxamide | 468 | 1.55 1.57 | E L |

TABLE 6-continued

| Ex. No. | Structure | Name | [M + H]+ | Ret Time (min.) | HPLC Methods |
|---|---|---|---|---|---|
| 188 | 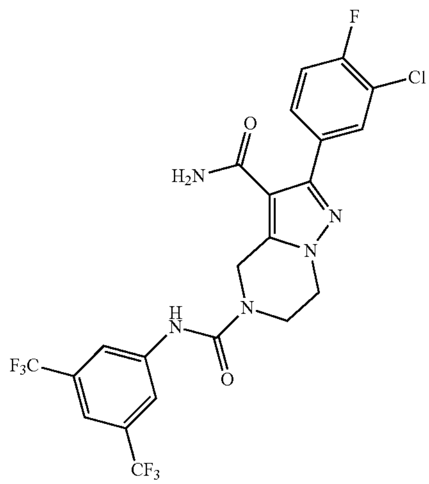 [SMILES: NC(=O)c1c(-c2ccc(F)c(Cl)c2)nn2c1CN(C(=O)Nc1cc(C(F)(F)F)cc(C(F)(F)F)c1)CC2] | N5-(3,5-Bis(trifluoromethyl)phenyl)-2-(3-chloro-4-fluorophenyl)-6,7-dihydropyrazolo[1,5-a]pyrazine-3,5(4H)-dicarboxamide | 550 | 1.90<br>1.93 | E<br>L |
| 189 | 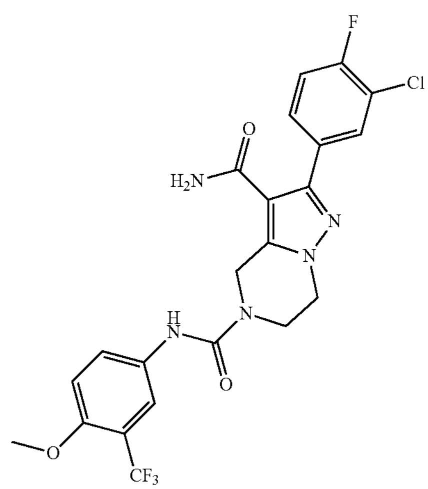 [SMILES: COc1ccc(NC(=O)N2CCn3nc(-c4ccc(F)c(Cl)c4)c(C(N)=O)c3C2)cc1C(F)(F)F] | 2-(3-Chloro-4-fluorophenyl)-N5-(4-methoxy-3-(trifluoromethyl)phenyl)-6,7-dihydropyrazolo[1,5-a]pyrazine-3,5(4H)-dicarboxamide | 512 | 1.56<br>1.58 | E<br>L |
| 190 | 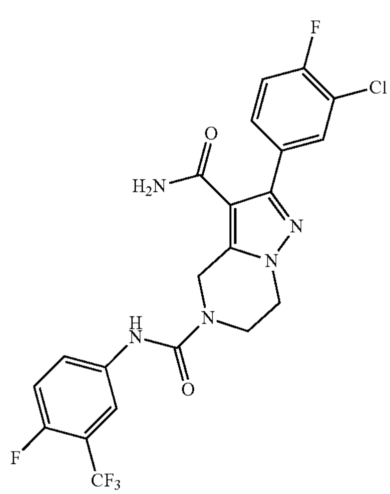 [SMILES: NC(=O)c1c(-c2ccc(F)c(Cl)c2)nn2c1CN(C(=O)Nc1ccc(F)c(C(F)(F)F)c1)CC2] | 2-(3-Chloro-4-fluorophenyl)-N5-(4-fluoro-3-(trifluoromethyl)phenyl)-6,7-dihydropyrazolo[1,5-a]pyrazine-3,5(4H)-dicarboxamide | 500 | 1.64<br>1.65 | E<br>L |

TABLE 6-continued

| Ex. No. | Structure | Name | [M + H]+ | Ret Time (min.) | HPLC Methods |
|---|---|---|---|---|---|
| 191 | 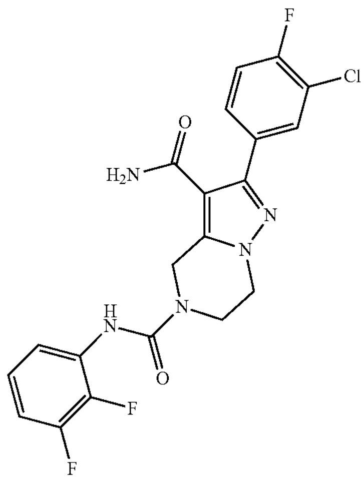 [SMILES: NC(=O)c1c(-c2ccc(F)c(Cl)c2)nn2c1CN(C(=O)Nc1cccc(F)c1F)CC2] | 2-(3-Chloro-4-fluorophenyl)-N5-(2,3-difluorophenyl)-6,7-dihydropyrazolo[1,5-a]pyrazine-3,5(4H)-dicarboxamide | 450 | 1.33<br>1.34 | E<br>L |
| 192 | 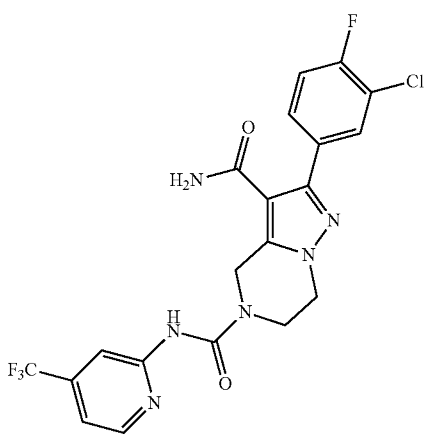 [SMILES: NC(=O)c1c(-c2ccc(F)c(Cl)c2)nn2c1CN(C(=O)Nc1cc(C(F)(F)F)ccn1)CC2] | 2-(3-Chloro-4-fluorophenyl)-N5-(4-(trifluoromethyl)pyridin-2-yl)-6,7-dihydropyrazolo[1,5-a]pyrazine-3,5(4H)-dicarboxamide | 483 | 9.543<br>9.052 | A<br>B |
| 193 | 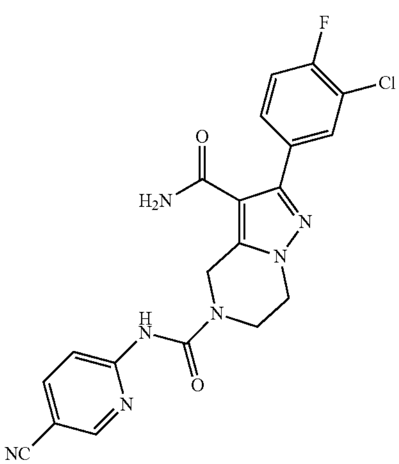 [SMILES: N#Cc1ccc(NC(=O)N2CCn3nc(-c4ccc(F)c(Cl)c4)c(C(N)=O)c3C2)nc1] | 2-(3-Chloro-4-fluorophenyl)-N5-(5-cyanopyridin-2-yl)-6,7-dihydropyrazolo[1,5-a]pyrazine-3,5(4H)-dicarboxamide | 440 | 8.188<br>8.113 | A<br>B |

TABLE 6-continued

| Ex. No. | Structure | Name | [M + H]+ | Ret Time (min.) | HPLC Methods |
|---|---|---|---|---|---|
| 194 | 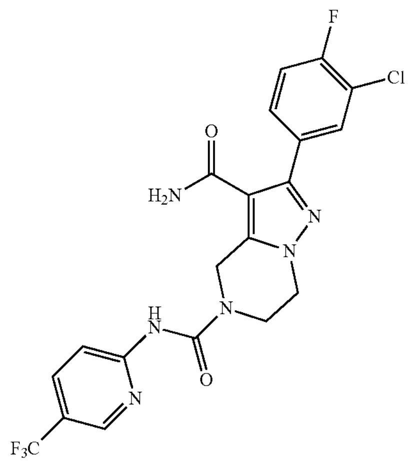 [SMILES: NC(=O)c1c(-c2ccc(F)c(Cl)c2)nn2c1CN(C(=O)Nc1ccc(C(F)(F)F)cn1)CC2] | 2-(3-Chloro-4-fluorophenyl)-$N^5$-(5-(trifluoromethyl)pyridin-2-yl)-6,7-dihydropyrazolo[1,5-a]pyrazine-3,5(4H)-dicarboxamide | 483 | 9.567 9.094 | A B |
| 195 | 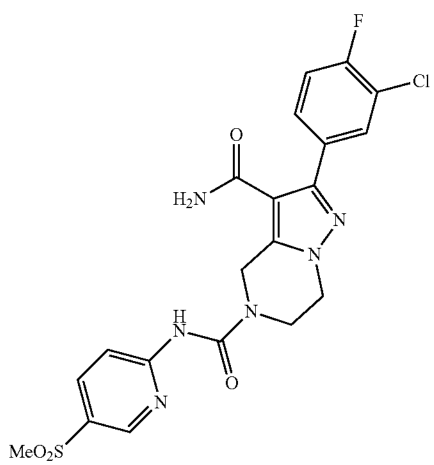 [SMILES: CS(=O)(=O)c1ccc(NC(=O)N2CCn3nc(-c4ccc(F)c(Cl)c4)c(C(N)=O)c3C2)nc1] | 2-(3-Chloro-4-fluorophenyl)-$N^5$-(5-(methylsulfonyl)pyridin-2-yl)-6,7-dihydropyrazolo[1,5-a]pyrazine-3,5(4H)-dicarboxamide | 493 | 7.596 7.664 | A B |
| 196 | 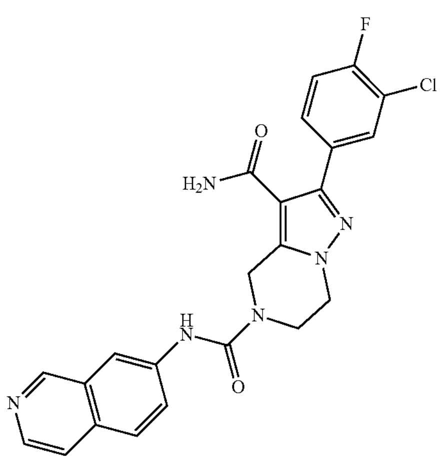 | 2-(3-Chloro-4-fluorophenyl)-$N^5$-(isoquinolin-7-yl)-6,7-dihydropyrazolo[1,5-a]pyrazine-3,5(4H)-dicarboxamide | 465 | 1.224 0.932 | E L |

TABLE 6-continued

| Ex. No. | Structure | Name | [M + H]+ | Ret Time (min.) | HPLC Methods |
|---|---|---|---|---|---|
| 197 | 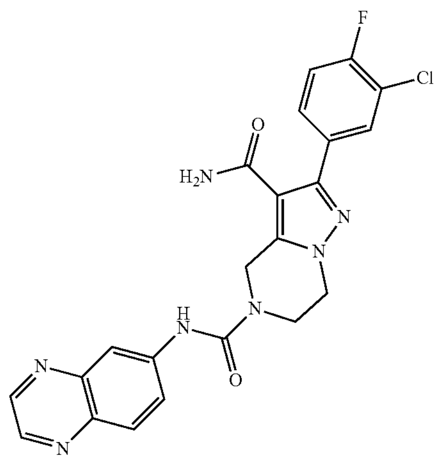 [SMILES: NC(=O)c1c(-c2ccc(F)c(Cl)c2)nn2c1CN(C(=O)Nc1ccc3nccnc3c1)CC2] | 2-(3-Chloro-4-fluorophenyl)-N5-(quinoxalin-6-yl)-6,7-dihydropyrazolo[1,5-a]pyrazine-3,5(4H)-dicarboxamide | 466 | 1.792<br>1.795 | K<br>J |
| 198 | 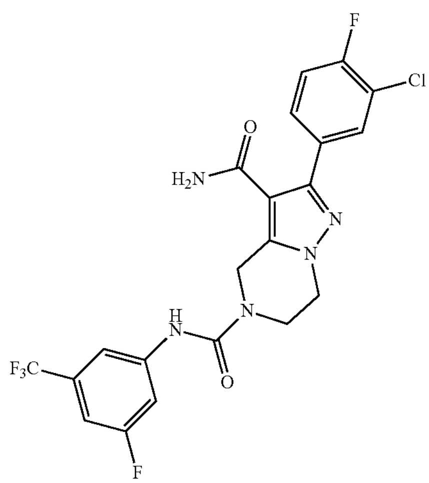 [SMILES: NC(=O)c1c(-c2ccc(F)c(Cl)c2)nn2c1CN(C(=O)Nc1cc(F)cc(C(F)(F)F)c1)CC2] | 2-(3-Chloro-4-fluorophenyl)-N5-(3-fluoro-5-(trifluoromethyl)phenyl)-6,7-dihydropyrazolo[1,5-a]pyrazine-3,5(4H)-dicarboxamide | 450 | 9.61<br>0.04 | A<br>B |
| 199 | 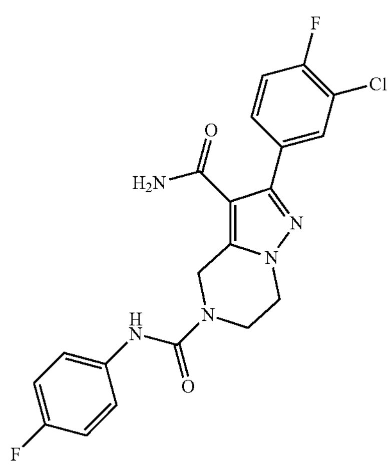 [SMILES: NC(=O)c1c(-c2ccc(F)c(Cl)c2)nn2c1CN(C(=O)Nc1ccc(F)cc1)CC2] | 2-(3-Chloro-4-fluorophenyl)-N5-(4-fluorophenyl)-6,7-dihydropyrazolo[1,5-a]pyrazine-3,5(4H)-dicarboxamide | 433 | 8.82<br>8.72 | A<br>B |

TABLE 6-continued

| Ex. No. | Structure | Name | [M + H]+ | Ret Time (min.) | HPLC Methods |
|---|---|---|---|---|---|
| 200 | 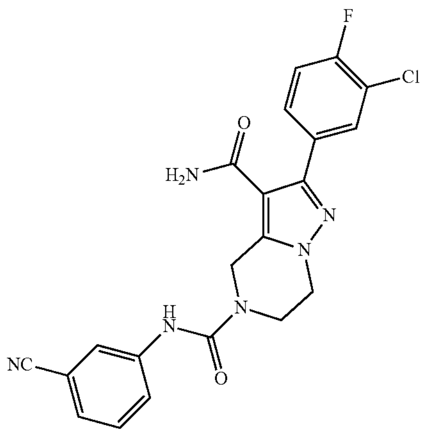 [SMILES: N#Cc1cccc(NC(=O)N2CCn3nc(-c4ccc(F)c(Cl)c4)c(C(N)=O)c3C2)c1] | 2-(3-Chloro-4-fluorophenyl)-N5-(3-cyanophenyl)-6,7-dihydropyrazolo[1,5-a]pyrazine-3,5(4H)-dicarboxamide | 439 | 8.82<br>8.57 | A<br>B |
| 201 | 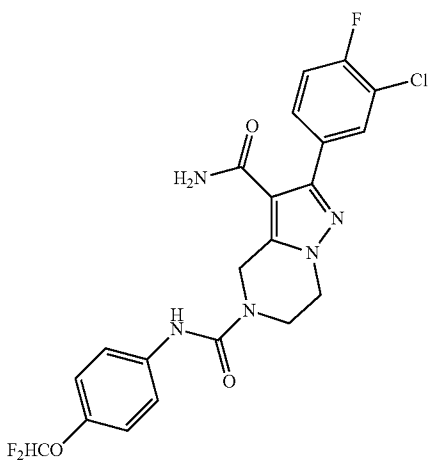 [SMILES: NC(=O)c1c(-c2ccc(F)c(Cl)c2)nn2c1CN(C(=O)Nc1ccc(OC(F)F)cc1)CC2] | 2-(3-Chloro-4-fluorophenyl)-N5-(4-(difluoromethoxy)phenyl)-6,7-dihydropyrazolo[1,5-a]pyrazine-3,5(4H)-dicarboxamide | 474 | 8.89<br>8.88 | A<br>B |
| 202 | 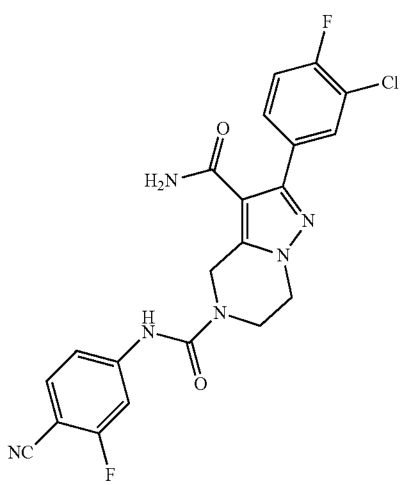 [SMILES: N#Cc1ccc(NC(=O)N2CCn3nc(-c4ccc(F)c(Cl)c4)c(C(N)=O)c3C2)cc1F] | 2-(3-Chloro-4-fluorophenyl)-N5-(4-cyano-3-fluorophenyl)-6,7-dihydropyrazolo[1,5-a]pyrazine-3,5(H)-dicarboxamide | 458 | 9.30<br>9.21 | A<br>B |

TABLE 6-continued
| Ex. No. | Structure | Name | [M + H]⁺ | Ret Time (min.) | HPLC Methods |
|---|---|---|---|---|---|
| 203 | 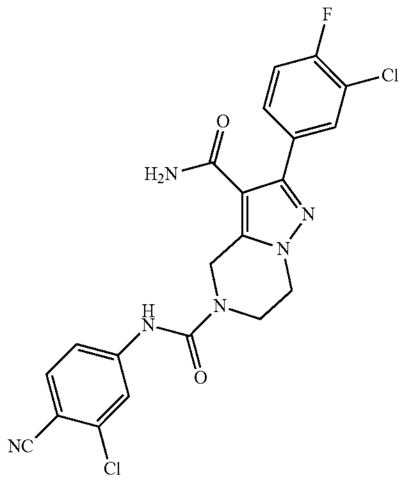 [SMILES: N#Cc1ccc(NC(=O)N2CCn3nc(-c4ccc(F)c(Cl)c4)c(C(N)=O)c3C2)cc1Cl] | N⁵-(3-Chloro-4-cyanophenyl)-2-(3-chloro-4-fluorophenyl)-6,7-dihydropyrazolo[1,5-a]pyrazine-3,5(4H)-dicarboxamide | 473 | 9.63<br>9.45 | A<br>B |
| 204 | 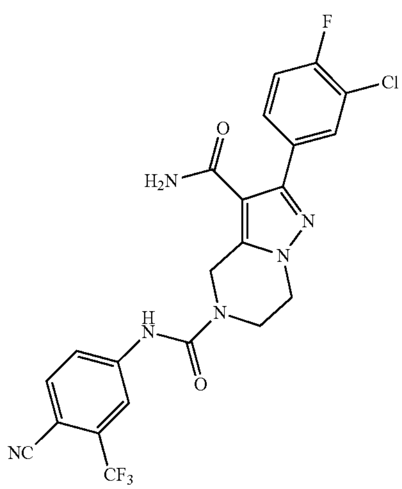 [SMILES: N#Cc1ccc(NC(=O)N2CCn3nc(-c4ccc(F)c(Cl)c4)c(C(N)=O)c3C2)cc1C(F)(F)F] | 2-(3-Chloro-4-fluorophenyl)-N⁵-(4-cyano-3-(trifluoromethyl)phenyl)-6,7-dihydropyrazolo[1,5-a]pyrazine-3,5(4H)-dicarboxamide | 507 | 10.258<br>9.696 | A<br>B |
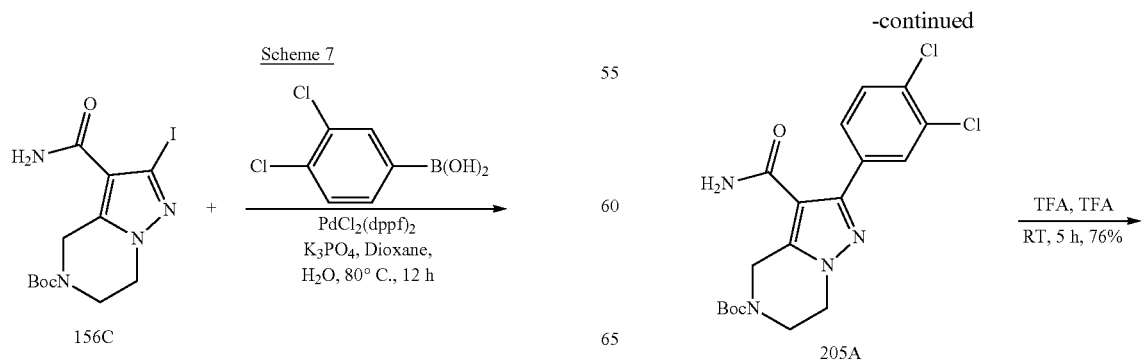

-continued

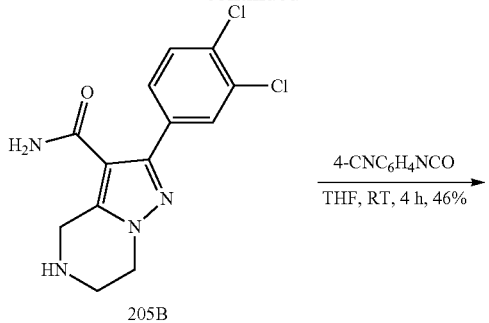

205B

4-CNC₆H₄NCO
―――――――――→
THF, RT, 4 h, 46%

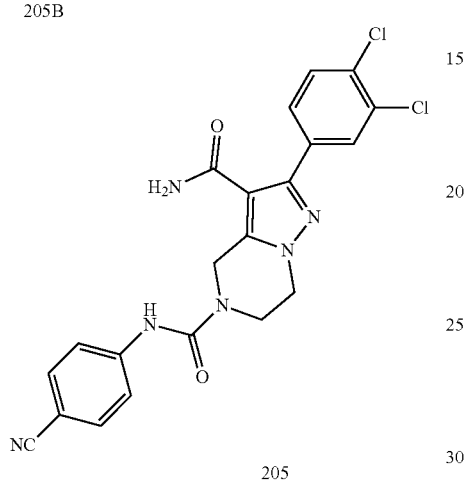

205

Intermediate 205A: tert-Butyl 3-carbamoyl-2-(3,4-dichlorophenyl)-6,7-dihydropyrazolo[1,5-a]pyrazine-5(4H)-carboxylate

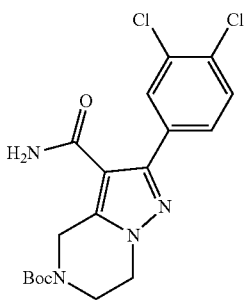 [SMILES: CC(C)(C)OC(=O)N1CCn2nc(-c3ccc(Cl)c(Cl)c3)c(C(N)=O)c2C1]

To a stirred solution of Intermediate 156C (9 g, 23 mmol), (3,4-dichlorophenyl) boronic acid (6.57 g, 34.4 mmol) in 1,4-dioxane (150 mL) and water (10 mL) was added K₃PO₄ (14.61 g, 68.8 mmol) and the reaction mixture was purged with nitrogen for 15 min. PdCl₂(dppf)-CH₂Cl₂ (1.124 g, 1.377 mmol) was added and the reaction mixture was stirred at 80° C. for 12 h. The reaction mixture was diluted with water (300 mL) and extracted with EtOAc (3×80 mL). The combined organic layer was washed with brine, dried over Na₂SO₄, filtered and the filtrate concentrated. The crude reaction mixture was purified by silica gel chromatography (40 g REDISEP® column, eluting with 65% EtOAc in hexanes). Fractions were collected and concentrated to afford Intermediate 205A as a pale yellow solid (8 g, 85%). MS(ES): m/z=411.0 [M+1]⁺; ¹H NMR: (400 MHz, DMSO-d₆) δ ppm 7.92-7.87 (m, 1H), 7.69-7.64 (m, 2H), 7.44-7.18 (m, 2H), 4.74 (s, 2H), 4.17 (t, 2H), 3.84 (t, 2H), 1.45 (s, 9H).

Intermediate 205B: 2-(3,4-Dichlorophenyl)-4,5,6,7-tetrahydropyrazolo[1,5-a]pyrazine-3-carboxamide

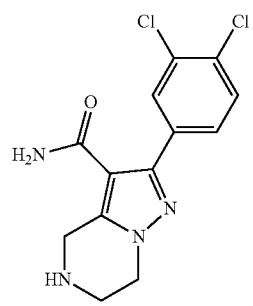 [SMILES: NC(=O)c1c(-c2ccc(Cl)c(Cl)c2)nn2c1CNCC2]

To a stirred solution of 205A (9 g, 21.88 mmol) in DCM (20 mL) was added dropwise TFA (15 mL, 21.88 mmol) at 0° C. and the reaction mixture was stirred at RT for 12 h. The volatiles were removed under reduced pressure and the crude product was basified with a 10% aq. NaOH solution and stirred for 10 min. The solid product separated was filtered, washed with water, and dried under vacuum to afford 205B as an off-white solid (5.2 g, 76%). MS(ES): m/z=311.0 [M+1]⁺; ¹H NMR: (400 MHz, DMSO-d₆) δ ppm 7.92 (s, 1H), 7.67 (m, 2H), 7.32-7.09 (m, 2H), 4.02 (s, 4H), 3.12 (br. s., 2H), 2.70-2.58 (m, 1H).

Compound 205: N⁵-(4-Cyanophenyl)-2-(3,4-dichlorophenyl)-6,7-dihydropyrazolo[1,5-a]pyrazine-3,5(4H)-dicarboxamide

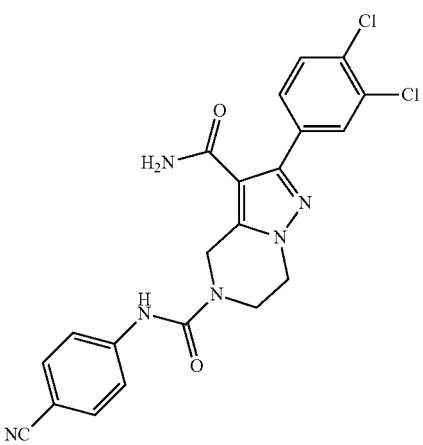 [SMILES: N#Cc1ccc(NC(=O)N2CCn3nc(-c4ccc(Cl)c(Cl)c4)c(C(N)=O)c3C2)cc1]

To a solution of Intermediate 205B (0.20 g, 0.643 mmol) in THF (5 mL) was added 4-isocyanatobenzonitrile (0.111 g, 0.771 mmol) and the reaction mixture was stirred at RT for 14 h. The reaction mixture was quenched with water and extracted with ethyl acetate (3×5 mL). The combined organic layer was washed with a 10% aqueous solution of NaHCO$_3$, brine, dried over Na$_2$SO$_4$, filtered and the filtrate concentrated. The crude product was purified by preparative HPLC to afford Compound 205 as an off-white solid (135 mg, 46%). HPLC retention times 9.44 min. and 9.06 min. (Methods A and B respectively). MS(ES): m/z=405 [M+H]$^+$; $^1$H NMR (400 MHz, DMSO-d$_6$) d ppm 9.50 (br. s., 1H), 7.91 (s, 1H), 7.65-7.75 (m, 6H), 7.25-7.45 (d, 2H), 4.92 (s, 2H), 4.26 (t, J=5.27 Hz, 2H), 4.01 (t, J=5.52 Hz, 2H).

The Compounds shown in Table 7 have been prepared similar to Compound 205 by coupling of Intermediate 205B with various readily available isocyanates or in-situ generated from respective anilines.

TABLE 7

| Ex. No. | Structure | Name | [M + H]$^+$ | Ret Time (min.) | HPLC Methods |
|---|---|---|---|---|---|
| 206 | 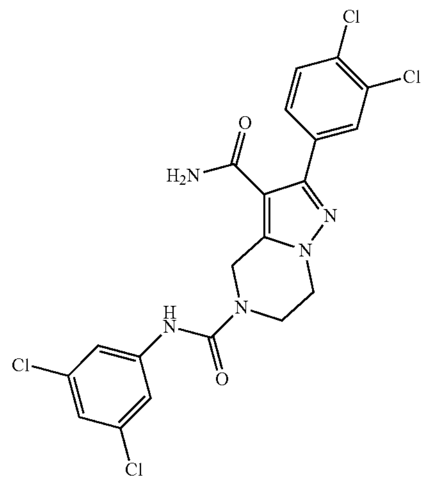 | 2-(3,4-Dichlorophenyl-N$^5$-(3,5-dichlorophenyl)-6,7-dihydropyrazolo[1,5-a]pyrazine-3,5(4H)-dicarboxamide | 498 | 10.698<br>11.357 | B<br>A |
| 207 | 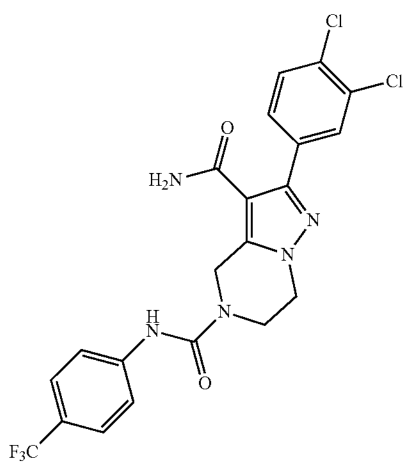 [SMILES: NC(=O)c1c(-c2ccc(Cl)c(Cl)c2)nn2c1CN(C(=O)Nc1ccc(C(F)(F)F)cc1)CC2] | 2-(3,4-Dichlorophenyl)-N$^5$-(4-(trifluoromethyl)phenyl)-6,7-dihydropyrazolo[1,5-a]pyrazine-3,5(4H)-dicarboxamide | 498.2 | 10.91<br>10.14 | A<br>B |
| 208 | 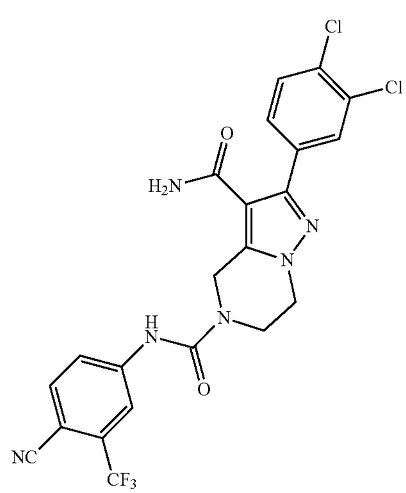 [SMILES: N#Cc1ccc(NC(=O)N2CCn3nc(-c4ccc(Cl)c(Cl)c4)c(C(N)=O)c3C2)cc1C(F)(F)F] | N$^5$-(4-Cyano-3-(trifluoromethyl)phenyl)-2-(3,4-dichlorophenyl)-6,7-dihydropyrazolo[1,5-a]pyrazine-3,5(4H)-dicarboxamide | 521 | 10.14<br>10.8 | B<br>A |

TABLE 7-continued

| Ex. No. | Structure | Name | [M + H]+ | Ret Time (min.) | HPLC Methods |
|---|---|---|---|---|---|
| 209 | 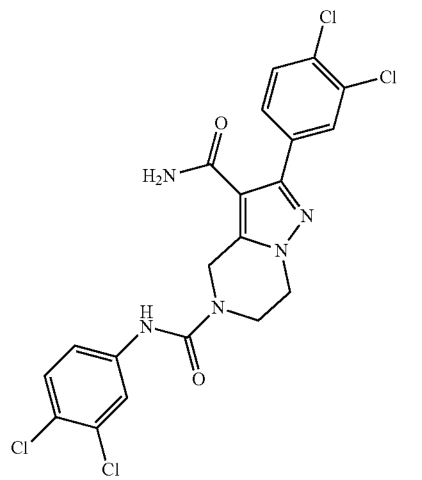 [SMILES: NC(=O)c1c(-c2ccc(Cl)c(Cl)c2)nn2c1CN(C(=O)Nc1ccc(Cl)c(Cl)c1)CC2] | N5,2-Bis(3,4-dichlorophenyl)-6,7-dihydropyrazolo[1,5-a](pyrazine-3,5(4H)-dicarboxamide | 499.7 | 1.75<br>1.75 | E<br>L |
| 210 | 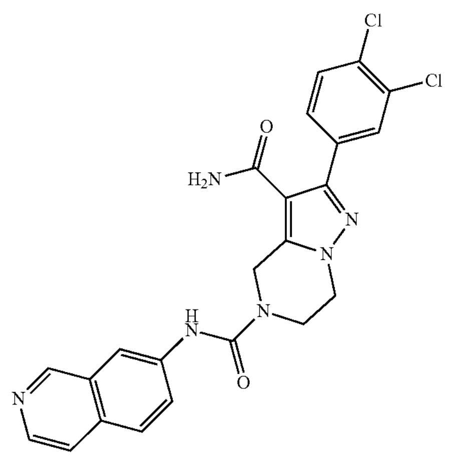 [SMILES: NC(=O)c1c(-c2ccc(Cl)c(Cl)c2)nn2c1CN(C(=O)Nc1ccc3ccncc3c1)CC2] | 2-(3,4-Dichlorophenyl)-N5-(isoquinolin-7-yl)-6,7-dihydropyrazolo[1,5-a]pyrazine-3,5(4H)-dicarboxamide | 481 | 1.349<br>1.039 | E<br>L |
| 211 | 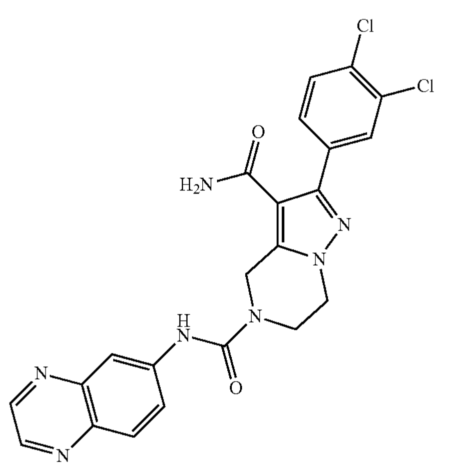 [SMILES: NC(=O)c1c(-c2ccc(Cl)c(Cl)c2)nn2c1CN(C(=O)Nc1ccc3nccnc3c1)CC2] | 2-(3,4-Dichlorophenyl)-N5-(quinoxalin-6-yl)-6,7-dihydropyrazolo[1,5-a]pyrazine-3,5(4H)-dicarboxamide | 482 | 1.935<br>1.943 | J<br>K |

TABLE 7-continued

| Ex. No. | Structure | Name | [M + H]+ | Ret Time (min.) | HPLC Methods |
|---|---|---|---|---|---|
| 212 | 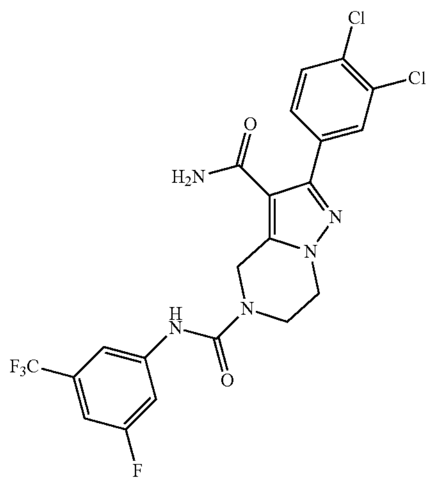 | 2-(3,4-Dichlorophenyl)-N5-(3-fluoro-5-(trifluoromethyl)phenyl)-6,7-dihydropyrazolo[1,5-a]pyrazine-3,5(4H)-dicarboxamide | 516 | 11.51<br>10.49 | A<br>B |
| 213 | 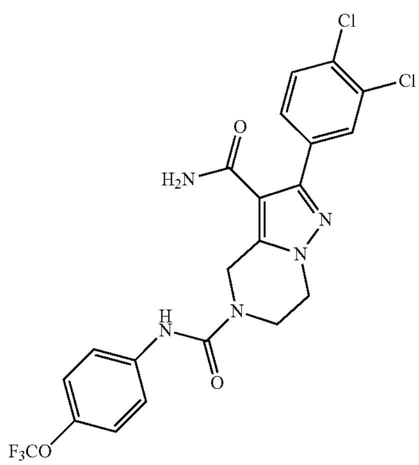 [SMILES: NC(=O)c1c(-c2ccc(Cl)c(Cl)c2)nn2c1CN(C(=O)Nc1ccc(OC(F)(F)F)cc1)CC2] | 2-(3,4-Dichlorophenyl)-N5-(4-(trifluoromethoxy)phenyl)-6,7-dihydropyrazolo[1,5-a]pyrazine-3,5(4H)-dicarboxamide | 512 | 10.90<br>10.21 | A<br>B |
| 214 | 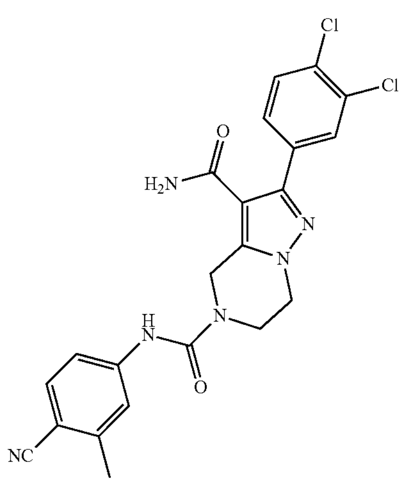 [SMILES: Cc1cc(NC(=O)N2CCn3nc(-c4ccc(Cl)c(Cl)c4)c(C(N)=O)c3C2)ccc1C#N] | N5-(4-Cyano-3-methylphenyl)-2-(3,4-dichlorophenyl)-6,7-dihydropyrazolo[1,5-a]pyrazine-3,5(4H)-dicarboxamide | 470 | 9.78<br>9.31 | A<br>B |

Scheme 8

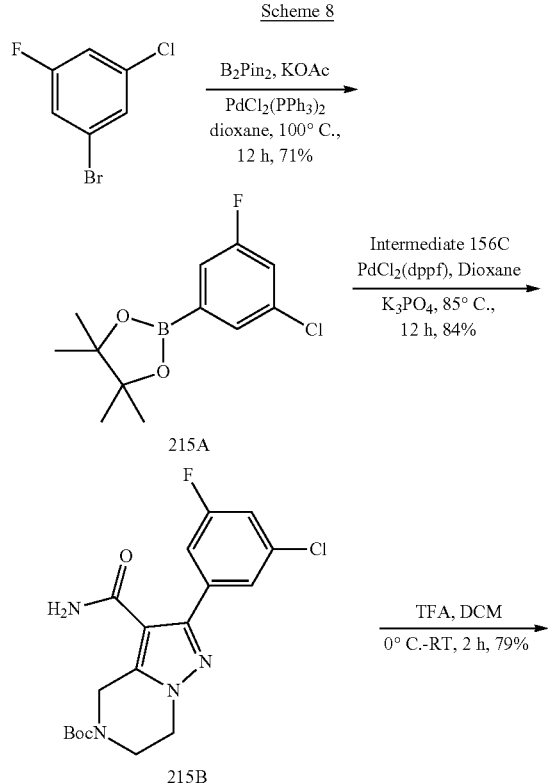

Intermediate 215A: 2-(3-Chloro-5-fluorophenyl)-4,4,5,5-tetramethyl-1,3,2-dioxaborolane

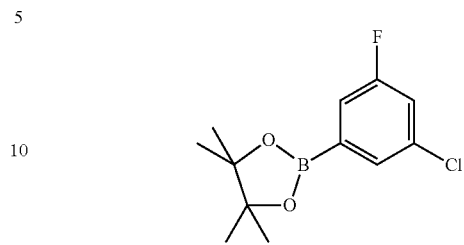

To a solution of 1-bromo-3-chloro-5-fluorobenzene (1.5 g, 7.16 mmol) and bis(pinacolato)diboron (2.182 g, 8.59 mmol) in dioxane (5 mL) was added KOAc (2.109 g, 21.49 mmol) and the reaction mixture was degassed with $N_2$ gas for 15 min. $Pd_2(PPh_3)_2Cl_2$ (0.302 g, 0.430 mmol) was added and the reaction mixture was heated at 100° C. and stirred for 12 h. The reaction mixture was filtered through CELITE® pad and concentrated. The crude product was purified by silica gel chromatography (12 g REDISEP® column, eluting with 1% EtOAc in hexanes). Fractions containing the product were combined and evaporated to afford the Intermediate 215A as colorless liquid (1.3 g, 71%). $^1$H NMR (400 MHz, DMSO-$d_6$) δ ppm 7.59 (td, J=2.3, 9.0 Hz, 1H), 7.46 (dd, J=1.0, 2.0 Hz, 1H), 7.34 (ddd, J=1.0, 2.5, 8.5 Hz, 1H), 1.31 (s, 12H).

Intermediate 215B: tert-Butyl 3-carbamoyl-2-(3-chloro-5-fluorophenyl)-6,7-dihydropyrazolo[1,5-a]pyrazine-5(4H)-carboxylate

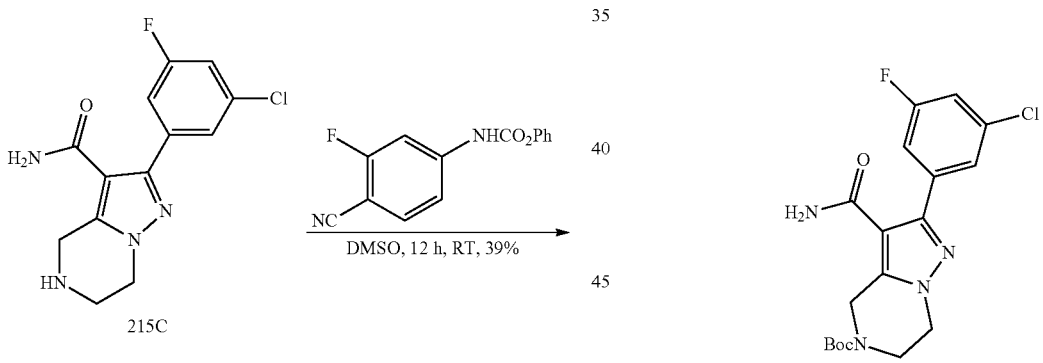

To a stirred solution of Intermediate 156C (1 g, 2.55 mmol), Intermediate 215A (981 mg, 3.82 mmol) in 1,4-dioxane (20 mL) was added $K_3PO_4$ (1624 mg, 7.65 mmol) in water (1.0 mL) and the reaction mixture was purged with nitrogen for 5 min. $PdCl_2(dppf)$-$CH_2Cl_2$ (125 mg, 0.153 mmol) was added and the reaction mixture was stirred at 80° C. for 12 h. The reaction mixture was diluted with water (25 mL) and extracted with EtOAc (3×25 mL). The combined organic layer was washed with brine, dried over $Na_2SO_4$, filtered and the filtrate concentrated. The crude reaction mixture was purified by silica gel chromatography (24 g REDISEP® column, eluting with 70% EtOAc in hexanes). Fractions were collected and concentrated to afford Intermediate 215B as an off-white solid (850 mg, 84%). MS(ES): m/z=575 [M+H]$^+$; $^1$H NMR (300 MHz, DMSO-$d_6$) δ ppm 7.60 (t, J=1.5 Hz, 1H), 7.54-7.47 (m, 1H), 7.47-7.32 (m, 3H), 4.74 (s, 2H), 4.18 (t, J=5.5 Hz, 2H), 3.84 (t, J=5.3 Hz, 2H), 1.45 (s, 9H).

Intermediate 215C: 2-(3-Chloro-5-fluorophenyl)-4,5,6,7-tetrahydropyrazolo[1,5-a]pyrazine-3-carboxamide

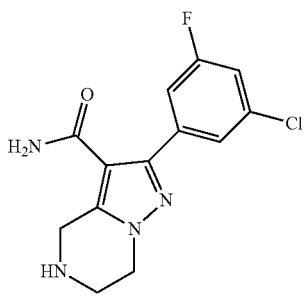 [SMILES: NC(=O)c1c(-c2cc(F)cc(Cl)c2)nn2c1CNCC2]

To a solution of Intermediate 215B (850 mg, 2.153 mmol) in DCM (7 mL) was added TFA (5 mL) at 0° C. and the resulting solution was allowed to warm to RT and stirred for 2 h. The volatiles were removed under a reduced pressure and the residue was triturated with Et$_2$O. The solid product separated was treated with a 10% aqueous solution of NaOH at RT and stirred vigorously for 2 h. The solid product separated was filtered, washed with water and azeotroped with toluene to afford Intermediate 215C as an off-white solid (500 mg, 79%). MS(ES): m/z=295.2 [M+H]$^+$; $^1$H NMR (400 MHz, DMSO-d$_6$) δ ppm 7.63 (t, J=1.5 Hz, 1H), 7.56-7.50 (m, 1H), 7.40 (td, J=2.1, 8.8 Hz, 1H), 7.27 (br. s., 2H), 4.07-3.99 (m, 4H), 3.13 (q, J=5.5 Hz, 2H), 2.68-2.60 (m, 1H).

Compound 215: 2-(3-Chloro-5-fluorophenyl)-N$^5$-(4-cyano-3-fluorophenyl)-6,7-dihydropyrazolo[1,5-a]pyrazine-3,5(4H)-dicarboxamide

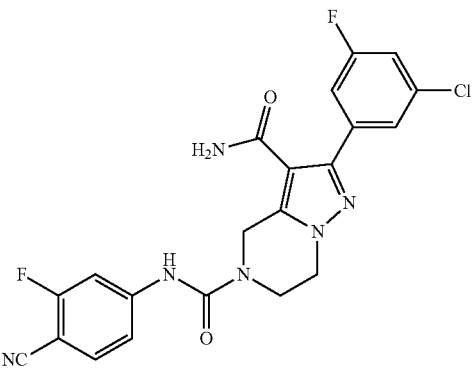 [SMILES: N#Cc1ccc(NC(=O)N2CCn3nc(-c4cc(F)cc(Cl)c4)c(C(N)=O)c3C2)cc1F]

To a solution of Intermediate 215C (30 mg, 0.102 mmol) in DMSO (1 mL) was added phenyl(4-cyano-3-fluorophenyl)carbamate (39.1 mg, 0.153 mmol) and the resulting solution was stirred at RT for 12 h. The reaction mixture was diluted with water and the solid product filtered and dried. The crude product was purified by preparative HPLC to afford Compound 215 as an off-white solid. HPLC retention times 9.31 min. and 9.25 min. (Methods A and B respectively). MS(ES): m/z=457 [M+H]$^+$; $^1$H NMR: (400 MHz, DMSO-d$_6$) δ ppm 9.62 (s, 1H), 7.75-7.84 (m, 1H), 7.70 (dd, J=12.80, 1.76 Hz, 1H), 7.62 (t, J=1.51 Hz, 1H), 7.31-7.56 (m, 5H), 4.92 (s, 2H), 4.27 (t, J=5.27 Hz, 2H), 4.01 (t, J=5.27 Hz, 2H).

The Compounds shown in Table 8 have been prepared similar to Compound 215 by reaction of Intermediate 215C with respective anilines phenylcarbamates or with readily available isocyanates.

TABLE 8

| Ex. No. | Structure | Name | [M + H]$^+$ | Ret Time (min.) | HPLC Methods |
|---|---|---|---|---|---|
| 216 | 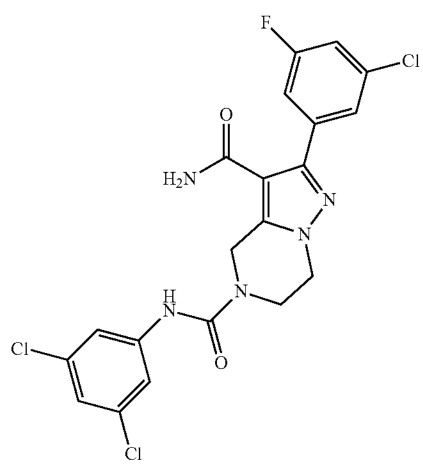 [SMILES: NC(=O)c1c(-c2cc(F)cc(Cl)c2)nn2c1CN(C(=O)Nc1cc(Cl)cc(Cl)c1)CC2] | 2-(3-Chloro-5-fluorophenyl)-N$^5$-(3,5-dichlorophenyl)-6,7-dihydropyrazolo[1,5-a]pyrazine-3,5(4H)-dicarboxamide | 484 | 10.347<br>11.365 | B<br>A |

TABLE 8-continued

| Ex. No. | Structure | Name | [M + H]+ | Ret Time (min.) | HPLC Methods |
|---|---|---|---|---|---|
| 217 | 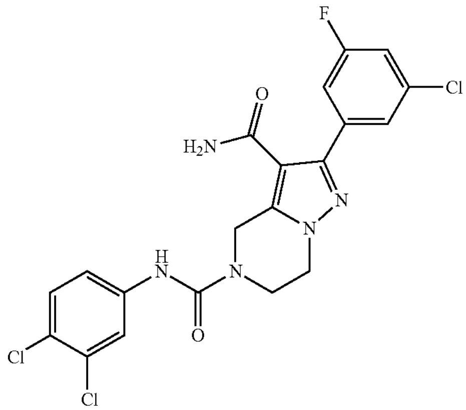 [SMILES: NC(=O)c1c(-c2cc(F)cc(Cl)c2)nn2c1CN(C(=O)Nc1ccc(Cl)c(Cl)c1)CC2] | 2-(3-Chloro-5-fluorophenyl)-$N^5$-(3,4-dichlorophenyl)-6,7-dihydropyrazolo[1,5-a]pyrazine-3,5(4H)-dicarboxamide | 484.0 | 10.78<br>10.15 | A<br>B |
| 218 | 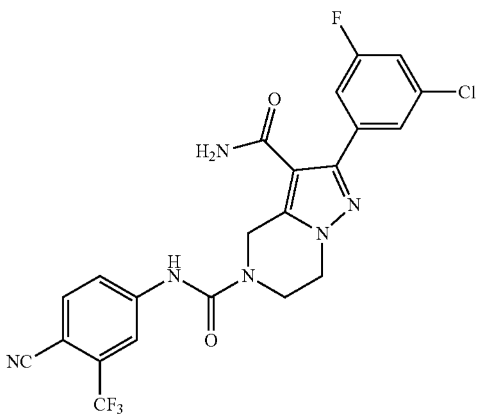 [SMILES: N#Cc1ccc(NC(=O)N2CCn3nc(-c4cc(F)cc(Cl)c4)c(C(N)=O)c3C2)cc1C(F)(F)F] | 2-(3-Chloro-5-fluorophenyl)-$N^5$-(4-cyano-3-(trifluoromethyl)phenyl)-6,7-dihydropyrazolo[1,5-a]pyrazine-3,5(4H)-dicarboxamide | 507.2 | 9.65<br>10.64 | B<br>A |
| 219 | 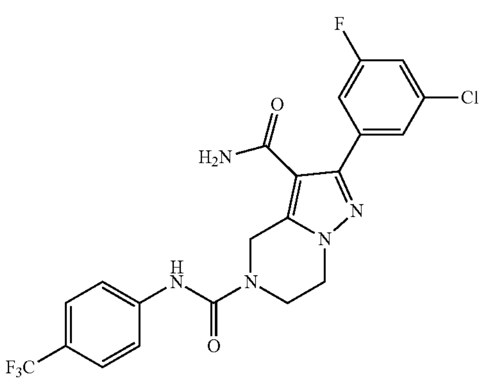 [SMILES: NC(=O)c1c(-c2cc(F)cc(Cl)c2)nn2c1CN(C(=O)Nc1ccc(C(F)(F)F)cc1)CC2] | 2-(3-Chloro-5-fluorophenyl)-$N^5$-(4-(trifluoromethyl)phenyl) 6,7-dihydropyrazolo[1,5-a]pyrazine-3,5(4H)-dicarboxamide | 482.2 | 14.98<br>17.52 | B<br>A |

TABLE 8-continued

| Ex. No. | Structure | Name | [M + H]+ | Ret Time (min.) | HPLC Methods |
|---|---|---|---|---|---|
| 220 | 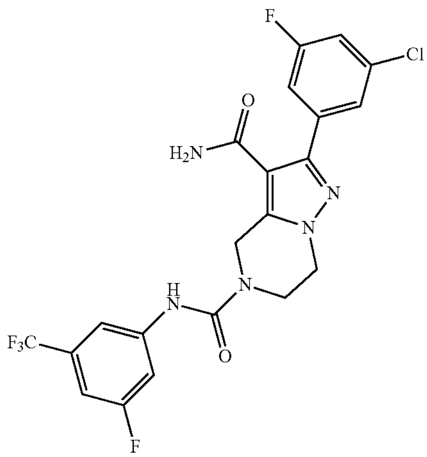 [SMILES: NC(=O)c1c(-c2cc(F)cc(Cl)c2)nn2c1CN(C(=O)Nc1cc(F)cc(C(F)(F)F)c1)CC2] | 2-(3-Chloro-5-fluorophenyl)-N5-(3-fluoro-5-(trifluoromethyl)phenyl)-6,7-dihydropyrazolo[1,5-a]pyrazine-3,5(4H)-dicarboxamide | 498 | 11.13<br>10.22 | A<br>B |
| 221 | 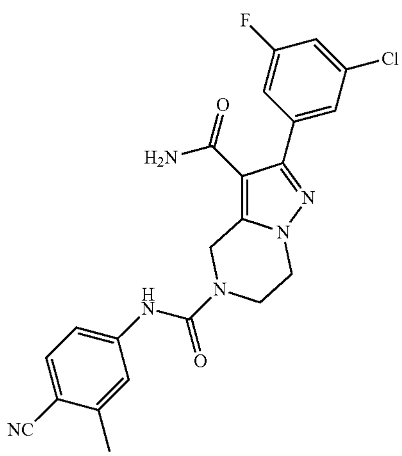 [SMILES: Cc1cc(NC(=O)N2CCn3nc(-c4cc(F)cc(Cl)c4)c(C(N)=O)c3C2)ccc1C#N] | 2-(3-Chloro-5-fluorophenyl)-N5-(4-cyano-3-methylphenyl)-6,7-dihydropyrazolo[1,5-a]pyrazine-3,5(4H)-dicarboxamide | 453 | 9.10<br>9.07 | A<br>B |
| 222 | 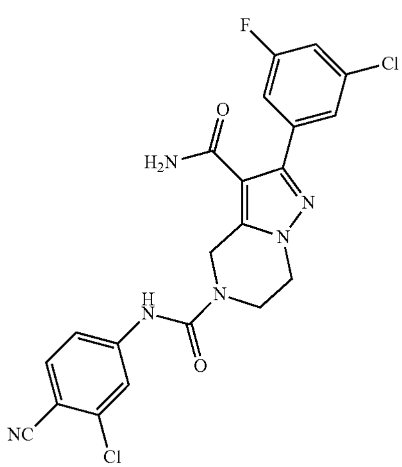 [SMILES: N#Cc1ccc(NC(=O)N2CCn3nc(-c4cc(F)cc(Cl)c4)c(C(N)=O)c3C2)cc1Cl] | N5-(3-Chloro-4-cyanophenyl)-2-(3-chloro-5-fluorophenyl)-6,7-dihydropyrazolo[1,5-a]pyrazine-3,5(4H)-dicarboxamide | 475 | 9.67<br>9.55 | A<br>B |

Scheme 9

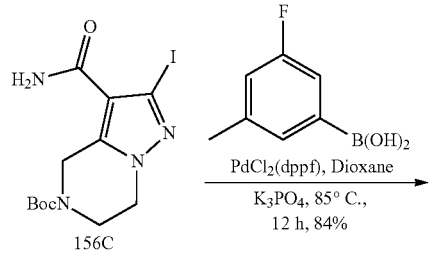

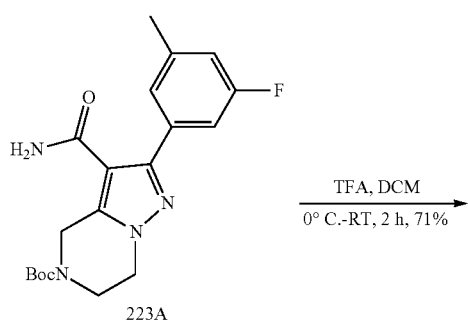

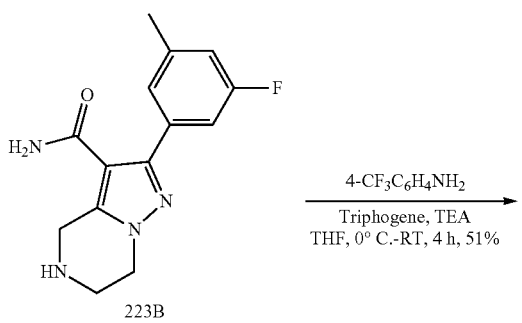

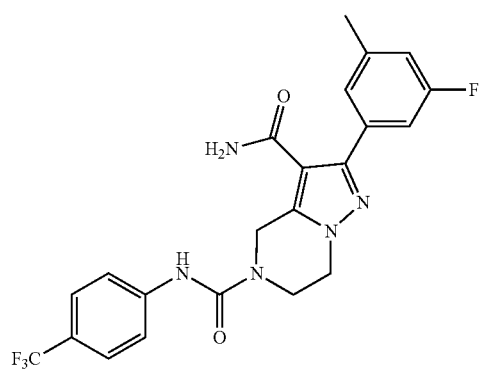 [SMILES: Cc1cc(F)cc(-c2nn3c(c2C(N)=O)CN(C(=O)Nc2ccc(C(F)(F)F)cc2)CC3)c1]

Intermediate 223A: tert-Butyl 3-carbamoyl-2-(3-fluoro-5-methylphenyl)-6,7-dihydropyrazolo[1,5-a]pyrazine-5(4H)-carboxylate

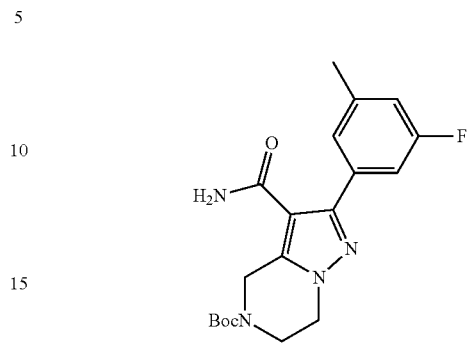

To a solution of Intermediate 156C (500 mg, 1.275 mmol) and (3-fluoro-5-methylphenyl)boronic acid (294 mg, 1.912 mmol) in 1,4-dioxane (10 mL) was added $K_3PO_4$ (812 mg, 3.82 mmol) in water (1 mL) and reaction mixture was degassed with $N_2$ for 15 min. $PdCl_2(dppf)CH_2Cl_2$ (62.5 mg, 0.076 mmol) was added and the reaction mixture was heated at 85° C. and stirred for 12 h. The reaction mixture was concentrated under a reduced pressure and the crude product was purified by silica gel chromatography (24 g REDISEP® column, eluting with 65% EtOAc in hexanes). Fractions containing the product were combined and evaporated to afford the Intermediate 223A as a pale yellow solid (0.4 g, 84%). MS(ES): m/z=375.2 [M+H]$^+$; $^1$H NMR (300 MHz, DMSO-d$_6$) δ ppm 7.34 (d, J=0.8 Hz, 2H), 7.28-7.21 (m, 1H), 7.15-7.07 (m, 1H), 7.07-7.00 (m, 1H), 4.73 (s, 2H), 4.15 (t, J=5.3 Hz, 2H), 3.88-3.80 (m, 2H), 2.35 (s, 3H), 1.45 (s, 9H).

Intermediate 223B: 2-(3-Fluoro-5-methylphenyl)-4,5,6,7-tetrahydropyrazolo[1,5-a]pyrazine-3-carboxamide

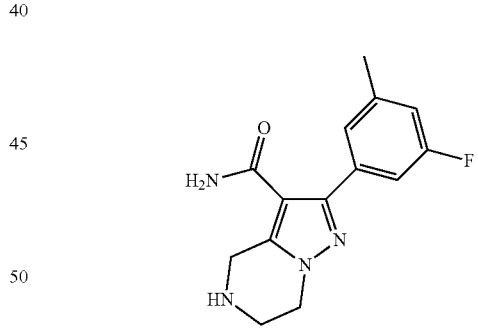

To a solution of Intermediate 223A (400 mg, 1.068 mmol) in DCM (4 mL) was added TFA (2.5 mL) at 0° C. and the resulting solution was allowed to warm to RT and stirred for 2 h. The volatiles were removed under a reduced pressure and the crude product was triturated with Et$_2$O (2×20 mL). The TFA salt was suspended in a 10% aqueous solution of NaOH and stirred vigorously at RT for 2 h. The solid product separated was filtered, washed with water, azeotroped with toluene to afford Intermediate 223B as an off-white solid (0.210 g, 71%). MS(ES): m/z=275.1 [M+H]$^+$; $^1$H NMR (300 MHz, DMSO-d$_6$) δ ppm 9.38 (br. s., 1H), 7.42 (br. s., 1H), 7.33 (s, 1H), 7.24 (d, J=9.4 Hz, 1H), 7.08 (d, J=9.4 Hz, 2H), 4.55 (s, 2H), 4.36 (t, J=5.7 Hz, 2H), 3.69 (t, J=5.7 Hz, 2H), 2.36 (s, 3H).

Compound 223: 2-(3-Fluoro-5-methylphenyl)-N-(4-(trifluoromethyl)phenyl)-6,7-dihydropyrazolo[1,5-a]pyrazine-3,5(4H)-dicarboxamide

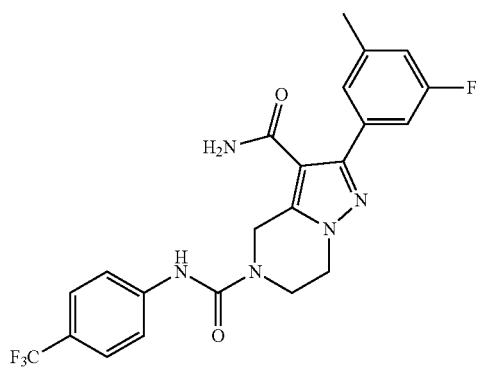

To a solution of 4-(trifluoromethyl)aniline (29.0 mg, 0.180 mmol) and TEA (0.063 mL, 0.449 mmol) in THF (3 mL) was added triphosgene (26.7 mg, 0.090 mmol) at 0° C. and the resulting solution was stirred at the same temperature for 30 min. A solution of Intermediate 223B (25 mg, 0.090 mmol) in THF (2 mL) was added and the reaction mixture was stirred at RT for 3 h. The reaction mixture was quenched with water and extracted with ethyl acetate (3×5 mL). The combined organic layer was washed with a 10% aqueous solution of NaHCO$_3$, brine, dried over Na$_2$SO$_4$, filtered and the filtrate concentrated. The crude product was purified by preparative HPLC to afford Compound 223 as a white solid (22 mg, 51%). HPLC retention times 1.65 min. (Method E). MS(ES): m/z=462 [M+H]$^+$; $^1$H NMR (400 MHz, DMSO-d$_6$) δ ppm 9.30 (s, 1H), 7.67-7.74 (m, 2H), 7.59-7.66 (m, 2H), 7.36 (s, 2H), 7.28 (d, J=10.04 Hz, 1H), 7.13 (br. s., 1H), 7.04 (d, J=9.54 Hz, 1H), 4.91 (s, 2H), 4.24 (t, J=5.27 Hz, 2H), 4.01 (t, J=5.27 Hz, 2H), 2.30-2.35 (s, 3H).

The Compounds shown in Table 9 have been prepared similar to Compound 223 by reaction of Intermediate 223B with respective anilines phenylcarbamates or with readily available/in-situ generated isocyanates.

TABLE 9

| Ex. No. | Structure | Name | [M + H]$^+$ | Ret Time (min.) | HPLC Methods |
|---|---|---|---|---|---|
| 224 | 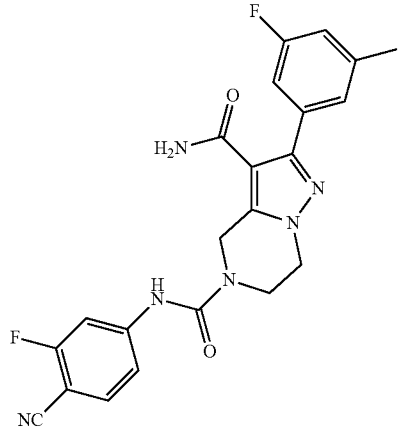 [SMILES: Cc1cc(F)cc(-c2nn3c(c2C(N)=O)CN(C(=O)Nc2ccc(C#N)c(F)c2)CC3)c1] | N$^5$-(4-Cyano-3-fluorophenyl)-2-(3-fluoro-5-methylphenyl)-6,7-dihydropyrazolo[1,5-a]pyrazine-3,5(4H)-dicarboxamide | 437.0 | 1.44 | E |
| 225 | 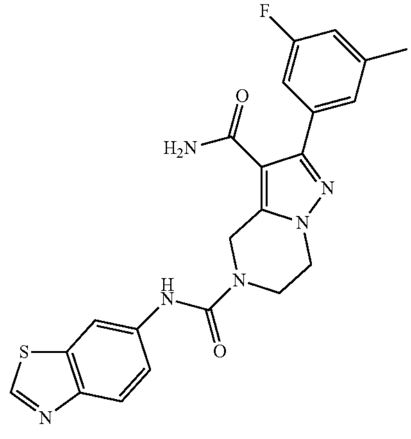 [SMILES: Cc1cc(F)cc(-c2nn3c(c2C(N)=O)CN(C(=O)Nc2ccc4ncsc4c2)CC3)c1] | N$^5$-(Benzo[d]thiazol-6-yl)-2-(3-fluoro-5-methylphenyl)-6,7-dihydropyrazolo[1,5-a]pyrazine-3,5(4H)-dicarboxamide | 451.0 | 1.23 | E |

TABLE 9-continued

| Ex. No. | Structure | Name | [M + H]+ | Ret Time (min.) | HPLC Methods |
|---|---|---|---|---|---|
| 226 | 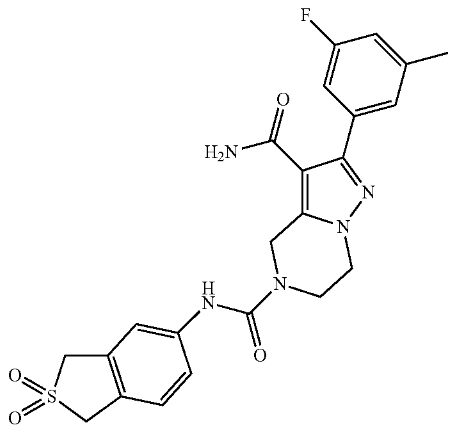 [SMILES: Cc1cc(F)cc(-c2nn3c(c2C(N)=O)CN(C(=O)Nc2ccc4c(c2)CS(=O)(=O)C4)CC3)c1] | N5-(2,2-Dioxido-1,3-dihydrobenzo[c]thiophen-5-yl)-2-(3-fluoro-5-methylphenyl)-6,7-dihydropyrazolo[1,5-a]pyrazine-3,5(4H)-dicarboxamide | 484.0 | 1.14 | E |
| 227 | 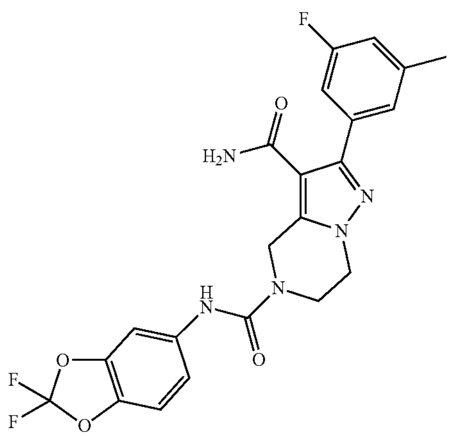 [SMILES: Cc1cc(F)cc(-c2nn3c(c2C(N)=O)CN(C(=O)Nc2ccc4c(c2)OC(F)(F)O4)CC3)c1] | N5-(2,2-Difluorobenzo[d][1,3]dioxol-5-yl)-2-(3-fluoro-5-methylphenyl)-6,7-dihydropyrazolo[1,5-a]pyrazine-3,5(4H)-dicarboxamide | 474.0 | 1.62 | E |
| 228 | 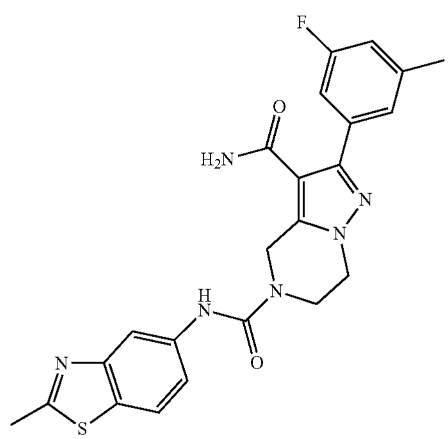 | 2-(3-Fluoro-5-methylphenyl)-N5-(2-methylbenzo[d]thiazol-5-yl)-6,7-dihydropyrazolo[1,5-a]pyrazine-3,5(4H)-dicarboxamide | 465.0 | 1.31 | E |

TABLE 9-continued
| Ex. No. | Structure | Name | [M + H]+ | Ret Time (min.) | HPLC Methods |
|---|---|---|---|---|---|
| 229 | 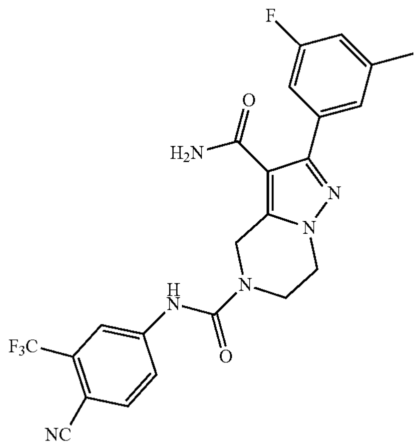 [SMILES: Cc1cc(F)cc(-c2nn3c(c2C(N)=O)CN(C(=O)Nc2ccc(C#N)c(C(F)(F)F)c2)CC3)c1] | $N^5$-(4-Cyano-3-(trifluoromethyl)phenyl)-2-(3-fluoro-5-methylphenyl)-6,7-dihydropyrazolo[1,5-a]pyrazine-3,5(4H)-dicarboxamide | 487.0 | 1.61 | E |
| 230 | 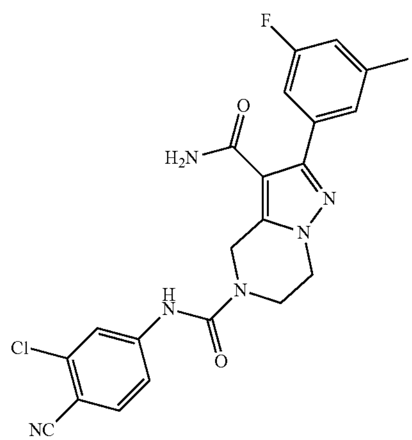 [SMILES: Cc1cc(F)cc(-c2nn3c(c2C(N)=O)CN(C(=O)Nc2ccc(C#N)c(Cl)c2)CC3)c1] | $N^5$-(3-Chloro-4-cyanophenyl)-2-(3-fluoro-5-methylphenyl)-6,7-dihydropyrazolo[1,5-a]pyrazine-3,5(4H)-dicarboxamide | 452.9 | 1.51 | E |
Scheme 10
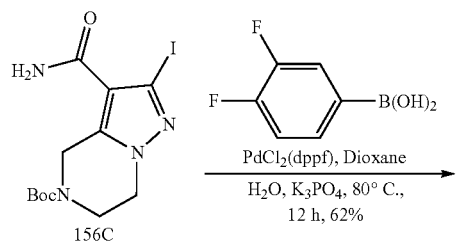
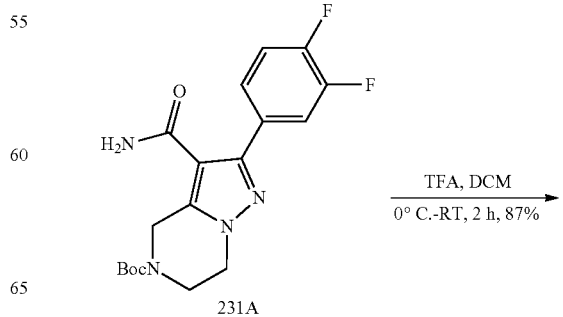

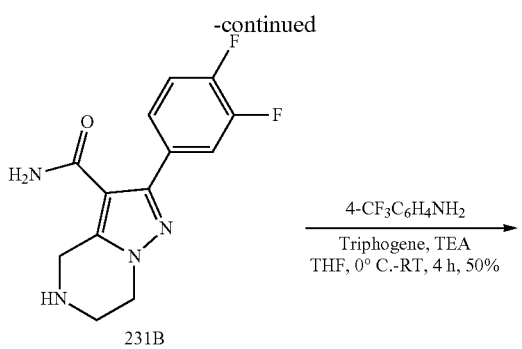

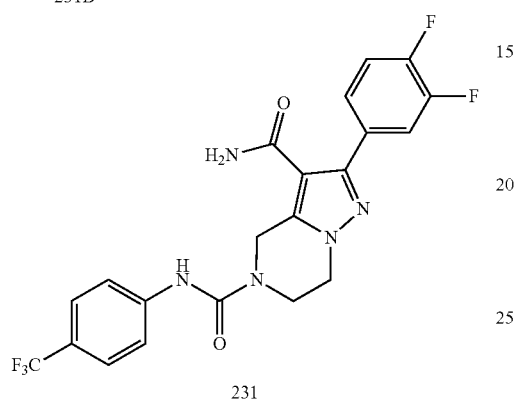

Intermediate 231A: tert-Butyl 3-carbamoyl-2-(3,4-difluorophenyl)-6,7-dihydropyrazolo[1,5-a]pyrazine-5(4H)-carboxylate

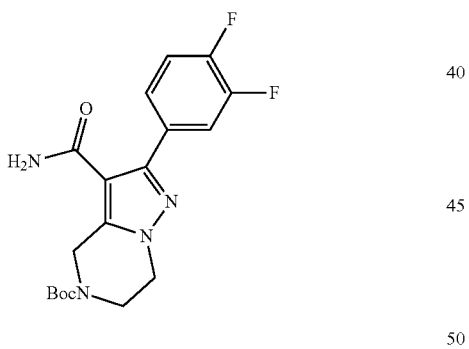

To a solution of Intermediate 156C (1.0 g, 2.55 mmol) and (3,4-difluorophenyl) boronic acid (0.604 g, 3.82 mmol) in 1,4-dioxane (10 mL) was added K₃PO₄ (1.624 g, 7.65 mmol) in water (2 mL) and the reaction mixture was purged with nitrogen for 5 min. PdCl₂(dppf)-CH₂Cl₂ (0.125 g, 0.153 mmol) was added, the reaction mixture was heated to 80° C. and stirred for 5 h. The reaction mixture was quenched with water and extracted with ethyl acetate (3×25 mL). The combined organic layer was washed with water, brine, dried over Na₂SO₄, filtered and the filtrate concentrated. The crude was purified by silica gel chromatography (40 g REDISEP® column, eluting with 5% MeOH in CHCl₃). Fractions containing the product were combined and evaporated to afford the Intermediate 231A as a white solid (0.6 g, 62%). MS(ES): m/z=379 [M+H]⁺; ¹H NMR (400 MHz, DMSO-d₆) δ ppm 7.69 (ddd, J=12.30, 8.03, 1.76 Hz, 1H), 7.42-7.58 (m, 2H), 7.30 (br. s., 1H), 7.16 (br. s., 1H), 4.74 (s, 2H), 4.11-4.22 (m, 2H), 3.85 (d, J=5.52 Hz, 2H), 1.46 (s, 9).

Intermediate 231B: 2-(3,4-Difluorophenyl)-4,5,6,7-tetrahydropyrazolo[1,5-a]pyrazine-3-carboxamide

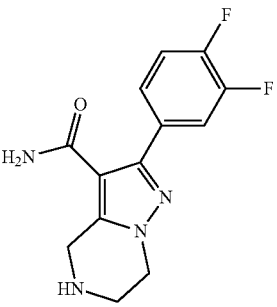 [SMILES: NC(=O)c1c(-c2ccc(F)c(F)c2)nn2c1CNCC2]

To the solution of Intermediate 231A (0.5 g, 1.321 mmol) in DCM (10 mL) at 0° C. was added TFA (0.509 mL, 6.61 mmol) and the resulting solution was stirred at RT for 3 h. The volatiles were removed under reduced pressure and the residue was suspended in a 10% aqueous solution of NaOH (10 mL) and stirred for 30 min. The solid filtered through a Buchner funnel, rinsed with diethyl ether and dried to afford Intermediate 231B (0.32 g, 87%). MS(ES): m/z=279 [M+H]⁺; ¹H NMR (300 MHz, DMSO-d₆) δ ppm 7.71 (ddd, J=12.28, 7.93, 2.08 Hz, 1H), 7.39-7.60 (m, 1H), 6.99-7.31 (m, 1H), 3.94-4.07 (m, 2H), 3.26-3.53 (m, 4H), 3.11 (q, J=5.67 Hz, 1H).

Compound 231: 2-(3,4-Difluorophenyl)-N⁵-(4-(trifluoromethyl)phenyl)-6,7-dihydropyrazolo[1,5-a]pyrazine-3,5(4H)-dicarboxamide

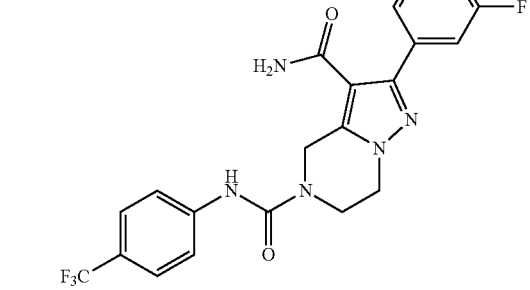

To a solution of 4-(trifluoromethyl)aniline (29.0 mg, 0.180 mmol) and TEA (0.063 mL, 0.449 mmol) in THF (3 mL) was added triphosgene (26.7 mg, 0.090 mmol) at 0° C. and the resulting solution was stirred at the same temperature for 30 min. A solution of Intermediate 231B (25 mg, 0.090 mmol) in THF (2 mL) was added and the reaction mixture was stirred at RT for 3 h. The reaction mixture was quenched with water and extracted with ethyl acetate (3×5 mL). The combined organic layer was washed with a 10% aqueous solution of NaHCO$_3$, brine, dried over Na$_2$SO$_4$, filtered and the filtrate concentrated. The crude product was purified by preparative HPLC to afford Compound 231 as a white solid (21 mg, 50%). HPLC retention time is 1.58 min. (Method E). MS(ES): m/z=466 [M+H]$^+$; $^1$H NMR (400 MHz, DMSO-d$_6$) δ ppm 9.31 (s, 1H), 7.66-7.78 (m, 3H), 7.62 (s, 2H), 7.44-7.59 (m, 2H), 7.37 (br. s., 1H), 7.20 (br. s., 1H), 4.92 (s, 2H), 4.25 (d, J=10.54 Hz, 2H), 4.01 (d, J=10.54 Hz, 2H).

The Compounds shown in Table 10 have been prepared similar to Compound 231 by coupling of Intermediate 231B with various readily available isocyanates or in-situ generated from respective anilines.

TABLE 10

| Ex. No. | Structure | Name | [M + H]$^+$ | Ret Time (min.) | HPLC Methods |
|---------|-----------|------|-------------|-----------------|--------------|
| 232 | 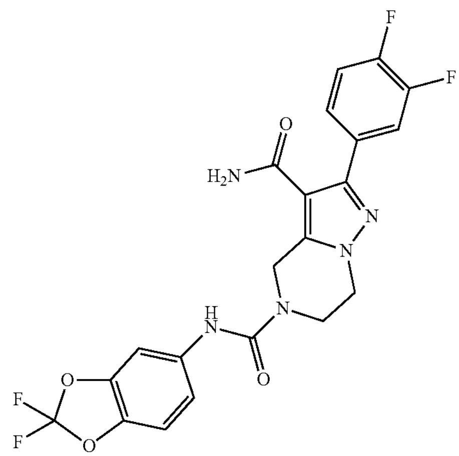 [SMILES: NC(=O)c1c(-c2ccc(F)c(F)c2)nn2c1CN(C(=O)Nc1ccc3c(c1)OC(F)(F)O3)CC2] | N$^5$-(2,2-Difluorobenzo[d][1,3]dioxol-5-yl)-2-(3,4-difluorophenyl)-6,7-dihydropyrazolo[1,5-a]pyrazine-3,5(4H)-dicarboxamide | 478.0 | 1.56 | E |
| 233 | 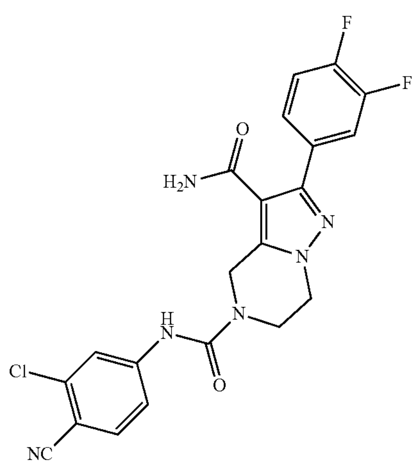 [SMILES: N#Cc1ccc(NC(=O)N2CCn3nc(-c4ccc(F)c(F)c4)c(C(N)=O)c3C2)cc1Cl] | N$^5$-(3-Chloro-4-cyanophenyl)-2-(3,4-difluorophenyl)-6,7-dihydropyrazolo[1,5-a]pyrazine-3,5(4H)-dicarboxamide | 455.0 | 1.43 | E |
| 234 | 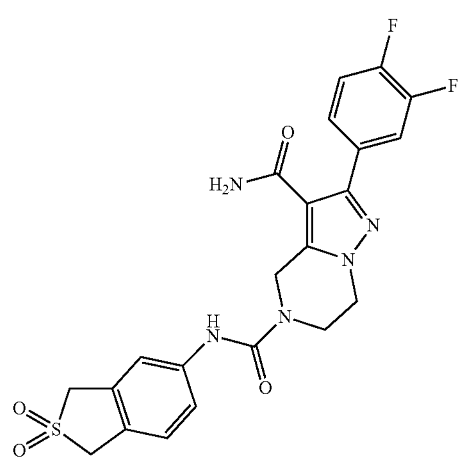 [SMILES: NC(=O)c1c(-c2ccc(F)c(F)c2)nn2c1CN(C(=O)Nc1ccc3c(c1)CS(=O)(=O)C3)CC2] | 2-(3,4-Difluorophenyl)-N$^5$-(2,2-dioxido-1,3-dihydrobenzo[c]thiophen-5-yl)-6,7-dihydropyrazolo[1,5-a]pyrazine-3,5(4H)-dicarboxamide | 488.0 | 1.07 | E |

TABLE 10-continued

| Ex. No. | Structure | Name | [M + H]+ | Ret Time (min.) | HPLC Methods |
|---|---|---|---|---|---|
| 235 | 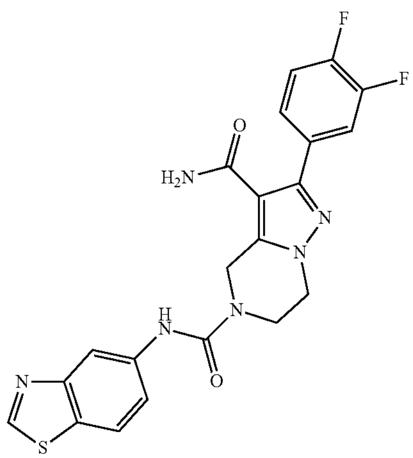 [SMILES: NC(=O)c1c(-c2ccc(F)c(F)c2)nn2c1CN(C(=O)Nc1ccc3scnc3c1)CC2] | N5-(Benzo[d]thiazol-6-yl)-2-(3,4-difluorophenyl)-6,7-dihydropyrazolo[1,5-a]pyrazine-3,5(4H)-dicarboxamide | 455.0 | 1.14 | E |
| 236 | 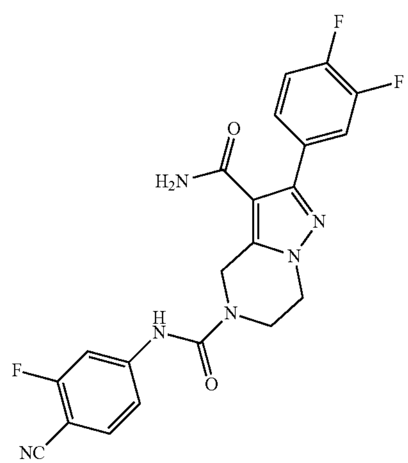 [SMILES: N#Cc1ccc(NC(=O)N2CCn3nc(-c4ccc(F)c(F)c4)c(C(N)=O)c3C2)cc1F] | N5-(4-Cyano-3-fluorophenyl)-2-(3,4-difluorophenyl)-6,7-dihydropyrazolo[1,5-a]pyrazine-3,5(4H)-dicarboxamide | 439.0 | 1.36 | E |
| 237 | 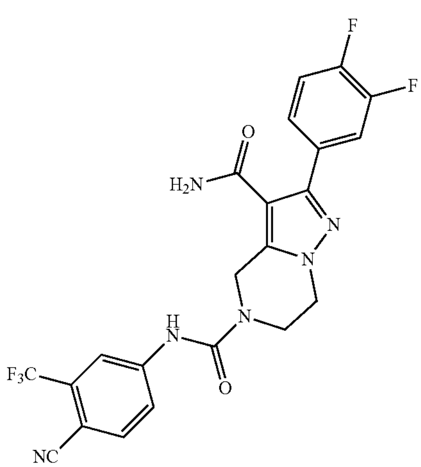 [SMILES: N#Cc1ccc(NC(=O)N2CCn3nc(-c4ccc(F)c(F)c4)c(C(N)=O)c3C2)cc1C(F)(F)F] | N5-(4-Cyano-3-(trifluoromethyl)phenyl)-2-(3,4-difluorophenyl)-6,7-dihydropyrazolo[1,5-a]pyrazine-3,5(4H)-dicarboxamide | 491.0 | 1.54 | E |

TABLE 10-continued

| Ex. No. | Structure | Name | [M + H]+ | Ret Time (min.) | HPLC Methods |
|---|---|---|---|---|---|
| 238 | 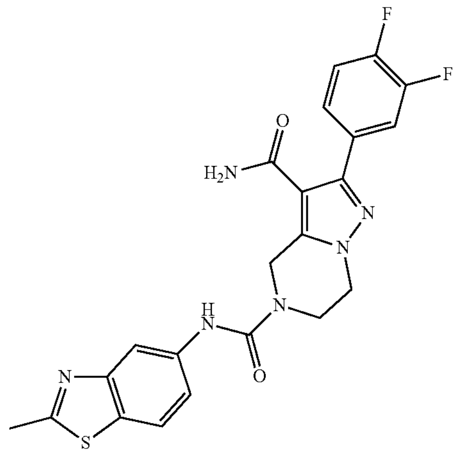 [SMILES: Cc1nc2cc(NC(=O)N3CCn4nc(-c5ccc(F)c(F)c5)c(C(N)=O)c4C3)ccc2s1] | 2-(3,4-Difluorophenyl)-N⁵-(2-methylbenzo[d]thiazol-5-yl)-6,7-dihydropyrazolo[1,5-a]pyrazine-3,5(4H)-dicarboxamide | 469.0 | 1.25 | E |

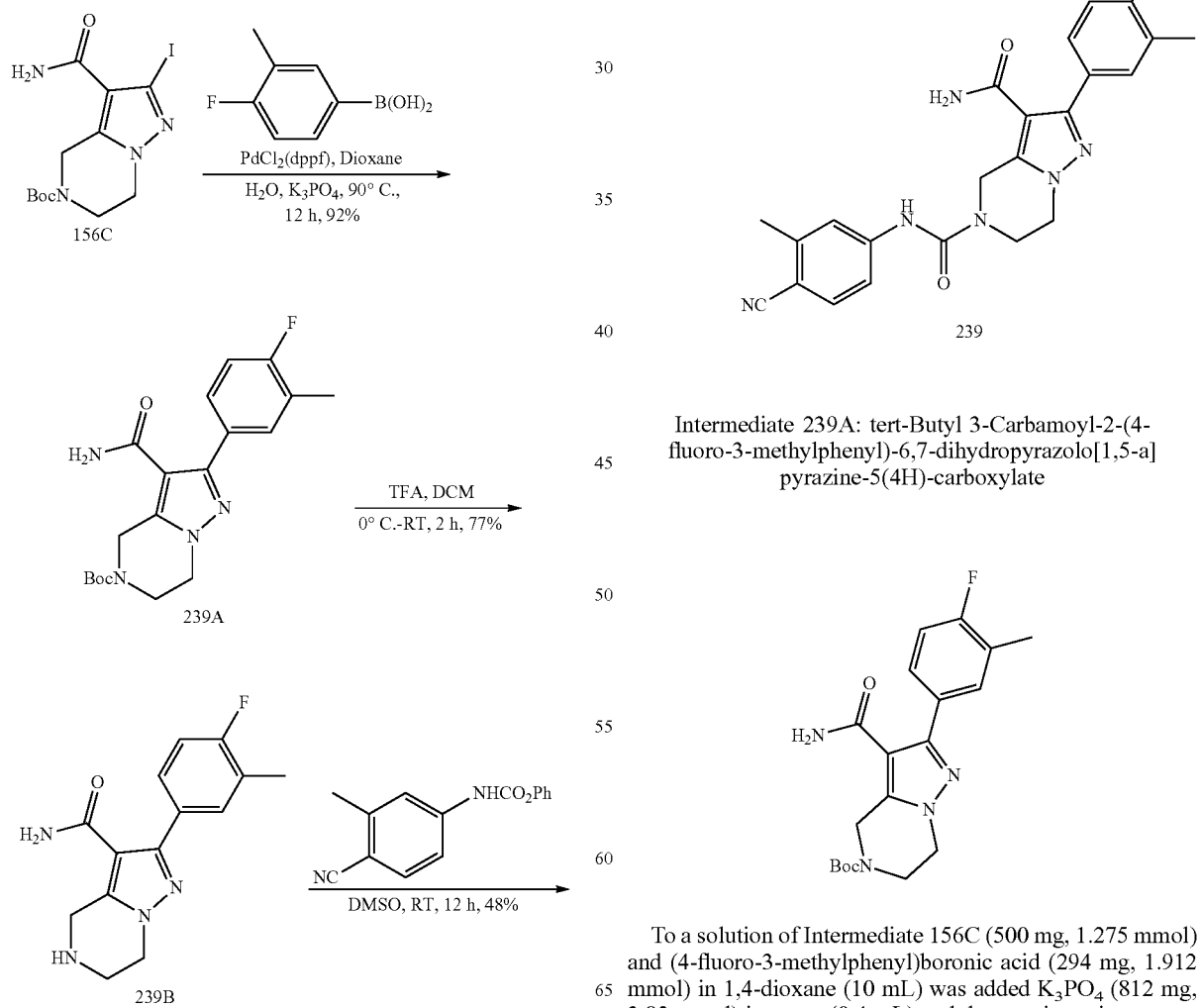

Intermediate 239A: tert-Butyl 3-Carbamoyl-2-(4-fluoro-3-methylphenyl)-6,7-dihydropyrazolo[1,5-a]pyrazine-5(4H)-carboxylate To a solution of Intermediate 156C (500 mg, 1.275 mmol) and (4-fluoro-3-methylphenyl)boronic acid (294 mg, 1.912 mmol) in 1,4-dioxane (10 mL) was added $K_3PO_4$ (812 mg, 3.82 mmol) in water (0.4 mL) and the reaction mixture was degassed with $N_2$ for 15 min. $PdCl_2$(dppf)$CH_2Cl_2$ (62.5 mg, 0.076 mmol) was added and the reaction mixture was heated to 85° C. and stirred for 14 h. The reaction mixture was concentrated under reduced pressure and the crude product was purified by silica gel chromatography (24 g REDISEP® column, eluting with 65% EtOAc in hexanes). Fractions containing the product were combined and evaporated to afford Intermediate 239A as a pale yellow solid (0.44 g, 92%). $^1$H NMR (300 MHz, DMSO-$d_6$) δ ppm 7.54 (d, J=7.2 Hz, 1H), 7.47 (ddd, J=2.3, 5.4, 8.2 Hz, 1H), 7.24 (hr. s., 1H), 7.22-7.13 (m, 1H), 6.88 (br. s., 1H), 4.73 (s, 2H), 4.14 (t, J=5.5 Hz, 2H), 3.84 (t, J=5.3 Hz, 2H), 2.26 (d, J=1.5 Hz, 3H), 1.45 (s, 9H).

Intermediate 239B: 2-(4-Fluoro-3-methylphenyl)-4,5,6,7-tetrahydropyrazolo[1,5-a]pyrazine-3-carboxamide

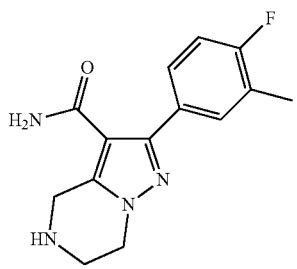 [SMILES: Cc1cc(-c2nn3c(c2C(N)=O)CNCC3)ccc1F]

To a solution of Intermediate 239A (440 mg, 1.175 mmol) in DCM (5 mL) was added TFA (4 mL) at 0° C. and the resulting solution was allowed to warm to RT and stirred for 2 h. The volatiles were removed under pressure and the residue was triturated with Et$_2$O (2×20 mL). The solid compound was suspended in a 10% aqueous solution of NaOH and stirred vigorously at RT for 2 h. The solid was filtered, washed with water and azeotroped with toluene to afford Intermediate 239B as a brown color solid (0.250 g, 77%). MS(ES): m/z=275.2 [M+H]$^+$. $^1$H NMR (300 MHz, DMSO-$d_6$) δ ppm 7.56 (d, J=7.9 Hz, 1H), 7.49 (ddd, J=2.3, 5.3, 8.3 Hz, 1H), 7.21-7.08 (m, 2H), 6.85 (br. s., 1H), 4.06-3.95 (m, 4H), 3.11 (d, J=4.9 Hz, 2H), 2.62 (br. s., 1H), 2.25 (d, J=1.5 Hz, 3H).

Compound 239: $N^5$-(4-Cyano-3-methylphenyl)-2-(4-fluoro-3-methylphenyl)-6,7-dihydropyrazolo[1,5-a]pyrazine-3,5(4H)-dicarboxamide

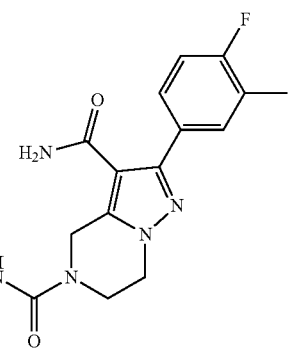

To a stirred solution of Intermediate 239B (30 mg, 0.109 mmol) in DMSO (1 mL) was added phenyl(4-cyano-3-methylphenyl)carbamate (41.4 mg, 0.164 mmol) and the resulting solution was stirred at RT for 12 h. The reaction mixture was diluted with water and solid product was separated isolated and purified by reverse phase preparative HPLC to afford Compound 239 as a white solid (23 mg, 48%). HPLC retention times are 8.47 min. and 8.96 min. (Methods A and B respectively). MS(ES): m/z=433 [M+H]$^+$; $^1$H NMR: (400 MHz, DMSO-$d_6$) δ ppm 9.32 (s, 1H), 7.65 (d, J=8.53 Hz, 1H), 7.57 (s, 2H), 7.45-7.53 (m, 2H), 7.30 (br. s., 1H), 7.14-7.23 (m, 1H), 6.91 (br. s., 1H), 4.90 (s, 2H), 4.22 (t, J=5.27 Hz, 2H), 4.00 (t, J=5.27 Hz, 2H), 2.40-2.47 (m, 3H), 2.27 (d, J=1.51 Hz, 3H).

The Compounds shown in Table 11 have been prepared similar to Compound 239 by reaction of Intermediate 239B with respective anilines phenylcarbamates or with readily available/in-situ generated isocyanates.

TABLE 11

| Ex. No. | Structure | Name | [M + H]$^+$ | Ret Time (min.) | HPLC Methods |
|---|---|---|---|---|---|
| 240 | 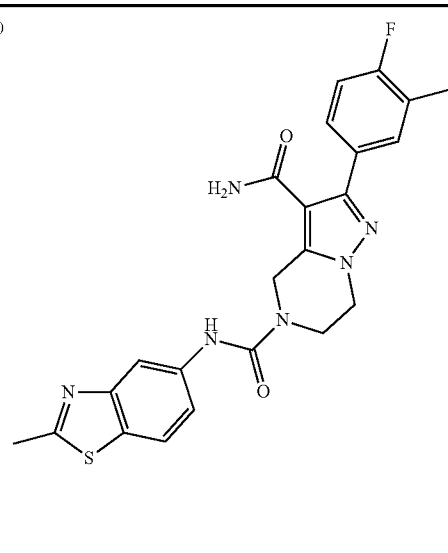 | 2-(4-Fluoro-3-methylphenyl)-$N^5$-(2-methylbenzo[d]thiazol-5-yl)-6,7-dihydropyrazolo[1,5-a]pyrazine-3,5(4H)-dicarboxamide | 465.0 | 1.30 | E |

TABLE 11-continued

| Ex. No. | Structure | Name | [M + H]+ | Ret Time (min.) | HPLC Methods |
|---|---|---|---|---|---|
| 241 | 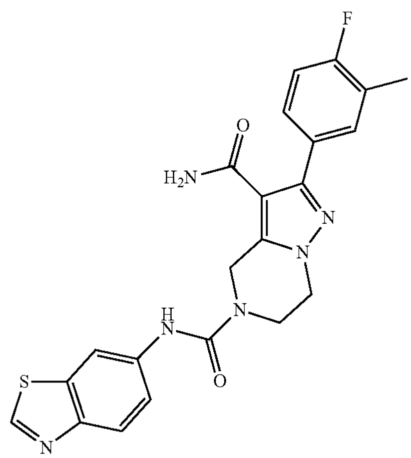 [SMILES: Cc1cc(-c2nn3c(c2C(N)=O)CN(C(=O)Nc2ccc4ncsc4c2)CC3)ccc1F] | N5-(Benzo[d]thiazol-6-yl)-2-(4-fluoro-3-methylphenyl)-6,7-dihydropyrazolo[1,5-a]pyrazine-3,5(4H)-dicarboxamide | 451.0 | 1.20 | E |
| 242 | 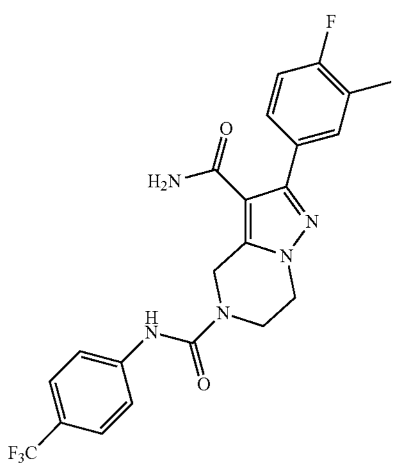 [SMILES: Cc1cc(-c2nn3c(c2C(N)=O)CN(C(=O)Nc2ccc(C(F)(F)F)cc2)CC3)ccc1F] | 2-(4-Fluoro-3-methylphenyl)-N5-(4-(trifluoromethyl)phenyl)-6,7-dihydropyrazolo[1,5-a]pyrazine-3,5(4H)-dicarboxamide | 462.0 | 1.64 | E |
| 243 | 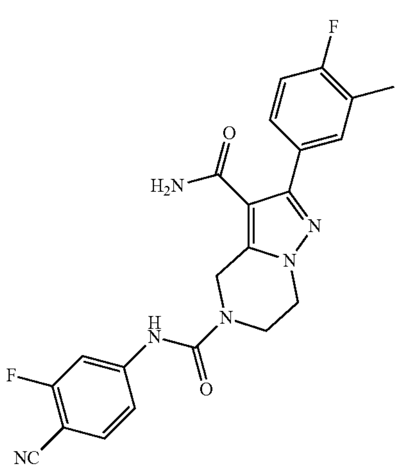 [SMILES: Cc1cc(-c2nn3c(c2C(N)=O)CN(C(=O)Nc2ccc(C#N)c(F)c2)CC3)ccc1F] | N5-(4-Cyano-3-fluorophenyl)-2-(4-fluoro-3-methylphenyl)-6,7-dihydropyrazolo[1,5-a]pyrazine-3,5(4H)-dicarboxamide | 437.0 | 1.42 | E |

TABLE 11-continued

| Ex. No. | Structure | Name | [M + H]+ | Ret Time (min.) | HPLC Methods |
|---|---|---|---|---|---|
| 244 | 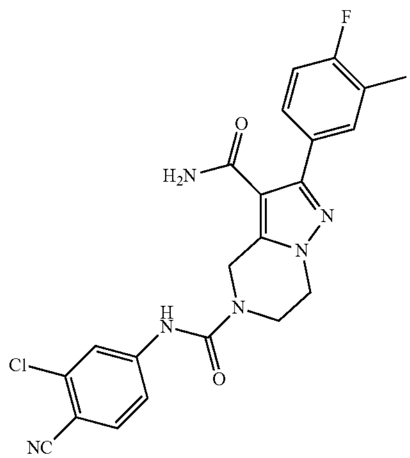 [SMILES: Cc1cc(-c2nn3c(c2C(N)=O)CN(C(=O)Nc2ccc(C#N)c(Cl)c2)CC3)ccc1F] | N5-(3-Chloro-4-cyanophenyl)-2-(4-fluoro-3-methylphenyl)-6,7-dihydropyrazolo[1,5-a]pyrazine-3,5(4H)-dicarboxamide | 453 | 1.49 | E |
| 245 | 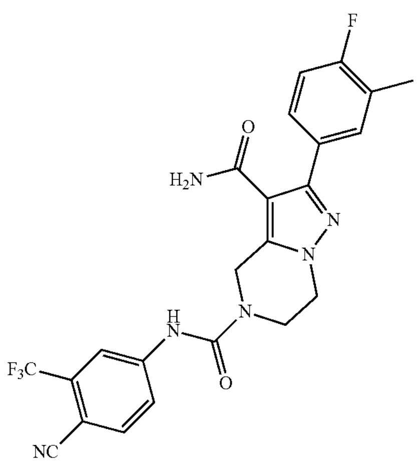 [SMILES: Cc1cc(-c2nn3c(c2C(N)=O)CN(C(=O)Nc2ccc(C#N)c(C(F)(F)F)c2)CC3)ccc1F] | N5-(4-Cyano-3-(trifluoromethyl)phenyl)-2-(4-fluoro-3-methylphenyl)-6,7-dihydropyrazolo[1,5-a]pyrazine-3,5(4H)-dicarboxamide | 487.0 | 1.61 | E |
| 246 | 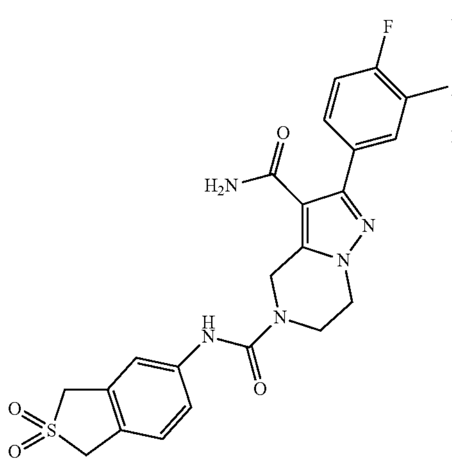 | N5-(2,2-Dioxido-1,3-dihydrobenzo[c]thiophen-5-yl)-2-(4-fluoro-3-methylphenyl)-6,7-dihydropyrazolo[1,5-a]pyrazine-3,5(4H)-dicarboxamide | 484.0 | 1.13 | E |

TABLE 11-continued
| Ex. No. | Structure | Name | [M + H]$^+$ | Ret Time (min.) | HPLC Methods |
|---|---|---|---|---|---|
| 247 | 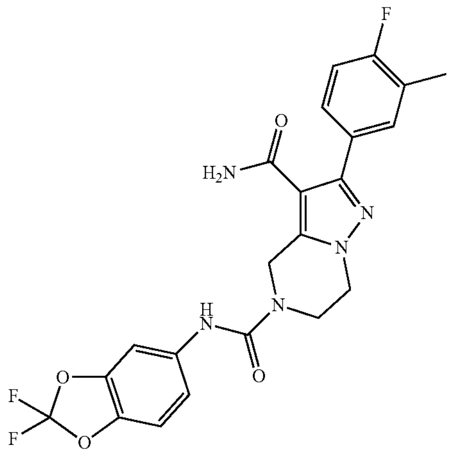 [SMILES: Cc1cc(-c2nn3c(c2C(N)=O)CN(C(=O)Nc2ccc4c(c2)OC(F)(F)O4)CC3)ccc1F] | N$^5$-(2,2-Difluorobenzo[d][1,3]dioxol-5-yl)-2-(4-fluoro-3-methylphenyl)-6,7-dihydropyrazolo[1,5-a]pyrazine-3,5(4H)-dicarboxamide | 474.0 | 1.60 | E |
| 248 | 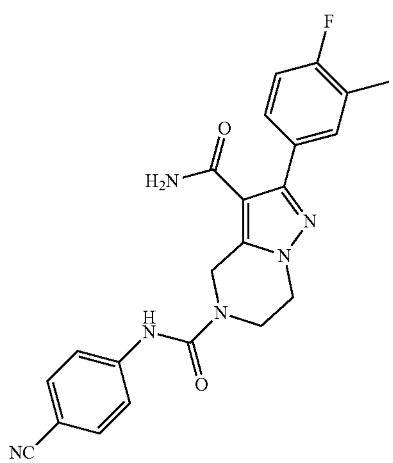 [SMILES: Cc1cc(-c2nn3c(c2C(N)=O)CN(C(=O)Nc2ccc(C#N)cc2)CC3)ccc1F] | N$^5$-(4-Cyanophenyl)-2-(4-fluoro-3-methylphenyl)-6,7-dihydropyrazolo[1,5-a]pyrazine-3,5(4H)-dicarboxamide | 419.0 | 1.27 | E |
Scheme 12
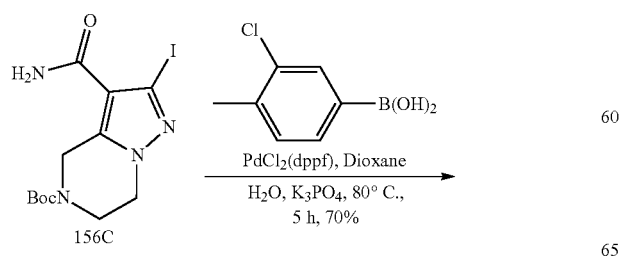
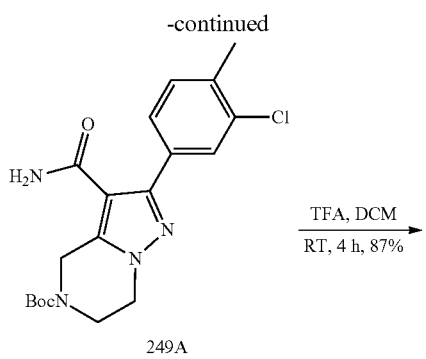
-continued

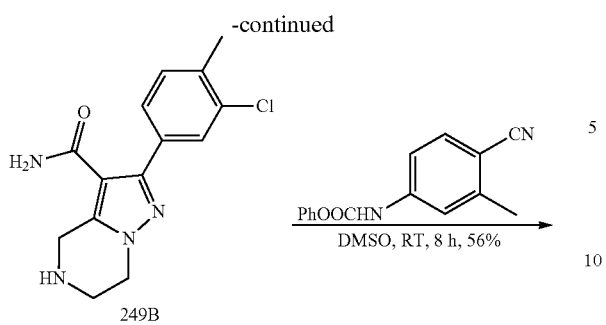

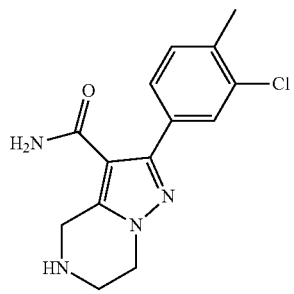 [SMILES: Cc1ccc(-c2nn3c(c2C(N)=O)CNCC3)cc1Cl]

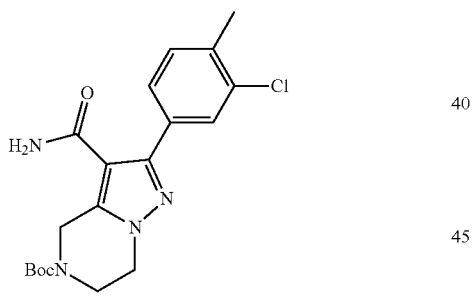

Intermediate 249A: tert-Butyl 3-carbamoyl-2-(3-chloro-4-methylphenyl)-6,7-dihydropyrazolo[1,5-a]pyrazine-5(4H)-carboxylate To a solution of Intermediate 156C (1 g, 2.55 mmol) in 1,4-dioxane (15 mL) and water (1.5 mL) was added (3-chloro-4-methylphenyl)boronic acid (0.652 g, 3.82 mmol), K₃PO₄ (1.624 g, 7.65 mmol) and the reaction mixture was purged with N₂ for 5 min. PdCl₂(dppf)-CH₂Cl₂ adduct (0.125 g, 0.153 mmol) was added and the reaction mixture was heated to 80° C. and stirred for 5 h. The reaction mixture was cooled to RT, filtered through CELITE® pad and the filtrate was concentrated under vacuum. The crude product was diluted with water and extracted with ethyl acetate (3×25 mL). The combined organic layer was washed with brine, dried over Na₂SO₄ and concentrated. The crude product was purified by silica gel chromatography (40 g REDISEP® column, eluting with 5% MeOH in CHCl₃). Fractions containing the product were combined and evaporated to afford the Compound 249A as a pale brown solid (0.68 g, 70%). MS(ES): m/z=391 [M+1]⁺; ¹H NMR (300 MHz, DMSO-d₆) δ ppm 7.69 (d, J=1.5 Hz, 1H), 7.56-7.51 (m, 1H), 7.40 (s, 1H), 7.34-7.26 (m, 1H), 7.16-7.06 (m, 1H), 4.73 (s, 2H), 4.15 (s, 2H), 3.84 (s, 2H), 2.35 (s, 3H), 1.45 (s, 9H).

Intermediate 249B: 2-(3-Chloro-4-methylphenyl)-4,5,6,7-tetrahydropyrazolo[1,5-a]pyrazine-3-carboxamide

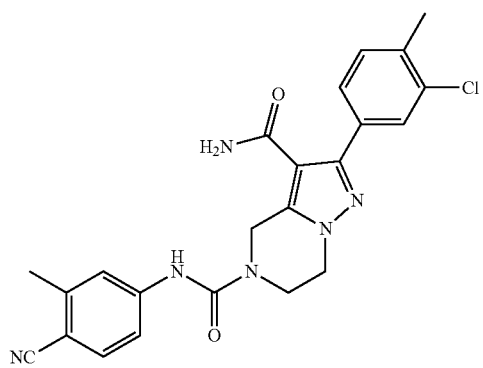 [SMILES: Cc1ccc(-c2nn3c(c2C(N)=O)CN(C(=O)Nc2ccc(C#N)c(C)c2)CC3)cc1Cl]

To a solution of Intermediate 249A (680 mg, 1.740 mmol) in DCM (5 mL) was added TFA (2.011 mL, 26.1 mmol) dropwise at 0° C. and the resulting solution was warmed to RT and stirred for 4 h. The reaction mixture was concentrated and the crude product was suspended in a 20% aqueous solution of NaOH at 0° C. and stirred at RT for 2 h. The solid separated was filtered and dried to afford Intermediate 249B as a grey solid (450 mg, 87%). MS(ES): m/z=291 [M+1]⁺; ¹H NMR (400 MHz, DMSO-d₆) δ ppm 7.71 (d, J=1.5 Hz, 1H), 7.55 (dd, J=7.8, 1.8 Hz, 1H), 7.36 (d, J=8.0 Hz, 1H), 7.25-6.97 (m, 2H), 4.06-3.91 (m, 4H), 3.12 (br. s., 2H), 2.69-2.58 (m, 1H), 2.35 (s, 3H).

Compound 249: 2-(3-Chloro-4-methylphenyl)-N⁵-(4-cyano-3-methylphenyl)-6,7-dihydropyrazolo[1,5-a]pyrazine-3,5(4H)-dicarboxamide To a stirred solution of Intermediate 249B (30 mg, 0.103 mmol) in DMSO (3 mL) was added phenyl(4-cyano-3-methylphenyl)carbamate (31.2 mg, 0.124 mmol) and the resulting solution was stirred at RT for 8 h. The reaction mixture was diluted with water, stirred vigorously for 5 min and the crude product separated was filtered and dried under vacuum. The crude product was purified by preparative HPLC to afford Compound 249 as an off-white solid (25.97 mg, 56%). HPLC retention times 8.79 min. and 9.72 min. (Methods B and A respectively). MS(ES): m/z=449 [M+1]⁺; ¹H NMR: (400 MHz, DMSO-d₆) δ ppm 9.32 (s, 1H), 7.71

(d, J=1.51 Hz, 1H), 7.65 (d, J=8.53 Hz, 1H), 7.45-7.59 (m, 3H), 7.30-7.44 (m, 2H), 7.14 (br. s., 1H), 4.90 (s, 2H), 4.24 (t, J=5.27 Hz, 2H), 4.00 (t, J=5.27 Hz, 2H), 2.43 (s, 3H), 2.31-2.39 (m, 3H).

The Compounds shown in Table 12 have been prepared similar to Compound 249 by reaction of Intermediate 249B with respective anilines phenylcarbamates or with readily available/in-situ generated isocyanates.

TABLE 12

| Ex. No. | Structure | Name | [M + H]⁺ | Ret Time (min.) | HPLC Methods |
|---------|-----------|------|----------|-----------------|--------------|
| 250 | 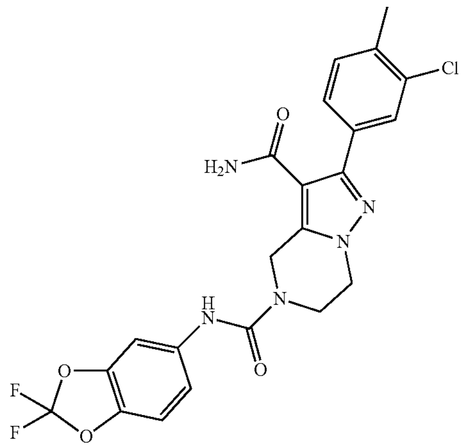 [SMILES: Cc1ccc(-c2nn3c(c2C(N)=O)CN(C(=O)Nc2ccc4c(c2)OC(F)(F)O4)CC3)cc1Cl] | 2-(3-Chloro-4-methylphenyl)-$N^5$-(2,2-difluorobenzo[d][1,3]dioxol-5-yl)-6,7-dihydropyrazolo[1,5-a]pyrazine-3,5(4H)-dicarboxamide | 490.0 | 1.73 | E |
| 251 | 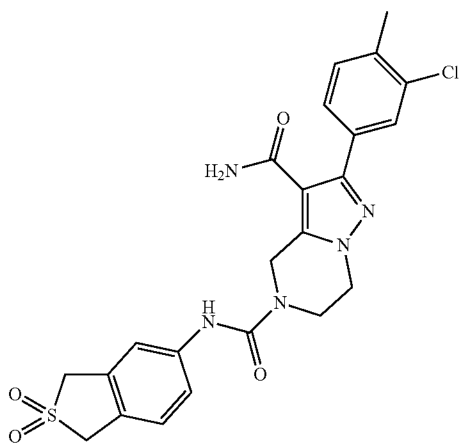 [SMILES: Cc1ccc(-c2nn3c(c2C(N)=O)CN(C(=O)Nc2ccc4c(c2)CS(=O)(=O)C4)CC3)cc1Cl] | 2-(3-Chloro-4-methylphenyl)-$N^5$-(2,2-dioxido-1,3-dihydrobenzo[c]thiophen-5-yl)-6,7-dihydropyrazolo[1,5-a]pyrazine-3,5(4H)-dicarboxamide | 500.0 | 1.26 | E |
| 252 | 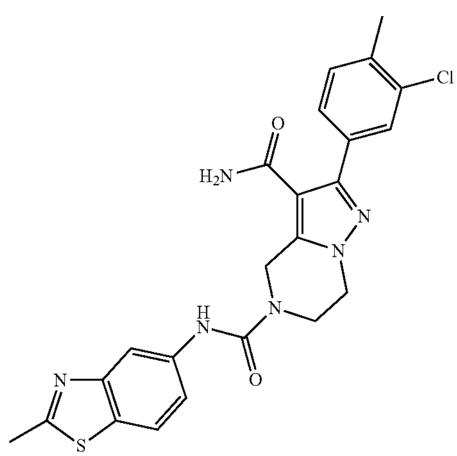 [SMILES: Cc1nc2cc(NC(=O)N3CCn4nc(-c5ccc(C)c(Cl)c5)c(C(N)=O)c4C3)ccc2s1] | 2-(3-Chloro-4-methylphenyl)-$N^5$-(2-methylbenzo[d]thiazol-5-yl)-6,7-dihydropyrazolo[1,5-a]pyrazine-3,5(4H)-dicarboxamide | 481.0 | 1.42 | E |

TABLE 12-continued

| Ex. No. | Structure | Name | [M + H]⁺ | Ret Time (min.) | HPLC Methods |
|---|---|---|---|---|---|
| 253 | 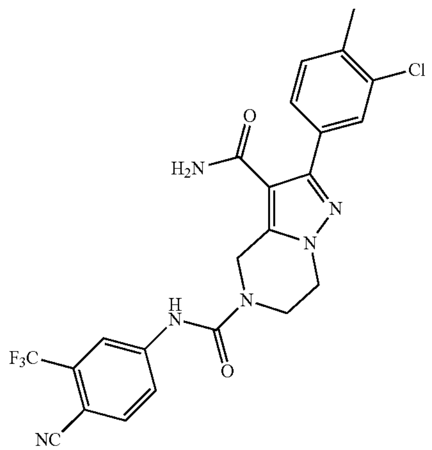 [SMILES: Cc1ccc(-c2nn3c(c2C(N)=O)CN(C(=O)Nc2ccc(C#N)c(C(F)(F)F)c2)CC3)cc1Cl] | 2-(3-Chloro-4-methylphenyl)-N⁵-(4-cyano-3-(trifluoromethyl)phenyl)-6,7-dihydropyrazolo[1,5-a]pyrazine-3,5(4H)-dicarboxamide | 503.0 | 1.73 | E |
| 254 | 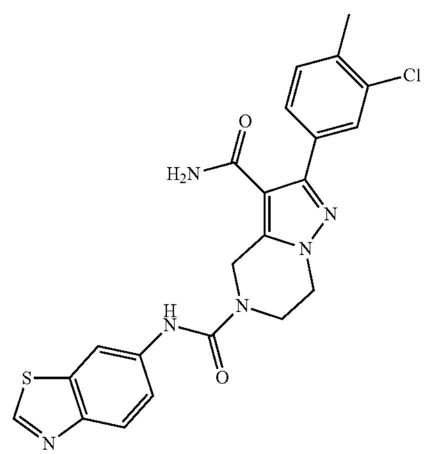 [SMILES: Cc1ccc(-c2nn3c(c2C(N)=O)CN(C(=O)Nc2ccc4ncsc4c2)CC3)cc1Cl] | N⁵-(Benzo[d]thiazol-6-yl)-2-(3-chloro-4-methylphenyl)-6,7-dihydropyrazolo[1,5-a]pyrazine-3,5(4H)-dicarboxamide | 467.0 | 1.34 | E |
| 255 | 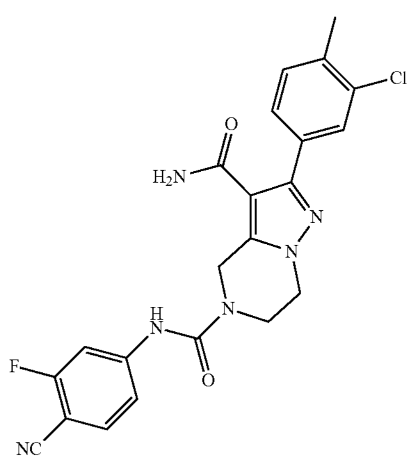 [SMILES: Cc1ccc(-c2nn3c(c2C(N)=O)CN(C(=O)Nc2ccc(C#N)c(F)c2)CC3)cc1Cl] | 2-(3-Chloro-4-methylphenyl)-N⁵-(4-cyano-3-fluorophenyl)-6,7-dihydropyrazolo[1,5-a]pyrazine-3,5(4H)-dicarboxamide | 453.0 | 1.56 | E |

TABLE 12-continued
| Ex. No. | Structure | Name | [M + H]+ | Ret Time (min.) | HPLC Methods |
|---|---|---|---|---|---|
| 256 | 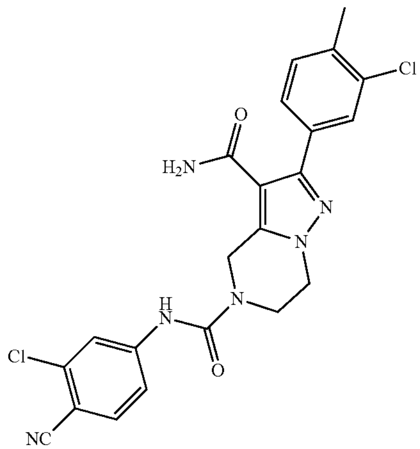 [SMILES: Cc1ccc(-c2nn3c(c2C(N)=O)CN(C(=O)Nc2ccc(C#N)c(Cl)c2)CC3)cc1Cl] | N5-(3-Chloro-4-cyanophenyl)-2-(3-chloro-4-methylphenyl)-6,7-dihydropyrazolo[1,5-a]pyrazine-3,5(4H)-dicarboxamide | 468.8 | 1.62 | E |
| 257 | 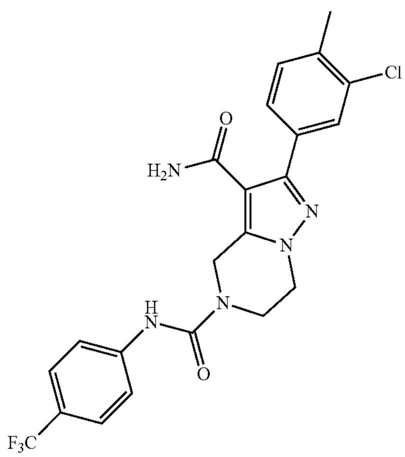 [SMILES: Cc1ccc(-c2nn3c(c2C(N)=O)CN(C(=O)Nc2ccc(C(F)(F)F)cc2)CC3)cc1Cl] | 2-(3-Chloro-4-methylphenyl)-N5-(4-(trifluoromethyl)phenyl)-6,7-dihydropyrazolo[1,5-a]pyrazine-3,5(4H)-dicarboxamide | 478.0 | 1.76 | E |
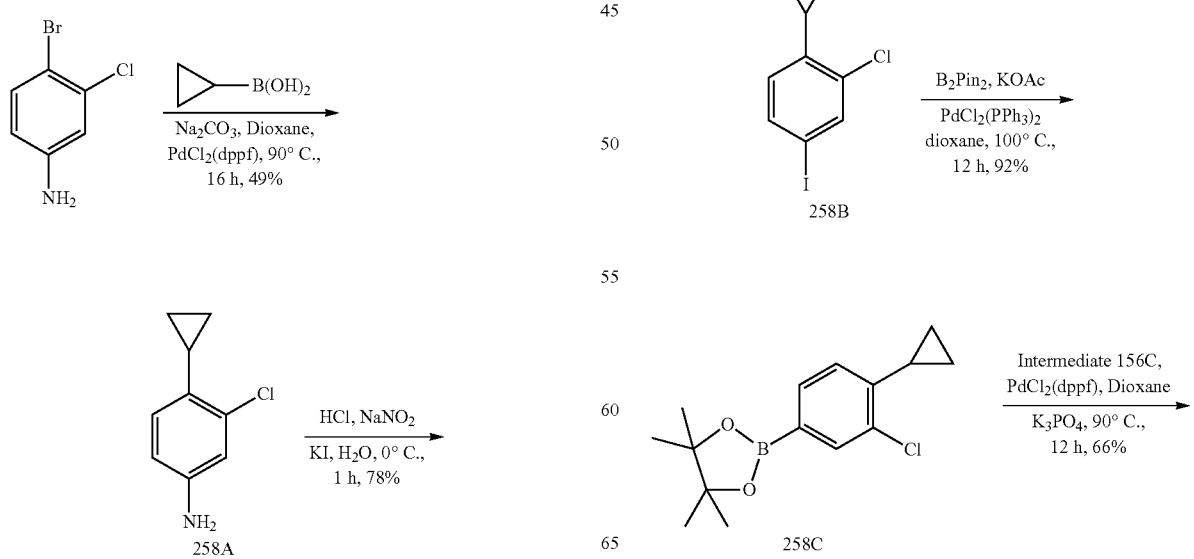
Scheme 13

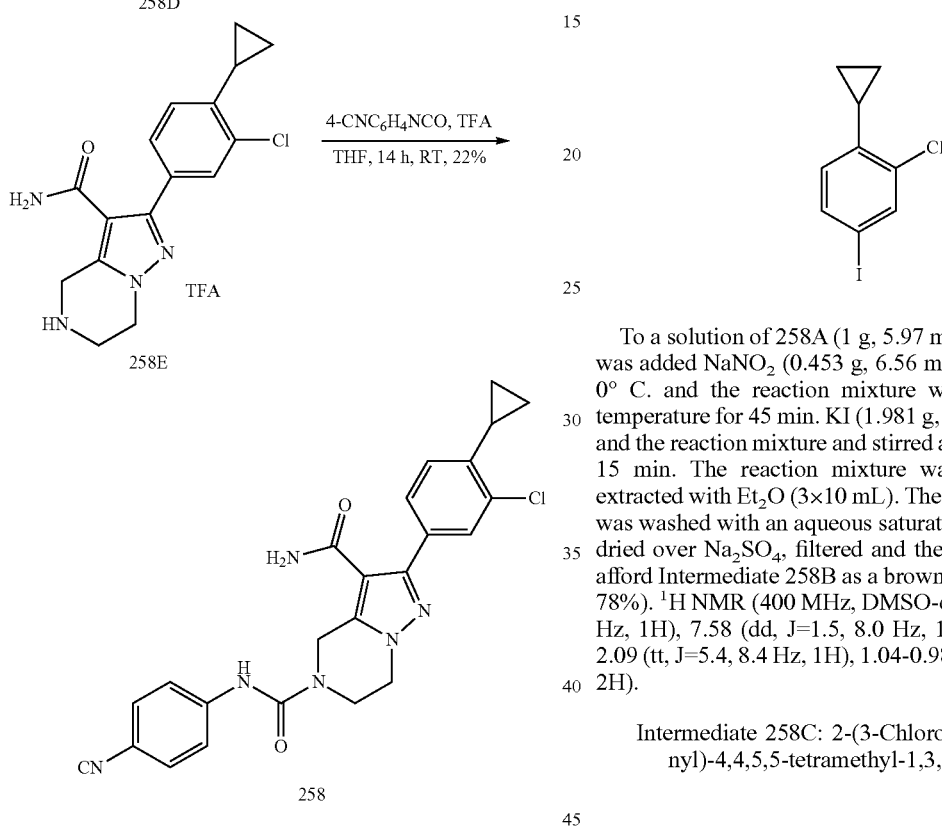

Intermediate 258A: 3-Chloro-4-cyclopropylaniline

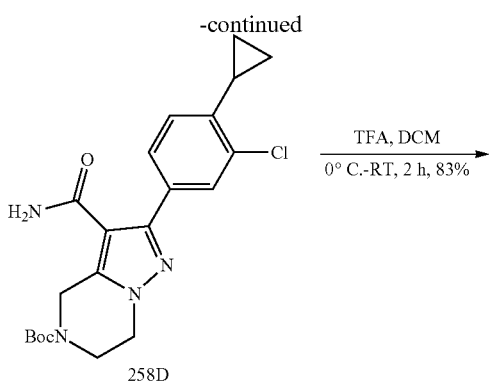

To a solution 4-bromo-3-chloroaniline (3 g, 14.53 mmol) and cyclopropylboronic acid (1.872 g, 21.80 mmol) in 1,4-dioxane (30 mL) was added Na$_2$CO$_3$ (4.62 g, 43.6 mmol) in water (0.4 mL) and the reaction mixture was degassed with N$_2$ for 15 min. PdCl$_2$(dppf)CH$_2$Cl$_2$ (1.187 g, 1.453 mmol) was added and the reaction mixture was heated to 85° C. and stirred for 16 h. The reaction mixture was concentrated under a reduced pressure and the crude product was purified by silica gel chromatography (40 g REDISEP® column, eluting with 70% EtOAc in hexanes). Fractions containing the product were combined and evaporated to afford the Intermediate 258A as a colorless semi-solid (1.2 g, 49%). $^1$H NMR (400 MHz, DMSO-d$_6$) δ ppm 6.70 (d, J=8.5 Hz, 1H), 6.62-6.60 (m, 1H), 6.43 (dd, J=2.3, 8.3 Hz, 1H), 5.15 (s, 2H), 1.90 (tt, J=5.1, 8.4 Hz, 1H), 0.87-0.81 (m, 2H), 0.53-0.48 (m, 2H).

Intermediate 258B: 2-Chloro-1-cyclopropyl-4-iodobenzene

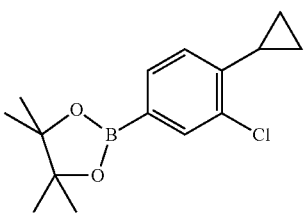 [SMILES: CC1(C)OB(c2ccc(C3CC3)c(Cl)c2)OC1(C)C]

To a solution of 258A (1 g, 5.97 mmol) in 6N HCl (5 mL) was added NaNO$_2$ (0.453 g, 6.56 mmol) in water (1 mL) at 0° C. and the reaction mixture was stirred at the same temperature for 45 min. KI (1.981 g, 11.93 mmol) was added and the reaction mixture and stirred at 0° C. for an additional 15 min. The reaction mixture was warmed to RT and extracted with Et$_2$O (3×10 mL). The combined organic layer was washed with an aqueous saturated solution of NaHSO$_3$, dried over Na$_2$SO$_4$, filtered and the filtrate concentrated to afford Intermediate 258B as a brown color semi-solid (1.3 g, 78%). $^1$H NMR (400 MHz, DMSO-d$_6$) δ ppm 7.77 (d, J=2.0 Hz, 1H), 7.58 (dd, J=1.5, 8.0 Hz, 1H), 6.84-6.79 (m, 1H), 2.09 (tt, J=5.4, 8.4 Hz, 1H), 1.04-0.98 (m, 2H), 0.72-0.66 (m, 2H).

Intermediate 258C: 2-(3-Chloro-4-cyclopropylphenyl)-4,4,5,5-tetramethyl-1,3,2-dioxaborolane To a solution of Intermediate 258B (1.3 g, 4.67 mmol) and bis(pinacolato)diboron (1.422 g, 5.60 mmol) in dioxane (20 mL) was added KOAc (1.374 g, 14.00 mmol) and the reaction mixture was degassed with N$_2$ gas for 15 min. PdCl$_2$(PPh$_3$)$_2$ (0.197 g, 0.280 mmol) was added and reaction mixture was heated to 100° C. and stirred for 12 h. The reaction mixture was concentrated under a reduced pressure and the crude product was purified by silica gel chromatography (40 g REDISEP® column, eluting with 8% EtOAc in hexanes). Fractions containing the product were combined and evaporated to afford the Intermediate 258C as a colorless semi-solid (1.2 g, 92%). $^1$H NMR (400 MHz, DMSO-d$_6$) δ ppm 7.60-7.58 (m, 1H), 7.53-7.48 (m, 1H), 7.02 (d, J=7.5 Hz, 1H), 2.19 (tt, J=5.1, 8.4 Hz, 1H), 1.17 (s, 12H), 1.08-1.02 (m, 2H), 0.76-0.70 (m, 2H).

Intermediate 258D: tert-Butyl 3-carbamoyl-2-(3-chloro-4-cyclopropylphenyl)-6,7-dihydropyrazolo[1,5-a]pyrazine-5(4H)-carboxylate

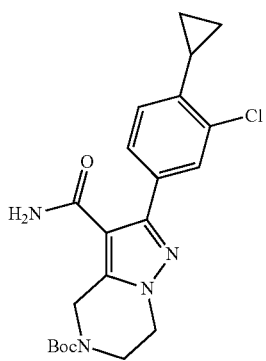 [SMILES: CC(C)(C)OC(=O)N1CCn2nc(-c3ccc(C4CC4)c(Cl)c3)c(C(N)=O)c2C1]

To a solution of Intermediate 156C (500 mg, 1.275 mmol) and 258C (533 mg, 1.912 mmol) in 1,4-dioxane (3 mL) was added K$_3$PO$_4$ (812 mg, 3.82 mmol) in water (0.4 mL) and the reaction mixture was degassed with N$_2$ for 15 min. PdCl$_2$(dppf)CH$_2$Cl$_2$ adduct (62.5 mg, 0.076 mmol) was added and the reaction mixture was heated to 85° C. and stirred for 12 h. The reaction mixture was concentrated under a reduced pressure and the crude product was purified by silica gel chromatography (24 g REDISEP® column, eluting with 60% EtOAc in hexanes). Fractions containing the product were combined and evaporated to afford the Intermediate 258D as an off-white solid (350 mg, 66%). MS(ES): m/z=417.2 [M+H]$^+$; $^1$H NMR (400 MHz, DMSO-d$_6$) δ ppm 7.69 (d, J=2.0 Hz, 1H), 7.53 (dd, J=2.0, 8.0 Hz, 1H), 7.35-7.09 (m, 2H), 7.06 (d, J=8.0 Hz, 1H), 4.73 (s, 2H), 4.15 (t, J=5.5 Hz, 2H), 3.87-3.81 (m, 2H), 2.21-2.12 (m, 1H), 1.45 (s, 9H), 1.06-1.00 (m, 2H), 0.77-0.71 (m, 2H).

Intermediate 258E: 2-(3-Chloro-4-cyclopropylphenyl)-4,5,6,7-tetrahydropyrazolo[1,5-a]pyrazine-3-carboxamide TFA salt

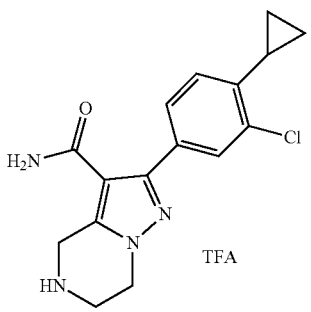 [SMILES: NC(=O)c1c(-c2ccc(C3CC3)c(Cl)c2)nn2c1CNCC2]

To solution of Intermediate 258D (350 mg, 0.840 mmol) in DCM (7 mL) was added TFA (5 mL) at 0° C. and the resulting solution was allowed to warm to RT and stirred for 2 h. The volatiles were removed under a reduced pressure and the residue was triturated with Et$_2$O to afford TFA salt of Intermediate 258E as an off-white solid (300 mg, 83%). MS(ES): m/z=317.2 [M+H]$^+$; $^1$H NMR (300 MHz, DMSO-d$_6$) δ ppm 9.43 (br. s., 1H), 7.68 (d, J=1.9 Hz, 1H), 7.52 (dd, J=1.7, 8.1 Hz, 1H), 7.40 (br. s., 1H), 7.15 (br. s., 1H), 7.08 (d, J=8.3 Hz, 1H), 4.55 (s, 2H), 4.40-4.32 (m, 2H), 3.69 (t, J=5.9 Hz, 2H), 2.22-2.12 (m, 1H), 1.08-1.00 (m, 2H), 0.78-0.70 (m, 2H).

Compound 258: 2-(3-Chloro-4-cyclopropylphenyl)-N$^5$-(4-cyanophenyl)-6,7-dihydropyrazolo[1,5-a]pyrazine-3,5(4H)-dicarboxamide

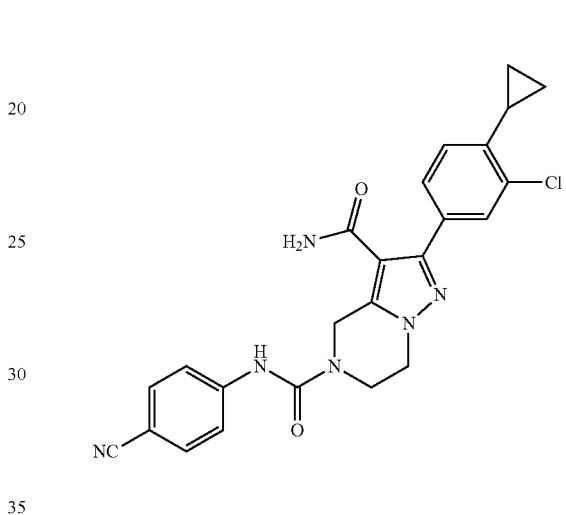

To a solution of Intermediate 258E (80 mg, 0.186 mmol) in THF (5 mL) was added TEA (0.259 mL, 1.857 mmol) and the resulting solution was stirred at RT for 30 min. 4-Isocyanatobenzonitrile (26.8 mg, 0.186 mmol) was added and the reaction mixture was stirred at RT for 14 h. The reaction mixture was diluted with EtOAc, washed with water, brine, dried over Na$_2$SO$_4$, filtered and the filtrate concentrated. The crude product was purified by preparative HPLC to afford Compound 258 as an off-white solid (0.02 g, 22%). HPLC retention times 1.571 min. and 1.556 min. (Methods J and K respectively). MS(ES): m/z=461.2 [M+H]$^+$; $^1$H NMR (400 MHz, DMSO-d$_6$) δ ppm 9.39 (s, 1H), 7.62-7.80 (m, 5H), 7.52-7.59 (m, 1H), 7.37 (br. s., 1H), 7.17 (br. s., 1H), 7.06 (d, J=8.03 Hz, 1H), 4.90 (s, 2H), 4.24 (t, J=5.27 Hz, 2H), 4.00 (t, J=5.27 Hz, 2H), 2.17 (ddd, J=13.55, 8.28, 5.27 Hz, 1H), 0.93-1.10 (m, 2H), 0.66-0.82 (m, 2H).

Scheme 14

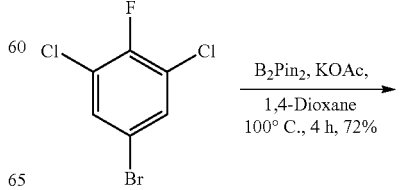

265

-continued

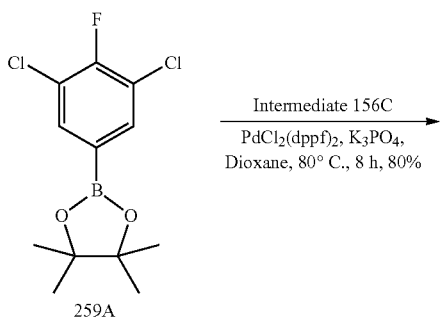

259A

Intermediate 156C
PdCl₂(dppf)₂, K₃PO₄,
Dioxane, 80° C., 8 h, 80%

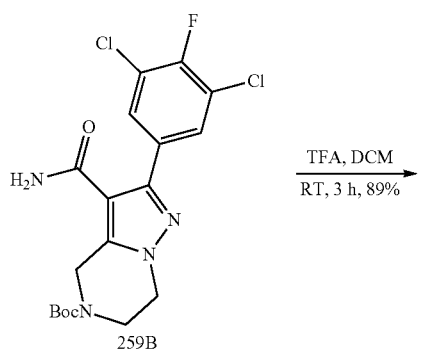

259B

TFA, DCM
RT, 3 h, 89%

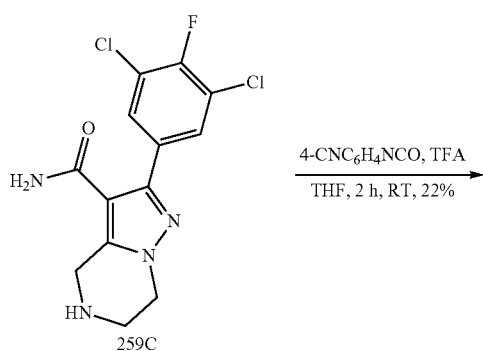

259C

4-CNC₆H₄NCO, TFA
THF, 2 h, RT, 22%

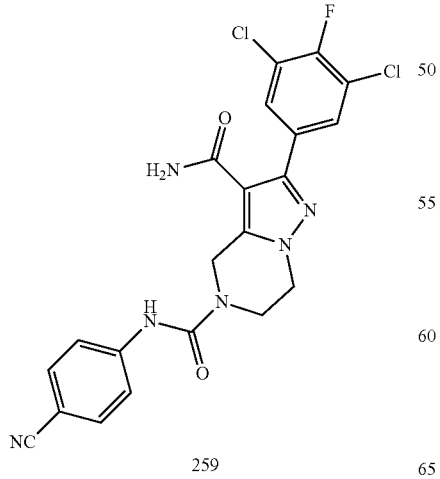

259

266

Intermediate 259A: 2-(3,5-Dichloro-4-fluorophe-nyl)-4,4,5,5-tetramethyl-1,3,2-dioxaborolane

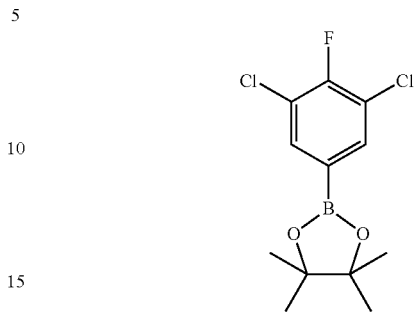

To a stirred solution of 5-bromo-1,3-dichloro-2-fluorobenzene (1.5 g, 6.15 mmol) in 1,4-dioxane (3.0 mL) was added B₂Pin₂ (2.343 g, 9.23 mmol), PdCl₂(dppf)-CH₂C2 (0.301 g, 0.369 mmol), KOAc (1.509 g, 15.38 mmol) and the reaction mixture was degasified with nitrogen for 10 min. The reaction mixture was then heated to 100° C. and stirred for 4 h. The reaction mixture was diluted with ethyl acetate filtered through CELITE® and the filtrate was washed with water, dried over sodium sulfate, filtered and the filtrate concentrated. The crude compound was purified by silica gel chromatography (24 g REDISEP® column, eluting with 3% EtOAc in hexanes). Fractions containing the product were combined and evaporated to afford the Intermediate 259A as a colorless oil (1.3 g, 72%). ¹H NMR (400 MHz, DMSO-d₆) δ ppm 7.71 (d, J=6.53 Hz, 2H), 1.29-1.32 (m, 12H).

Intermediate 259B: tert-Butyl 3-carbamoyl-2-(3,5-dichloro-4-fluorophenyl)-6,7-dihydropyrazolo[1,5-a]pyrazine-5(4H)-carboxylate

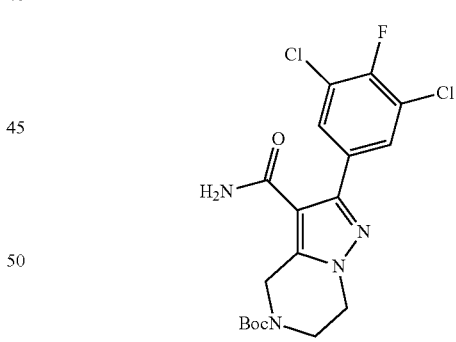

To a stirred suspension of Intermediate 156C (1.2 g, 3.06 mmol) in 1,4-dioxane (10.0 mL) was added Intermediate 259A (1.335 g, 4.59 mmol), K₃PO₄ (1.948 g, 9.18 mmol) and the reaction mixture was degasified for 10 min. PdCl₂(dppf)-CH₂Cl₂ (0.150 g, 0.184 mmol) was added and the reaction mixture was heated to 80° C. and stirred for 8 h. The reaction mixture was diluted with ethyl acetate (20 mL), washed with water, brine, dried over Na₂SO₄, filtered and the filtrate concentrated. The crude compound was purified by silica gel chromatography (24 g REDISEP® column, eluting with 60% EtOAc in hexanes). Fractions containing the product were combined and evaporated to afford the Intermediate 259B as a white solid (1.1 g, 80%). MS(ES):

m/z=429 [M+H]⁺; $^1$H NMR (400 MHz, DMSO-d$_6$) ppm 7.85 (d, J=6.53 Hz, 2H), 7.35 (br. s., 2H), 4.75 (s, 2H), 4.17 (t, J=5.52 Hz, 2H), 3.84 (t, J=5.52 Hz, 2H), 1.45 (s, 9H).

Intermediate 259C: 2-(3,5-Dichloro-4-fluorophenyl)-4,5,6,7-tetrahydropyrazolo[1,5-a]pyrazine-3-carboxamide

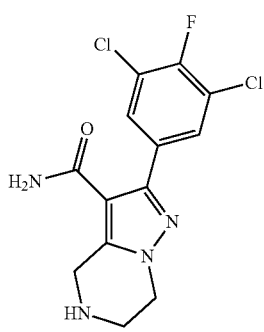 [SMILES: NC(=O)c1c(-c2cc(Cl)c(F)c(Cl)c2)nn2c1CNCC2]

To a solution of Intermediate 259B (1.1 g, 2.56 mmol) in DCM (5.0 mL) was added TFA (10 mL, 130 mmol) and the resulting solution was stirred at RT for 3 h. The volatiles were removed under reduced pressure. The residue was added a saturated aqueous solution of NaHCO$_3$ and stirred for 1 h. The solid was filtered and dried under vacuum to afford Intermediate 259C as an off-white solid (0.75 g, 89%). MS(ES): m/z=329 [M+H]⁺; $^1$H NMR (400 MHz, DMSO-d$_6$) δ ppm 7.89 (d, J=6.53 Hz, 2H), 7.27 (br. s., 2H), 3.95-4.13 (m, 4H), 3.13 (t, J=5.52 Hz, 2H), 2.68 (br. s., 1H).

Compound 259: N⁵-(4-Cyanophenyl)-2-(3,5-dichloro-4-fluorophenyl)-6,7-dihydropyrazolo[1,5-a]pyrazine-3,5(4H)-dicarboxamide

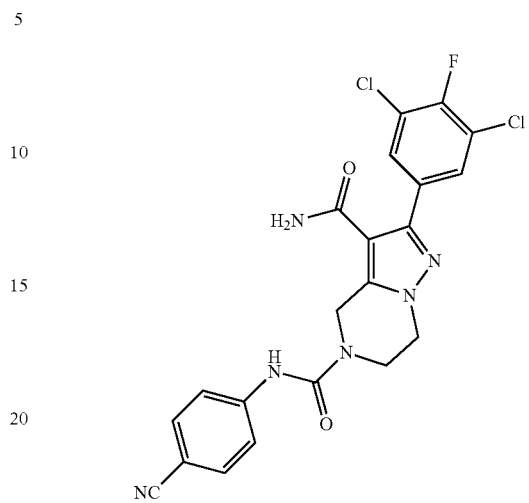

To a solution of Intermediate 259C (0.1 g, 0.304 mmol) in THF (2 mL) was added TEA (0.085 mL, 0.608 mmol) and the resulting solution was stirred at RT for 30 min. 4-Isocyanatobenzonitrile (0.053 g, 0.365 mmol) was added and the reaction mixture was stirred at RT for 2 h. The reaction mixture was diluted with EtOAc, washed with water, brine, dried over Na$_2$SO$_4$, filtered and the filtrate concentrated. The crude product was purified by preparative HPLC to afford Compound 259 as an off-white solid (0.02 g, 22%). HPLC retention times 10.01 min. and 9.05 min. (Methods A and B respectively). MS(ES): m/z=473 [M+H]⁺; $^1$H NMR (400 MHz, DMSO-d$_6$) δ ppm 9.39 (s, 1H), 7.88 (d, J=6.53 Hz, 2H), 7.63-7.76 (m, 4H), 7.26-7.51 (m, 2H), 4.93 (s, 2H), 4.26 (t, J=5.52 Hz, 2H), 4.01 (t, J=5.52 Hz, 2H).

The Compounds shown in Table 13 have been prepared similar to Compound 259 by coupling of Intermediate 259C with various readily available isocyanates or in-situ generated from respective anilines.

TABLE 13

| Ex. No. | Structure | Name | [M + H]⁺ | Ret Time (min.) | HPLC Methods |
|---|---|---|---|---|---|
| 260 | 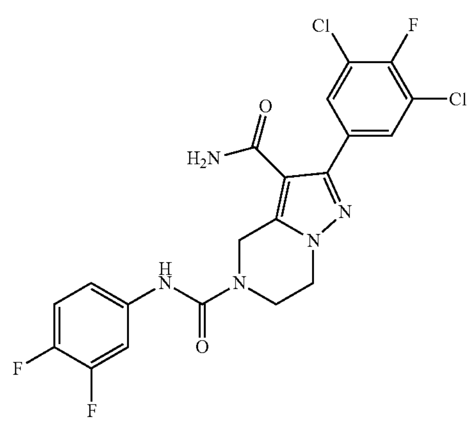 [SMILES: NC(=O)c1c(-c2cc(Cl)c(F)c(Cl)c2)nn2c1CN(C(=O)Nc1ccc(F)c(F)c1)CC2] | 2-(3,5-Dichloro-4-fluorophenyl)-N⁵-(3,4-difluorophenyl)-6,7-dihydropyrazolo[1,5-a]pyrazine-3,5(4H)-dicarboxamide | 486 | 10.44<br>8.90 | A<br>B |

TABLE 13-continued

| Ex. No. | Structure | Name | [M + H]+ | Ret Time (min.) | HPLC Methods |
|---|---|---|---|---|---|
| 261 | 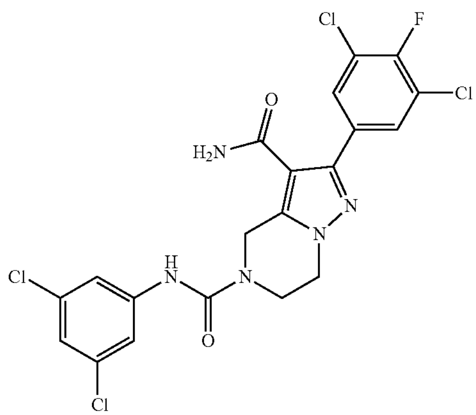 [SMILES: NC(=O)c1c(-c2cc(Cl)c(F)c(Cl)c2)nn2c1CN(C(=O)Nc1cc(Cl)cc(Cl)c1)CC2] | 2-(3,5-Dichloro-4-fluorophenyl)-N⁵-(3,5-dichlorophenyl)-6,7-dihydropyrazolo[1,5-a]pyrazine-3,5(4H)-dicarboxamide | 518 [M + H] | 11.006 12.208 | B A |
| 262 | 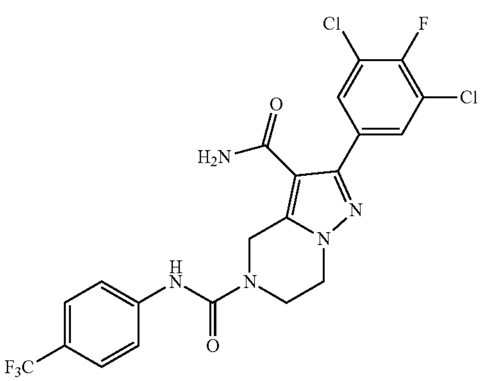 [SMILES: NC(=O)c1c(-c2cc(Cl)c(F)c(Cl)c2)nn2c1CN(C(=O)Nc1ccc(C(F)(F)F)cc1)CC2] | 2-(3,5-Dichloro-4-fluorophenyl)-N⁵-(4-(trifluoromethyl)phenyl)-6,7-dihydropyrazolo[1,5-a]pyrazine-3,5(4H)-dicarboxamide | 518.0 | 10.48 11.39 | B A |
| 263 | 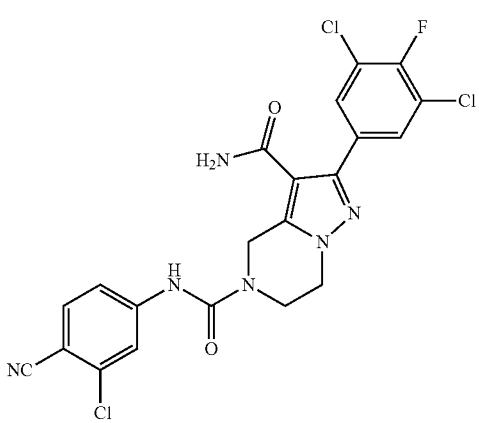 | N⁵-(3-Chloro-4-cyanophenyl)-2-(3,5-dichloro-4-fluorophenyl)-6,7-dihydropyrazolo[1,5-a]pyrazine-3,5(4H)-dicarboxamide | 507 | 1.669 1.769 | E L |

TABLE 13-continued
| Ex. No. | Structure | Name | [M + H]+ | Ret Time (min.) | HPLC Methods |
|---|---|---|---|---|---|
| 264 | 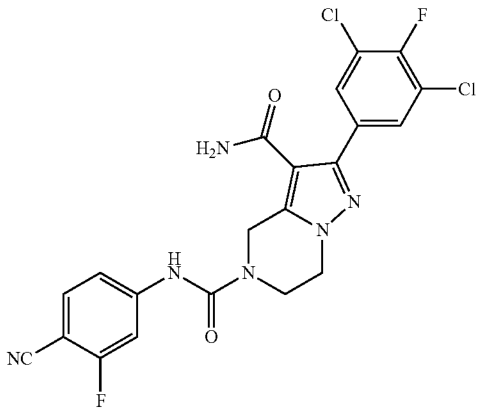 [SMILES: N#Cc1ccc(NC(=O)N2CCn3nc(-c4cc(Cl)c(F)c(Cl)c4)c(C(N)=O)c3C2)cc1F] | N5-(4-Cyano-3-fluorophenyl)-2-(3,5-dichloro-4-fluorophenyl)-6,7-dihydropyrazolo[1,5-a]pyrazine-3,5(4H)-dicarboxamide | 492 | 1.602<br>1.707 | E<br>L |
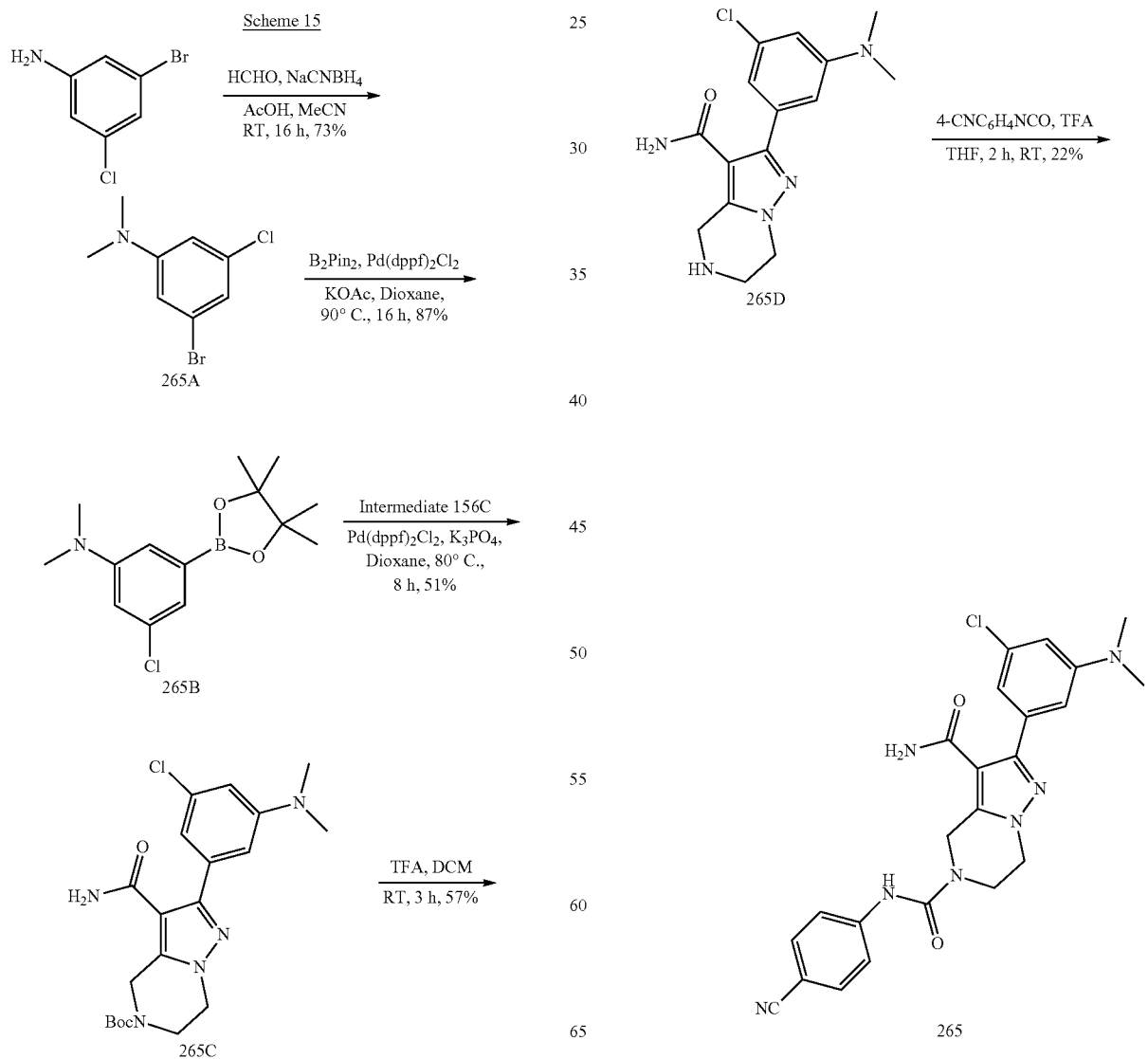

Intermediate 265A:
3-Bromo-5-chloro-N,N-dimethylaniline

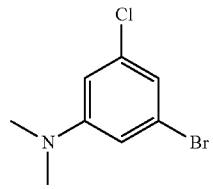

To a stirred solution of 3-bromo-5-chloroaniline (0.3 g, 1.453 mmol) in acetonitrile (5.0 mL) was added 37% aqueous formaldehyde solution (1.082 mL, 14.53 mmol) followed by sodium cyanoborohydride (0.274 g, 4.36 mmol) at RT. Acetic acid (0.3 mL, 5.24 mmol) was added over a period of 10 min and the reaction mixture was stirred at RT for 16 h. To the reaction mixture was added a 10% aqueous solution of NaOH and extracted with ethyl acetate (2×15 mL). The combined organic layer was washed with water, brine, dried over sodium sulfate, filtered and the filtrate concentrated. The crude compound was purified by silica gel chromatography (12 g REDISEP® column, eluting with 20% EtOAc in hexanes). Fractions containing the product were combined and evaporated to afford the Intermediate 265A as a pale yellow solid (0.25 g, 73%). $^1$H NMR (300 MHz, chloroform-d) δ ppm 6.83 (t, J=1.70 Hz, 1H), 6.68-6.72 (m, 1H), 6.56-6.60 (m, 1H), 2.96 (s, 6H).

Intermediate 265B: 3-Chloro-N,N-dimethyl-5-(4,4,5,5-tetramethyl-1,3,2-dioxaborolan-2-yl)aniline

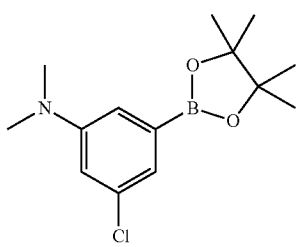

To a stirred solution of Intermediate 265A (0.25 g, 1.066 mmol) in 1,4-dioxane (8 mL) was added B$_2$Pin$_2$ (0.677 g, 2.67 mmol), KOAc (0.262 g, 2.67 mmol), PdCl$_2$(dppf)$_2$-CH$_2$Cl$_2$ adduct (0.052 g, 0.064 mmol) and the reaction mixture was purged with nitrogen for 5 min. The reaction mixture was then heated to 90° C. and stirred 16 h. The reaction mixture was concentrated and the residue was extracted with ethyl acetate (3×15 mL). The combined organic layer was washed with water, brine, dried over Na$_2$SO$_4$, filtered and the filtrate concentrated. The crude product was purified by silica gel chromatography (24 g REDISEP® column, eluting with 2% EtOAc in hexanes). Fractions containing the product were combined and evaporated to afford the Intermediate 265B as an off-white solid (0.26 g, 87%). MS(ES): m/z=200 [M−82)]; $^1$H NMR (400 MHz, chloroform-d) δ ppm 7.11 (d, J=2.01 Hz, 1H), 7.01 (d, J=2.01 Hz, 1H), 6.70-6.78 (m, 1H), 2.96 (s, 6H), 1.31-1.35 (m, 12H).

Intermediate 265C: tert-Butyl 3-carbamoyl-2-(3-chloro-5-(dimethylamino)phenyl)-6,7-dihydropyrazolo[1,5-a]pyrazine-5(4H)-carboxylate

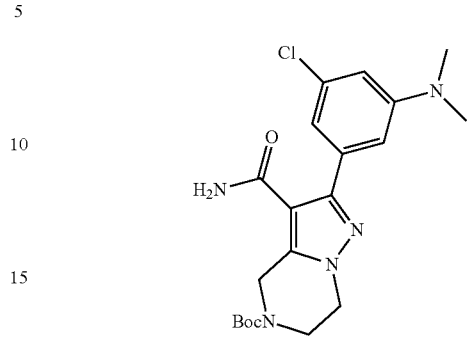

To a stirred suspension of Intermediate 156C (1.0 g, 2.55 mmol) in 1,4-dioxane (20.0 mL) was added Intermediate 265B (1.077 g, 3.82 mmol), K$_3$PO$_4$ (1.624 g, 7.65 mmol), PdCl$_2$(dppf)-CH$_2$Cl$_2$ (0.125 g, 0.153 mmol) and the reaction mixture was purged with nitrogen for 10 min. The reaction mixture was then heated to 80° C. and stirred for 8 h. The reaction mixture was concentrated and extracted with ethyl acetate (3×20 mL). The combined organic layer was washed with water, brine, dried over Na$_2$SO$_4$, filtered and the filtrate concentrated. The crude product was purified by silica gel chromatography (24 g REDISEP® column, eluting with 1% MeOH in chloroform). Fractions containing the product were combined and evaporated to afford the Intermediate 265C as brown solid (0.55 g, 51%). MS(ES): m/z=420 [M+H]$^+$; $^1$H NMR (400 MHz, DMSO-d$_6$) δ ppm 7.26-7.35 (m, 1H), 6.87-7.01 (m, 3H), 6.71 (t, J=2.01 Hz, 1H), 4.73 (s, 2H), 4.15 (t, J=5.27 Hz, 2H), 3.84 (t, J=5.52 Hz, 2H), 2.93 (s, 6H), 1.46 (s, 9H).

Intermediate 265D: 2-(3-Chloro-5-(dimethylamino)phenyl)-4,5,6,7-tetrahydropyrazolo[1,5-a]pyrazine-3-carboxamide

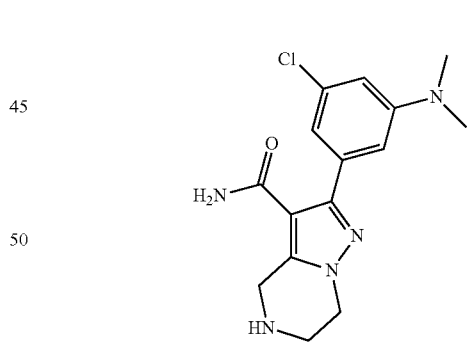

To a solution of Intermediate 265C (0.55 g, 1.310 mmol) in DCM (10 mL) was added TFA (2.027 mL, 26.3 mmol) dropwise at 0° C. and the resulting solution was warmed to RT and stirred for 4 h. The reaction mixture was concentrated and to the crude product was added a saturated aqueous solution of NaHCO$_3$ at 0° C. and stirred at RT for 1 h. The solid separated was filtered and dried to afford Intermediate 265D as a brown solid (0.24 g, 57%). MS(ES): m/z=320 [M+H]$^+$; $^1$H NMR (400 MHz, DMSO-d$_6$) δ ppm 7.20 (br. s., 1H), 6.86-7.04 (m, 3H), 6.68 (t, J=2.01 Hz, 1H), 3.88-4.04 (m, 4H), 3.12 (d, J=4.02 Hz, 2H), 2.93 (s, 6H) 2.50 (br. s, 1H).

Compound 265: 2-(3-Chloro-5-(dimethylamino)phenyl)-N⁵-(4-cyanophenyl)-6,7-dihydropyrazolo[1,5-a]pyrazine-3,5(4H)-dicarboxamide

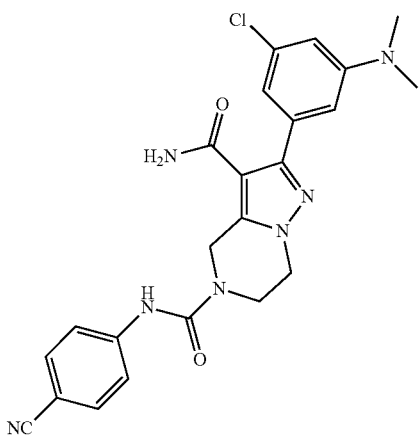 [SMILES: CN(C)c1cc(Cl)cc(-c2nn3c(c2C(N)=O)CN(C(=O)Nc2ccc(C#N)cc2)CC3)c1]

Compound 265 was synthesized from Intermediate 265D using a synthetic sequence analogous to the preparation of Compound 259. HPLC retention times 8.19 min. and 8.53 min. (Methods A and B respectively). MS(ES): m/z=464 [M+H]⁺; ¹H NMR (400 MHz, DMSO-d₆) δ ppm 9.41 (s, 1H), 7.79-7.62 (m, 4H), 7.37 (br. s., 1H), 7.07-6.89 (m, 3H), 6.72 (t, J=2.0 Hz, 1H), 4.90 (s, 2H), 4.24 (t, J=5.3 Hz, 2H), 4.06-3.94 (m, 2H), 3.01-2.86 (s, 6H).

The Compounds shown in Table 14 have been prepared similar to Compound 265 by coupling of Intermediate 265D with various readily available isocyanates or in-situ generated from respective anilines.

TABLE 14

| Ex. No. | Structure | Name | [M + H]⁺ | Ret Time (min) | HPLC Methods |
|---|---|---|---|---|---|
| 266 | 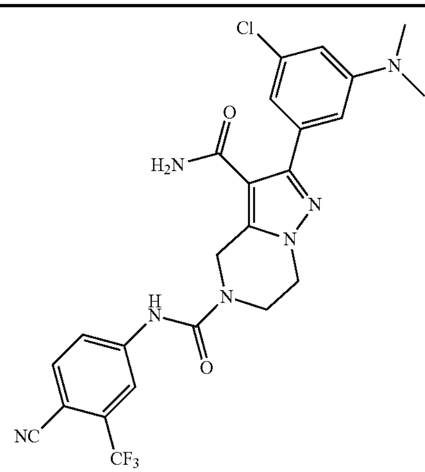 | 2-(3-Chloro-5-(dimethylamino)phenyl)-N⁵-(4-cyano-3-(trifluoromethyl)phenyl)-6,7-dihydropyrazolo[1,5-a]pyrazine-3,5(H)-dicarboxamide | 532 | 10.286 9.755 | A B |
| 267 | 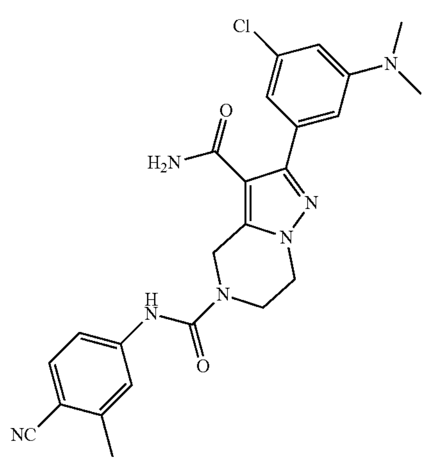 [SMILES: Cc1cc(NC(=O)N2CCn3nc(-c4cc(Cl)cc(N(C)C)c4)c(C(N)=O)c3C2)ccc1C#N] | 2-(3-Chloro-5-(dimethylamino)phenyl)-N⁵-(4-cyano-3-methylphenyl)-6,7-dihydropyrazolo[1,5-a]pyrazine-3,5(4H)-dicarboxamide | 478 | 9.349 8.940 | A B |

TABLE 14-continued
| Ex. No. | Structure | Name | [M + H]+ | Ret Time (min) | HPLC Methods |
|---|---|---|---|---|---|
| 268 | 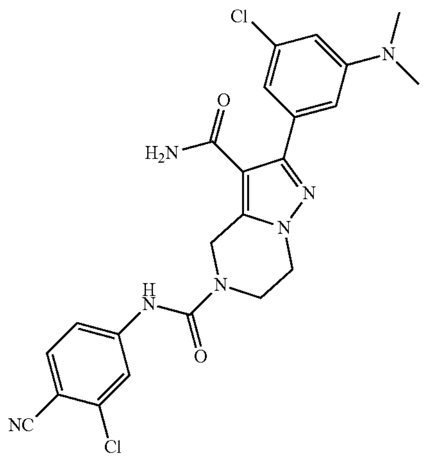 [SMILES: CN(C)c1cc(Cl)cc(-c2nn3c(c2C(N)=O)CN(C(=O)Nc2ccc(C#N)c(Cl)c2)CC3)c1] | N5-(3-Chloro-4-cyanophenyl)-2-(3-chloro-5-(dimethyl-amino)phenyl)-6,7-dihydropyrazolo[1,5-a]pyrazine-3,5(4H)-dicarboxamide | 498 | 9.913<br>9.452 | A<br>B |
| 269 | 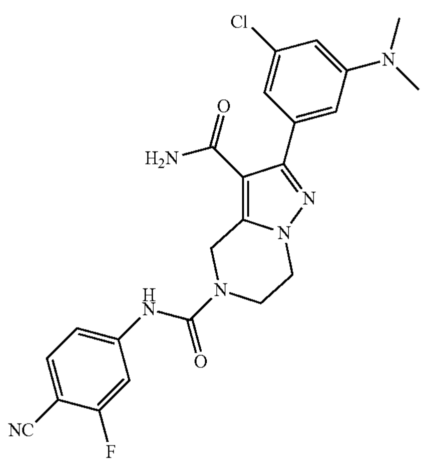 [SMILES: CN(C)c1cc(Cl)cc(-c2nn3c(c2C(N)=O)CN(C(=O)Nc2ccc(C#N)c(F)c2)CC3)c1] | 2-(3-Chloro-5-(dimethylamino)phenyl)-N5-(4-cyano-3-fluorophenyl)-6,7-dihydropyrazolo[1,5-a]pyrazine-3,5(4H)-dicarboxamide | 482 | 9.557<br>9.132 | A<br>B |
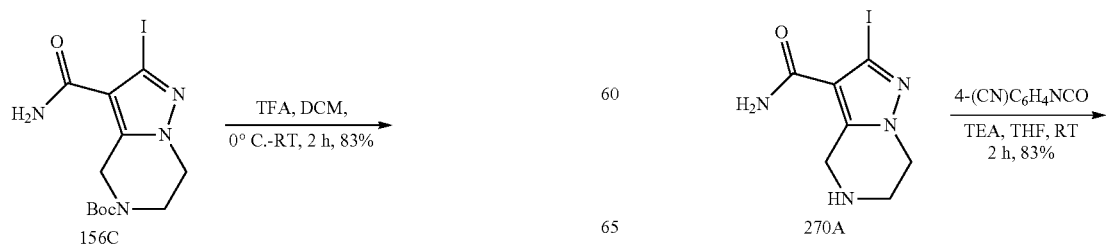
Scheme 16

279
-continued

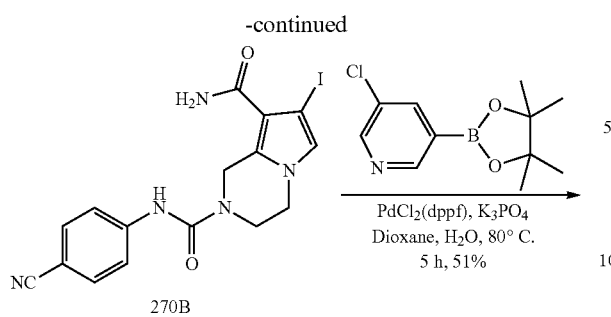

Intermediate 270A: 2-Iodo-4,5,6,7-tetrahydropyrazolo[1,5-a]pyrazine-3-carboxamide

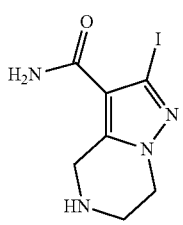

To a stirred solution of Intermediate 156C (1.500 g, 3.82 mmol) in DCM (15 mL) was added TFA (8 mL) slowly at RT and the reaction mixture was allowed to stir at RT for 2 h. The reaction mixture was diluted with a 10% aqueous solution of NaOH and the solid formed was filtered through a Buchner funnel, dried under vacuum to afford Intermediate 270A (0.95 g, 85%) as an off-white solid. MS(ES): m/z=293 [M+H]$^+$; $^1$H NMR (400 MHz, DMSO-d$_6$) δ ppm 7.23 (br. s., 1H), 6.78 (br. s., 1H), 4.02 (d, J=5.5 Hz, 2H), 3.97 (t, J=5.5 Hz, 2H), 3.06 (q, J=5.0 Hz, 2H), 2.59 (t, J=5.5 Hz, 1H).

280

Intermediate 270B: N$^5$-(4-Cyanophenyl)-2-iodo-6,7-dihydropyrazolo[1,5-a]pyrazine-3,5(4H)-dicarboxamide

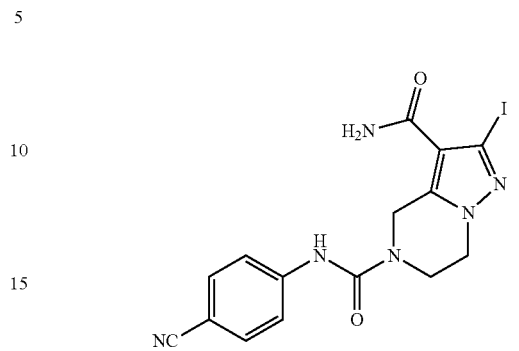

To a solution of Intermediate 270A (2.5 g, 6.16 mmol) in THF (100 mL) was added 4-cyanophenylisocyanate (1.065 g, 7.39 mmol) and the reaction mixture was stirred at room temperature for 2 h. The reaction mixture was concentrated under reduced pressure and the residue was dissolved in DCM (50 ml), washed with a saturated aqueous solution of NaHCO$_3$, water and brine. The organic layer was dried over Na$_2$SO$_4$, filtered and the filtrate concentrated. The crude product was triturated with diethyl ether (3×50 mL). The solid was filtered through a Buchner funnel and rinsed with hexane to afford Intermediate 270B as a white solid (2.5 g, 93%). MS(ES): m/z=437 [M+H]$^+$; $^1$H NMR (400 MHz, DMSO-d$_6$) δ ppm 9.36 (s, 1H), 7.59-7.77 (m, 4H), 7.43 (br. s., 1H), 6.89 (br. s., 1H), 4.90 (s, 2H), 4.21 (t, J=5.27 Hz, 2H), 3.95 (d, J=5.52 Hz, 2H).

Compound 270: 2-(5-Chloropyridin-3-yl)-N$^5$-(4-cyanophenyl)-6,7-dihydropyrazolo[1,5-a]pyrazine-3,5(4H)-dicarboxamide

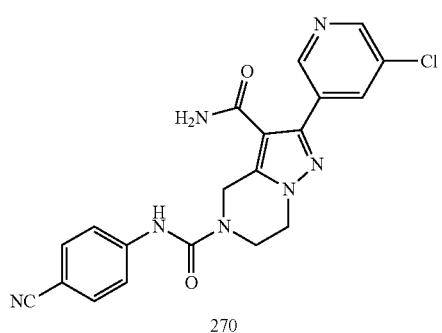

To a solution of Intermediate 270B (40 mg, 0.092 mmol), 3-chloro-5-(4,4,5,5-tetramethyl-1,3,2-dioxaborolan-2-yl) pyridine (32.9 mg, 0.138 mmol) in 1,4-dioxane (2 mL) was added K$_3$PO$_4$ (58.4 mg, 0.275 mmol) in water (0.5 ml) and the resulting reaction mixture was purged with N$_2$ for 5 min. PdCl$_2$(dppf)-CH$_2$Cl$_2$ adduct (4.49 mg, 5.50 µmol) was added, the reaction mixture was heated to 80° C. and stirred for 5 h. The reaction mixture was quenched with water and extracted with ethyl acetate (3×5 mL). The combined organic layer was washed with water, brine, dried over Na$_2$SO$_4$, filtered and the filtrate concentrated to afford the crude compound, which was purified via preparative HPLC to afford Compound 270 as an off-white solid (20 mg, 51%). HPLC retention times are 7.01 min. and 6.85 min. (Methods A and B). MS(ES): m/z=422 [M+H]$^+$; $^1$H NMR (400 MHz, DMSO-d$_6$) δ ppm 9.41 (s, 1H), 8.80 (d, J=1.51 Hz, 1H), 8.63 (d, J=2.51 Hz, 1H), 8.15 (t, J=2.01 Hz, 1H), 7.71 (q, J=9.04 Hz, 4H), 7.37 (br. s., 2H), 4.95 (s, 2H), 4.29 (t, J=5.27 Hz, 2H), 4.02 (t, J=5.27 Hz, 2H).

The Compounds shown in Table 15 have been prepared similar to Compound 270 by Suzuki coupling of Intermediate 270B with various readily available boronic acids.

TABLE 15

| Ex. No. | Structure | Name | [M + H]$^+$ | Ret Time (min.) | HPLC Methods |
|---|---|---|---|---|---|
| 271 | 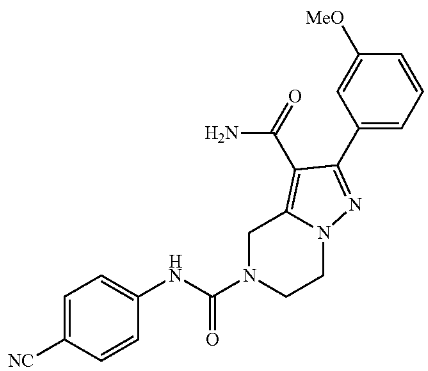 [SMILES: COc1cccc(-c2nn3c(c2C(N)=O)CN(C(=O)Nc2ccc(C#N)cc2)CC3)c1] | N$^5$-(4-Cyanophenyl)-2-(3-methoxyphenyl)-6,7-dihydropyrazolo[1,5-a]pyrazine-3,5(4H)-dicarboxamide | 415.2 | 7.85<br>7.88 | B<br>A |
| 272 | 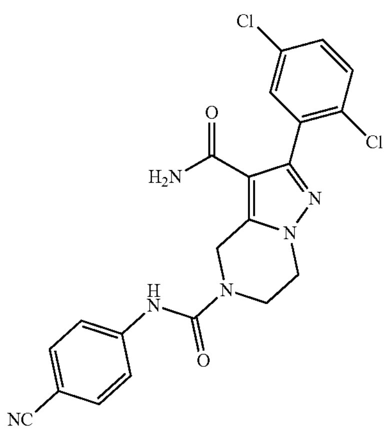 [SMILES: N#Cc1ccc(NC(=O)N2CCn3nc(-c4cc(Cl)ccc4Cl)c(C(N)=O)c3C2)cc1] | N$^5$-(4-Cyanophenyl)-2-(2,5-dichlorophenyl)-6,7-dihydropyrazolo[1,5-a]pyrazine-3,5(4H)-dicarboxamide | 454.8 | 1.33 | E |
| 273 | 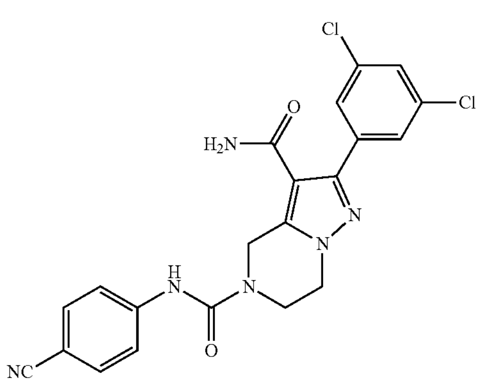 [SMILES: N#Cc1ccc(NC(=O)N2CCn3nc(-c4cc(Cl)cc(Cl)c4)c(C(N)=O)c3C2)cc1] | N$^5$-(4-Cyanophenyl)-2-(3,5-dichlorophenyl)-6,7-dihydropyrazolo[1,5-a]pyrazine-3,5(4H)-dicarboxamide | 456 | 9.881<br>9.179 | A<br>B |

TABLE 15-continued

| Ex. No. | Structure | Name | [M + H]+ | Ret Time (min.) | HPLC Methods |
|---|---|---|---|---|---|
| 274 | 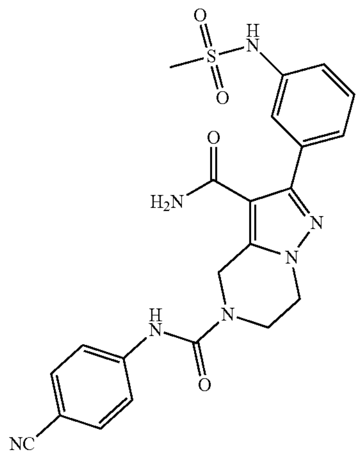 [SMILES: CS(=O)(=O)Nc1cccc(-c2nn3c(c2C(N)=O)CN(C(=O)Nc2ccc(C#N)cc2)CC3)c1] | N5-(4-Cyanophenyl)-2-(3-(methylsulfonamido)phenyl)-6,7-dihydropyrazolo[1,5-a]pyrazine-3,5(4H)-dicarboxamide | 480.0 | 0.95 | E |
| 275 | 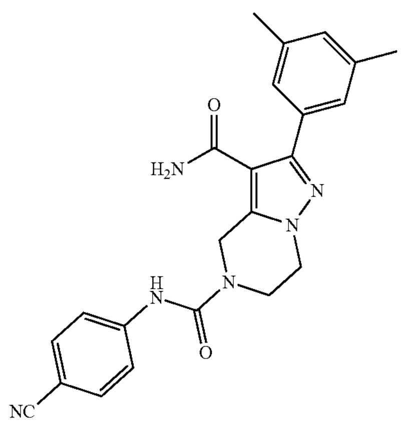 [SMILES: Cc1cc(C)cc(-c2nn3c(c2C(N)=O)CN(C(=O)Nc2ccc(C#N)cc2)CC3)c1] | N5-(4-Cyanophenyl)-2-(3,5-dimethylphenyl)-6,7-dihydropyrazolo[1,5-a]pyrazine-3,5(4H)-dicarboxamide | 415.0 | 1.36 | E |
| 276 | 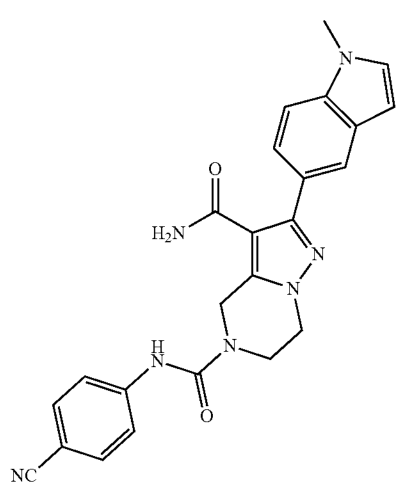 [SMILES: Cn1ccc2cc(-c3nn4c(c3C(N)=O)CN(C(=O)Nc3ccc(C#N)cc3)CC4)ccc21] | N5-(4-Cyanophenyl)-2-(1-methyl-1H-indol-5-yl)-6,7-dihydropyrazolo[1,5-a]pyrazine-3,5(4H)-dicarboxamide | 440.0 | 1.22 | E |

TABLE 15-continued

| Ex. No. | Structure | Name | [M + H]+ | Ret Time (min.) | HPLC Methods |
|---|---|---|---|---|---|
| 277 | 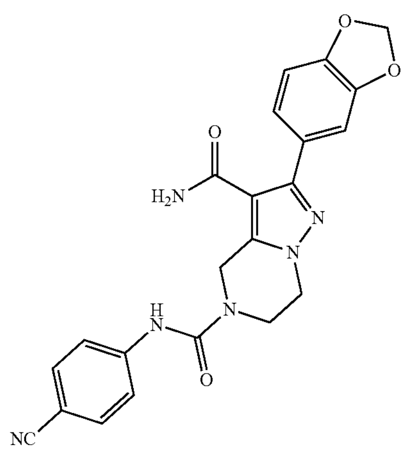 [SMILES: N#Cc1ccc(NC(=O)N2CCn3nc(-c4ccc5c(c4)OCO5)c(C(N)=O)c3C2)cc1] | 2-(Benzo[d][1,3]dioxol-5-yl)-N5-(4-cyanophenyl)-6,7-dihydropyrazolo[1,5-a]pyrazine-3,5(4H)-dicarboxamide | 431.0 | 1.09 | E |
| 278 | 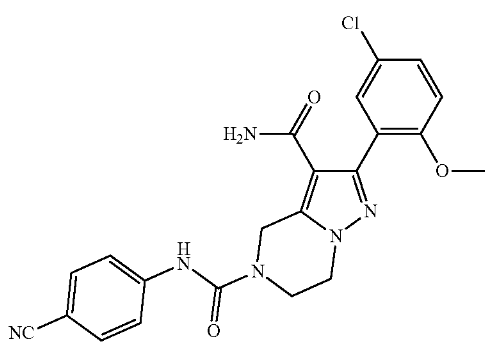 [SMILES: COc1ccc(Cl)cc1-c1nn2c(c1C(N)=O)CN(C(=O)Nc1ccc(C#N)cc1)CC2] | 2-(5-Chloro-2-methoxyphenyl)-N5-(4-cyanophenyl)-6,7-dihydropyrazolo[1,5-a]pyrazine-3,5(4H)-dicarboxamide | 451.0 | 1.26 | E |
| 279 | 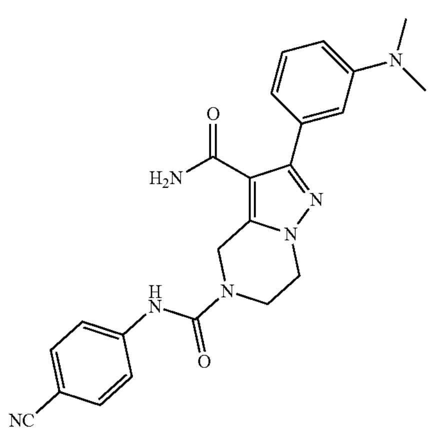 [SMILES: CN(C)c1cccc(-c2nn3c(c2C(N)=O)CN(C(=O)Nc2ccc(C#N)cc2)CC3)c1] | N5-(4-Cyanophenyl)-2-(3-(dimethylamino)phenyl)-6,7-dihydropyrazolo[1,5-a]pyrazine-3,5(4H)-dicarboxamide | 430.0 | 1.23 | E |

TABLE 15-continued

| Ex. No. | Structure | Name | [M + H]+ | Ret Time (min.) | HPLC Methods |
|---|---|---|---|---|---|
| 280 | 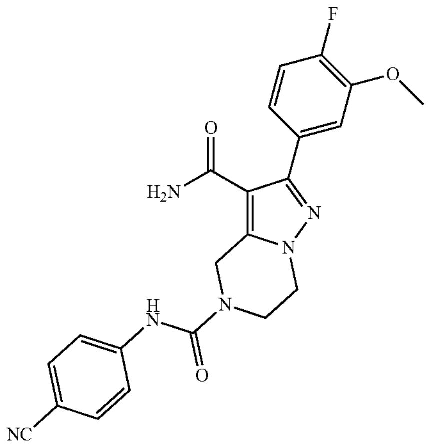 [SMILES: COc1cc(-c2nn3c(c2C(N)=O)CN(C(=O)Nc2ccc(C#N)cc2)CC3)ccc1F] | N5-(4-Cyanophenyl)-2-(4-fluoro-3-methoxyphenyl)-6,7-dihydropyrazolo[1,5-a]pyrazine-3,5(4H)-dicarboxamide | 435.0 | 1.17 | E |
| 281 | 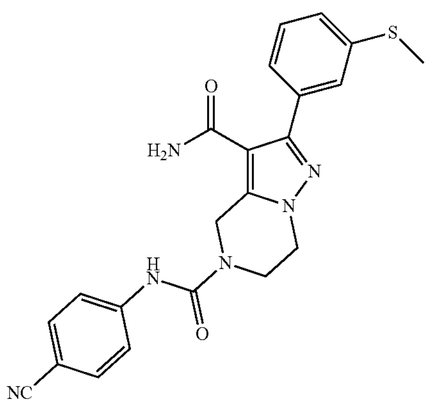 [SMILES: CSc1cccc(-c2nn3c(c2C(N)=O)CN(C(=O)Nc2ccc(C#N)cc2)CC3)c1] | N5-(4-Cyanophenyl)-2-(3-(methylthio)phenyl)-6,7-dihydropyrazolo[1,5-a]pyrazine-3,5(4H)-dicarboxamide | 433.0 | 1.26 | E |
| 282 | 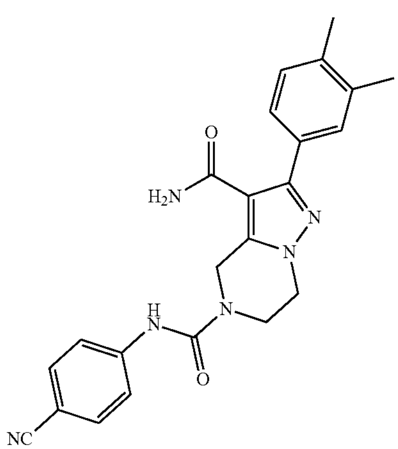 [SMILES: Cc1ccc(-c2nn3c(c2C(N)=O)CN(C(=O)Nc2ccc(C#N)cc2)CC3)cc1C] | N5-(4-Cyanophenyl)-2-(3,4-dimethylphenyl)-6,7-dihydropyrazolo[1,5-a]pyrazine-3,5(4H)-dicarboxamide | 415.0 | 1.35 | E |

TABLE 15-continued

| Ex. No. | Structure | Name | [M + H]⁺ | Ret Time (min.) | HPLC Methods |
|---|---|---|---|---|---|
| 283 | 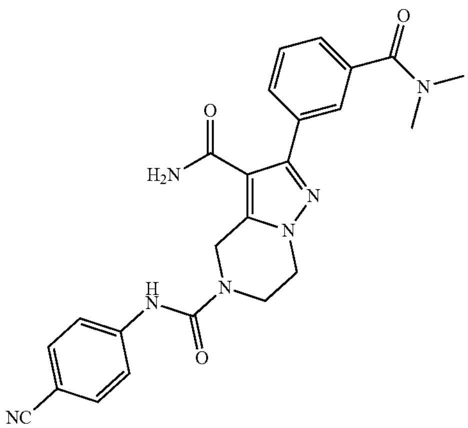 [SMILES: CN(C)C(=O)c1cccc(-c2nn3c(c2C(N)=O)CN(C(=O)Nc2ccc(C#N)cc2)CC3)c1] | N⁵-(4-Cyanophenyl)-2-(3-(dimethylcarbamoyl)phenyl)-6,7-dihydropyrazolo[1,5-a]pyrazine-3,5(4H)-dicarboxamide | 458.0 | 0.92 | E |
| 284 | 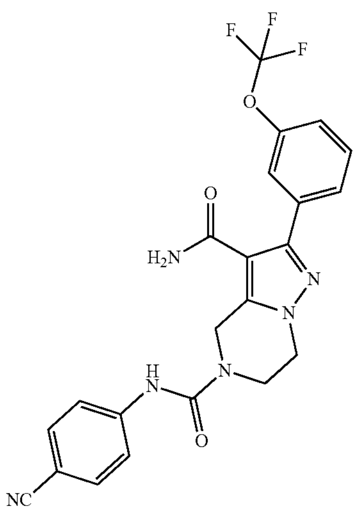 [SMILES: N#Cc1ccc(NC(=O)N2CCn3nc(-c4cccc(OC(F)(F)F)c4)c(C(N)=O)c3C2)cc1] | N⁵-(4-Cyanophenyl)-2-(3-(trifluoromethoxy)phenyl)-6,7-dihydropyrazolo[1,5-a]pyrazine-3,5(4H)-dicarboxamide | 471.0 | 1.45 | E |
| 285 | 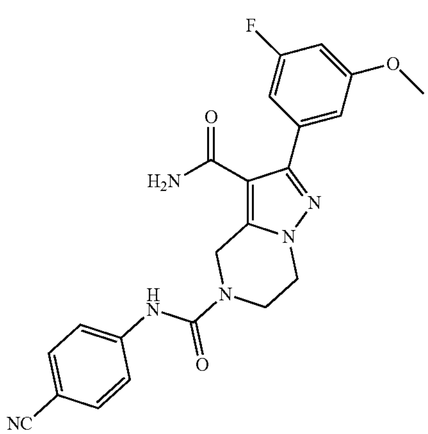 [SMILES: COc1cc(F)cc(-c2nn3c(c2C(N)=O)CN(C(=O)Nc2ccc(C#N)cc2)CC3)c1] | N⁵-(4-Cyanophenyl)-2-(3-fluoro-5-methoxyphenyl)-6,7-dihydropyrazolo[1,5-a]pyrazine-3,5(4H)-dicarboxamide | 435.0 | 1.22 | E |

TABLE 15-continued

| Ex. No. | Structure | Name | [M + H]+ | Ret Time (min.) | HPLC Methods |
|---|---|---|---|---|---|
| 286 | 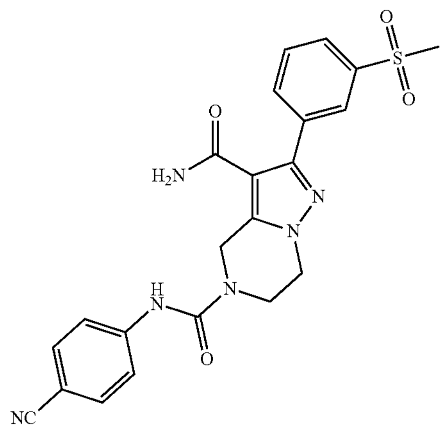 [SMILES: CS(=O)(=O)c1cccc(-c2nn3c(c2C(N)=O)CN(C(=O)Nc2ccc(C#N)cc2)CC3)c1] | N5-(4-Cyanophenyl)-2-(3-(methylsulfonyl)phenyl)-6,7-dihydropyrazolo[1,5-a]pyrazine-3,5(4H)-dicarboxamide | 482.0 | 0.93 | E |
| 287 | 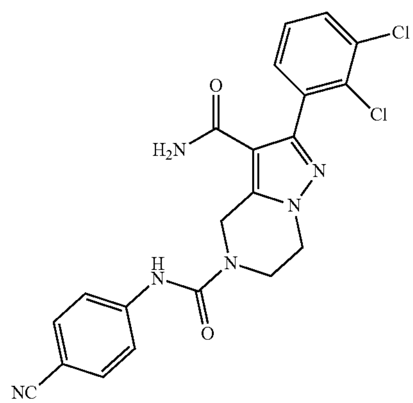 [SMILES: N#Cc1ccc(NC(=O)N2CCn3nc(-c4cccc(Cl)c4Cl)c(C(N)=O)c3C2)cc1] | N5-(4-Cyanophenyl)-2-(2,3-dichlorophenyl)-6,7-dihydropyrazolo[1,5-a]pyrazine-3,5(4H)-dicarboxamide | 454.8 | 1.30 | E |
| 288 | 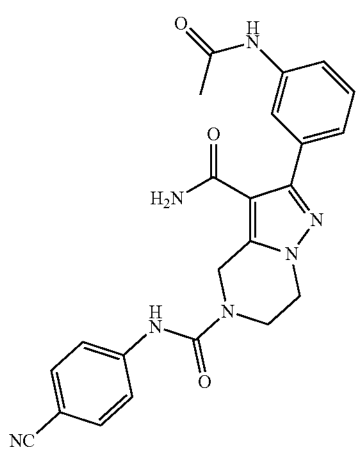 [SMILES: CC(=O)Nc1cccc(-c2nn3c(c2C(N)=O)CN(C(=O)Nc2ccc(C#N)cc2)CC3)c1] | 2-(3-Acetamidophenyl)-N5-(4-cyanophenyl)-6,7-dihydropyrazolo[1,5-a]pyrazine-3,5(4H)-dicarboxamide | 444.0 | 0.90 | E |

TABLE 15-continued

| Ex. No. | Structure | Name | [M + H]+ | Ret Time (min.) | HPLC Methods |
|---|---|---|---|---|---|
| 289 | 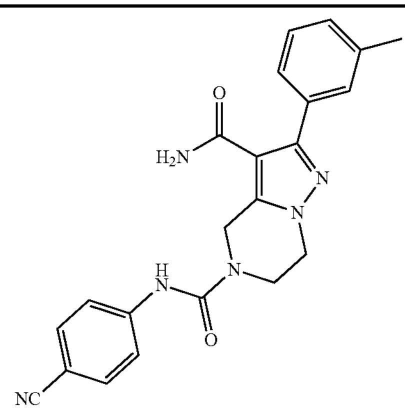 | N5-(4-Cyanophenyl)-2-(m-tolyl)-6,7-dihydropyrazolo[1,5-a]pyrazine-3,5(4H)-dicarboxamide | 401.0 | 1.22 | E |
| 290 | 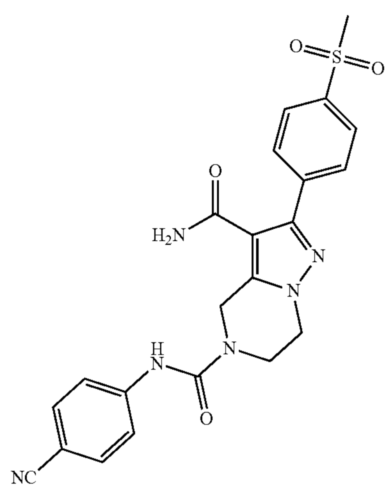 [SMILES: CS(=O)(=O)c1ccc(-c2nn3c(c2C(N)=O)CN(C(=O)Nc2ccc(C#N)cc2)CC3)cc1] | N5-(4-Cyanophenyl)-2-(4-(methylsulfonyl)phenyl)-6,7-dihydropyrazolo[1,5-a]pyrazine-3,5(4H)-dicarboxamide | 481.8 | 0.92 | E |
| 291 | 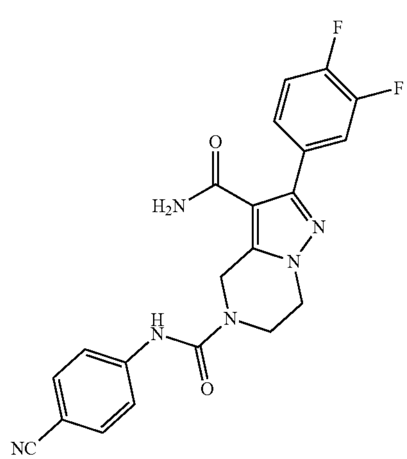 [SMILES: N#Cc1ccc(NC(=O)N2CCn3nc(-c4ccc(F)c(F)c4)c(C(N)=O)c3C2)cc1] | N5-(4-Cyanophenyl)-2-(3,4-difluorophenyl)-6,7-dihydropyrazolo[1,5-a]pyrazine-3,5(4H)-dicarboxamide | 423.0 | 1.22 | E |

Scheme 17

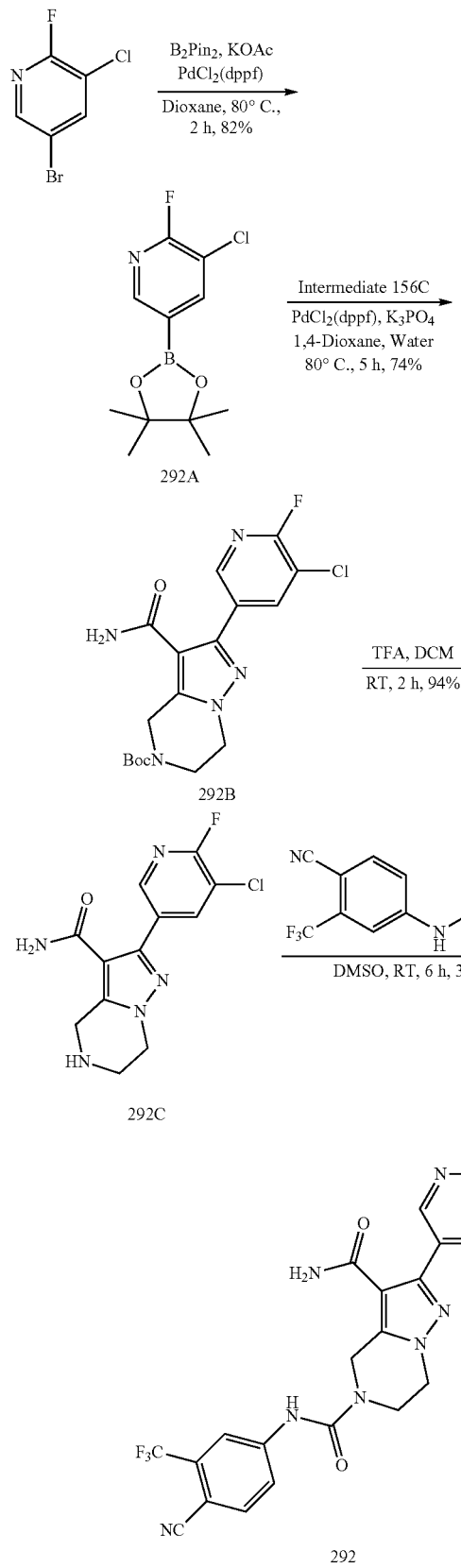

Intermediate 292A: 3-Chloro-2-fluoro-5-(4,4,5,5-tetramethyl-1,3,2-dioxaborolan-2-yl)pyridine

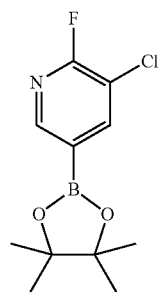

To a solution of 5-bromo-3-chloro-2-fluoropyridine (0.5 g, 2.376 mmol) in 1,4-dioxane (2 mL) was added bis(pinacolato)diboron (0.724 g, 2.85 mmol) and KOAc (0.350 g, 3.56 mmol) and the reaction mixture was purged with nitrogen for 10 min. PdCl$_2$(dppf)-CH$_2$Cl$_2$ adduct (0.097 g, 0.119 mmol) was added and the reaction mixture was allowed to stir at 80 OC for 3 h. The volatiles were removed under a reduced pressure and the residue was extracted with EtOAc (3×20 mL). The combined organic layer was concentrated and the residue was triturated with n-hexanes to afford Intermediate 292A (0.5 g, 82%) as a brown solid. MS(ES): m/z=176 [M−84]$^+$; $^1$H NMR (300 MHz, DMSO-d$_6$) δ ppm 8.34-8.39 (m, 1H), 8.17-8.26 (m, 1H), 1.32 (s, 12H).

Intermediate 292B: tert-Butyl 3-carbamoyl-2-(5-chloro-6-fluoropyridin-3-yl)-6,7-dihydropyrazolo[1,5-a]pyrazine-5(4H)-carboxylate

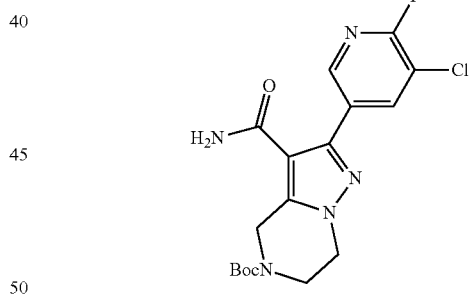

To a solution of Intermediate 156C (0.2 g, 0.510 mmol) in 1,4-dioxane (10 mL) was added Intermediate 292A (0.197 g, 0.765 mmol) and K$_3$PO$_4$ (0.325 g, 1.53 mmol) in water (2 mL) and the resulting reaction mixture was purging with N$_2$ for 10 min. PdCl$_2$(dppf)-CH$_2$Cl$_2$ adduct (0.025 g, 0.031 mmol) was added and the reaction mixture was then allowed to heat to 80° C. and stir for 5 h. The reaction mixture was diluted with water and extracted with ethyl acetate (3×25 mL). The combined organic layer was washed with water, brine, dried over Na$_2$SO$_4$, and concentrated in vacuo. The crude reaction mixture was purified by silica gel chromatography (24 g REDISEP® column, eluting with gradient from 0 to 2% MeOH in CHCl$_3$). Fractions containing the product were combined and evaporated to afford the Intermediate 292B (0.15 g, 74%) as an off-white solid. MS(ES): m/z=396 [M+H]$^+$; $^1$H NMR (400 MHz, DMSO-d$_6$) δ ppm 8.32-8.47 (m, 2H), 7.29 (br. s., 2H), 4.79 (s, 2H), 4.15-4.27 (m, 2H), 3.86 (d, J=5.52 Hz, 2H), 1.44 (s, 9H).

Intermediate 292C: 2-(5-Chloro-6-fluoropyridin-3-yl)-4,5,6,7-tetrahydropyrazolo[1,5-a]pyrazine-3-carboxamide

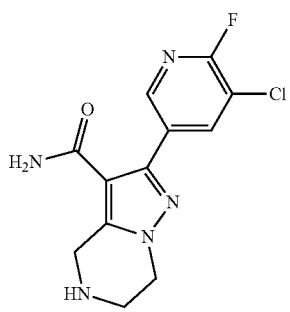 [SMILES: NC(=O)c1c(-c2cnc(F)c(Cl)c2)nn2c1CNCC2]

To a solution of Intermediate 292B (0.15 g, 0.379 mmol) in DCM (10 mL) at 0° C. was added TFA (0.146 mL, 1.895 mmol) and the resulting solution was stirred at RT for 3 h. The volatiles were removed under reduced pressure and the residue was treated with 10% aqueous solution of NaOH. The solid was filtered, washed with hexanes and dried in vacuo to afford Intermediate 292C (0.1 g, 94%) as a pale yellow solid. MS(ES): m/z=296 [M+H]$^+$; $^1$H NMR (400 MHz, DMSO-d$_6$) δ ppm 8.35-8.51 (m, 2H), 7.05-7.30 (br. s, 2H), 3.96-4.16 (m, 4H), 3.14 (d, J=5.02 Hz, 2H), 2.61-2.74 (m, 1H).

Compound 292: 2-(5-Chloro-6-fluoropyridin-3-yl)-N$^5$-(4-cyano-3-(trifluoromethyl)phenyl)-6,7-dihydropyrazolo[1,5-a]pyrazine-3,5(4H)-dicarboxamide

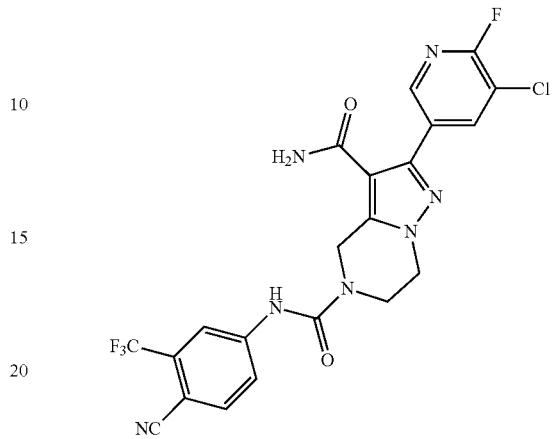

A solution of Intermediate 292C (20 mg, 0.067) and intermediate phenyl(4-cyano-3-(trifluoromethyl)phenyl)carbamate (24.86 mg, 0.081 mmol) in DMSO (3 mL) was stirred at RT for 6 h. The reaction mixture was diluted with water and the solid precipitated was filtered and dried. The crude was purified by silica gel chromatography (4 g REDISEP® column, eluting with a gradient from 0 to 5% MeOH in DCM). Fractions containing the product were combined and evaporated to afford the Compound 292 (12 mg, 32%) as a pale yellow solid. MS(ES): m/z=439 [M+H]$^+$; $^1$H NMR (400 MHz, DMSO-d$_6$) δ ppm 9.60 (br s, 1H), 8.37-8.47 (m, 2H), 8.16 (d, J=2.01 Hz, 1H), 8.05 (d, J=8.53 Hz, 1H), 7.93-7.99 (m, 1H), 7.24-7.43 (br s, 2H), 4.98 (s, 2H), 4.25-4.33 (m, 2H), 4.04 (d, J=5.52 Hz, 2H).

The Compounds shown in Table 16 have been prepared similar to Compound 292 by reaction of Intermediate 292C with respective anilines phenylcarbamates or with readily available/in-situ generated isocyanates.

TABLE 16

| Ex. No. | Structure | Name | [M + H]$^+$ | Ret Time (min.) | HPLC Methods |
|---|---|---|---|---|---|
| 293 | 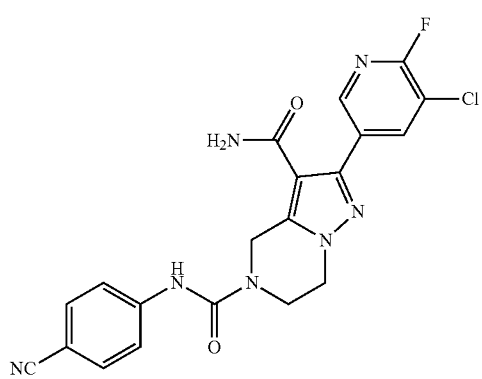 [SMILES: N#Cc1ccc(NC(=O)N2CCn3nc(-c4cnc(F)c(Cl)c4)c(C(N)=O)c3C2)cc1] | 2-(5-Chloro-6-fluoropyridin-3-yl)-N$^5$-(4-cyanophenyl)-6,7-dihydropyrazolo[1,5-a]pyrazine-3,5(4H)-dicarboxamide | 441 | 8.10<br>7.84 | A<br>B |

TABLE 16-continued

| Ex. No. | Structure | Name | [M + H]⁺ | Ret Time (min.) | HPLC Methods |
|---|---|---|---|---|---|
| 294 | 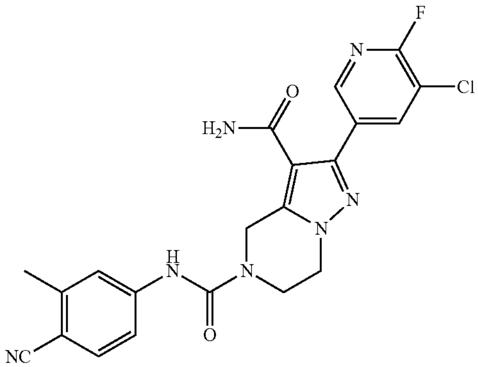 [SMILES: Cc1cc(NC(=O)N2CCn3nc(-c4cnc(F)c(Cl)c4)c(C(N)=O)c3C2)ccc1C#N] | 2-(5-Chloro-6-fluoropyridin-3-yl)-N⁵-(4-cyano-3-methylphenyl)-6,7-dihydropyrazolo[1,5-a]pyrazine-3,5(4H)-dicarboxamide | 454 | 8.60<br>8.31 | A<br>B |
| 295 | 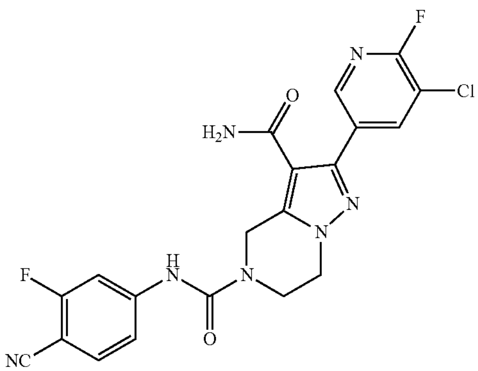 | 2-(5-Chloro-6-fluoropyridin-3-yl)-N⁵-(4-cyano-3-fluorophenyl)-6,7-dihydropyrazolo[1,5-a]pyrazine-3,5(4H)-dicarboxamide | 458 | 8.81<br>8.48 | A<br>B |
| 296 | 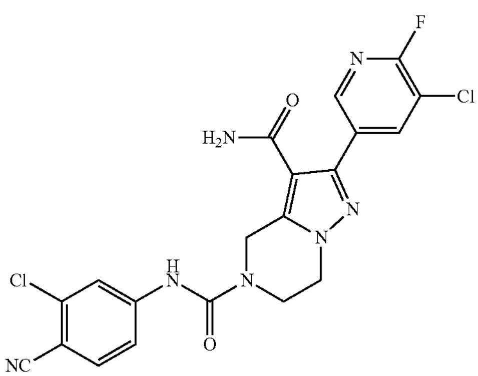 [SMILES: N#Cc1ccc(NC(=O)N2CCn3nc(-c4cnc(F)c(Cl)c4)c(C(N)=O)c3C2)cc1Cl] | N⁵-(3-Chloro-4-cyanophenyl)-2-(5-chloro-6-fluoropyridin-3-yl)-6,7-dihydropyrazolo[1,5-a]pyrazine-3,5(4H)-dicarboxamide | 474 | 14.12<br>13.39 | C<br>D |

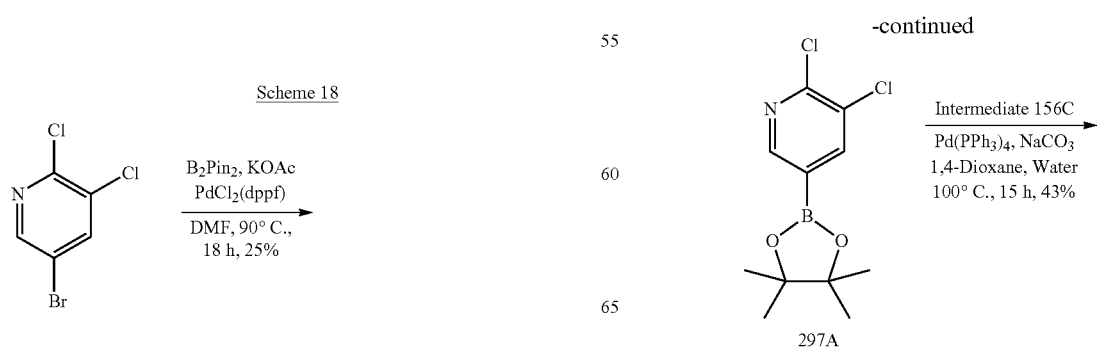

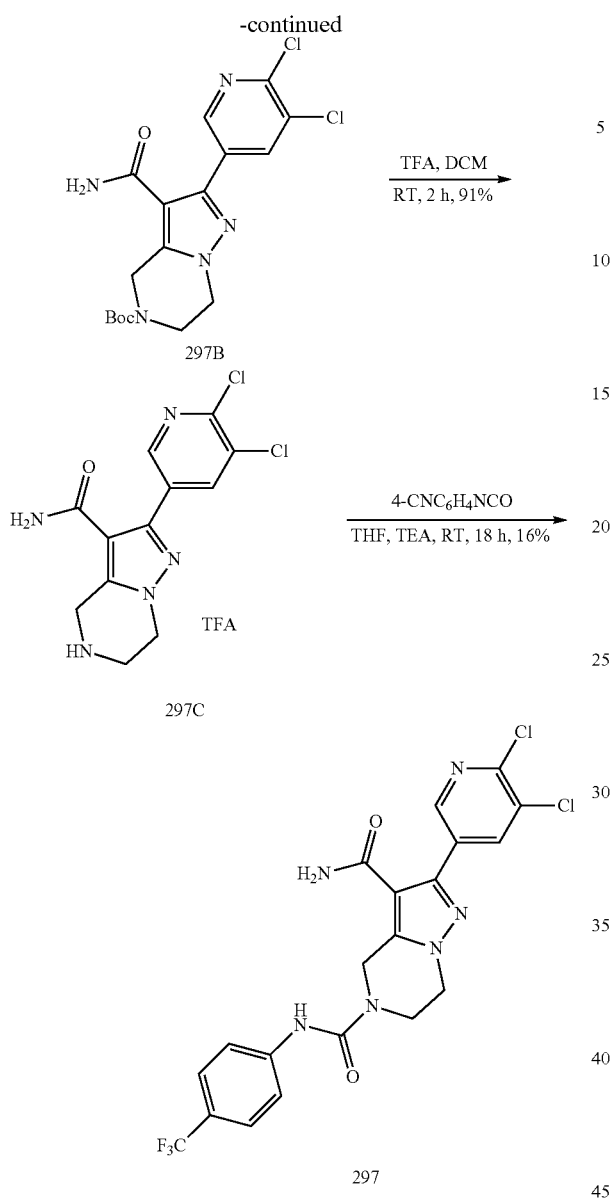

Intermediate 297A: 2,3-Dichloro-5-(4,4,5,5-tetramethyl-1,3,2-dioxaborolan-2-yl)pyridine

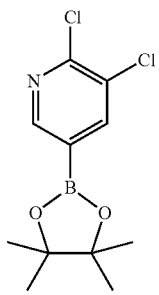

To a solution of 5-bromo-2,3-dichloropyridine (0.25 g, 1.102 mmol) in DMF (3 mL) was added KOAc (0.324 g, 3.31 mmol), bis(pinacolato)diboron (0.336 g, 1.322 mmol) and the resulting reaction mixture was purged with $N_2$ for 5 min. $PdCl_2$(dppf)-$CH_2Cl_2$ (0.048 g, 0.066 mmol) was added and the reaction mixture was heated to 90° C. and stirred for 18 h. The reaction mixture was cooled to RT, diluted with water and extracted with EtOAc (2×50 mL). The combined organic layer was dried over anhydrous $Na_2SO_4$, filtered and the filtrate concentrated under reduced pressure. The crude compound was purified by silica gel chromatography (12 g REDISEP® column, eluting with a gradient from 0-10% of EtOAc in hexanes). Fractions containing the product were combined and evaporated to afford the Intermediate 297A (0.08 g, 25%). MS(ES): m/z=272.4 [M+H]$^+$; $^1$H NMR (300 MHz, DMSO-$d_6$) δ ppm 8.89 (d, J=2.3 Hz, 1H), 8.69 (d, J=2.3 Hz, 1H), 1.17 (s, 12H).

Intermediate 297B: tert-Butyl 3-carbamoyl-2-(5,6-dichloropyridin-3-yl)-6,7-dihydropyrazolo[1,5-a]pyrazine-5(4H)-carboxylate To a stirred solution of Intermediate 156C (0.1 g, 0.255 mmol) and Intermediate 297A (0.070 g, 0.255 mmol) in 1,4-dioxane (2 mL was added a solution of $Na_2CO_3$ (0.081 g, 0.765 mmol) in water (0.5 mL) and the reaction mixture was purged with $N_2$ gas for 5 min. Pd(PPh$_3$)$_4$(0.015 g, 0.013 mmol) was added and the reaction mixture was heated to 100° C. and stirred for 15 h. The reaction mixture was diluted with water and extracted with EtOAc (2×50 mL). The organic layer was washed with brine, dried over $Na_2SO_4$ and concentrated under reduced pressure. The crude compound was purified by silica gel chromatography (12 g REDISEP® column, eluting with a gradient from 0-60% of EtOAc in hexanes). Fractions containing the product were combined and evaporated to afford Intermediate 297B (0.05 g, 43%) as an off-white solid. MS(ES): m/z=412.1 [M+H]$^+$; $^1$H NMR (300 MHz, DMSO-$d_6$) δ ppm 8.62 (d, J=1.9 Hz, 1H), 8.33 (s, 1H), 7.66-7.52 (m, 1H), 7.34 (br. s., 1H), 4.77 (s, 2H), 4.20 (t, J=5.3 Hz, 2H), 3.85 (t, J 5.3 Hz, 2H), 1.43 (s, 9H).

Intermediate 297C: 2-(5,6-Dichloropyridin-3-yl)-4,5,6,7-tetrahydropyrazolo[1,5-a]pyrazine-3-carboxamide TFA

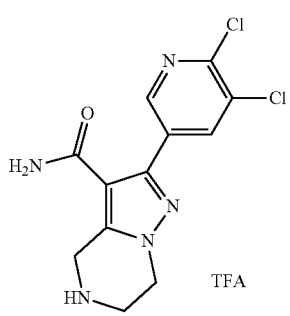 [SMILES: NC(=O)c1c(-c2cnc(Cl)c(Cl)c2)nn2c1CNCC2]

A solution of Intermediate 297B (0.35 g, 0.849 mmol) in DCM (15 mL) was added TFA (0.327 mL, 4.24 mmol) and the resultant solution was allowed to stir at RT for 1 h. The volatiles were removed under reduced pressure and the reaction mixture was triturated with diethyl ether to afford Intermediate 297C (0.3 g, 91%) as a pale yellow solid. MS(ES): m/z=312.0 [M+H]$^+$.

Intermediate 297: $N^5$-(4-Cyanophenyl)-2-(5,6-dichloropyridin-3-yl)-6,7-dihydropyrazolo[1,5-a]pyrazine-3,5(4H)-dicarboxamide

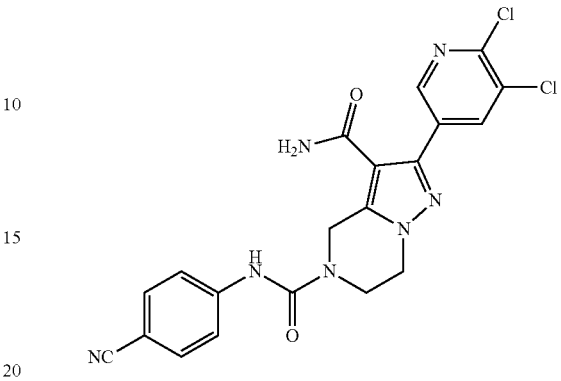

To a stirred solution of Intermediate 297C (0.05 g, 0.082 mmol) and 4-isocyanatobenzonitrile (0.012 g, 0.082 mmol) in THF (1 mL) was added TEA (0.034 mL, 0.246 mmol) and the resulting reaction mixture was allowed to stir at RT for 18 h. The reaction mixture was diluted with EtOAc, washed with water and brine. The organic layer was dried over Na$_2$SO$_4$, filtered and the filtrate concentrated under reduced pressure. The crude product was purified by preparative HPLC to afford Compound 297 (0.006 g, 16%) as an off-white solid. The HPLC retention times are 1.357 min. and 1.365 min. (Methods E and L respectively). MS(ES): m/z=456.1 [M+H]$^+$; $^1$H NMR (400 MHz, DMSO-d$_6$) δ ppm 9.40 (s, 1H), 8.64 (d, J=2.5 Hz, 1H), 8.34 (d, J=2.0 Hz, 1H), 7.77-7.63 (m, 4H), 7.43 (br. s., 1H), 7.33 (br. s., 1H), 4.94 (s, 2H), 4.28 (t, J=5.3 Hz, 2H), 4.01 (t, J=5.3 Hz, 2H).

The Compound shown in Table 17 has been prepared similar to Compound 297 by coupling of Intermediate 297C with various readily available isocyanates or in-situ generated from respective anilines.

TABLE 17

| Ex. No. | Structure | Name | [M + H]$^+$ | Ret Time (min.) | HPLC Methods |
|---|---|---|---|---|---|
| 298 | 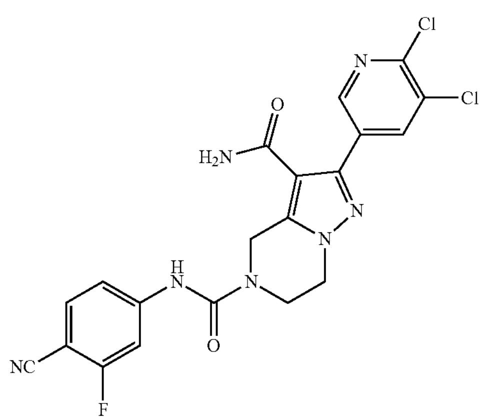 [SMILES: N#Cc1ccc(NC(=O)N2CCn3nc(-c4cnc(Cl)c(Cl)c4)c(C(N)=O)c3C2)cc1F] | $N^5$-(4-Cyano-3-fluorophenyl)-2-(5,6-dichloropyridin-3-yl)-6,7-dihydropyrazolo[1,5-a]pyrazine-3,5(4H)-dicarboxamide | 474.0 | 8.716<br>9.350 | A<br>B |

Scheme 19

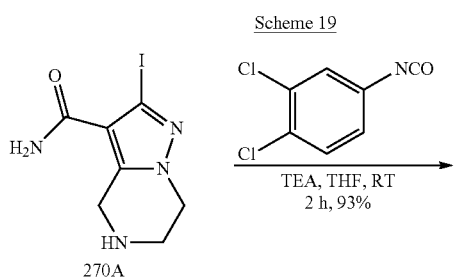

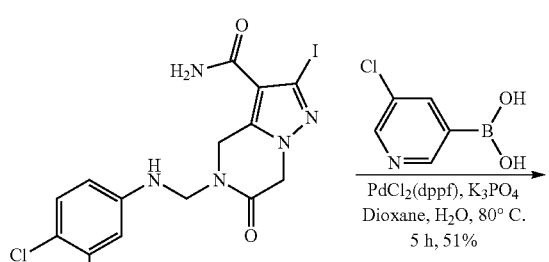

299A

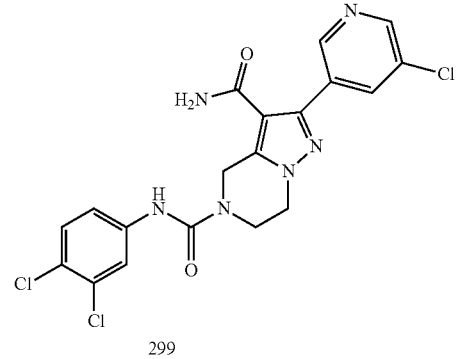

299

Intermediate 299A: N⁵-(3,4-Dichlorophenyl)-2-iodo-6,7-dihydropyrazolo[1,5-a]pyrazine-3,5(4H)-dicarboxamide

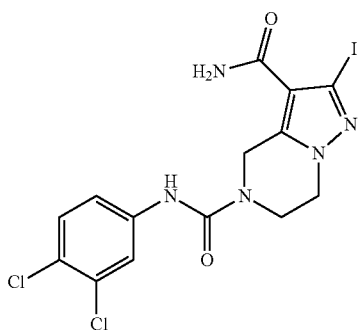 [SMILES: NC(=O)c1c(I)nn2c1CN(C(=O)Nc1ccc(Cl)c(Cl)c1)CC2]

To a solution of Intermediate 270A (350 mg, 1.198 mmol) in THF (20 mL) was added TEA (0.501 mL, 3.59 mmol), 1,2-dichloro-4-isocyanatobenzene (270 mg, 1.438 mmol) and the reaction mixture was stirred at room temperature for 2 h. The reaction mixture was concentrated under reduced pressure and the residue was dissolved in ethyl acetate (50 mL), washed with a saturated aqueous solution of NaHCO₃, water and brine. The organic layer was dried over Na₂SO₄, filtered and the filtrate concentrated. The crude product was triturated with diethyl ether (3×50 mL) and the solid was filtered through a Buchner funnel and rinsed with hexane to afford Intermediate 299A as a white solid (350 mg 59%). MS(ES): m/z=477.8 [M−H]⁻; ¹H NMR (400 MHz, DMSO-d₆) δ ppm 9.17 (s, 1H), 7.81 (d, J=2.5 Hz, 1H), 7.53-7.41 (m, 3H), 6.90 (br. s., 1H), 4.89 (s, 2H), 4.24-4.15 (m, 2H), 3.92 (t, J=5.3 Hz, 2H).

Compound 299: 2-(5-Chloropyridin-3-yl)-N⁵-(3,4-dichlorophenyl)-6,7-dihydropyrazolo[1,5-a]pyrazine-3,5(4H)-dicarboxamide

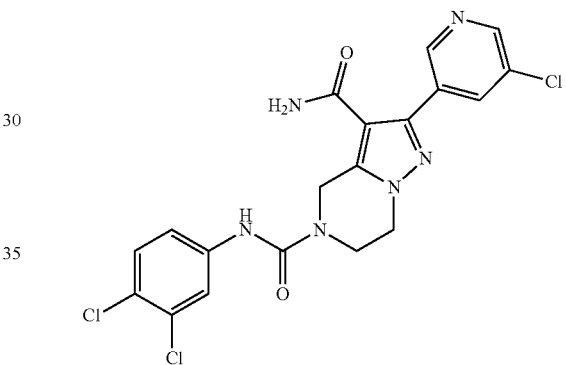

To a solution of Intermediate 299A (40 mg, 0.083 mmol), (5-chloropyridin-3-yl)boronic acid (19.67 mg, 0.125 mmol) in 1,4-dioxane (1.5 mL) was added K₃PO₄ (53.1 mg, 0.250 mmol) in water (0.5 mL) and the resulting reaction mixture was purged with N₂ for 5 min. PdCl₂(dppf)-CH₂Cl₂ adduct (3.4 mg, 4.17 μmol) was added, the reaction mixture was heated to 80° C. and stirred for 5 h. The reaction mixture was quenched with water and extracted with ethyl acetate (3×5 mL). The combined organic layer was washed with water, brine, dried over Na₂SO₄, filtered and the filtrate concentrated to afford. The crude compound was purified via preparative HPLC to afford Compound 299 as an off-white solid (18 mg, 46%). The HPLC retention times are 1.357 min. and 1.365 min. (Methods J and K respectively). MS(ES): m/z=464.8 [M+H]⁺; ¹H NMR (400 MHz, methanol-d₄) δ ppm 8.80 (d, J=2.01 Hz, 1H), 8.58 (d, J=2.51 Hz, 1H), 8.19 (t, J=2.26 Hz, 1H), 7.74 (d, J=2.51 Hz, 1H), 7.27-7.48 (m, 2H), 5.02 (s, 2H), 4.29-4.40 (m, 2H), 4.09 (t, J=5.27 Hz, 2H).

The Compounds shown in Table 18 have been prepared similar to Compound 299 by coupling of Intermediate 299A with various readily available boronic acids.

TABLE 18
| Ex. No. | Structure | Name | [M + H]+ | Ret Time (min.) | HPLC Methods |
|---|---|---|---|---|---|
| 300 | 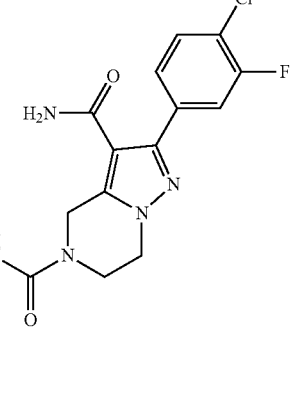 | 2-(4-Chloro-3-fluorophenyl)-N$^5$-(3,4-dichlorophenyl)-6,7-dihydropyrazolo[1,5-a]pyrazine-3,5(4H)-dicarboxamide | 483 | 10.58<br>9.96 | A<br>B |
| 301 | 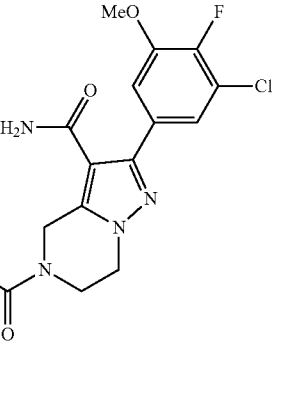 | 2-(3-Chloro-4-fluoro-5-methoxyphenyl)-N$^5$-(3,4-dichlorophenyl)-6,7-dihydropyrazolo[1,5-a]pyrazine-3,5(4H)-dicarboxamide | 513 | 10.72<br>10.19 | A<br>B |
| 302 | 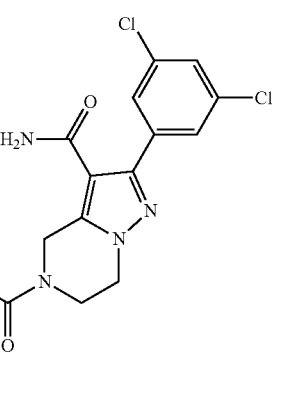 | N$^5$-(3,4-Dichlorophenyl)-2-(3,5-dichlorophenyl)-6,7-dihydropyrazolo[1,5-a]pyrazine-3,5(4H)-dicarboxamide | 498 | 11.42<br>10.82 | A<br>B |

TABLE 18-continued
| Ex. No. | Structure | Name | [M + H]+ | Ret Time (min.) | HPLC Methods |
|---|---|---|---|---|---|
| 303 | 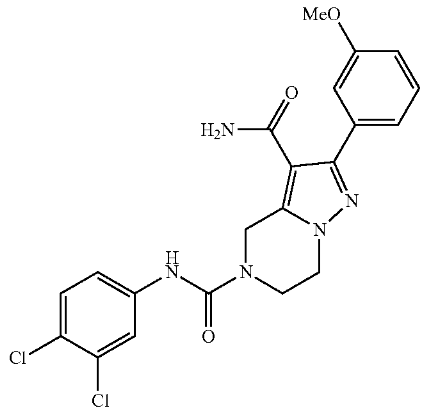 [SMILES: COc1cccc(-c2nn3c(c2C(N)=O)CN(C(=O)Nc2ccc(Cl)c(Cl)c2)CC3)c1] | N5-(3,4-Dichlorophenyl)-2-(3-methoxyphenyl)-6,7-dihydropyrazolo[1,5-a]pyrazine-3,5(4H)-dicarboxamide | 460 | 1.47<br>1.47 | E<br>L |
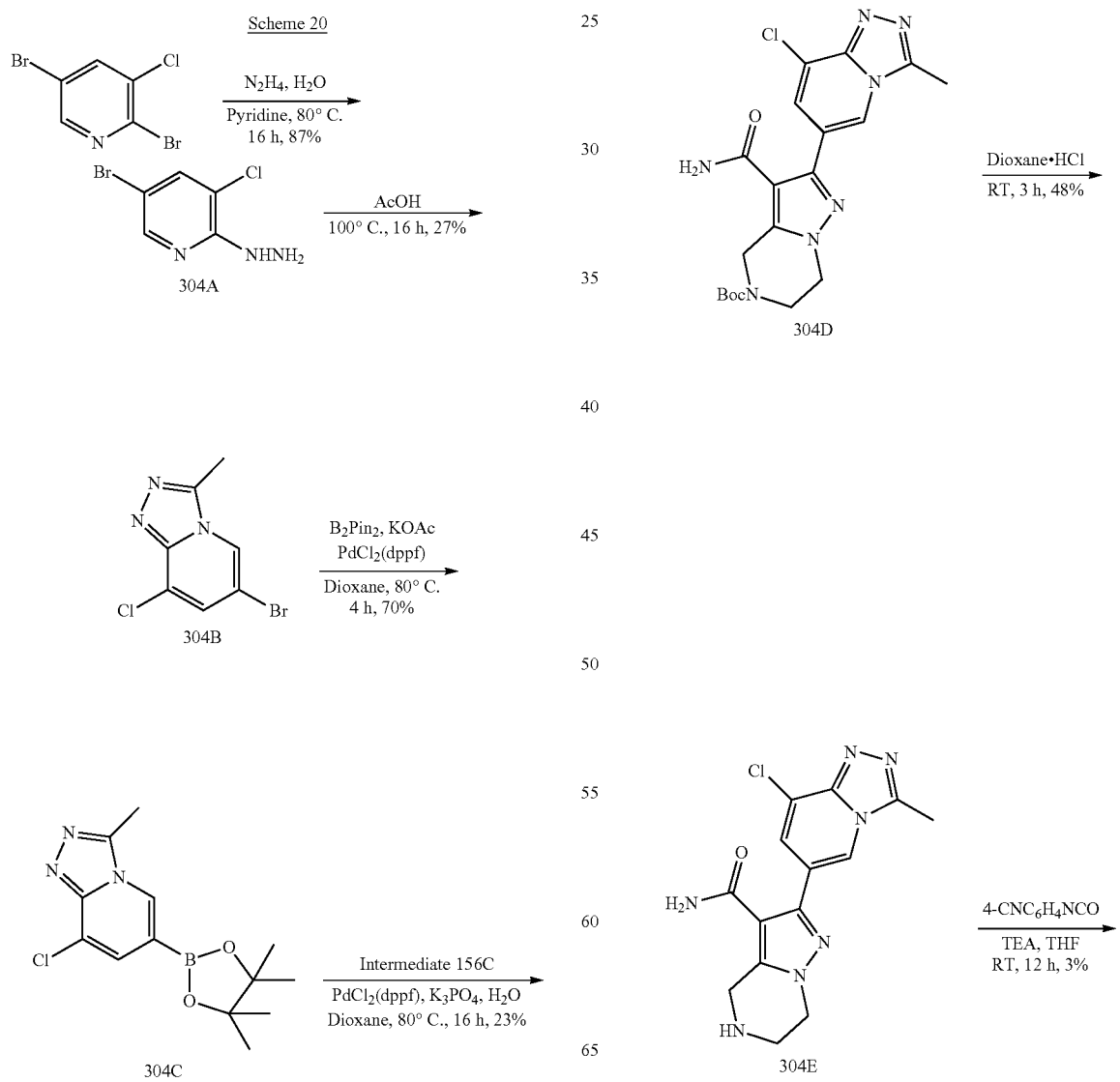

-continued

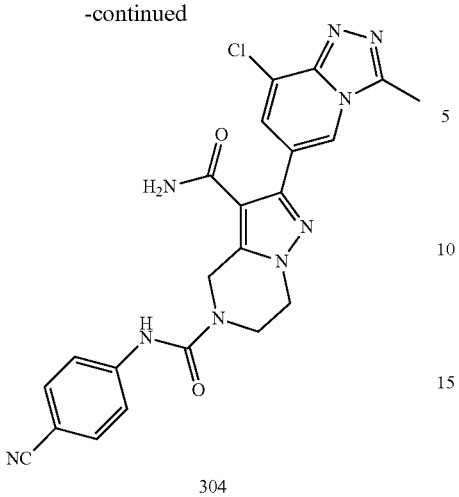

304

Intermediate 304A: 5-Bromo-4-chloro-2-hydrazinylpyridine

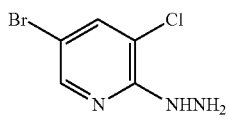

To a stirred solution of 2,5-dibromo-3-chloropyridine (0.5 g, 1.843 mmol) in pyridine (2.5 mL) was added hydrazine hydrate (0.099 mL, 2.027 mmol) and the reaction mixture was heated to 80° C. for 16 h. The reaction mixture was concentrated and azeotroped with toluene to afford Intermediate 304A (0.4 g, 87%) as a yellow solid which was taken to the next step without further purification. MS(ES): m/z=224[M+2]$^+$.

Intermediate 304B: 6-Bromo-8-chloro-3-methyl-[1,2,4]triazolo[4,3-a]pyridine

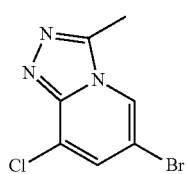

A solution of Intermediate 304A (0.9 g, 4.05 mmol) in acetic acid (10 mL, 175 mmol) was heated to 110° C. and stirred for 16 h. The reaction mixture was concentrated under reduced pressure and the crude compound was purified by silica gel chromatography (12 g REDISEP® column, eluting with a gradient of 3-8% MeOH in CHCl$_3$). Fractions containing the product were combined and evaporated to afford Intermediate 304B (0.3 g, 27%) as an off-white solid. MS(ES): m/z=248 [M+2]$^+$; $^1$H NMR (400 MHz, DMSO-d$_6$) δ ppm 8.79 (d, J=1.5 Hz, 1H), 7.80 (d, J=1.5 Hz, 1H), 2.70-2.68 (m, 3H).

Intermediate 304C: 8-Chloro-3-methyl-6-(4,4,5,5-tetramethyl-1,3,2-dioxaborolan-2-yl)-[1,2,4]triazolo[4,3-a]pyridine

To a solution of Intermediate 304B (0.5 g, 2.028 mmol) in dioxane (10 mL) was added bis(pinacolato)diboron (1.030 g, 4.06 mmol), KOAc (0.597 g, 6.09 mmol) and the resulting reaction mixture was degasified with N$_2$ for 5 min. PdCl$_2$(dppf)-CH$_2$Cl$_2$ adduct (0.083 g, 0.101 mmol) was added and the reaction mixture was heated to 80° C. and stirred for 4 h. The reaction mixture concentrated under reduced pressure and the residue was extracted with ethyl acetate. The combined organic layer was washed with water, dried over Na$_2$SO$_4$, filtered and the filtrate concentrated to afford Intermediate 304C (0.5 g, 70%) as a brown oil which was taken to Suzuki coupling without further purification.

Intermediate 304D: tert-Butyl 3-carbamoyl-2-(8-chloro-3-methyl-[1,2,4]triazolo[4,3-a]pyridin-6-yl)-6,7-dihydropyrazolo[1,5-a]pyrazine-5(4H)-carboxylate

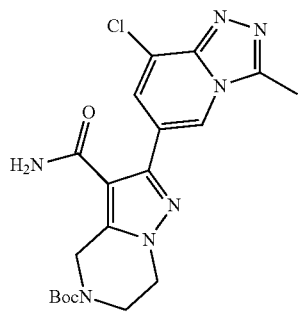 [SMILES: Cc1nnc2c(Cl)cc(-c3nn4c(c3C(N)=O)CN(C(=O)OC(C)(C)C)CC4)cn12]

To a solution of Intermediate 156C (0.5 g, 1.275 mmol) and Intermediate 304C (1.123 g, 3.82 mmol) in dioxane (2 mL) was added a solution of K$_3$PO$_4$ (0.812 g, 3.82 mmol) in water (0.5 mL) and the reaction mixture was degasified with N$_2$ for 10 min. PdCl$_2$(dppf)-CH$_2$Cl$_2$ (0.078 g, 0.096 mmol) was added and the reaction mixture was heated to 80° C. and stirred for 16 h. The reaction mixture was diluted with ethyl acetate and filtered through CELITE®. The filtrate was washed with water, dried over Na$_2$SO$_4$, filtered and the filtrate concentrated. The crude compound was purified by silica gel chromatography (12 g REDISEP® column, eluting with a gradient of 60-100% EtOAc in hexanes). Fractions containing the product were combined and evaporated to afford Intermediate 304D (0.160 g, 23%) as brown oil. MS(ES): m/z=430[M−H]$^+$; $^1$H NMR (300 MHz, DMSO-d$_6$) δ ppm 8.70 (d, J=1.1 Hz, 1H), 7.72 (d, J=1.5 Hz, 1H), 7.55

(d, J=8.3 Hz, 2H), 4.80 (s, 2H), 4.20 (t, J=5.5 Hz, 2H), 3.86 (t, J=5.5 Hz, 2H), 2.74-2.67 (m, 3H), 1.45 (s, 9H).

Intermediate 304E: 2-(8-Chloro-3-methyl-[1,2,4]triazolo[4,3-a]pyridin-6-yl)-4,5,6,7-tetrahydropyrazolo[1,5-a]pyrazine-3-carboxamide HCl salt

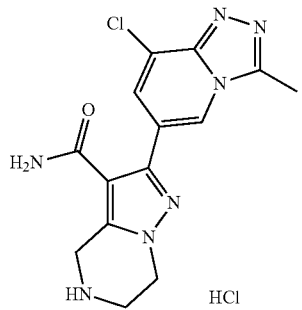 [SMILES: Cc1nnc2c(Cl)cc(-c3nn4c(c3C(N)=O)CNCC4)cn12 ; Cl]

A solution of Intermediate 304D (0.34 g, 0.787 mmol) in 4M HCl in dioxane (3 mL, 0.787 mmol) was stirred at RT for 3 h. The volatiles were removed under a reduced pressure and the residue was triturated with diethyl ether to afford Intermediate 304E (0.14 g, 48%) as a brown solid MS(ES): m/z=332[M+H]$^+$; $^1$H NMR (300 MHz, DMSO-d$_6$) δ ppm 10.00 (br. s., 2H), 8.73 (d, J=1.1 Hz, 1H), 7.73 (d, J=1.5 Hz, 1H), 4.60 (br. s., 2H), 4.44 (t, J=5.5 Hz, 2H), 3.75-3.63 (t, J=5.5 Hz, 2H), 2.77-2.67 (m, 3H).

Compound 304: 2-(8-Chloro-3-methyl-[1,2,4]triazolo[4,3-a]pyridin-6-yl)-N$^5$-(4-cyanophenyl)-6,7-dihydropyrazolo[1,5-a]pyrazine-3,5(4H)-dicarboxamide

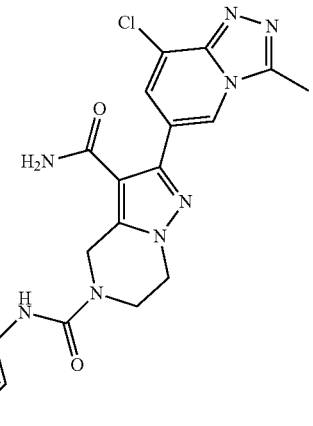

To a solution of Intermediate 304E (0.05 g, 0.151 mmol) in THF (1 mL) was added 4-isocyanatobenzonitrile (0.22 g, 0.151 mmol) followed by and TEA (0.063 mL, 0.452 mmol) and the resulting solution was allowed to stir at RT for 12 h. The reaction mixture was quenched with water (2 mL) and concentrated under vacuum. The crude product was purified by preparative HPLC to afford Compound 304 (2 mg, 3%) as a white solid. HPLC retention times 1.03 min. and 1.02 min. (Methods E and L respectively). MS(ES): m/z=476 [M+H]$^+$; $^1$H NMR (400 MHz, DMSO-d$_6$) δ ppm 9.42 (s, 1H), 8.72 (d, J=1.0 Hz, 1H), 7.75-7.65 (m, 5H), 7.46-7.15 (m, 2H), 4.97 (s, 2H), 4.28 (t, J=5.3 Hz, 2H), 4.02 (t, J=5.3 Hz, 2H), 2.72 (s, 3H).

The Compound shown in Table 19 has been prepared similar to Compound 304 by coupling of Intermediate 304E with in-situ generated isocyanate from respective aniline.

TABLE 19

| Ex. No. | Structure | Name | [M + H]$^+$ | Ret Time (min.) | HPLC Methods |
|---|---|---|---|---|---|
| 305 | 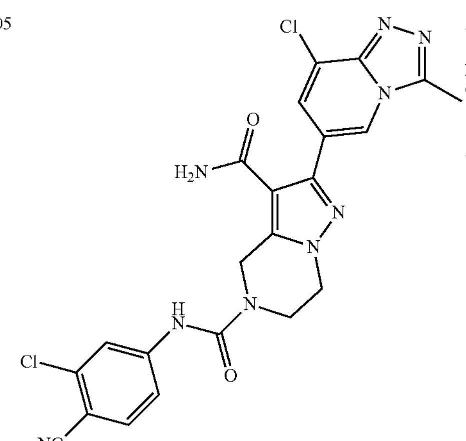 | 2-(8-Chloro-3-methyl-[1,2,4]triazolo[4,3-a]pyridin-6-yl)-N$^5$-(3-chloro-4-cyanophenyl)-6,7-dihydropyrazolo[1,5-a]pyrazine-3,5(4H)-dicarboxamide | 571 | 1.19<br>1.18 | E<br>L |

Scheme 21

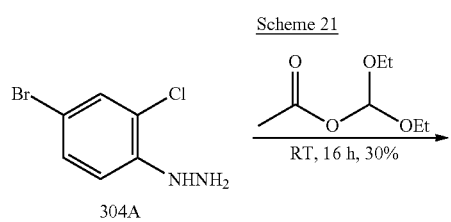

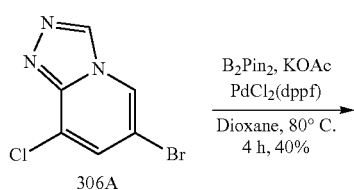

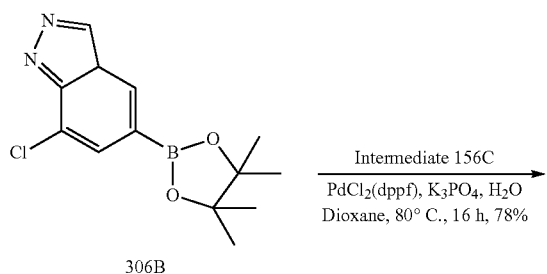

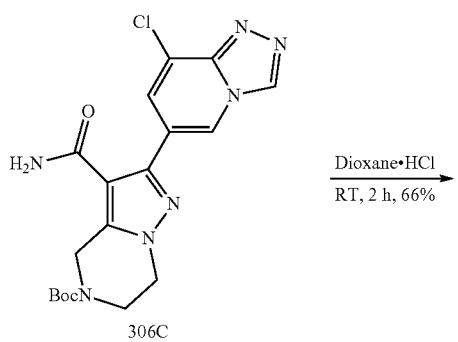

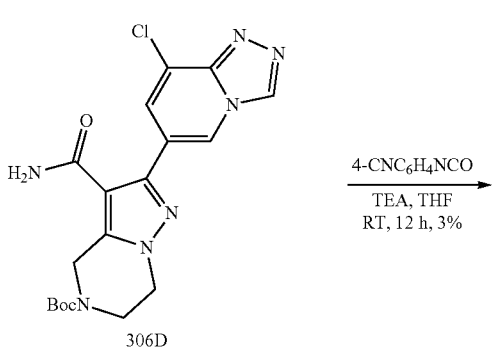

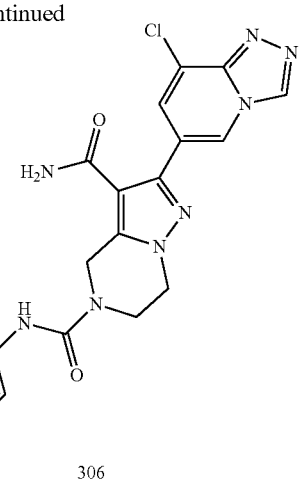

Intermediate 306A:
6-Bromo-8-chloro-[1,2,4]triazolo[4,3-a]pyridine

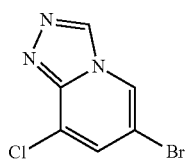 [SMILES: Clc1cc(Br)cn2cnnc12]

A solution of Intermediate 304A (4 g, 17.98 mmol) in diethoxymethyl acetate (20 mL, 17.98 mmol) was stirred at RT for 16 h. The reaction mixture was diluted with water and extracted with EtOAc (3×100 mL). The combined organic layer was dried over $Na_2SO_4$, filtered and the filtrate concentrated under vacuum. The crude compound was purified by silica gel chromatography (40 g REDISEP® column, eluting with gradient from 0-7% MeOH in $CHCl_3$). Fractions containing the product were combined and evaporated to afford Intermediate 306A (1.4 g, 30%) as an off-white solid. MS(ES): m/z=232 $[M=H]^+$; $^1$H NMR (400 MHz, DMSO-$d_6$) δ ppm 9.28 (s, 1H), 8.93 (d, J=1.51 Hz, 1H), 7.86 (d, J=1.00 Hz, 1H).

Intermediate 306B: 8-Chloro-6-(4,4,5,5-tetramethyl-1,3,2-dioxaborolan-2-yl)-[1,2,4]triazolo[4,3-a]pyridine

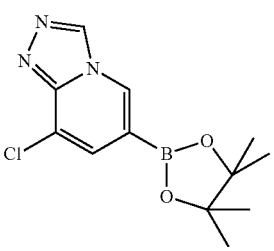 [SMILES: CC1(C)OB(c2cc(Cl)c3nncn3c2)OC1(C)C]

To a stirred solution of Intermediate 306A (0.5 g, 2.151 mmol) in dioxane (2 mL) was added bis(pinacolato)diboron (1.092 g, 4.30 mmol), KOAc (0.633 g, 6.45 mmol) and the reaction mixture was degasified with $N_2$ for 5 min. $PdCl_2$(dppf)-$CH_2Cl_2$ (0.088 g, 0.108 mmol) was added and the reaction mixture was heated to 80° C. and stirred for 4 h. The reaction mixture was cooled to RT filtered through CELITE® and the CELITE® pad was washed with ethyl acetate (100 mL). The filtrate was washed with water, dried over $Na_2SO_4$, filtered and the filtrate concentrated to afford crude Intermediate 306B (200 mg, 40%) which was taken to Suzuki coupling without purification.

Intermediate 306C: tert-Butyl 3-carbamoyl-2-(8-chloro-[1,2,4]triazolo[4,3-a]pyridin-6-yl)-6,7-dihydropyrazolo[1,5-a]pyrazine-5(4H)-carboxylate

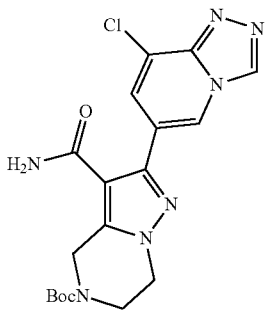 [SMILES: CC(C)(C)OC(=O)N1CCn2nc(-c3cc(Cl)c4nncn4c3)c(C(N)=O)c2C1]

Intermediate 306C was synthesized from Intermediate 306B using a synthetic sequence analogous to the preparation of Intermediate 304D. MS(ES): m/z=418 [M+H]$^+$; $^1$H NMR (300 MHz, DMSO-$d_6$) δ ppm 9.46 (s, 1H), 8.93 (d, J=1.1 Hz, 1H), 7.77 (d, J=1.5 Hz, 1H), 7.38-7.18 (m, 2H), 4.79 (s, 2H), 4.19 (t, J=4.9 Hz, 2H), 3.86 (t, J=1.0 Hz, 2H) 1.43 (s, 9H).

Intermediate 306D: 2-(8-Chloro-[1,2,4]triazolo[4,3-a]pyridin-6-yl)-4,5,6,7-tetrahydropyrazolo[1,5-a]pyrazine-3-carboxamide TFA salt

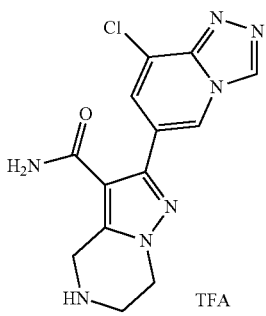 [SMILES: NC(=O)c1c(-c2cc(Cl)c3nncn3c2)nn2c1CNCC2]

Intermediate 306D was synthesized from Intermediate 306C using a synthetic sequence analogous to the preparation of Intermediate 304E. MS(ES): m/z=318 [M+H]$^+$; $^1$H NMR (300 MHz, DMSO-$d_6$) δ ppm 10.07 (br. s., 2H), 9.47 (s, 1H), 8.96 (d, J=1.5 Hz, 1H), 7.77 (d, J=1.1 Hz, 1H), 7.50-7.22 (m, 2H), 4.58 (br. s., 2H), 4.44 (t, J=5.5 Hz, 2H), 3.68 (t, J=5.5 Hz, 2H).

Compound 306: 2-(8-Chloro-[1,2,4]triazolo[4,3-a]pyridin-6-yl)-$N^5$-(4-cyanophenyl)-6,7-dihydropyrazolo[1,5-a]pyrazine-3,5(4H)-dicarboxamide

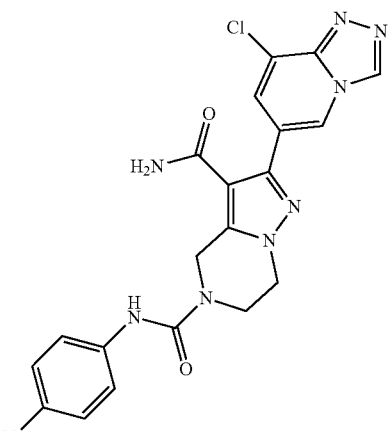

Compound 306 was synthesized from Intermediate 306D using a synthetic sequence analogous to the preparation of Compound 304. HPLC retention times 0.98 min. and 1.01 min. (Methods E and L respectively). MS(ES): m/z=462 [M+H]$^+$; $^1$H NMR (400 MHz, DMSO-$d_6$) δ ppm 9.46 (s, 1H), 9.42 (s, 1H), 8.95 (d, J=1.5 Hz, 1H), 7.78 (d, J=1.5 Hz, 1H), 7.74-7.65 (m, 4H), 7.41-7.21 (m, 2H), 4.95 (s, 2H), 4.28 (t, J=5.3 Hz, 2H), 4.02 (t, J=5.5 Hz, 2H).

The Compound shown in Table 20 has been prepared similar to Compound 306 by coupling of Intermediate 306D with in-situ generated from respective anilines.

TABLE 20

| Ex. No. | Structure | Name | [M + H]+ | Ret Time (min.) | HPLC Methods |
|---|---|---|---|---|---|
| 307 | 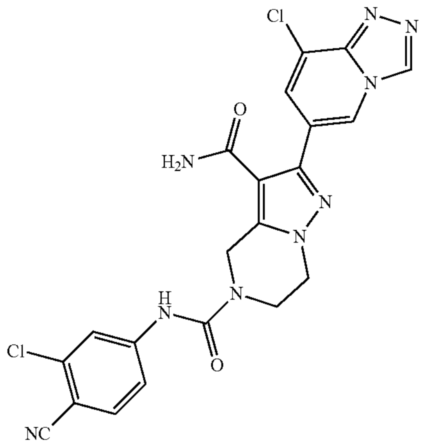 [SMILES: N#Cc1ccc(NC(=O)N2CCn3nc(-c4cc(Cl)c5nncn5c4)c(C(N)=O)c3C2)cc1Cl] | N5-(3-Chloro-4-cyanophenyl)-2-(8-chloro-[1,2,4]triazolo[4,3-a]pyridin-6-yl)-6,7-dihydropyrazolo[1,5-a]pyrazine-3,5(4H)-dicarboxamide | 496 | 1.17<br>1.17 | E<br>L |

Scheme 22

-continued

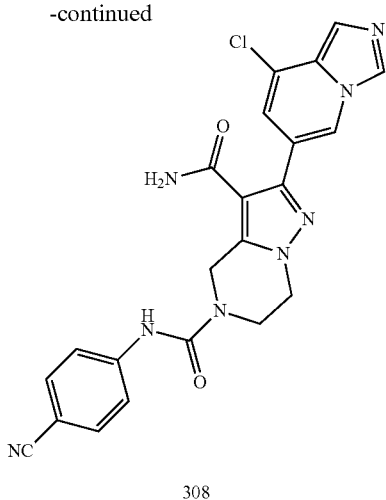

308

Intermediate 308A: (5-Bromo-3-chloropyridin-2-yl)methanol

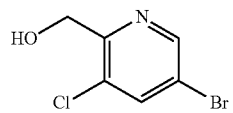

A solution of 2,5-dibromo-3-chloropyridine (3.0 g, 11.06 mmol) in toluene (5 mL) was cooled to −78° C. under $N_2$. To this solution was added n-BuLi (8.29 mL, 13.27 mmol) dropwise and allowed to stir for 2 h at −78° C. prior to addition of DMF (1.712 mL, 22.11 mmol). The reaction mixture was allowed to warm to RT. To this reaction mixture was added MeOH (3 mL) and $NaBH_4$ (0.418 g, 11.06 mmol) and stirred at RT for 30 min. The reaction mixture was quenched with saturated aq. ammonium chloride solution and extracted with ethyl acetate (2×50 mL). The combined organic layer was washed with brine, dried over anhydrous $Na_2SO_4$, filtered and the filtrate concentrated. The crude reaction mixture was purified by silica gel chromatography (24 g REDISEP® column, eluting with a gradient of 0-10% EtOAc in hexanes). Fractions containing the product were combined and evaporated to afford the Intermediate 308A (2.6 g, 53%) as a pale yellow crystals. $^1$H NMR (400 MHz, DMSO-$d_6$) δ ppm 8.66 (d, J=2.01 Hz, 1H), 8.31 (s, 1H), 5.33 (d, J=12.05 Hz, 1H), 4.61 (s, 2H).

Intermediate 308B:
(5-Bromo-3-chloropyridin-2-yl)methyl methanesulfonate

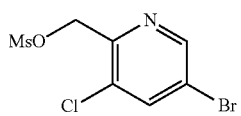

To a cooled solution of Intermediate 308A (150 mg, 0.674 mmol) in DCM (3 mL) at 5° C. was added TEA (94 L, 0.674 mmol) followed by the slow addition of methanesulfonyl chloride (54.4 μL, 0.674 mmol). The resulting reaction mixture was stirred for 2 h at the same temperature. The reaction mixture was diluted with DCM (20 mL), washed with water and brine. The organic layer was dried over $Na_2SO_4$ and evaporated under vacuum. The crude Intermediate 308B (2.7 g, 100%) was taken to the next transformation without any purification. MS(ES): m/z=302.4 [M+H]$^+$.

Intermediate 308C:
(5-Bromo-3-chloropyridin-2-yl)methanamine

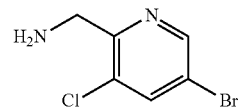

A solution of Intermediate 308B (2.7 g, 5.84 mmol) in IPA (50 mL) was saturated with $NH_3$ gas and the resulting solution was allowed to stir at RT for 12 h. The volatiles were removed under vacuum and the crude product was triturated with n-hexanes to afford Intermediate 308C (1.0 g, 77%) as a pale yellow solid. MS(ES): m/z=223.4. $^1$H NMR (400 MHz, DMSO-$d_6$) δ ppm 8.80 (d, J=2.01 Hz, 1H), 8.08-8.65 (m, 1H), 6.82 (br. s., 2H), 4.27 (s, 2H).

Intermediate 308D:
N-((5-Bromo-3-chloropyridin-2-yl)methyl)formamide

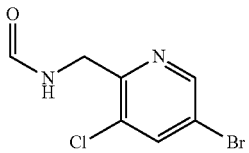 [SMILES: O=CNCc1ncc(Br)cc1Cl]

A solution of Intermediate 308C (600 mg, 1.896 mmol) in formic acid (10 mL, 9.48 mmol) was heated to 100° C. and stirred for 12 h. The reaction mixture was cooled to 0° C. and the pH was carefully adjusted to 8 by the slow addition of 25% aqueous solution of ammonium hydroxide. The reaction mixture was diluted with water and the aqueous layer was extracted with dichloromethane (3×10 mL). The combined organic layer was dried over $Na_2SO_4$, filtered and the filtrate concentrated under vacuum to afford Intermediate 308D (300 mg, 63%). The crude product was used for the next step without further purification. MS(ES): m/z=251.3 [M+H]$^+$.

Intermediate 308E:
6-Bromo-8-chloroimidazo[1,5-a]pyridine

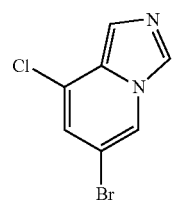 [SMILES: Clc1cc(Br)cn2cncc12]

To a solution of Intermediate 308D (300 mg, 1.202 mmol) in toluene (5 mL) was added phosphoryl trichloride (1073 mg, 7 mmol) slowly and the reaction mixture was heated to 100° C. and stirred for 4 h. The reaction mixture was cooled to 0° C. and carefully quenched with ice-cold water. The pH of the reaction mixture was adjusting to 9 with an aq. solution of 25% ammonium hydroxide and extracted with dichloromethane (3×10 mL). The combined organic layer was dried over Na$_2$SO$_4$, and concentrated. The crude reaction mixture was purified by silica gel chromatography (12 g REDISEP® column, eluting with a gradient of 0-6% MeOH in CHCl$_3$). Fractions containing the product were combined and evaporated to afford the Intermediate 308E (110 mg, 40%) as a brown oil. MS(ES): m/z=233.3 [M+H]$^+$.

Intermediate 308F: 8-Chloro-6-(4,4,5,5-tetramethyl-1,3,2-dioxaborolan-2-yl)imidazo[1,5-a]pyridine

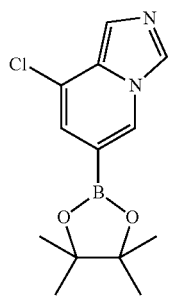 [SMILES: CC1(C)OB(c2cc(Cl)c3cncn3c2)OC1(C)C]

To a solution of Intermediate 308E (50 mg, 0.216 mmol) in DMF (2 mL) was added KOAc (63.6 mg, 0.648 mmol), bis(pinacolato)diboron (65.8 mg, 0.259 mmol) and the reaction mixture was purged with N$_2$ for 5 min. Pd(dppf)Cl$_2$CH$_2$Cl$_2$ (9.48 mg, 0.013 mmol) was added and the reaction mixture was heated to 90 OC and stirred for 18 h. The reaction mixture was diluted with water and extracted with ethyl acetate (2×25 mL). The combined organic layer was dried over anhydrous Na$_2$SO$_4$ and concentrated under reduced pressure to afford crude Intermediate 308F (50 mg, 70%) which was taken to Suzuki coupling without further purification.

Intermediate 308G: tert-Butyl 3-carbamoyl-2-(8-chloroimidazo[1,5-a]pyridin-6-yl)-6,7-dihydropyrazolo[1,5-a]pyrazine-5(4H)-carboxylate

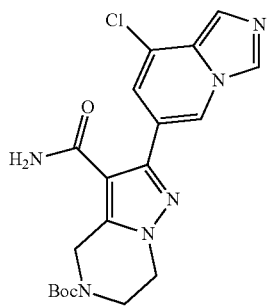 [SMILES: CC(C)(C)OC(=O)N1CCn2nc(-c3cc(Cl)c4cncn4c3)c(C(N)=O)c2C1]

To a solution of Intermediate 156C (20 mg, 0.051 mmol) and Intermediate 308F (78 mg, 0.056 mmol) in DMF (1 mL) was added a solution of Na$_2$CO$_3$ (16.21 mg, 0.153 mmol) in water (1 mL) and the resulting solution was purged with N$_2$ gas for 5 min. Pd(PPh$_3$)$_4$(2.95 mg, 2.55 mmol) was added and the reaction mixture was heated to 100° C. and allowed to stir for 18 h. The reaction mixture was diluted with water and extracted with ethyl acetate (2×25 mL). The combined organic layer was dried over anhydrous Na$_2$SO$_4$ and concentrated under reduced pressure. The crude reaction mixture was purified by silica gel chromatography (12 g REDISEP® column, eluting with a gradient of 0-6% MeOH in CHCl$_3$). Fractions containing the product were combined and evaporated to afford Intermediate 308G (20 mg, 7%). MS(ES): m/z=417.5 [M+H]$^+$.

Compound 308: 2-(8-Chloroimidazo[1,5-a]pyridin-6-yl)-N-(4-cyanophenyl)-6,7-dihydropyrazolo[1,5-a]pyrazine-3,5(4H)-dicarboxamide

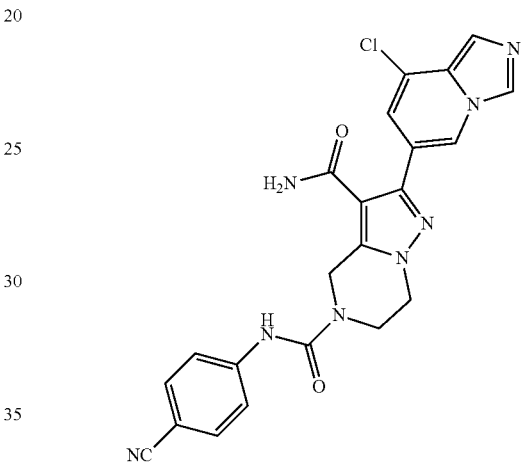

To a solution of Intermediate 308G (30 mg, 5.04 mmol) in DCM (2 mL) was slowly added TFA (0.776 L, 10.08 mmol) and stirred for 2 h. The volatiles were evaporated under vacuum and the residue was dissolved in THF (2 mL). 4-Isocyanatobenzonitrile (0.726 mg, 5.04 μmol) and TEA (1.404 μl, 10.08 μmol) were added and the reaction mixture was stirred at RT for 12 h. The reaction mixture was quenched with water and extracted with EtOAc (3×5 mL). The combined organic layer was dried over Na$_2$SO$_4$, filtered and the filtrate evaporated. The crude product was purified by preparative HPLC to afford Compound 308 (21 mg, 41%) as a pale yellow solid. The HPLC retention times are 2.063 min. and 1.801 min. (Methods E and L respectively); MS(ES): m/z=461.2 [M+H]$^+$; $^1$H NMR (400 MHz, DMSO-d$_6$) δ ppm 9.39 (s, 1H), 8.76 (s, 1H), 7.62-7.77 (m, 5H), 7.18-7.25 (m, 2H), 7.08 (s, 1H), 6.95 (s, 1H), 4.94 (s, 2H), 4.26 (t, J=5.05 Hz, 2H), 4.01 (t, J=5.21 Hz, 2H).

Scheme 23

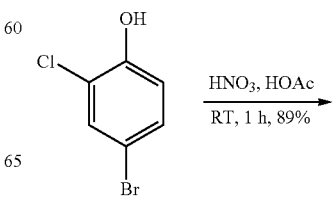

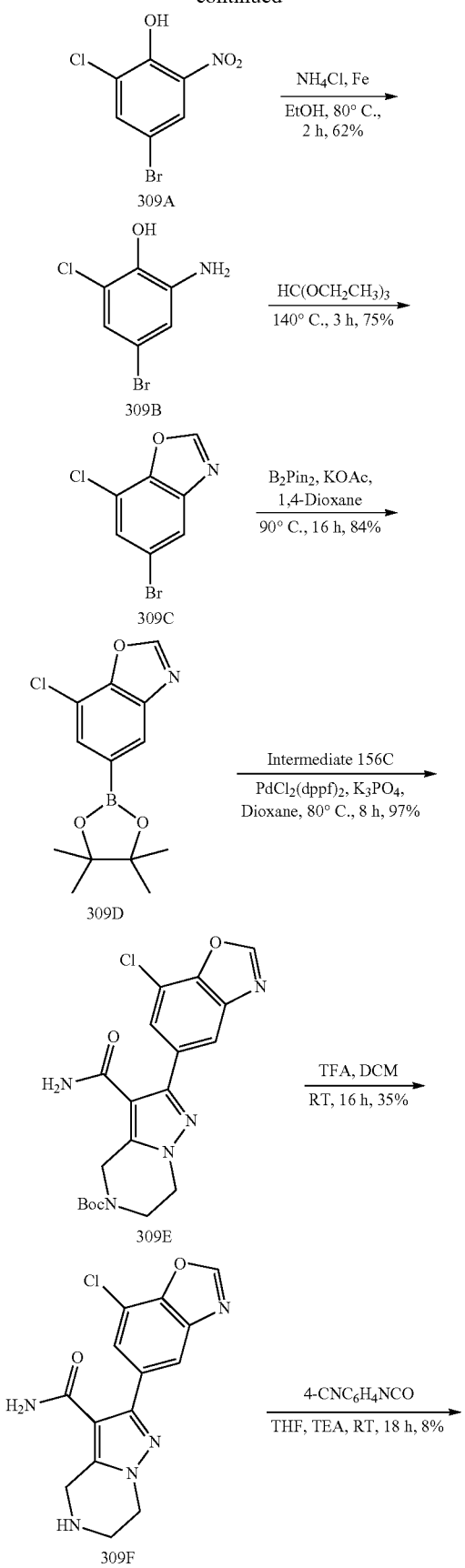

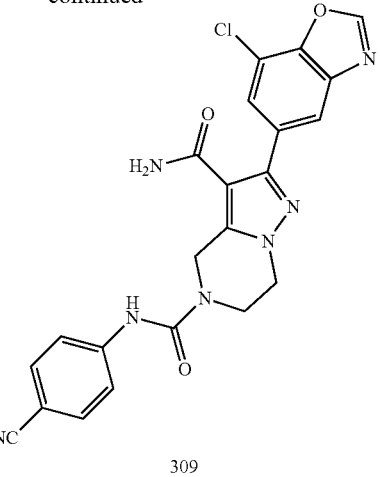

Intermediate 309A: 4-Bromo-2-chloro-6-nitrophenol

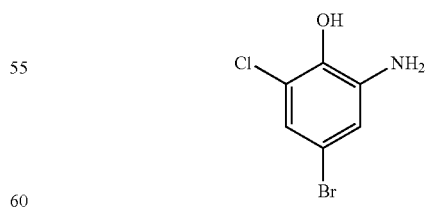

To a stirred solution of 4-bromo-2-chlorophenol (15.0 g, 72.3 mmol) in acetic acid (60 mL) was slowly added HNO$_3$ (9.23 mL, 145 mmol) over a period of 15 min and the reaction mixture was stirred at RT for 1 h. The reaction was quenched with ice-cold water and the pale yellow solid was filtered and dried. The crude compound was purified by silica gel chromatography (120 g REDISEP® column, eluting a gradient from 0 to 20% EtOAc in hexanes). Fractions containing the product were combined and evaporated to afford the Intermediate 309A (16.2 g, 89%) as a pale yellow solid. MS(ES): m/z=250 [M−1]$^+$; $^1$H NMR (400 MHz, DMSO-d$_6$) δ ppm 11.43 (br. s., 1H), 8.05-8.12 (m, 2H).

Intermediate 309B: 2-Amino-4-bromo-6-chlorophenol

To a stirred solution of Intermediate 309A (10 g, 21.79 mmol) in EtOH (80.0 mL) was added saturated aq. solution of NH$_4$Cl (80 mL, 218 mmol) followed by iron powder (9.73 g, 174 mmol). The resulting suspension was heated to 80° C. and allowed to stir for 2 h. The reaction mixture was cooled to RT, filtered through CELITE® and the filtrate was concentrated. The reaction mixture was diluted with EtOAc (100 mL), washed with water and brine. The organic layer was dried over sodium sulfate, filtered and the filtrate concentrated under reduced pressure. The crude compound was purified by silica gel chromatography (120 g REDISEP® column, eluting with a gradient from 0 to 5% EtOAc in hexanes). Fractions containing the product were combined and evaporated to afford Intermediate 309B (3.02 g, 62%) as a brown solid. MS(ES): m/z=221 [M+H]$^+$; $^1$H NMR (400 MHz, DMSO-d$_6$) δ ppm 9.00 (br. s., 1H), 6.50-6.76 (m, 2H), 5.21 (br. s., 2H).

Intermediate 309C:
5-Bromo-7-chlorobenzo[d]oxazole

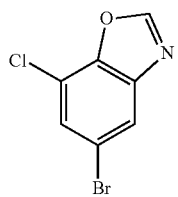 [SMILES: Clc1cc(Br)cc2ncoc12]

A suspension of Intermediate 309B (0.7 g, 3.15 mmol) in triethylorthoformate (14.0 ml, 84 mmol) was stirred at 140° C. for 3 h. The reaction mixture was cooled to RT, diluted with water and extracted with EtOAc (3×25 mL). The combined organic layer was washed with brine, dried over sodium sulfate, filtered and the filtrate concentrated under reduced pressure. The crude compound was purified by silica gel chromatography (12 g REDISEP® column, eluting with a gradient from 0 to 5% EtOAc in hexanes). Fractions containing the product were combined and evaporated to afford Intermediate 309C as an off-white solid (0.55 g, 75%). MS(ES): m/z=233 [M+H]$^+$; $^1$H NMR (300 MHz, DMSO-d$_6$) δ ppm 8.93 (s, 1H), 8.10 (d, J=1.51 Hz, 1H), 7.86 (d, J=1.51 Hz, 1H).

Intermediate 309D: 7-Chloro-5-(4,4,5,5-tetramethyl-1,3,2-dioxaborolan-2-yl)benzo[d]oxazole

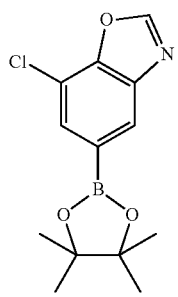 [SMILES: CC1(C)OB(c2cc(Cl)c3ocnc3c2)OC1(C)C]

To a stirred solution of Intermediate 309C (0.7 g, 3.01 mmol) in 1,4-dioxane (8.0 mL) was added bis(pinacolato)diboron (1.147 g, 4.52 mmol) and KOAc (0.739 g, 7.53 mmol) and the reaction mixture was purged with N$_2$ for 10 min. PdCl$_2$(dppf)-CH$_2$Cl$_2$ (0.148 g, 0.181 mmol) was added and the reaction mixture was heated to 90° C. and stirred for 16 h. The reaction mixture was concentrated and extracted with ethyl acetate (3×25 mL). The combined organic layer was washed with water, brine, dried over sodium sulfate and concentrated. The crude reaction mixture was purified by silica gel chromatography (24 g REDISEP® column, eluting with a gradient from 0 to 5% EtOAc in hexanes). Fractions containing the product were combined and evaporated to afford the Intermediate 309D (0.71 g, 84%) as a white solid. MS(ES): m/z=279 [M+H]$^+$; $^1$H NMR (300 MHz, DMSO-d$_6$) δ ppm 8.92 (s, 1H), 7.94-8.00 (m, 1H), 7.71 (s, 1H), 1.33 (s, 12H).

Intermediate 309E: tert-Butyl 3-carbamoyl-2-(7-chlorobenzo[d]oxazol-5-yl)-6,7-dihydropyrazolo[1,5-a]pyrazine-5(4H)-carboxylate

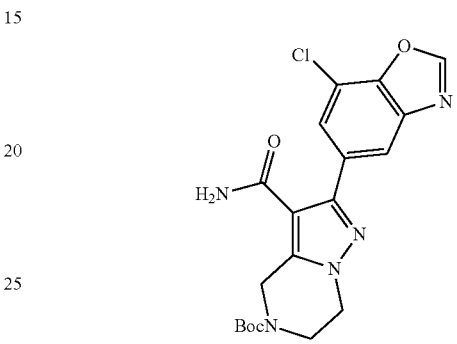

To a stirred suspension of Intermediate 309D (0.7 g, 1.785 mmol) in 1,4-dioxane (2.0 mL) was added Intermediate 156C (1.247 g, 4.46 mmol), K$_3$PO$_4$ (2.68 mL, 5.35 mmol) and the reaction mixture was purged with N$_2$ for 10 min. PdCl$_2$(dppf)-CH$_2$Cl$_2$ (0.087 g, 0.107 mmol) was added and the reaction mixture was heated to 80° C. and stirred for 8 h. The reaction mixture was concentrated and extracted with ethyl acetate (3×25 mL). The combined organic layer was washed with water, brine, dried over sodium sulfate and concentrated. The crude was purified by silica gel chromatography (24 g REDISEP® column, eluting with a gradient from 0 to 1% MeOH in chloroform) to afford Intermediate 309E (0.31 g, 97%) as an off-white solid. MS(ES): m/z=418 [M+H]$^+$; $^1$H NMR (300 MHz, DMSO-d$_6$) δ ppm 8.90 (s, 1H), 8.01 (d, J=1.51 Hz, 1H), 7.81 (s, 1H), 7.11-7.35 (m, 2H), 4.73 (s, 2H), 4.14 (t, J=5.29 Hz, 2H), 3.84-3.86 (t, 2H), 1.45 (s, 9H).

Intermediate 309F: 2-(7-Chlorobenzo[d]oxazol-5-yl)-4,5,6,7-tetrahydropyrazolo[1,5-a]pyrazine-3-carboxamide

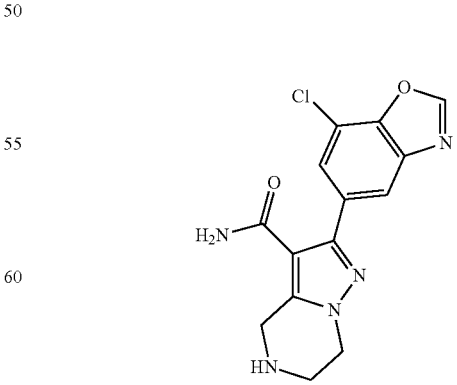

To a stirred solution of Intermediate 309E (0.3 g, 0.718 mmol) in DCM (3.0 mL) was added TFA (3.0 mL, 38.9 mmol) and allowed to stir at RT for 16 h. The reaction mixture was concentrated and slowly added saturated aq. solution of NaHCO₃ and extracted with chloroform. The organic layer was washed with water, brine, dried over sodium sulfate and concentrated under reduced pressure to afford Intermediate 309F (0.08 g, 35%) as a brown solid. $^1$H NMR (400 MHz, DMSO-d₆) δ ppm 8.89 (s, 1H), 8.05 (d, J=1.51 Hz, 1H), 7.85 (d, J=1.00 Hz, 1H), 7.01-7.32 (m, 2H), 3.93-4.10 (m, 4H), 3.14 (d, J=5.02 Hz, 2H), 2.64 (br. s., 1H).

Compound 309: 2-(7-Chlorobenzo[d]oxazol-5-yl)-N⁵-(4-cyanophenyl)-6,7-dihydropyrazolo[1,5-a]pyrazine-3,5(4H)-dicarboxamide

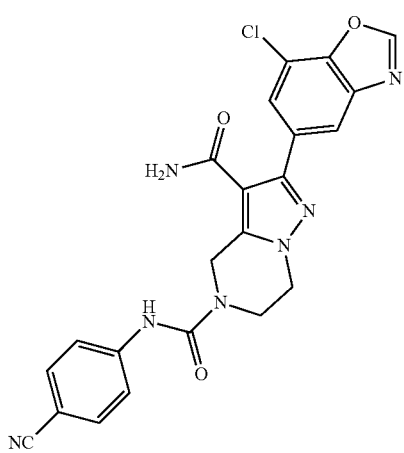 [SMILES: N#Cc1ccc(NC(=O)N2CCn3nc(-c4cc(Cl)c5ocnc5c4)c(C(N)=O)c3C2)cc1]

To a stirred solution of Intermediate 309F (0.035 g, 0.110 mmol) in THF (3.0 mL) was added TEA (0.015 mL, 0.110 mmol) followed by 4-isocyanatobenzonitrile (0.019 g, 0.132 mmol) and the resulting solution was allowed to stir at RT for 2 h. The reaction mixture was diluted with ethyl acetate, washed with water and brine. The organic layer was dried over sodium sulfate, filtered and the filtrate concentrated under reduced pressure. The crude product was purified by preparative HPLC to afford Compound 309 (4.5 mg, 8%) as a pale yellow solid. HPLC retention times 1.14 min. and 1.12 min. (Methods E and L respectively). MS(ES): m/z=462 [M+H]⁺; $^1$H NMR (400 MHz, DMSO-d₆) δ ppm 9.41 (s, 1H), 8.92 (s, 1H), 8.04 (d, J=1.51 Hz, 1H), 7.84 (d, J=1.51 Hz, 1H), 7.61-7.76 (m, 4H), 7.11-7.45 (m, 2H), 4.94 (s, 2H), 4.28 (t, J=5.27 Hz, 2H), 4.02 (t, J=5.27 Hz, 2H).

The Compound shown in Table 21 has been prepared similar to Compound 309 by coupling of Intermediate 309F with in-situ generated isocyanates from respective aniline.

TABLE 21

| Ex. No. | Structure | Name | [M + H]⁺ | Ret Time (min) | HPLC Methods |
|---|---|---|---|---|---|
| 310 | 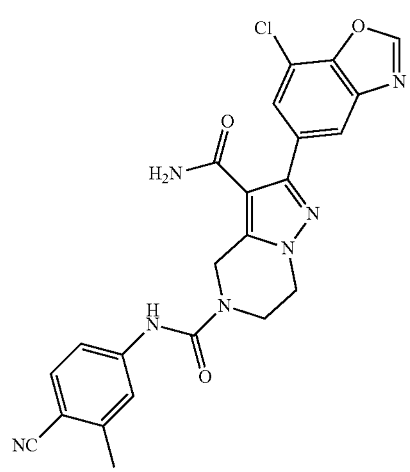 [SMILES: Cc1cc(NC(=O)N2CCn3nc(-c4cc(Cl)c5ocnc5c4)c(C(N)=O)c3C2)ccc1C#N] | 2-(7-Chlorobenzo[d]oxazol-5-yl)-N⁵-(4-cyano-3-methylphenyl)-6,7-dihydropyrazolo[1,5-a]pyrazine-3,5(4H)-dicarboxamide | 476 | 1.27 | E |

Scheme 24

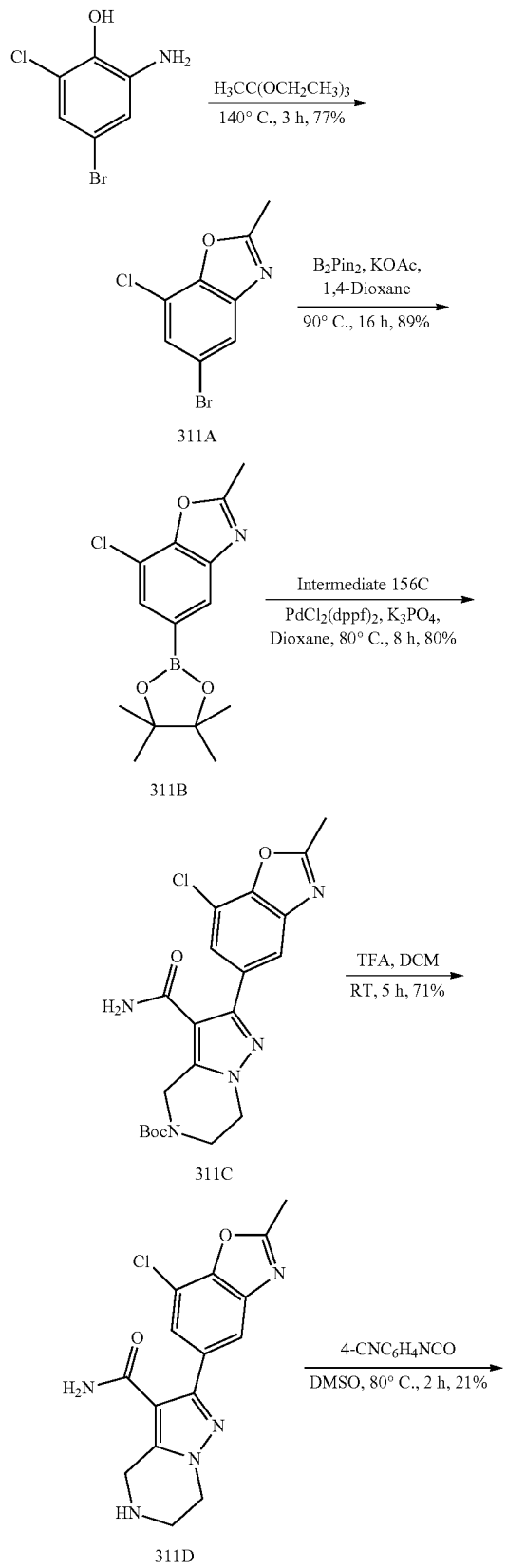

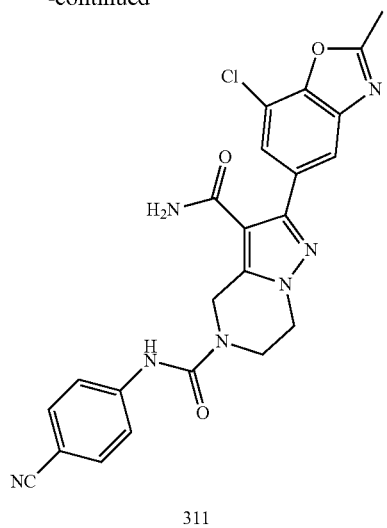

311

Intermediate 311A:
5-Bromo-7-chloro-2-methylbenzo[d]oxazole

To a stirred solution of 2-amino-4-bromo-6-chlorophenol (1.0 g, 4.50 mmol) in triethyl orthoacetate (0.829 mL, 4.50 mmol) was heated to 140° C. and stirred for 3 h. The reaction mixture was diluted with EtOAc (25 mL), washed with water and brine. The organic layer was dried over sodium sulfate, filtered and the filtrate concentrated under reduced pressure. The crude compound was purified by silica gel chromatography (120 g REDISEP® column, eluting with a gradient from 0 to 5% EtOAc in hexanes). Fractions containing the product were combined and evaporated to afford the Intermediate 311A (0.85 g, 77%) as a brown solid. MS(ES): m/z=246 [M+H]$^+$; $^1$H NMR (300 MHz, DMSO-d$_6$) δ ppm 7.93 (d, J=1.89 Hz, 1H), 7.74 (s, 1H), 2.67 (s, 3H).

Intermediate 311B: 7-Chloro-2-methyl-5-(4,4,5,5-tetramethyl-1,3,2-dioxaborolan-2-yl)benzo[d]oxazole

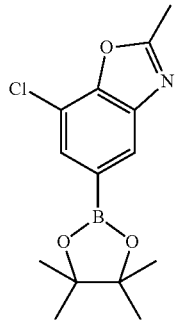 [SMILES: Cc1nc2cc(B3OC(C)(C)C(C)(C)O3)cc(Cl)c2o1]

Intermediate 311B was synthesized from Intermediate 311A using a synthetic sequence analogous to the preparation of Intermediate 309D. MS(ES): m/z=212 [M−82)]+; ¹H NMR (400 MHz, chloroform-d) δ ppm 7.72 (d, J=7.03 Hz, 2H), 2.04 (s, 3H), 1.31-1.38 (m, 12H).

Intermediate 311C: tert-Butyl 3-carbamoyl-2-(7-chloro-2-methylbenzo[d]oxazol-5-yl)-6,7-dihydropyrazolo[1,5-a]pyrazine-5(4H)-carboxylate

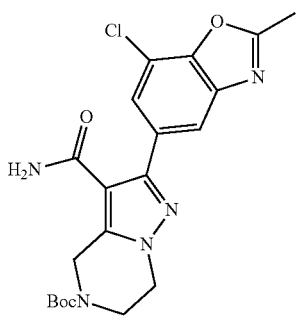 [SMILES: Cc1nc2cc(-c3nn4c(c3C(N)=O)CN(C(=O)OC(C)(C)C)CC4)cc(Cl)c2o1]

Intermediate 311C was synthesized from Intermediates 311B and 156C using a synthetic sequence analogous to the preparation of Intermediate 309E. MS(ES): m/z=432 [M+H]+; ¹H NMR (400 MHz, DMSO-d₆) δ ppm 7.87 (d, J=1.51 Hz, 1H), 7.72 (d, J=1.00 Hz, 1H), 7.04-7.40 (m, 2H), 4.76 (s, 2H), 4.18 (t, J=5.27 Hz, 2H), 3.85 (t, J 5.52 Hz, 2H), 2.68 (s, 3H), 1.46 (s, 9H).

Intermediate 311D: 2-(7-Chloro-2-methylbenzo[d]oxazol-5-yl)-4,5,6,7-tetrahydropyrazolo[1,5-a]pyrazine-3-carboxamide

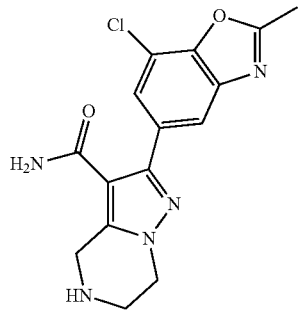 [SMILES: Cc1nc2cc(-c3nn4c(c3C(N)=O)CNCC4)cc(Cl)c2o1]

Intermediate 311D was synthesized from Intermediate 311C using a synthetic sequence analogous to the preparation of Intermediate 309F. MS(ES): m/z=332 [M+H]+; ¹H NMR (300 MHz, DMSO-d₆) δ ppm 7.89 (d, J=1.13 Hz, 1H) 7.74 (s, 1H), 6.95-7.30 (m, 2H), 3.95-4.09 (m, 4H), 3.13 (t, J=5.10 Hz, 2H), 2.62 (s, 3H).

Compound 311: 2-(7-Chloro-2-methylbenzo[d]oxazol-5-yl)-N⁵-(4-cyanophenyl)-6,7-dihydropyrazolo[1,5-a]pyrazine-3,5(4H)-dicarboxamide

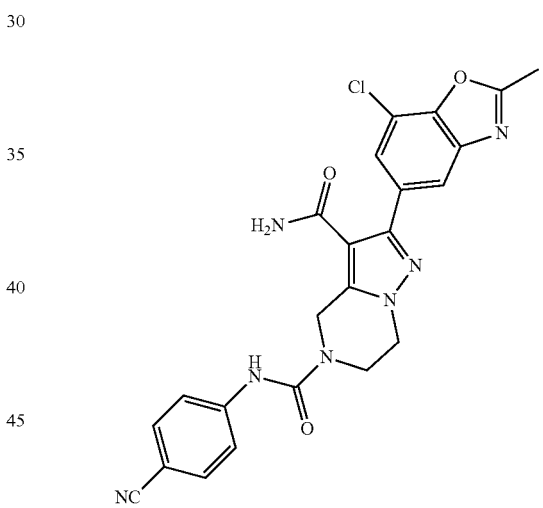

To a solution of Intermediate 311D (0.03 g, 0.090 mmol) in DMSO (1.0 mL) was added 4-isocyanatobenzonitrile (0.016 g, 0.109 mmol) and the resulting solution was heated to 80° C. and stirred for 2 h. The reaction mixture was diluted with EtOAc (10 mL), washed with water and brine. The organic layer was dried over sodium sulfate, filtered and the filtrate concentrated under reduced pressure. The crude compound was purified by preparative HPLC to afford the Compound 311 (9.2 mg, 21%) as an off-white solid. HPLC retention times 8.08 min. and 7.98 min. (Methods A and B respectively). MS(ES): m/z=476 [M+H]+; ¹H NMR (400 MHz, DMSO-d₆) δ ppm 9.41 (s, 1H), 7.90 (s, 1H), 7.66-7.77 (m, 5H), 7.09-7.45 (m, 2H), 4.93 (s, 2H), 4.27 (t, J=5.27 Hz, 2H), 4.02 (t, J=5.27 Hz, 2H) 2.5 (s, 3H).

The Compounds shown in Table 22 have been prepared similar to Compound 311 by coupling of Intermediate 311D with various readily available isocyanates or in-situ generated from respective anilines.

TABLE 22

| Ex. No. | Structure | Name | [M + H]+ | Ret Time (min) | HPLC Methods |
|---|---|---|---|---|---|
| 312 | 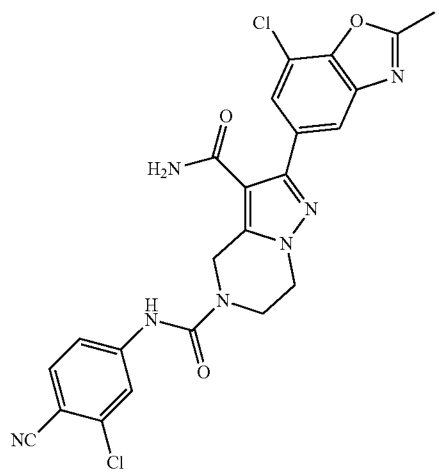 [SMILES: Cc1nc2cc(-c3nn4c(c3C(N)=O)CN(C(=O)Nc3ccc(C#N)c(Cl)c3)CC4)cc(Cl)c2o1] | 2-(7-Chloro-2-methylbenzo[d]oxazol-5-yl)-N5-(3-chloro-4-cyanophenyl)-6,7-dihydropyrazolo[1,5-a]pyrazine-3,5(4H)-dicarboxamide | 511 | 9.23<br>8.61 | A<br>B |
| 313 | 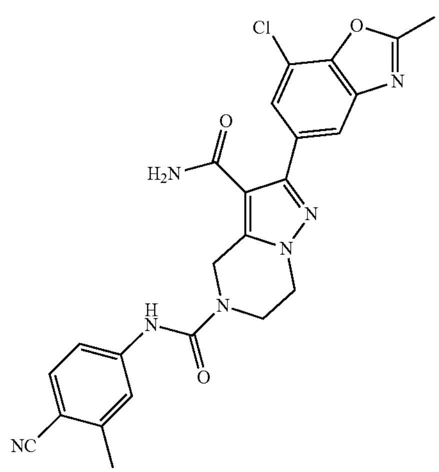 [SMILES: Cc1nc2cc(-c3nn4c(c3C(N)=O)CN(C(=O)Nc3ccc(C#N)c(C)c3)CC4)cc(Cl)c2o1] | 2-(7-Chloro-2-methylbenzo[d]oxazol-5-yl)-N5-(4-cyano-3-methylphenyl)-6,7-dihydropyrazolo[1,5-a]pyrazine-3,5(4H)-dicarboxamide | 490 | 1.34<br>1.32 | E<br>L |
| 314 | 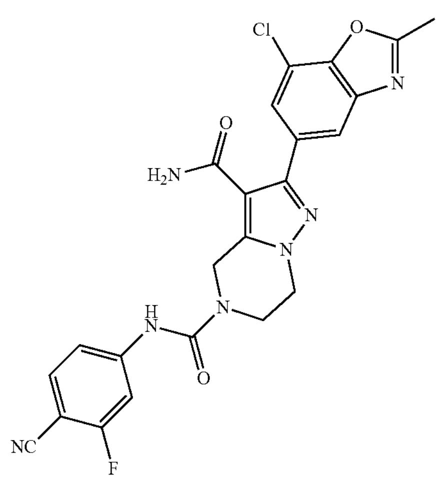 [SMILES: Cc1nc2cc(-c3nn4c(c3C(N)=O)CN(C(=O)Nc3ccc(C#N)c(F)c3)CC4)cc(Cl)c2o1] | 2-(7-Chloro-2-methylbenzo[d]oxazol-5-yl)-N5-(4-cyano-3-fluorophenyl)-6,7-dihydropyrazolo[1,5-a]pyrazine-3,5(4H)-dicarboxamide | 494 | 8.56<br>8.61 | M<br>B |

Scheme 25

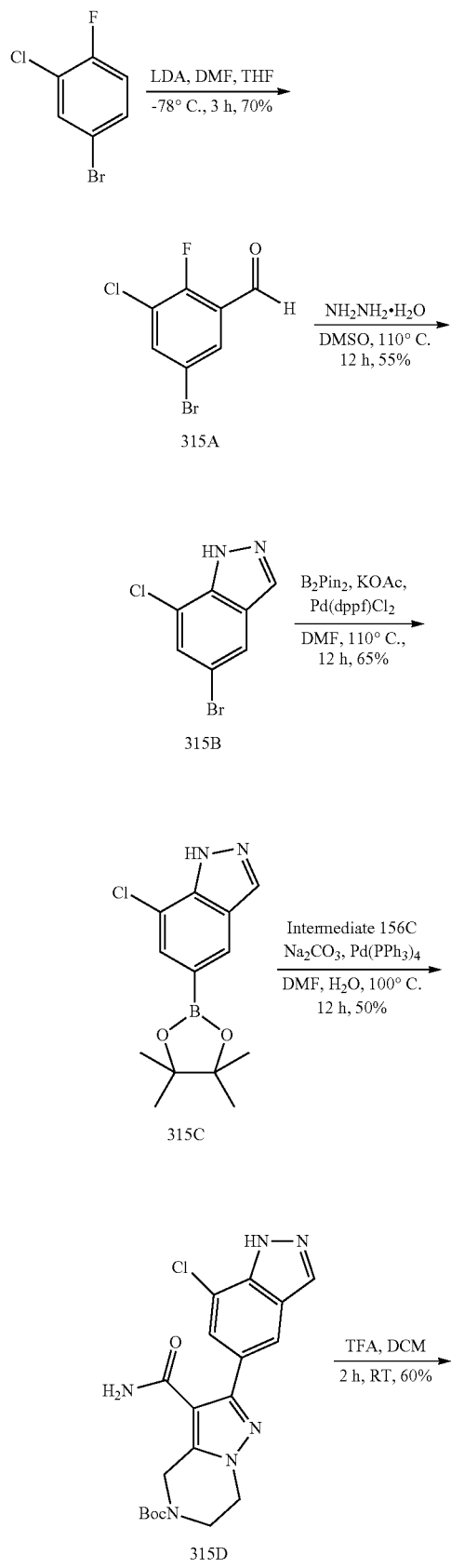

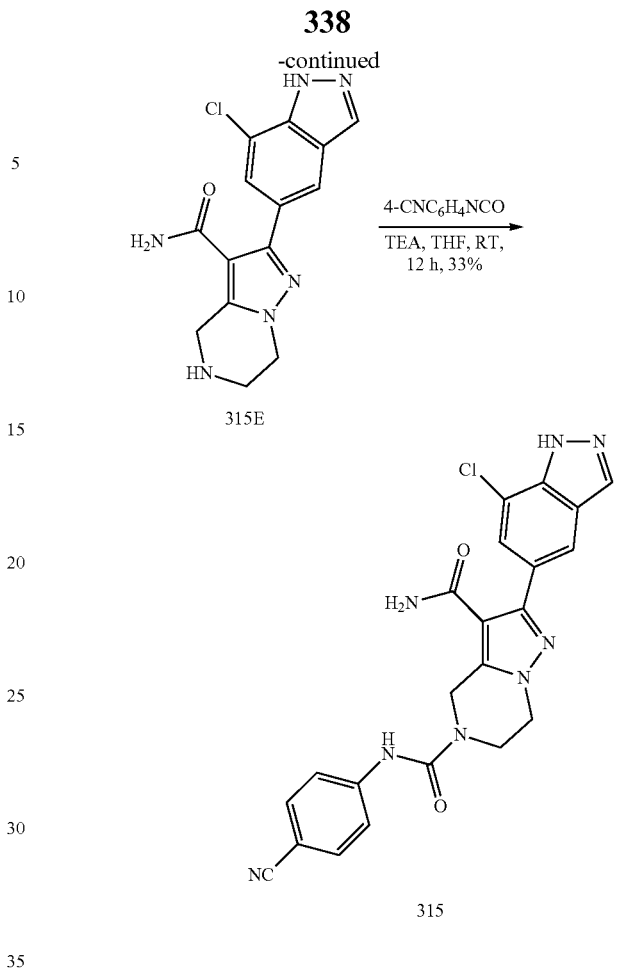

Intermediate 315A:
5-Bromo-3-chloro-2-fluorobenzaldehyde

To a solution 4-bromo-2-chloro-1-fluorobenzene (5.000 g, 23.87 mmol) in THF (50 mL) was added LDA (17.90 mL, 35.8 mmol, 1M in THF) dropwise at −78° C. and the reaction mixture was stirred at same temperature for 45 min. DMF (2.218 mL, 28.6 mmol) was added and reaction mixture was allowed to warm to RT and stirred for 3 h. The reaction mixture was quenched with saturated NH$_4$Cl solution and extracted with EtOAc (3×75 mL). The combined organic layer was washed with brine, dried over Na$_2$SO$_4$, filtered and concentrated. The crude product was purified by silica gel chromatography (40 g REDISEP® column, eluting with a gradient from 0 to 20% EtOAc in petroleum ether). Fractions containing the product were combined and evaporated to afford Intermediate 315A (3.5 g, 70%) as a yellow color solid. $^1$H NMR (300 MHz, DMSO-d$_6$) δ ppm 10.10 (d, J=0.8 Hz, 1H), 8.26 (dd, J=6.4, 2.6 Hz, 1H), 7.94 (dd, J=5.5, 2.5 Hz, 1H).

Intermediate 315B: 5-Bromo-7-chloro-1H-indazole

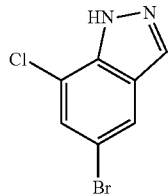 [SMILES: Clc1cc(Br)cc2cn[nH]c12]

To a solution of Intermediate 315A (3.00 g, 12.63 mmol) in DMSO (30 mL) was added hydrazine hydrate (1.2 mL, 25.5 mmol) and the resulting solution was heated to 110° C. and stirred for 12 h. The reaction mixture was cooled to 0° C., diluted with ice-cold water and the solid formed was filtered, dried under vacuum to afford the Intermediate 315B (1.5 g, 55%) as a white color solid. MS(ES): m/z=231 [M+H]$^+$; $^1$H NMR (300 MHz, DMSO-d$_6$) δ ppm 13.80 (br. s., 1H), 8.19 (s, 1H), 8.02 (d, J=1.5 Hz, 1H), 7.65 (d, J=1.5 Hz, 1H).

Intermediate 315C: 7-Chloro-5-(4,4,5,5-tetramethyl-1,3,2-dioxaborolan-2-yl)-1H-indazole

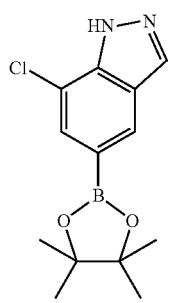 [SMILES: CC1(C)OB(c2cc(Cl)c3[nH]ncc3c2)OC1(C)C]

To a solution of Intermediate 315B (0.8 g, 3.46 mmol) and bis(pinacolato)diboron (1.053 g, 4.15 mmol) in DMF (8 mL) was added KOAc (1.018 g, 10.37 mmol) and the reaction mixture was degasified with N$_2$ for 10 min. PdCl$_2$(dppf)-CH$_2$Cl$_2$ (0.169 g, 0.207 mmol) was added and the resulting reaction mixture was heated to 110° C. and stirred for 12 h. The reaction mixture was diluted EtOAc, washed with water, brine, dried over Na$_2$SO$_4$, filtered and the filtrate concentrated to afford Intermediate 315C (0.7 g, 65%) as a brown color liquid. The crude product was taken for Suzuki coupling without purification. MS(ES): m/z=279 [M+H]$^+$.

Intermediate 315D: tert-Butyl 3-carbamoyl-2-(7-chloro-1H-indazol-5-yl)-6,7-dihydropyrazolo[1,5-a]pyrazine-5(4H)-carboxylate

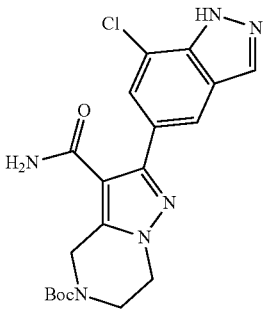 [SMILES: CC(C)(C)OC(=O)N1CCn2nc(-c3cc(Cl)c4[nH]ncc4c3)c(C(N)=O)c2C1]

To a solution of Intermediate 156C (500 mg, 1.275 mmol) and Intermediate 315C (462 mg, 1.657 mmol) in DMF (5 mL) and H$_2$O (0.5 mL) was added Na$_2$CO$_3$ (405 mg, 3.82 mmol) and the reaction mixture was purged with N$_2$ gas for 10 min. Pd(PPh$_3$)$_4$(73.7 mg, 0.064 mmol) was added and the resulting reaction mixture was heated to 100° C. and stirred for 12 h. The reaction mixture was diluted with water (50 mL) and extracted with EtOAc (3×25 mL). The combined organic layer was washed with brine, dried over Na$_2$SO$_4$, filtered and the filtrate concentrated. The crude product was purified by silica gel chromatography (40 g REDISEP® column, eluting with a gradient from 0 to 5% MeOH in Chloroform). Fractions containing the product were combined and evaporated to afford Intermediate 315D (0.3 g, 55%) as a yellow color solid. MS(ES): m/z=417 [M+H]$^+$; $^1$H NMR (400 MHz, DMSO-d$_6$) δ ppm 13.66 (s, 1H), 8.26 (d, J=1.5 Hz, 1H), 8.03 (s, 1H), 7.71 (d, J=1.0 Hz, 1H), 7.26 (br. s., 1H), 7.02 (br. s., 1H), 4.76 (s, 2H), 4.17 (t, J=5.3 Hz, 2H), 3.86 (t, J=5.3 Hz, 2H), 1.42 (s, 9H).

Intermediate 315E: 2-(7-Chloro-1H-indazol-5-yl)-4,5,6,7-tetrahydropyrazolo[1,5-a]pyrazine-3-carboxamide

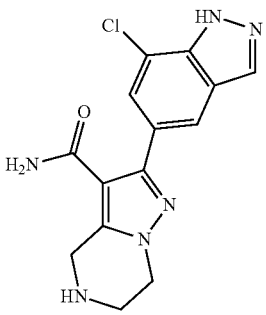 [SMILES: NC(=O)c1c(-c2cc(Cl)c3[nH]ncc3c2)nn2c1CNCC2]

Intermediate 315E was synthesized from Intermediate 315D using a synthetic sequence analogous to the preparation of Intermediate 309F. MS(ES): m/z=317 [M+H]$^+$; $^1$H NMR (400 MHz, DMSO-d$_6$) δ ppm 13.6 (s, 1H), 8.28 (d, J=1.5 Hz, 1H), 8.29-8.20 (s, 1H), 7.82 (d, J=1.5 Hz, 1H), 7.17 (br. s., 1H), 6.96 (br. s., 1H), 4.65 (s, 2H), 4.02 (t, J=5.5 Hz, 2H), 3.73 (t, J=5.5 Hz, 1H), 2.26 (br. s., 1H).

Compound 315: 2-(7-Chloro-1H-indazol-5-yl)-N⁵-(4-cyanophenyl)-6,7-dihydropyrazolo[1,5-a]pyrazine-3,5(4H)-dicarboxamide

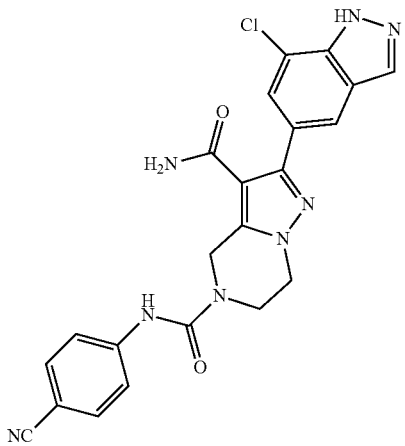 [SMILES: N#Cc1ccc(NC(=O)N2CCn3nc(-c4cc(Cl)c5[nH]ncc5c4)c(C(N)=O)c3C2)cc1]

Compound 315 was synthesized from Intermediate 315E using a synthetic sequence analogous to the preparation of Compound 309. HPLC retention times 7.266 min. and 6.71 min. (Methods A and B respectively). MS(ES): m/z=461.2 [M+H]$^+$; $^1$H NMR (400 MHz, DMSO-d$_6$) δ ppm 9.41 (s, 1H), 8.28 (s, 1H), 8.05 (d, J=1.00 Hz, 1H), 7.65-7.76 (m, 5H), 7.33 (br. s., 1H), 7.06 (br. s., 1H), 4.93 (s, 2H), 4.26 (t, J=5.27 Hz, 2H), 4.02 (t, J=5.27 Hz, 2H).

The Compounds shown in Table 23 have been prepared similar to Compound 315 by coupling of Intermediate 315E with various readily available isocyanates or in-situ generated from respective anilines.

TABLE 23

| Ex. No. | Structure | Name | [M + H]⁺ | Ret Time (min.) | HPLC Methods |
|---|---|---|---|---|---|
| 316 | 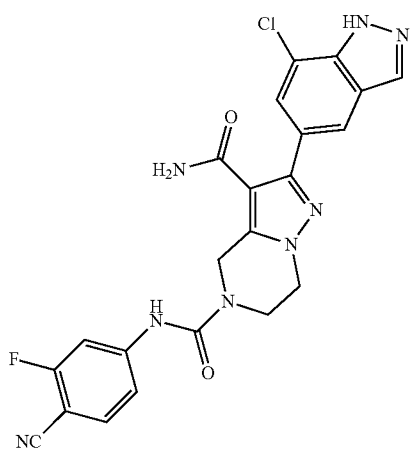 [SMILES: N#Cc1ccc(NC(=O)N2CCn3nc(-c4cc(Cl)c5[nH]ncc5c4)c(C(N)=O)c3C2)cc1F] | 2-(7-Chloro-1H-indazol-5-yl)-N⁵-(4-cyano-3-fluorophenyl)-6,7-dihydropyrazolo[1,5-a]pyrazine-3,5(4H)-dicarboxamide | 478.8 | 1.13<br>1.13 | E<br>L |
| 317 | 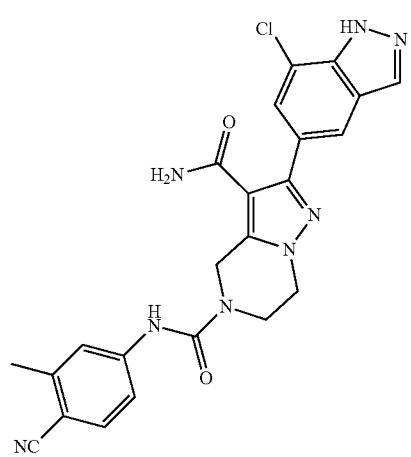 [SMILES: Cc1cc(NC(=O)N2CCn3nc(-c4cc(Cl)c5[nH]ncc5c4)c(C(N)=O)c3C2)ccc1C#N] | 2-(7-Chloro-1H-indazol-5-yl)-N⁵-(4-cyano-3-methylphenyl)-6,7-dihydropyrazolo[1,5-a]pyrazine-3,5(4H)-dicarboxamide | 474.8 | 1.11<br>1.11 | E<br>L |

Scheme 26

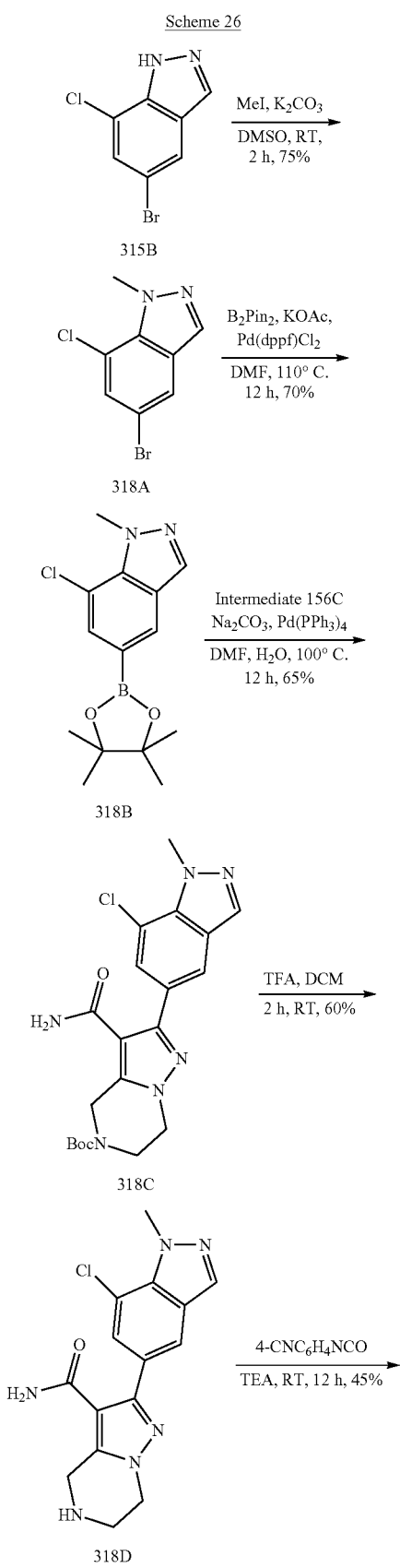 [SMILES: Clc1cc(Br)cc2cn[nH]c12 ; Cn1ncc2cc(Br)cc(Cl)c21 ; Cn1ncc2cc(B3OC(C)(C)C(C)(C)O3)cc(Cl)c21 ; Cn1ncc2cc(-c3nn4c(c3C(N)=O)CN(C(=O)OC(C)(C)C)CC4)cc(Cl)c21 ; Cn1ncc2cc(-c3nn4c(c3C(N)=O)CNCC4)cc(Cl)c21]

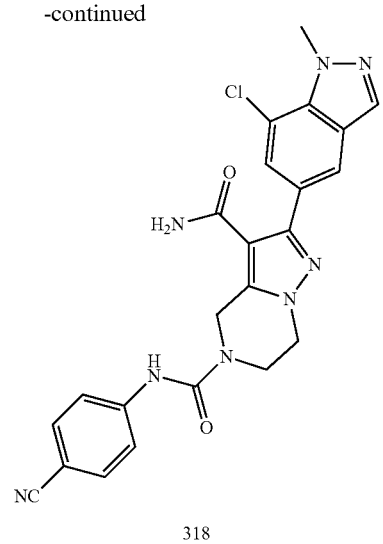

318

Intermediate 318A: 5-Bromo-7-chloro-1-methyl-1H-indazole

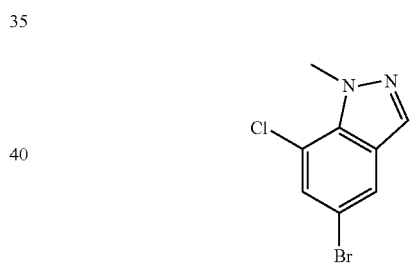

To a solution of Intermediate 315B (1.500 g, 6.48 mmol) and K$_2$CO$_3$ (4.48 g, 32.4 mmol) in DMSO (15 mL) was added MeI (0.486 mL, 7.78 mmol) at RT and the resulting reaction mixture was stirred at RT for 2 h. The reaction mixture was diluted with ice-cold water and the solid formed was filtered through a Buchner funnel, dried under vacuum. The crude product was purified by silica gel chromatography (40 g REDISEP® column, eluting with a gradient from 0 to 5% EtOAc in petroleum ether). Fractions containing the products were combined and evaporated to afford the Intermediate 318A (0.85 g, 50%) as a yellow solid. $^1$H NMR (400 MHz, DMSO-d$_6$) δ ppm 8.12 (s, 1H), 8.01 (d, J=1.5 Hz, 1H), 7.64 (d, J=1.5 Hz, 1H), 4.31 (s, 3H).

Intermediate 318B: 7-Chloro-1-methyl-5-(4,4,5,5-tetramethyl-1,3,2-dioxaborolan-2-yl)-1H-indazole

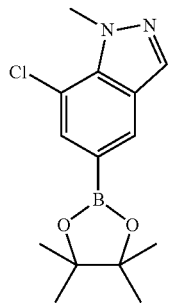 [SMILES: Cn1ncc2cc(B3OC(C)(C)C(C)(C)O3)cc(Cl)c21]

To a solution of Intermediate 318A (0.85 g, 3.46 mmol) and bis(pinacolato)diboron (1.055 g, 4.15 mmol) in DMF (8 mL) was added KOAc (1.018 g, 10.37 mmol) and the reaction mixture was degasified with $N_2$ for 10 min. $PdCl_2$(dppf)-$CH_2Cl_2$ (0.113 g, 0.138 mmol) was added and the resulting reaction mixture was heated to 110° C. and stirred for 12 h. The reaction mixture was diluted EtOAc, washed with water, brine, dried over $Na_2SO_4$, filtered and the filtrate concentrated to afford Intermediate 318B (0.75 g 75%) as a brown color liquid. The crude product was taken for Suzuki coupling without purification. MS(ES): m/z=293 [M+H]$^+$.

Intermediate 318C: tert-Butyl 3-carbamoyl-2-(7-chloro-1-methyl-1H-indazol-5-yl)-6,7-dihydropyrazolo[1,5-a]pyrazine-5(4H)-carboxylate

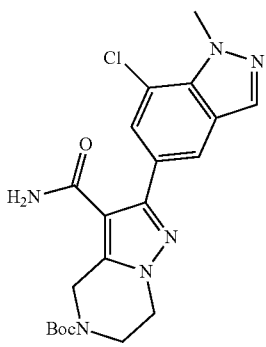 [SMILES: Cn1ncc2cc(-c3nn4c(c3C(N)=O)CN(C(=O)OC(C)(C)C)CC4)cc(Cl)c21]

Intermediate 318C was synthesized from Intermediate 318B using a synthetic sequence analogous to the preparation of Intermediate 315D. MS(ES): m/z=431.6 [M+H]$^+$; $^1$H NMR (400 MHz, DMSO-d$_6$) δ ppm 8.21 (s, 1H), 8.04 (d, J=1.5 Hz, 1H), 7.73 (d, J=1.5 Hz, 1H), 7.34 (s, 1H), 7.10 (s, 1H), 4.76 (s, 2H), 4.34 (s, 3H), 4.18 (t, J=5.5 Hz, 2H), 3.86 (t, J=5.5 Hz, 2H), 1.46 (s, 9H).

Intermediate 318D: 2-(7-Chloro-1-methyl-1H-indazol-5-yl)-4,5,6,7-tetrahydropyrazolo[1,5-a]pyrazine-3-carboxamide

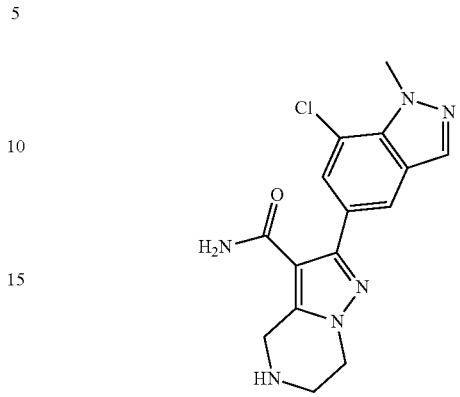

Intermediate 318D was synthesized from Intermediate 318C using a synthetic sequence analogous to the preparation of Intermediate 309F. MS(ES): m/z=331 [M+H]$^+$; $^1$H NMR (400 MHz, DMSO-d$_6$) δ ppm 8.19 (s, 1H), 8.06 (d, J=1.0 Hz, 1H), 7.76 (d, J=1.0 Hz, 1H), 7.21 (br. s., 1H), 7.04 (br. s., 1H), 4.33 (s, 3H), 4.07-3.99 (m, 4H), 3.16-3.12 (m, 2H), 2.65 (t, J=5.8 Hz, 1H).

Compound 318: 2-(7-Chloro-1-methyl-1H-indazol-5-yl)-N$^5$-(4-cyanophenyl)-6,7-dihydropyrazolo[1,5-a]pyrazine-3,5(4H)-dicarboxamide

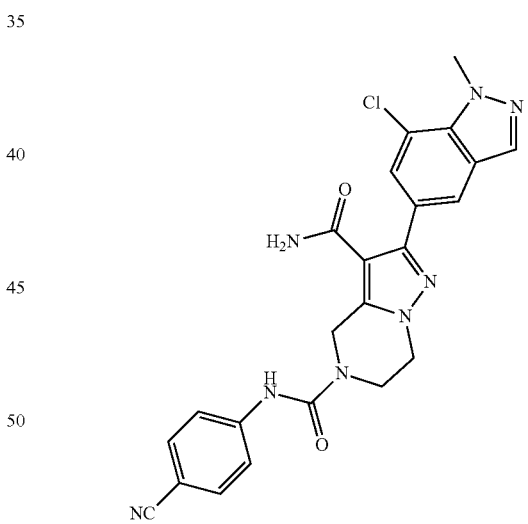

Compound 318 was synthesized from Intermediate 318D using a synthetic sequence analogous to the preparation of Compound 309. HPLC retention time 15.26 min. and 15.76 min. (Methods C and D respectively). MS(ES): m/z=475 [M+H]$^+$; $^1$H NMR (400 MHz, DMSO-d$_6$) δ ppm 9.40 (s, 1H), 8.21 (s, 1H), 8.06 (s, 1H), 7.64-7.77 (m, 5H), 7.34 (br. s., 1H), 7.10 (br. s., 1H), 4.93 (s, 2H), 4.34 (s, 3H), 4.26 (t, J=5.27 Hz, 2H), 3.80 (t, J=5.27 Hz, 2H).

The Compound shown in Table 24 has been prepared similar to Compound 318 by coupling of Intermediate 318D with in-situ generated from respective aniline.

TABLE 24
| Ex. No. | Structure | Name | [M + H]+ | Ret Time (min) | HPLC Methods |
|---|---|---|---|---|---|
| 319 | 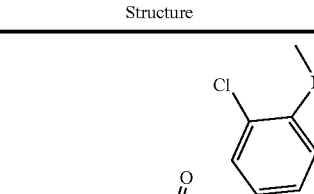 | 2-(7-Chloro-1-methyl-1H-indazol-5-yl)-N5-(3-chloro-4-cyanophenyl)-6,7-dihydropyrazolo[1,5-a]pyrazine-3,5(4H)-dicarboxamide | 509.6 | 1.44<br>1.45 | E<br>L |
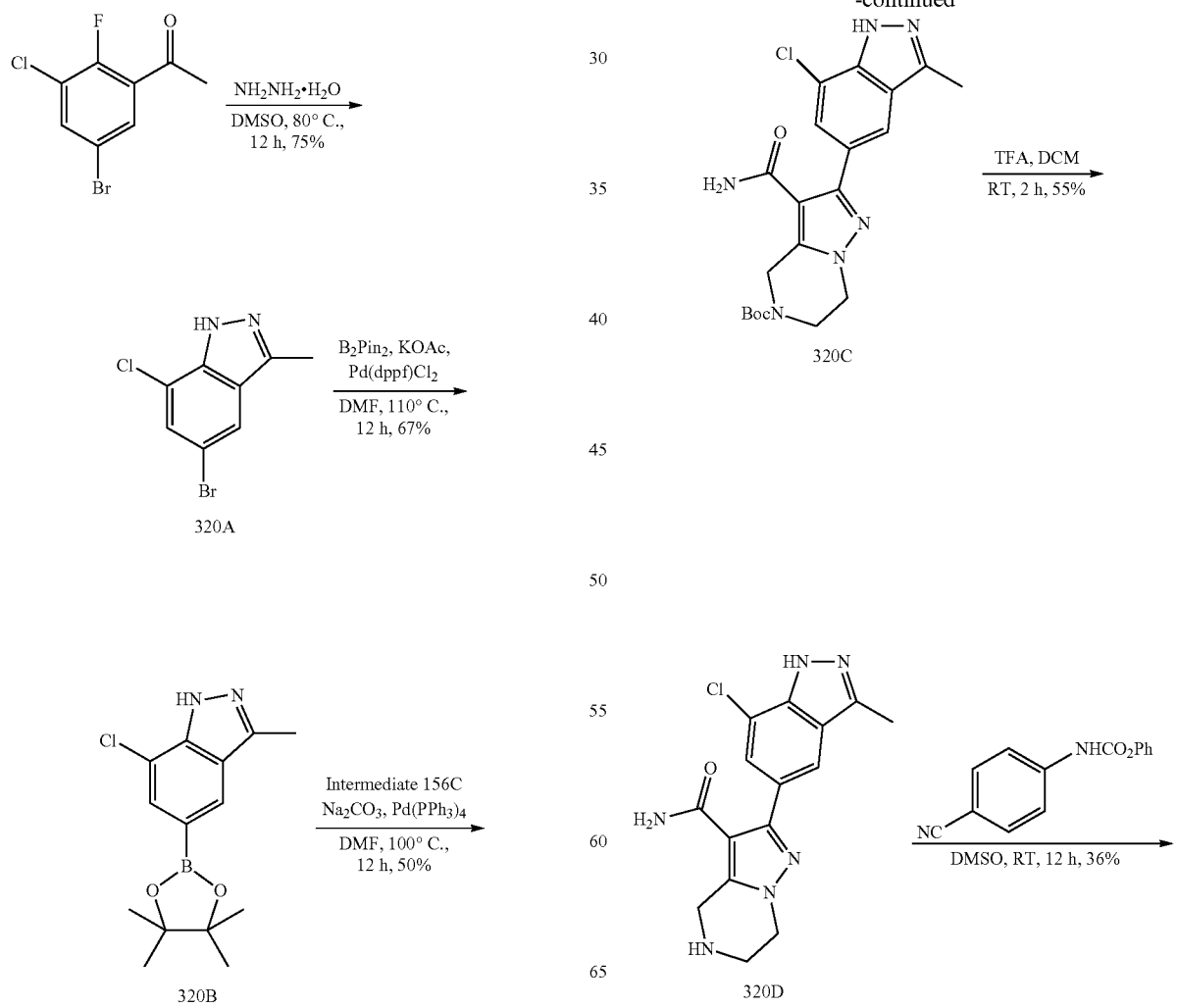

-continued

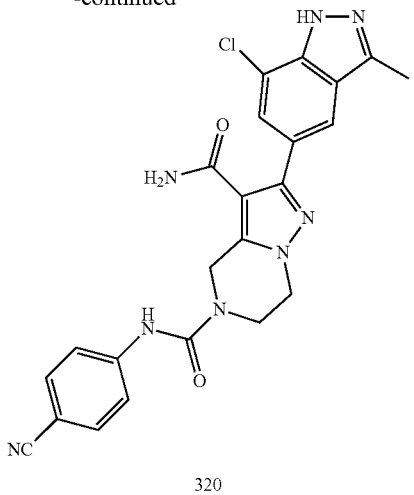

320

Intermediate 320A:
5-Bromo-7-chloro-3-methyl-1H-indazole

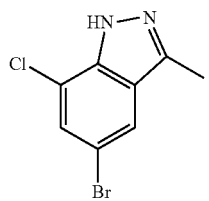

To a solution of 1-(5-bromo-3-chloro-2-fluorophenyl)ethanone (4.0 g, 15.91 mmol) in DMSO (40 mL) was added hydrazine monohydrate (0.998 mL, 31.8 mmol) and the reaction mixture was allowed to stir at 80° C. for 12 h. The reaction mixture was cooled to 0° C., diluted with ice-cold water and the solid was filtered through a Buchner funnel, and dried under vacuum to afford Intermediate 320A (3.1 g, 75%) as a white solid. $^1$H NMR (300 MHz, chloroform-d) ppm δ 10.19 (br. s., 1H), 7.75 (d, J=1.5 Hz, 1H), 7.52-7.44 (m, 1H), 2.58 (s, 3H).

Intermediate 320B: 7-Chloro-3-methyl-5-(4,4,5,5-tetramethyl-1,3,2-dioxaborolan-2-yl)-1H-indazole

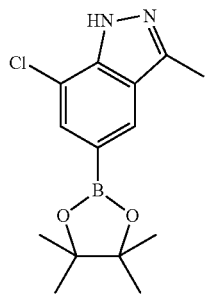 [SMILES: Cc1n[nH]c2c(Cl)cc(B3OC(C)(C)C(C)(C)O3)cc12]

To a solution of Intermediate 320A (1.0 g, 4.07 mmol), bis(pinacolato)diboron (1.345 g, 5.30 mmol) in DMF (10 mL) was added KOAc (1.199 g, 12.22 mmol) and the reaction mixture was purged with N$_2$ for 10 min. PdCl$_2$(dppf)-CH$_2$Cl$_2$ (0.200 g, 0.244 mmol) was added and the reaction mixture was heated to 100° C. and stirred for 12 h. The reaction mixture was diluted with water (50 mL) and extracted with ethyl acetate (2×50 mL). The combined organic layer was washed with brine, dried over Na$_2$SO$_4$, filtered and the filtrate concentrated to afford Intermediate 320B (0.8 g, 67%) as brown color gummy liquid. The crude product was taken to Suzuki coupling without purification. MS(ES): m/z=293 [M+H]$^+$.

Intermediate 320C: tert-Butyl 3-carbamoyl-2-(7-chloro-3-methyl-1H-indazol-5-yl)-6,7-dihydropyrazolo[1,5-a]pyrazine-5(4H)-carboxylate

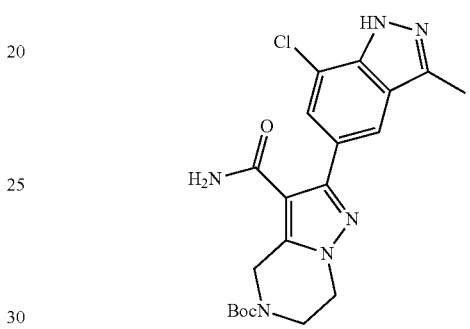

Intermediate 320C was synthesized from Intermediate 320B using a synthetic sequence analogous to the preparation of Intermediate 315D. MS(ES): m/z=431 [M+H]$^+$; $^1$H NMR (300 MHz, chloroform-d) δ ppm 10.25 (br. s., 1H), 7.83 (d, J=1.1 Hz, 1H), 7.61 (d, J=1.5 Hz, 1H), 7.29 (br. s., 1H), 6.97 (br. s., 1H), 5.01 (s, 2H), 4.25 (t, J=5.3 Hz, 2H), 3.98 (t, J=5.3 Hz, 2H), 1.54 (s, 9H).

Intermediate 320D: 2-(7-Chloro-3-methyl-1H-indazol-5-yl)-4,5,6,7-tetrahydropyrazolo[1,5-a]pyrazine-3-carboxamide

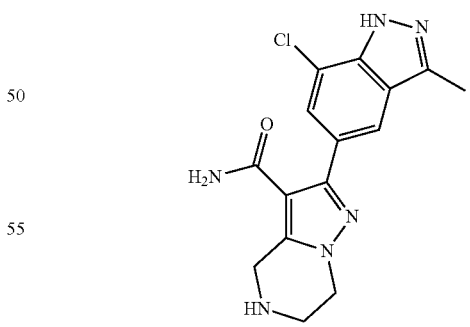

Intermediate 320D was synthesized from Intermediate 320C using a synthetic sequence analogous to the preparation of Intermediate 309F. MS(ES): m/z=331 [M+H]$^+$; $^1$H NMR (400 MHz, DMSO-d$_6$) ppm 13.22 (br. s., 1H), 7.98 (d, J=1.0 Hz, 1H), 7.70 (d, J=1.0 Hz, 1H), 7.20 (br. s., 1H), 6.95 (br. s., 1H), 4.08-3.94 (m, 4H), 3.13 (d, J=4.5 Hz, 2H), 2.69-2.59 (m, 1H), 2.4 (s, 3H).

351

Compound 320: 2-(7-Chloro-3-methyl-1H-indazol-5-yl)-N⁵-(4-cyanophenyl)-6,7-dihydropyrazolo[1,5-a]pyrazine-3,5(4H)-dicarboxamide

352

Scheme 28

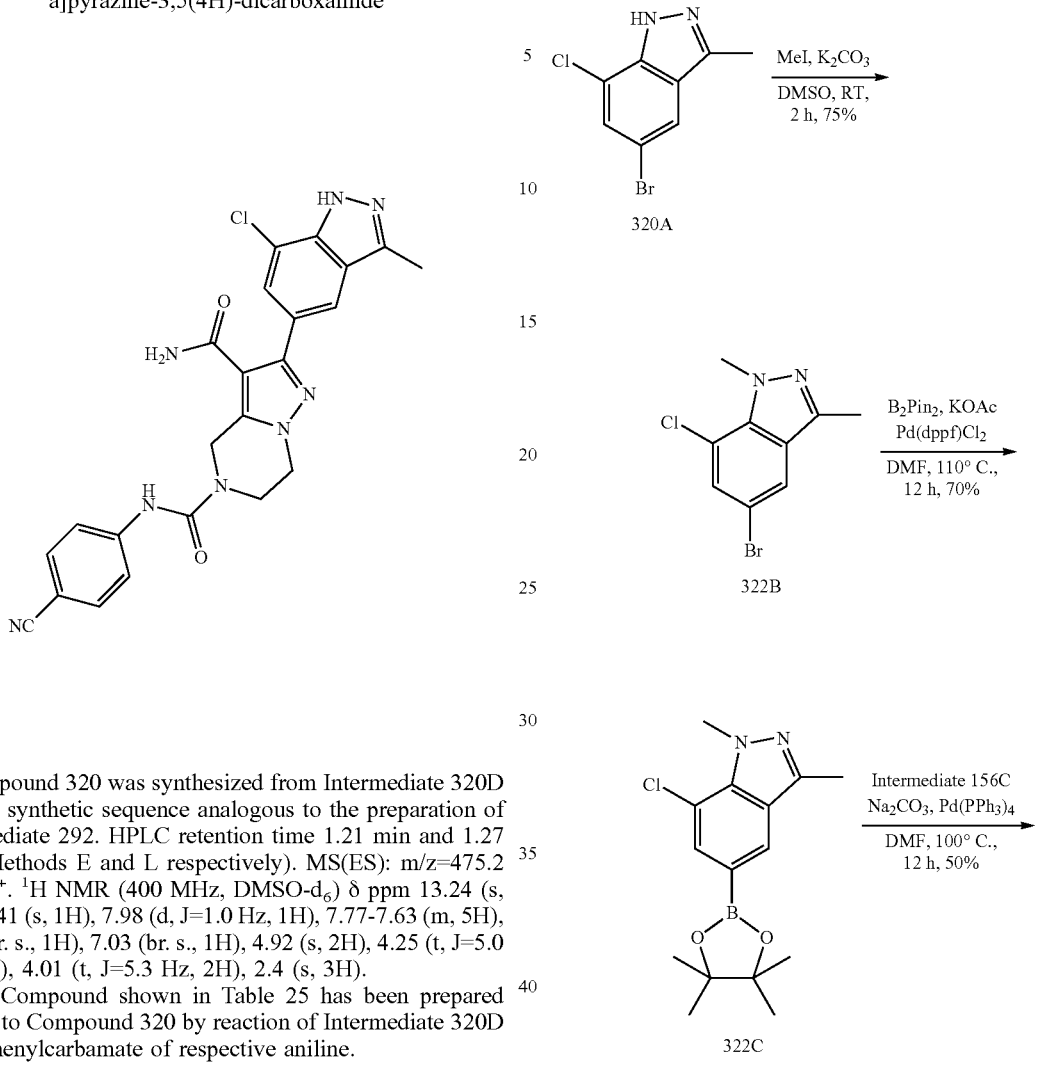

Compound 320 was synthesized from Intermediate 320D using a synthetic sequence analogous to the preparation of Intermediate 292. HPLC retention time 1.21 min and 1.27 min (Methods E and L respectively). MS(ES): m/z=475.2 [M+H]⁺. ¹H NMR (400 MHz, DMSO-$d_6$) δ ppm 13.24 (s, 1H), 9.41 (s, 1H), 7.98 (d, J=1.0 Hz, 1H), 7.77-7.63 (m, 5H), 7.36 (br. s., 1H), 7.03 (br. s., 1H), 4.92 (s, 2H), 4.25 (t, J=5.0 Hz, 2H), 4.01 (t, J=5.3 Hz, 2H), 2.4 (s, 3H).

The Compound shown in Table 25 has been prepared similar to Compound 320 by reaction of Intermediate 320D with phenylcarbamate of respective aniline.

TABLE 25

| Ex. No. | Structure | Name | [M + H]⁺ | Ret Time (min) | HPLC Methods |
|---|---|---|---|---|---|
| 321 | 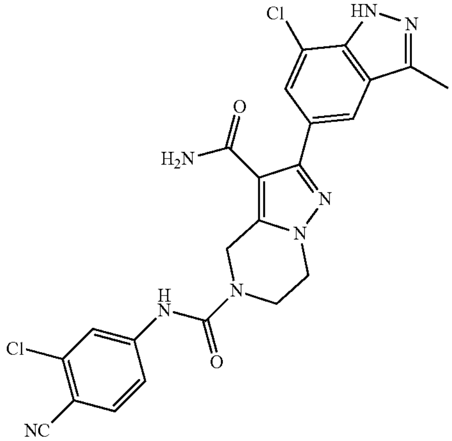 [SMILES: Cc1n[nH]c2c(Cl)cc(-c3nn4c(c3C(N)=O)CN(C(=O)Nc3ccc(C#N)c(Cl)c3)CC4)cc12] | 2-(7-Chloro-3-methyl-1H-indazol-5-yl)-N⁵-(3-chloro-4-cyanophenyl)-6,7-dihydropyrazolo[1,5-a]pyrazine-3,5(4H)-dicarboxamide | 509.2 | 1.39<br>1.43 | E<br>L |

353
-continued

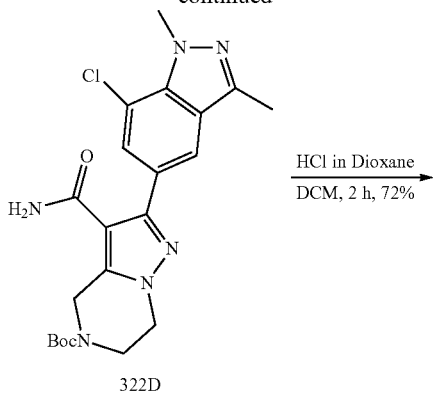

322D

HCl in Dioxane
────────────→
DCM, 2 h, 72%

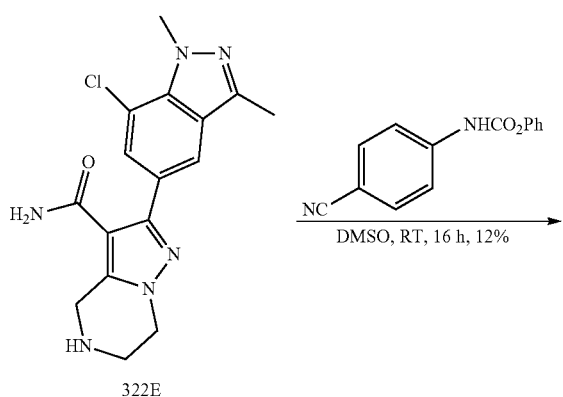

322E

354

Intermediate 322A:
5-Bromo-7-chloro-1,3-dimethyl-1H-indazole

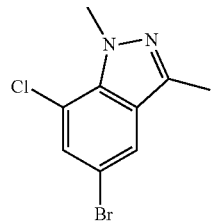

To a solution of Intermediate 320A (2.00 g, 8.15 mmol) and $K_2CO_3$ (3.38 g, 24.44 mmol) in DMSO (20 mL) was added methyl iodide (1.528 mL, 24.44 mmol) at 0° C. and the reaction mixture was stirred at RT for 12 h. The reaction mixture was diluted with ice-cold water, solid formed was filtered through a Buchner funnel and dried under vacuum. The crude product was purified by silica gel chromatography (40 g REDISEP® column, eluting with a gradient from 25% EtOAc in hexanes to isolate major isomer). Fractions containing the product were combined and evaporated to afford Intermediate 322A (1.1 g, 47%) as an off-white solid. $^1$H NMR (300 MHz, chloroform-d) δ ppm 7.67 (d, J=1.5 Hz, 1H), 7.44 (d, J=1.9 Hz, 1H), 4.31 (s, 3H), 2.51 (s, 3H).

Intermediate 322B: 7-Chloro-1,3-dimethyl-5-(4,4,5,5-tetramethyl-1,3,2-dioxaborolan-2-yl)-1H-indazole

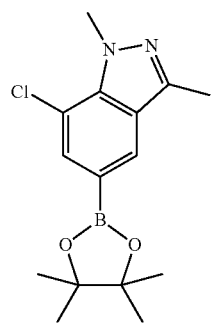 [SMILES: Cc1nn(C)c2c(Cl)cc(B3OC(C)(C)C(C)(C)O3)cc12]

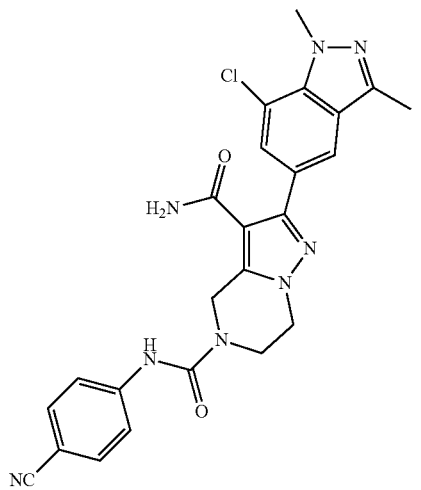

322

To a solution of Intermediate 322A (1.2 g, 4.62 mmol), bis(pinacolato)diboron (1.53 g, 6.01 mmol) in DMF (12 mL) was added KOAc (1.361 g, 13.87 mmol) and the reaction mixture was purged with $N_2$ gas for 0 min. $PdCl_2$(dppf)-$CH_2Cl_2$ (0.227 g, 0.277 mmol) was added and the reaction mixture was heated to 110° C. and stirred for 12 h. The reaction mixture was cooled to RT, diluted with EtOAc, and filtered through CELITE®. The filtrate was washed with water, brine, dried over $Na_2SO_4$, filtered and concentrated to afford Intermediate 322B (1.0 g, 70%) as brown liquid MS(ES): m/z=307 [M+H]$^+$.

Intermediate 322C: tert-Butyl 3-carbamoyl-2-(7-chloro-1,3-dimethyl-1H-indazol-5-yl)-6,7-dihydropyrazolo[1,5-a]pyrazine-5(4H)-carboxylate

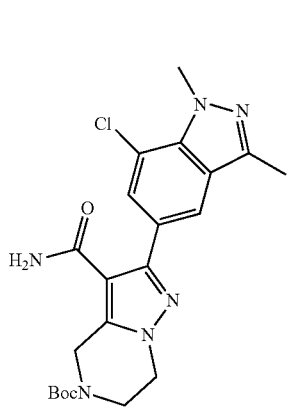 [SMILES: Cc1nn(C)c2c(Cl)cc(-c3nn4c(c3C(N)=O)CN(C(=O)OC(C)(C)C)CC4)cc12]

Intermediate 322C was synthesized from Intermediate 322B using a synthetic sequence analogous to the preparation of Intermediate 315D. MS(ES): m/z=445 [M+H]$^+$; $^1$H NMR (300 MHz, DMSO-d$_6$) δ ppm 8.32 (s, 1H), 7.70 (d, J=1.1 Hz, 1H), 7.02 (br. s., 1H), 6.89 (br. s., 1H), 4.25 (s, 3H), 4.16 (t, J=6 Hz, 2H), 3.85 (t, J=6 Hz, 2H), 2.47 (s, 3H).

Intermediate 322D: 2-(7-Chloro-1,3-dimethyl-1H-indazol-5-yl)-4,5,6,7-tetrahydropyrazolo[1,5-a]pyrazine-3-carboxamide, HCl

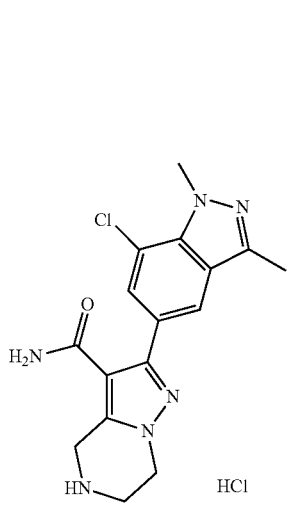 [SMILES: Cc1nn(C)c2c(Cl)cc(-c3nn4c(c3C(N)=O)CNCC4)cc12 ; Cl]

Intermediate 322D was synthesized from Intermediate 322C using a synthetic sequence analogous to the preparation of Intermediate 304E. MS(ES): m/z=335 [M+H]$^+$; $^1$H NMR (300 MHz, DMSO-d$_6$) δ ppm 7.97 (d, J=1.5 Hz, 1H), 7.68 (d, J=1.5 Hz, 1H), 7.40 (br. s., 1H), 7.06 (br. s., 1H), 4.55 (s., 2H), 4.42 (t, J=5.5 Hz, 2H), 4.25 (s, 3H), 3.67 (m, 3H), 2.46 (s, 3H).

Compound 322: 2-(7-Chloro-1,3-dimethyl-1H-indazol-5-yl)-N-(4-cyanophenyl)-6,7-dihydropyrazolo[1,5-a]pyrazine-3,5(4H)-dicarboxamide

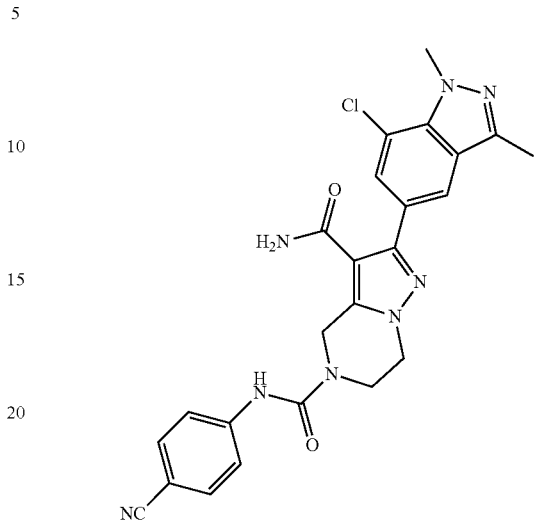

Compound 322 was synthesized from Intermediate 322D using a synthetic sequence analogous to the preparation of Compound 292. MS(ES): m/z=489.3 [M+H]$^+$; HPLC retention time 1.37 min and 1.42 min (Methods E and L respectively). $^1$H NMR (400 MHz, DMSO-d$_6$) δ ppm 9.42 (s, 1H), 7.99 (d, J=1.0 Hz, 1H), 7.77-7.64 (m, 5H), 7.39 (br. s., 1H), 7.08 (br. s., 1H), 4.93 (s, 2H), 4.28-4.26 (t, J=5.3 Hz, 2H), 4.24 (s, 3H), 4.02 (t, J=5.3 Hz, 2H), 2.48 (s, 3H).

Scheme 29

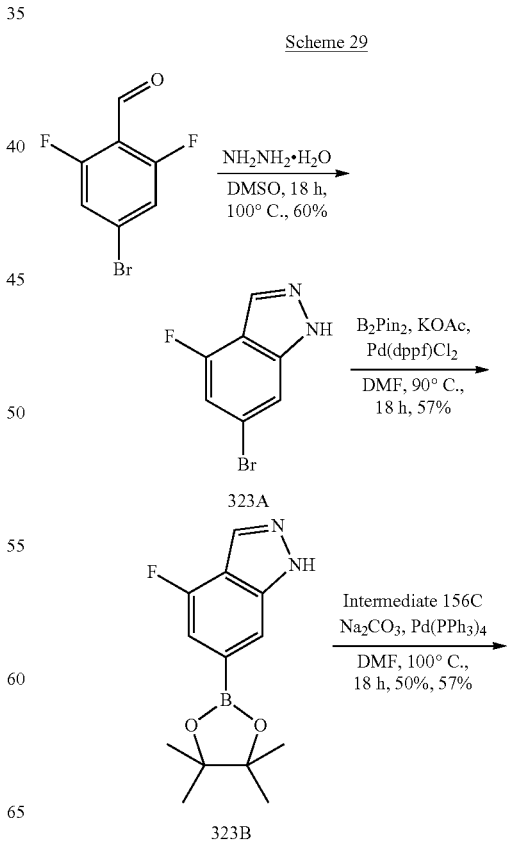

357
-continued

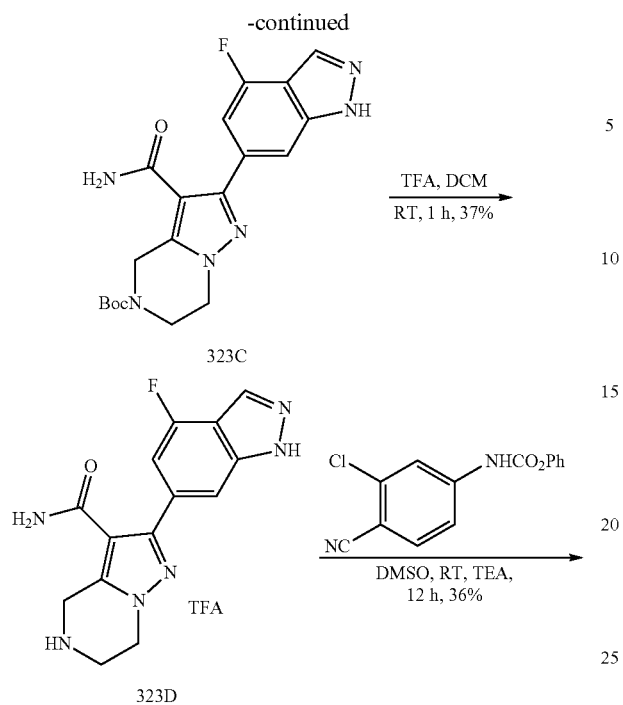

323C

323D

323

Intermediate 323A: 6-Bromo-4-fluoro-1H-indazole

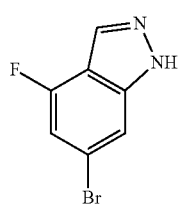 [SMILES: Fc1cc(Br)cc2[nH]ncc12]

To a solution of 4-bromo-2,6-difluorobenzaldehyde (0.1 g, 0.452 mmol) in DMSO (0.5 mL) was added hydrazine hydrate (0.023 g, 0.452 mmol) and the resultant solution was heated to 100° C. and stirred for 18 h. The reaction mixture cooled to RT and diluted with water. The solid separated was filtered, washed with water and dried under vacuum to afford Intermediate 323A (0.065 g, 60%) as a white solid. MS(ES):

m/z=214.9 [M+H]$^+$; $^1$H NMR (300 MHz, DMSO-d$_6$) δ ppm 13.53 (br. s., 1H), 8.22 (s, 1H), 7.65 (s, 1H), 7.17 (d, J=9.4 Hz, 1H).

Intermediate 323B: 4-Fluoro-6-(4,4,5,5-tetramethyl-1,3,2-dioxaborolan-2-yl)-1H-indazole

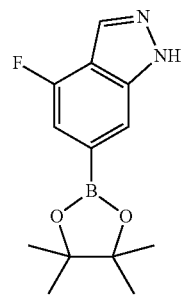

Intermediate 323B was synthesized from Intermediate 323A using a synthetic sequence analogous to the preparation of Intermediate 297A. MS(ES): m/z=181.0 [M+H]$^+$; $^1$H NMR (300 MHz, DMSO-d$_6$) δ ppm 13.53 (br. s., 1H), 8.22 (s, 1H), 7.69 (s, 1H), 6.99 (d, J=10.6 Hz, 1H), 1.32 (s, 12H).

Intermediate 323C: tert-Butyl 3-carbamoyl-2-(4-fluoro-1H-indazol-6-yl)-6,7-dihydropyrazolo[1,5-a]pyrazine-5(4H)-carboxylate

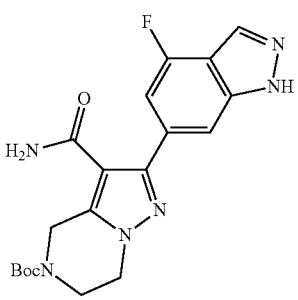 [SMILES: CC(C)(C)OC(=O)N1CCn2nc(-c3cc(F)c4cn[nH]c4c3)c(C(N)=O)c2C1]

Intermediate 323C was synthesized from Intermediate 323B using a synthetic sequence analogous to the preparation of Intermediate 315D MS(ES): m/z=401.2 [M+H]$^+$; $^1$H NMR (300 MHz, DMSO-d$_6$) δ ppm 12.86 (br. s., 1H), 8.19 (s, 1H), 7.73 (s, 1H), 7.36 (br. s., 1H), 7.20-7.16 (m, 2H), 4.75 (s, 2H), 4.18 (t, J=5.1 Hz, 2H), 3.90-3.77 (m, 2H), 1.54 (s, 9H).

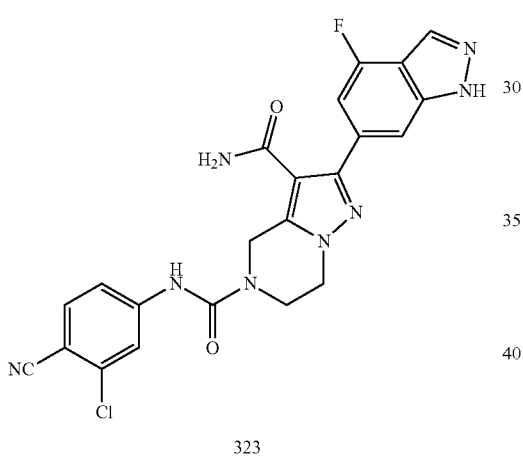

359

Intermediate 323D: 2-(4-Fluoro-1H-indazol-6-yl)-4,5,6,7-tetrahydropyrazolo[1,5-a]pyrazine-3-carboxamide TFA

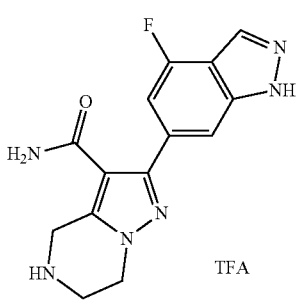 [SMILES: NC(=O)c1c(-c2cc(F)c3cn[nH]c3c2)nn2c1CNCC2]

Intermediate 323D was synthesized from Intermediate 323C using a synthetic sequence analogous to the preparation of Intermediate 297C. MS(ES): m/z=301.0 [M+H]$^+$.

360

Compound 323: N$^5$-(3-Chloro-4-cyanophenyl)-2-(4-fluoro-1H-indazol-6-yl)-6,7-dihydropyrazolo[1,5-a]pyrazine-3,5(4H)-dicarboxamide

To a stirred solution of Intermediate 323D (0.05 g, 0.121 mmol) in DMSO (1 mL) was added phenyl(3-chloro-4-cyanophenyl)carbamate (0.033 g, 0.121 mmol), TEA (0.050 mL, 0.362 mmol) and the resulting reaction mixture was allowed to stir at RT for 12 h. The reaction mixture was diluted with water and the solid separated was filtered and dried. The crude product was purified by preparative HPLC to afford Compound 323 (2 mg, 4%). The retention times are 1.271 min. and 1.265 min. (Methods E and L respectively): MS(ES): m/z=478.8 [M+H]$^+$; $^1$H NMR (400 MHz, DMSO-d$_6$) δ ppm 13.49 (s, 1H), 9.59 (s, 1H), 8.20 (s, 1H), 7.92 (d, J=2.0 Hz, 1H), 7.86 (d, J=8.5 Hz, 2H), 7.75 (s, 1H), 7.64-7.60 (m, 1H), 7.21 (d, J=11.5 Hz, 2H), 4.93 (s, 2H), 4.28 (s, 2H), 4.02 (s, 2H).

The Compounds shown in Table 26 have been prepared similar to Compound 323 by reaction of Intermediate 323D with phenylcarbamates of respective anilines.

TABLE 26

| Ex. No. | Structure | Name | [M + H]$^+$ | Ret Time (min.) | HPLC Methods |
|---|---|---|---|---|---|
| 324 | 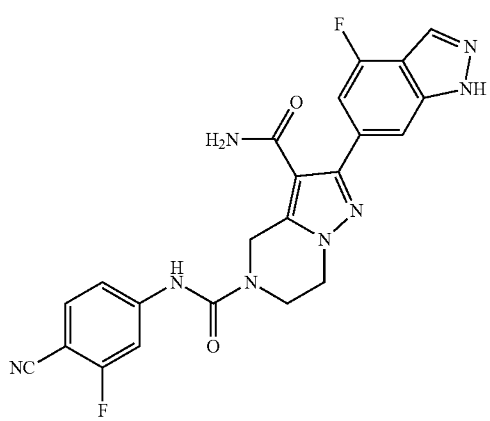 [SMILES: N#Cc1ccc(NC(=O)N2CCn3nc(-c4cc(F)c5cn[nH]c5c4)c(C(N)=O)c3C2)cc1F] | N$^5$-(4-Cyano-3-fluorophenyl)-2-(4-fluoro-1H-indazol-6-yl)-6,7-dihydropyrazolo[1,5-a]pyrazine-3,5(4H)-dicarboxamide | 462.9 | 1.270<br>1.154 | E<br>L |

TABLE 26-continued
| Ex. No. | Structure | Name | [M + H]+ | Ret Time (min.) | HPLC Methods |
|---|---|---|---|---|---|
| 325 | 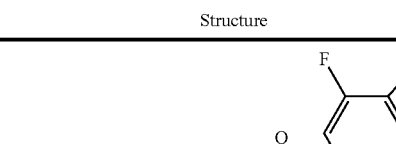 | N5-(4-Cyano-3-methylphenyl)-2-(4-fluoro-1H-indazol-6-yl)-6,7-dihydropyrazolo[1,5-a]pyrazine-3,5(4H)-dicarboxamide | 459.0 | 1.258<br>1.134 | E<br>L |
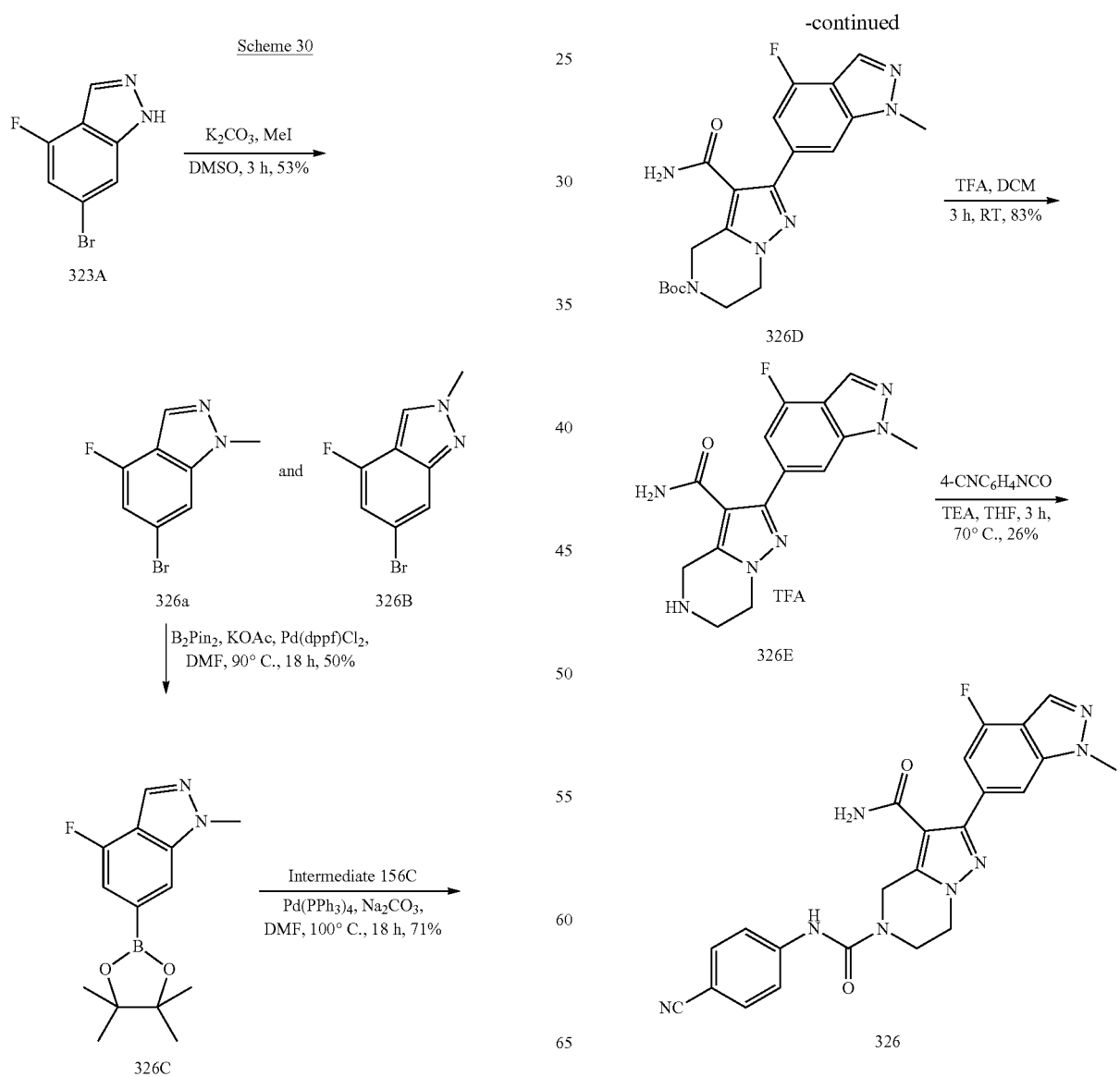

Intermediates 326A and 326B: 6-Bromo-4-fluoro-1-methyl-1H-indazole (326A), and 6-Bromo-4-fluoro-2-methyl-2H-indazole (326B)

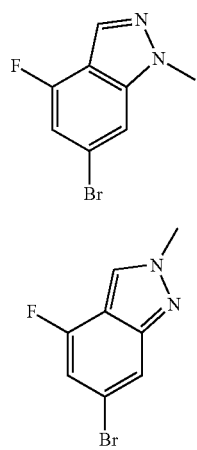

To a solution of Intermediate 323A (0.25 g, 1.163 mmol) in DMSO (3 mL) was added K$_2$CO$_3$ (0.321 g, 2.325 mmol) followed by MeI (0.087 mL, 1.395 mmol) and the resulting reaction mixture was stirred at RT for 3 h. The reaction mixture was quenched with water and extracted with EtOAc (2×50 mL). The combined organic layer was washed with brine, dried over Na$_2$SO$_4$ and concentrated under reduced pressure. The crude compound was purified by silica gel chromatography (12 g REDISEP® column, eluting with a gradient from 0-10% EtOAc in hexanes). Fractions containing the different products were combined and evaporated to afford Intermediate 326A (0.15 g, 54%) and Intermediate 326B (0.075 g, 27%). $^1$H NMR (300 MHz, DMSO-d$_6$, 326A) δ ppm 8.19 (s, 1H), 7.89 (s, 1H), 7.19 (dd, J=9.6, 0.9 Hz, 1H), 4.05 (s, 3H). $^1$H NMR (400 MHz, DMSO-d$_6$, 326B) δ ppm 8.61 (s, 1H), 7.74 (d, J=1.0 Hz, 1H), 7.05 (dd, J=1.3, 9.8 Hz, 1H), 4.18 (s, 3H).

Intermediate 326C: 4-Fluoro-1-methyl-6-(4,4,5,5-tetramethyl-1,3,2-dioxaborolan-2-yl)-1H-indazole

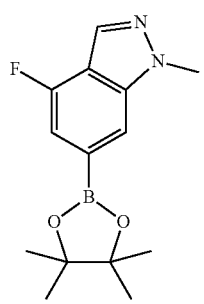 [SMILES: Cn1ncc2c(F)cc(B3OC(C)(C)C(C)(C)O3)cc21]

Intermediate 326C was synthesized from Intermediate 326A using a synthetic sequence analogous to the preparation of Intermediate 297A. MS(ES): m/z=277.1 [M+H]$^+$; $^1$H NMR (400 MHz, DMSO-d$_6$) δ ppm 8.20 (s, 1H), 7.80 (s, 1H), 7.04 (d, J=10.5 Hz, 1H), 4.13 (s, 3H), 1.34 (s, 12H).

Intermediate 326D: tert-Butyl 3-carbamoyl-2-(4-fluoro-1-methyl-1H-indazol-6-yl)-6,7-dihydropyrazolo[1,5-a]pyrazine-5(4H)-carboxylate

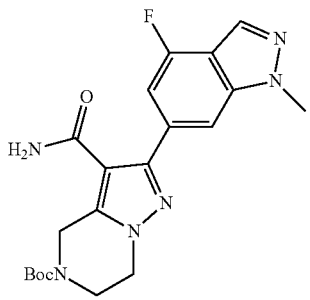 [SMILES: Cn1ncc2c(F)cc(-c3nn4c(c3C(N)=O)CN(C(=O)OC(C)(C)C)CC4)cc21]

Intermediate 326D was synthesized from Intermediate 326C using a synthetic sequence analogous to the preparation of Intermediate 315D. MS(ES): m/z=415.2 [M+H]$^+$; $^1$H NMR (400 MHz, chloroform-d) δ ppm 8.09 (s, 1H), 7.43 (s, 1H), 7.04 (d, J=10.5 Hz, 1H), 4.99 (s, 2H), 4.28-4.19 (m, 2H), 4.10 (s, 3H), 4.01-3.90 (m, 2H), 1.52 (s, 9H).

Intermediate 326E: 2-(4-Fluoro-1-methyl-1H-indazol-6-yl)-4,5,6,7-tetrahydropyrazolo[1,5-a]pyrazine-3-carboxamide TFA

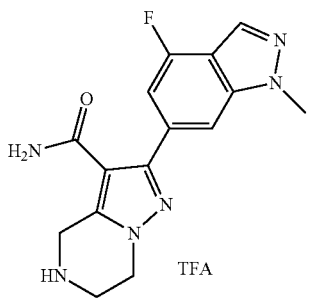 [SMILES: Cn1ncc2c(F)cc(-c3nn4c(c3C(N)=O)CNCC4)cc21]

Intermediate 326E was synthesized from Intermediate 326D using a synthetic sequence analogous to the preparation of Intermediate 297C. MS(ES): m/z=315.1[M+H]$^+$; $^1$H NMR (400 MHz, DMSO-d$_6$) δ ppm 9.46 (br. s., 1H), 8.21 (s, 1H), 7.79 (s, 1H), 7.34 (br. s., 1H), 7.21-7.14 (m, 1H), 7.05 (br. s., 1H), 4.60 (s, 2H), 4.41 (t, J=5.8 Hz, 2H), 4.10 (s, 3H), 3.73 (t, J=5.8 Hz, 2H).

Compound 326: N⁵-(4-Cyanophenyl)-2-(4-fluoro-1-methyl-1H-indazol-6-yl)-6,7-dihydropyrazolo[1,5-a]pyrazine-3,5(4H)-dicarboxamide Scheme 31

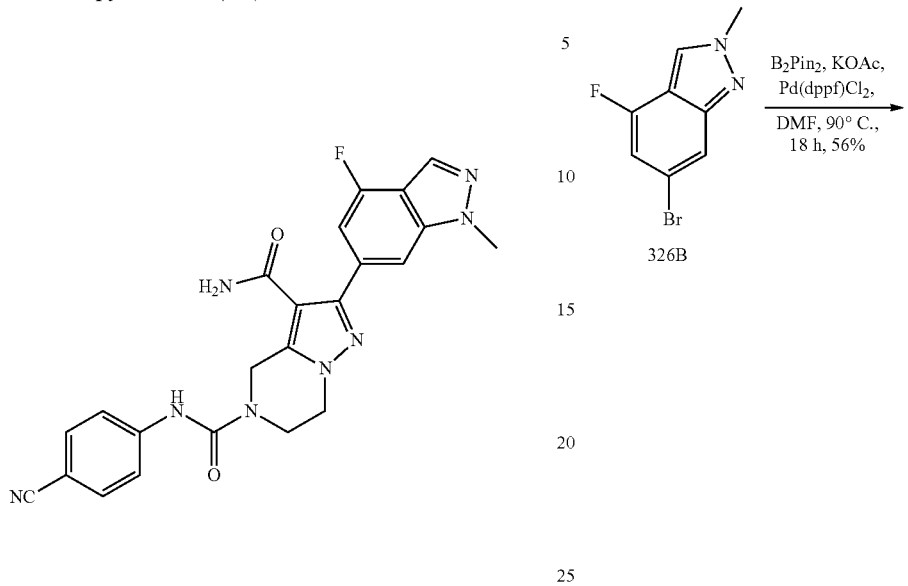

To a stirred solution of Intermediate 326E (0.04 g, 0.093 mmol) and 4-isocyanatobenzonitrile (0.013 g, 0.093 mmol) in THF (1 mL) was added TEA (0.039 mL, 0.280 mmol) and the resultant solution was heated to 70° C. and stirred for 3 h. The reaction mixture was diluted with EtOAc, washed with water and brine. The organic layer was dried over anhydrous Na₂SO₄, filtered and the filtrate concentrated. The crude product was purified by preparative HPLC to afford Compound 326 (0.011 g, 26%) as an off-white solid. MS(ES): m/z=459.2 [M+H]⁺; HPLC retention times are 1.768 min. and 1.777 min. (Methods E and L respectively). ¹H NMR (400 MHz, DMSO-d₆) δ ppm 9.41 (s, 1H), 8.19 (s, 1H), 7.81 (s, 1H), 7.75-7.66 (m, 4H), 7.39 (br. s., 1H), 7.21 (dd, J=1.0, 11.5 Hz, 1H), 7.11 (br. s., 1H), 4.95 (s, 2H), 4.28 (t, J=5.5 Hz, 2H), 4.09 (s, 3H), 4.04-3.98 (m, 2H).

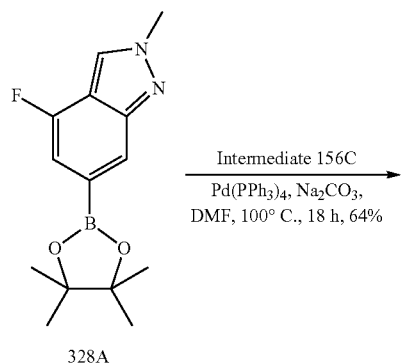

The Compound shown in Table 27 has been prepared similar to Compound 326 by coupling of Intermediate 326E with in-situ generated isocyanates from respective aniline.

TABLE 27

| Ex. No. | Structure | Name | [M + H]⁺ | Ret Time (min.) | HPLC Methods |
|---|---|---|---|---|---|
| 327 | 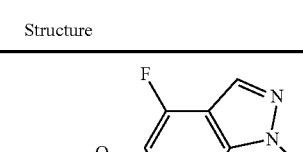 | N⁵-(4-Cyano-3-methylphenyl)-2-(4-fluoro-1-methyl-1H-indazol-6-yl)-6,7-dihydropyrazolo[1,5-a]pyrazine-3,5(4H)-dicarboxamide | 473.0 | 1.882<br>1.870 | E<br>L |

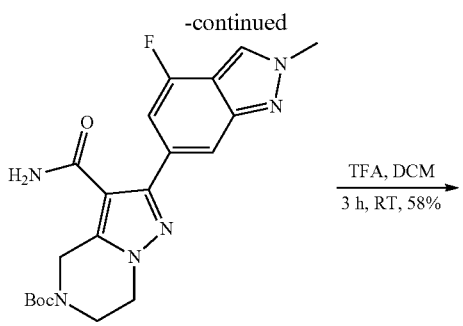

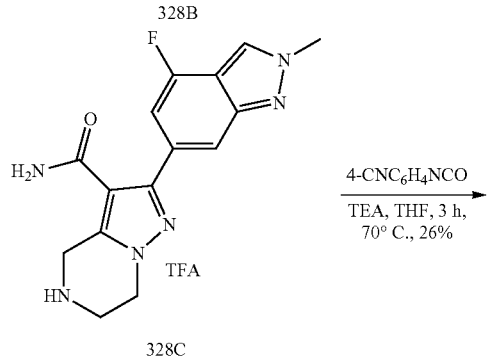

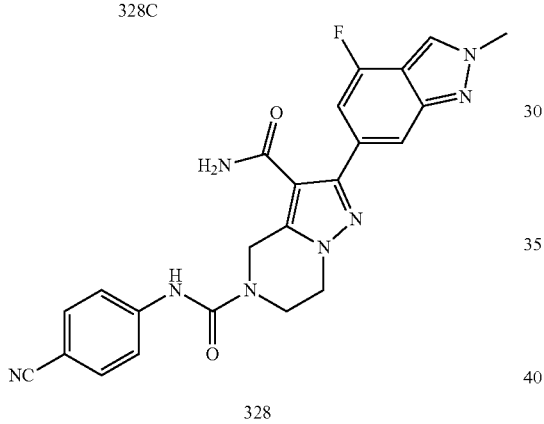

Intermediate 328A: 4-Fluoro-2-methyl-6-(4,4,5,5-tetramethyl-1,3,2-dioxaborolan-2-yl)-2H-indazole

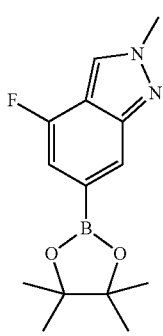 [SMILES: Cn1cc2c(F)cc(B3OC(C)(C)C(C)(C)O3)cc2n1]

Intermediate 328A was synthesized from Intermediate 326B using a synthetic sequence analogous to the preparation of Intermediate 297A. MS(ES): m/z=277.2 [M+H]$^+$; $^1$H NMR (400 MHz, DMSO-d$_6$) δ ppm 8.56 (s, 1H), 7.79 (s, 1H), 6.88 (d, J=10.5 Hz, 1H), 4.22 (s, 3H), 1.32 (s, 12H).

Intermediate 328B: tert-Butyl 3-carbamoyl-2-(4-fluoro-2-methyl-2H-indazol-6-yl)-6,7-dihydropyrazolo[1,5-a]pyrazine-5(4H)-carboxylate

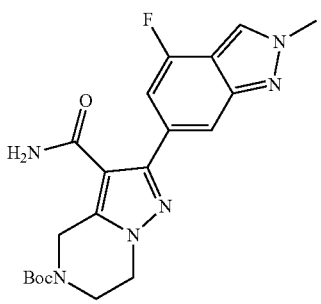 [SMILES: Cn1cc2c(F)cc(-c3nn4c(c3C(N)=O)CN(C(=O)OC(C)(C)C)CC4)cc2n1]

Intermediate 328B was synthesized from Intermediate 328A using a synthetic sequence analogous to the preparation of Intermediate 315D. MS(ES): m/z=415.2 [M+H]$^+$; $^1$H NMR (400 MHz, chloroform-d) δ ppm 8.06 (s, 1H), 7.72 (s, 1H), 6.88 (d, J=10.5 Hz, 1H), 5.02-4.97 (m, 2H), 4.27 (s, 2H), 4.25-4.20 (m, 3H), 4.00-3.89 (m, 2H), 1.52 (s, 9H).

Intermediate 328C: 2-(4-Fluoro-2-methyl-2H-indazol-6-yl)-4,5,6,7-tetrahydropyrazolo[1,5-a]pyrazine-3-carboxamide TFA

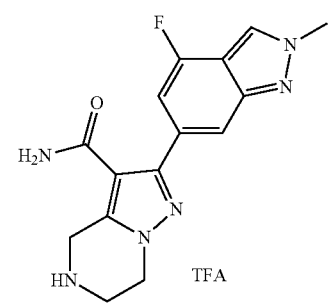 [SMILES: Cn1cc2c(F)cc(-c3nn4c(c3C(N)=O)CNCC4)cc2n1]

Intermediate 328C was synthesized from Intermediate 328B using a synthetic sequence analogous to the preparation of Intermediate 297C. MS(ES): m/z=315.2 [M+H]$^+$; $^1$H NMR (400 MHz, DMSO-d$_6$) δ ppm 9.52-9.32 (m, 1H), 8.58 (s, 1H), 7.74 (s, 1H), 7.45 (s, 1H), 7.15-6.97 (m, 2H), 4.58 (s, 2H), 4.40 (s, 2H), 4.21 (s, 3H), 3.72 (s, 2H).

369

Intermediate 328: N⁵-(3-Chloro-4-cyanophenyl)-2-(4-fluoro-2-methyl-2H-indazol-6-yl)-6,7-dihydropyrazolo[1,5-a]pyrazine-3,5(4H)-dicarboxamide

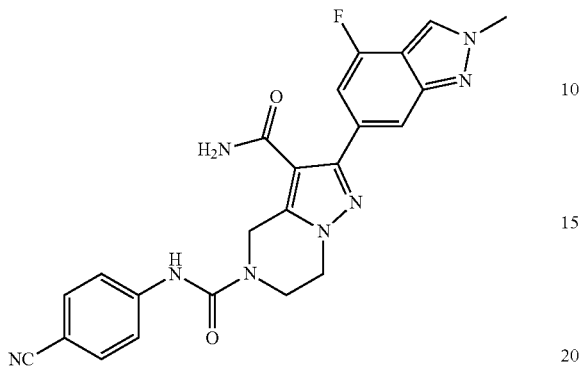

Compound 328 was synthesized from Intermediate 328C using a synthetic sequence analogous to the preparation of Compound 326. HPLC retention times are 1.653 min. and 1.653 min. (Methods H and I respectively). MS(ES): m/z=459.0 [M+H]⁺; ¹H NMR (400 MHz, DMSO-d₆) δ ppm 9.41 (s, 1H), 8.55 (s, 1H), 7.78-7.66 (m, 5H), 7.38 (br. s., 1H), 7.10 (dd, J=1.0, 11.5 Hz, 2H), 4.92 (s, 2H), 4.27 (t, J=5.3 Hz, 2H), 4.20 (s, 3H), 4.02 (t, J=5.3 Hz, 2H).

370

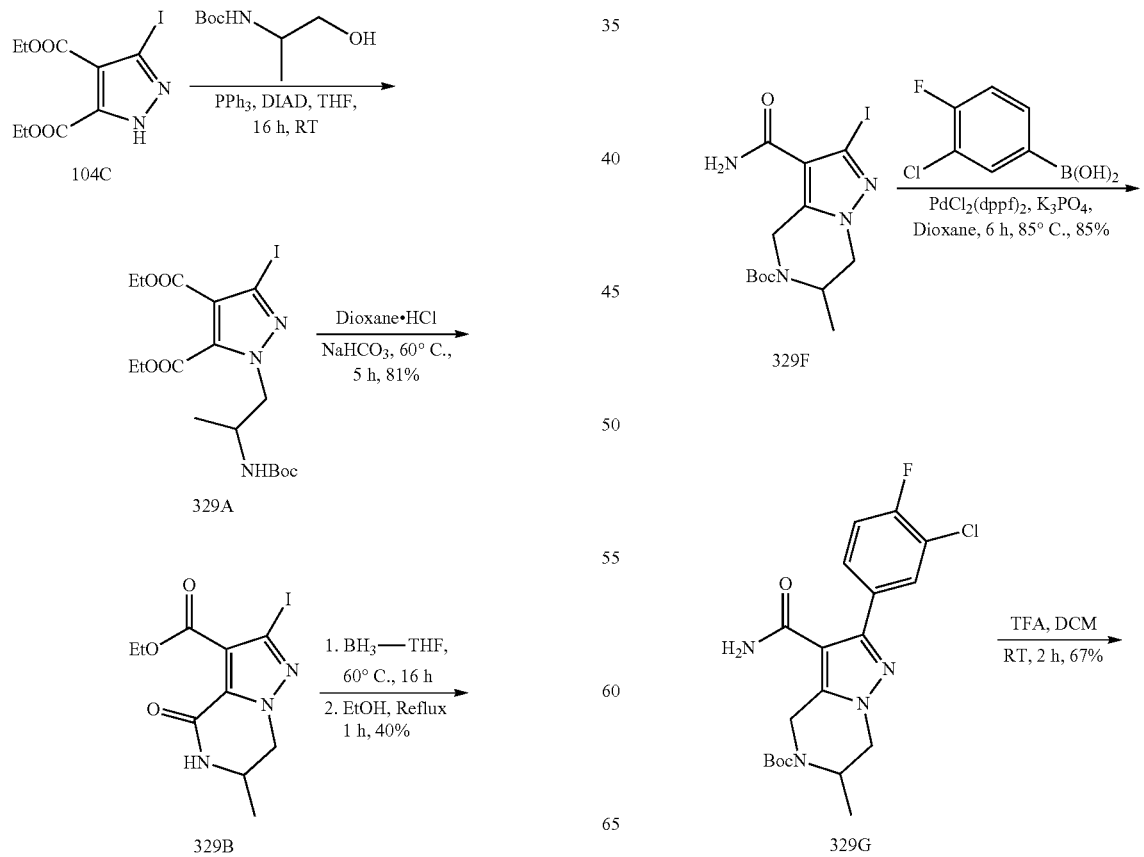

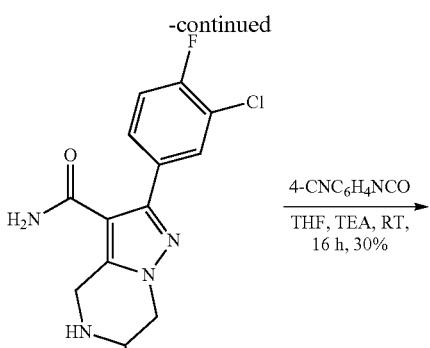

329H

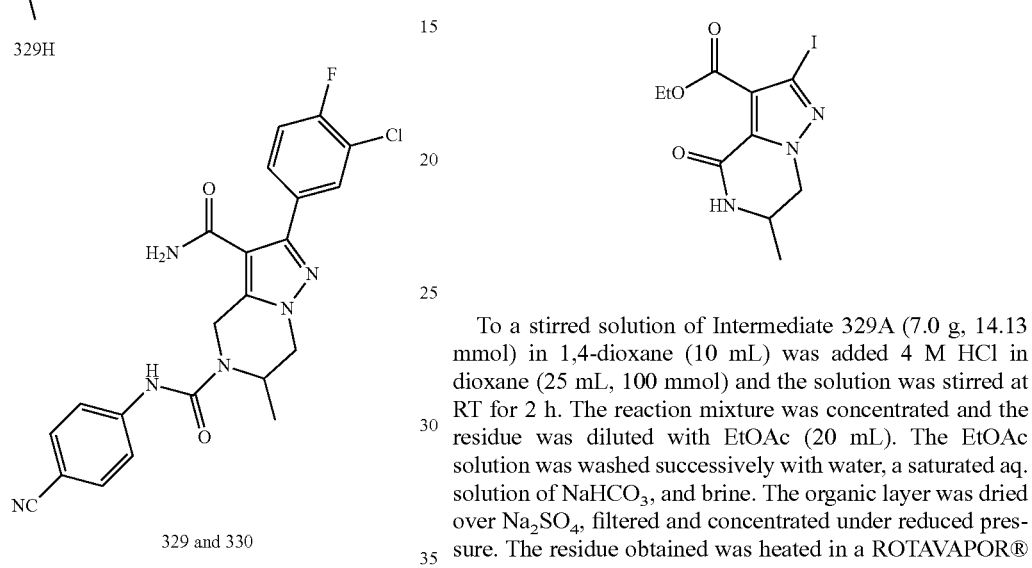

329 and 330

Intermediate 329A: Diethyl 1-(2-((Tert-butoxycarbonyl)amino)propyl)-3-iodo-1H-pyrazole-4,5-dicarboxylate To a stirred suspension of PPh$_3$ (12.41 g, 47.3 mmol) in THF (100 mL) was added DIAD (9.20 mL, 47.3 mmol) at −10° C. and allowed to stir at 0° C. for 0.5 h. Intermediate 104C (8.0 g, 23.66 mmol) was added as a solution in THF (10 mL) at 0° C. and stirred at RT for 45 min. The reaction mixture was cooled again to 0° C. and tert-butyl(1-hydroxypropan-2-yl)carbamate (5.39 g, 30.8 mmol) was added as a solution in THF (10 mL) and the mixture was stirred at RT for 16 h. The reaction mixture was diluted with ethyl acetate (100 mL), washed with water and brine. The organic layer was dried over Na$_2$SO$_4$, filtered and the filtrate concentrated under reduced pressure. The crude compound was purified by silica gel chromatography (40 g REDISEP® column, eluting with 15% EtOAc in hexane). Fractions containing the product were combined and evaporated to afford the Intermediate 329A as a brown liquid (7.0 g) contaminated with impurities arising from the coupling reagents. MS(ES): m/z=496 [M+H]$^+$. The crude intermediate was taken to the next step without further purification.

Intermediate 329B: Ethyl 2-iodo-6-methyl-4-oxo-4,5,6,7-tetrahydropyrazolo[1,5-a]pyrazine-3-carboxylate

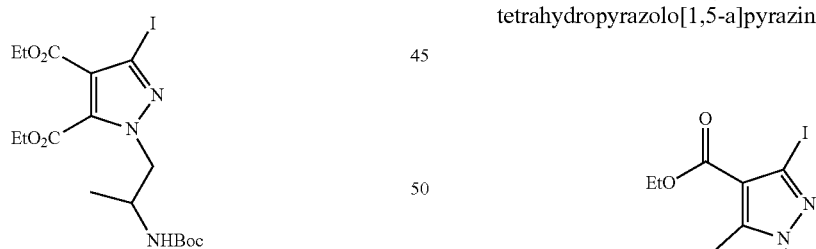

To a stirred solution of Intermediate 329A (7.0 g, 14.13 mmol) in 1,4-dioxane (10 mL) was added 4 M HCl in dioxane (25 mL, 100 mmol) and the solution was stirred at RT for 2 h. The reaction mixture was concentrated and the residue was diluted with EtOAc (20 mL). The EtOAc solution was washed successively with water, a saturated aq. solution of NaHCO$_3$, and brine. The organic layer was dried over Na$_2$SO$_4$, filtered and concentrated under reduced pressure. The residue obtained was heated in a ROTAVAPOR® at 60° C. for 5 h. The solid product was washed with ether to afford Intermediate 329B (4.0 g, 87%). MS(ES): m/z=350 [M+H]$^+$; $^1$H NMR (300 MHz, DMSO-d$_6$) δ ppm 8.49 (s, 1H), 4.27-4.49 (m, 1H), 4.11-4.26 (m, 2H), 4.03 (d, J=11.71 Hz, 2H), 1.06-1.39 (m, 6H).

Intermediate 329C: Ethyl 2-iodo-6-methyl-4,5,6,7-tetrahydropyrazolo[1,5-a]pyrazine-3-carboxylate To a solution of Intermediate 329B (4.0 g, 11.46 mmol) in THF (40 mL) was added BH$_3$.THF (40.1 mL, 80 mmol, 1M in THF) and the reaction mixture was stirred at 70° C. for 16 h. Ethanol (10 mL) was added and the reaction mixture was heated to reflux for 1 h. The reaction mixture was concentrated to afford Intermediate 329C (1.9 g, 40% yield) as a pale brown liquid. MS(ES): m/z=336 [M+H]$^+$. The crude compound was taken to the next step without further purification

Intermediate 329D: 5-tert-Butyl 3-ethyl2-iodo-6-methyl-6,7-dihydropyrazolo[1,5-a]pyrazine-3,5(4H)-dicarboxylate

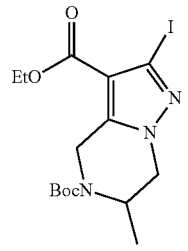

To a stirred solution of Intermediate 329C (0.81 g, 2.417 mmol) in DCM (10 mL) was added TEA (0.404 mL, 2.90 mmol) followed by Boc₂O (0.617 mL, 2.66 mmol) and the resulting solution was stirred at RT for 16 h. It was then diluted with DCM (10 mL) washed with water and brine. The crude compound was purified by silica gel chromatography (12 g REDISEP® column, eluting with 1% MeOH in CHCl₃). Fractions containing the product were combined and evaporated to afford Intermediate 329D as a colorless semi-solid (0.7 g, 67%). MS(ES): m/z=435 [M+H]⁺; ¹H NMR (400 MHz, DMSO-d₆) δ ppm 5.07 (d, J=18.57 Hz, 1H), 4.69 (br. s., 1H), 4.39 (d, J=18.57 Hz, 1H), 4.06-4.28 (m, 4H), 1.45 (s, 9H), 1.23-1.34 (m, 3H), 1.08 (d, J=7.03 Hz, 3H).

Intermediate 329E: 5-(tert-Butoxycarbonyl)-2-iodo-6-methyl-4,5,6,7-tetrahydropyrazolo[1,5-a]pyrazine-3-carboxylic acid

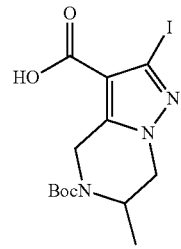 [SMILES: CC1Cn2nc(I)c(C(=O)O)c2CN1C(=O)OC(C)(C)C]

To a stirred solution of Intermediate 329D (0.85 g, 1.953 mmol) in EtOH (2.0 mL) was added a solution of NaOH (0.391 g, 9.76 mmol) in water (1.0 mL) and the resulting solution was stirred at RT for 16 h. The reaction mixture was concentrated and the residue was acidified by the addition of a 1N aq. solution of HCl (5 mL) which was allowed to stir for 10 min. The generated precipitate was filtered and dried to afford Intermediate 329E as a white solid (0.65 g, 82%). MS(ES): m/z=408 [M+H]⁺; ¹H NMR (300 MHz, DMSO-d₆) δ ppm 5.05 (d, J=18.89 Hz, 1H), 4.67 (br. s., 1H), 4.36 (d, J=18.13 Hz, 1H), 4.13-4.25 (m, 1H), 3.93-4.13 (m, 2H), 1.44 (s, 9H), 1.08 (t, J=6.99 Hz, 3H).

Intermediate 329F: tert-Butyl 3-carbamoyl-2-iodo-6-methyl-6,7-dihydropyrazolo[1,5-a]pyrazine-5(4H)-carboxylate

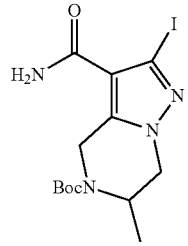 [SMILES: CC1Cn2nc(I)c(C(N)=O)c2CN1C(=O)OC(C)(C)C]

To a stirred solution of Intermediate 329E (0.65 g, 1.596 mmol) in DMF (3.0 mL) was added NH₄Cl (0.427 g, 7.98 mmol), HATU (1.214 g, 3.19 mmol) and DIPEA (0.836 mL, 4.79 mmol) and the resulting solution was allowed to stir at RT for 3 h. It was diluted with ethyl acetate (10 mL), washed with water, brine, dried over Na₂SO₄, filtered and the filtrate concentrated. The crude compound was purified by silica gel chromatography (12 g REDISEP® column, eluting with 2% MeOH in CHCl₃). Fractions containing the product were combined and evaporated to afford Intermediate 329F as a colorless liquid (0.38 g, 59%). MS(ES): m/z=407 [M+H]⁺; ¹H NMR (300 MHz, DMSO-d₆) δ ppm 6.79-7.56 (m, 2H), 5.01 (d, J=18.51 Hz, 1H), 4.66 (br. s., 1H), 4.39 (d, J=18.13 Hz, 1H), 3.96-4.20 (m, 2H), 1.44 (s, 9H), 1.07 (d, J=6.80 Hz, 3H).

Intermediate 329G: tert-Butyl 3-carbamoyl-2-iodo-6-methyl-6,7-dihydropyrazolo[1,5-a]pyrazine-5(4H)-carboxylate

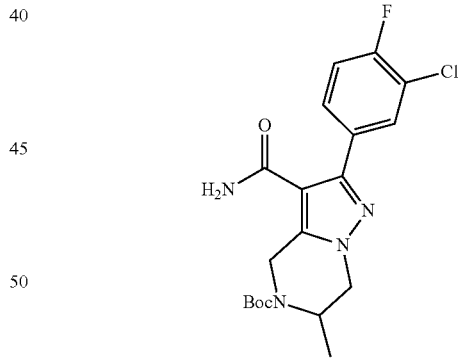

To a stirred suspension of Intermediate 329F (0.32 g, 0.788 mmol) in 1,4-dioxane (8.0 mL) was added (3-chloro-4-fluorophenyl)boronic acid (0.179 g, 1.024 mmol), K₃PO₄ (1.292 g, 2.58 mmol) and the contents of the flask were purged with N₂ for 10 min. PdCl₂(dppf)-CH₂Cl₂ (0.042 g, 0.052 mmol) was then added and the reaction mixture was stirred at 80° C. for 6 h. The reaction mixture was cooled to RT; diluted with ethyl acetate (10 mL), washed with water, dried over Na₂SO₄, filtered and the filtrate concentrated under reduced pressure. The crude compound was purified by silica gel chromatography (12 g REDISEP® column, eluting with 2% MeOH in CHCl₃). Fractions containing the product were combined and evaporated to afford Intermediate 329G as a pale yellow solid (0.27 g, 84%). MS(ES): m/z=408 [M+H]⁺; ¹H NMR (300 MHz, DMSO-d₆) δ ppm 7.85-7.92 (m, 1H), 7.71 (ddd, J=8.69, 4.91, 2.27 Hz, 1H), 7.46 (d, J=17.75 Hz, 1H), 7.24-7.38 (m, 2H), 4.99 (d, J=17.75 Hz, 1H), 4.72 (br. s., 1H), 4.44 (d, J=17.75 Hz, 1H), 4.08-4.28 (m, 2H), 1.46 (s, 9H), 1.15 (s, 3H).

Intermediate 329H: 2-(3-Chloro-4-fluorophenyl)-6-methyl-4,5,6,7-tetrahydropyrazolo[1,5-a]pyrazine-3-carboxamide, TFA

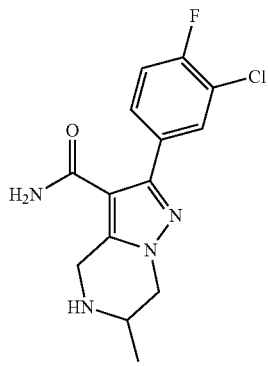 [SMILES: CC1Cn2nc(-c3ccc(F)c(Cl)c3)c(C(N)=O)c2CN1]

To a stirred solution of Intermediate 329G (0.09 g, 0.220 mmol) in DCM (3.0 mL) was added TFA (0.017 mL, 0.220 mmol) and the resulting solution was stirred at RT for 2 h. It was then concentrated and the residue was triturated with hexane to afford Intermediate 329H as a white solid (0.1 g). MS(ES): m/z=308 (M+H]+; ¹H NMR (400 MHz, DMSO-d₆) δ ppm 7.80-7.85 (m, 1H), 7.64-7.71 (m, 1H), 7.40-7.55 (m, 2H), 7.13-7.27 (m, 1H), 4.71 (d, J=16.06 Hz, 1H) 4.53 (dd, J=13.55, 4.02 Hz, 2H), 3.90-4.11 (m, 2H), 1.40 (d, J=6.53 Hz, 3H).

Compounds 329 and 330: 2-(3-Chloro-4-fluorophenyl)-N⁵-(4-cyanophenyl)-6-methyl-6,7-dihydropyrazolo[1,5-a]pyrazine-3,5(4H)-dicarboxamide

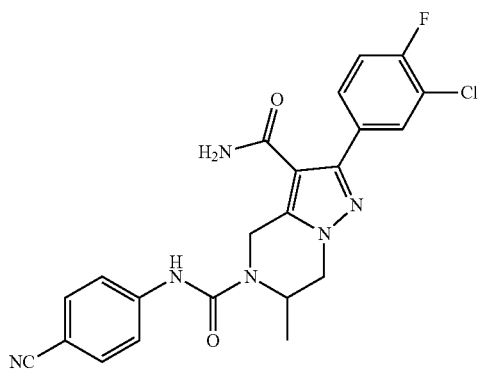 [SMILES: CC1Cn2nc(-c3ccc(F)c(Cl)c3)c(C(N)=O)c2CN1C(=O)Nc1ccc(C#N)cc1]

Compounds 329 and 330 were synthesized from Intermediate 329H using a synthetic sequence analogous to the preparation of Compound 297. Individual isomers were separated by chiral SFC purification (Column: CHIRALCEL® OD-H (4.6×250) mm, 5µ, Flow rate 4 ml/min; Isocratic: 40%, Mobile Phase B. Temperature: Ambient at 264 nm (Mobile Phase A: CO₂, Mobile Phase B: 0.3% diethylamine in methanol), Back pressure: 98 bar, Diluents: methanol).

Compound 329: (Elapsed time 2.52 min); MS(ES): m/z=453 [M+H]⁺. HPLC retention times 9.24 min. and 8.72 min (Methods A and B respectively). ¹H NMR (400 MHz, DMSO-d₆) δ ppm 9.33 (s, 1H), 7.84-7.98 (m, 1H), 7.63-7.76 (m, 5H), 7.25-7.50 (m, 3H), 5.27 (s, 1H), 4.86-5.00 (m, 1H), 4.60 (s, 1H), 4.08-4.32 (m, 2H), 1.23 (s, 3H).

Compound 330: (Elapsed time 3.42 min); MS(ES): m/z=453 [M+H]⁺. HPLC retention times 9.25 min. and 8.74 min (Methods A and B respectively). ¹H NMR (400 MHz, DMSO-d₆) δ ppm ¹H NMR (400 MHz, DMSO-d₆) δ ppm 9.33 (s, 1H), 7.84-7.98 (m, 1H), 7.63-7.76 (m, 5H), 7.25-7.50 (m, 3H), 5.27 (s, 1H), 4.86-5.00 (m, 1H), 4.60 (s, 1H), 4.08-4.32 (m, 2H), 1.23 (s, 3H).

Compounds 331 and 332: 2-(3-Chlorophenyl)-N⁵-(4-cyanophenyl)-6-methyl-6,7-dihydropyrazolo[1,5-a]pyrazine-3,5(4H)-dicarboxamide

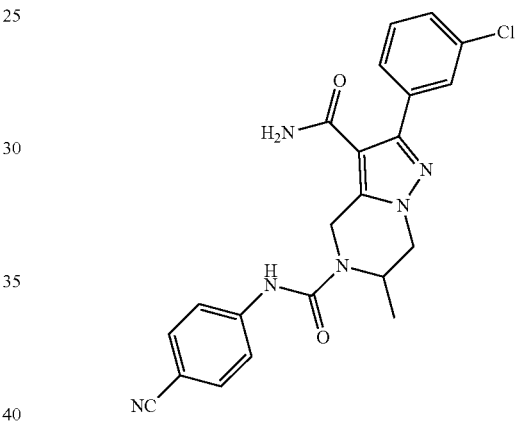

Compounds 331 and 332 were synthesized from Intermediate 329F using a synthetic sequence analogous to the preparation of Compound 330 using Suzuki coupling with 3,4-dichloroboronic acid followed by deprotection of N-Boc group and urea formation with 4-isocyanatobenzonitrile. Individual isomers were separated by chiral SFC purification (Column: CHIRALPAK® IC (250×4.6) mm, 5µ, Flow rate 3 ml/min; Isocratic: 40% Mobile Phase B. Temperature: Ambient at 264 nm (Mobile Phase A: CO₂, Mobile Phase B: 0.3% diethylamine in IPA), Back pressure: 100 bar, Diluents: isopropanol).

Compound 331: (Elapsed time 3.94 min); MS(ES): m/z=435 [M+H]⁺. HPLC retention times 8.66 min. and 9.26 min (Methods B and M respectively). ¹H NMR (400 MHz, DMSO-d₆) δ ppm 9.33 (s, 1H), 7.66-7.79 (m, 6H), 7.41-7.49 (m, 3H), 7.33 (br. s., 1H), 5.25 (d, J=17.57 Hz, 1H), 4.91-4.99 (m, 1H), 4.57 (d, J=17.57 Hz, 1H), 4.18-4.33 (m, 2H), 1.19-1.27 (m, 3H).

Compound 332: (Elapsed time 11.35 min); MS(ES): m/z=435 [M+H]⁺. HPLC retention times 8.66 min. and 9.26 min (Methods B and M respectively). ¹H NMR (400 MHz, DMSO-d₆) δ ppm 9.33 (s, 1H), 7.66-7.79 (m, 6H), 7.41-7.49 (m, 3H), 7.33 (br. s., 1H), 5.25 (d, J=17.57 Hz, 1H), 4.91-4.99 (m, 1H), 4.57 (d, J=17.57 Hz, 1H), 4.18-4.33 (m, 2H), 1.19-1.27 (m, 3H).

Compounds 333 and 334: N⁵-(4-Cyanophenyl)-2-(3,4-dichlorophenyl)-6-methyl-6,7-dihydropyrazolo[1,5-a]pyrazine-3,5(4H)-dicarboxamide

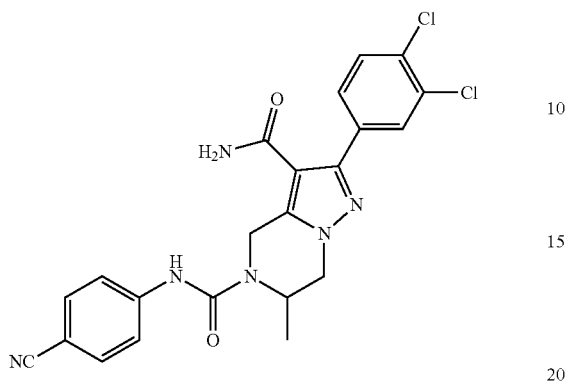

Compounds 333 and 334 were synthesized from Intermediate 329F using a synthetic sequence analogous to the preparation of Compound 330 using Suzuki coupling with 3,4-dichloroboronic acid followed by deprotection of N-Boc group and urea formation with 4-isocyanatobenzonitrile. The individual isomers were separated by chiral SFC separation (Column: CHIRALCEL® OJH (250×4.6) mm, 5 t, Flow rate 3 ml/min; Isocratic: 30% Mobile Phase B. Temperature: Ambient at 263 nm (Mobile Phase A: CO₂, Mobile Phase B: 0.3% diethylamine in methanol), Back pressure: 100 bar, Diluents: methanol).

Compound 333: (Elapsed time 3.53 min); MS(ES): m/z=469 [M+H]⁺. HPLC retention times 9.27 min. and 10.05 min (Methods B and A respectively). ¹H NMR (400 MHz, DMSO-d₆) δ ppm 9.32 (s, 1H), 7.95 (d, J=2.01 Hz, 1H), 7.64-7.76 (m, 6H), 7.42 (br. s., 2H), 5.24 (d, J=17.57 Hz, 1H), 4.88-5.00 (m, 1H), 4.57 (d, J=17.57 Hz, 1H), 4.12-4.32 (m, 2H), 1.18-1.24 (m, 3H).

Compound 334: (Elapsed time 4.15 min); MS(ES): m/z=469 [M+H]⁺. HPLC retention times 9.27 min. and 10.05 min (Methods B and A respectively). ¹H NMR (400 MHz, DMSO-d₆) δ ppm 9.32 (s, 1H), 7.95 (d, J=2.01 Hz, 1H), 7.64-7.76 (m, 6H), 7.42 (br. s., 2H), 5.24 (d, J=17.57 Hz, 1H), 4.88-5.00 (m, 1H), 4.57 (d, J=17.57 Hz, 1H), 4.12-4.32 (m, 2H), 1.18-1.24 (m, 3H).

Scheme 33

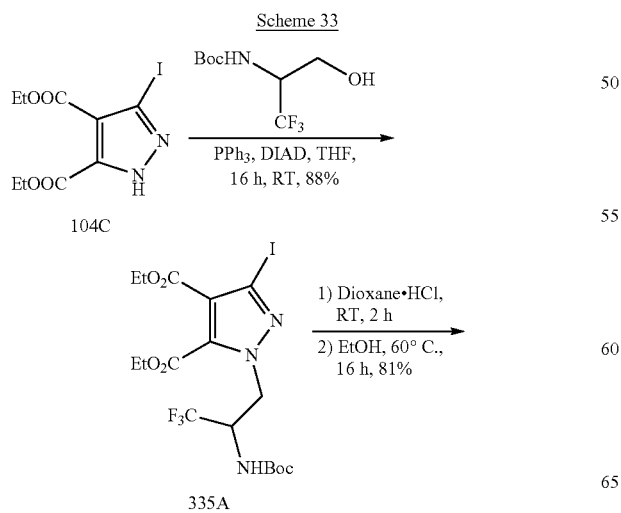

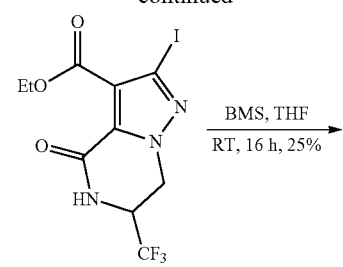

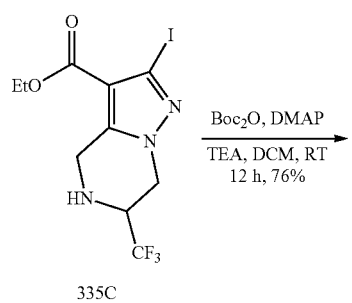

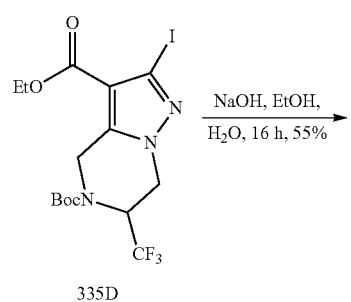

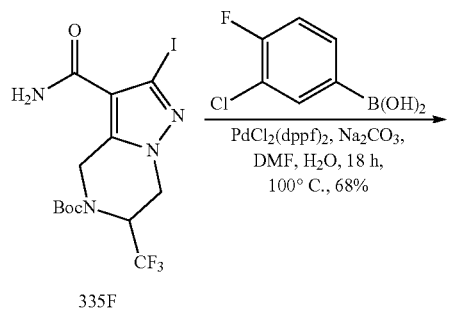

379
-continued

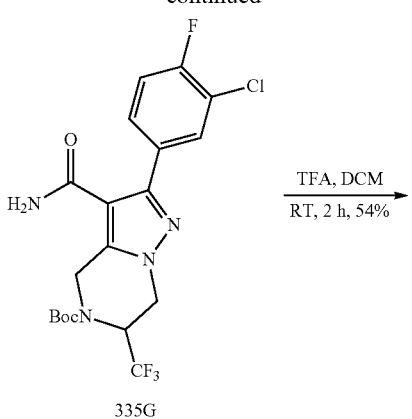

335G

→ TFA, DCM
RT, 2 h, 54%

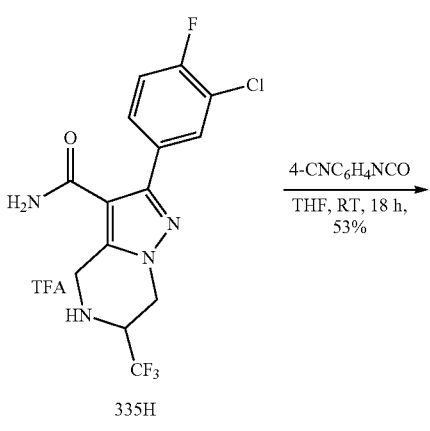

335H

→ 4-CNC₆H₄NCO
THF, RT, 18 h,
53%

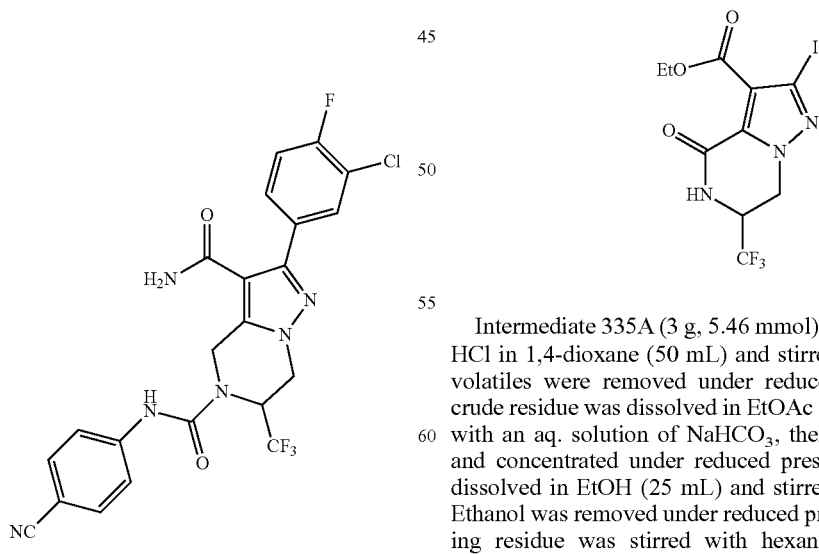

335 and 336

380

Intermediate 335A: Diethyl 1-(2-((Tert-butoxycarbonyl)amino)-3,3,3-trifluoropropyl)-3-iodo-1H-pyrazole-4,5-dicarboxylate

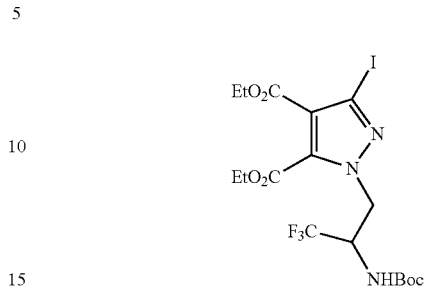

To a stirred solution of PPh₃ (3.10 g, 11.83 mmol) in THF (50 mL) was added DIAD (2.300 mL, 11.83 mmol) at 0° C. and the mixture stirred for 15 min prior to the addition of Intermediate 104C (2 g, 5.92 mmol) in THF (10 mL) which was allowed to stir for 15 min. A solution of tert-butyl(1,1,1-trifluoro-3-hydroxypropan-2-yl)carbamate (1.763 g, 7.69 mmol) in THF (10 mL) was then added and the solution was stirred at RT for 16 h. The reaction mixture was poured into water and extracted with EtOAc (2×100 mL). The combined organic layer was washed with brine, dried over anhydrous Na₂SO₄, filtered and the filtrate concentrated under reduced pressure. The crude compound was purified by silica gel chromatography (24 g REDISEP® column, eluting with 10% EtOAc in hexanes). Fractions containing the product were combined and evaporated to afford Intermediate 335A (3 g, 88%) as an oil. ¹H NMR (400 MHz, DMSO-d₆) δ ppm 7.94-7.84 (m, 1H), 4.87-4.80 (m, 1H), 4.79-4.67 (m, 1H), 4.40-4.31 (m, 3H), 4.30-4.21 (m, 2H), 1.33 (s, 9H), 1.30-1.25 (m, 6H).

Intermediate 335B: Ethyl 2-iodo-4-oxo-6-(trifluoromethyl)-4,5,6,7-tetrahydropyrazolo[1,5-a]pyrazine-3-carboxylate Intermediate 335A (3 g, 5.46 mmol) was dissolved in 4 M HCl in 1,4-dioxane (50 mL) and stirred at RT for 2 h. The volatiles were removed under reduced pressure, and the crude residue was dissolved in EtOAc (250 mL) and washed with an aq. solution of NaHCO₃, then dried over Na₂SO₄ and concentrated under reduced pressure. The crude was dissolved in EtOH (25 mL) and stirred at 60° C. for 16 h. Ethanol was removed under reduced pressure and the resulting residue was stirred with hexanes for 15 min. The triturated solid was filtered and dried to afford Intermediate 335B (0.96 g, 41.4%) as an off-white solid. MS(ES): −m/z=404.0 [M+H]⁺; ¹H NMR (400 MHz, DMSO-d₆) δ ppm 9.34 (d, J=4.5 Hz, 1H), 4.84-4.73 (m, 2H), 4.71-4.60 (m, 1H), 4.34-4.20 (m, 2H), 1.32-1.23 (m, 3H).

Intermediate 335C: Ethyl 2-iodo-6-(trifluoromethyl)-4,5,6,7-tetrahydropyrazolo[1,5-a]pyrazine-3-carboxylate

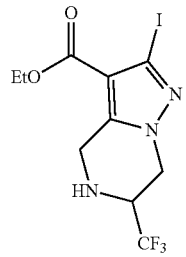 [SMILES: CCOC(=O)c1c(I)nn2c1CNC(C(F)(F)F)C2]

To a stirred solution of Intermediate 335B (0.1 g, 0.248 mmol) in THF (1 mL) was added BH$_3$.DMS complex (0.236 mL, 2.481 mmol) under nitrogen and the reaction mixture was stirred at RT for 16 h. The reaction mixture was then cooled to 0° C., quenched with methanol (1 mL) and stirred for 15 min at RT. The volatiles were removed under reduced pressure and the crude compound was purified by silica gel chromatography (12 g REDISEP® column, eluting with 25% EtOAc in hexanes). Fractions containing the product were combined and evaporated to afford Intermediate 335C as a white solid (0.025 g, 25%). MS(ES): −m/z=390.4 [M+H]$^+$; $^1$H NMR (400 MHz, DMSO-d$_6$) δ ppm 4.37-4.27 (m, 2H), 4.22 (q, J=7.4 Hz, 3H), 4.12-4.00 (m, 3H), 1.33-1.26 (m, 3H).

Intermediate 335D: 5-tert-Butyl 3-ethyl2-iodo-6-(trifluoromethyl)-6,7-dihydropyrazolo[1,5-a]pyrazine-3,5(4H)-dicarboxylate

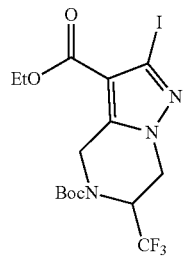 [SMILES: CCOC(=O)c1c(I)nn2c1CN(C(=O)OC(C)(C)C)C(C(F)(F)F)C2]

To a stirred solution of Intermediate 335C (0.025 g, 0.064 mmol) in DCM (5 mL) was added TEA (0.027 mL, 0.193 mmol) and DMAP (0.785 mg, 6.42 µmol), followed by Boc$_2$O (0.018 mL, 0.077 mmol) and the resulting solution was allowed to stir at RT for 12 h. The reaction mixture was then diluted with DCM (20 mL), washed with water, dried over anhydrous Na$_2$SO$_4$, filtered and the filtrate concentrated under reduced pressure. The crude compound was purified by silica gel chromatography (12 g REDISEP® column, eluting with 20% EtOAc in hexanes). Fractions containing the product were combined and evaporated to afford Intermediate 335D as a white solid (0.025 g, 76%). MS(ES): m/z=490.4 [M+H]$^+$; $^1$H NMR (400 MHz, DMSO-d$_6$) δ ppm 5.55-5.38 (m, 1H), 5.18-5.08 (m, 1H), 4.54 (br. s., 3H), 4.24 (d, J=7.0 Hz, 2H), 1.48 (s, 9H), 1.31 (t, J=7.3 Hz, 3H).

Intermediate 335E: 5-(tert-Butoxycarbonyl)-2-iodo-6-(trifluoromethyl)-4,5,6,7-tetrahydropyrazolo[1,5-a]pyrazine-3-carboxylic acid

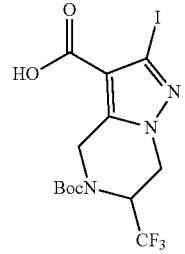

To a solution of Intermediate 335D (0.22 g, 0.450 mmol) in ethanol (2 mL) and water (2 mL) was added NaOH (0.036 g, 0.899 mmol) and the solution was stirred at RT for 16 h. The reaction mixture was concentrated under reduced pressure and the pH of the crude product was adjusted to 2 with an aqueous solution of 1.5N HCl and extracted with EtOAc (2×20 mL). The combined organic layer was dried over anhydrous Na$_2$SO$_4$, filtered and the filtrate concentrated under reduced pressure to afford Intermediate 335E as a white solid (0.12 g, 55%). MS(ES): m/z=462.4 [M+H]$^+$; $^1$H NMR (400 MHz, DMSO-d$_6$) δ ppm 12.4 (br, s., 1H), 5.55-5.38 (m, 1H), 5.18-5.08 (m, 1H), 4.54 (m, 3H), 1.48 (s, 9H).

Intermediate 335F: tert-Butyl 3-carbamoyl-2-iodo-6-(trifluoromethyl)-6,7-dihydropyrazolo[1,5-a]pyrazine-5(4H)-carboxylate

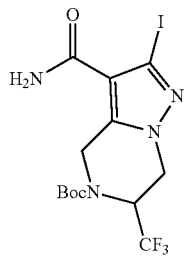 [SMILES: CC(C)(C)OC(=O)N1Cc2c(C(N)=O)c(I)nn2CC1C(F)(F)F]

To a solution of Intermediate 335E (0.12 g, 0.260 mmol) in DMF (1 mL) was added NH$_4$Cl (0.028 g, 0.520 mmol), HATU (0.099 g, 0.260 mmol) and DIPEA (0.136 mL, 0.781 mmol) under nitrogen and the resulting solution was stirred at RT for 16 h. The reaction mixture was poured into water and the aqueous layer was extracted with EtOAc (2×25 mL). The combined organic layers were dried over anhydrous Na$_2$SO$_4$ and concentrated under reduced pressure. The crude compound was purified by silica gel chromatography (12 g REDISEP® column, eluting with 3% MeOH in CHCl$_3$). Fractions containing the product were combined and evaporated to afford Intermediate 335F as a white solid (0.07 g, 50%). MS(ES): m/z=460.9 [M+H]$^+$.

Intermediate 335G: tert-Butyl 3-carbamoyl-2-(3-chloro-4-fluorophenyl)-6-(trifluoromethyl)-6,7-dihydropyrazolo[1,5-a]pyrazine-5(4H)-carboxylate

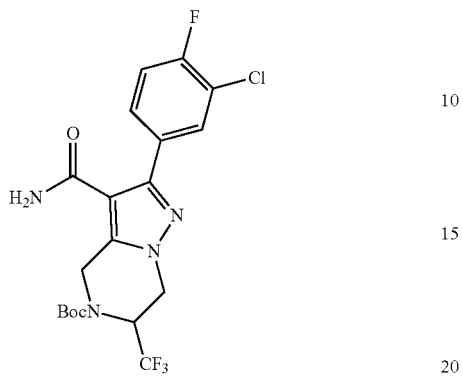

To a solution of Intermediate 335F (0.35 g, 0.761 mmol) and (3-chloro-4-fluorophenyl)boronic acid (0.215 g, 0.837 mmol) in DMF (2 mL) was added a solution of $Na_2CO_3$ (0.242 g, 2.282 mmol) in water (1 mL) and the reaction mixture was purged with nitrogen for 5 min. $Pd(PPh_3)_4$ (0.044 g, 0.038 mmol) was then added and the reaction mixture was stirred at 100° C. for 18 h. The reaction mixture was cooled to RT and extracted with EtOAc (2×50 mL). The combined organic layer was dried over anhydrous $Na_2SO_4$, filtered and the filtrate concentrated under reduced pressure. The crude compound was purified by silica gel chromatography (12 g REDISEP® column, eluting with 5% MeOH in $CHCl_3$). Fractions containing the product were combined and evaporated to afford Intermediate 335G as a white solid (0.25 g, 68%). MS(ES): m/z=464.5 [M+H]$^+$; $^1$H NMR (400 MHz, DMSO-$d_6$) δ ppm 7.92-7.82 (m, 1H), 7.73-7.67 (m, 1H), 7.65-7.52 (m, 1H), 7.51-7.44 (m, 1H), 7.41-7.21 (m, 2H), 5.17-5.05 (m, 1H), 4.65-4.48 (m, 3H), 1.50 (s, 9H).

Intermediate 335H: 2-(3-Chloro-4-fluorophenyl)-6-(trifluoromethyl)-4,5,6,7-tetrahydropyrazolo[1,5-a]pyrazine-3-carboxamide.TFA

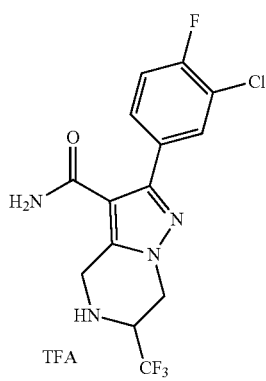 [SMILES: NC(=O)c1c(-c2ccc(F)c(Cl)c2)nn2c1CNC(C(F)(F)F)C2]

To a solution of Intermediate 335G (0.3 g, 0.648 mmol) in DCM (5 mL) was added TFA (0.499 mL, 6.48 mmol) under nitrogen and the resulting solution was stirred at RT for 2 h. The volatiles were removed under reduced pressure and the crude product was triturated with diethyl ether to afford Intermediate 335H as a white solid (0.21 g, 54%). MS(ES): m/z=363.4 [M+H]$^+$;

Compounds 335 and 336: 2-(3-Chloro-4-fluorophenyl)-$N^5$-(4-cyanophenyl)-6-(trifluoromethyl)-6,7-dihydropyrazolo[1,5-a]pyrazine-3,5(4H)-dicarboxamide

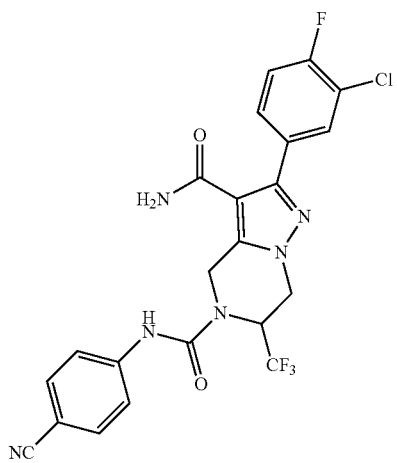 [SMILES: N#Cc1ccc(NC(=O)N2Cc3c(C(N)=O)c(-c4ccc(F)c(Cl)c4)nn3CC2C(F)(F)F)cc1]

Compounds 335 and 336 were synthesized from Intermediate 335H using a synthetic sequence analogous to the preparation of Compound 297. The individual isomers were separated by preparative chiral SFC purification (Column: CHIRALPAK® IC (250×4.6) mm, 54, Flow rate 3 ml/min; Isocratic: 30% Mobile Phase B. Temperature: Ambient at 267 nm (Mobile Phase A: $CO_2$, Mobile Phase B: 0.3% diethylamine in methanol), Back pressure: 100 bar, Diluents: methanol).

Compound 335 (19 mg, 24%); (Elapsed time 2.65 min); MS(ES): m/z=507.0 [M+H]$^+$; $^1$H NMR (400 MHz, DMSO-$d_6$) δ ppm 9.58 (s, 1H), 7.85-7.90 (m, 1H), 7.76 (br. s., 2H), 7.64-7.73 (m, 3H), 7.41-7.52 (m, 2H), 7.31 (br. s., 1H), 5.80 (br. s., 1H), 5.35 (d, J=17.07 Hz, 1H), 4.78 (d, J=18.57 Hz, 1H), 4.62 (br. s., 2H).

Compound 336 (23 mg, 29%); (Elapsed time 5.43 min); MS(ES): m/z=507.0 [M+H]$^+$; $^1$H NMR (400 MHz, DMSO-$d_6$) δ ppm 9.58 (s, 1H), 7.85-7.90 (m, 1H), 7.76 (br. s., 2H), 7.64-7.73 (m, 3H), 7.41-7.52 (m, 2H), 7.31 (br. s., 1H), 5.80 (br. s., 1H), 5.35 (d, J=17.07 Hz, 1H), 4.78 (d, J=18.57 Hz, 1H), 4.62 (br. s., 2H).

Compounds 337 and 338: 2-(3-Chlorophenyl)-N⁵-(4-cyanophenyl)-6-(trifluoromethyl)-6,7-dihydropyrazolo[1,5-a]pyrazine-3,5(4H)-dicarboxamide

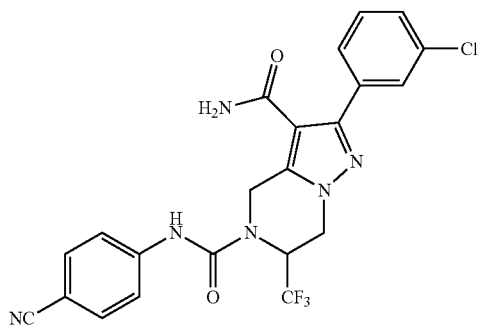

Compounds 337 and 338 were synthesized from Intermediate 335F using a synthetic sequence analogous to the preparation of Compound 335 using Suzuki coupling with 3-chloroboronic acid followed by deprotection of N-Boc group and urea formation with 4-isocyanatobenzonitrile. The individual isomers were separated by preparative chiral SFC (Column: CHIRALPAK® IC (250×4.6) mm, 5 t, Flow rate 3 ml/min; Isocratic: 40% Mobile Phase B. Temperature: Ambient at 267 nm (Mobile Phase A: $CO_2$, Mobile Phase B: 0.3% diethylamine in methanol), Back pressure: 100 bar, Diluents: methanol.

Compound 337: (Elapsed time 1.65 min); MS(ES): m/z=489.5 [M+H]⁺; ¹H NMR (400 MHz, DMSO-d₆) δ ppm 9.58 (s, 1H), 7.82-7.64 (m, 6H), 7.49-7.43 (m, 3H), 7.30 (br. s., 1H), 5.80 (d, J=9.0 Hz, 1H), 5.33 (d, J=17.1 Hz, 1H), 4.79 (d, J=17.1 Hz, 1H), 4.63 (br. s., 2H).

Compound 338: (Elapsed time 5.11 min): MS(ES): m/z=489.5 [M+H]⁺; ¹H NMR (400 MHz, DMSO-d₆) δ ppm 9.58 (s, 1H), 7.82-7.64 (m, 6H), 7.49-7.43 (m, 3H), 7.30 (br. s., 1H), 5.80 (d, J=9.0 Hz, 1H), 5.33 (d, J=17.1 Hz, 1H), 4.79 (d, J=17.1 Hz, 1H), 4.63 (br. s., 2H).

Compounds 339 and 340: N⁵-(4-Cyanophenyl)-2-(3,4-dichlorophenyl)-6-(trifluoromethyl)-6,7-dihydropyrazolo[1,5-a]pyrazine-3,5(4H)-dicarboxamide

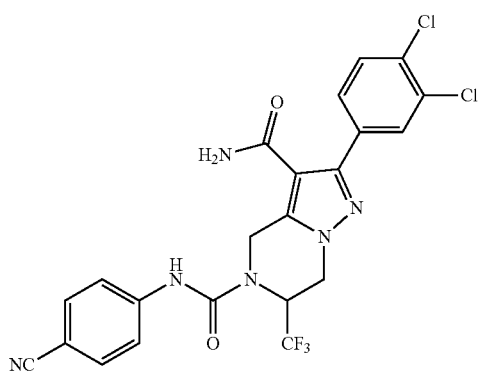

Compounds 339 and 340 were synthesized from Intermediate 335F using a synthetic sequence analogous to the preparation of Compound 335 using Suzuki coupling with 3,4-dichloroboronic acid followed by deprotection of N-Boc group and urea formation with 4-isocyanatobenzonitrile. The individual isomers were separated by preparative chiral SFC (Column: CHIRALPAK® IC (250×4.6) mm, 5 t, Flow rate 3 ml/min; Isocratic: 40%; Mobile Phase B. Temperature: Ambient at 267 nm (Mobile Phase A: $CO_2$, Mobile Phase B: 0.3% diethylamine in methanol), Back pressure: 100 bar, Diluents: methanol.

Compound 339: (Elapsed time 1.79 min); MS(ES): m/z=523.5 [M+H]⁺; ¹H NMR (400 MHz, DMSO-d₆) δ ppm 9.58 (s, 1H), 7.93 (s, 1H), 7.83-7.75 (m, 2H), 7.73-7.66 (m, 4H), 7.48 (br. s., 1H), 7.38 (br. s., 1H), 5.82 (br. s., 1H), 5.34 (d, J=17.1 Hz, 1H), 4.79 (d, J=17.1 Hz, 1H), 4.64 (br. s., 2H).

Compound 340: (Elapsed time 3.38 min); MS(ES): m/z=523.5 [M+H]⁺; ¹H NMR (400 MHz, DMSO-d₆) δ ppm 9.58 (s, 1H), 7.93 (s, 1H), 7.83-7.75 (m, 2H), 7.73-7.66 (m, 4H), 7.48 (br. s., 1H), 7.38 (br. s., 1H), 5.82 (br. s., 1H), 5.34 (d, J=17.1 Hz, 1H), 4.79 (d, J=17.1 Hz, 1H), 4.64 (br. s., 2H).

Scheme 34

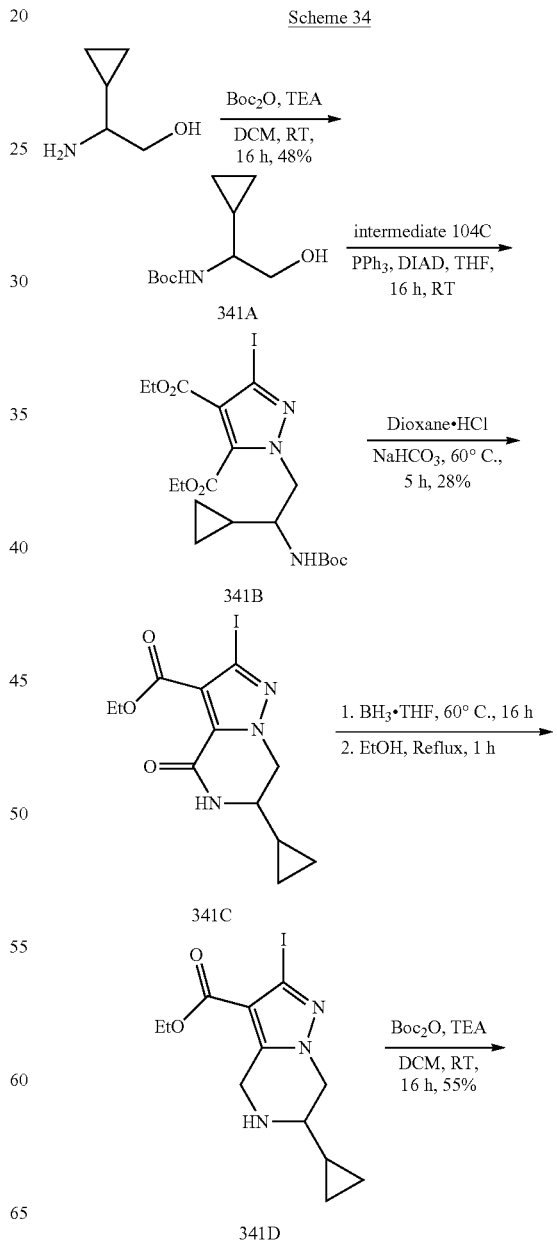

387
-continued

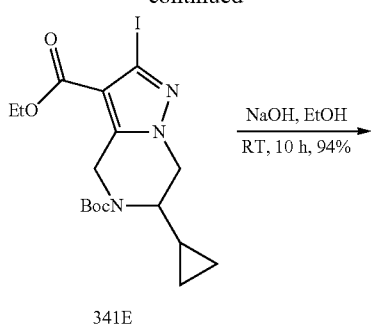

341E

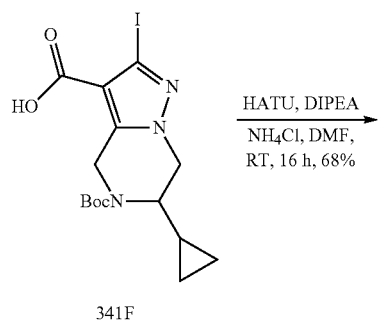

341F

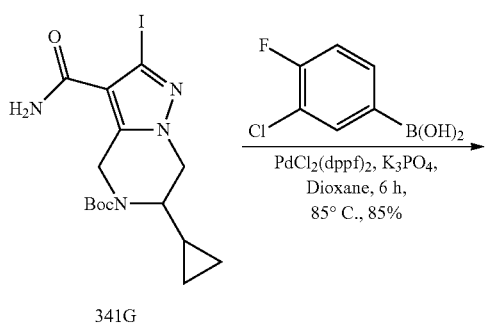

341G

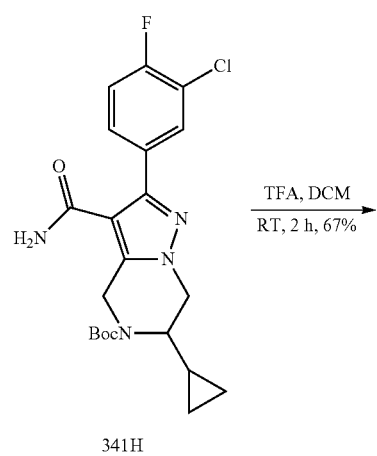

341H

388
-continued

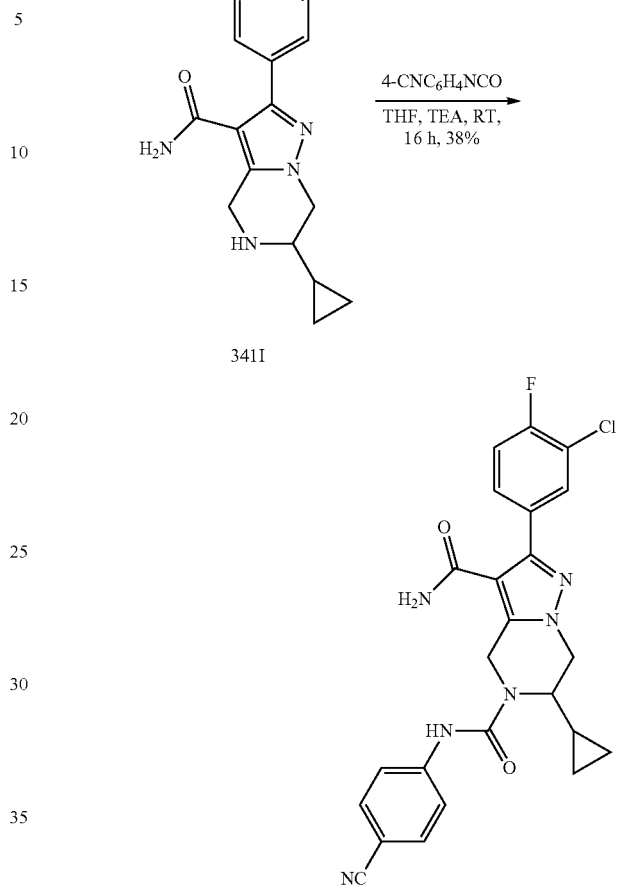

341I 341 and 342

Intermediate 341A:
tert-Butyl(1-cyclopropyl-2-hydroxyethyl)carbamate

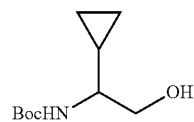

To a stirred solution of tert-butyl(1-cyclopropyl-2-hydroxyethyl)carbamate (6.5 g, 64.3 mmol) in DCM (10.0 mL) was added TEA (10.75 mL, 77 mmol), followed by Boc$_2$O (16.41 mL, 70.7 mmol) and the resulting solution was stirred at RT for 16 h. The reaction mixture was concentrated and the residue was extracted with DCM (50 mL). The organic layer was washed with water, brine, dried over Na$_2$SO$_4$, filtered and the filtrate concentrated under reduced pressure. The crude compound was purified by silica gel chromatography (120 g REDISEP® column, eluting with 20% EtOAc in hexanes). Fractions containing the product were combined and evaporated to afford Intermediate 341A as a colorless liquid (6.2 g, 48%). $^1$H NMR (400 MHz, DMSO-d$_6$) δ ppm 6.47 (d, J=7.03 Hz, 1H), 4.45-4.58 (m, 1H), 3.38-3.45 (m, 2H), 2.98 (br. s., 1H), 1.31-1.47 (m, 9H), 0.76-0.89 (m, 1H), 0.34-0.45 (m, 1H), 0.18-0.32 (m, 2H), 0.07-0.15 (m, 1H).

Intermediate 341B: Diethyl 1-(2-((Tert-butoxycarbonyl)amino)-2-cyclopropylethyl)-3-iodo-1H-pyrazole-4,5-dicarboxylate

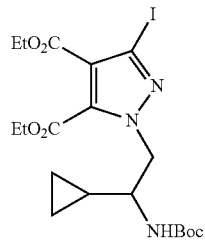 [SMILES: CCOC(=O)c1c(I)nn(CC(NC(=O)OC(C)(C)C)C2CC2)c1C(=O)OCC]

To a stirred solution of PPh₃ (15.52 g, 59.2 mmol) in THF (40.0 mL) cooled to −10° C. was added DIAD (11.50 mL, 59.2 mmol) and the resulting solution was stirred at 0° C. for 0.5 h. Intermediate 104C (10 g, 29.6 mmol) was added as a solution in THF (10 mL) at 0° C. and stirred at RT for 45 min. A solution of Intermediate 341A (7.74 g, 38.5 mmol) in THF (10 mL) at was added at 0° C. and the reaction mixture was allowed to stir at RT for 16 h. The reaction mixture was diluted with EtOAc (50 mL) washed with water and brine. The organic layer was dried over Na₂SO₄ and concentrated under reduced pressure. The crude compound was purified by silica gel chromatography (120 g REDISEP® column, eluting with 15% EtOAc in hexanes). Fractions containing the product were combined and evaporated to afford Intermediate 341B along with impurities arising from the coupling reagents (8.01 g, 84%); the crude material was taken to the next step without further purification. MS(ES): m/z=522 [M+H]⁺.

Intermediate 341C: Ethyl 6-cyclopropyl-2-iodo-4-oxo-4,5,6,7-tetrahydropyrazolo[1,5-a]pyrazine-3-carboxylate

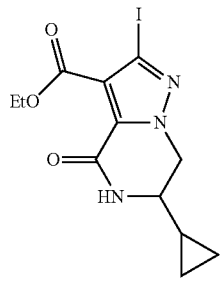 [SMILES: CCOC(=O)c1c(I)nn2c1C(=O)NC(C1CC1)C2]

To a stirred solution of Intermediate 341B (8.0 g, 15.34 mmol) in 1,4-dioxane (10.0 mL) was added 4 M HCl in dioxane (40.0 mL, 160 mmol) and the resulting solution was stirred at RT for 2 h. The reaction mixture was concentrated and diluted with EtOAc (50 mL). The organic layer was washed successively with water, a saturated aq. solution of NaHCO₃, and brine, then dried over Na₂SO₄, filtered and the filtrate concentrated under reduced pressure. The residue obtained was heated in a ROTAVAPOR® at 60° C. for 5 h. The solid product was triturated with diethyl ether to afford Intermediate 341C as an off-white solid (1.6 g, 28%). MS(ES): m/z=376 [M+H]⁺; ¹H NMR (300 MHz, DMSO-d₆) δ ppm 8.67 (d, J=2.27 Hz, 1H), 4.47 (dd, J=13.22, 4.53 Hz, 1H), 4.17-4.33 (m, 3H), 3.15 (d, J=9.07 Hz, 1H), 1.28 (s, 3H), 0.90 (d, J=8.69 Hz, 1H), 0.40-0.54 (m, 2H), 0.20-0.37 (m, 2H).

Intermediate 341D: Ethyl 6-cyclopropyl-2-iodo-4,5,6,7-tetrahydropyrazolo[1,5-a]pyrazine-3-carboxylate

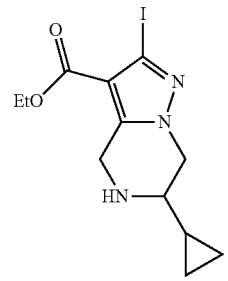 [SMILES: CCOC(=O)c1c(I)nn2c1CNC(C1CC1)C2]

To a solution of Intermediate 341C (1.3 g, 3.47 mmol) in THF (10 mL) was added BH₃.THF (6.06 mL, 12.13 mmol, 1 M in THF) and the resulting solution was stirred at 60° C. for 16 h. The reaction mixture was quenched with ethanol (10 mL) and heated to reflux for 1 h. The reaction mixture was concentrated under reduced pressure to afford crude Intermediate 341D (1.2 g), which was taken to the next step without further purification. MS(ES): m/z=362 [M+H]⁺.

Intermediate 341E: 5-tert-Butyl 3-ethyl6-cyclopropyl-2-iodo-6,7-dihydropyrazolo[1,5-a]pyrazine-3,5(4H)-dicarboxylate

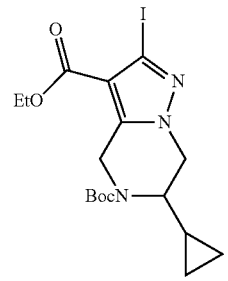 [SMILES: CCOC(=O)c1c(I)nn2c1CN(C(=O)OC(C)(C)C)C(C1CC1)C2]

To a solution of Intermediate 341D (1.2 g, 3.32 mmol) in DCM (10.0 mL) was added TEA (0.556 mL, 3.99 mmol), followed by Boc₂O (0.849 mL, 3.65 mmol) and the solution was stirred at RT for 16 h. The reaction mixture was diluted with DCM (15 mL) and the organic layer was washed with water, brine, dried over Na₂SO₄, filtered and the filtrate concentrated. The crude compound was purified by silica gel chromatography (24 g REDISEP® column, eluting with 25% EtOAc in hexane). Fractions containing the product were combined and evaporated to afford the Intermediate 341E as a colorless semi-solid (0.85 g, 55%). MS(ES): m/z=462 [M+H]⁺; ¹H NMR (300 MHz, DMSO-d₆) δ ppm 5.13 (d, J=18.89 Hz, 1H), 4.48 (d, J=18.89 Hz, 1H), 4.13-4.31 (m, 4H), 3.84 (br. s., 1H), 1.38-1.47 (m, 9H), 1.31 (s, 3H), 0.84-0.96 (m, 1H), 0.46 (d, J=8.31 Hz, 2H), 0.38 (d, J=4.91 Hz, 2H).

Intermediate 341F: 5-(tert-Butoxycarbonyl)-6-cyclopropyl-2-iodo-4,5,6,7-tetrahydropyrazolo[1,5-a]pyrazine-3-carboxylic acid

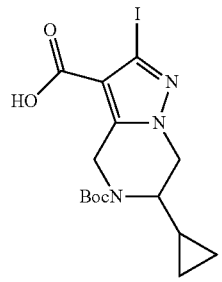 [SMILES: CC(C)(C)OC(=O)N1Cc2c(C(=O)O)c(I)nn2CC1C1CC1]

To a stirred solution of Intermediate 341E (0.85 g, 1.843 mmol) in ethanol (2 mL) and water (1 mL) was added NaOH (0.369 g, 9.21 mmol) and the resulting solution was stirred at RT for 10 h. The reaction mixture was diluted with DCM (10 mL) and washed successively with an aqueous solution of 1N HCl, water and brine. The organic layer was then dried over $Na_2SO_4$, filtered and the filtrate concentrated under reduced pressure to afford the Intermediate 341F as an off-white solid (0.75 g, 94%). MS(ES): m/z=434 [M+H]$^+$; $^1$H NMR (300 MHz, DMSO-$d_6$) δ 8 ppm 12.6 (br. s., 1H), 5.11 (d, J=18.89 Hz, 1H), 4.45 (d, J=18.51 Hz, 1H), 4.16-4.25 (m, 2H), 3.82 (br. s., 1H), 1.43 (s, 9H), 0.82-0.96 (m, 1H), 0.47 (d, J=7.93 Hz, 2H), 0.35 (dd, J=6.80, 4.91 Hz, 2H).

Intermediate 341G: tert-Butyl 3-carbamoyl-6-cyclopropyl-2-iodo-6,7-dihydropyrazolo[1,5-a]pyrazine-5(4H)-carboxylate

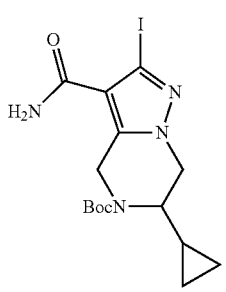 [SMILES: CC(C)(C)OC(=O)N1Cc2c(C(N)=O)c(I)nn2CC1C1CC1]

To a stirred solution of Intermediate 341F (0.75 g, 1.731 mmol) in DMF (4.0 mL) was added $NH_4Cl$ (0.463 g, 8.66 mmol), HATU (1.316 g, 3.46 mmol) and DIPEA (1.512 mL, 8.66 mmol) and the resulting solution was stirred at RT for 16 h. The reaction mixture was diluted with ethyl acetate (10 mL), washed with water and brine. The organic layer was dried over $Na_2SO_4$, filtered and the filtrate concentrated under reduced pressure. The crude compound was purified by silica gel chromatography (24 g REDISEP® column, eluting with 65% EtOAc in hexanes). Fractions containing the product were combined and evaporated to afford Intermediate 341G as a colorless liquid (0.51 g, 68%). MS(ES): m/z=433 [M+H]$^+$; $^1$H NMR (300 MHz, DMSO-$d_6$) δ ppm 6.83-7.50 (m, 2H), 5.07 (d, J=18.13 Hz, 1H), 4.50 (d, J=18.51 Hz, 1H), 4.20 (d, J=2.27 Hz, 2H), 3.84 (br. s., 1H), 1.43 (s, 9H), 0.89 (d, J=9.82 Hz, 1H), 0.47 (d, J=7.93 Hz, 2H), 0.27-0.40 (m, 2H).

Intermediate 341H: tert-Butyl 3-carbamoyl-2-(3-chloro-4-fluorophenyl)-6-cyclopropyl-6,7-dihydropyrazolo[1,5-a]pyrazine-5(4H)-carboxylate

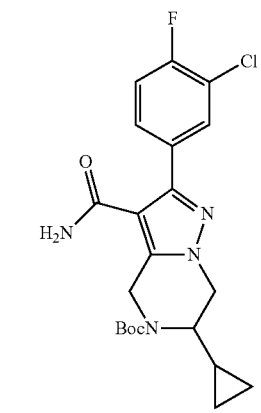 [SMILES: CC(C)(C)OC(=O)N1Cc2c(C(N)=O)c(-c3ccc(F)c(Cl)c3)nn2CC1C1CC1]

To a stirred suspension of Intermediate 341G (0.47 g, 1.087 mmol) in 1,4-dioxane (5 mL) was added $K_3PO_4$ (1.631 mL, 3.26 mmol), (3-chloro-4-fluorophenyl)boronic acid (0.246 g, 1.414 mmol) and the reaction mixture was purged with nitrogen for 10 min. $PdCl_2$(dppf)-$CH_2Cl_2$ (0.053 g, 0.065 mmol) was then added and the reaction mixture was heated to 80° C. and stirred for 6 h. The reaction mixture was filtered through CELITE® and the filtrate was diluted with ethyl acetate (10 mL), and washed with water and brine. The organic layer was dried over $Na_2SO_4$, filtered and the filtrate concentrated under reduced pressure. The crude compound was purified by silica gel chromatography (12 g REDISEP® column, eluting with 2% MeOH in $CHCl_3$). Fractions containing the product were combined and evaporated to afford Intermediate 341H as an off-white solid (0.4 g, 85%). MS(ES): m/z=435 [M+H]$^+$; $^1$H NMR (300 MHz, DMSO-$d_6$) δ ppm 7.85-7.95 (m, 1H), 7.66-7.77 (m, 1H), 7.47 (t, J=9.07 Hz, 1H), 7.20-7.39 (m, 2H), 5.05 (d, J=17.37 Hz, 1H), 4.55 (d, J=17.37 Hz, 1H), 4.24 (br. s., 2H), 3.89 (br. s., 1H), 1.45 (s, 9H), 0.87-1.05 (m, 1H), 0.31-0.55 (m, 4H).

Intermediate 3411: 2-(3-Chloro-4-fluorophenyl)-6-cyclopropyl-4,5,6,7-tetrahydropyrazolo[1,5-a]pyrazine-3-carboxamide

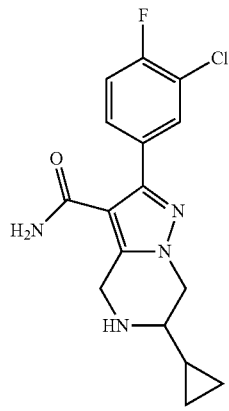 [SMILES: NC(=O)c1c(-c2ccc(F)c(Cl)c2)nn2c1CNC(C1CC1)C2]

To a stirred solution of Intermediate 341H (0.43 g, 0.989 mmol) in DCM (8.0 mL) was added TFA (4.0 mL, 51.9 mmol) and the resulting solution was stirred at RT for 2 h. The reaction mixture was concentrated and the residue was extracted with DCM (10 mL), and washed successively with water, a saturated aq. NaHCO$_3$ solution and brine.

The organic layer was dried over Na$_2$SO$_4$, filtered and the filtrate concentrated under reduced pressure to afford Intermediate 3411 as an off-white solid (0.3 g, 67%). MS(ES): m/z=335 [M+H]$^+$; $^1$H NMR (400 MHz, DMSO-d$_6$) δ ppm 7.80-7.91 (m, 1H), 7.64-7.70 (m, 1H), 7.35-7.50 (m, 1H), 7.02-7.29 (m, 2H), 4.12-4.25 (m, 2H), 3.93 (d, J=16.56 Hz, 1H), 3.68-3.81 (m, 2H), 2.40 (br. s., 1H), 0.82-0.98 (m, 1H), 0.48 (d, J=8.03 Hz, 2H), 0.37 (d, J=5.02 Hz, 2H).

Compounds 341 and 342: 2-(3-Chloro-4-fluorophenyl)-6-cyclopropyl-N$^5$-(3,3-difluoro-1-methylcyclobutyl)-6,7-dihydropyrazolo[1,5-a]pyrazine-3,5(4H)-dicarboxamide

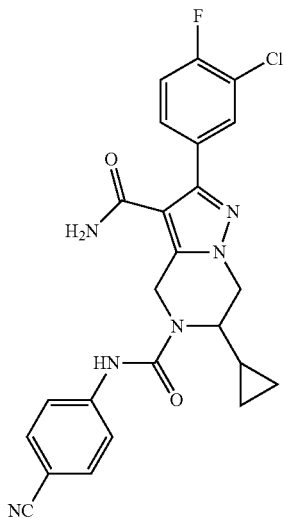 [SMILES: N#Cc1ccc(NC(=O)N2Cc3c(C(N)=O)c(-c4ccc(F)c(Cl)c4)nn3CC2C2CC2)cc1]

Compounds 341 and 342 were synthesized from Intermediate 3411 using a synthetic sequence analogous to the preparation of Compound 297. The individual isomers were separated by preparative chiral SFC purification (Column: CHIRALPAK® IC (4.6×250) mm, 5μ, Flow rate: 4 ml/min; Isocratic: 35%; Mobile Phase B. Temperature: Ambient at 267 nm (Mobile Phase A: CO$_2$, Mobile Phase B: 0.2% diethylamine in methanol).

Compound 341: Elapsed at 5.26 min; HPLC retention times 10.33 min. and 9.39 min. (Methods M and B). MS(ES): m/z=479 [M+H]$^+$; $^1$H NMR (400 MHz, DMSO-d$_6$) δ ppm 9.31 (s, 1H), 7.91 (dd, J=7.28, 2.26 Hz, 1H), 7.69-7.76 (m, 3H), 7.61-7.67 (m, 2H), 7.33-7.51 (m, 3H), 5.26 (d, J=17.57 Hz, 1H), 4.73 (d, J=17.57 Hz, 1H), 4.31 (d, J=2.51 Hz, 2H), 4.11 (d, J=9.54 Hz, 1H), 1.04-1.15 (m, 1H), 0.35-0.61 (m, 4H).

Compound 342: Elapsed at 9.02 min; HPLC retention times 10.33 min. and 9.39 min. (Methods M and B). MS(ES): m/z=479 [M+H]$^+$; $^1$H NMR (400 MHz, DMSO-d$_6$) δ ppm 9.31 (s, 1H), 7.91 (dd, J=7.28, 2.26 Hz, 1H), 7.69-7.76 (m, 3H), 7.61-7.67 (m, 2H), 7.33-7.51 (m, 3H), 5.26 (d, J=17.57 Hz, 1H), 4.73 (d, J=17.57 Hz, 1H), 4.31 (d, J=2.51 Hz, 2H), 4.11 (d, J=9.54 Hz, 1H), 1.04-1.15 (m, 1H), 0.35-0.61 (m, 4H).

Scheme 35

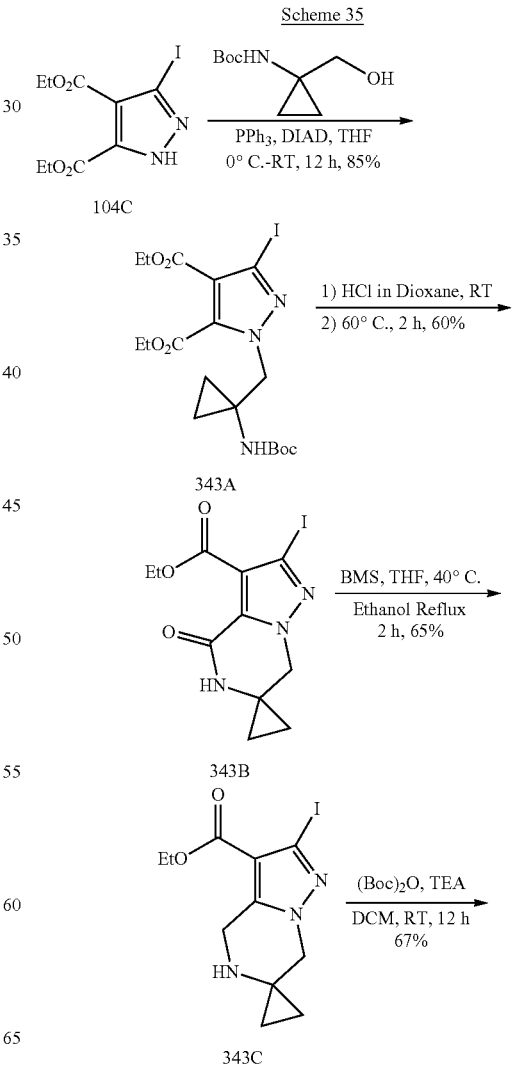

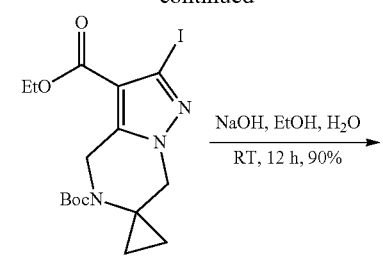

343D

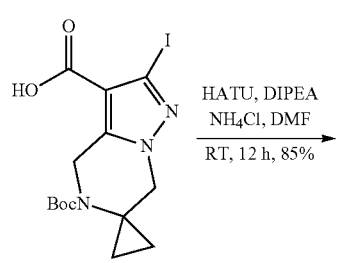

343E

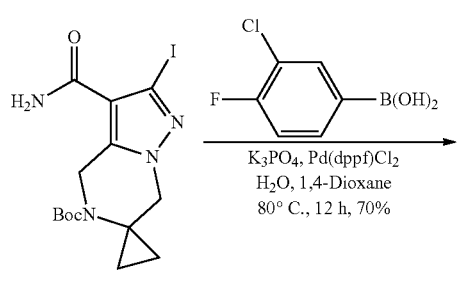

343F

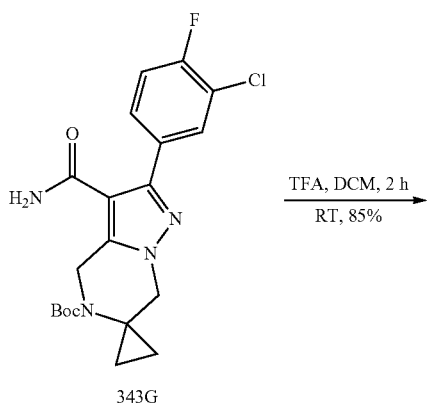

343G

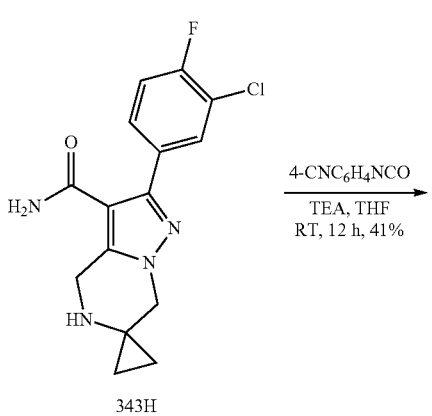

343H

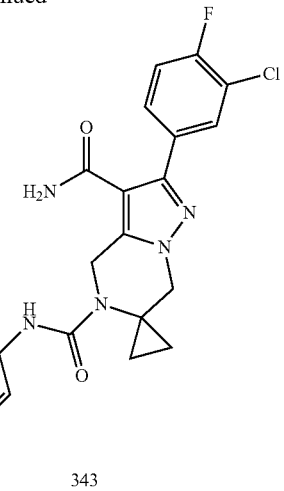

343

Intermediate 343A: Diethyl 1-((1-((Tert-Butoxycarbonyl)amino)cyclopropyl)methyl)-3-iodo-1H-pyrazole-4,5-dicarboxylate

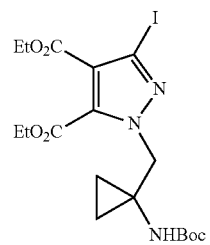

To a stirred solution of PPh$_3$ (15.52 g, 59.2 mmol) in THF (80.0 mL) cooled to 0° C. was added DIAD (11.50 mL, 59.2 mmol) and the resulting solution was stirred at 0° C. for 0.5 h. Intermediate 104C (8.00 g, 23.66 mmol) was added as a solution in THF (20 mL) at 0° C. and stirred at RT for 45 min. A solution of tert-butyl(1-(hydroxymethyl)cyclopropyl)carbamate (5.32 g, 28.4 mmol) in THF (10 mL) was added at 0° C. and the reaction mixture was allowed to stir at RT for 16 h. The reaction mixture was diluted with water (250 mL) and extracted with EtOAc (2×200 mL). The combined organic layer was washed with brine, dried over Na$_2$SO$_4$, filtered and concentrated. The crude product was purified by silica gel chromatography (220 g REDISEP® column, eluting with 20% EtOAc in hexane). Fractions containing the product were combined and evaporated to afford Intermediate 343A as a pale yellow liquid (10 g, 85%). MS(ES): m/z=508 [M+H]$^+$; $^1$H NMR (400 MHz, chloroform-d) δ ppm 4.45 (s, 2H), 4.41-4.25 (m, 4H), 1.46 (s, 9H), 1.40-1.30 (m, 4H), 1.24 (s, 3H), 1.03-0.94 (m, 2H), 0.90-0.78 (m, 2H).

Intermediate 343B: Ethyl 2'-iodo-4'-oxo-5',7'-di-hydro-4'H-spiro[cyclopropane-1,6'-pyrazolo[1,5-a]pyrazine]-3'-carboxylate

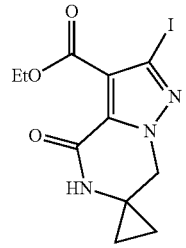 [SMILES: CCOC(=O)c1c(I)nn2c1C(=O)NC1(CC1)C2]

To a stirred solution of Intermediate 343A (2.1 g, 4.14 mmol) in 1,4-dioxane (10.0 mL) was added 4 M HCl in dioxane (10 mL, 41 mmol) and the resulting solution was stirred at RT for 1 h. The reaction mixture was concentrated and diluted with EtOAc (50 mL). The organic layer was washed successively with water, a saturated aq. solution of NaHCO$_3$, and brine, then dried over Na$_2$SO$_4$, filtered and the filtrate concentrated under reduced pressure. The residue obtained was heated in a ROTAVAPOR® at 60° C. for 5 h. The solid product was triturated with diethyl ether to afford Intermediate 343B as a pale yellow solid (1.1 g, 60%). MS(ES): m/z=362 [M+H]$^+$; $^1$H NMR (400 MHz, chloroform-d) δ ppm 6.93 (s, 1H), 4.41 (q, J=7.0 Hz, 2H), 4.26 (s, 2H), 1.41 (t, J=7.0 Hz, 3H), 1.11-0.85 (m, 4H).

Intermediate 343C: Ethyl 2'-iodo-5',7'-dihydro-4'H-spiro[cyclopropane-1,6'-pyrazolo[1,5-a]pyrazine]-3'-carboxylate

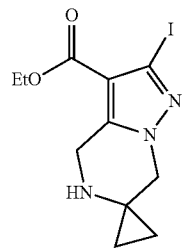

To a solution of Intermediate 343B (1.1 g, 3.05 mmol) in THF (10 mL) was added BH$_3$.DMS (0.578 mL, 6.09 mmol, 2M) and the resulting solution was stirred at 40 OC for 18 h. The reaction mixture was cooled to RT, quenched with ethanol (10 mL) and heated to reflux for 1 h. The reaction mixture was concentrated under reduced pressure. The crude product was purified by silica gel chromatography (24 g REDISEP® column, eluting with 2% MeOH in CHCl$_3$). Fractions containing the product were combined and evaporated to afford Intermediate 343C (0.7 g, 66%) as a gummy solid. MS(ES): m/z=348 [M+H]$^+$. $^1$H NMR (400 MHz, chloroform-d) δ ppm 4.41 (q, J=7.0 Hz, 2H), 3.92 (s, 1H), 1.38 (m, 4H), 1.36 (t, J=7.0 Hz, 3H), 0.90 (m, 2H), 0.68 (m, 2H).

Intermediate 343D: 5'-tert-Butyl 3'-ethyl2'-iodo-4'H-spiro[cyclopropane-1,6'-pyrazolo[1,5-a]pyrazine]-3',5'(7'H)-dicarboxylate

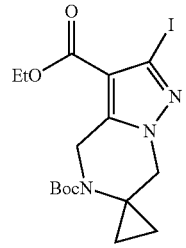 [SMILES: CCOC(=O)c1c(I)nn2c1CN(C(=O)OC(C)(C)C)C1(CC1)C2]

To a solution of Intermediate 343C (0.70 g, 2.016 mmol) in DCM (10.0 mL) was added TEA (0.281 mL, 2.016 mmol), followed by Boc$_2$O (0.702 mL, 3.02 mmol) and the solution was stirred at RT for 16 h. The reaction mixture was diluted with DCM (25 mL) and the organic layer was washed with water, brine, dried over Na$_2$SO$_4$, filtered and the filtrate concentrated. The crude product was purified by silica gel chromatography (24 g REDISEP® column, eluting with 30% EtOAc in petroleum ether). Fractions containing the product were combined and evaporated to afford Intermediate 343D as an off-white solid (0.6 g, 67%). MS(ES): m/z=448 [M+H]$^+$; $^1$H NMR (400 MHz, chloroform-d) 6 ppm 4.88 (br. s., 2H), 4.33 (q, J=7.0 Hz, 2H), 4.03 (br. s., 2H), 1.48 (m, 9H), 1.41 (t, J=7.0 Hz, 3H), 1.17 (m, 2H), 0.97-0.85 (m, 2H).

Intermediate 343E: 5'-(tert-Butoxycarbonyl)-2'-iodo-5',7'-dihydro-4'H-spiro[cyclopropane-1,6'-pyrazolo[1,5-a]pyrazine]-3'-carboxylic acid

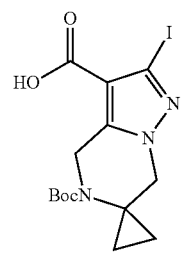 [SMILES: CC(C)(C)OC(=O)N1Cc2c(C(=O)O)c(I)nn2CC12CC2]

To a stirred solution of Intermediate 343D (0.500 g, 1.118 mmol) in ethanol (10 mL) and water (1 mL) was added NaOH (0.369 g, 9.21 mmol) and the resulting solution was stirred at RT for 12 h. The volatiles were removed under reduced pressure and the residue was acidified with an aqueous solution of 1.5 N HCl. The solid product separated was filtered through a Buchner funnel and dried under vacuum to afford Intermediate 343E as a white solid (0.43 g, 90%). MS(ES): m/z=420 [M+H]$^+$; $^1$H NMR (400 MHz, chloroform-d) δ ppm 6.19 (br. s., 1H), 4.92 (br. s., 2H), 4.06 (br. s., 2H), 1.48 (s, 9H), 1.19 (br. s., 2H), 1.01-0.83 (m, 2H).

Intermediate 343F: tert-Butyl 3'-carbamoyl-2'-iodo-4'H-spiro[cyclopropane-1,6'-pyrazolo[1,5-a]pyrazine]-5'(7'H)-carboxylate

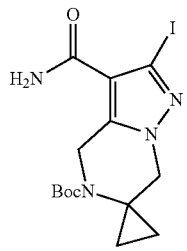 [SMILES: CC(C)(C)OC(=O)N1Cc2c(C(N)=O)c(I)nn2CC12CC2]

To a stirred solution of Intermediate 343E (0.43 g, 1.026 mmol) in DMF (4 mL) was added $NH_4Cl$ (0.274 g, 5.13 mmol), HATU (0.780 g, 2.051 mmol) and DIPEA (0.537 mL, 3.08 mmol) and the resulting solution was stirred at RT for 16 h. The reaction mixture was diluted with water (50 mL) and extracted with EtOAc (3×25 mL). The combined organic layer was washed with brine, dried over $Na_2SO_4$, filtered and the filtrate concentrated. The residue was triturated with diethyl ether, filtered and dried to afford Intermediate 343F as an off-white solid (0.4 g, 89%). MS(ES): m/z=419 [M+H]$^+$; $^1$H NMR (400 MHz, chloroform-d) δ ppm 6.56 (br. s., 1H), 5.54 (br. s., 1H), 4.96 (br. s., 2H), 4.04 (br. s., 2H), 1.44 (s, 9H), 1.18 (m, 2H), 0.97-0.84 (m, 2H).

Intermediate 343G: tert-Butyl 3'-carbamoyl-2'-(3-chloro-4-fluorophenyl)-4'H-spiro[cyclopropane-1,6'-pyrazolo[1,5-a]pyrazine]-5'(7'H)-carboxylate

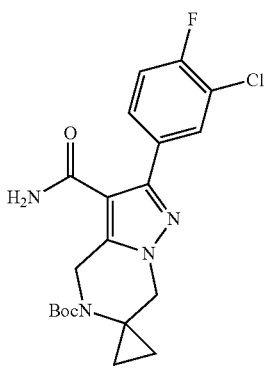 [SMILES: CC(C)(C)OC(=O)N1Cc2c(C(N)=O)c(-c3ccc(F)c(Cl)c3)nn2CC12CC2]

To a stirred suspension of Intermediate 343F (0.400 g, 0.956 mmol) in 1,4-dioxane (5 mL) was added $K_3PO_4$ (0.500 g, 2.80 mmol), (3-chloro-4-fluorophenyl) boronic acid (0.250 g, 1.435 mmol) and the reaction mixture was purged with nitrogen for 10 min. $PdCl_2(dppf)-CH_2Cl_2$ (0.047 g, 0.057 mmol) was then added and the reaction mixture was heated to 80° C. and stirred for 12 h. The reaction mixture was diluted with water (25 mL) and extracted with EtOAc (3×25 mL). The combined organic layers were washed with brine, dried over $Na_2SO_4$, filtered and the filtrate concentrated. The crude product was purified by silica gel chromatography (24 g REDISEP® column, eluting with 3% MeOH in $CHCl_3$) Fractions containing the product were combined and evaporated to afford Intermediate 343G as a pale yellow solid (0.29 g, 70%). MS(ES): m/z=421 [M+H]$^+$; $^1$H NMR (400 MHz, chloroform-d) δ ppm 7.69 (dd, J=7.0, 2.3 Hz, 1H), 7.50 (ddd, J=8.5, 4.6, 2.1 Hz, 1H), 7.33-7.15 (m, 1H), 5.34 (br. s., 2H), 4.97 (br. s., 2H), 4.05 (br. s., 2H), 1.44 (s, 9H), 1.22-1.24 (m, 2H), 1.02-0.79 (m, 2H).

Intermediate 343H: 2'-(3-Chloro-4-fluorophenyl)-5',7'-dihydro-4'H-spiro[cyclopropane-1,6'-pyrazolo[1,5-a]pyrazine]-3'-carboxamide

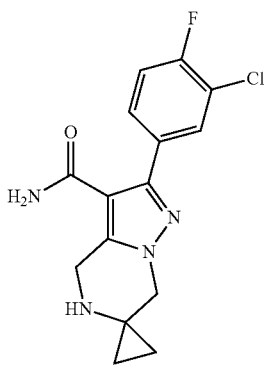 [SMILES: NC(=O)c1c(-c2ccc(F)c(Cl)c2)nn2c1CNC1(CC1)C2]

To a solution of Intermediate 343G (0.29 g, 0.689 mmol) in DCM (5 mL) was added TFA (3 mL) and the resulting solution was stirred at RT for 2 h. The volatiles were removed under reduced pressure. The residue was basified with a 10% aqueous solution of $NaHCO_3$ and extracted with EtOAc (3×20 mL). The combined organic layer was washed with brine, dried over $Na_2SO_4$, filtered and the filtrate concentrated to afford Intermediate 343H as a yellow solid (0.2 g, 85%). MS(ES): m/z=321 [M+H]$^+$; $^1$H NMR (300 MHz, chloroform-d) δ ppm 7.71 (dd, J=7.2, 2.3 Hz, 1H), 7.51 (ddd, J=8.3, 4.5, 2.3 Hz, 1H), 7.33-7.11 (m, 1H), 5.33 (br. s., 2H), 4.40 (s, 2H), 4.03 (s, 2H), 1.02-0.88 (m, 2H), 0.80-0.59 (m, 2H).

Compound 343: 2'-(3-Chloro-4-fluorophenyl)-N$^5$'-(4-cyanophenyl)-4'H-spiro[cyclopropane-1,6'-pyrazolo[1,5-a]pyrazine]-3',5'(7'H)-dicarboxamide

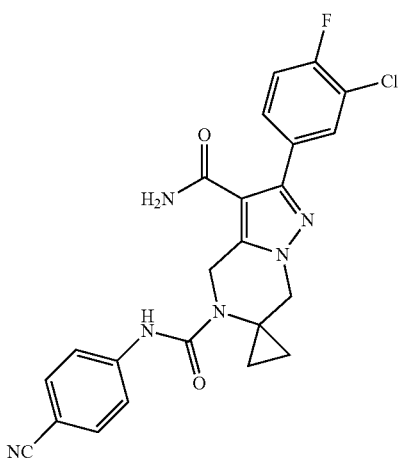 [SMILES: N#Cc1ccc(NC(=O)N2Cc3c(C(N)=O)c(-c4ccc(F)c(Cl)c4)nn3CC23CC3)cc1]

Compound 343 was synthesized from Intermediate 343H using a synthetic sequence analogous to the preparation of Compound 297. HPLC retention times 9.16 min. and 8.83 min. (Methods A and B). MS(ES): m/z=465 [M+H]+; 1H NMR (400 MHz, DMSO-d6) δ ppm 9.11 (s, 1H), 7.86 (dd, J=7.31, 2.16 Hz, 1H), 7.66-7.73 (m, 5H), 7.45 (t, J=9 Hz, 1H), 7.35 (br.s, 1H), 7.23 (br.s, 1H), 4.92 (br.s, 2H), 4.25 (br.s, 2H), 1.16 (s, 4H).

The Compounds shown in Table 28 have been prepared similar to Compound 343 by coupling of Intermediate 343H with various readily available isocyanates or in-situ generated from respective anilines.

TABLE 28

| Ex. No. | Structure | Name | [M + H]+ | Ret Time (min.) | HPLC Methods |
|---|---|---|---|---|---|
| 344 | 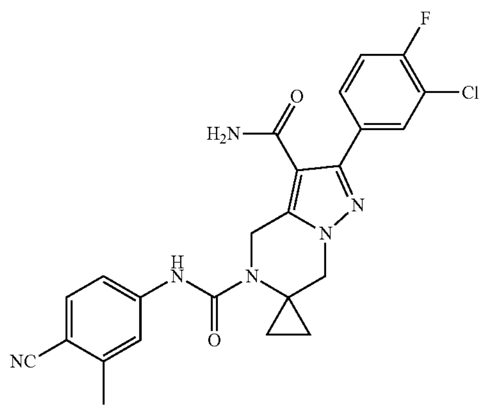 [SMILES: Cc1cc(NC(=O)N2Cc3c(C(N)=O)c(-c4ccc(F)c(Cl)c4)nn3CC23CC3)ccc1C#N] | 2'-(3-Chloro-4-fluorophenyl)-N5'-(4-cyano-3-methylphenyl)-4'H-spiro[cyclopropane-1,6'-pyrazolo[1,5-a]pyrazine]-3',5'(7'H)-dicarboxamide | 479.2 | 9.60<br>9.23 | A<br>B |
| 345 | 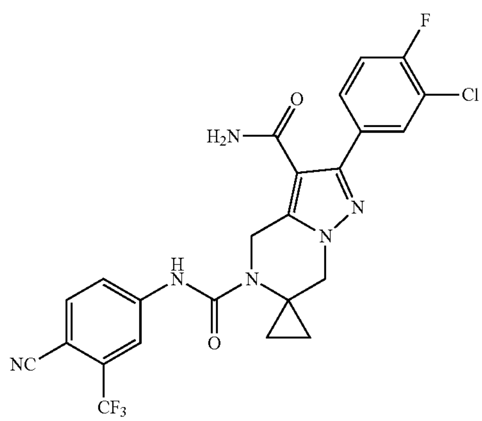 [SMILES: N#Cc1ccc(NC(=O)N2Cc3c(C(N)=O)c(-c4ccc(F)c(Cl)c4)nn3CC23CC3)cc1C(F)(F)F] | 2'-(3-Chloro-4-fluorophenyl)-N5'-(4-cyano-3-(trifluoromethyl)phenyl)-4'H-spiro[cyclopropane-1,6'-pyrazolo[1,5-a]pyrazine]-3',5'(7'H)-dicarboxamide | 533.2 | 10.47<br>9.93 | A<br>B |

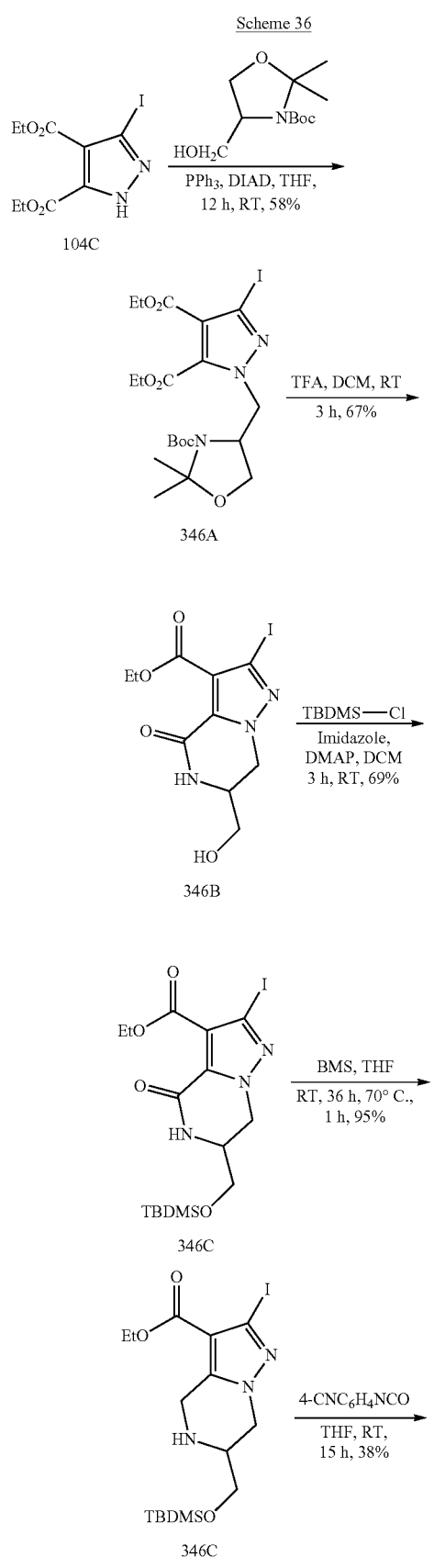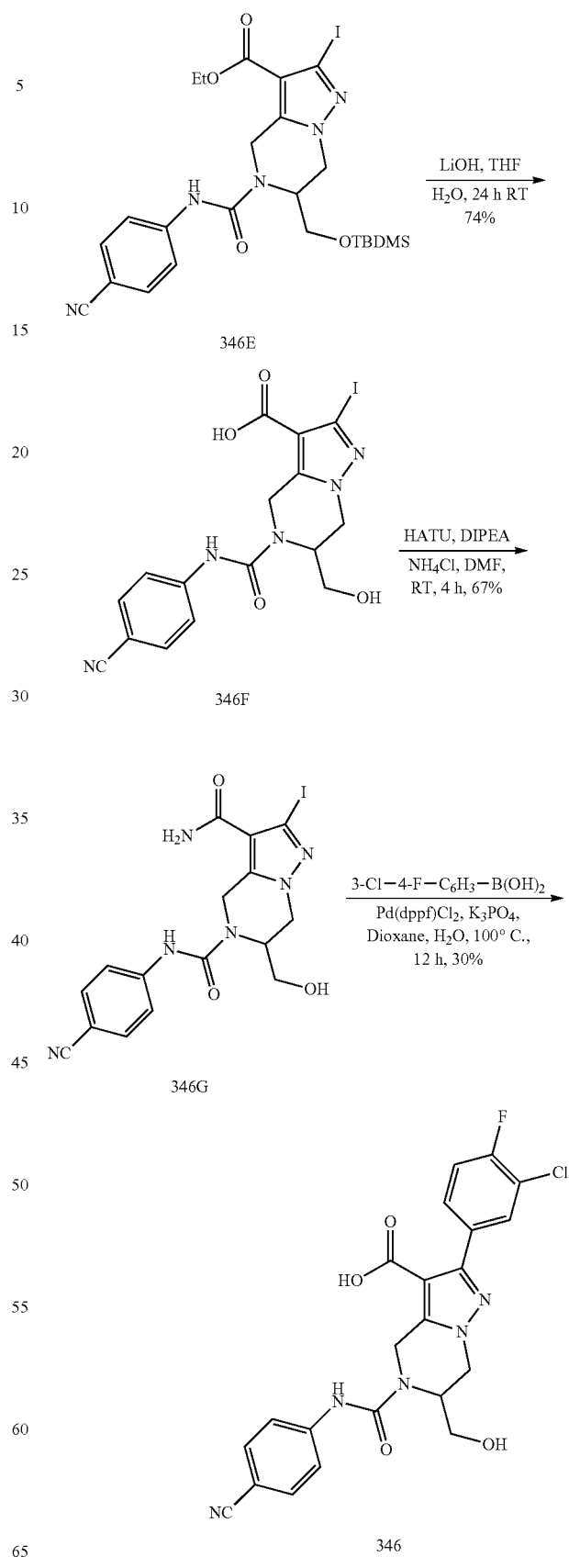

Intermediate 346A: Diethyl 1-((3-(tert-butoxycarbonyl)-2,2-dimethyloxazolidin-4-yl)methyl)-3-iodo-1H-pyrazole-4,5-dicarboxylate

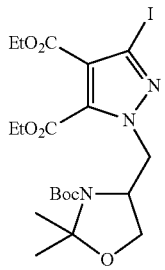 [SMILES: CCOC(=O)c1c(I)nn(CC2COC(C)(C)N2C(=O)OC(C)(C)C)c1C(=O)OCC]

To a stirred solution of triphenylphosphine (5.84 g, 22.25 mmol) in THF (20 mL) was added DIAD (4.50 g 22.25 mmol) dropwise at 0° C. and the resulting solution was stirred for 15 min. Intermediate 104C (3.0 g, 8.90 mmol) in THF (20 mL) was added slowly at 0° C. and stirred at room temperature for 45 min. Intermediate tert-butyl 4-(hydroxymethyl)-2,2-dimethyloxazolidine-3-carboxylate (2.470 g, 10.68 mmol) in THF (20 mL) was added at 0° C. and resulting solution was stirred at room temperature overnight. The volatiles were removed under reduced pressure and the crude compound was purified by silica gel chromatography (40 g REDISEP® column, eluting with 10-13% ethyl acetate in hexanes). Fractions containing the product were combined and evaporated to afford Intermediate 346A (3.5 g, 58.5%) as a pale yellow oil. MS(ES): m/z=552 [M+H]$^+$; $^1$H NMR (300 MHz, DMSO-d$_6$) δ ppm 4.53-4.18 (m, 6H), 3.96-3.82 (m, 2H), 1.50-1.21 (m, 21H).

Intermediate 346B: Ethyl 6-(hydroxymethyl)-2-iodo-4-oxo-4,5,6,7-tetrahydropyrazolo[1,5-a]pyrazine-3-carboxylate

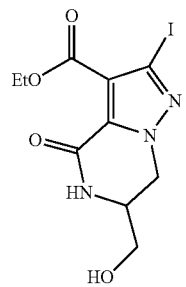 [SMILES: CCOC(=O)c1c(I)nn2c1C(=O)NC(CO)C2]

To a solution of Intermediate 346A (3.3 g, 5.99 mmol) in dioxane (10 mL) was added 4 M HCl in dioxane (5 mL, 5.99 mmol) and the resulting reaction mixture was stirred at RT for 3 h. The reaction mixture was concentrated and the crude product was basified with a 10% aqueous solution of sodium bicarbonate and extracted with EtOAc (3×100 mL). The combined organic layer was dried over sodium sulfate, filtered and concentrated slowly (2 to 3 h) using a rotary evaporator at 60° C. to obtain Intermediate 346B (1.6 g, 67.4%) as a white solid. MS(ES): m/z=366 [M+H]$^+$; $^1$H NMR (400 MHz, DMSO-d$_6$) δ ppm 8.43 (d, J=3.0 Hz, 1H), 5.14 (t, J=5.5 Hz, 1H), 4.46-4.41 (m, 1H), 4.37-4.30 (m, 1H), 4.25 (q, J=7.0 Hz, 2H), 3.84-3.75 (m, 1H), 3.54-3.47 (m, 1H), 3.36 (s, 1H), 1.28 (t, J=7.0 Hz, 3H).

Intermediate 346C: Ethyl 6-(((tert-butyldimethylsilyl)oxy)methyl)-2-iodo-4-oxo-4,5,6,7-tetrahydropyrazolo[1,5-a]pyrazine-3-carboxylate

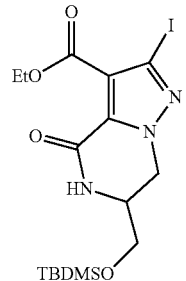 [SMILES: CCOC(=O)c1c(I)nn2c1C(=O)NC(CO[Si](C)(C)C(C)(C)C)C2]

To a solution of Intermediate 346B (1.2 g, 3.29 mmol) in DCM (12 mL) was added imidazole (0.336 g, 4.93 mmol), TBDMS-Cl (0.644 g, 4.27 mmol), DMAP (0.028 g, 0.23 mmol) and the reaction mixture was stirred at RT for 3 h. The reaction mixture was diluted with water and extracted with DCM (3×40 mL). The combined organic layer was washed with water, dried over sodium sulfate and concentrated. The crude product obtained was purified by silica gel chromatography (40 g REDISEP® column, eluting with 50% ethyl acetate in hexanes). Fractions containing the product were combined and evaporated to afford Intermediate 346C (1.1 g, 69%), MS(ES): m/z=480.2 [M+H]$^+$; $^1$H NMR (400 MHz, DMSO-d$_6$) δ ppm 8.43 (d, J=4.0 Hz, 1H), 4.52-4.45 (m, 1H), 4.35 (dd, J=4.0, 13.6 Hz, 1H), 4.27-4.18 (m, 2H), 3.86-3.79 (m, 1H), 3.71 (dd, J=4.0, 10.5 Hz, 1H), 3.55 (dd, J=6.0, 10.5 Hz, 1H), 1.27 (t, J=7.0 Hz, 3H), 0.81-0.75 (m, 9H), −0.02 (d, J=1.0 Hz, 6H).

Intermediate 346D: Ethyl 6-(((tert-butyldimethylsilyl)oxy)methyl)-2-iodo-4,5,6,7-tetrahydropyrazolo[1,5-a]pyrazine-3-carboxylate

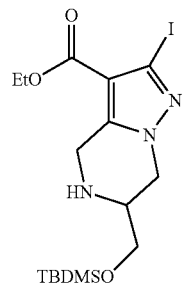 [SMILES: CCOC(=O)c1c(I)nn2c1CNC(CO[Si](C)(C)C(C)(C)C)C2]

To a solution of Intermediate 346C (1.2 g, 2.503 mmol) in THF (120 ml) was added neat borane dimethylsulfide complex (0.713 mL, 7.51 mmol) dropwise and the resulting solution was heated at 40 OC for 36 h. The reaction mixture was cooled to room temperature and ethanol (10 mL) was added dropwise. The reaction mixture was stirred at 70° C. for 1 h and concentrated to afford Intermediate 346D as a white semi-solid (1.23 g, 95%), which was taken to the next step without further purification. MS(ES): m/z=466 [M+H]$^+$.

Intermediate 346E: Ethyl 6-(((tert-butyldimethylsilyl)oxy)methyl)-5-((4-cyanophenyl)carbamoyl)-2-iodo-4,5,6,7-tetrahydropyrazolo[1,5-a]pyrazine-3-carboxylate

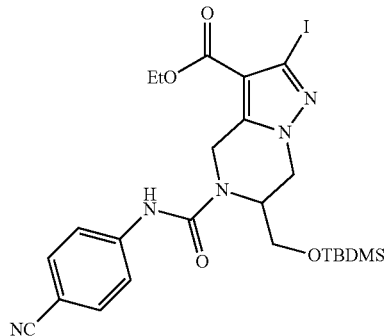 [SMILES: CCOC(=O)c1c(I)nn2c1CN(C(=O)Nc1ccc(C#N)cc1)C(CO[Si](C)(C)C(C)(C)C)C2]

To a solution of Intermediate 346D (1.2 g, 2.58 mmol) in THF (12 ml) was added 4-isocyanatobenzonitrile (0.446 g, 3.09 mmol) and the solution was stirred at room temperature overnight. The reaction mixture was concentrated and the crude product was purified by silica gel chromatography (40 g REDISEP® column, eluting with 16% EtOAc in hexanes). Fractions containing the product were combined and evaporated to afford Intermediate 346E (0.6 g, 38%) as a white solid. MS(ES): m/z=610 [M+H]$^+$; $^1$H NMR (400 MHz, DMSO-d$_6$) δ ppm 9.32 (s, 1H), 7.75-7.63 (m, 4H), 5.24 (d, J=18.6 Hz, 1H), 4.85-4.77 (m, 1H), 4.47 (d, J=18.6 Hz, 1H), 4.35 (d, J=2.5 Hz, 2H), 4.30-4.22 (m, 2H), 3.73-3.64 (m, 2H), 1.31 (t, J=7.0 Hz, 3H), 0.76-0.71 (m, 9H), −0.04 (m, 6H).

Intermediate 346F: 5-((4-Cyanophenyl)carbamoyl)-6-(hydroxymethyl)-2-iodo-4,5,6,7-tetrahydropyrazolo[1,5-a]pyrazine-3-carboxylic acid

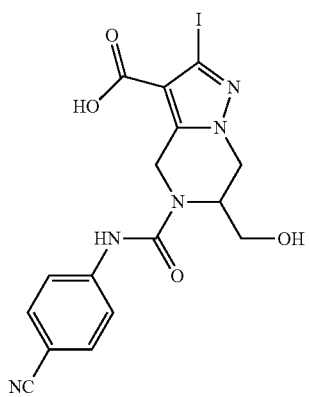 [SMILES: N#Cc1ccc(NC(=O)N2Cc3c(C(=O)O)c(I)nn3CC2CO)cc1]

To a solution of Intermediate 346E (0.7 g, 1.148 mmol) in THF (10 mL) and water (5 ml) was added LiOH (0.083 g, 3.45 mmol) and the reaction mass was stirred at RT for 24 h. The volatiles were evaporated; the residue was diluted with water (10 mL) and neutralized with an aqueous solution of 1.0 N HCl. The solid product separated was filtered and dried to afford Intermediate 346F (0.4 g, 74%) as an off-white solid which was taken to the next step without further purification. MS(ES): m/z=468 [M+H]$^+$; $^1$H NMR (300 MHz, DMSO-d$_6$) δ ppm 12.35-12.80 (br, 1H), 9.33 (s, 1H), 7.69-7.74 (m, 2H), 7.62-7.68 (m, 2H), 5.20-5.30 (m, 1H), 5.10-5.19 (m, 1H), 4.72 (d, J=4.53 Hz, 1H), 4.46 (d, J=18.51 Hz, 1H), 4.27-4.38 (m, 2H), 3.40-3.48 (m, 2H).

Intermediate 346G: N-(4-Cyanophenyl)-6-(hydroxymethyl)-2-iodo-6,7-dihydropyrazolo[1,5-a]pyrazine-3,5(4H)-dicarboxamide

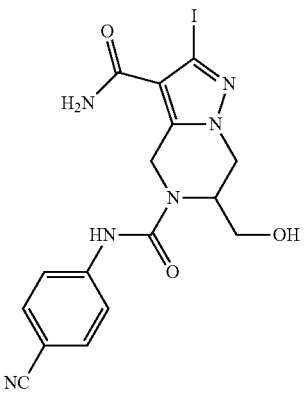 [SMILES: N#Cc1ccc(NC(=O)N2Cc3c(C(N)=O)c(I)nn3CC2CO)cc1]

To a solution of Intermediate 346F (0.12 g, 0.257 mmol) in dry DMF (3 mL) was added HATU (0.195 g, 0.512 mmol), diisopropylethylamine (224 μL, 1.128 mmol) and ammonium chloride (0.0687 g, 1.128 mmol) and the reaction mixture was stirred at room temperature for 4 h. The reaction mixture was concentrated completely to dryness and the crude was partitioned between ethyl acetate and water. The organic layer was separated, washed with brine, dried over Na$_2$SO$_4$, filtered and the filtrate concentrated. The crude product was purified by silica gel chromatography (12 g REDISEP® column, eluting with 3-5% methanol in chloroform). Fractions containing the product were combined to afford Intermediate 346G (0.08 g, 67%) as an off-white solid. MS(ES): m/z=467 [M+H]$^+$; $^1$H NMR (400 MHz, DMSO-d$_6$) δ ppm 9.29 (s, 1H), 7.69-7.74 (m, 2H), 7.63-7.69 (m, 2H), 7.37-7.48 (m, 1H), 6.93 (br. s., 1H), 5.22 (d, J=18.07 Hz, 1H), 5.13 (t, J=5.27 Hz, 1H), 4.72 (d, J=4.52 Hz, 1H), 4.51 (d, J=18.57 Hz, 1H), 4.31-4.38 (m, 1H), 4.20-4.28 (m, 1H), 3.43 (t, J=6.02 Hz, 2H).

Compound 346: 2-(3-Chloro-4-fluorophenyl)-$N^5$-(4-cyanophenyl)-6-(hydroxymethyl)-6,7-dihydropyrazolo[1,5-a]pyrazine-3,5(4H)-dicarboxamide

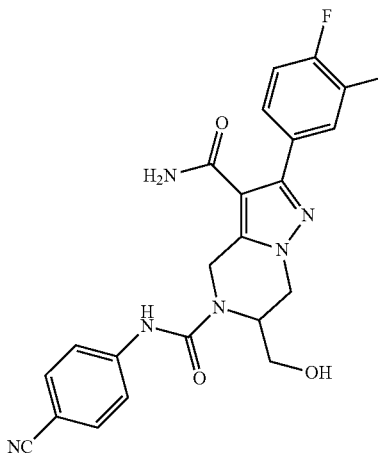

A solution of Intermediate 346G (0.07 g, 0.15 mmol), (3-chloro-4-fluorophenyl) boronic acid (0.0393 g, 0.225 mmol) and $K_3PO_4$ (0.096, 0.45 mmol) in 1,4-dioxane (3 mL) and water (0.5 mL) was degassed with nitrogen for 10 min. $PdCl_2$(dppf)-$CH_2Cl_2$ adduct (7.36 mg, 9.01 μmol) was added and the reaction mixture was stirred at 80° C. for 12 h. The reaction mixture was concentrated and crude was partitioned between ethyl acetate and water. The organic layer was separated, washed with brine, dried over $Na_2SO_4$, filtered and the filtrate concentrated. The crude was purified via preparative HPLC to afford 346 as an off-white solid (20 mg, 30%). HPLC retention times 8.10 min. and 7.95 min. (Methods A and B); MS(ES): m/z=469 [M+H]$^+$; $^1$H NMR (400 MHz, DMSO-$d_6$) δ ppm 9.35 (br. s., 1H), 7.90 (dd, J=7.28, 2.26 Hz, 1H), 7.66-7.76 (m, 5H), 7.45-7.51 (m, 1H), 7.30-7.43 (m, 2H), 5.20 (d, J=17.57 Hz, 2H), 4.80 (d, J=5.02 Hz, 1H), 4.54 (d, J=17.57 Hz, 1H), 4.36-4.42 (m, 1H), 4.24-4.31 (m, 1H), 3.50 (d, J=6.02 Hz, 2H).

Scheme 37

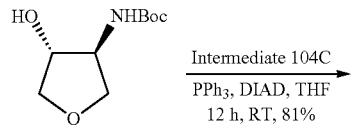

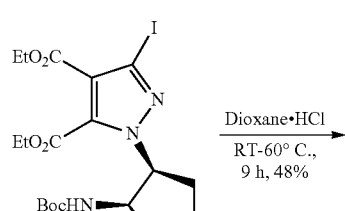

347A

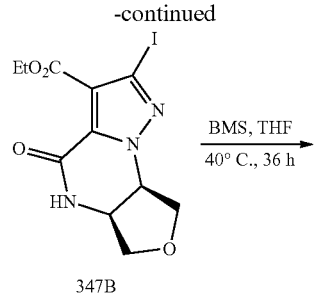

347B

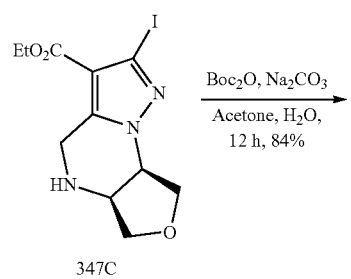

347C

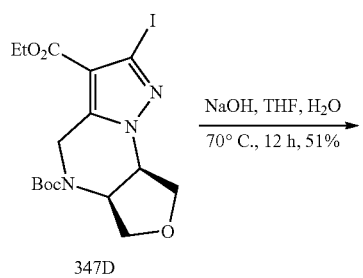

347D

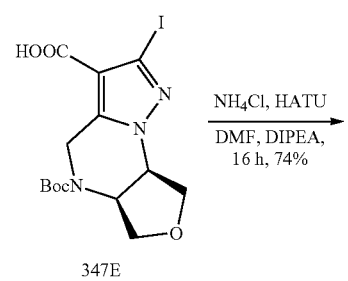

347E

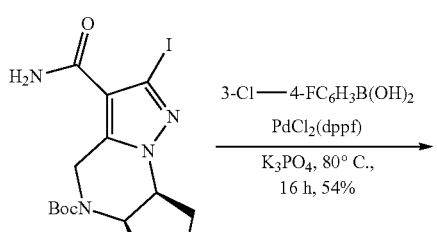

347F

411

-continued

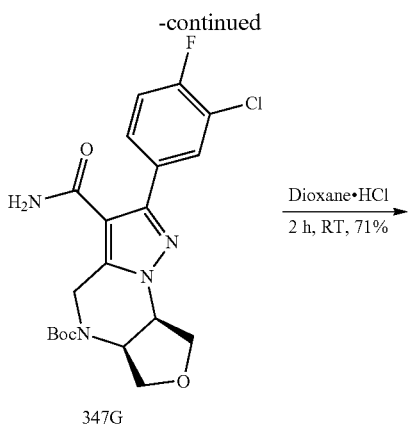

347G

| Dioxane•HCl |
|---|
| 2 h, RT, 71% |

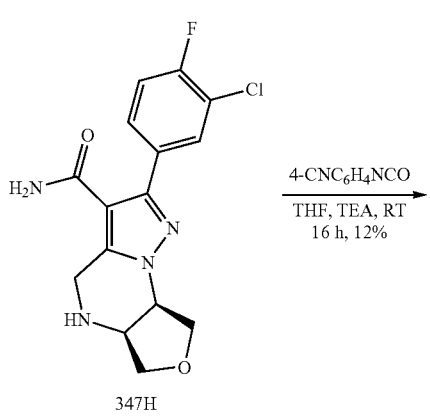

347H

| 4-CNC6H4NCO |
|---|
| THF, TEA, RT |
| 16 h, 12% |

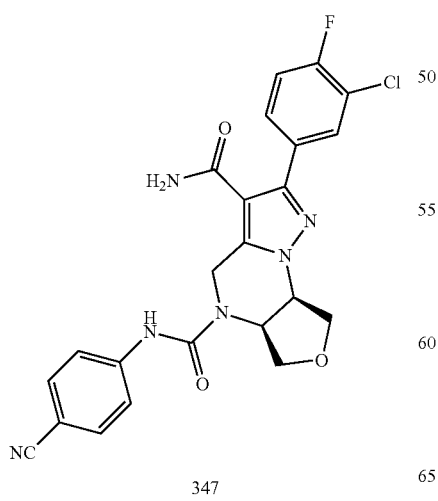

347

412

Intermediate 347A: Diethyl 1-((3R,4S)-4-((Tert-butoxycarbonyl)amino)tetrahydrofuran-3-yl)-3-iodo-1H-pyrazole-4,5-dicarboxylate

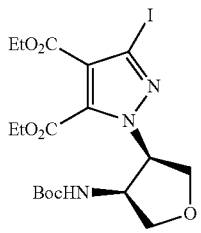 [SMILES: CCOC(=O)c1c(I)nn([C@H]2COC[C@H]2NC(=O)OC(C)(C)C)c1C(=O)OCC]

To a solution of PPh₃ (2.72 g, 10.35 mmol) in THF (10 mL) at 0° C. was added DIAD (2.013 mL, 10.35 mmol) dropwise and stirred for 15 min. A solution of Intermediate 104C (1.4 g, 4.14 mmol) in THF (10 mL) was added to the above reaction mixture and was stirred at 0° C. for 45 min. A solution of tert-butyl((3S,4R)-4-hydroxytetrahydrofuran-3-yl)carbamate (1.683 g, 8.28 mmol) in THF (10 mL) was added dropwise at 0° C. and the reaction mixture was stirred at RT for 12 h. The reaction mixture was then concentrated and the crude compound was purified by silica gel chromatography (24 g REDISEP® column, eluting with 30% EtOAc in hexanes). Fractions containing the product were combined and evaporated to afford Intermediate 347A (1.7 g, 81%) as a white solid. MS(ES): m/z=522 [M–H]⁺; The crude product was taken to the next step without further purification.

Intermediate 347B: (5aS,8aR)-Ethyl 2-iodo-4-oxo-4,5,5a,6,8,8a-hexahydrofuro[3,4-e]pyrazolo[1,5-a]pyrazine-3-carboxylate

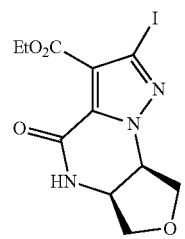 [SMILES: CCOC(=O)c1c(I)nn2c1C(=O)N[C@@H]1COC[C@@H]12]

To an ice-cold solution of Intermediate 347A (6.0 g, 11.5 mmol) in dioxane (20 mL) was added a 4 M solution of HCl in dioxane (100 mL, 11.47 mmol) and the reaction mixture was stirred at RT for 4 h. The reaction mixture was concentrated; the pH of the residue was adjusted to 8 with a 10% aqueous solution of NaHCO₃ and the mixture was stirred at RT for 30 min. then was extracted with EtOAc (3×100 mL). The combined organic layers were washed with water, dried over Na₂SO₄, concentrated and kept under vacuum at 60° C. for 6 h to obtain Intermediate 347B as an off-white solid (2.1 g, 48%). MS(ES): –m/z=378 [M+H]⁺; ¹H NMR (400 MHz, DMSO-d₆) δ ppm 8.67 (d, J=3.5 Hz, 1H), 5.11-5.04 (m, 1H), 4.45 (dq, J=4.0, 6.5 Hz, 1H), 4.31-4.12 (m, 4H), 4.04-3.94 (m, 1H), 3.57 (dd, J=6.0, 9.0 Hz, 1H), 1.32-1.22 (m, 3H).

Intermediate 347C: (5aS,8aR)-Ethyl 2-iodo-4,5,5a,6,8,8a-hexahydrofuro[3,4-e]pyrazolo[1,5-a]pyrazine-3-carboxylate

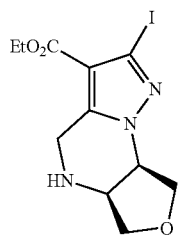 [SMILES: CCOC(=O)c1c(I)nn2c1CN[C@@H]1COC[C@@H]12]

To a stirred solution of Intermediate 347B (0.5 g, 1.33 mmol) in THF (1 mL) was added borane dimethyl sulfide complex (0.378 mL, 3.98 mmol) and the reaction mixture was stirred at 40° C. for 16 h. Additional quantity of borane dimethyl sulfide complex (0.126 mL, 1.326 mmol) was added and the reaction was stirred further for 16 h. The reaction was quenched by adding ethanol (3 mL) and allowing the solution to heat to reflux for 2 h. The reaction mixture was concentrated to afford crude Intermediate 347C as an off-white semi-solid which was taken as such for next step without further purification

Intermediate 347D: (5aS,8aR)-5-tert-Butyl 3-ethyl2-iodo-5a,6,8,8a-tetrahydrofuro[3,4-e]pyrazolo[1,5-a]pyrazine-3,5(4H)-dicarboxylate

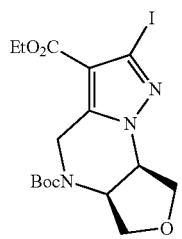 [SMILES: CCOC(=O)c1c(I)nn2c1CN(C(=O)OC(C)(C)C)[C@@H]1COC[C@@H]12]

To a stirred solution of Intermediate 347C (1.0 g, 2.75 mmol) in DCM (10 mL) was added TEA (1.151 mL, 8.26 mmol) and stirred for 10 min., followed by the addition of Boc$_2$O (0.767 mL, 3.30 mmol). The reaction mixture was allowed to stir at RT for 16 h., at which point it was diluted with water (50 mL) and extracted with DCM (3×50 mL). The combined organic layers were washed with water, dried over Na$_2$SO$_4$ and concentrated. The crude compound was purified by silica gel chromatography (12 g REDISEP® column, eluting with 50% EtOAc in hexanes). Fractions containing the product were combined and evaporated to afford Intermediate 347D (0.56, 44% yield) as an off-white solid. MS(ES): –m/z=464 [M+H]$^+$; $^1$H NMR (300 MHz, DMSO-d$_6$) δ ppm 5.30 (d, J=18.5 Hz, 1H), 4.88 (dd, J=3.0, 7.2 Hz, 1H), 4.51-4.36 (m, 1H), 4.33-4.14 (m, 2H), 4.13-4.00 (m, 1H), 3.98-3.86 (m, 1H), 3.82-3.71 (m, 1H), 1.49-1.39 (m, 9H), 1.35-1.25 (m, 3H).

Intermediate 347E: (5aS,8aR)-5-(tert-Butoxycarbonyl)-2-iodo-4,5,5a,6,8,8a-hexahydrofuro[3,4-e]pyrazolo[1,5-a]pyrazine-3-carboxylic acid

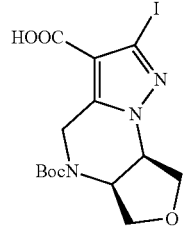 [SMILES: CC(C)(C)OC(=O)N1Cc2c(C(=O)O)c(I)nn2[C@H]2COC[C@H]21]

To a stirred solution of Intermediate 347D (0.85 g, 1.835 mmol) in THF (5 mL) was added a solution of NaOH (0.220 g, 5.50 mmol) in water (4 mL) and the reaction mixture was heated to 70° C. for 16 h. The reaction mixture was concentrated and the pH of the residue was adjusted to 4-5 using an aqueous solution of citric acid. The formed precipitate was filtered, washed with n-hexanes and dried to afford Intermediate 347E (0.48 g, 51%) as an off-white solid. MS(ES): –m/z=434 [M–H]$^+$; $^1$H NMR (300 MHz, DMSO-d$_6$) δ ppm 12.80-12.67 (m, 1H), 5.30 (d, J=18.5 Hz, 2H), 4.87 (dd, J=3.4, 6.8 Hz, 1H), 4.46-4.32 (m, 1H), 4.12-4.04 (m, 1H), 3.98-3.90 (m, 1H), 3.89-3.82 (m, 1H), 3.80-3.69 (m, 1H), 1.43 (s, 9H).

Intermediate 347F: (5aS,8aR)-tert-Butyl 3-carbamoyl-2-iodo-5a,6,8,8a-tetrahydrofuro[3,4-e]pyrazolo[1,5-a]pyrazine-5(4H)-carboxylate

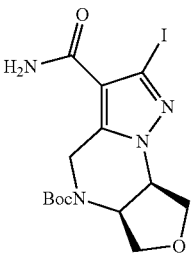 [SMILES: CC(C)(C)OC(=O)N1Cc2c(C(N)=O)c(I)nn2[C@H]2COC[C@H]21]

To a stirred solution of Intermediate 347E (0.480 g, 1.103 mmol) in DMF (10 mL) at RT was added DIPEA (0.963 mL, 5.51 mmol), HATU (0.839 g, 2.206 mmol), and NH$_4$Cl (0.295 g, 5.51 mmol). After stirring for 12 h, the reaction mixture was diluted with water and extracted with EtOAc (3×50 mL). The combined organic layers were washed with water, dried over Na$_2$SO$_4$ and concentrated to afford Intermediate 347F (0.39 g, 74%) as a pale yellow oil. MS(ES): m/z=435 [M+H]$^+$; $^1$H NMR (300 MHz, DMSO-d$_6$) δ ppm 7.95 (s, 2H), 5.30-5.13 (m, 2H), 4.86 (dd, J=3.4, 7.6 Hz, 1H), 4.38 (d, J=15.9 Hz, 1H), 4.14-4.03 (m, 1H), 3.98-3.82 (m, 2H), 3.75 (dd, J=6.6, 9.3 Hz, 1H), 1.43 (s, 9H).

Intermediate 347G: (5aS,8aR)-tert-Butyl 3-carbamoyl-2-(3-chloro-4-fluorophenyl)-5a,6,8,8a-tetrahydrofuro[3,4-e]pyrazolo[1,5-a]pyrazine-5(4H)-carboxylate

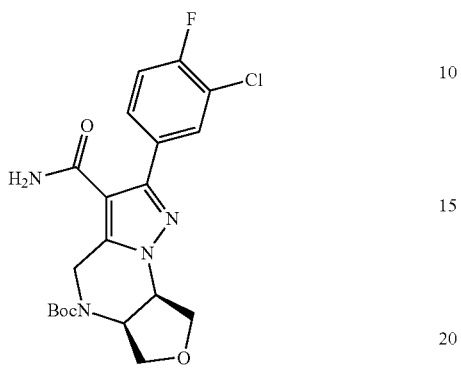

To a stirred solution of Intermediate 347F (0.370 g, 0.852 mmol) and (3-chloro-4-fluorophenyl)boronic acid (0.297 g, 1.704 mmol) in dioxane (2 mL) was added a solution of $K_3PO_4$ (0.543 g, 2.56 mmol) in water (0.5 mL) and the reaction mixture was purged with nitrogen for 10 min. $PdCl_2(dppf)CH_2Cl_2$ (0.052 g, 0.064 mmol) was then added and the reaction mixture was heated to 80° C. and stirred for 16 h. The reaction mixture was diluted with water and extracted with EtOAc (3×30 mL). The combined organic layers were washed with water, dried over $Na_2SO_4$ and concentrated. The crude compound was purified by silica gel chromatography (12 g REDISEP® column, eluting with 4% MeOH in $CHCl_3$). Fractions containing the product were combined and evaporated to afford Intermediate 347G (0.270 g, 54%) as an off-white solid. MS(ES): m/z=437 [M+H]⁺.

Intermediate 347H: (5aS,8aR)-2-(3-Chloro-4-fluorophenyl)-4,5,5a,6,8,8a-hexahydrofuro[3,4-e]pyrazolo[1,5-a]pyrazine-3-carboxamide HC

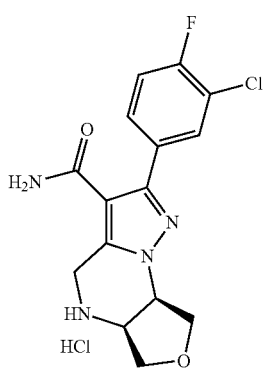 [SMILES: NC(=O)c1c(-c2ccc(F)c(Cl)c2)nn2c1CN[C@@H]1COC[C@@H]12 ; Cl]

To a stirred solution of Intermediate 347G (0.2 g, 0.458 mmol) in dioxane (1 mL) was added a solution of HCl in dioxane (2 mL, 8.0 mmol, 4 M). After stirring at RT for 2 h, the reaction mixture was concentrated and the crude product was triturated with hexanes to afford Intermediate 347H (0.17 g, 71%) as an off-white solid. MS(ES): −m/z=337 [M+H]⁻ ¹H NMR (400 MHz, DMSO-d₆) δ ppm 7.90 (ddd, J=1.8, 7.5, 14.3 Hz, 1H), 7.80-7.68 (m, 2H), 7.54-7.47 (m, 1H), 7.38 (dd, J=8.3, 9.8 Hz, 1H), 5.10 (br. s., 1H), 4.63 (br. s., 1H), 4.56 (s, 2H), 4.20-3.98 (m, 4H), 3.57 (s, 1H).

Compound 347: (5aS,8aR)-2-(3-Chloro-4-fluorophenyl)-N⁵-(4-cyanophenyl)-5a,6,8,8a-tetrahydrofuro[3,4-e]pyrazolo[1,5-a]pyrazine-3,5(4H)-dicarboxamide

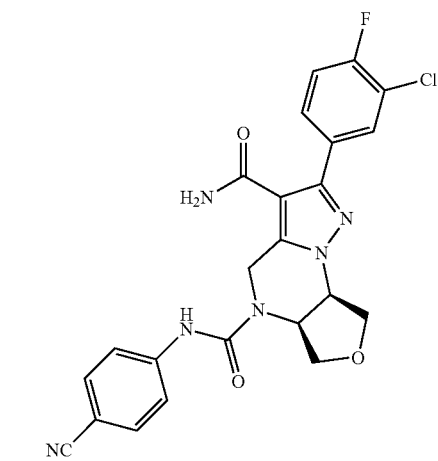 [SMILES: N#Cc1ccc(NC(=O)N2Cc3c(C(N)=O)c(-c4ccc(F)c(Cl)c4)nn3[C@H]3COC[C@H]32)cc1]

Compound 347 was synthesized from Intermediate 347H using a synthetic sequence analogous to the preparation of Compound 297. HPLC retention times 1.51 min. and 1.51 min. (Methods E and L respectively). MS(ES): m/z=481 [M+H]⁺; ¹H NMR (400 MHz, DMSO-d₆) δ ppm 9.52 (s, 1H), 7.90 (dd, J=2.0, 7.5 Hz, 1H), 7.76-7.69 (m, 3H), 7.67-7.61 (m, 2H), 7.48 (t, J=9.0 Hz, 1H), 7.44-7.33 (m, 2H), 5.50 (q, J=7.4 Hz, 1H), 5.36 (d, J=17.1 Hz, 1H), 4.93 (dd, J=3.0, 7.0 Hz, 1H), 4.54 (d, J=17.1 Hz, 1H), 4.22 (d, J=10.0 Hz, 1H), 4.04-3.96 (m, 2H), 3.89 (dd, J=6.5, 9.0 Hz, 1H).

The Compounds shown in Table 29 have been prepared similar to Compound 347 by coupling of 347F with different boronic acids followed by de-protection of N-Boc group and coupling with 4-isocyanatobenzonitrile.

TABLE 29
| Ex. No. | Structure | Name | [M + H]+ | Ret Time (min.) | HPLC Methods |
|---|---|---|---|---|---|
| 348 | 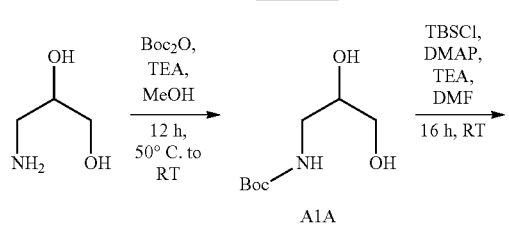 | (5aS,8aR)-2-(3-Chlorophenyl)-N5-(4-cyanophenyl)-5a,6,8,8a-tetrahydrofuro[3,4-e]pyrazolo[1,5-a]pyrazine-3,5(4H)-dicarboxamide | 463 | 1.422<br>1.422 | E<br>L |
| 349 | 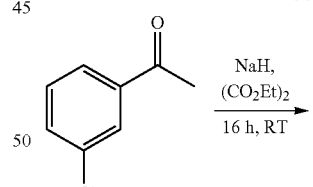 | (5aS,8aR)-N5-(4-Cyanophenyl)-2-(3,4-dichlorophenyl)-5a,6,8,8a-tetrahydrofuro[3,4-e]pyrazolo[1,5-a]pyrazine-3,5(4H)-dicarboxamide | 497 | 1.607<br>1.624 | E<br>L |
Scheme 38
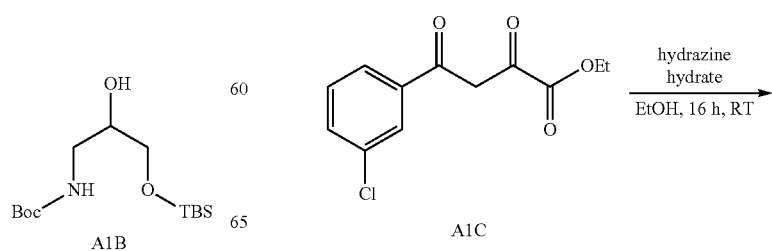

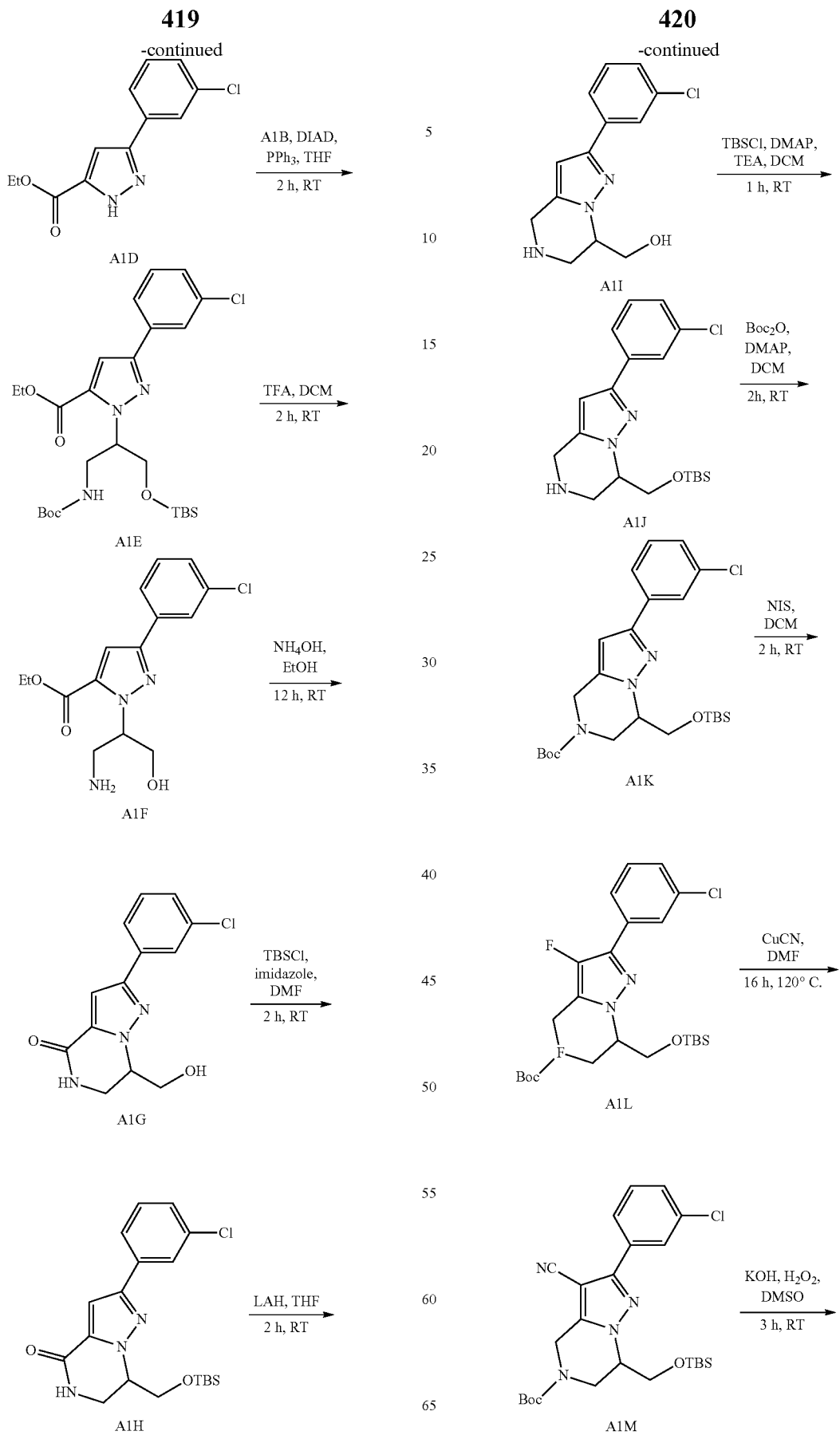

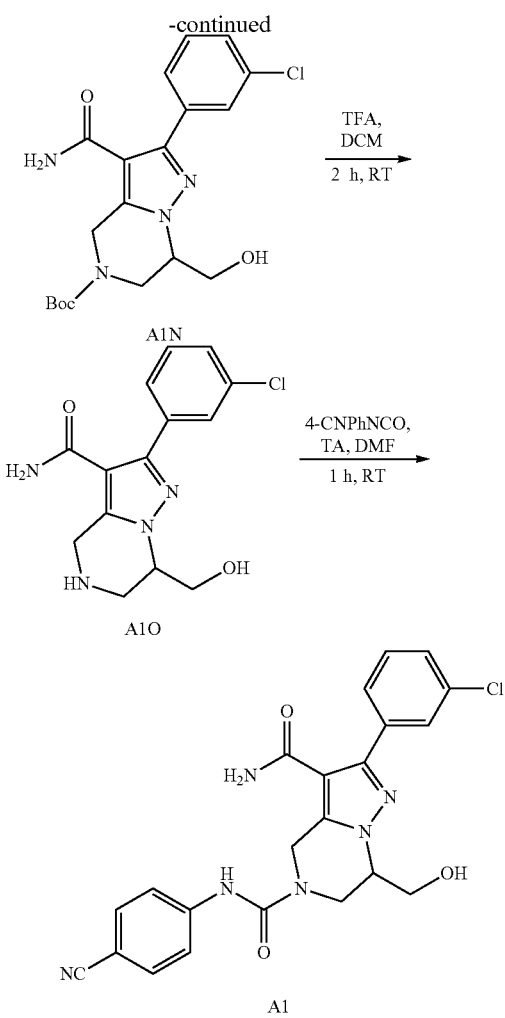

Intermediate A1A:
tert-Butyl(2,3-dihydroxypropyl)carbamate

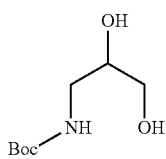 [SMILES: CC(C)(C)OC(=O)NCC(O)CO]

The above Intermediate was synthesized according to a patent literature procedure reported in U.S. Publication No. 2006/69156 A1 (2006).

To a solution of 3-aminopropane-1,2-diol (10.0 g, 110 mmol) in MeOH (407 mL) was added Boc₂O (35.9 g, 165 mmol) and TEA (55 mL, 395 mmol) and the reaction mixture was heated at 50° C. for 20 min., followed by stirring at room temperature for 12 h. The reaction was then concentrated under reduced pressure to provide a residue. It was purified by silica gel chromatography (330 g REDISEP® column, eluting with 5% MeOH in DCM). Fractions containing the product were combined and evaporated to afford Intermediate A1A (20.14 g, 96%) as a colorless oil. ¹H NMR (400 MHz, DMSO-d₆) δ ppm 6.61 (br. s., 1H), 4.63 (d, J=4.9 Hz, 1H), 4.47 (t, J=5.6 Hz, 1H), 3.45 (d, J=5.6 Hz, 1H), 3.31-3.23 (m, 2H), 3.09-2.98 (m, 1H), 2.85 (d, J=6.6 Hz, 1H), 1.38 (s, 9H).

Intermediate A1B: tert-Butyl(3-((Tert-butyldimethylsilyl)oxy)-2-hydroxypropyl) carbamate

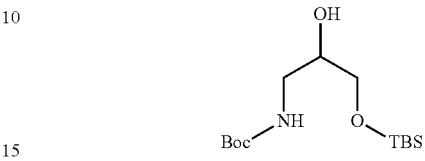

The above Intermediate was synthesized according to a patent literature procedure reported in U.S. Publication No. 2003/187026 A1 (2003).

To a solution of Intermediate A1A (20.14 g, 105 mmol) in DCM (168 mL) were added TEA (17.62 mL, 126 mmol), TBSCl (18.00 g, 116 mmol) and DMAP (0.515 g, 4.21 mmol) and the reaction mixture was stirred at room temperature for 16 h. The mixture was then diluted with DCM (100 mL) and the organic layer was washed with water (3×100 mL), brine, dried over anhydrous MgSO₄, filtered and the filtrate was concentrated under reduced pressure to provide a crude residue. It was purified by silica gel chromatography (330 g REDISEP® column, eluting with a gradient of 0 to 30% EtOAc in hexanes). Fractions containing the product were combined and evaporated to afford Intermediate A1B (24.46 g, 76%) as a pale yellow oil. ¹H NMR (400 MHz, DMSO-d₆) δ ppm 6.58 (br. s., 1H), 4.69 (d, J=4.4 Hz, 1H), 3.55-3.42 (m, 3H), 1.37 (s, 9H), 0.92-0.82 (m, 9H).

Intermediate A1C: Ethyl 4-(3-chlorophenyl)-2,4-dioxobutanoate

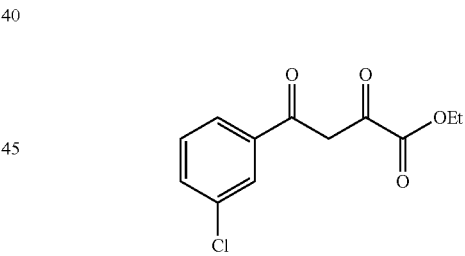

To an ice-cold solution of 1-(3-chlorophenyl)ethanone (16.79 mL, 129 mmol) and diethyl oxalate (18.05 mL, 136 mmol) in DMF (78.0 mL) was added, portionwise over 30 min., NaH (6.09 g, 155 mmol, 60% dispersion in mineral oil) and the resultant mixture was stirred at that temperature for 20 min. and then at room temperature for 16 h. The reaction mixture was diluted with water and acidified to pH 4-5 with 1N aq. HCl. The mixture was further diluted with copious amounts of water. The aq. layer was extracted with EtOAc (4×100 mL) and the combined organic layer was washed with water, brine, dried over anhydrous MgSO₄, filtered and the filtrate was concentrated under reduced pressure to provide a crude residue. It was purified by silica gel chromatography (220 g REDISEP® column, eluting with a 0 to 15% EtOAc in hexanes). Fractions containing the product were combined and evaporated to afford Intermediate A1C (27.1 g, 84%) as a solid. MS(ES): m/z=277.10

[M+Na]+; 1H NMR (400 MHz, chloroform-d) δ ppm 7.99 (t, J=1.8 Hz, 1H), 7.95-7.86 (m, 1H), 7.60 (ddd, J=8.0, 2.1, 1.0 Hz, 1H), 7.48 (t, J=7.9 Hz, 1H), 7.06 (s, 1H), 4.43 (q, J=7.3 Hz, 2H), 1.44 (t, J=7.2 Hz, 3H).

Intermediate A1D: Ethyl 3-(3-chlorophenyl)-1H-pyrazole-5-carboxylate

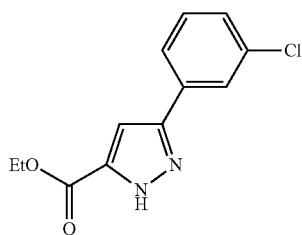 [SMILES: CCOC(=O)c1cc(-c2cccc(Cl)c2)n[nH]1]

To a suspension of Intermediate A1C (14.57 g, 57.2 mmol) in EtOH (191 mL) was added hydrazine hydrate (5.57 mL, 57.2 mmol, 64% solution) and the reaction mixture was stirred at room temperature for 16 h. The reaction turned homogenous over time and then a solid precipitated out. The thick precipitate was filtered off. The filter cake was washed with a little EtOH to afford the product as a white solid. The filtrate was rotavaped to dryness to afford the crude product as a yellow solid. It was suspended in a minimum amount of EtOH or MeCN and filtered off to give more of the product. The process of rotavaping the filtrate to dryness and suspending the subsequent solid in EtOH or MeCN was repeated 2-3 more times to provide more white product during each filtration cycle. The combined solid was dried under vacuum for 3 h to afford Intermediate A1D (10.9 g, 76%). MS(ES): m/z=273 [M+Na]+; 1H NMR (400 MHz, DMSO-d6) ppm 13.91 (br. s., 1H), 7.97 (t, J=1.8 Hz, 1H), 7.86 (dt, J=7.8, 1.4 Hz, 1H), 7.55-7.33 (m, 4H), 4.34 (q, J=7.2 Hz, 2H), 1.34 (t, J=7.2 Hz, 3H).

Intermediate A1E: Ethyl 3-(3-chlorophenyl)-1-(2,2,3,3,11,11-hexamethyl-9-oxo-4,10-dioxa-8-aza-3-siladodecan-6-yl)-1H-pyrazole-5-carboxylate

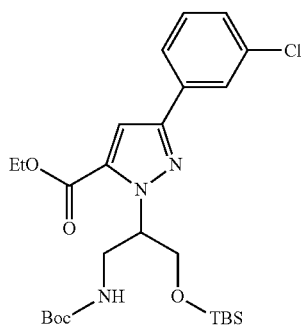

To an ice-cold suspension of Intermediate A1D (7.0 g, 27.9 mmol) and PPh3 (10.99 g, 41.9 mmol) in THF (112 mL) was added a solution of DIAD (8.57 mL, 41.9 mmol) in THF (15 mL). Soon the reaction mixture turned homogenous. It was stirred at that temperature for 30 min., followed by the addition of a solution of Intermediate A1B (10.24 g, 33.5 mmol) in THF (15 mL). The resultant reaction mixture was stirred at room temperature for 2 h and then diluted with EtOAc (150 mL). The organic layer was washed with brine, dried over anhydrous MgSO4, filtered and the filtrate was concentrated under reduced pressure to provide a crude oil. It was purified by silica gel chromatography (220 g REDISEP® column, eluting with 0 to 15% EtOAc in hexanes). Fractions containing the product were combined and evaporated to afford Intermediate A1E (12.5 g, 83%) as a thick syrup. MS(ES): m/z=438.1 [M-Boc]+; 1H NMR (400 MHz, chloroform-d) δ ppm 7.97 (s, 1H), 7.91-7.83 (m, 1H), 7.53-7.37 (m, 3H), 7.01 (s, 1H), 5.54 (br. s., 1H), 4.32 (q, J=7.0 Hz, 2H), 3.94 (d, J=6.0 Hz, 2H), 3.48 (s, 1H), 3.39 (d, J=7.5 Hz, 1H), 1.41-1.29 (m, 12H), 0.74 (s, 9H).

Intermediate A1F: Ethyl 1-(1-amino-3-hydroxypropan-2-yl)-3-(3-chlorophenyl)-1H-pyrazole-5-carboxylate, 2HCl

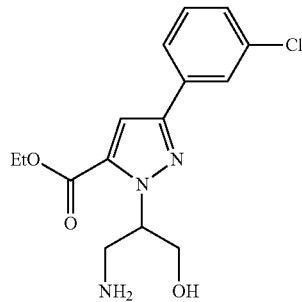 [SMILES: CCOC(=O)c1cc(-c2cccc(Cl)c2)nn1C(CN)CO]

To a solution of Intermediate A1E (21.0 g, 39 mmol) in 1,4-dioxane (156 mL) was added a solution of HCl (166 mL, 663 mmol, 4M in 1,4-dioxane) and the reaction mixture was stirred at room temperature for 12 h. The white precipitate that was generated was filtered off and the filter cake was washed with a little dioxane. The solid was dried under vacuum for 4 h to afford Intermediate A1F as a bis HCl salt (11.9 g, 77%). MS(ES): m/z=324.0 [M+H]+.

Intermediate A1G: 2-(3-Chlorophenyl)-7-(hydroxymethyl)-6,7-dihydropyrazolo[1,5-a]pyrazin-4(5H)-one

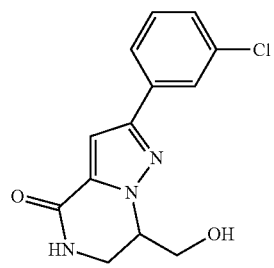 [SMILES: O=C1NCC(CO)n2nc(-c3cccc(Cl)c3)cc21]

To a suspension of Intermediate A1F (5.23 g, 13.18 mmol) in EtOH (132 mL) was added NH4OH (171 mL, 1318 mmol) and the reaction mixture was stirred at RT for 16 h. Soon the mixture became homogenous and a white precipitate formed overnight. The solid was filtered off and the filtrate was concentrated under reduced pressure to provide more product. The combined white solid was dried overnight to afford Intermediate A1G (3.5 g, 96%). MS(ES): m/z=278.0 [M+H]$^+$. $^1$H NMR (400 MHz, DMSO-d$_6$) ppm 8.22 (br. s., 1H), 7.94 (t, J=1.6 Hz, 1H), 7.86 (dt, J=7.7, 1.3 Hz, 1H), 7.52-7.38 (m, 2H), 7.34 (s, 1H), 7.07 (br. s., 1H), 5.29 (t, J=5.8 Hz, 1H), 4.54-4.42 (m, 1H), 3.86-3.71 (m, 3H), 3.65 (dt, J=13.4, 4.1 Hz, 1H).

Intermediate A1H: 7-(((tert-Butyldimethylsilyl)oxy)methyl)-2-(3-chlorophenyl)-6,7-dihydropyrazolo[1,5-a]pyrazin-4(5H)-one

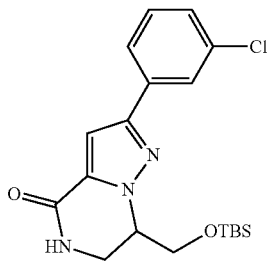 [SMILES: CC(C)(C)[Si](C)(C)OCC1CNC(=O)c2cc(-c3cccc(Cl)c3)nn21]

To a solution of Intermediate A1G (4.365 g, 15.72 mmol) in DMF (157 mL) was added imidazole (1.380 g, 20.28 mmol) and TBSCl (2.84 g, 18.86 mmol) and the reaction mixture was stirred at room temperature for 2 h. Most of the DMF was concentrated under reduced pressure and the residue was diluted with water to generate a white precipitate. This solid was filtered off and the filter cake was dried under vacuum for 4 h to afford Intermediate A1H (5.1 g, 83%). MS(ES): m/z=392.1 [M+H]$^+$. $^1$H NMR (400 MHz, DMSO-d$_6$) δ ppm 8.21 (br. s., 1H), 7.94 (t, J=1.6 Hz, 1H), 7.86 (dt, J=7.5, 1.3 Hz, 1H), 7.52-7.37 (m, 2H), 7.35 (s, 1H), 4.58 (br. s., 1H), 4.09-3.92 (m, 2H), 3.63 (s, 1H), 0.91-0.79 (m, 9H).

Intermediate A1I: (2-(3-Chlorophenyl)-4,5,6,7-tetrahydropyrazolo[1,5-a]pyrazin-7-yl)methanol

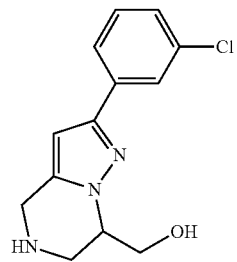 [SMILES: OCC1CNCc2cc(-c3cccc(Cl)c3)nn21]

To a solution of Intermediate A1H (4.945 g, 12.61 mmol) in THF (126 mL) was added, dropwise at −15° C., a 1M solution of LAH in THF (31.5 mL, 31.5 mmol) and the reaction mixture was stirred at that temperature for 3 h. LC-MS shows mainly unreacted starting material. Hence, more 1M LAH solution in THF (6.31 mL, 6.31 mmol, 0.5 equivalent) was added dropwise at −15° C. and the RM was allowed to gradually warm to room temperature and stir further for 16 h. The reaction mixture was carefully quenched at −15° C. with sequential addition of H$_2$O (31.5 mL), NaOH (15% aq. solution, 31.5 mL), and H$_2$O (92 mL). The slurry was then allowed to stir at room temperature for ~30 min., followed by the addition of anhydrous MgSO$_4$. The mixture was stirred further for 15 min. and then the inorganics were filtered off. The filter cake was washed with THF (150 mL). The biphasic filtrate was concentrated under reduced pressure to remove THF. The residual aq. layer was extracted with DCM (3×50 mL). The combined organic layer was washed with brine, dried over anhydrous MgSO$_4$, filtered and concentrated under reduced pressure to afford TBS cleaved Intermediate A1I (3.1 g, 93%) as a slightly impure yellow sticky solid. MS(ES): m/z=264.0 [M+H]$^+$.

Intermediate A1J: 7-(((tert-Butyldimethylsilyl)oxy)methyl)-2-(3-chlorophenyl)-4,5,6,7-tetrahydropyrazolo[1,5-a]pyrazine

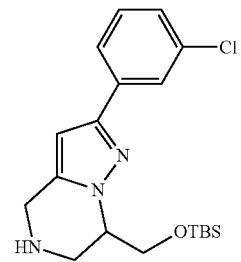 [SMILES: CC(C)(C)[Si](C)(C)OCC1CNCc2cc(-c3cccc(Cl)c3)nn21]

To a solution of Intermediate A1I (2.37 g, 8.97 mmol) in DCM (90 mL) were added TBSCl (2.57 g, 17.05 mmol), DMAP (0.164 g, 1.346 mmol) and TEA (3.75 mL, 26.9 mmol) and the reaction mixture was stirred at room temperature for 6 h. It was then diluted with a saturated solution of aq. NaHCO$_3$ and the two layers were separated. The aq. layer was back-extracted with DCM (2×50 mL). The combined organic layer was washed with water, brine, dried over anhydrous MgSO$_4$, filtered and concentrated under reduced pressure to give an oil. It was purified by silica gel chromatography (120 g REDISEP® column, eluting with a gradient of 40-65% EtOAc in hexanes). Fractions containing the product were combined and evaporated to afford Intermediate A1J (3.194 g, 94%) as a colorless oil. MS(ES): m/z=378.1 [M+H]$^+$.

Intermediate A1K: tert-Butyl 7-(((tert-butyldimethylsilyl)oxy)methyl)-2-(3-chlorophenyl)-6,7-dihydropyrazolo[1,5-a]pyrazine-5(4H)-carboxylate

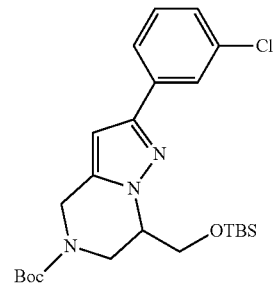 [SMILES: CC(C)(C)OC(=O)N1Cc2cc(-c3cccc(Cl)c3)nn2C(CO[Si](C)(C)C(C)(C)C)C1]

To a solution of Intermediate A1J (3.194 g, 8.45 mmol) in DCM (85 mL) were added Boc$_2$O (2.213 g, 10.14 mmol), DMAP (0.103 g, 0.845 mmol) and TEA (3.53 mL, 25.4 mmol) and the reaction mixture was stirred at room temperature for 2 h. It was then quenched with a saturated solution of aq. NaHCO$_3$ and the two layers were separated.

The aq. layer was back-extracted with DCM (2×50 mL). The combined organic layer was washed with brine, dried, over anhydrous MgSO$_4$, filtered and concentrated under reduced pressure to give a solid. It was purified by silica gel chromatography (120 g REDISEP® column, eluting with 20% EtOAc in hexanes). Fractions containing the product were combined and evaporated to afford Intermediate A1K (3.392 g, 84%) as an oil. MS(ES): m/z=478.08 [M+H]$^+$.

Intermediate A1L: tert-Butyl 7-(((tert-butyldimethylsilyl)oxy)methyl)-2-(3-chlorophenyl)-3-iodo-6,7-dihydropyrazolo[1,5-a]pyrazine-5(4H)-carboxylate

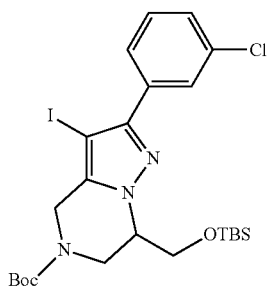 [SMILES: CC(C)(C)OC(=O)N1Cc2c(I)c(-c3cccc(Cl)c3)nn2C(CO[Si](C)(C)C(C)(C)C)C1]

To a solution of Intermediate A1K (3.392 g, 7.09 mmol) in DCM (37.8 mL) and MeOH (9.46 mL) was added NIS (7.66 g, 34.1 mmol) and the reaction mixture was stirred at RT for 2 h. The solution was then concentrated under reduced pressure to provide a solid. It was purified by silica gel chromatography (120 g REDISEP® column, eluting with a gradient of 10 to 15% EtOAc in hexanes). Fractions containing the product were combined and evaporated to afford Intermediate A1L (4.28 g, >99%) as a semi-solid. MS(ES): m/z=604.08 [M+H]$^+$.

Intermediate A1M: tert-Butyl 7-(((tert-butyldimethylsilyl)oxy)methyl)-2-(3-chlorophenyl)-3-cyano-6,7-dihydropyrazolo[1,5-a]pyrazine-5(4H)-carboxylate

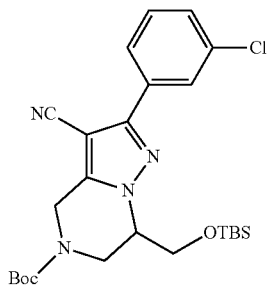 [SMILES: CC(C)(C)OC(=O)N1Cc2c(C#N)c(-c3cccc(Cl)c3)nn2C(CO[Si](C)(C)C(C)(C)C)C1]

To a solution of Intermediate A1L (1.0 g, 1.656 mmol) in DMF (16.56 mL) was added CuCN (0.371 g, 4.14 mmol) and the reaction mixture was heated in a sealed tube in an oil bath at 120° C. for 16 h. The inorganics were then filtered off and the filter cake was washed with EtOAc. The combined filtrate was concentrated under reduced pressure to give a crude residue. It was purified by silica gel chromatography (80 g REDISEP® column, eluting with a gradient of 10 to 15% EtOAc in hexanes). Fractions containing the product were combined and evaporated to afford Intermediate A1M (0.425 g, 51%) as an oil. MS(ES): m/z=504.08 [M+H]$^+$; $^1$H NMR (400 MHz, DMSO-d$_6$) δ ppm 7.90-7.78 (m, 2H), 7.69-7.50 (m, 2H), 4.88 (d, J=17.6 Hz, 1H), 4.71 (d, J=17.6 Hz, 1H), 4.48 (br. s., 1H), 4.13 (br. s., 1H), 4.00-3.91 (m, 2H), 3.81 (br. s., 1H), 1.53-1.43 (m, 9H), 0.88-0.77 (m, 9H).

Intermediate A1N: tert-Butyl 3-carbamoyl-2-(3-chlorophenyl)-7-(hydroxymethyl)-6,7-dihydropyrazolo[1,5-a]pyrazine-5(4H)-carboxylate

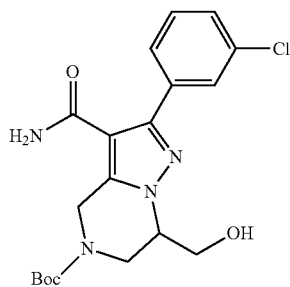 [SMILES: CC(C)(C)OC(=O)N1Cc2c(C(N)=O)c(-c3cccc(Cl)c3)nn2C(CO)C1]

To a solution of Intermediate A1M (1.4 g, 2.78 mmol) in DMSO (27 mL) was added a 5M aq. solution of KOH (2.78 mL, 13.91 mmol) and H$_2$O$_2$(5.68 mL, 55.7 mmol, 30% w/v in H$_2$O) and the reaction mixture was stirred at room temperature for 3 h. It was then diluted with a lot of water and the aq. phase was extracted with EtOAc (3×50 mL). The combined organic layer was washed with water, brine, dried over anhydrous MgSO$_4$, filtered and concentrated under reduced pressure to give a crude solid. It was purified by silica gel chromatography (80 g REDISEP® column, eluting with 100% EtOAc). Fractions containing the product were combined and evaporated to afford TBS cleaved Intermediate A1N (0.95 g, 84%) as a white solid. MS(ES): m/z=407 [M+H]$^+$.

Intermediate A1O: 2-(3-Chlorophenyl)-7-(hydroxymethyl)-4,5,6,7-tetrahydropyrazolo[1,5-a]pyrazine-3-carboxamide

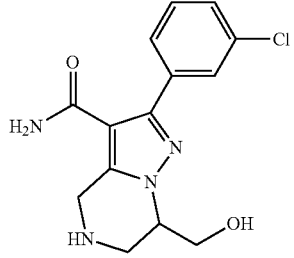 [SMILES: NC(=O)c1c(-c2cccc(Cl)c2)nn2c1CNCC2CO]

To a solution of Intermediate A1N (0.17 g, 0.418 mmol) in DCM (4.18 mL) was added TFA (0.644 mL, 8.36 mmol) and the reaction mixture was stirred at room temperature for 1 h. The volatiles were then evaporated under reduced pressure and the residue was basified with saturated aq. solution of NaHCO$_3$. The two layers were separated and the aq. layer was extracted with DCM (3×10 mL). The combined organic layer was washed with brine, dried over anhydrous MgSO$_4$, filtered and concentrated under reduced pressure to give a crude solid. It was purified by silica gel chromatography (25 g REDISEP® column, eluting with 35% MeOH in DCM). Fractions containing the product were combined and evaporated to afford Intermediate A1O (0.073 g, 57%) as a white solid. MS(ES): m/z=307 [M+H]$^+$.

Compound A1: 2-(3-Chlorophenyl)-N$^5$-(4-cyanophenyl)-7-(hydroxymethyl)-6,7-dihydropyrazolo[1,5-a]pyrazine-3,5(4H)-dicarboxamide

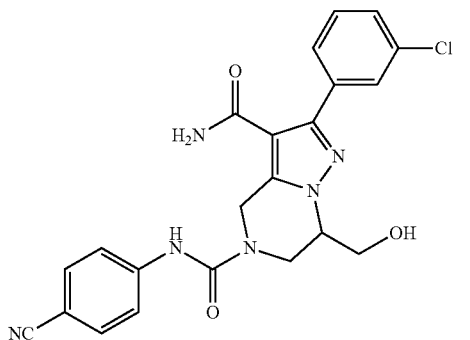 [SMILES: N#Cc1ccc(NC(=O)N2Cc3c(C(N)=O)c(-c4cccc(Cl)c4)nn3C(CO)C2)cc1]

To a solution of Intermediate A1O (0.027 g, 0.088 mmol) in DMF (1.76 mL) were added 4-isocyanatobenzonitrile (0.019 g, 0.132 mmol) and TEA (0.037 mL, 0.264 mmol) and the reaction mixture was stirred at room temperature for 2 h. The mixture was then filtered off and the filtrate was purified via preparative LC/MS. Fractions containing the desired product were combined and evaporated to afford Compound A1 (0.029 g, 70%). MS(ES): m/z=451 [M+H]$^+$; HPLC Ret. Time 1.41 min. and 2.16 min. (HPLC Methods H and I); $^1$H NMR (600 MHz, DMSO-d$_6$) δ ppm 7.77-7.69 (m, 3H), 7.69-7.60 (m, 3H), 7.50-7.40 (m, 2H), 7.38 (br. s., 1H), 7.23 (br. s., 1H), 4.99-4.84 (m, 2H), 4.38-4.28 (m, 1H), 4.12-4.01 (m, 2H), 3.96-3.87 (m, 1H), 3.81 (dd, J=11.0, 7.3 Hz, 1H), 1.91 (s, 1H).

The Compounds described in Table 30 were synthesized by reacting Intermediate A1O with the corresponding aniline.

TABLE 30

| Ex. No. | Structure | Name | Synthetic Method | [M + H]$^+$ | Ret. Time (min.) | HPLC Method |
|---|---|---|---|---|---|---|
| A2 | 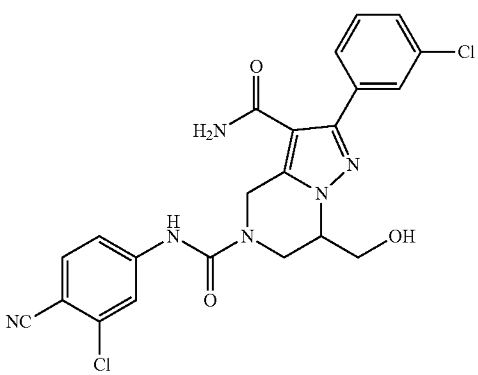 [SMILES: N#Cc1ccc(NC(=O)N2Cc3c(C(N)=O)c(-c4cccc(Cl)c4)nn3C(CO)C2)cc1Cl] | N$^5$-(3-Chloro-4-cyanophenyl)-2-(3-chlorophenyl)-7-(hydroxymethyl)-6,7-dihydropyrazolo[1,5-a]pyrazine-3,5(4H)-dicarboxamide | A | 485.2 | 1.43<br>2.32 | H<br>I |
| A3 | 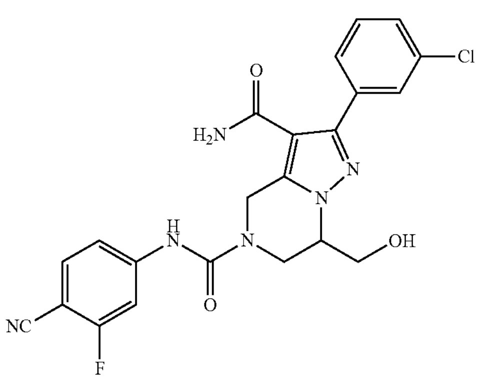 [SMILES: N#Cc1ccc(NC(=O)N2Cc3c(C(N)=O)c(-c4cccc(Cl)c4)nn3C(CO)C2)cc1F] | 2-(3-Chlorophenyl)-N$^5$-(4-cyano-3-fluorophenyl)-7-(hydroxymethyl)-6,7-dihydropyrazolo[1,5-a]pyrazine-3,5(4H)-dicarboxamide | A | 469.2 | 1.52<br>2.31 | H<br>I |

TABLE 30-continued

| Ex. No. | Structure | Name | Synthetic Method | [M + H]+ | Ret. Time (min.) | HPLC Method |
|---|---|---|---|---|---|---|
| A4 | 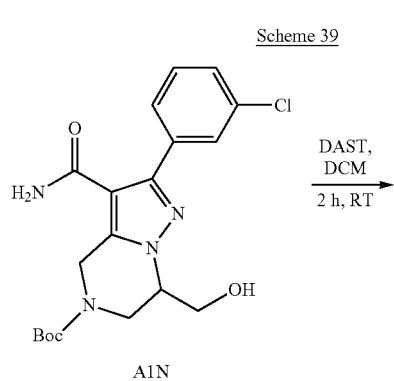 | 2-(3-Chlorophenyl)-N⁵-(3,5-dichlorophenyl)-7-(hydroxymethyl)-6,7-dihydropyrazolo[1,5-a]pyrazine-3,5(4H)-dicarboxamide | A | 495.90 | 2.29, 2.70 | H I |

Scheme 39

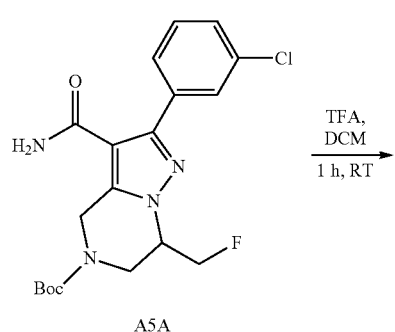

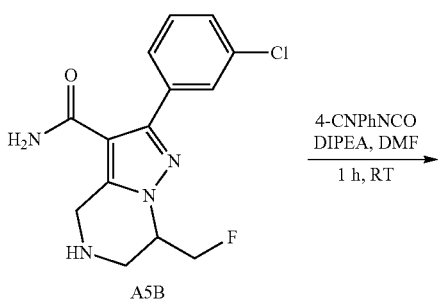

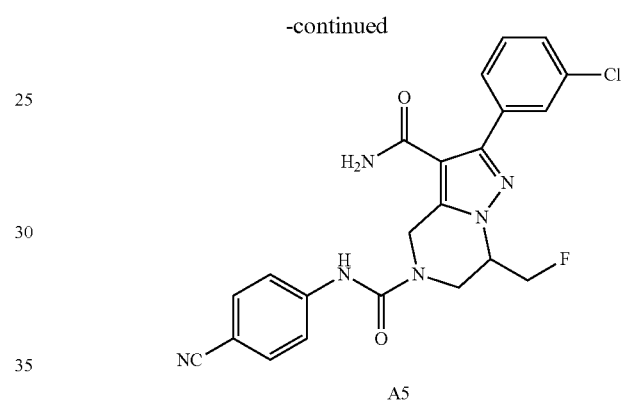

Intermediate A5A: tert-Butyl 3-carbamoyl-2-(3-chlorophenyl)-7-(fluoromethyl)-6,7-dihydropyrazolo[1,5-a]pyrazine-5(4H)-carboxylate

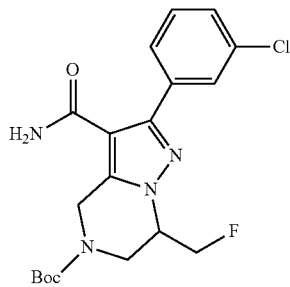 [SMILES: CC(C)(C)OC(=O)N1Cc2c(C(N)=O)c(-c3cccc(Cl)c3)nn2C(CF)C1]

To a suspension of Intermediate A1N (0.15 g, 0.369 mmol) in DCM (4.92 mL) cooled to −78° C., was added DAST (0.073 mL, 0.553 mmol). Soon the reaction mixture turned homogenous. The reaction was stirred at room temperature for 2 h. It was quenched with a saturated aq. solution of NaHCO₃. The organic layer was separated and the aq. layer was extracted with DCM (3×10 mL). The combined organic layer was washed with brine, dried over anhydrous MgSO₄, filtered and the filtrate concentrated under reduced pressure to give an oil. It was purified by silica gel chromatography (25 g REDISEP® column, eluting with 55% EtOAc in hexanes). Fractions containing the product were combined and evaporated to afford Intermediate A5A (0.054 g, 35.8%) as a white solid. MS(ES): m/z=409 [M+H]+.

Intermediate A5B: 2-(3-Chlorophenyl)-7-(fluoromethyl)-4,5,6,7-tetrahydropyrazolo[1,5-a]pyrazine-3-carboxamide, 2 TFA

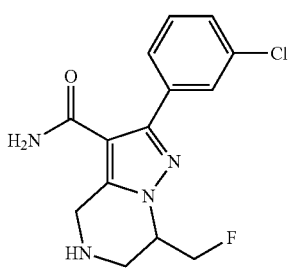 [SMILES: NC(=O)c1c(-c2cccc(Cl)c2)nn2c1CNCC2CF]

To a solution of Intermediate A5A (0.054 g, 0.132 mmol) in DCM (1.321 mL) was added TFA (0.102 mL, 1.321 mmol) and the reaction mixture was stirred at room temperature for 1 h. It was then concentrated under reduced pressure to provide a residue. The residue was dried under vacuum to afford Intermediate A5B as the bis TFA salt (0.071 g, >99%). MS(ES): m/z=309.0 [M+H]+.

Compound A5: 2-(3-Chlorophenyl)-N5-(4-cyanophenyl)-7-(fluoromethyl)-6,7-dihydropyrazolo[1,5-a]pyrazine-3,5(4H)-dicarboxamide

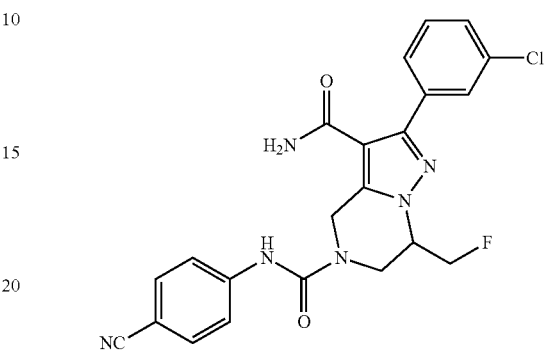

To a solution of Intermediate A5B (0.035 g, 0.065 mmol) in DMF (0.65 mL) were added 4-isocyanatobenzonitrile (0.019 g, 0.130 mmol) and DIPEA (0.057 mL, 0.326 mmol) and the reaction mixture was stirred at room temperature for 1 h. The mixture was then filtered off and the filtrate was purified via preparative LC/MS. Fractions containing the desired product were combined and evaporated to afford Compound A5 (0.017 g, 59%). MS(ES): m/z=453.30 [M+H]+; HPLC Ret. Time 1.44 min. and 2.31 min. (HPLC Methods H and I); 1H NMR (500 MHz, DMSO-d6) δ ppm 7.73 (d, J=7.6 Hz, 3H), 7.67 (d, J=8.5 Hz, 3H), 7.51-7.38 (m, 3H), 7.31 (br. s., 1H), 5.08 (d, J=5.8 Hz, 1H), 5.04-4.86 (m, 3H), 4.81 (d, J=7.9 Hz, 1H), 4.70 (br. s., 1H), 4.65 (br. s., 1H), 4.18 (d, J=10.1 Hz, 1H), 4.04 (dd, J=14.0, 6.4 Hz, 1H).

The Compounds described in Table 31 were synthesized by reacting Intermediate A5B with the corresponding reagents.

TABLE 31

| Ex. No. | Structure | Name | Synthetic Method | [M + H]+ | Ret. Time (min.) | HPLC Method |
|---|---|---|---|---|---|---|
| A6 | 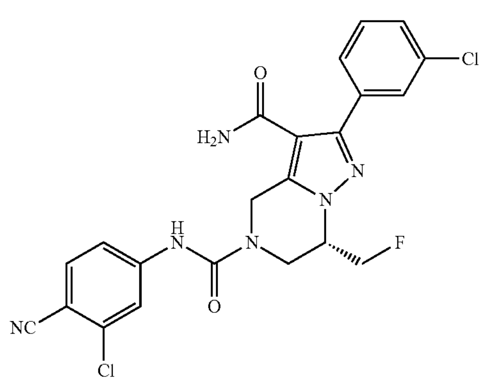 [SMILES: N#Cc1ccc(NC(=O)N2Cc3c(C(N)=O)c(-c4cccc(Cl)c4)nn3[C@H](CF)C2)cc1Cl] | (S)-N5-(3-Chloro-4-cyanophenyl)-2-(3-chlorophenyl)-7-(fluoromethyl)-6,7-dihydropyrazolo[1,5-a]pyrazine-3,5(4H)-dicarboxamide | B | 487.3 | 1.70, 2.62 | H I |

TABLE 31-continued

| Ex. No. | Structure | Name | Synthetic Method | [M + H]+ | Ret. Time (min.) | HPLC Method |
|---|---|---|---|---|---|---|
| A7 | 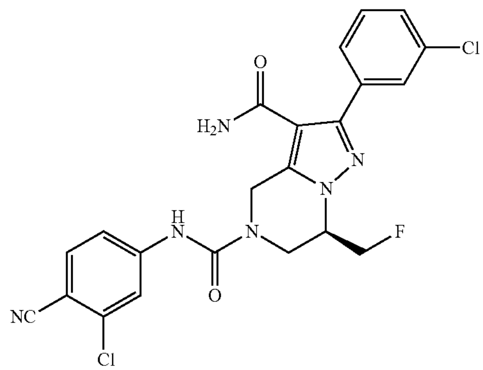 [SMILES: N#Cc1ccc(NC(=O)N2Cc3c(C(N)=O)c(-c4cccc(Cl)c4)nn3[C@@H](CF)C2)cc1Cl] | (R)-N5-(3-Chloro-4-cyanophenyl)-2-(3-chlorophenyl)-7-(fluoromethyl)-6,7-dihydropyrazolo[1,5-a]pyrazine-3,5(4H)-dicarboxamide | B | 487.4 | 1.70, 2.64 | H I |
| A8 | 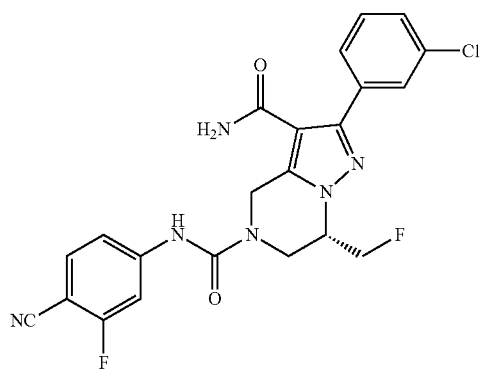 [SMILES: N#Cc1ccc(NC(=O)N2Cc3c(C(N)=O)c(-c4cccc(Cl)c4)nn3[C@H](CF)C2)cc1F] | (S)-2-(3-Chlorophenyl)-N5-(4-cyano-3-fluorophenyl)-7-(fluoromethyl)-6,7-dihydropyrazolo[1,5-a]pyrazine-3,5(4H)-dicarboxamide | B | 471.3 | 1.64, 2.53 | H I |
| A9 | 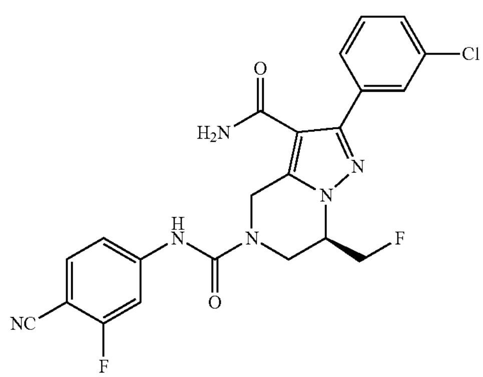 [SMILES: N#Cc1ccc(NC(=O)N2Cc3c(C(N)=O)c(-c4cccc(Cl)c4)nn3[C@@H](CF)C2)cc1F] | (R)-2-(3-Chlorophenyl)-N5-(4-cyano-3-fluorophenyl)-7-(fluoromethyl)-6,7-dihydropyrazolo[1,5-a]pyrazine-3,5(4H)-dicarboxamide | B | 471.4 | 1.61, 2.55 | H I |
| A10 | 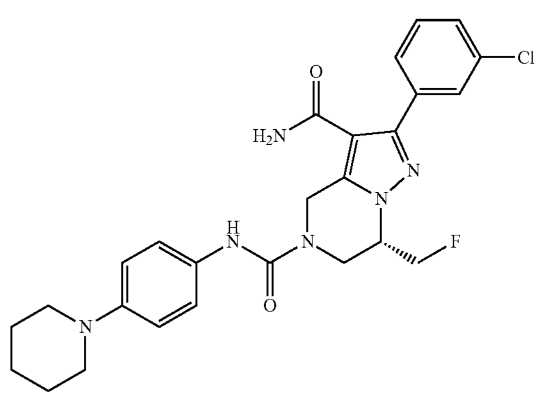 [SMILES: NC(=O)c1c(-c2cccc(Cl)c2)nn2c1CN(C(=O)Nc1ccc(N3CCCCC3)cc1)C[C@H]2CF] | (S)-2-(3-Chlorophenyl)-7-(fluoromethyl)-N5-(4-(piperidin-1-yl)phenyl)-6,7-dihydropyrazolo[1,5-a]pyrazine-3,5(4H)-dicarboxamide | D | 511.2 | 1.794, 3.106 | H I |

TABLE 31-continued
| Ex. No. | Structure | Name | Synthetic Method | [M + H]+ | Ret. Time (min.) | HPLC Method |
|---|---|---|---|---|---|---|
| A11 | 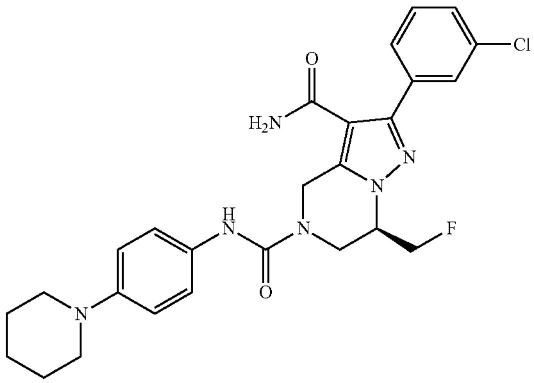 [SMILES: NC(=O)c1c(-c2cccc(Cl)c2)nn2c1CN(C(=O)Nc1ccc(N3CCCCC3)cc1)C[C@@H]2CF] | (R)-2-(3-Chlorophenyl)-7-(fluoromethyl)-$N^5$-(4-(piperidin-1-yl)phenyl)-6,7-dihydropyrazolo[1,5-a]pyrazine-3,5(4H)-dicarboxamide | D | 511.2 | 1.785, 3.115 | H I |
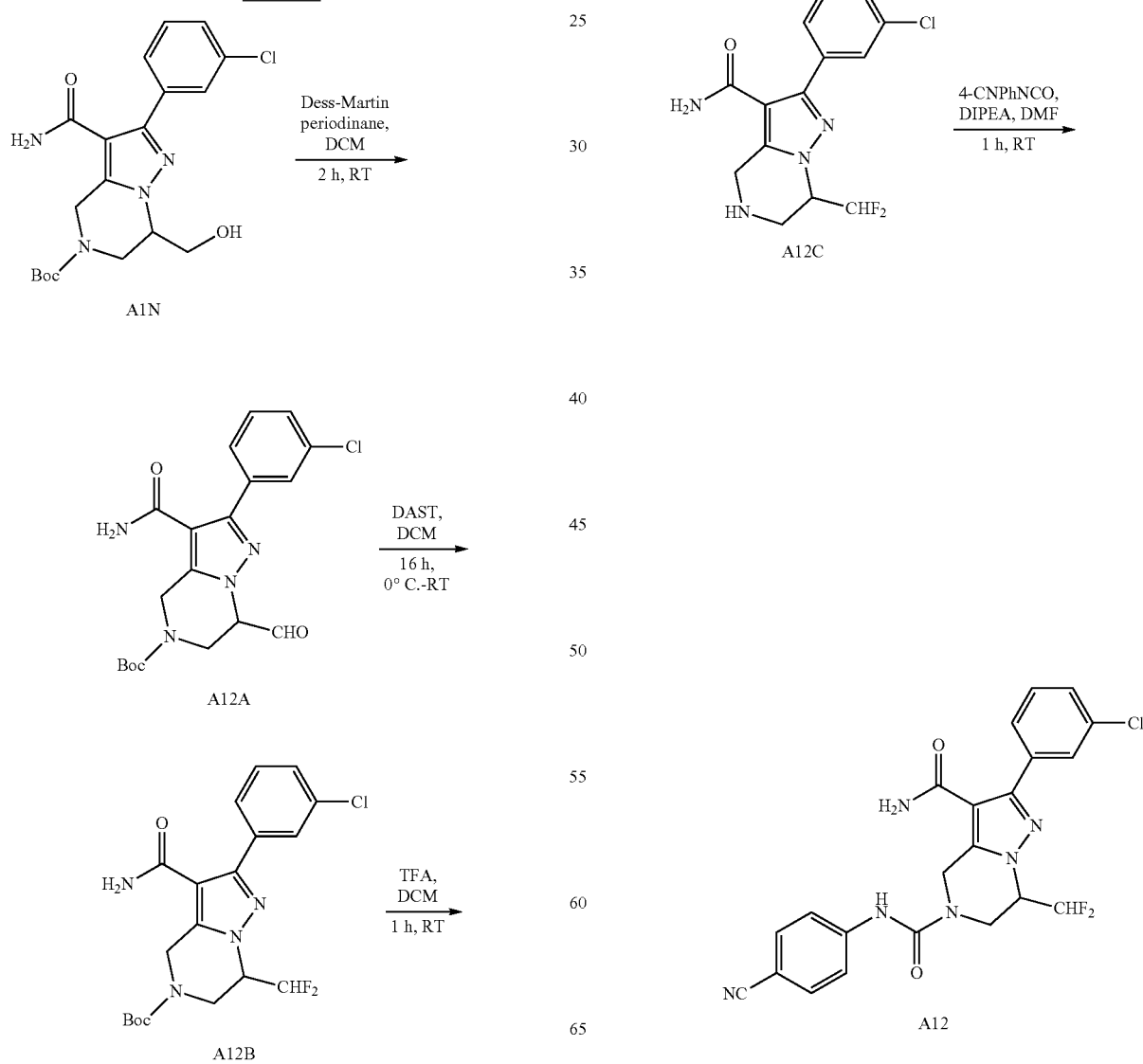
Scheme 40

Intermediate A12A: tert-Butyl 3-carbamoyl-2-(3-chlorophenyl)-7-formyl-6,7-dihydropyrazolo[1,5-a]pyrazine-5(4H)-carboxylate

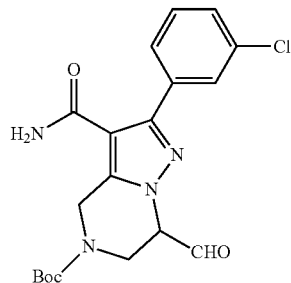 [SMILES: CC(C)(C)OC(=O)N1Cc2c(C(N)=O)c(-c3cccc(Cl)c3)nn2C(C=O)C1]

To a suspension of Intermediate A1N (0.2 g, 0.492 mmol) in DCM (4.92 mL) was added Dess-Martin periodinane (0.271 g, 0.639 mmol) and the reaction mixture was stirred at RT for 16 h. The mixture was then quenched with a saturated solution of aq. NaHCO$_3$. The two layers were separated and the aq. layer was extracted with DCM (2×10 mL). The combined organic layer was washed with brine, dried over anhydrous MgSO$_4$, filtered and the filtrate was concentrated under reduced pressure to give an oil. It was purified by silica gel chromatography (40 g REDISEP® column, eluting with a gradient of 75% EtOAc in hexanes to 100% EtOAc). Fractions containing the product were combined and evaporated to afford Intermediate A12A (0.054 g, 35.8%) as a white solid. MS(ES): m/z=409 [M+H]$^+$; $^1$H NMR (400 MHz, chloroform-d) δ ppm 9.75 (s, 1H), 7.65-7.54 (m, 1H), 7.54-7.33 (m, 4H), 5.50 (br. s., 1H), 4.96 (d, J=16.8 Hz, 2H), 4.77 (br. s., 1H), 4.59 (d, J=16.1 Hz, 1H), 3.65 (d, J=12.3 Hz, 1H), 1.58-1.37 (m, 9H).

Intermediate A12B: tert-Butyl 3-carbamoyl-2-(3-chlorophenyl)-7-(difluoromethyl)-6,7-dihydropyrazolo[1,5-a]pyrazine-5(4H)-carboxylate

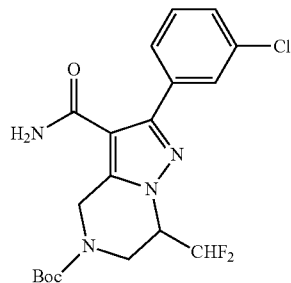 [SMILES: CC(C)(C)OC(=O)N1Cc2c(C(N)=O)c(-c3cccc(Cl)c3)nn2C(C(F)F)C1]

To a solution of Intermediate A12A (0.105 g, 0.259 mmol) in DCM (2.59 mL) at 0° C. was added, DAST (0.103 mL, 0.778 mmol) and the reaction mixture was stirred at room temperature for 16 h. The reaction was then quenched with a saturated aq. solution of NaHCO$_3$. The two layers were separated and the aq. layer was extracted with DCM (2×10 mL). The combined organic layer was washed with brine, dried over anhydrous MgSO$_4$, filtered and the filtrate concentrated under reduced pressure to give an oil. It was purified by silica gel chromatography (25 g REDISEP® column, eluting with a gradient of 55 to 65% EtOAc in hexanes). Fractions containing the product were combined and evaporated to afford Intermediate A12B as a yellow solid. MS(ES): m/z=427 [M+H]$^+$.

Intermediate A12C: 2-(3-Chlorophenyl)-7-(difluoromethyl)-4,5,6,7-tetrahydropyrazolo[1,5-a]pyrazine-3-carboxamide, 2 TFA

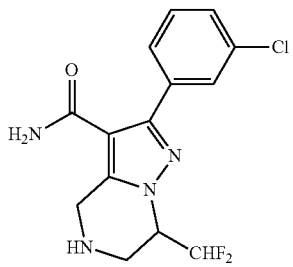 [SMILES: NC(=O)c1c(-c2cccc(Cl)c2)nn2c1CNCC2C(F)F]

Intermediate A12C was synthesized analogous to Intermediate A5B (Scheme 39) by reacting Intermediate A12B with TFA. Intermediate A12C (0.029 g, 20%) was subjected to analoging as the bis TFA salt. MS(ES): m/z=327 [M+H]$^+$.

Compound A12: 2-(3-Chlorophenyl)-N$^5$-(4-cyanophenyl)-7-(difluoromethyl)-6,7-dihydropyrazolo[1,5-a]pyrazine-3,5(4H)-dicarboxamide

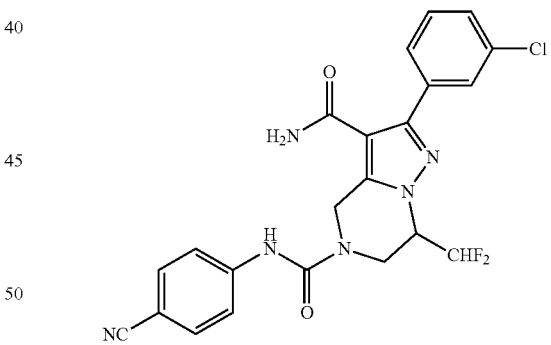

Compound A12 was synthesized analogous to Compound A5 by reacting Intermediate A12C with 4-isocyanatobenzonitrile. MS(ES): m/z=471.08 [M+H]$^+$; HPLC Ret. time 1.48 min. and 2.35 min. (HPLC Methods H and I respectively); $^1$H NMR (500 MHz, DMSO-d$_6$) δ ppm 7.96 (s, 1H), 7.78-7.70 (m, 3H), 7.67 (d, J=8.5 Hz, 3H), 7.54-7.42 (m, 3H), 7.35 (br. s., 1H), 6.55 (br. s., 1H), 5.16 (d, J=17.1 Hz, 1H), 4.93 (br. s., 1H), 4.82 (d, J=17.4 Hz, 1H), 4.50 (dd, J=14.3, 3.1 Hz, 1H), 3.93-3.79 (m, 1H).

Scheme 41

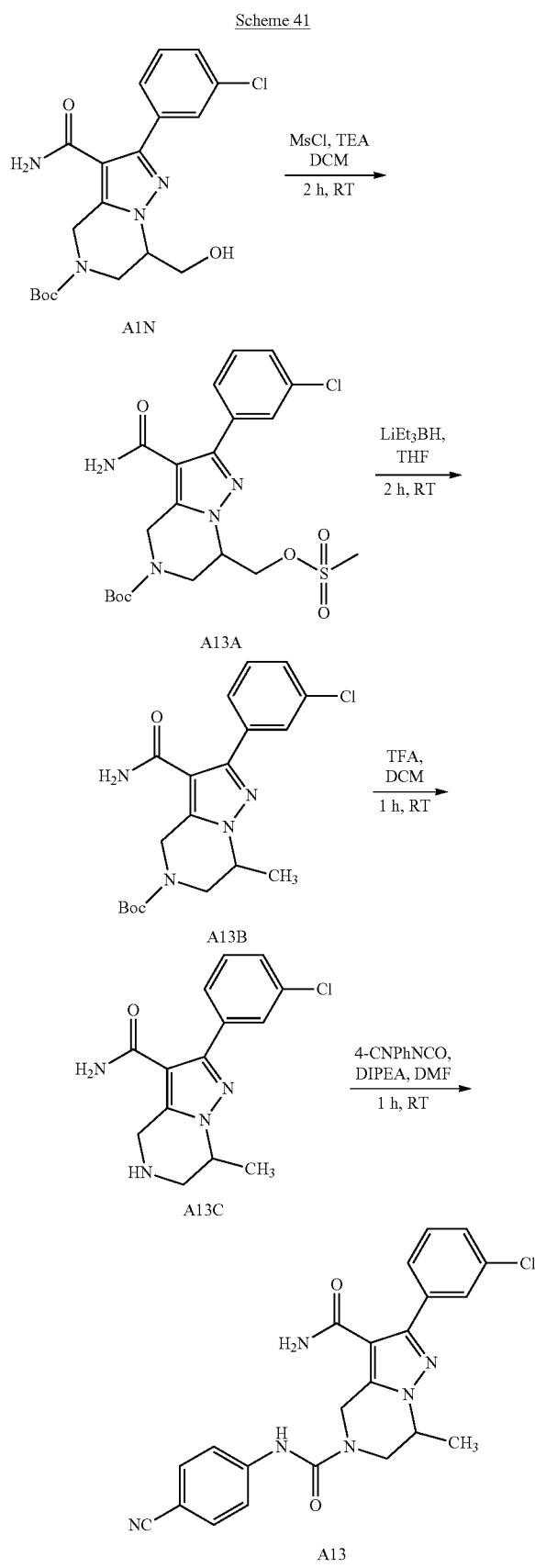

Intermediate A13A: tert-Butyl 3-carbamoyl-2-(3-chlorophenyl)-7-(((methylsulfonyl)oxy)methyl)-6,7-dihydropyrazolo[1,5-a]pyrazine-5(4H)-carboxylate

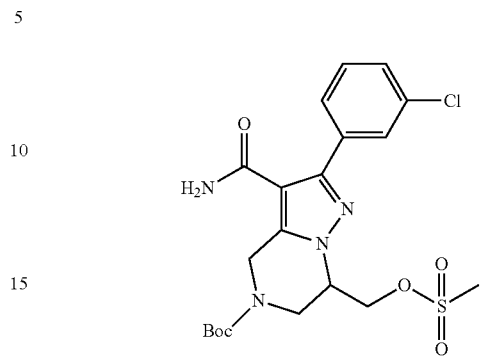

To an ice-cold suspension of Intermediate A1N (0.3 g, 0.737 mmol) in DCM (7.37 mL) was added TEA (0.123 mL, 0.885 mmol), followed by a dropwise addition of methanesulfonyl chloride (0.063 mL, 0.811 mmol). The resultant homogenous reaction mixture was stirred at room temperature for 2 h. The reaction was then quenched with a saturated aq. solution of NaHCO$_3$. The two layers were separated and the aq. layer was extracted with DCM (2×10 mL). The combined organic layer was washed with brine, dried over anhydrous MgSO$_4$, filtered and the filtrate was concentrated under reduced pressure to give an oil. It was purified by silica gel chromatography (40 g REDISEP® column, eluting with a gradient of 75% to 85% EtOAc in hexanes). Fractions containing the product were combined and evaporated to afford Intermediate A13A (0.208 g, 58.2%) as a white foam. MS(ES): m/z=485 [M+H]$^+$.

Intermediate A13B: tert-Butyl 3-carbamoyl-2-(3-chlorophenyl)-7-methyl-6,7-dihydropyrazolo[1,5-a]pyrazine-5(4H)-carboxylate

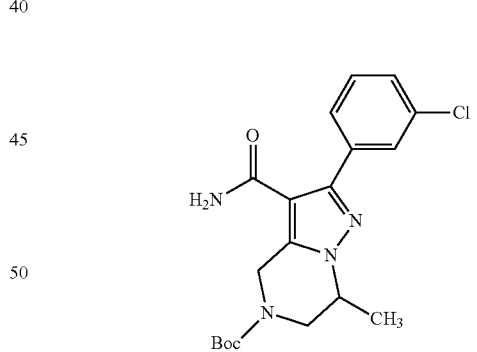

To a solution of Intermediate A13A (0.08 g, 0.165 mmol) in THF (3.30 mL) was added dropwise at room temperature, a 1M solution of LiEt$_3$BH in THF (1.650 mL, 1.650 mmol) and the reaction mixture was stirred for 2 h. It was then carefully quenched with water and extracted with DCM (3×10 mL). The combined organic layer was washed with brine, dried over anhydrous MgSO$_4$, filtered and the filtrate concentrated under reduced pressure to give an oil. It was purified by silica gel chromatography (25 g REDISEP® column, eluting with a 50% EtOAc in hexanes). Fractions containing the product were combined and evaporated to afford Intermediate A13B (0.053 g, 81%) as a white foam. MS(ES): m/z=391.1 [M+H]$^+$.

Intermediate A13C: 2-(3-Chlorophenyl)-7-methyl-4,5,6,7-tetrahydropyrazolo[1,5-a]pyrazine-3-carboxamide, 2 TFA

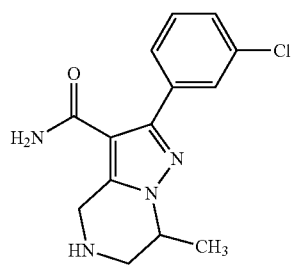 [SMILES: CC1CNCc2c(C(N)=O)c(-c3cccc(Cl)c3)nn21]

Intermediate A13C was synthesized analogous to Intermediate A5B by reacting Intermediate A13B with TFA. Intermediate A13C (0.07 g, >99%) was subjected to analoging as the bis TFA salt. MS(ES): m/z=291 [M+H]$^+$.

Compound A13: 2-(3-Chlorophenyl)-N$^5$-(4-cyanophenyl)-7-methyl-6,7-dihydropyrazolo[1,5-a]pyrazine-3,5(4H)-dicarboxamide

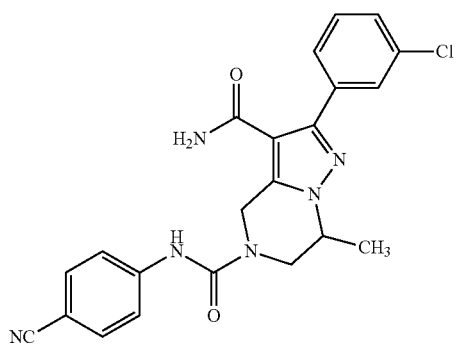 [SMILES: CC1CN(C(=O)Nc2ccc(C#N)cc2)Cc2c(C(N)=O)c(-c3cccc(Cl)c3)nn21]

Compound A13 was synthesized analogous to Compound A5 by reacting Intermediate A13C with 4-isocyanatobenzonitrile. MS(ES): m/z=435.0 [M+H]$^+$; HPLC Ret. Time 1.48 min. and 2.41 min. (Methods H and I respectively); $^1$H NMR (500 MHz, DMSO-d$_6$) δ ppm 9.38 (s, 1H), 7.77-7.59 (m, 6H), 7.49-7.41 (m, 2H), 7.38 (br. s., 1H), 7.22 (br. s., 1H), 4.97 (d, J=17.1 Hz, 1H), 4.86 (d, J=17.1 Hz, 1H), 4.53-4.38 (m, 1H), 4.11 (dd, J=13.7, 3.7 Hz, 1H), 3.72 (dd, J=14.2, 6.9 Hz, 1H), 2.89 (s, 1H), 2.73 (s, 1H), 1.49 (d, J=6.4 Hz, 3H).

Scheme 42

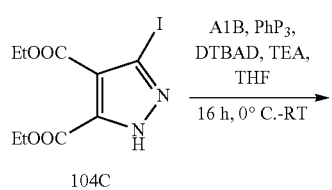

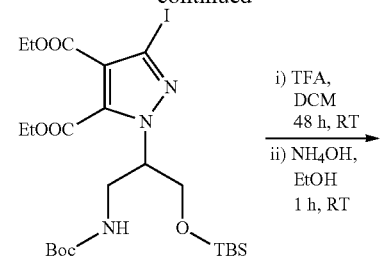

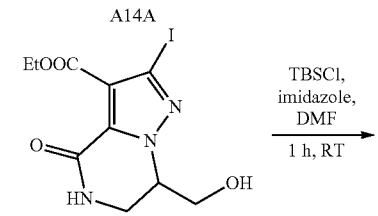

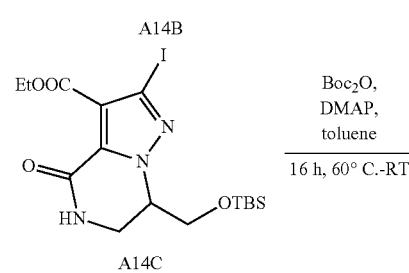

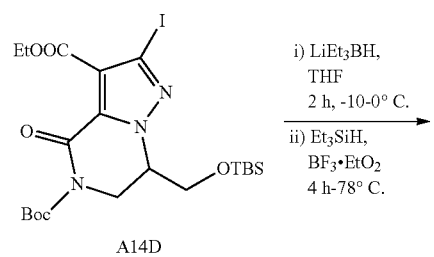

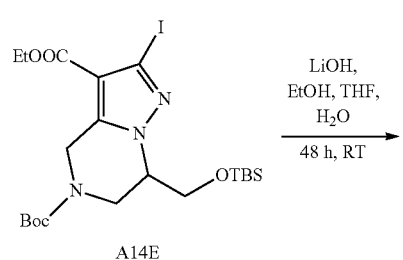

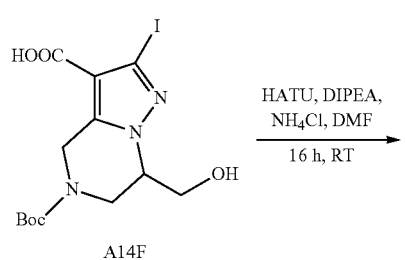

-continued

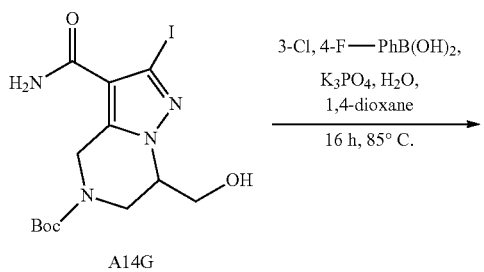

A14G

3-Cl, 4-F—PhB(OH)₂,
K₃PO₄, H₂O,
1,4-dioxane
───────────────→
16 h, 85° C.

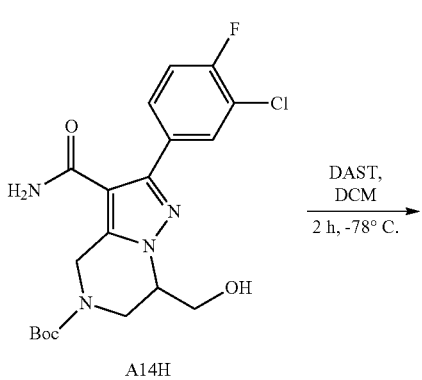

A14H

DAST,
DCM
──────→
2 h, -78° C.

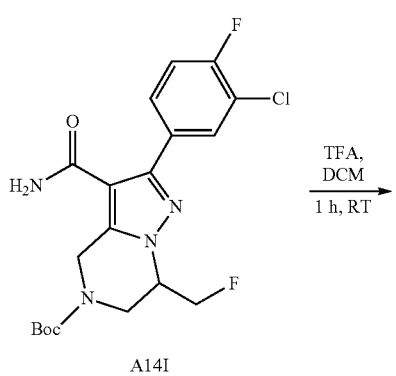

A14I

TFA,
DCM
──────→
1 h, RT

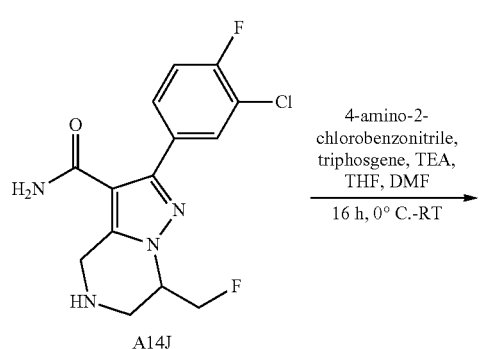

A14J 4-amino-2-
chlorobenzonitrile,
triphosgene, TEA,
THF, DMF
──────────────→
16 h, 0° C.-RT -continued

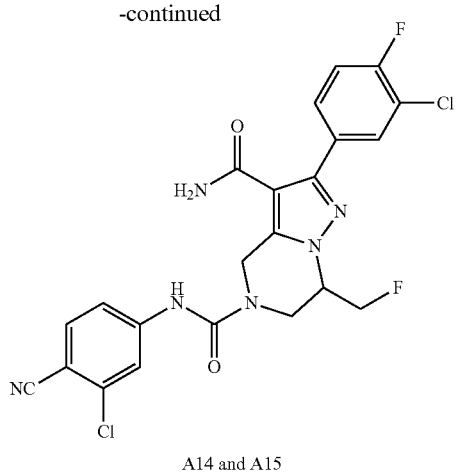

A14 and A15

Intermediate A14A: Diethyl 1-(2,2,3,3,11,11-hex-amethyl-9-oxo-4,10-dioxa-8-aza-3-siladodecan-6-yl)-3-iodo-1H-pyrazole-4,5-dicarboxylate

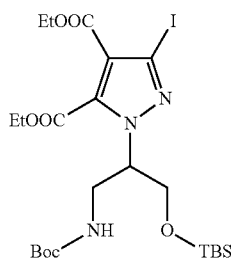

A solution of Intermediate 104C (1.0 g, 2.96 mmol), Intermediate A1B (1.13 g, 3.70 mmol), triphenylphosphine (0.78 g, 2.96 mmol) and TEA (0.41 mL, 2.96 mmol) in THF (14.79 mL) was cooled to 0° C. and to it was added DTBAD (0.7 g, 2.96 mmol). The reaction mixture was then allowed to stir at room temperature for 16 h and then diluted with water and EtOAc. The two layers were separated and the aq. layer was extracted with EtOAc (2×20 mL). The combined organic layer was washed with brine, dried over anhydrous MgSO₄, filtered and the filtrate was concentrated to give an oil. It was purified by silica gel chromatography (80 g REDISEP® column, eluting with a gradient of 0 to 15% EtOAc in hexanes). Fractions containing the product were combined and evaporated to afford Intermediate A14A (1.2 g, 65%) as a solid. MS(ES): m/z=648.1 [M+Na]⁺.

Intermediate A14B: Ethyl 7-(hydroxymethyl)-2-iodo-4-oxo-4,5,6,7-tetrahydropyrazolo[1,5-a]pyrazine-3-carboxylate

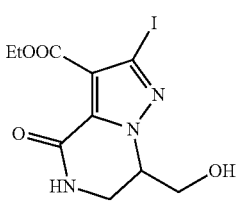 [SMILES: CCOC(=O)c1c(I)nn2c1C(=O)NCC2CO]

To a solution of Intermediate A14A (21.5 g, 34.4 mmol) in DCM (344 mL) was added TFA (47.7 mL, 619 mmol) and the reaction mixture was allowed to stir at room temperature for 48 h. The volatiles were then concentrated under reduced pressure. The residue thus obtained was directly taken up in EtOH (75 mL) and to it was added ammonium hydroxide (581 mL, 447 mmol, 30% aq.). Soon a precipitate was generated. The stirring was continued for 1 h at room temperature. The generated solid was filtered off. The filter cake was rinsed with a small amount of EtOH. The combined filtrate was partially evaporated under reduced pressure to generate more precipitate. This solid was combined with the initial filter cake and air-dried to afford Intermediate A14B (18 g, 71.6%) as a white solid. MS(ES): m/z=365.8 [M+H]$^+$.

Intermediate A14C: Ethyl 7-(((tert-butyldimethylsilyl)oxy)methyl)-2-iodo-4-oxo-4,5,6,7-tetrahydropyrazolo[1,5-a]pyrazine-3-carboxylate

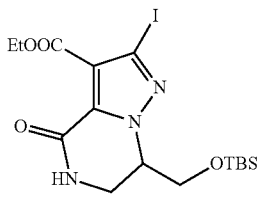 [SMILES: CCOC(=O)c1c(I)nn2c1C(=O)NCC2CO[Si](C)(C)C(C)(C)C]

To a solution of Intermediate A14B (16.79 g, 46.0 mmol) in DMF (230 mL) was added TBSCl (8.32 g, 55.2 mmol), followed by imidazole (4.70 g, 69.0 mmol) and the reaction mixture was stirred at room temperature for 1 h. The mixture was then concentrated to dryness, the residue was diluted with water and extracted with DCM (2×200 mL). The combined organic layer was washed with brine, dried over anhydrous MgSO$_4$, filtered and the filtrate was concentrated to give an oil. It was purified by silica gel chromatography (REDISEP® 330 g, eluting with a gradient of 10 to 55% EtOAc in hexanes). Fractions containing the product were combined and evaporated to afford Intermediate A14C (16 g, 72.6%) as a solid. MS(ES): m/z=479.9 [M+H]$^+$.

Intermediate A14D: 5-tert-Butyl 3-ethyl7-(((tert-butyldimethylsilyl)oxy)methyl)-2-iodo-4-oxo-6,7-dihydropyrazolo[1,5-a]pyrazine-3,5(4H)-dicarboxylate

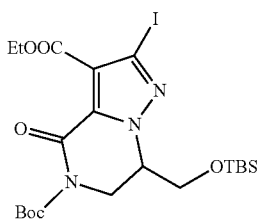 [SMILES: CCOC(=O)c1c(I)nn2c1C(=O)N(C(=O)OC(C)(C)C)CC2CO[Si](C)(C)C(C)(C)C]

To a solution of Intermediate A14C (11.74 g, 24.49 mmol) in toluene (188 mL) was added DMAP (4.49 g, 36.7 mmol), followed by Boc$_2$O (6.41 g, 29.4 mmol) and the reaction mixture was heated in an oil bath at 60° C. for 1 h and then at room temperature for 16 h. It was then concentrated to dryness to afford a solid residue, which was purified by silica gel chromatography (REDISEP® 220 g, eluting with a gradient of 5 to 25% EtOAc in hexanes). Fractions containing the product were combined and evaporated to afford Intermediate A14D (13.7 g, 96%) as a white solid. MS(ES): m/z=580.1 [M+H]$^+$.

Intermediate A14E: 5-tert-Butyl 3-ethyl7-(((tert-butyldimethylsilyl)oxy)methyl)-2-iodo-6,7-dihydropyrazolo[1,5-a]pyrazine-3,5(4H)-dicarboxylate

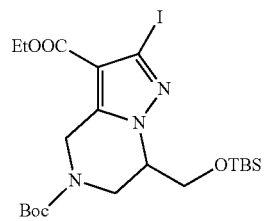 [SMILES: CCOC(=O)c1c(I)nn2c1CN(C(=O)OC(C)(C)C)CC2CO[Si](C)(C)C(C)(C)C]

To a −10° C. solution of Intermediate A14D (1.0 g, 1.726 mmol) in THF (4.31 mL), was added SUPER-HYDRIDE® (2.07 mL, 2.071 mmol, 1M in THF) dropwise over 30 min., and the reaction mixture was stirred at 0° C. for 2 h. It was then quenched with water and extracted with EtOAc (2×25 mL). The combined organic layer was washed with brine, dried over anhydrous MgSO$_4$, filtered and the filtrate was concentrated to afford the partially reduced Intermediate as a foam. MS(ES): m/z=604.15 [M+Na]$^+$. It was used in the next step without further purification.

To a −78° C. solution of the above Intermediate in DCM (~8 mL) was added, triethylsilane (0.85 mL, 5.18 mmol), followed by BF$_3$.OEt$_2$ (0.65 mL, 5.18 mmol) and the reaction mixture was stirred at that temperature for 1 h. Thereafter, more triethylsilane (0.852 mL, 5.18 mmol) and BF$_3$.OEt$_2$ (0.656 mL, 5.18 mmol) were added and stirring continued at −78° C. for 3 h. The reaction was quenched with a satd. aq. solution of NaHCO$_3$, the two layers were separated and the aq. layer was extracted with DCM (2×15 mL). The combined organic layer was washed with brine, dried over anhydrous MgSO$_4$, filtered and the filtrate was concentrated to afford an oil. It was purified by silica gel chromatography (80 g REDISEP® column, eluting with a gradient of 5 to 15% EtOAc in hexanes). Fractions containing the product were combined and evaporated to afford Intermediate A14E (0.42 g, 43%) as a white solid. MS(ES): m/z=566.15 [M+H]$^+$.

Intermediate A14F: 5-(tert-Butoxycarbonyl)-7-(hydroxymethyl)-2-iodo-4,5,6,7-tetrahydropyrazolo[1,5-a]pyrazine-3-carboxylic acid

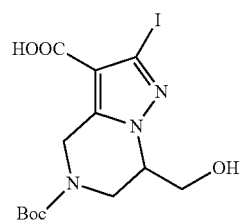 [SMILES: CC(C)(C)OC(=O)N1Cc2c(C(=O)O)c(I)nn2C(CO)C1]

To a solution of Intermediate A14E (10.0 g, 17.68 mmol) in ethanol (26.8 mL) and THF (53.6 mL) was added a suspension of LiOH (6.05 g, 248 mmol) in water (17.86 mL) and the reaction mixture was stirred at room temperature for 48 h. The volatiles were concentrated under reduced pressure and the aq. residue was extracted with Et$_2$O. The Et$_2$O layer was discarded and the aq. layer was acidified with a 1N aqueous solution of HCl to pH=2. It was then extracted with DCM (4×50 mL). The combined organic layer was washed with brine, dried over anhydrous MgSO$_4$, filtered and the filtrate was concentrated to afford Intermediate A14F (6.87 g, 92%) as a white solid, with the concomitant loss of the TBS group. MS(ES): m/z=446.1 [M+Na]$^+$.

Intermediate A14G: tert-Butyl 3-carbamoyl-7-(hydroxymethyl)-2-iodo-6,7-dihydropyrazolo[1,5-a]pyrazine-5(4H)-carboxylate

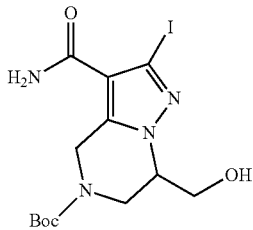

To a solution of Intermediate A14F (6.87 g, 16.23 mmol) in DMF (27.1 mL) were added DIPEA (11.34 mL, 64.9 mmol) and HATU (12.34 g, 32.5 mmol) and the mixture was stirred at room temperature for 30 min., followed by the addition of NH$_4$Cl (3.47 g, 64.9 mmol). The resultant mixture continued to stir at room temperature for 16 h. It was diluted with water (250 mL) and extracted with DCM (3×70 mL). The combined organic layer was washed with copious amounts of water, brine, dried over anhydrous MgSO$_4$, filtered and the filtrate was concentrated to afford an oil. It was purified by silica gel chromatography (120 g REDISEP® column, eluting with 5% EtOAc in hexanes). Fractions containing the product were combined and evaporated to afford Intermediate A9G (6.75 g, 98%) as a solid. MS(ES): m/z=423.1 [M+H]$^+$.

Intermediate A14H: tert-Butyl 3-carbamoyl-2-(3-chloro-4-fluorophenyl)-7-(hydroxymethyl)-6,7-dihydropyrazolo[1,5-a]pyrazine-5(4H)-carboxylate

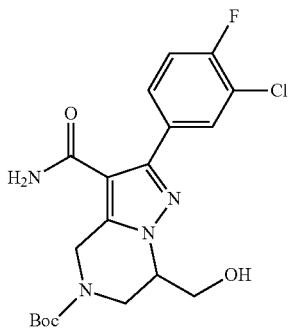 [SMILES: CC(C)(C)OC(=O)N1Cc2c(C(N)=O)c(-c3ccc(F)c(Cl)c3)nn2C(CO)C1]

To a degassed solution of Intermediate A14G (5.1 g, 12.08 mmol) and (3-chloro-4-fluorophenyl)boronic acid (3.16 g, 18.12 mmol) in a 2M aqueous solution of K$_3$PO$_4$ (18.12 mL, 36.2 mmol) and 1,4-dioxane (121 mL) was added PdCl$_2$(dppf) (0.884 g, 1.208 mmol). The reaction mixture was degassed again for 5 min. and then heated in a sealed tube in an oil bath at 85° C. for 16 h. The mixture was concentrated under reduced pressure to near dryness, the residue was partitioned between DCM and water, the two layers were separated and the aq. layer was extracted with DCM (2×40 mL). The combined organic layers were washed with brine, dried over anhydrous MgSO$_4$, filtered and the filtrate was concentrated to afford an oil. It was purified by silica gel chromatography (120 g REDISEP® column, eluting with a gradient of 65 to 90% EtOAc in hexanes). Fractions containing the product were combined and evaporated to afford Intermediate A14H (5.08 g, >99%) as a pale brown solid. MS(ES): m/z=425.2 [M+H]$^+$.

Intermediate A14I: tert-Butyl 3-carbamoyl-2-(3-chloro-4-fluorophenyl)-7-(fluoromethyl)-6,7-dihydropyrazolo[1,5-a]pyrazine-5(4H)-carboxylate

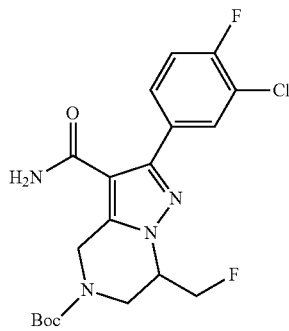 [SMILES: CC(C)(C)OC(=O)N1Cc2c(C(N)=O)c(-c3ccc(F)c(Cl)c3)nn2C(CF)C1]

To a −78° C. solution of Intermediate A14H (1.84 g, 4.33 mmol) in DCM (43.3 mL) was added DAST (0.57 mL, 4.33 mmol) dropwise and then the reaction mixture was allowed to stir at room temperature for 2 h. It was quenched with a satd. aq. solution of NaHCO$_3$, the organic layer was separated and the aq. layer was extracted with DCM (2×20 mL). The combined organic layer was washed with brine, dried over anhydrous MgSO$_4$, filtered and the filtrate was concentrated under reduced pressure to give a solid. It was purified by silica gel chromatography (120 g REDISEP® column, eluting with a gradient of 10 to 55% EtOAc in hexanes). Fractions containing the product were combined and evaporated to afford Intermediate A14I (0.56 g, 30.2%) as a white solid. MS(ES): m/z=427.2 [M+H]$^+$.

Intermediate A14J: 2-(3-Chloro-4-fluorophenyl)-7-(fluoromethyl)-4,5,6,7-tetrahydropyrazolo[1,5-a]pyrazine-3-carboxamide

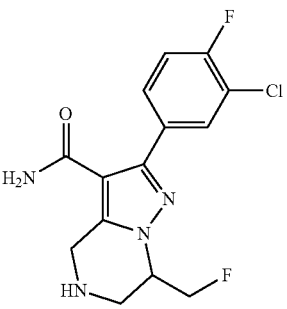

To a solution of Intermediate A14I (0.2 g, 0.466 mmol) in DCM (4.66 mL) was added TFA (0.72 mL, 9.32 mmol) and the reaction mixture was stirred at room temperature for 2 h. The volatiles were evaporated and the residue was basified with a satd. aq. solution of NaHCO$_3$ and extracted with a 5% solution of MeOH in DCM (3×10 mL). The combined organic layer was washed with brine, dried over anhydrous MgSO$_4$, filtered and the filtrate was concentrated under reduced pressure to give Intermediate A14J (0.15 g, 100%) as an off-white solid. MS(ES): m/z=327.2 [M+H]$^+$.

Compounds A14 and A15: N$^5$-(3-Chloro-4-cyanophenyl)-2-(3-chloro-4-fluorophenyl)-7-(fluoromethyl)-6,7-dihydropyrazolo[1,5-a]pyrazine-3,5(4H)-dicarboxamide A solution of 4-amino-2-chlorobenzonitrile (0.047 g, 0.306 mmol) and TEA (0.085 mL, 0.612 mmol) in THF (3.4 mL) was added dropwise to an ice-cold solution of triphosgene (0.034 g, 0.115 mmol) in THF (3.4 mL). This mixture was continued to stir at that temperature for 30 min., followed by the addition of a solution of Intermediate A14J (0.05 g, 0.153 mmol) in DMF (1.7 mL). The resultant reaction mixture was stirred at room temperature for 16 h. The volatiles were evaporated under reduced pressure and the residue was purified by preparative HPLC to afford a racemic mixture of Compounds A14 and A15. The individual enantiomers A14 and A15 were separated by chiral SFC purification using CHIRALPAK® IA preparative column (30×250) mm, 5 μm column, mobile phase 40% MeOH in CO$_2$, back pressure 150 bar, temperature 35° C., flow rate 70.0 mL/min for 11 min. UV monitored at 265 nm. Compound A14 (S)-isomer was eluted at 7.24 min. (12.2 mg, 100% ee, Yield=15.78%) and Compound A15 (R)-isomer was eluted at 8.61 min. (13.4 mg, 100% ee, Yield=17.33%). MS: m/z=505.3 [M+H]$^+$; HPLC Ret. Time 1.73 min. and 2.69 min. (Methods H and I respectively); $^1$H NMR (500 MHz, DMSO-d$_6$) δ ppm 7.92-7.80 (m, 3H), 7.75-7.66 (m, 1H), 7.59 (d, J=9.2 Hz, 1H), 7.49 (t, J=9.0 Hz, 1H), 7.43 (br. s., 1H), 7.31 (br. s., 1H), 5.02-4.92 (m, 2H), 4.90 (d, J=13.9 Hz, 1H), 4.80 (d, J=9.9 Hz, 1H), 4.69 (br. s., 1H), 4.65 (br. s., 1H), 4.17 (dd, J=14.3, 4.4 Hz, 1H), 4.05 (dd, J=14.1, 6.8 Hz, 1H).

The Compounds described in Table 32 were synthesized by reacting Intermediate A14J with the corresponding aniline.

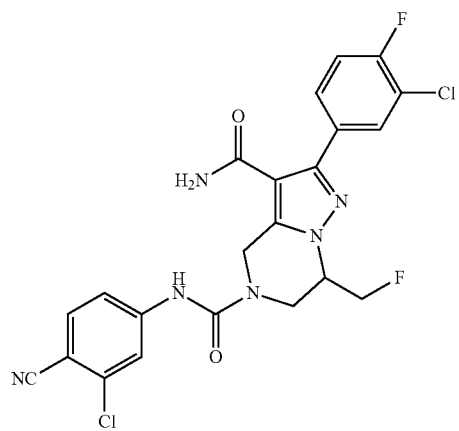 [SMILES: N#Cc1ccc(NC(=O)N2Cc3c(C(N)=O)c(-c4ccc(F)c(Cl)c4)nn3C(CF)C2)cc1Cl]

TABLE 32

| Ex. No. | Structure | Name | Synthetic Method | [M + H]$^+$ | Ret. Time (min.) | HPLC Method |
|---|---|---|---|---|---|---|
| A16 | 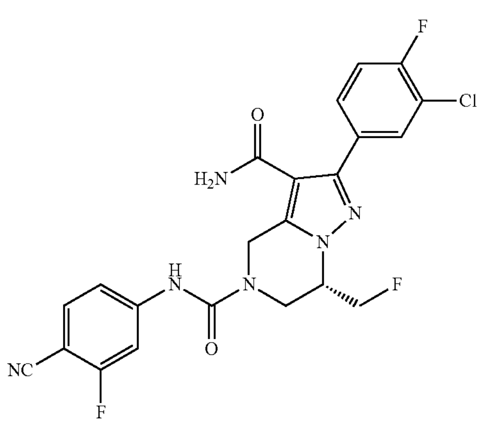 [SMILES: N#Cc1ccc(NC(=O)N2Cc3c(C(N)=O)c(-c4ccc(F)c(Cl)c4)nn3[C@H](CF)C2)cc1F] | (S)-2-(3-Chloro-4-fluorophenyl)-N$^5$-(4-cyano-3-fluorophenyl)-7-(fluoromethyl)-6,7-dihydropyrazolo[1,5-a]pyrazine-3,5(4H)-dicarboxamide | B | 489.3 | 1.67, 2.59 | H I |

TABLE 32-continued
| Ex. No. | Structure | Name | Synthetic Method | [M + H]+ | Ret. Time (min.) | HPLC Method |
|---|---|---|---|---|---|---|
| A17 | 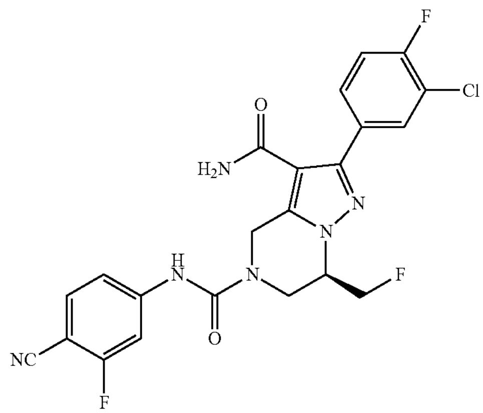 [SMILES: N#Cc1ccc(NC(=O)N2Cc3c(C(N)=O)c(-c4ccc(F)c(Cl)c4)nn3[C@@H](CF)C2)cc1F] | (R)-2-(3-Chloro-4-fluorophenyl)-N5-(4-cyano-3-fluorophenyl)-7-(fluoromethyl)-6,7-dihydropyrazolo[1,5-a]pyrazine-3,5(4H)-dicarboxamide | B | 489.3 | 1.64, 2.59 | H I |
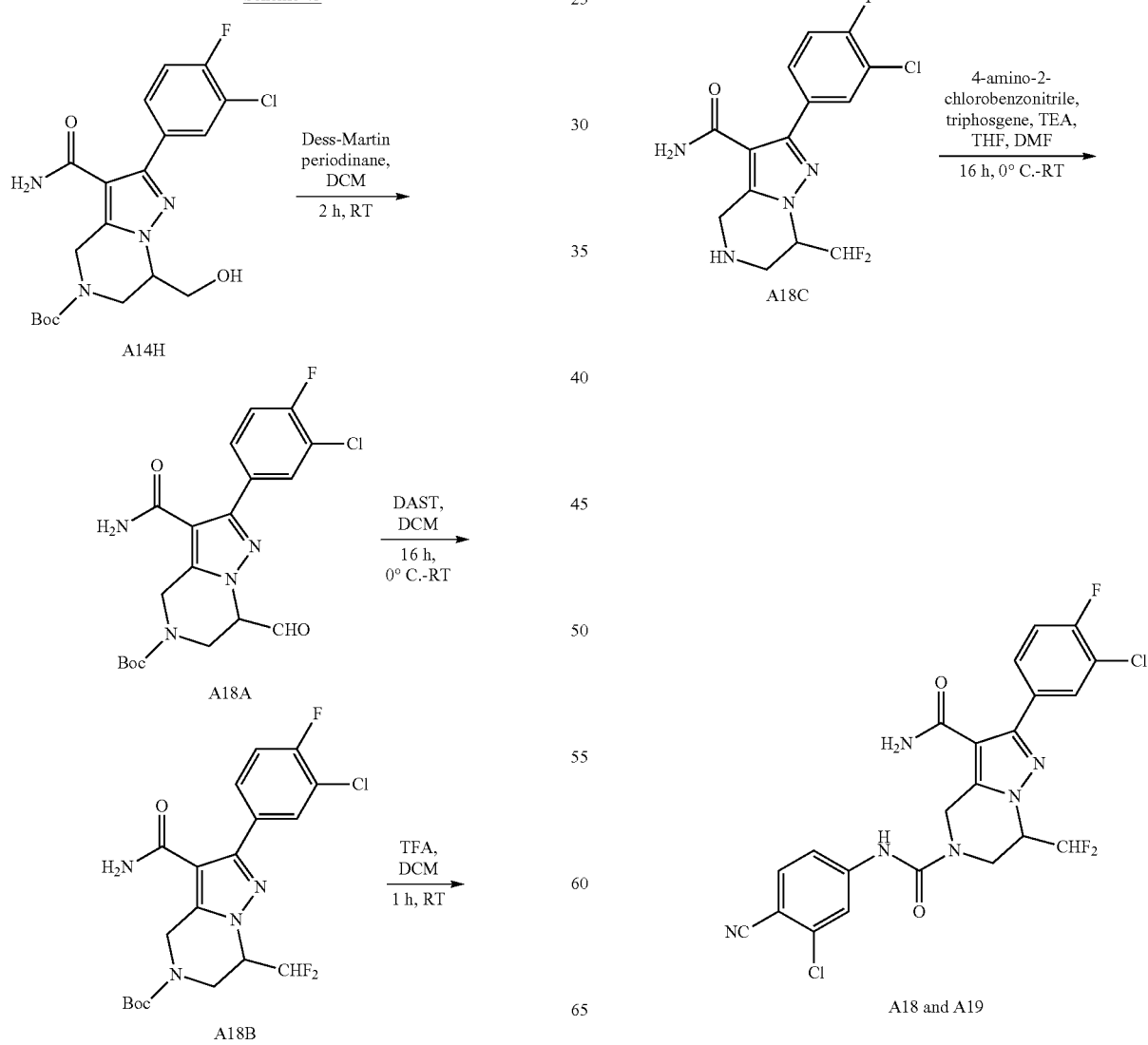
Scheme 43

455

Intermediate A18C: 2-(3-Chloro-4-fluorophenyl)-7-(difluoromethyl)-4,5,6,7-tetrahydropyrazolo[1,5-a]pyrazine-3-carboxamide

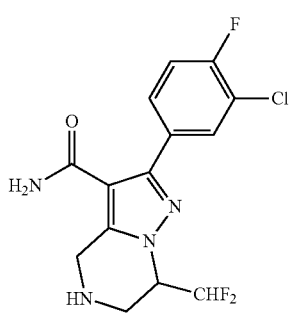 [SMILES: NC(=O)c1c(-c2ccc(F)c(Cl)c2)nn2c1CNCC2C(F)F]

Intermediate A18C was synthesized from Intermediate A14H by following the synthetic sequence shown in Scheme 40 for the synthesis of Intermediate A12C. MS(ES): m/z=345.0 [M+H]$^+$.

456

Compounds A18 and A19: (S)—N$^5$-(3-Chloro-4-cyanophenyl)-2-(3-chloro-4-fluorophenyl)-7-(difluoromethyl)-6,7-dihydropyrazolo[1,5-a]pyrazine-3,5(4H)-dicarboxamide

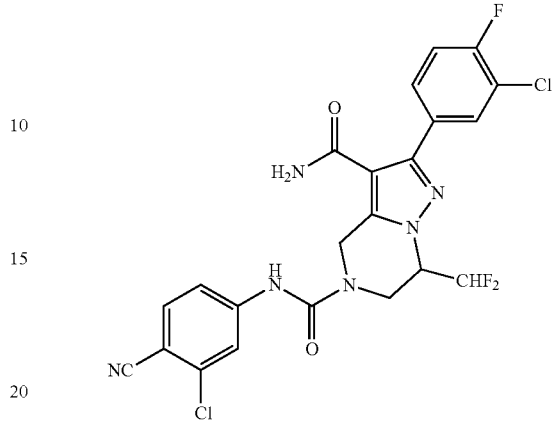

The racemic mixture of Compounds A18 and A19 was synthesized analogous to Compounds A14 and A15 (Scheme 42) by reacting Intermediate A18C with 4-amino-2-chlorobenzonitrile. The individual enantiomers A18 and A19 were separated by chiral SFC purification using CHIRALPAK® AS preparative column (21×250) mm, 10 m column, Solvent A: 0.1% diethylamine in heptane, Solvent B: 100% EtOH, start % B: 30, isocratic, flow rate 15.0 mL/min for 32 min. UV monitored at 254 nm. Compound A18 (S)-isomer was eluted at 21.012 min. (10.4 mg, 100% ee, Yield=12.65%) and A19 (R)-isomer was eluted at 11.008 min. (10.6 mg, 100% ee, Yield=12.76%). MS(ES): m/z=523.3 [M−H]$^+$; HPLC Ret. Time 1.77 min. and 2.70 min. (Methods H and I respectively); $^1$H NMR (500 MHz, DMSO-d$_6$) δ ppm 7.93-7.80 (m, 3H), 7.69 (d, J=4.8 Hz, 1H), 7.60 (d, J=8.1 Hz, 1H), 7.55-7.44 (m, 2H), 7.40 (br. s., 1H), 5.18 (d, J=17.2 Hz, 1H), 4.93 (br. s., 1H), 4.82 (d, J=16.9 Hz, 1H), 4.51 (d, J=11.7 Hz, 1H), 3.88 (d, J=13.6 Hz, 1H), 3.39 (br. s., 1H).

The Compounds described in Table 33 were synthesized analogous to Compounds A18 and A19 by reacting Intermediate A18C with the corresponding reagents.

TABLE 33

| Ex. No. | Structure | Name | Synthetic Method | [M + H]$^+$ | Ret. Time (min.) | HPLC Method |
|---|---|---|---|---|---|---|
| A20 | 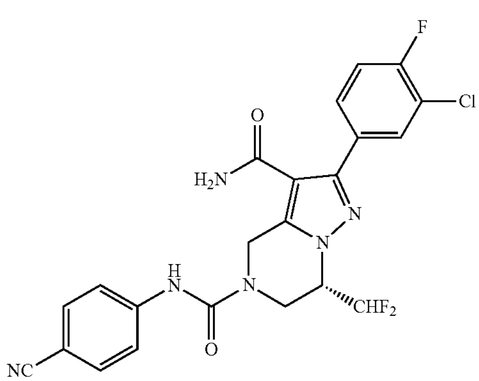 [SMILES: N#Cc1ccc(NC(=O)N2Cc3c(C(N)=O)c(-c4ccc(F)c(Cl)c4)nn3[C@H](C(F)F)C2)cc1] | (S)-2-(3-Chloro-4-fluorophenyl)-N$^5$-(4-cyanophenyl)-7-(difluoromethyl)-6,7-dihydropyrazolo[1,5-a]pyrazine-3,5(4H)-dicarboxamide | A | 489.4 | 1.62<br>2.43 | H<br>I |

TABLE 33-continued

| Ex. No. | Structure | Name | Synthetic Method | [M + H]+ | Ret. Time (min.) | HPLC Method |
|---|---|---|---|---|---|---|
| A21 | 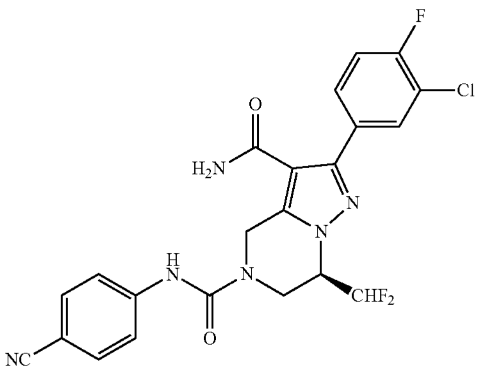 [SMILES: N#Cc1ccc(NC(=O)N2Cc3c(C(N)=O)c(-c4ccc(F)c(Cl)c4)nn3[C@@H](C(F)F)C2)cc1] | (R)-2-(3-Chloro-4-fluorophenyl)-N5-(4-cyanophenyl)-7-(difluoromethyl)-6,7-dihydropyrazolo[1,5-a]pyrazine-3,5(4H)-dicarboxamide | A | 489.3 | 1.60 2.42 | H I |
| A22 | 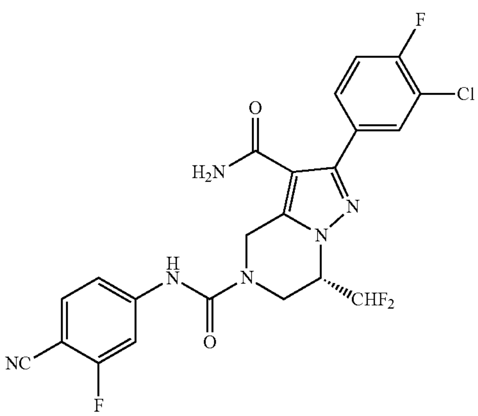 [SMILES: N#Cc1ccc(NC(=O)N2Cc3c(C(N)=O)c(-c4ccc(F)c(Cl)c4)nn3[C@H](C(F)F)C2)cc1F] | (S)-2-(3-Chloro-4-fluorophenyl)-N5-(4-cyano-3-fluorophenyl)-7-(difluoromethyl)-6,7-dihydropyrazolo[1,5-a]pyrazine-3,5(4H)-dicarboxamide | B | 507.2 | 1.65 2.48 | H I |
| A23 | 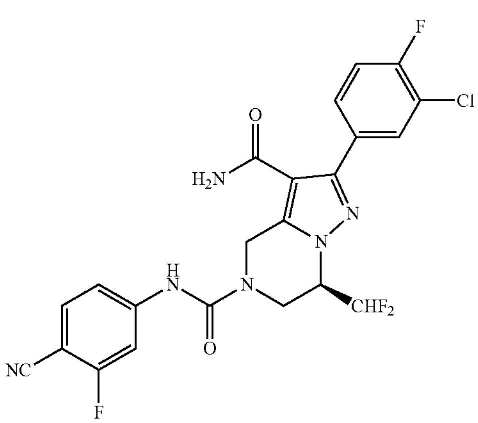 [SMILES: N#Cc1ccc(NC(=O)N2Cc3c(C(N)=O)c(-c4ccc(F)c(Cl)c4)nn3[C@@H](C(F)F)C2)cc1F] | (R)-2-(3-Chloro-4-fluorophenyl)-N5-(4-cyano-3-fluorophenyl)-7-(difluoromethyl)-6,7-dihydropyrazolo[1,5-a]pyrazine-3,5(4H)-dicarboxamide | B | 507.2 | 1.65 2.48 | H I |

Scheme 44

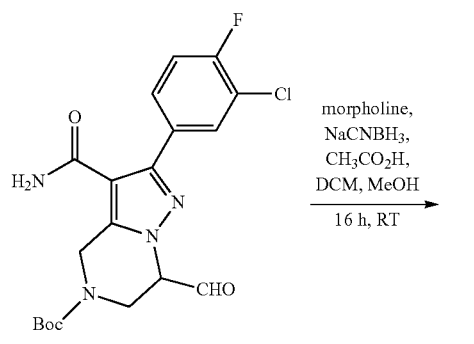
A18A

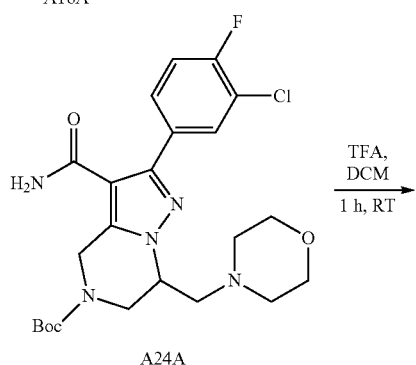
A24A

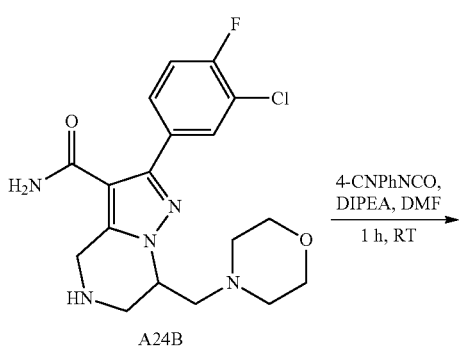
A24B

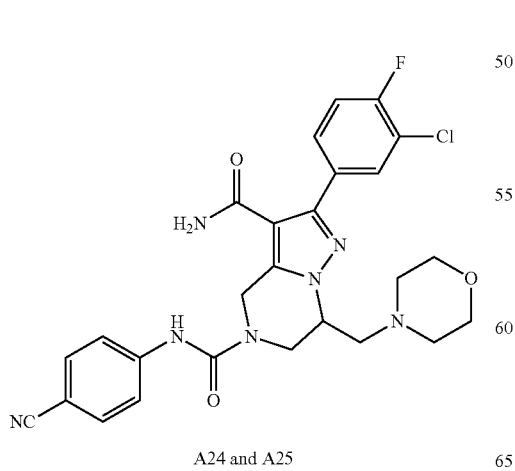
A24 and A25

Intermediate A24A: tert-Butyl 3-carbamoyl-2-(3-chloro-4-fluorophenyl)-7-(morpholinomethyl)-6,7-dihydropyrazolo[1,5-a]pyrazine-5(4H)-carboxylate

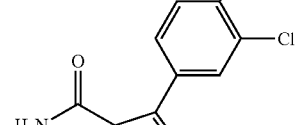

To a solution of Intermediate A18A (0.17 g, 0.402 mmol) in DCM (5.36 mL) and MeOH (2.68 mL) was added morpholine (0.088 mL, 1.005 mmol), followed by sodium cyanoborohydride (0.076 g, 1.21 mmol) and glacial acetic acid (0.023 mL, 0.402 mmol). The reaction mixture was stirred at room temperature for 8 h. It was quenched with a satd. aq. solution of NaHCO$_3$, the two layers were separated and the aq. layer was extracted with DCM (2×10 mL). The combined organic layer was washed with brine, dried over anhydrous MgSO$_4$, filtered and the filtrate was concentrated under reduced pressure to afford an oil. It was purified by silica gel chromatography (24 g REDISEP® column, eluting with a gradient of 40 to 60% EtOAc in DCM). Fractions containing the product were combined and evaporated to afford Intermediate A24A (0.086 g, 43.3%) as an off-white foam. MS(ES): m/z=494.1 [M+H]$^+$.

Intermediate A24B: 2-(3-Chloro-4-fluorophenyl)-7-(morpholinomethyl)-4,5,6,7-tetrahydropyrazolo[1,5-a]pyrazine-3-carboxamide, 2 TFA To a solution of Intermediate A24A (0.086 g, 0.174 mmol) in DCM (1.74 mL) was added TFA (0.134 mL, 1.741 mmol) and the reaction mixture was stirred at room temperature for 1 h. It was then concentrated to dryness under reduced pressure to afford crude Intermediate A24B (0.105 g, >99%) as the bis TFA salt. MS(ES): m/z=394.0.

Compounds A24 and A25: 2-(3-Chloro-4-fluorophenyl)-N5-(4-cyanophenyl)-7-(morpholinomethyl)-6,7-dihydropyrazolo[1,5-a]pyrazine-3,5(4H)-dicarboxamide

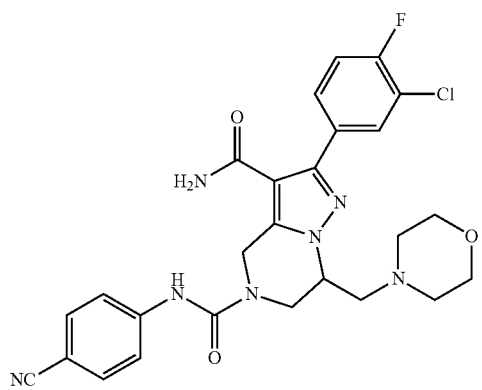 [SMILES: N#Cc1ccc(NC(=O)N2Cc3c(C(N)=O)c(-c4ccc(F)c(Cl)c4)nn3C(CN3CCOCC3)C2)cc1]

To a solution of Intermediate A24B (0.054 g, 0.087 mmol) in DMF (0.87 mL) was added DIPEA (0.091 mL, 0.521 mmol), followed by 4-isocyanatobenzonitrile (0.038 g, 0.260 mmol) and the reaction mixture was stirred at room temperature for 1 h. It was purified by preparative HPLC to afford a racemic mixture of compounds A24 and A25. The individual enantiomers A24 and A25 were separated by chiral SFC purification using CHIRALCEL® OD preparative column (21×250) mm, 10 μm column, Solvent A: 0.1% diethylamine in heptane, Solvent B: 100% EtOH, start % B: 25, isocratic, flow rate 15.0 mL/min for 35 min. UV monitored at 254 nm. Compound A24 (S)-isomer was eluted at 25.022 min. (9.7 mg, 100% ee, Yield=20.56%) and Compound A25 (R)-isomer was eluted at 18.054 min. (7.6 mg, 100% ee, Yield=15.94%). MS: m/z=538.2 [M+H]$^+$; HPLC Ret. Time 1.57 min. and 2.46 min. (Methods H and I respectively); $^1$H NMR (500 MHz, DMSO-d$_6$) δ ppm 7.85 (dd, J=7.3, 1.8 Hz, 1H), 7.78-7.64 (m, 5H), 7.48 (t, J=9.0 Hz, 1H), 7.41 (br. s., 1H), 7.25 (br. s., 1H), 5.20 (d, J=17.2 Hz, 1H), 4.71 (d, J=16.9 Hz, 1H), 4.61-4.50 (m, 1H), 4.45 (d, J=14.7 Hz, 1H), 3.85-3.71 (m, 1H), 3.55 (br. s., 4H), 2.83-2.74 (m, 2H), 2.64-2.52 (m, 3H), 2.38-2.25 (m, 2H).

Scheme 45

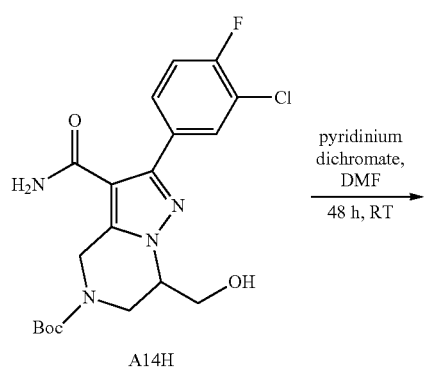

A14H

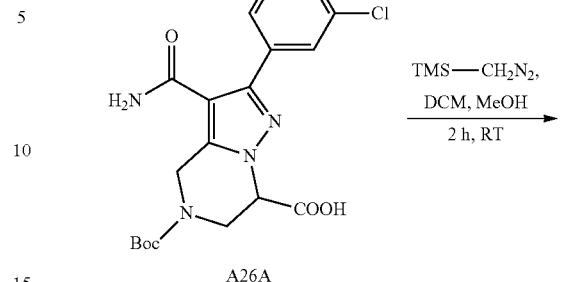

A26A

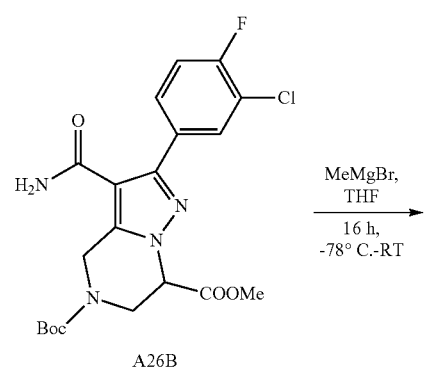

A26B

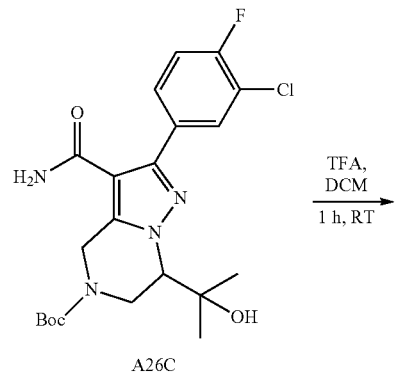

A26C

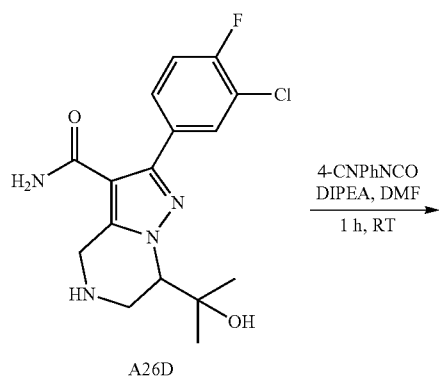

A26D

463
-continued

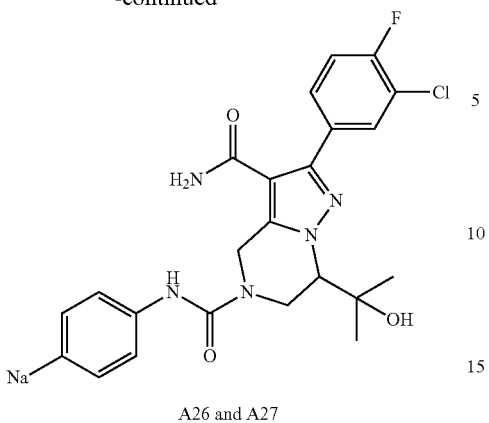

A26 and A27

Intermediate A26A: 5-(tert-Butoxycarbonyl)-3-carbamoyl-2-(3-chloro-4-fluorophenyl)-4,5,6,7-tetrahydropyrazolo[1,5-a]pyrazine-7-carboxylic acid

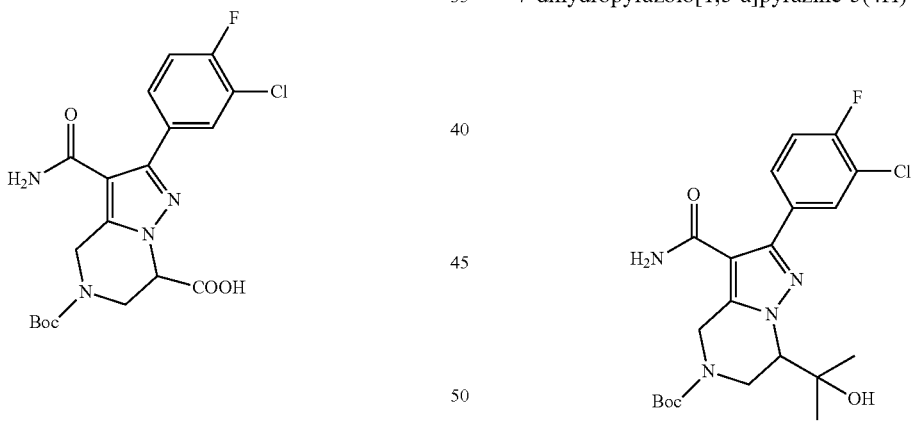

To a solution of Intermediate A14H (2.0 g, 4.71 mmol) in DMF (47.1 mL) was added pyridinium dichromate (12.40 g, 33.0 mmol) and the reaction mixture was stirred at room temperature for 48 h. It was then diluted with water (250 mL) and extracted with EtOAc (3×50 mL) The combined organic layer was washed with water, brine, dried over anhydrous MgSO₄, filtered and the filtrate was concentrated under reduced pressure to afford crude Intermediate A26A (1.47 g, 71.2%) as a brown solid. MS(ES): m/z=439.3 [M+H]⁺.

464

Intermediate A26B: 5-tert-Butyl 7-methyl 3-carbamoyl-2-(3-chloro-4-fluorophenyl)-6,7-dihydropyrazolo[1,5-a]pyrazine-5,7(4H)-dicarboxylate

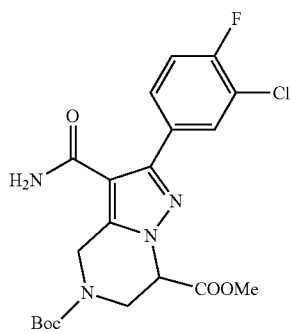 [SMILES: COC(=O)C1CN(C(=O)OC(C)(C)C)Cc2c(C(N)=O)c(-c3ccc(F)c(Cl)c3)nn21]

To a solution of crude Intermediate A26A (1.47 g, 3.35 mmol) in DCM (16.75 mL) and MeOH (16.75 mL) was added TMS-diazomethane (5.02 mL, 10.05 mmol, 2M solution in THF) and the reaction mixture was stirred at room temperature for 2 h. The mixture was then concentrated to dryness under reduced pressure. The residue was purified by silica gel chromatography (40 g REDISEP® column, eluting with a gradient of 45 to 55% EtOAc in hexanes). Fractions containing the product were combined and evaporated to afford Intermediate A26B (0.9 g, 59.4%) as a white amorphous solid. MS(ES): m/z=451.3 [M−H]⁺.

Intermediate A26C: tert-Butyl 3-carbamoyl-2-(3-chloro-4-fluorophenyl)-7-(2-hydroxypropan-2-yl)-6,7-dihydropyrazolo[1,5-a]pyrazine-5(4H)-carboxylate To a −78° C. solution of Intermediate A26B (0.9 g, 1.990 mmol) in THF (19.90 mL) was added a solution of methylmagnesium bromide (3.32 mL, 9.95 mmol, 3M in hexanes) dropwise. The reaction mixture was gradually allowed to attain room temperature and stirred for 16 h. It was quenched with a satd. aq. solution of NH₄Cl, the two layers were separated and the aq. layer was extracted with EtOAc (2×60 mL). The combined organic layer was washed with brine, dried over anhydrous MgSO₄, filtered and the filtrate was concentrated under reduced pressure to give an oil. It was purified by silica gel chromatography (80 g REDISEP® column, eluting with a gradient of 60 to 70% EtOAc in DCM). Fractions containing the product were combined and evaporated to afford Intermediate A26C (0.84 g, 93%) as a yellow solid. (ES): m/z=453.08 [M+H]⁺.

Intermediate A26D: 2-(3-Chloro-4-fluorophenyl)-7-(2-hydroxypropan-2-yl)-4,5,6,7-tetrahydropyrazolo[1,5-a]pyrazine-3-carboxamide

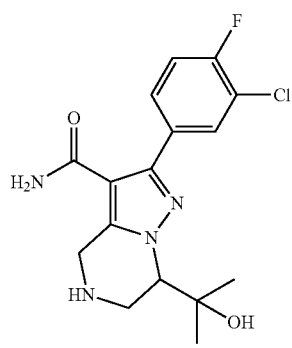 [SMILES: CC(C)(O)C1CNCc2c(C(N)=O)c(-c3ccc(F)c(Cl)c3)nn21]

To a solution of Intermediate A26C (0.45 g, 0.994 mmol) in DCM (10.0 mL) was added TFA (1.53 mL, 19.87 mmol) and the reaction mixture was stirred at room temperature for 1 h. The volatiles were concentrated under reduced pressure and the residue was neutralized with a satd. aq. solution of NaHCO$_3$ and extracted with a 5% solution of MeOH in DCM (3×20 mL). The combined organic layer was washed with brine, dried over anhydrous MgSO$_4$, filtered and the filtrate was concentrated under reduced pressure to give Intermediate A26D (0.34 g, 96%) as a solid. (ES): m/z=375.02 [M+Na]$^+$.

Compounds A26 and A27: 2-(3-Chloro-4-fluorophenyl)-N$^5$-(4-cyanophenyl)-7-(2-hydroxypropan-2-yl)-6,7-dihydropyrazolo[1,5-a]pyrazine-3,5(4H)-dicarboxamide

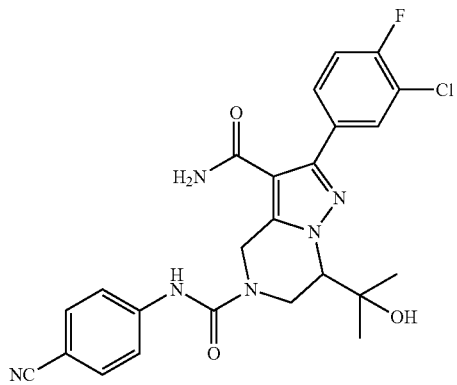 [SMILES: CC(C)(O)C1CN(C(=O)Nc2ccc(C#N)cc2)Cc2c(C(N)=O)c(-c3ccc(F)c(Cl)c3)nn21]

A solution of Intermediate A26D (0.05 g, 0.142 mmol), 4-isocyanatobenzonitrile (0.051 g, 0.354 mmol) and DIPEA (0.087 mL, 0.496 mmol) in DMF (1.42 mL) was stirred at room temperature for 1 h. The reaction mixture was purified via preparative HPLC to afford a racemic mixture of Compounds A26 and A27. Individual enantiomers A26 and A27 were separated by chiral SFC separation using CHIRALPAK® IA preparative column (30×250) mm, 5 μm column, mobile phase: 40% MeOH in CO$_2$, back pressure 150 bar, temperature 35° C., flow rate 70.0 mL/min for 16 min. UV monitored at 265 nm. Compound A26 (S)-isomer was eluted at 5.71 min. (13.5 mg, 100% ee, Yield=18.59%) and Compound A27 (R)-isomer was eluted at 11.43 min. (13.6 mg, 100% ee, Yield=19.12%). MS(ES): m/z=497.4 [M+H]$^+$; HPLC Ret. Time 1.50 min. and 2.41 min. (Methods H and I respectively); $^1$H NMR (500 MHz, DMSO-d$_6$) δ ppm 7.87 (d, J=7.3 Hz, 1H), 7.78-7.62 (m, 5H), 7.49 (t, J=9.0 Hz, 1H), 7.43 (br. s., 1H), 7.28 (br. s., 1H), 5.02 (d, J=16.9 Hz, 1H), 4.83 (d, J=16.9 Hz, 1H), 4.43 (dd, J=13.9, 3.7 Hz, 1H), 4.26 (t, J=3.9 Hz, 1H), 3.71 (dd, J=14.1, 4.2 Hz, 1H), 3.37 (d, J=5.1 Hz, 1H), 1.32 (s, 3H), 1.08 (s, 3H).

Scheme 46

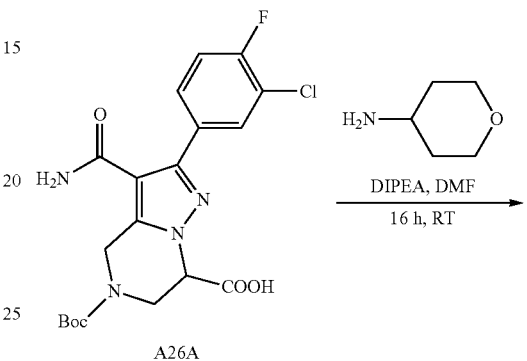

A26A

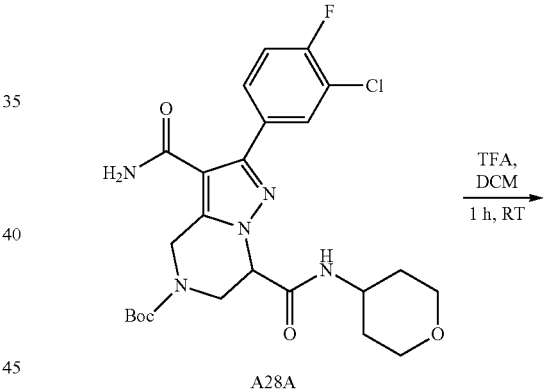

A28A

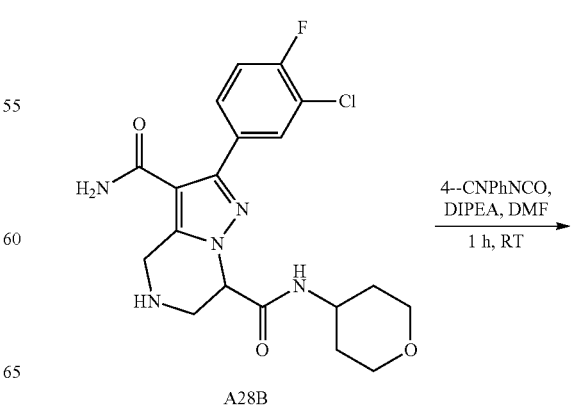

A28B

467
-continued

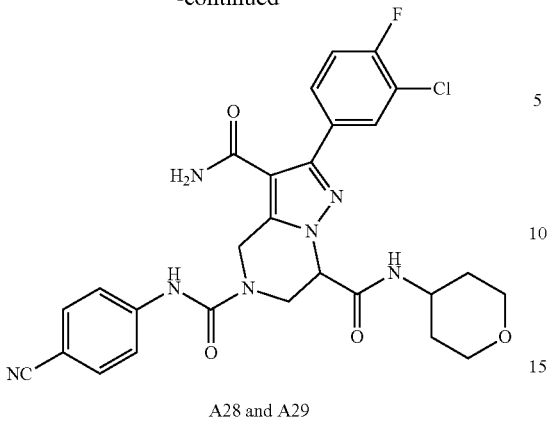

A28 and A29

Intermediate A28B: 2-(3-Chloro-4-fluorophenyl)-N⁷-(tetrahydro-2H-pyran-4-yl)-4,5,6,7-tetrahydropyrazolo[1,5-a]pyrazine-3,7-dicarboxamide, 2 TFA

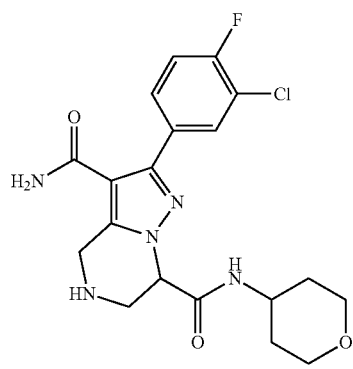 [SMILES: NC(=O)c1c(-c2ccc(F)c(Cl)c2)nn2c1CNCC2C(=O)NC1CCOCC1]

A solution of Intermediate A26A (0.103 g, 0.235 mmol), tetrahydro-2H-pyran-4-amine, HCl (0.13 g, 0.939 mmol), HATU (0.18 g, 0.469 mmol) and DIPEA (0.164 mL, 0.939 mmol) in DMF (2.35 mL) was stirred at room temperature for 16 h. The reaction mixture was diluted with water and extracted with EtOAc (3×10 mL). The combined organic layer was washed with water, brine, dried over anhydrous MgSO₄, filtered and concentrated to afford the intermediate amide A28A. MS(ES): m/z=544.1 [M+Na]⁺. The crude product was subjected to deprotection of the Boc group without purification.

To a solution of Intermediate A28A in DCM (2 mL) was added TFA (0.27 mL, 3.52 mmol) and the reaction mixture was stirred at room temperature for 1 h. The mixture was then concentrated to dryness to afford crude Intermediate A28B (0.15 g, >99%) as the bis TFA salt. MS(ES): m/z=422.0 [M+H]⁺.

468

Compounds A28 and A29: 2-(3-Chloro-4-fluorophenyl)-N⁵-(4-cyanophenyl)-N⁷-(tetrahydro-2H-pyran-4-yl)-6,7-dihydropyrazolo[1,5-a]pyrazine-3,5,7(4H)-tricarboxamide

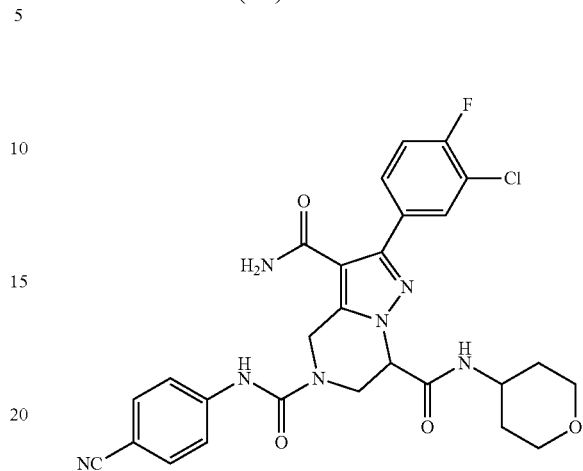

To a solution of Intermediate A28B (0.065 g, 0.100 mmol) in DMF (1.0 mL) was added DIPEA (0.087 mL, 0.500 mmol), followed by 4-isocyanatobenzonitrile (0.036 g, 0.250 mmol) and the reaction mixture was stirred at room temperature for 1 h. It was purified via preparative HPLC to afford a racemic mixture of Compounds A28 and A29. Individual enantiomers A28 and A29 were separated by chiral SFC separation using CHIRALPAK® IA preparative column (30×250) mm, 5 μm column, mobile phase: 45% MeOH in CO₂, temperature 35° C., flow rate 70.0 mL/min for 23 min. UV monitored at 266 nm. Compound A28 (S)-isomer was eluted at 5.43 min. (5.1 mg, 100% ee, Yield=8.92%) and Compound A29 (R)-isomer was eluted at 17.43 min. (5.0 mg, 100% ee, Yield=8.3%). MS(ES): m/z=566.3 [M+H]⁺; HPLC Ret. Time 1.60 min. and 2.17 min. (Methods H and I respectively); ¹H NMR (500 MHz, DMSO-d₆) δ ppm 8.52 (d, J=7.7 Hz, 1H), 7.82 (dd, J=7.3, 1.8 Hz, 1H), 7.74-7.57 (m, 5H), 7.47 (t, J=9.0 Hz, 1H), 7.40 (br. s., 1H), 7.27 (br. s., 1H), 5.19 (d, J=17.2 Hz, 1H), 4.97 (br. s., 1H), 4.76 (d, J=17.2 Hz, 1H), 4.52-4.38 (m, 1H), 3.97 (d, J=10.3 Hz, 1H), 3.84-3.77 (m, 1H), 3.75-3.60 (m, 2H), 3.41 (br. s., 1H), 3.37-3.27 (m, 1H), 3.27-3.14 (m, 1H), 1.70 (d, J=12.5 Hz, 1H), 1.58 (d, J=12.5 Hz, 1H), 1.50-1.28 (m, 2H).

Scheme 47

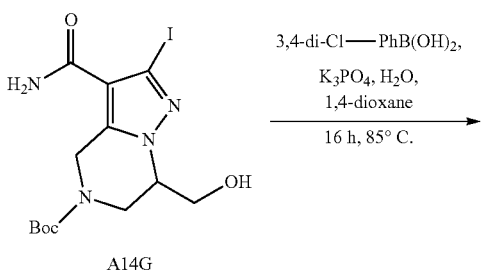

A14G

-continued

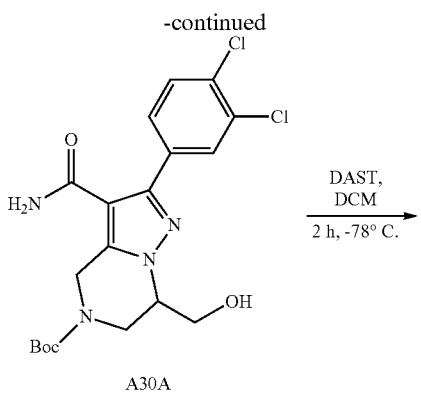

A30A

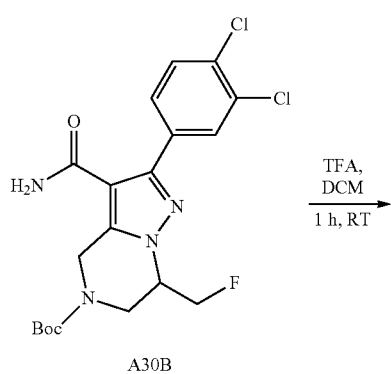

A30B

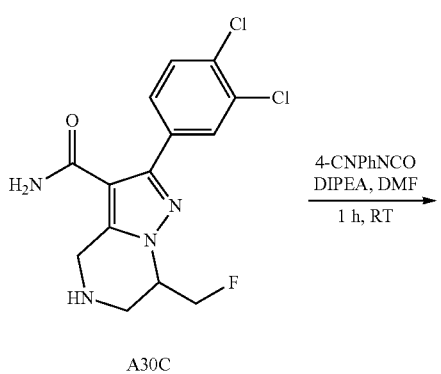

A30C

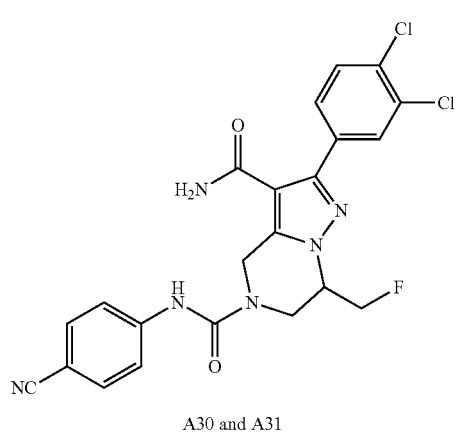

A30 and A31

Intermediate A30C: 2-(3,4-Dichlorophenyl)-7-(fluoromethyl)-4,5,6,7-tetrahydropyrazolo[1,5-a]pyrazine-3-carboxamide

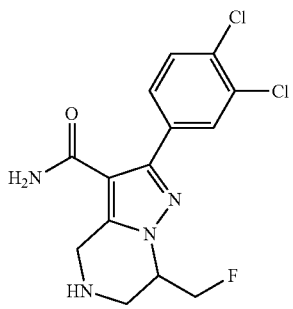 [SMILES: NC(=O)c1c(-c2ccc(Cl)c(Cl)c2)nn2c1CNCC2CF]

Intermediate A30C was synthesized analogous to Intermediate A14J by first coupling Intermediate A14G with 3,4-dichlorophenylboronic acid, followed by the synthetic sequence described in Scheme 42. MS(ES): m/z=343.1 [M+H]$^+$.

Compounds A30 and A31: N$^5$-(4-Cyanophenyl)-2-(3,4-dichlorophenyl)-7-(fluoromethyl)-6,7-dihydropyrazolo[1,5-a]pyrazine-3,5(4H)-dicarboxamide

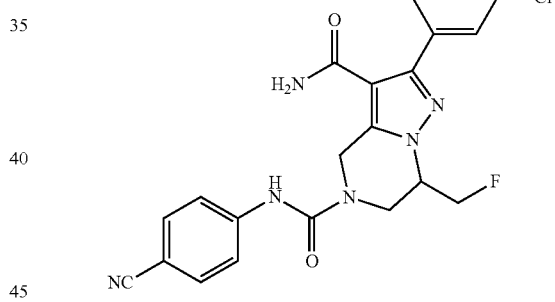

A solution of Intermediate A30C (0.05 g, 0.146 mmol), 4-isocyanatobenzonitrile (0.052 g, 0.364 mmol) and DIPEA (0.076 mL, 0.437 mmol) in DMF (1.46 mL) was stirred at room temperature for 1 h. The reaction mixture was purified by preparative HPLC to afford a racemic mixture of Compounds A30 and A31. The individual enantiomers A30 and A31 were separated by chiral SFC purification using CHIRALPAK® IA preparative column (30×250) mm, 5 μm column, flow rate 70.0 mL/min for 16 min.; mobile phase: 40% MeOH in CO$_2$. Temperature: 35° C., back pressure 150 bar, UV monitored at 265 nm, Back pressure: 150 bar. Compound A30 (S)-isomer was eluted at 9.23 min. (14.4 mg, 100% ee, Yield=20.28%) and Compound A31 (R)-isomer was eluted at 12.89 min. (14.0 mg, 100% ee, Yield=19.72%). MS(ES): m/z=487.3 [M+H]$^+$; HPLC Ret. Time 1.62 min. and 2.49 min. (Methods H and I respectively); $^1$H NMR (500 MHz, DMSO-d$_6$) δ ppm 7.89 (s, 1H), 7.77-7.59 (m, 6H), 7.42 (br. s., 1H), 7.38 (br. s., 1H), 5.06 (d, J=5.9 Hz, 1H), 5.02-4.91 (m, 3H), 4.88 (d, J=12.1 Hz, 1H), 4.78 (d, J=10.3 Hz, 1H), 4.68 (br. s., 1H), 4.63 (br. s., 1H), 4.20-4.11 (m, 1H), 4.11-4.01 (m, 1H).

Scheme 48

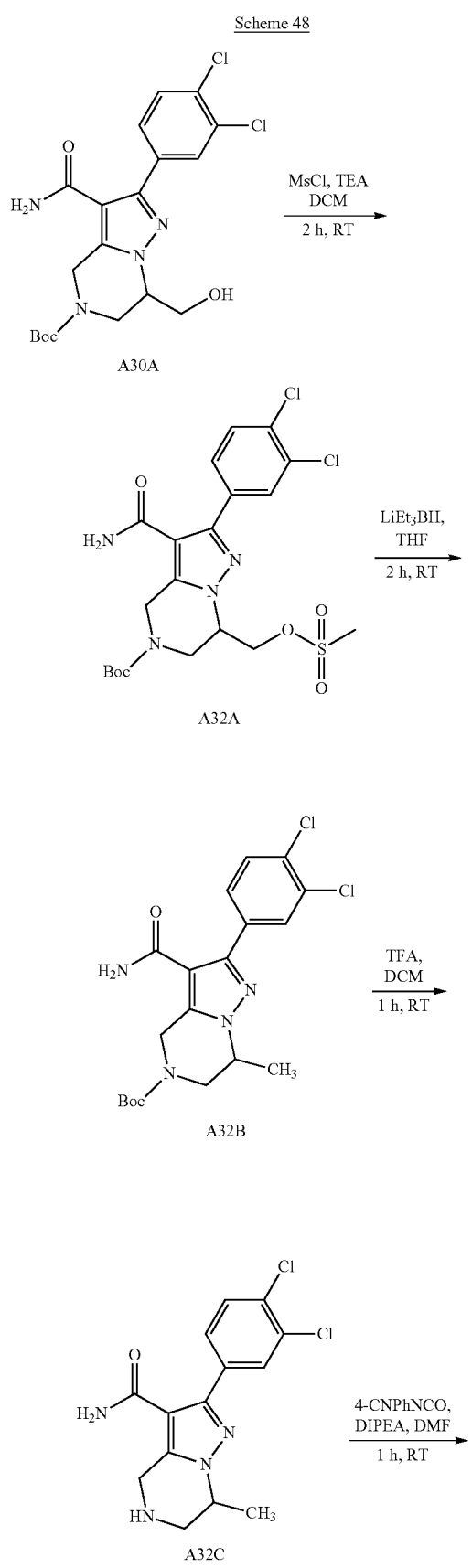

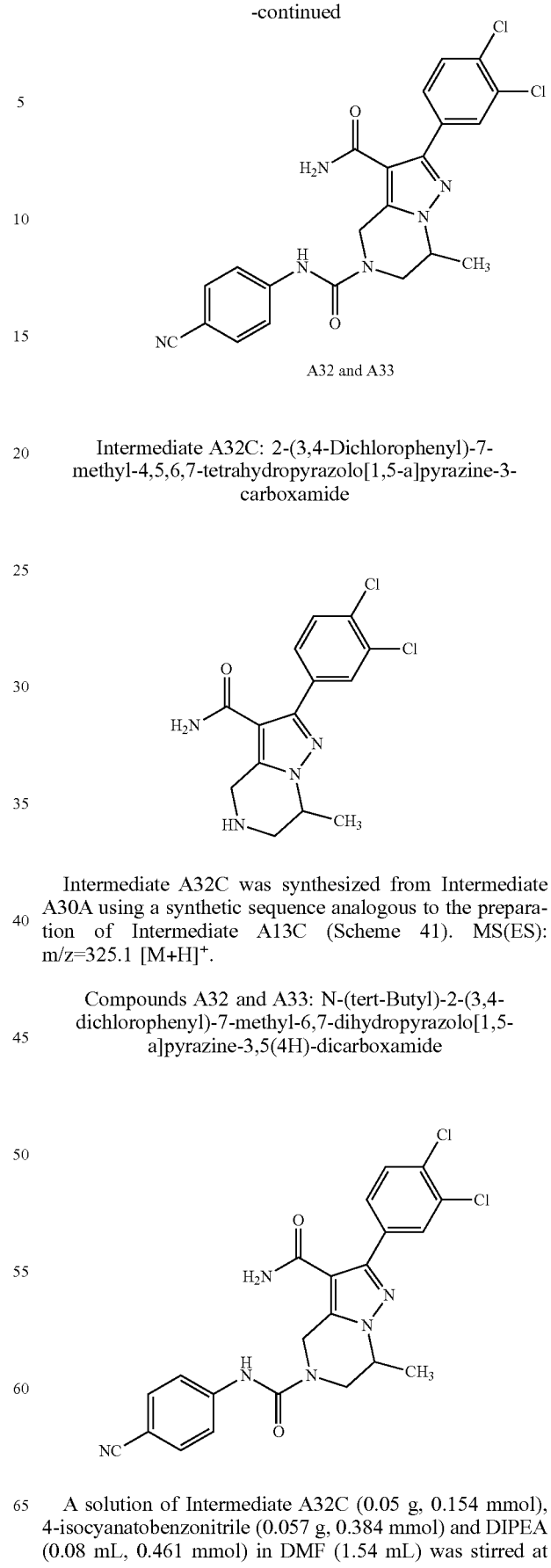

Intermediate A32C: 2-(3,4-Dichlorophenyl)-7-methyl-4,5,6,7-tetrahydropyrazolo[1,5-a]pyrazine-3-carboxamide Intermediate A32C was synthesized from Intermediate A30A using a synthetic sequence analogous to the preparation of Intermediate A13C (Scheme 41). MS(ES): m/z=325.1 [M+H]⁺.

Compounds A32 and A33: N-(tert-Butyl)-2-(3,4-dichlorophenyl)-7-methyl-6,7-dihydropyrazolo[1,5-a]pyrazine-3,5(4H)-dicarboxamide A solution of Intermediate A32C (0.05 g, 0.154 mmol), 4-isocyanatobenzonitrile (0.057 g, 0.384 mmol) and DIPEA (0.08 mL, 0.461 mmol) in DMF (1.54 mL) was stirred at room temperature for 1 h. The reaction mixture was purified by preparative HPLC to afford a racemic mixture of Compounds A32 and A33. The individual enantiomers A32 and A33 were separated by chiral SFC purification using CHIRALPAK® AD preparative column (21×250) mm, 10 μm column, Solvent A: 0.1% diethylamine in heptane, Solvent B: 100% EtOH, start % B: 5.0, isocratic, flow rate 15.0 mL/min for 70 min. UV monitored at 254 nm. Compound A32 (S)-isomer was eluted at 38.833 min. (18.7 mg, 100% ee, Yield=25.9%) and Compound A33 (R)-isomer was eluted at 48.49 min. (18.3 mg, 100% ee, Yield=25.4%). MS(ES): m/z=469.3; $^1$H NMR (500 MHz, DMSO-d$_6$) δ ppm 7.79-7.62 (m, 6H), 7.43 (br. s., 1H), 7.33 (br. s., 1H), 4.99 (d, J=17.2 Hz, 1H), 4.86 (d, J=16.9 Hz, 1H), 4.54-4.40 (m, 1H), 4.12 (dd, J=13.9, 3.7 Hz, 1H), 3.72 (dd, J=14.1, 6.8 Hz, 1H), 3.38 (d, J=4.8 Hz, 1H), 1.50 (d, J=6.2 Hz, 3H).

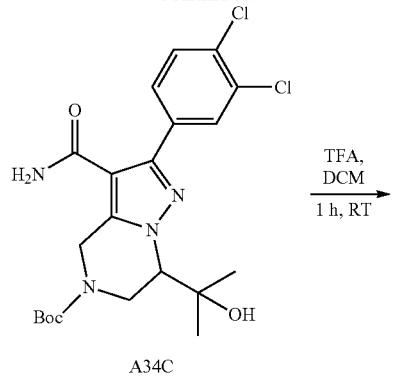

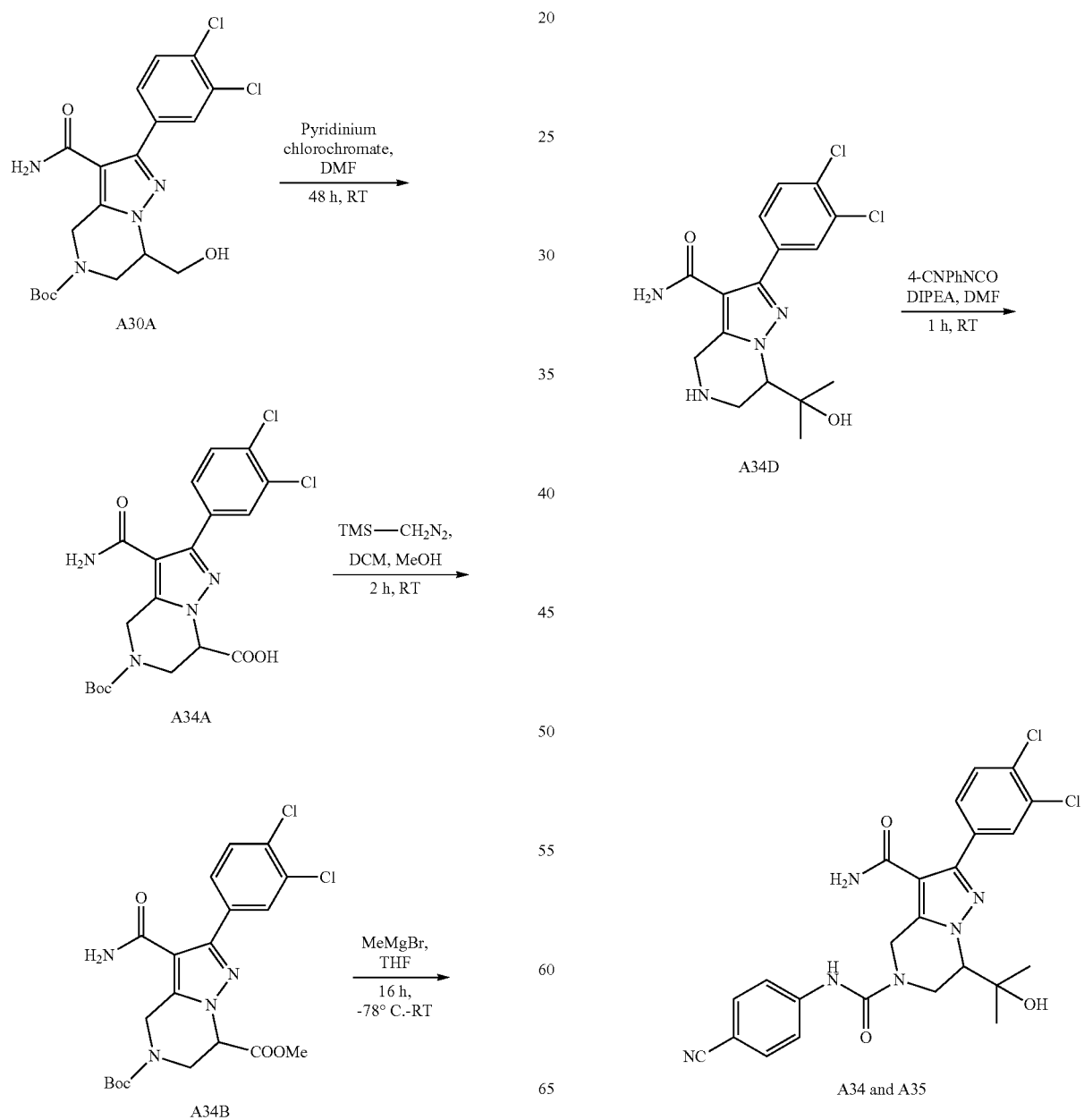

Scheme 49

Intermediate A34D: 2-(3,4-Dichlorophenyl)-7-(2-hydroxypropan-2-yl)-4,5,6,7-tetrahydropyrazolo[1,5-a]pyrazine-3-carboxamide

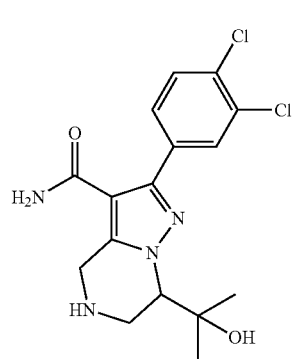 [SMILES: CC(C)(O)C1CNCc2c(C(N)=O)c(-c3ccc(Cl)c(Cl)c3)nn21]

Intermediate A34D was synthesized from Intermediate A30A using a synthetic sequence analogous to the preparation of Intermediate A26D (Scheme 45). MS(ES): m/z=369.1 [M+H]$^+$.

Compounds A34 and A35: N$^5$-(4-Cyanophenyl)-2-(3,4-dichlorophenyl)-7-(2-hydroxypropan-2-yl)-6,7-dihydropyrazolo[1,5-a]pyrazine-3,5(4H)-dicarboxamide

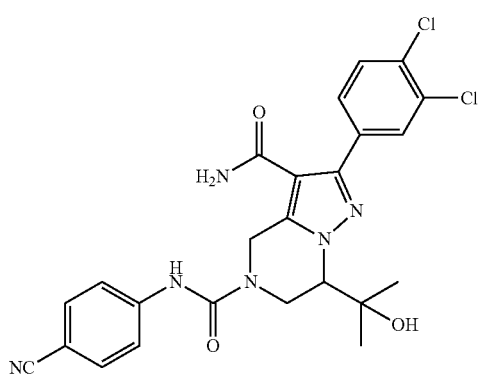 [SMILES: CC(C)(O)C1CN(C(=O)Nc2ccc(C#N)cc2)Cc2c(C(N)=O)c(-c3ccc(Cl)c(Cl)c3)nn21]

The racemic mixture of Compounds A34 and A35 was synthesized analogous to Compounds A26 and A27 (Scheme 45) by reacting Intermediate A34D with 4-isocyanatobenzonitrile. The reaction mixture was purified via preparative HPLC to afford a racemic mixture of Compounds A34 and A35. The individual enantiomers A34 and A35 were separated by chiral SFC separation using CHIRALPAK® IA preparative column (30×250) mm, 5 μm column, mobile phase: 40% MeOH in CO$_2$, temperature 35° C., back pressure 150 bar, flow rate 70.0 mL/min for 25 min. UV monitored at 265 nm. Compound A34 (S)-isomer was eluted at 7.45 min. (13.4 mg, 100% ee, Yield=19.28%) and Compound A35 (R)-isomer was eluted at 18.57 min. (12.8 mg, 100% ee, Yield=18.41%). MS(ES): m/z=513.3 [M+H]$^+$; HPLC Ret. Time 1.64 min. and 2.54 min. (Methods H and I respectively); $^1$H NMR (500 MHz, DMSO-d$_6$) δ ppm 7.90 (s, 1H), 7.77-7.59 (m, 7H), 7.43 (br. s., 1H), 7.36 (br. s., 1H), 5.01 (d, J=16.9 Hz, 1H), 4.81 (d, J=17.2 Hz, 1H), 4.43 (d, J=14.3 Hz, 1H), 4.27 (br. s., 1H), 3.69 (d, J=9.5 Hz, 1H), 1.32 (s, 3H), 1.13-1.04 (m, 3H).

Scheme 50

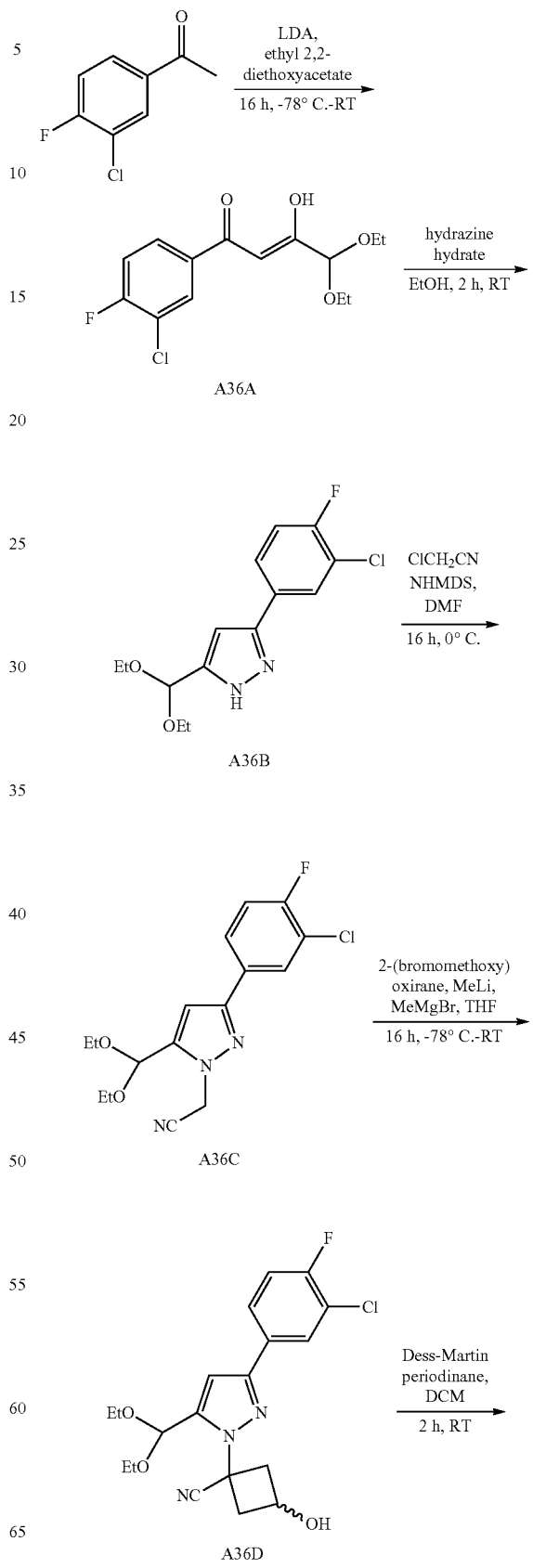

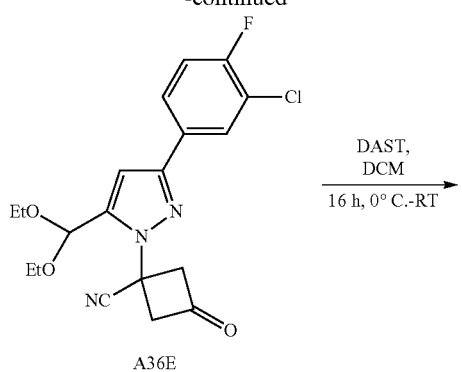
A36E
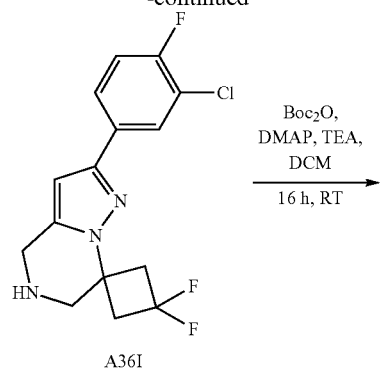
A36I
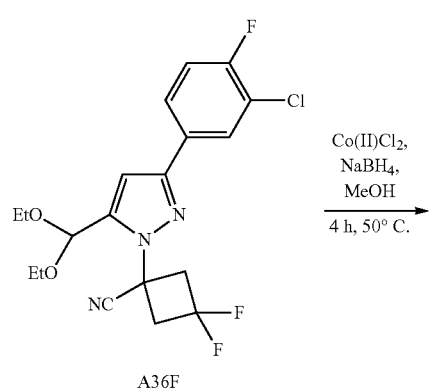
A36F
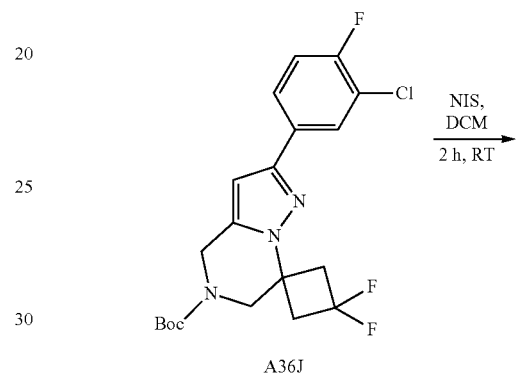
A36J
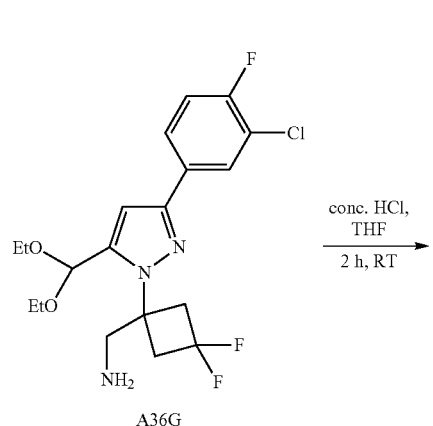
A36G
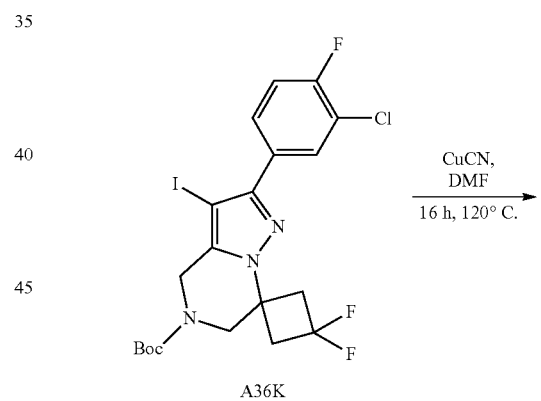
A36K
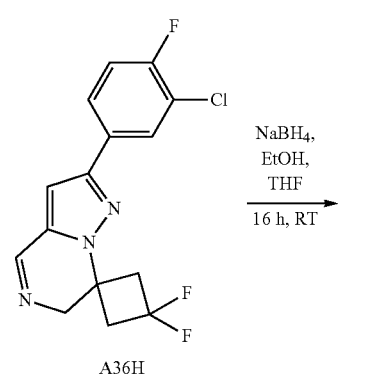
A36H
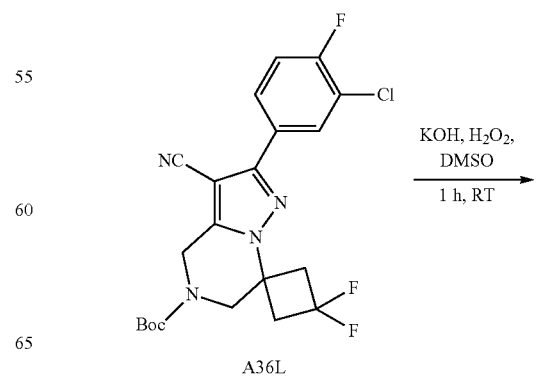
A36L

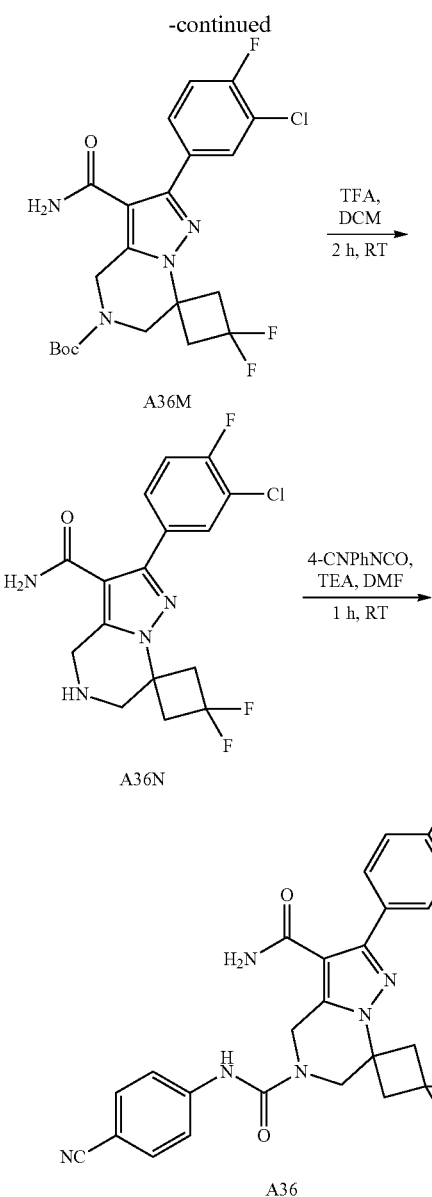

Intermediate A36A: (Z)-1-(3-Chloro-4-fluorophenyl)-4,4-diethoxy-3-hydroxybut-2-en-1-one

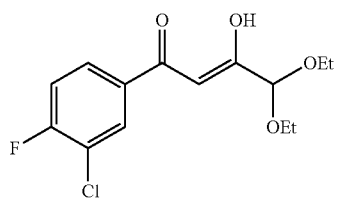 [SMILES: CCOC(OCC)/C(O)=C/C(=O)c1ccc(F)c(Cl)c1]

To a −78° C. solution of 1-(3-chloro-4-fluorophenyl) ethanone (16.25 g, 94 mmol) and ethyl 2,2-diethoxyacetate (20.73 mL, 113 mmol) in THF (392 mL) was added, dropwise, a solution of LDA (51.8 mL, 104 mmol, 2M in THF). The resultant reaction mixture was gradually allowed to reach room temperature and continued stirring for 16 h. The reaction was carefully quenched with water and diluted with EtOAc. The two layers were separated and the aq. layer was extracted with EtOAc (2×150 mL). The combined organic layer was washed with brine, dried over anhydrous MgSO$_4$, filtered and the filtrate was concentrated under reduced pressure to provide a crude oil. It was purified by silica gel chromatography (1500 g Commodity column, eluting with a 10% EtOAc in hexanes). Fractions containing the product were combined and evaporated to afford Intermediate A36A (9.97 g, 35%) as a solid. MS(ES): m/z=257 [M−OEt]$^+$.

Intermediate A36B: 3-(3-Chloro-4-fluorophenyl)-5-(diethoxymethyl)-1H-pyrazole

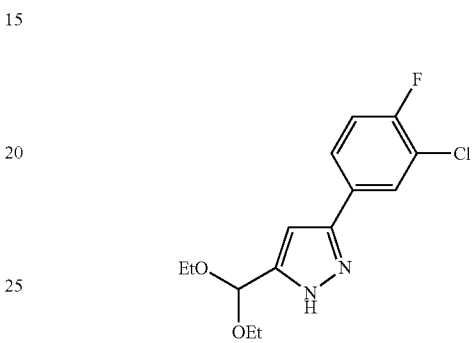

To a solution of Intermediate A36A (19.37 g, 64.0 mmol) in EtOH (128 mL) was added hydrazine hydrate (4.9 mL, 64.0 mmol, 64% solution) and the reaction continued stirring at room temperature for 2 h. Ethanol was concentrated under reduced pressure and the residue was partitioned between water and EtOAc. The two layers were separated and the aq. layer was extracted with EtOAc (2×200 mL). The combined organic layer was washed with water, brine, dried over anhydrous MgSO$_4$, filtered and the filtrate was concentrated under reduced pressure to provide a crude oil. It was purified by silica gel chromatography (330 g REDISEP® column, eluting with a gradient of 0 to 20% EtOAc in hexanes). Fractions containing the product were combined and evaporated to afford Intermediate A36B (17.08 g, 89%) as a bright yellow syrup that later on solidified. MS(ES): m/z=253 [M−OEt]$^+$; $^1$H NMR (400 MHz, chloroform-d) δ ppm 7.87 (dd, J=7.0, 2.3 Hz, 1H), 7.68 (ddd, J=8.5, 4.6, 2.1 Hz, 1H), 7.19 (t, J=8.7 Hz, 1H), 6.57 (s, 1H), 5.75 (s, 1H), 3.76-3.57 (m, 4H), 1.35-1.24 (m, 7H).

Intermediate A36C: 2-(3-(3-Chloro-4-fluorophenyl)-5-(diethoxymethyl)-1H-pyrazol-1-yl)acetonitrile

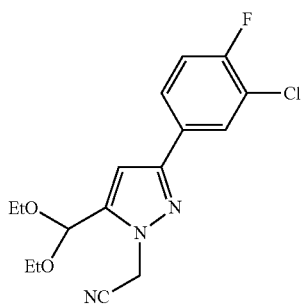 [SMILES: CCOC(OCC)c1cc(-c2ccc(F)c(Cl)c2)nn1CC#N]

To a 0° C. solution of Intermediate A36B (1.21 g, 4.04 mmol) in DMF (10.22 mL) was added a solution of NHMDS (4.24 mL, 4.24 mmol, 1M in THF) and the reaction continued to stir at that temperature for 30 min., followed by the addition of 2-chloroacetonitrile (0.283 mL, 4.44 mmol). The resultant mixture was stirred at room temperature for 16 h. It was quenched by the addition of a satd. aq. solution of NH$_4$Cl and the aq. layer was extracted with EtOAc (3×25 mL). The combined organic layer was washed with water, brine, dried over anhydrous MgSO$_4$, filtered, and the filtrate was concentrated under reduced pressure to provide a crude oil. It was purified by silica gel chromatography (120 g REDISEP® column, 20% EtOAc in hexanes). Fractions containing the product were combined and evaporated to afford Intermediate A36C (1.0 g, 73.3%) as a white solid. MS(ES): m/z=338.2 [M+H]$^+$.

Intermediate A36D: 1-(3-(3-Chloro-4-fluorophenyl)-5-(diethoxymethyl)-1H-pyrazol-1-yl)-3-hydroxycyclobutanecarbonitrile

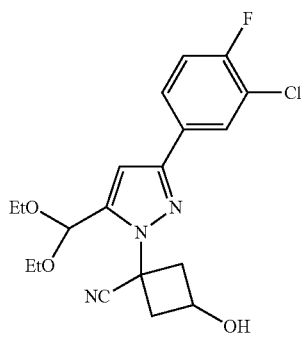 [SMILES: CCOC(OCC)c1cc(-c2ccc(F)c(Cl)c2)nn1C1(C#N)CC(O)C1]

To a −78° C. solution of Intermediate A36C (0.5 g, 1.480 mmol) in THF (7.40 mL) was added a solution of methyllithium (0.925 mL, 1.48 mmol, 1.6M in diethyl ether) dropwise and the reaction was allowed to stir at that temperature for 1 h. Subsequently, a solution of 2-(bromomethyl)oxirane (0.125 mL, 1.48 mmol) in THF (2 mL) was introduced dropwise. The reaction was allowed to stir at −78° C. for 1 h. Then, a solution of methylmagnesium bromide (0.493 mL, 1.48 mmol, 3M in diethyl ether) was added at −78° C. and the resultant reaction mixture was allowed to warm to room temperature. After 16 h, the reaction was quenched by adding a satd. aq. solution of NH$_4$Cl, the two layers were separated and the aq. layer was extracted with EtOAc (2×20 mL). The combined organic layer was washed with brine, dried over anhydrous MgSO$_4$, filtered and the filtrate was concentrated under reduced pressure to provide a crude oil. It was purified by silica gel chromatography (40 g REDISEP® column, eluting with a gradient of 0 to 20% EtOAc in hexanes). Fractions containing the product were combined and evaporated to afford Intermediate A36D (0.197 g, 33.8%) as a solid. MS(ES): m/z=394.1 [M+H]$^+$.

Intermediate A36E: 1-(3-(3-Chloro-4-fluorophenyl)-5-(diethoxymethyl)-1H-pyrazol-1-yl)-3-oxocyclobutanecarbonitrile

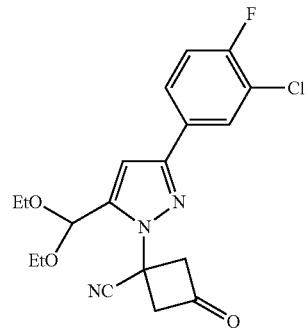 [SMILES: CCOC(OCC)c1cc(-c2ccc(F)c(Cl)c2)nn1C1(C#N)CC(=O)C1]

To a solution of Intermediate A36D (4.6 g, 11.68 mmol) in DCM (58.4 mL) was added Dess-Martin periodinane (7.43 g, 17.52 mmol) and the reaction mixture was stirred at room temperature for 2 h. It was then quenched with the addition of a satd. aq. solution of NaHCO$_3$ and a satd. aq. solution of sodium sulfite. The two layers were separated and the aq. layer was extracted with DCM (2×70 mL), the combined organic layers was washed with brine, dried over anhydrous MgSO$_4$, filtered and the filtrate was concentrated under reduced pressure to provide a crude oil. It was purified by silica gel chromatography (220 g REDISEP® column, eluting with a gradient of 0 to 15% EtOAc in hexanes). Fractions containing the product were combined and evaporated to afford Intermediate A36E (3.98 g, 87%) as a colorless syrup. MS(ES): m/z=392.1 [M+H]$^+$.

Intermediate A36F: 1-(3-(3-Chloro-4-fluorophenyl)-5-(diethoxymethyl)-1H-pyrazol-1-yl)-3,3-difluorocyclobutanecarbonitrile

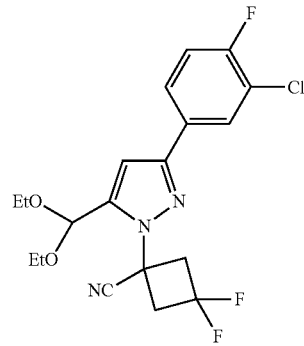 [SMILES: CCOC(OCC)c1cc(-c2ccc(F)c(Cl)c2)nn1C1(C#N)CC(F)(F)C1]

To a 0° C. solution of Intermediate A36E (3.98 g, 10.16 mmol) in DCM (67.7 mL) was added DAST (4.03 mL, 30.5 mmol) and the reaction mixture was stirred at room temperature for 18 h. It was quenched with a satd. aq. solution of NaHCO$_3$, the two layers were separated and the aq. layer was extracted with DCM (2×60 mL). The combined organic layer was washed with brine, dried over anhydrous MgSO$_4$, filtered and the filtrate was concentrated under reduced pressure to provide a crude oil. It was purified by silica gel chromatography (220 g REDISEP® column, eluting with a gradient of 10 to 15% EtOAc in hexanes). Fractions containing the product were combined and evaporated to afford Intermediate A36F (3.075 g, 73.2%) as a pale yellow oil. MS(ES): m/z=414.17 [M+H]⁺.

Intermediate A36G: (1-(3-(3-Chloro-4-fluorophenyl)-5-(diethoxymethyl)-1H-pyrazol-1-yl)-3,3-difluorocyclobutyl)methanamine

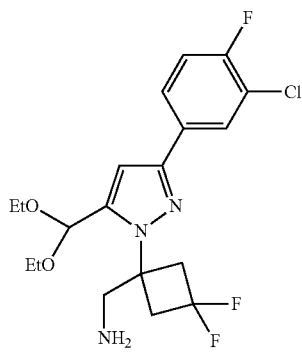 [SMILES: CCOC(OCC)c1cc(-c2ccc(F)c(Cl)c2)nn1C1(CN)CC(F)(F)C1]

To a 0° C. suspension of Intermediate A36F (3.075 g, 7.43 mmol) and cobalt(II) chloride (2.96 g, 22.29 mmol) in MeOH (74.3 mL) was slowly added NaBH₄ (2.81 g, 74.3 mmol). The reaction mixture instantly turned black and a vigorous gas evolution was observed. The reaction was heated in an oil bath at 50° C. for 4 h and then allowed to stir at room temperature for 16 h. The reaction mixture was then filtered through a CELITE® plug and the filtrate was concentrated under reduced pressure to afford a residue. This residue was suspended in DCM and filtered off. The filtrate was concentrated and purified by silica gel chromatography (120 g REDISEP® column, eluting with a gradient of 65 to 75% EtOAc in hexanes). Fractions containing the product were combined and evaporated to afford Intermediate A36G (1.1 g, 35.4%) as a colorless oil. ¹H NMR (400 MHz, chloroform-d) δ ppm 7.86 (dd, J=7.2, 2.1 Hz, 1H), 7.65 (ddd, J=8.6, 4.6, 2.1 Hz, 1H), 7.17 (t, J=8.7 Hz, 1H), 6.70 (s, 1H), 5.61 (s, 1H), 3.75-3.45 (m, 7H), 3.21 (s, 2H), 3.01 (ddd, J=15.4, 13.1, 4.9 Hz, 2H), 1.27 (t, J=7.0 Hz, 6H).

Intermediate A36H: 2'-(3-Chloro-4-fluorophenyl)-3,3-difluoro-6'H-spiro[cyclobutane-1,7'-pyrazolo[1,5-a]pyrazine]

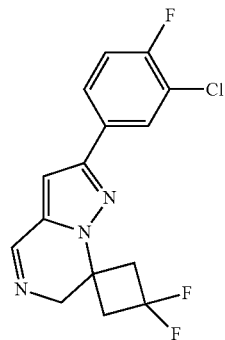 [SMILES: Fc1ccc(-c2cc3n(n2)C2(CN=C3)CC(F)(F)C2)cc1Cl]

To a solution of Intermediate A36G (1.017 g, 2.434 mmol) in THF (24.34 mL) was added a conc. aqueous solution of HCl (0.61 mL, 7.30 mmol). A precipitate formed and the reaction continued to stir at room temperature for 2 h. The solvent was evaporated and the aq. residue was basified with a satd. aq. solution of NaHCO₃ and extracted with EtOAc (3×25 mL). The combined organic layer was washed with brine, dried over anhydrous MgSO₄, filtered and the filtrate was concentrated under reduced pressure to afford crude Intermediate A36H (0.79 g, 100%) as a white solid. MS(ES): m/z=326.0 [M+H]⁺.

Intermediate A36I: 2'-(3-Chloro-4-fluorophenyl)-3,3-difluoro-5',6'-dihydro-4'H-spiro[cyclobutane-1,7'-pyrazolo[1,5-a]pyrazine]

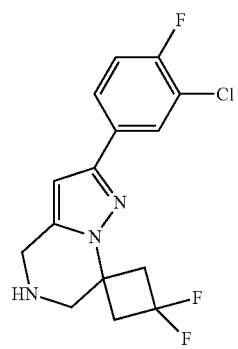 [SMILES: Fc1ccc(-c2cc3n(n2)C2(CNC3)CC(F)(F)C2)cc1Cl]

To a solution of Intermediate A36H (0.79 g, 2.425 mmol) in EtOH (24.25 mL) and THF (24.25 mL) was added NaBH₄ (0.459 g, 12.13 mmol) at room temperature and the reaction mixture was stirred for 16 h. It was diluted with water and extracted with DCM (3×25 mL). The combined organic layer was washed with brine, dried over anhydrous MgSO₄, filtered and the filtrate was concentrated under reduced pressure. It was purified by silica gel chromatography (12 g REDISEP® column, eluting with a gradient of 55 to 100% EtOAc in hexanes). Fractions containing the product were combined and evaporated to afford Intermediate A36I (0.139 g, 17.49%) as a white solid. MS(ES): m/z=328.1 [M+H]⁺.

Intermediate A36J: tert-Butyl 2'-(3-chloro-4-fluorophenyl)-3,3-difluoro-4'H-spiro[cyclobutane-1,7'-pyrazolo[1,5-a]pyrazine]-5'(6'H)-carboxylate

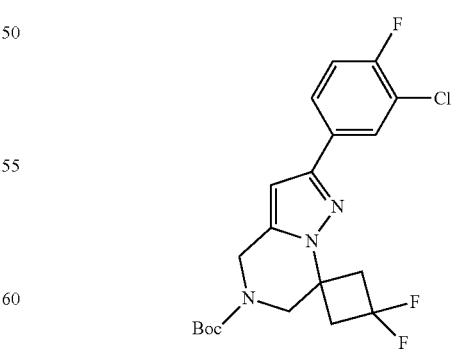

To a solution of Intermediate A36I (0.137 g, 0.418 mmol) in DCM (4.18 mL) were added TEA (0.175 mL, 1.254 mmol), DMAP (5.11 mg, 0.042 mmol) and Boc₂O (0.109 g, 0.502 mmol) and the reaction mixture was stirred for 16 h.

It was quenched by adding a satd. aq. solution of NaHCO₃, the two layers were separated and the aq. layer was extracted with DCM (2×10 mL). The combined organic layer was washed with brine, dried over anhydrous MgSO₄, filtered and the filtrate was concentrated under reduced pressure. It was purified by silica gel chromatography (24 g REDISEP® column, eluting with 21% EtOAc in hexanes). Fractions containing the product were combined and evaporated to afford Intermediate A36J (0.14 g, 78%) as a white solid. MS(ES): m/z=428.1 [M+H]⁺.

Intermediate A36K: tert-Butyl 2'-(3-chloro-4-fluorophenyl)-3,3-difluoro-3'-iodo-4'H-spiro[cyclobutane-1,7'-pyrazolo[1,5-a]pyrazine]-5'(6'H)-carboxylate

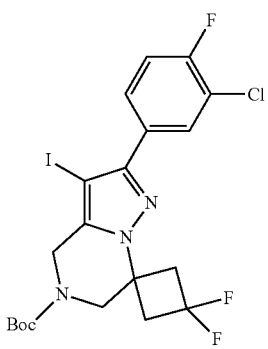 [SMILES: CC(C)(C)OC(=O)N1Cc2c(I)c(-c3ccc(F)c(Cl)c3)nn2C2(C1)CC(F)(F)C2]

To a solution of Intermediate A36J (0.14 g, 0.327 mmol) in DCM (2.62 mL) and MeOH (0.654 mL) was added NIS (0.221 g, 0.982 mmol) and the reaction mixture continued to stir at room temperature for 3 h. It was then concentrated under reduced pressure and the residue was purified by silica gel chromatography (24 g REDISEP® column, eluting with 18% EtOAc in hexanes). Fractions containing the product were combined and evaporated to afford Intermediate A36K (0.179 g, 100%) as a white foam. MS(ES): m/z=554.0 [M+H]⁺.

Intermediate A36L: tert-Butyl 2'-(3-chloro-4-fluorophenyl)-3'-cyano-3,3-difluoro-4'H-spiro[cyclobutane-1,7'-pyrazolo[1,5-a]pyrazine]-5'(6'H)-carboxylate

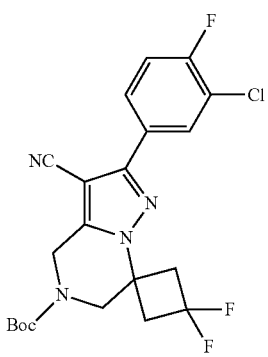 [SMILES: CC(C)(C)OC(=O)N1Cc2c(C#N)c(-c3ccc(F)c(Cl)c3)nn2C2(C1)CC(F)(F)C2]

To a degassed solution of Intermediate A36K (0.148 g, 0.267 mmol) in DMF (5.35 mL) was added copper(I) cyanide (0.061 g, 0.668 mmol) and the mixture was degassed again for 5 min. with N₂ and then heated in a sealed tube in an oil bath at 120° C. for 20 h. The reaction mixture was filtered and the filtrate concentrated under reduced pressure to afford a crude residue, which was purified by silica gel chromatography (12 g REDISEP® column, eluting with 30% EtOAc in hexanes). Fractions containing the product were combined and evaporated to afford Intermediate A36L (0.095 g, 52.59%) as an off-white solid. MS(ES): m/z=478.3 [M+Na]⁺.

Intermediate A36M: tert-Butyl 3'-carbamoyl-2'-(3-chloro-4-fluorophenyl)-3,3-difluoro-4'H-spiro[cyclobutane-1,7'-pyrazolo[1,5-a]pyrazine]-5'(6'H)-carboxylate

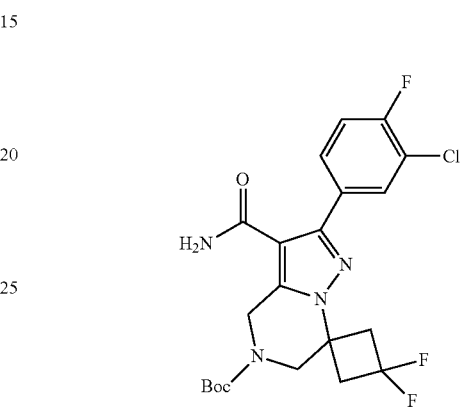

To an ice-cold solution of Intermediate A36L (0.095 g, 0.210 mmol) in DMSO (2.1 mL) was added a 5M aq. solution of KOH (0.21 mL, 1.049 mmol), followed by the dropwise addition of a 30% aq. solution of H₂O₂ (0.429 mL, 4.20 mmol). The reaction mixture was stirred at room temperature for 1 h. It was then diluted with water and extracted with EtOAc (2×10 mL). The combined organic layer was washed with brine, dried over anhydrous MgSO₄, filtered and the filtrate was concentrated under reduced pressure to give a yellow oil. It was purified by silica gel chromatography (12 g REDISEP® column, eluting with 30% EtOAc in DCM). Fractions containing the product were combined and evaporated to afford Intermediate A36M (0.073 g, 73.9%) as a white solid. MS(ES): m/z=471.1 [M+H]⁺.

Intermediate A36N: 2'-(3-Chloro-4-fluorophenyl)-3,3-difluoro-5',6'-dihydro-4'H-spiro[cyclobutane-1,7'-pyrazolo[1,5-a]pyrazine]-3'-carboxamide, TFA

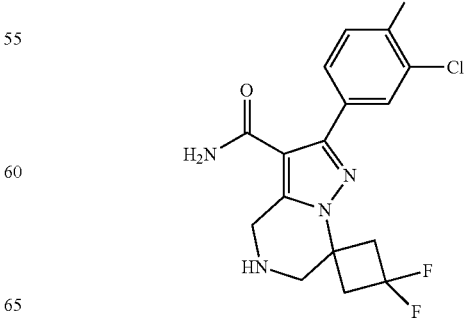

To a solution of Intermediate A36M (0.073 g, 0.155 mmol) in DCM (1.55 mL) was added TFA (0.24 mL, 3.10 mmol) and the reaction mixture continued to stir at room temperature for 2 h. It was then concentrated to dryness and the residue was dried under vacuum for 20 min. to afford crude Intermediate A36N (0.073 g, >99%) as the mono TFA salt.

Compound A36: 2'-(3-Chloro-4-fluorophenyl)-N$^{5'}$-(4-cyanophenyl)-3,3-difluoro-4'H-spiro[cyclobutane-1,7'-pyrazolo[1,5-a]pyrazine]-3',5'(6'H)-dicarboxamide

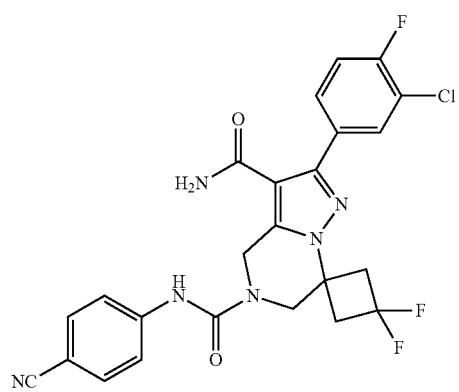 [SMILES: N#Cc1ccc(NC(=O)N2Cc3c(C(N)=O)c(-c4ccc(F)c(Cl)c4)nn3C3(C2)CC(F)(F)C3)cc1]

To a solution of Intermediate A36N (0.037 g, 0.076 mmol) and DIPEA (0.067 mL, 0.382 mmol) in DMF (1.0 mL) was added 4-isocyanatobenzonitrile (0.022 g, 0.153 mmol) and the reaction mixture continued to stir at room temperature for 2 h. It was then purified by preparative HPLC to afford Compound A36 (16.9 mg, 42.6%). MS(ES): m/z=515.3 [M+H]$^+$; HPLC Ret. Time 1.89 min. and 2.77 min. (HPLC Methods H and I); $^1$H NMR (500 MHz, DMSO-d$_6$) δ ppm 7.89 (d, J=5.9 Hz, 1H), 7.77-7.68 (m, 3H), 7.65 (d, J=8.8 Hz, 2H), 7.54-7.39 (m, 2H), 7.32 (br. s., 1H), 5.01 (s, 2H), 4.24-4.16 (m, 1H), 4.14 (s, 2H), 3.40 (d, J=14.7 Hz, 2H), 3.12-2.99 (m, 2H).

Scheme 51

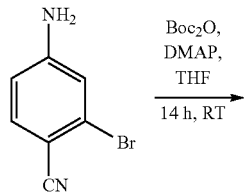

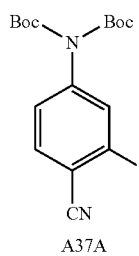 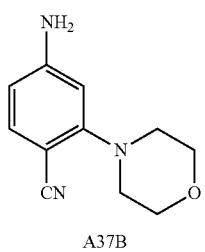

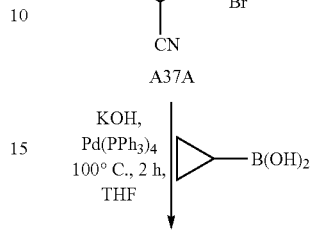

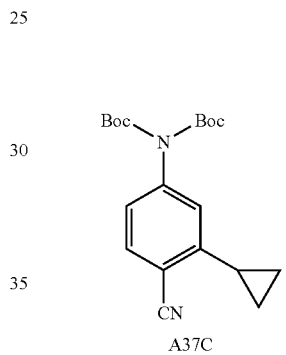 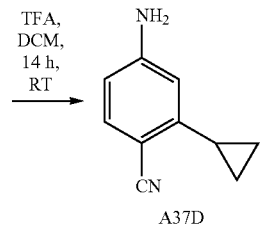

Intermediate A37A:
Di-tert-butyl(3-bromo-4-cyanophenyl)carbamate

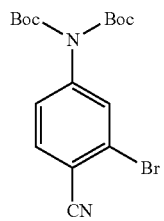

To a solution of 4-amino-2-bromobenzonitrile (4.68 g, 23.75 mmol) in THF (60 mL) were added TEA (6.62 mL, 47.5 mmol), DMAP (0.290 g, 2.375 mmol), and BOC-anhydride (5.63 mL, 24.23 mmol). The reaction mixture was allowed to stir at RT overnight. It was concentrated and the residue was purified by silica gel chromatography (80 g REDISEP® column, eluting with a gradient from 0-15% EtOAc in hexanes). Fractions containing the product were combined and evaporated to afford Intermediate A37A (3.8 g, 40.3%). MS(ES): m/z=420.8 [M+Na]$^+$; aH NMR (400 MHz, chloroform-d) δ ppm 7.71-7.53 (m, 2H), 7.50 (d, J=1.5 Hz, 1H), 1.48 (s, 18H).

Intermediate A37B:
4-Amino-2-morpholinobenzonitrile

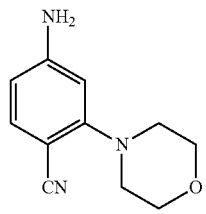 [SMILES: N#Cc1ccc(N)cc1N1CCOCC1]

To a vial were added Intermediate A37A (300 mg, 0.755 mmol), morpholine (132 mg, 1.510 mmol), sodium tert-butoxide (109 mg, 1.133 mmol), Pd$_2$(dba)$_3$ (69.2 mg, 0.076 mmol), XantPhos (87 mg, 0.151 mmol), and dioxane (8 mL). The reaction mixture was purged with nitrogen for 5 min. and capped. It was heated at 105° C. for 5 h. The reaction mixture was cooled to RT and diluted with equal parts water and DCM. The organic layer was separated and the aqueous layer was extracted twice more with DCM. The combined organic layer was washed with brine, dried over Na$_2$SO$_4$, and filtered. The filtrate was concentrated. The crude material was dissolved in DCM (15 mL) and treated with TFA (3 mL). The reaction mixture was stirred at RT overnight and concentrated. The residue was diluted with 20% MeOH in CHCl$_3$ and carefully quenched with a saturated aq. NaHCO$_3$ solution. The organic layer was separated and the aqueous layer was extracted twice more with CHCl$_3$. The combined organic layer was washed with brine, dried over Na$_2$SO$_4$, and filtered. The filtrate was concentrated. The crude product was purified by silica gel chromatography (40 g REDISEP® column, eluting with a gradient from 30-80% EtOAc in hexane). Fractions containing the product were combined and evaporated to afford Intermediate A37B (62 mg, 40.5%). MS(ES): m/z=204.1 [M+H]$^+$.

Intermediate A37D:
4-Amino-2-cyclopropylbenzonitrile

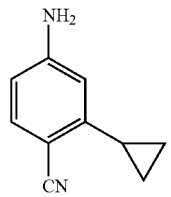 [SMILES: N#Cc1ccc(N)cc1C1CC1]

To a microwave vial were added cyclopropylboronic acid (441 mg, 5.14 mmol), Intermediate A37A (510 mg, 1.284 mmol), THF (8 mL), a 2 M aq. solution of potassium hydroxide (2.57 mL, 5.14 mmol), and Pd(Ph$_3$P)$_4$ (148 mg, 0.128 mmol). The reaction mixture was purged with nitrogen for 3 min. and heated at 100° C. in a microwave for 2 h. The reaction mixture was cooled to RT and diluted with equal parts water and DCM. The organic layer was separated and the aqueous layer was extracted twice more with DCM. The combined organic layer was washed with brine, dried over Na$_2$SO$_4$, and filtered. The filtrate was concentrated to afford crude Intermediate A37C which was used as such without further purification.

To a solution of crude Intermediate A37C in DCM (15 mL) was added TFA (6 mL). The reaction mixture was stirred at RT overnight and concentrated. The residue was purified by preparative HPLC. Fractions containing the product were combined and evaporated to afford Intermediate A37D (84 mg, 41.4%). MS(ES): m/z=159.2 [M+H]$^+$. $^1$H NMR (400 MHz, methanol-d$_4$)) δ ppm 7.22 (d, J=8.3 Hz, 1H), 6.54 (d, J=1.5 Hz, 1H), 6.39 (dd, J=8.0, 1.5 Hz, 1H), 1.91-1.74 (m, 1H), 1.06-0.94 (m, 2H), 0.80-0.63 (m, 2H).

Compound A37: 2-(3-Chlorophenyl)-N-(4-cyano-3-morpholinophenyl)-6,7-dihydropyrazolo[1,5-a]pyrazine-3,5(4H)-dicarboxamide

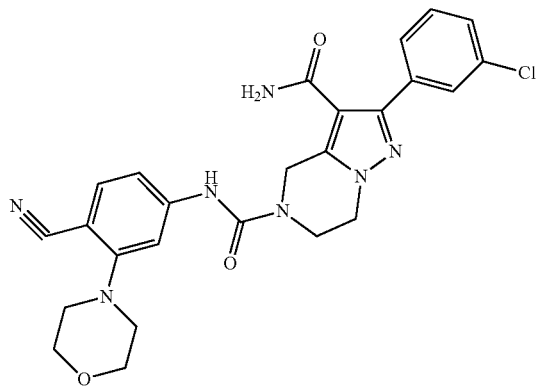 [SMILES: N#Cc1ccc(NC(=O)N2CCn3nc(-c4cccc(Cl)c4)c(C(N)=O)c3C2)cc1N1CCOCC1]

To a solution of triphosgene (25 mg, 0.084 mmol) in THF (2 mL) cooled to 0° C. was added a solution of Intermediate A37B (35 mg, 0.172 mmol) and TEA (0.096 mL, 0.689 mmol) in THF (2 mL). The resulting suspension was allowed to stir at 0° C. for 30 min. prior to the addition of a solution of Intermediate 156E (42.9 mg, 0.155 mmol) in DMF (1 mL). The reaction mixture was stirred at RT overnight and diluted with equal parts water and DCM. The organic layer was separated and the aqueous layer was extracted twice more with DCM. The combined organic layer was washed with brine, dried over Na$_2$SO$_4$, and filtered. The filtrate was concentrated to afford the crude material which was purified by preparative HPLC. Fractions containing the desired product were combined and dried under vacuum to afford Compound A37 (8.2 mg, 9.4%). MS(ES): m/z=506.3 [M+H$^+$; HPLC Ret. Time 1.57 min. and 2.17 min. (HPLC Methods H and I); $^1$H NMR (500 MHz, DMSO-d$_6$) δ ppm 9.09 (s, 1H), 7.73 (s, 1H), 7.66 (d, J=7.0 Hz, 1H), 7.54 (d, J=8.8 Hz, 1H), 7.50-7.42 (m, 2H), 7.39 (br. s., 1H), 7.20 (br. s., 1H), 6.90 (s, 1H), 6.84 (d, J=8.8 Hz, 1H), 4.91 (s, 2H), 4.25 (br. s., 2H), 4.01 (br. s., 2H), 3.73 (br. s., 4H), 3.28 (m., 3H), 3.34 (br. s., 1H).

The Compounds described in Table 34 were synthesized analogous to Compound A37 by reacting Intermediate 156E with corresponding amines.

TABLE 34

| Ex. No. | Structure | Name | [M + H]⁺ | Ret Time (min.) | HPLC Method |
|---|---|---|---|---|---|
| A38 | 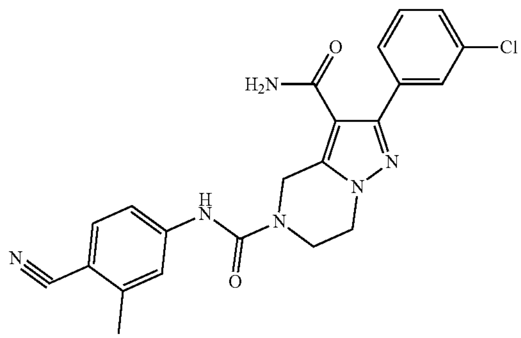 [SMILES: Cc1cc(NC(=O)N2CCn3nc(-c4cccc(Cl)c4)c(C(N)=O)c3C2)ccc1C#N] | 2-(3-Chlorophenyl)-N⁵-(4-cyano-3-methylphenyl)-6,7-dihydropyrazolo[1,5-a]pyrazine-3,5(4H)-dicarboxamide | 435.4 | 1.46<br>2.42 | H<br>I |
| A39 | 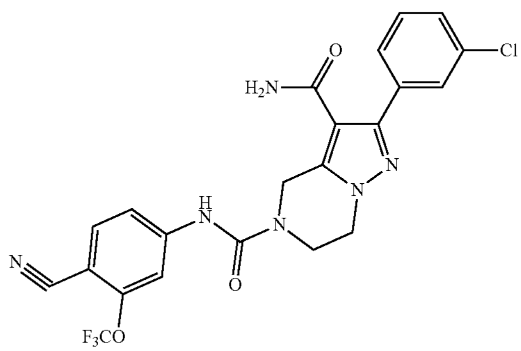 [SMILES: N#Cc1ccc(NC(=O)N2CCn3nc(-c4cccc(Cl)c4)c(C(N)=O)c3C2)cc1OC(F)(F)F] | 2-(3-Chlorophenyl)-N⁵-(4-cyano-3-(trifluoromethoxy)phenyl)-6,7-dihydropyrazolo[1,5-a]pyrazine-3,5(4H)-dicarboxamide | 505.4 | 1.68<br>2.59 | H<br>I |
| A40 | 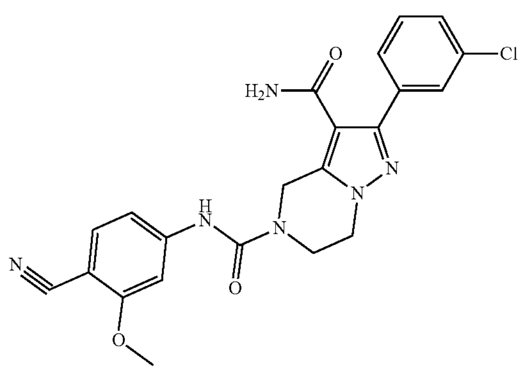 [SMILES: COc1cc(NC(=O)N2CCn3nc(-c4cccc(Cl)c4)c(C(N)=O)c3C2)ccc1C#N] | 2-(3-Chlorophenyl)-N⁵-(4-cyano-3-methoxyphenyl)-6,7-dihydropyrazolo[1,5-a]pyrazine-3,5(4H)-dicarboxamide | 451.5 | 1.44<br>2.35 | H<br>I |
| A41 | 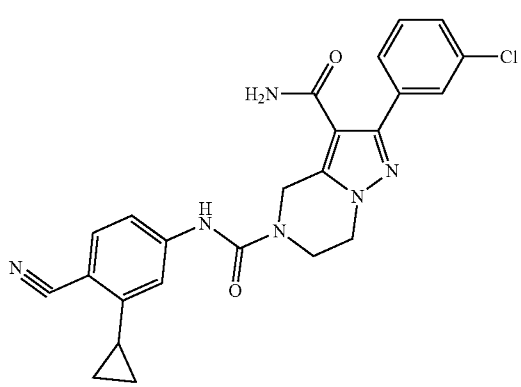 [SMILES: N#Cc1ccc(NC(=O)N2CCn3nc(-c4cccc(Cl)c4)c(C(N)=O)c3C2)cc1C1CC1] | 2-(3-Chlorophenyl)-N⁵-(4-cyano-3-cyclopropylphenyl)-6,7-dihydropyrazolo[1,5-a]pyrazine-3,5(4H)-dicarboxamide | 460.2 | 1.78<br>2.33 | H<br>I |

TABLE 34-continued

| Ex. No. | Structure | Name | [M + H]+ | Ret Time (min.) | HPLC Method |
|---|---|---|---|---|---|
| A42 | 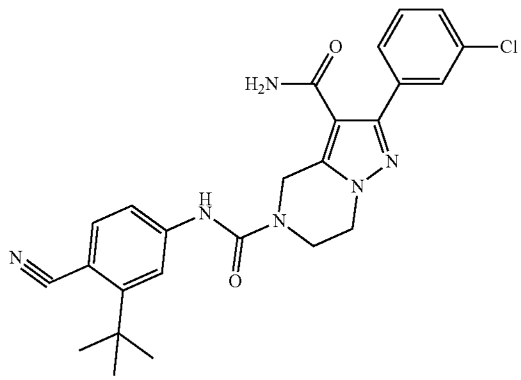 [SMILES: CC(C)(C)c1cc(NC(=O)N2CCn3nc(-c4cccc(Cl)c4)c(C(N)=O)c3C2)ccc1C#N] | $N^5$-(3-(tert-Butyl)-4-cyanophenyl)-2-(3-chlorophenyl)-6,7-dihydropyrazolo[1,5-a]pyrazine-3,5(4H)-dicarboxamide | 477.5 | 1.68<br>2.64 | H<br>I |
| A43 | 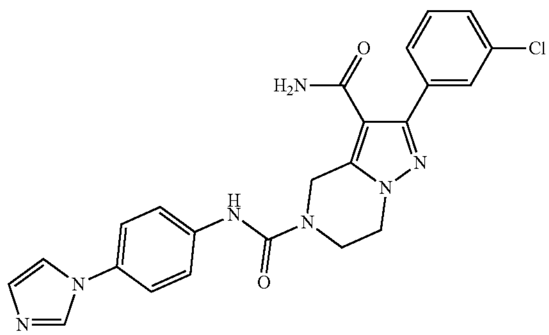 [SMILES: NC(=O)c1c(-c2cccc(Cl)c2)nn2c1CN(C(=O)Nc1ccc(-n3ccnc3)cc1)CC2] | $N^5$-(4-(1H-Imidazol-1-yl)phenyl)-2-(3-chlorophenyl)-6,7-dihydropyrazolo[1,5-a]pyrazine-3,5(4H)-dicarboxamide | 496.2 | 1.94<br>2.51 | H<br>I |
| A44 | 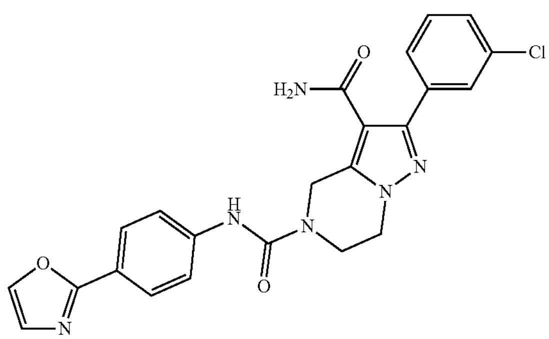 [SMILES: NC(=O)c1c(-c2cccc(Cl)c2)nn2c1CN(C(=O)Nc1ccc(-c3ncco3)cc1)CC2] | 2-(3-Chlorophenyl)-$N^5$-(4-(oxazol-2-yl)phenyl)-6,7-dihydropyrazolo[1,5-a]pyrazine-3,5(4H)-dicarboxamide | 463.3 | 1.48<br>2.33 | H<br>I |
| A45 | 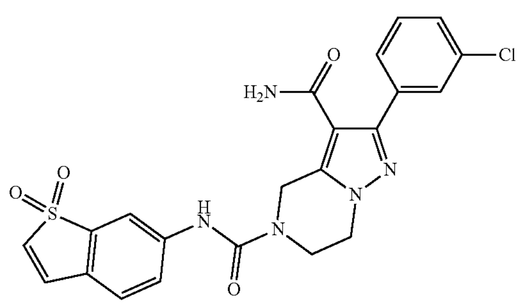 [SMILES: NC(=O)c1c(-c2cccc(Cl)c2)nn2c1CN(C(=O)Nc1ccc3c(c1)S(=O)(=O)C=C3)CC2] | 2-(3-Chlorophenyl)-$N^5$-(1,1-dioxidobenzo[b]thiophen-6-yl)-6,7-dihydropyrazolo[1,5-a]pyrazine-3,5(4H)-dicarboxamide | 484.1 | 1.59<br>2.09 | H<br>I |

TABLE 34-continued

| Ex. No. | Structure | Name | [M + H]+ | Ret Time (min.) | HPLC Method |
|---|---|---|---|---|---|
| A46 | 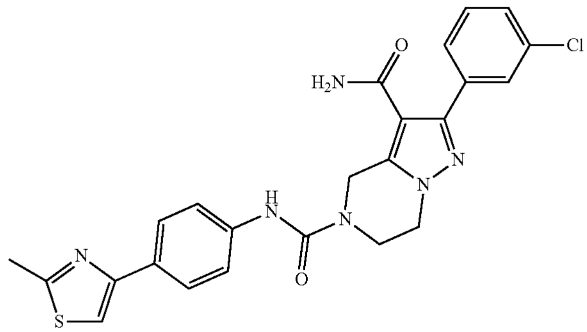 [SMILES: Cc1nc(-c2ccc(NC(=O)N3CCn4nc(-c5cccc(Cl)c5)c(C(N)=O)c4C3)cc2)cs1] | 2-(3-Chlorophenyl)-N5-(4-(2-methylthiazol-4-yl)phenyl)-6,7-dihydropyrazolo[1,5-a]pyrazine-3,5(4H)-dicarboxamide | 467.2 | 1.46<br>2.36 | H<br>I |
| A47 | 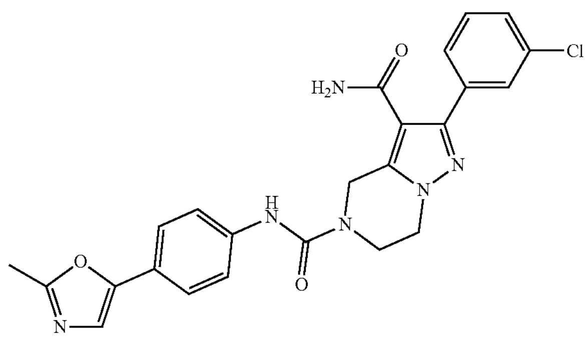 [SMILES: Cc1ncc(-c2ccc(NC(=O)N3CCn4nc(-c5cccc(Cl)c5)c(C(N)=O)c4C3)cc2)o1] | 2-(3-Chlorophenyl)-N5-(4-(2-methyloxazol-5-yl)phenyl)-6,7-dihydropyrazolo[1,5-a]pyrazine-3,5(4H)-dicarboxamide | 451.2 | 1.41<br>2.24 | H<br>I |

The Compounds described in Table 35 were synthesized analogous to Compound A37 by reacting Intermediate 172B with corresponding amines.

TABLE 35

| Ex. No. | Structure | Name | [M − H]+ | Ret Time (min.) | HPLC Method |
|---|---|---|---|---|---|
| A48 | 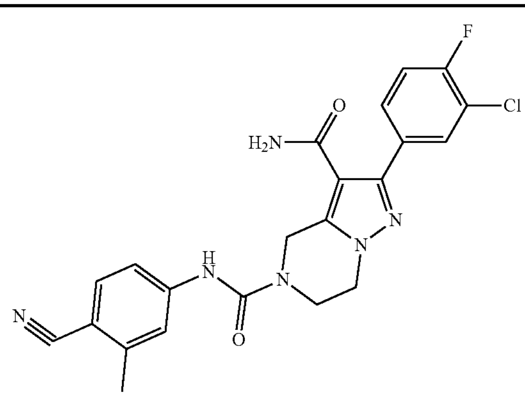 | 2-(3-Chloro-4-fluorophenyl)-N5-(4-cyano-3-methylphenyl)-6,7-dihydropyrazolo[1,5-a]pyrazine-3,5(4H)-dicarboxamide | 453.2 | 1.89<br>2.44 | H<br>I |

TABLE 35-continued

| Ex. No. | Structure | Name | [M − H]+ | Ret Time (min.) | HPLC Method |
|---|---|---|---|---|---|
| A49 | 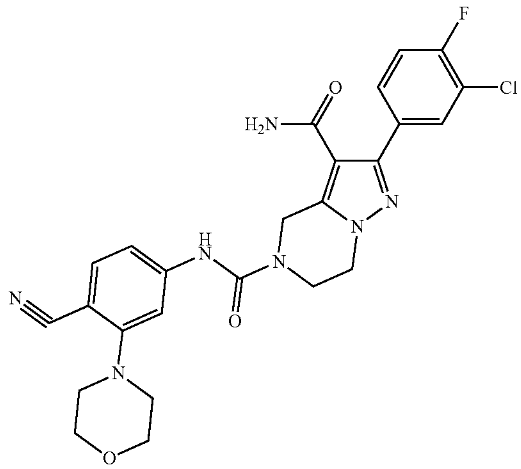 [SMILES: N#Cc1ccc(NC(=O)N2CCn3nc(-c4ccc(F)c(Cl)c4)c(C(N)=O)c3C2)cc1N1CCOCC1] | 2-(3-Chloro-4-fluorophenyl)-N5-(4-cyano-3-morpholinophenyl)-6,7-dihydropyrazolo[1,5-a]pyrazine-3,5(4H)-dicarboxamide | 524.2 | 1.42<br>2.43 | H<br>I |
| A50 | 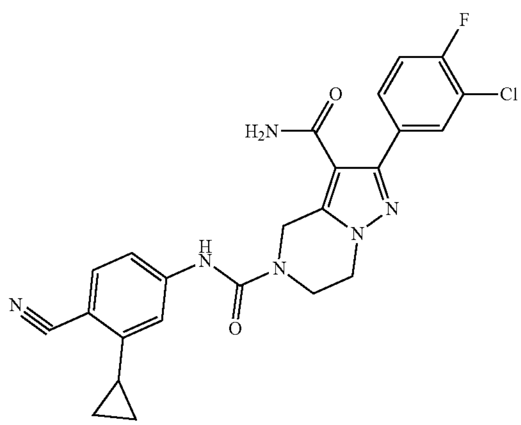 [SMILES: N#Cc1ccc(NC(=O)N2CCn3nc(-c4ccc(F)c(Cl)c4)c(C(N)=O)c3C2)cc1C1CC1] | 2-(3-Chloro-4-fluorophenyl)-N5-(4-cyano-3-cyclopropylphenyl)-6,7-dihydropyrazolo[1,5-a]pyrazine-3,5(4H)-dicarboxamide | 479.3 | 1.57<br>2.43 | H<br>I |
| A51 | 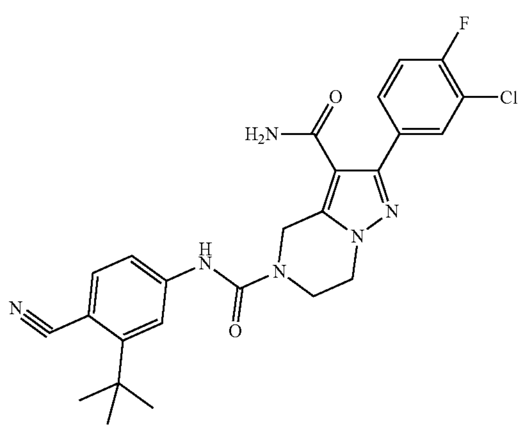 [SMILES: CC(C)(C)c1cc(NC(=O)N2CCn3nc(-c4ccc(F)c(Cl)c4)c(C(N)=O)c3C2)ccc1C#N] | N5-(3-(tert-Butyl)-4-cyanophenyl)-2-(3-chloro-4-fluorophenyl)-6,7-dihydropyrazolo[1,5-a]pyrazine-3,5(4H)-dicarboxamide | 495.3 | 1.95<br>2.63 | H<br>I |

TABLE 35-continued

| Ex. No. | Structure | Name | [M − H]+ | Ret Time (min.) | HPLC Method |
|---|---|---|---|---|---|
| A52 | 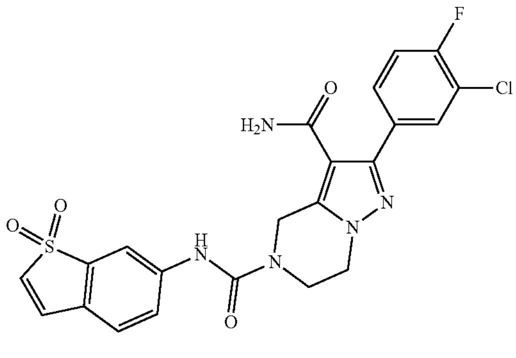 [SMILES: NC(=O)c1c(-c2ccc(F)c(Cl)c2)nn2c1CN(C(=O)Nc1ccc3c(c1)S(=O)(=O)C=C3)CC2] | 2-(3-Chloro-4-fluorophenyl)-N[5]-(1,1-dioxidobenzo[b]thiophen-6-yl)-6,7-dihydropyrazolo[1,5-a]pyrazine-3,5(4H)-dicarboxamide | 503.3 | 1.43<br>2.17 | H<br>I |
| A53 | 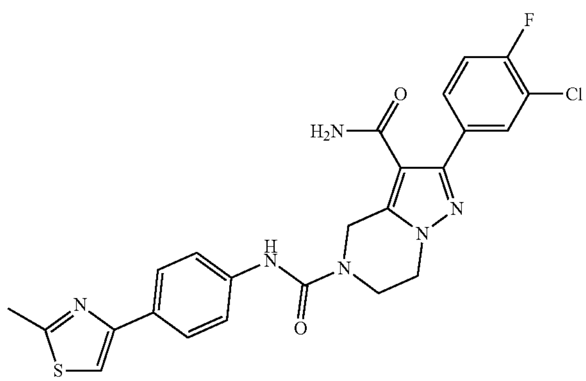 [SMILES: Cc1nc(-c2ccc(NC(=O)N3CCn4nc(-c5ccc(F)c(Cl)c5)c(C(N)=O)c4C3)cc2)cs1] | 2-(3-Chloro-4-fluorophenyl)-N[5]-(4-(2-methylthiazol-4-yl)phenyl)-6,7-dihydropyrazolo[1,5-a]pyrazine-3,5(4H)-dicarboxamide | 485.4 | 1.51<br>2.43 | H<br>I |
| A54 | 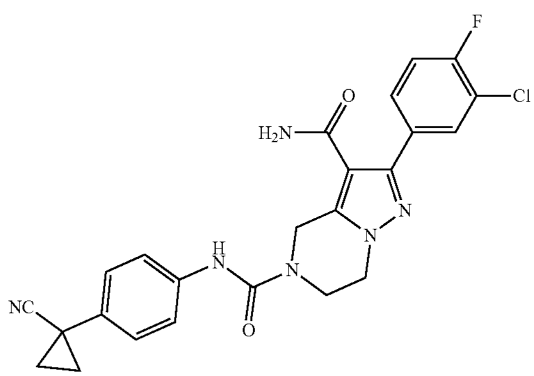 [SMILES: N#CC1(c2ccc(NC(=O)N3CCn4nc(-c5ccc(F)c(Cl)c5)c(C(N)=O)c4C3)cc2)CC1] | 2-(3-Chloro-4-fluorophenyl)-N[5]-(4-(1-cyanocyclopropyl)phenyl)-6,7-dihydropyrazolo[1,5-a]pyrazine-3,5(4H)-dicarboxamide | 479.2 | 1.56<br>2.36 | H<br>I |

The Compounds described in Table 36 were synthesized analogous to Compound A37 by reacting Intermediate 185A with corresponding amines.

TABLE 36

| Ex. No. | Structure | Name | [M − H]+ | Ret Time (min.) | HPLC Method |
|---|---|---|---|---|---|
| A55 | 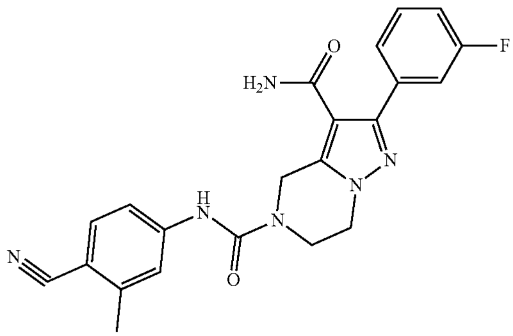 [SMILES: Cc1cc(NC(=O)N2CCn3nc(-c4cccc(F)c4)c(C(N)=O)c3C2)ccc1C#N] | N5-(4-Cyano-3-methylphenyl)-2-(3-fluorophenyl)-6,7-dihydropyrazolo[1,5-a]pyrazine-3,5(4H)-dicarboxamide | 419.3 | 1.62<br>2.18 | H<br>I |
| A56 | 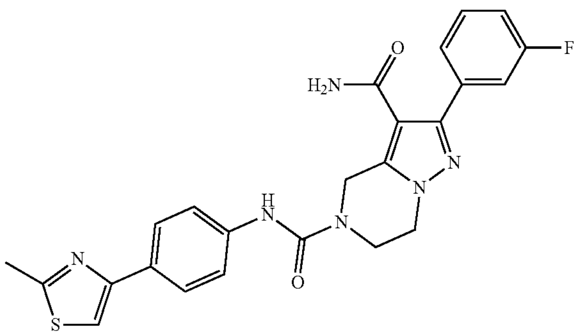 [SMILES: Cc1nc(-c2ccc(NC(=O)N3CCn4nc(-c5cccc(F)c5)c(C(N)=O)c4C3)cc2)cs1] | 2-(3-Fluorophenyl)-N5-(4-(2-methylthiazol-4-yl)phenyl)-6,7-dihydropyrazolo[1,5-a]pyrazine-3,5(4H)-dicarboxamide | 451.3 | 1.36<br>2.21 | H<br>I |
| A57 | 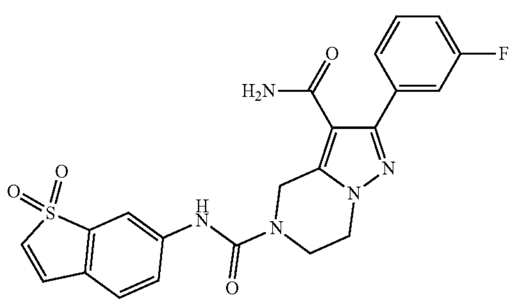 [SMILES: NC(=O)c1c(-c2cccc(F)c2)nn2c1CN(C(=O)Nc1ccc3c(c1)S(=O)(=O)C=C3)CC2] | N5-(1,1-Dioxidobenzo[b]thiophen-6-yl)-2-(3-fluorophenyl)-6,7-dihydropyrazolo[1,5-a]pyrazine-3,5(4H)-dicarboxamide | 468.2 | 1.23<br>1.91 | H<br>I |
| A58 | 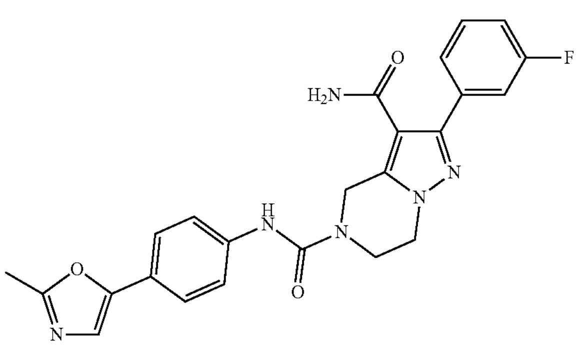 [SMILES: Cc1ncc(-c2ccc(NC(=O)N3CCn4nc(-c5cccc(F)c5)c(C(N)=O)c4C3)cc2)o1] | 2-(3-Fluorophenyl)-N5-(4-(2-methyloxazol-5-yl)phenyl)-6,7-dihydropyrazolo[1,5-a]pyrazine-3,5(4H)-dicarboxamide | 435.4 | 1.15<br>2.09 | H<br>I |

TABLE 36-continued

| Ex. No. | Structure | Name | [M − H]+ | Ret Time (min.) | HPLC Method |
|---|---|---|---|---|---|
| A59 | 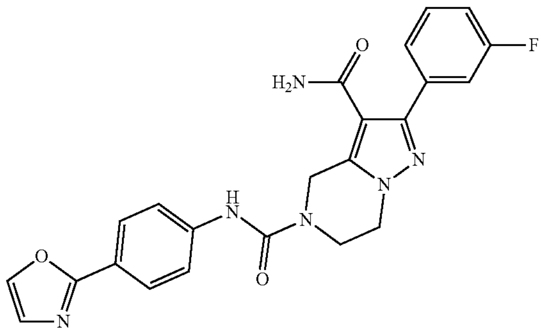 [SMILES: NC(=O)c1c(-c2cccc(F)c2)nn2c1CN(C(=O)Nc1ccc(-c3ncco3)cc1)CC2] | 2-(3-Fluorophenyl)-N⁵-(4-(oxazol-2-yl)phenyl)-6,7-dihydropyrazolo[1,5-a]pyrazine-3,5(4H)-dicarboxamide | 447.3 | 1.32<br>2.19 | H<br>I |

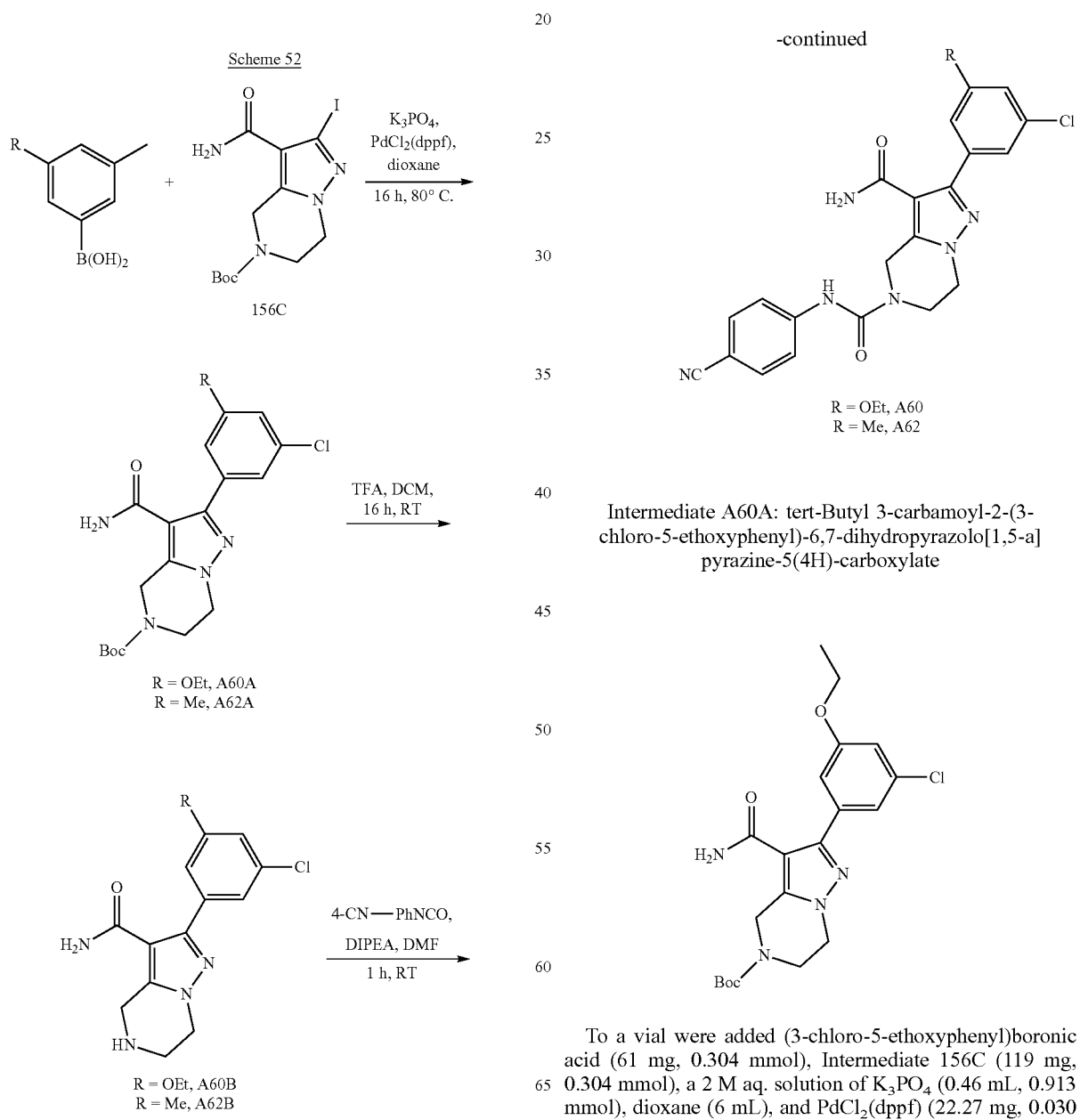

Intermediate A60A: tert-Butyl 3-carbamoyl-2-(3-chloro-5-ethoxyphenyl)-6,7-dihydropyrazolo[1,5-a]pyrazine-5(4H)-carboxylate To a vial were added (3-chloro-5-ethoxyphenyl)boronic acid (61 mg, 0.304 mmol), Intermediate 156C (119 mg, 0.304 mmol), a 2 M aq. solution of K₃PO₄ (0.46 mL, 0.913 mmol), dioxane (6 mL), and PdCl₂(dppf) (22.27 mg, 0.030 mmol). The reaction mixture was purged with nitrogen for 1 min. and then heated at 80° C. overnight. The reaction mixture was diluted with equal parts of water and DCM. The organic layer was separated and the aqueous layer was extracted twice more with DCM. The combined organic layer was washed with brine, dried over Na$_2$SO$_4$, and filtered. The filtrate was concentrated. The residue was purified by silica gel chromatography (40 g REDISEP® column, eluting with a gradient from 20-80% EtOAc in hexanes). Fractions containing the product were combined and evaporated to afford Intermediate A60A (62 mg, 40.5%). MS(ES): m/z=421.2 [M+H]$^+$; $^1$H NMR (400 MHz, chloroform-d)) δ ppm 7.16 (t, J=1.6 Hz, 1H), 7.00 (d, J=1.8 Hz, 2H), 4.99 (s, 2H), 4.23 (t, J=5.3 Hz, 2H), 4.07 (q, J=7.0 Hz, 2H), 3.96 (t, J=5.3 Hz, 2H), 1.53 (s, 9H), 1.44 (t, J=7.0 Hz, 3H).

Compound A60: 2-(3-Chloro-5-ethoxyphenyl)-N-(4-cyanophenyl)-6,7-dihydropyrazolo[1,5-a]pyrazine-3,5(4H)-dicarboxamide Compound A61: N$^5$-(3-Chloro-4-cyanophenyl)-2-(3-chloro-5-ethoxyphenyl)-6,7-dihydropyrazolo[1,5-a]pyrazine-3,5(4H)-dicarboxamide

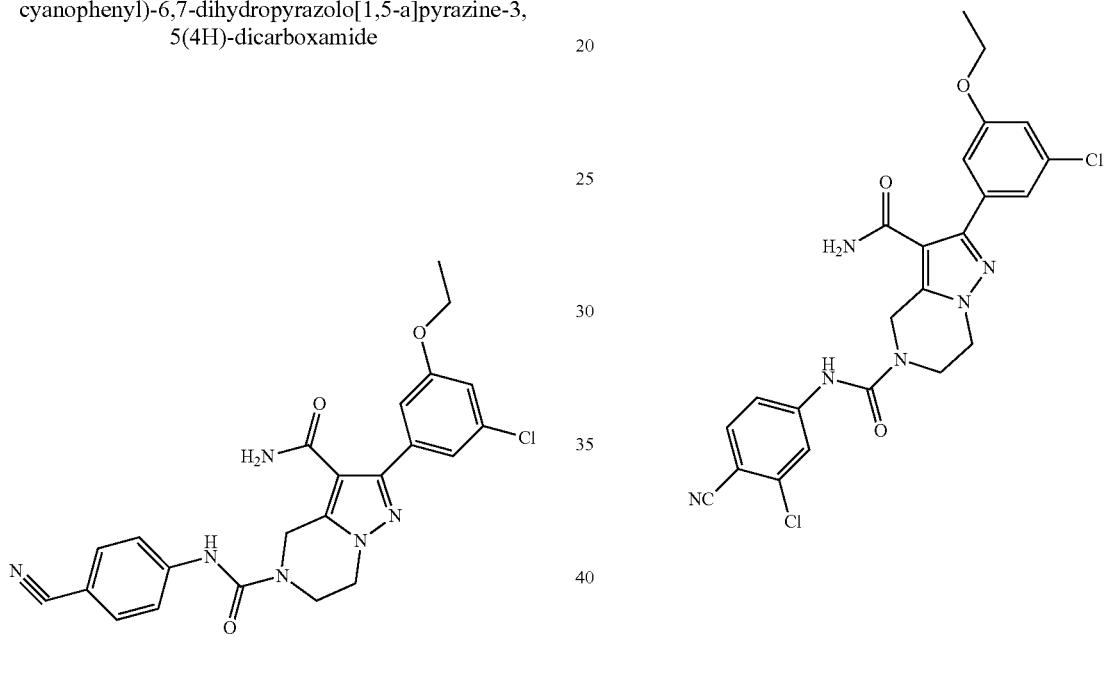

To a solution of Intermediate A60A (60 mg, 0.143 mmol) in DCM (10 mL) was added TFA (1 mL, 12.98 mmol). The reaction mixture was then allowed to stir at RT overnight prior to the removal of the volatiles to afford crude Intermediate A60B as a TFA salt. The TFA salt was then dissolved in DMF (1 mL) and treated with DIPEA (0.018 mL, 0.115 mmol). The resulting mixture was allowed to stir for 5 min. prior to the addition of 4-isocyanatobenzonitrile (8.29 mg, 0.057 mmol). The reaction mixture was stirred for 1 h, after which it was filtered and purified by preparative HPLC. Fractions containing the desired product were combined and dried under vacuum to afford Compound A60 (5.8 mg, 21.7%). MS(ES): m/z=463.3 [M−H]$^+$; HPLC Ret. Time 1.71 min. and 2.53 min. (HPLC Methods H and I); $^1$H NMR (500 MHz, DMSO-d$_6$)) δ ppm 7.78-7.64 (m, 4H), 7.29 (s, 2H), 7.22 (s, 2H), 7.01 (s, 1H), 4.90 (s, 2H), 4.25 (br. s., 2H), 4.07 (q, J=7.0 Hz, 2H), 4.00 (br. s., 2H), 3.37 (d, J=8.8 Hz, 2H), 3.18 (d, J=4.4 Hz, 1H), 1.34 (t, J=6.8 Hz, 3H).

To a solution of triphosgene (23.13 mg, 0.078 mmol) in THF (4 mL) was added a solution of 4-amino-2-chlorobenzonitrile (11.89 mg, 0.078 mmol) and TEA (0.043 mL, 0.312 mmol) in THF (1 mL) at 0° C. The reaction mixture was allowed to stir at 0° C. for 30 min. prior to the addition of a solution of Intermediate A60B (25 mg, 0.078 mmol) in DMF (1 ML). The reaction mixture was stirred for 1 h after which it was filtered and purified by preparative HPLC. Fractions containing the desired product were combined and dried under vacuum to afford Compound A61 (26.5 mg, 68.1%). MS(ES): m/z=497.3 [M−H]$^+$; HPLC Ret. Time 1.72 min. and 2.62 min. (HPLC Methods H and I); $^1$H NMR (500 MHz, DMSO-d$_6$) δ ppm 9.57 (s, 1H), 7.91 (d, J=1.8 Hz, 1H), 7.85 (d, J=8.8 Hz, 1H), 7.61 (dd, J=8.8, 1.8 Hz, 1H), 7.29 (s, 1H), 7.27-7.15 (m, 2H), 7.08-6.95 (m, 1H), 4.91 (s, 2H), 4.44-4.21 (m, 2H), 4.15-3.92 (m, 4H), 1.34 (t, J=7.0 Hz, 3H).

Compound A62: 2-(3-Chloro-5-methylphenyl)-N⁵-(4-cyanophenyl)-6,7-dihydropyrazolo[1,5-a]pyrazine-3,5(4H)-dicarboxamide

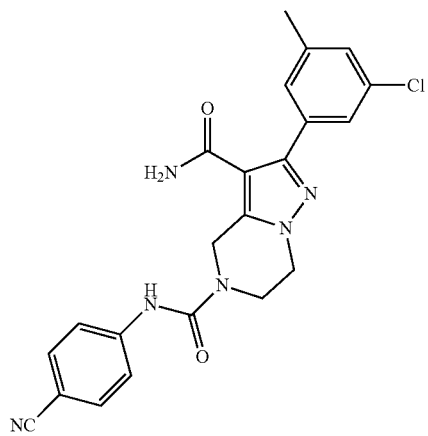 [SMILES: Cc1cc(Cl)cc(-c2nn3c(c2C(N)=O)CN(C(=O)Nc2ccc(C#N)cc2)CC3)c1]

Compound A62 was synthesized analogous to Compound A60 by reacting deprotected A62A with 4-isocyanatobenzonitrile. The compound was purified by preparative HPLC. MS(ES): m/z=433.3 [M–H]⁺; HPLC Ret. Time 1.65 min. and 2.51 min. (HPLC Methods H and I). ¹H NMR (500 MHz, DMSO-$d_6$)) δ ppm 7.78-7.59 (m, 4H), 7.51 (s, 1H), 7.46 (s, 1H), 7.38 (br. s., 1H), 7.27 (s, 1H), 7.21 (br. s., 1H), 4.90 (s, 2H), 4.24 (br. s., 2H), 4.01 (br. s., 2H), 2.34 (s, 3H).

Compound A63: N⁵-(3-Chloro-4-cyanophenyl)-2-(3-chloro-5-methylphenyl)-6,7-dihydropyrazolo[1,5-a]pyrazine-3,5(4H)-dicarboxamide

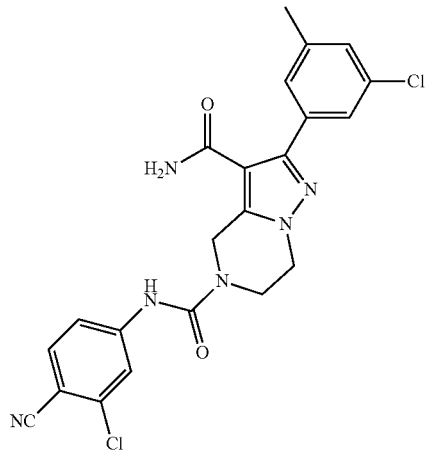 [SMILES: Cc1cc(Cl)cc(-c2nn3c(c2C(N)=O)CN(C(=O)Nc2ccc(C#N)c(Cl)c2)CC3)c1]

Compound A63 was synthesized analogous to Compound A61 by reacting deprotected A62A with 4-amino-2-chlorobenzonitrile. The compound was purified by preparative HPLC. MS(ES): m/z=467.2 [M–H]⁺; HPLC Ret. Time 2.07 min. and 2.71 min. (HPLC Methods H and I). ¹H NMR (500 MHz, DMSO-$d_6$) δ ppm 9.58 (s, 1H), 7.91 (s, 1H), 7.85 (d, J=8.8 Hz, 1H), 7.61 (d, J=8.8 Hz, 1H), 7.51 (s, 1H), 7.47 (s, 1H), 7.40 (br. s., 1H), 7.28 (s, 1H), 7.18 (br. s., 1H), 4.91 (s, 2H), 4.25 (t, J=5.0 Hz, 2H), 4.07-3.93 (m, 2H), 2.35 (s, 3H).

Scheme 53

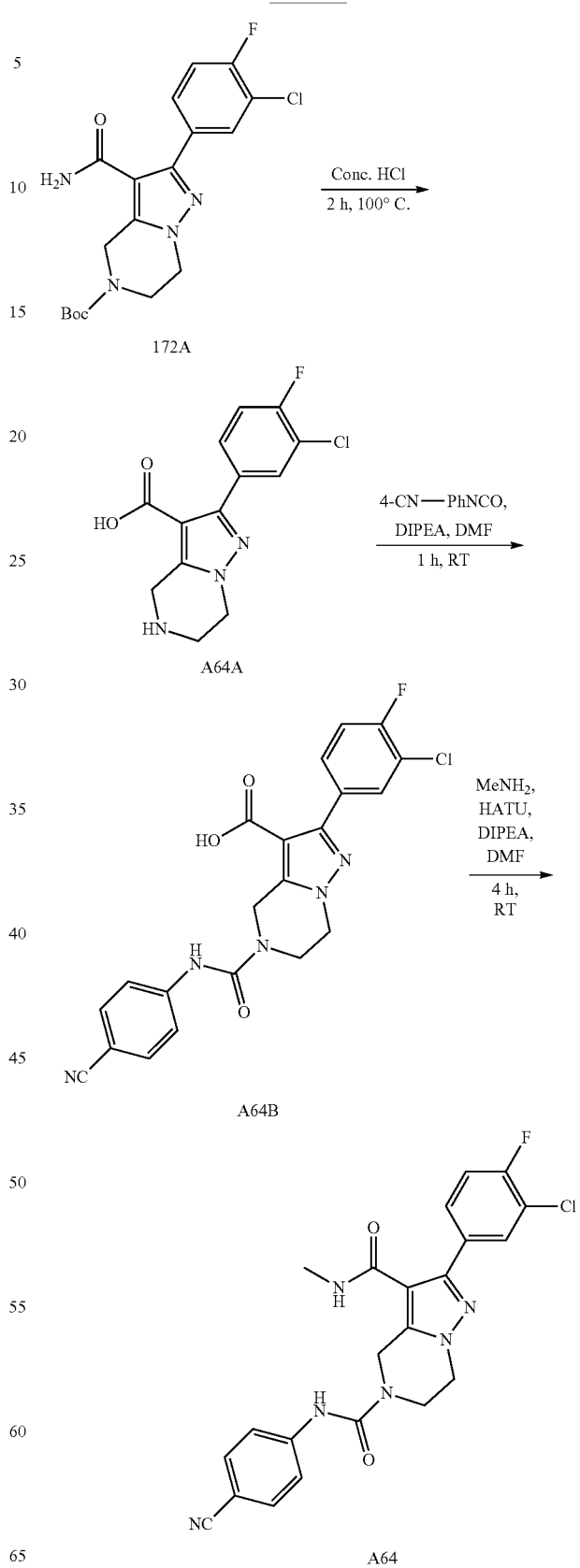

Intermediate A64A: 2-(3-Chloro-4-fluorophenyl)-4,5,6,7-tetrahydropyrazolo[1,5-a]pyrazine-3-carboxylic acid

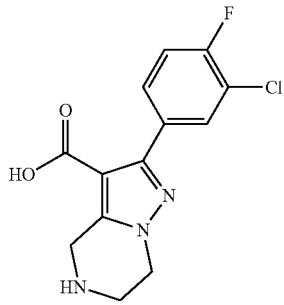 [SMILES: O=C(O)c1c(-c2ccc(F)c(Cl)c2)nn2c1CNCC2]

A suspension of Intermediate 172A (700 mg, 2.375 mmol) in a concentrated aq. solution of HCl (6 mL) was heated at 100° C. for 2 h and it became a solution. The reaction mixture was cooled to RT and treated with 1 N NaOH to PH 7. The resulting precipitate was collected by filtration, washed with water, and dried with vacuum to afford Intermediate A64A (250 mg, 35.6%) as a white powder. MS(ES): m/z=296.0 [M+H]$^+$.

Intermediate A64B: 2-(3-Chloro-4-fluorophenyl)-5-((4-cyanophenyl)carbamoyl)-4,5,6,7-tetrahydropyrazolo[1,5-a]pyrazine-3-carboxylic acid

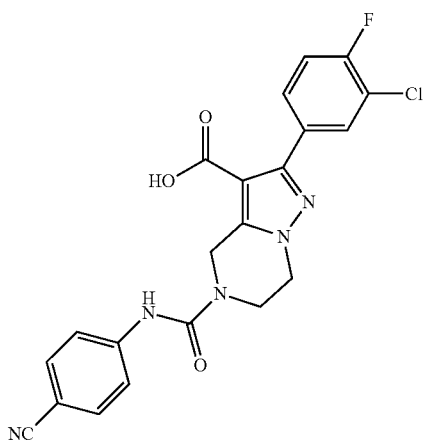 [SMILES: N#Cc1ccc(NC(=O)N2CCn3nc(-c4ccc(F)c(Cl)c4)c(C(=O)O)c3C2)cc1]

To a solution of Intermediate A64A (80 mg, 0.195 mmol) in DMF (3 mL) was added Hunig's base (0.068 mL, 0.391 mmol). The resulting mixture was allowed to stir for 5 min. prior to the addition of 4-isocyanatobenzonitrile (28.1 mg, 0.195 mmol). The reaction mixture was allowed to stir at RT for 2 h after which it was filtered and purified by preparative HPLC. Fractions containing the desired product were combined and dried under vacuum to afford Intermediate 28B (50 mg, 58%). MS(ES): m/z=440.1 [M+H]$^+$.

Compound A64: 2-(3-Chloro-4-fluorophenyl)-N$^5$-(4-cyanophenyl)-N3-methyl-6,7-dihydropyrazolo[1,5-a]pyrazine-3,5(4H)-dicarboxamide

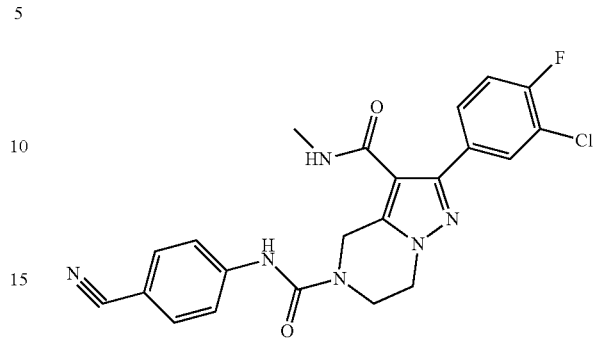

To a solution of Intermediate A64B (25 mg, 0.045 mmol) in DMF (1 mL) were added methylamine HCl salt (6.10 mg, 0.090 mmol), Hunig's base (0.032 mL, 0.181 mmol), and HATU (34.3 mg, 0.090 mmol). The reaction mixture was allowed stir at RT for 4 h after which it was filtered and purified by preparative HPLC. Fractions containing the desired product were combined and dried under vacuum to afford Compound A64 (10 mg, 48.9%). MS(ES): m/z=451.4 [M−H]$^+$; HPLC Ret. Time 1.55 min. and 2.43 min. (HPLC Methods H and I); $^1$H NMR (500 MHz, DMSO-d$_6$) δ ppm 7.87-7.77 (m, 2H), 7.77-7.59 (m, 6H), 7.47 (t, J=9.0 Hz, 1H), 4.88 (s, 2H), 4.25 (br. s., 2H), 4.01 (br. s., 2H), 3.35 (s, 3H).

Compound A65: 2-(3-Chloro-4-fluorophenyl)-N$^5$-(4-cyanophenyl)-N$^3$-cyclopropyl-6,7-dihydropyrazolo[1,5-a]pyrazine-3,5(4H)-dicarboxamide

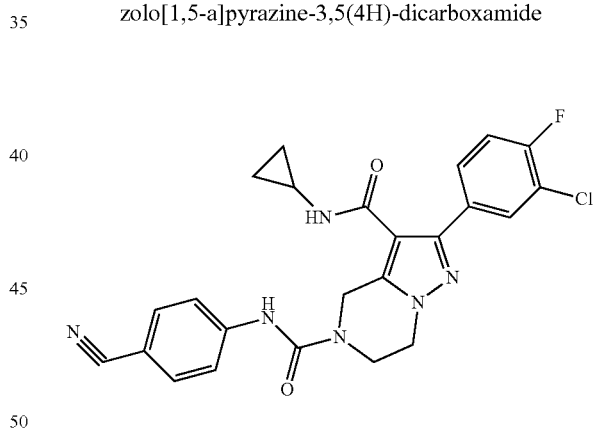

Compound A65 was synthesized analogous to Compound A64 by reacting Intermediate A64B with cyclopropylamine. The compound was purified by preparative HPLC. MS(ES): m/z=477.4 [M−H]$^+$; HPLC Ret. Time 1.64 min. and 2.51 min. (HPLC Methods H and I); $^1$H NMR (500 MHz, DMSO-d$_6$) δ ppm 9.41 (s, 1H), 8.02 (d, J=3.7 Hz, 1H), 7.78 (d, J=7.3 Hz, 1H), 7.75-7.59 (m, 5H), 7.47 (t, J=9.0 Hz, 1H), 4.84 (s, 2H), 4.24 (br. s., 2H), 4.00 (br. s., 2H), 2.79 (d, J=3.3 Hz, 1H), 0.68 (d, J=5.5 Hz, 2H), 0.46 (br. s., 2H).

Scheme 54

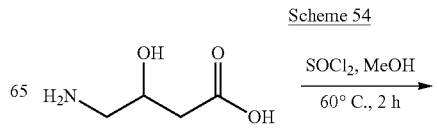

511
-continued

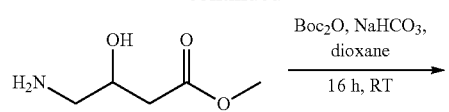
A66A

Boc₂O, NaHCO₃,
dioxane
──────────────→
16 h, RT

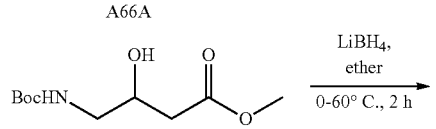
A66B

LiBH₄,
ether
──────────────→
0-60° C., 2 h

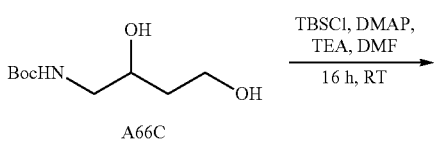
A66C

TBSCl, DMAP,
TEA, DMF
──────────────→
16 h, RT

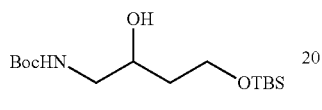
A66D

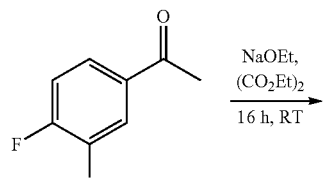

NaOEt,
(CO₂Et)₂
──────────────→
16 h, RT

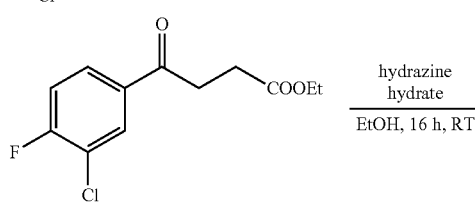
A66E hydrazine
hydrate
──────────────→
EtOH, 16 h, RT

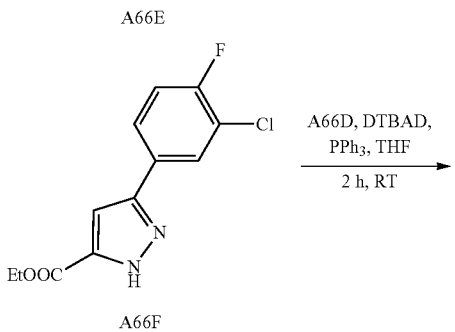
A66F

A66D, DTBAD,
PPh₃, THF
──────────────→
2 h, RT

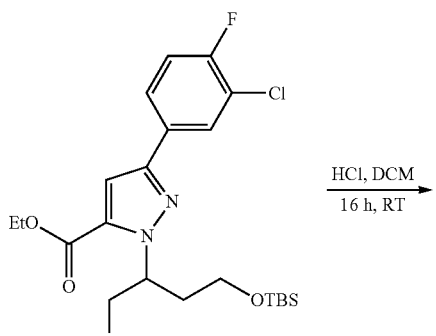
A66G

HCl, DCM
──────────────→
16 h, RT

512
-continued

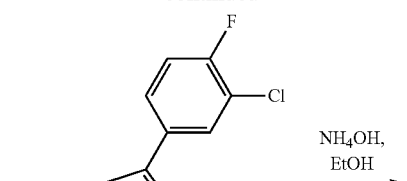
A66H

NH₄OH,
EtOH
──────────────→
4 h, RT

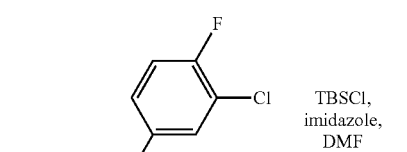
A66I

TBSCl,
imidazole,
DMF
──────────────→
2 h, RT

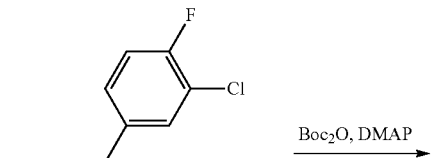
A66J

Boc₂O, DMAP
──────────────→
2 h, RT

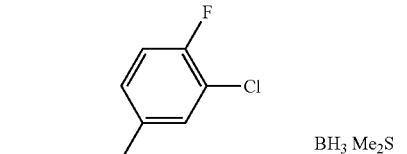
A66K

BH₃ Me₂S
──────────────→
70° C.

513

-continued

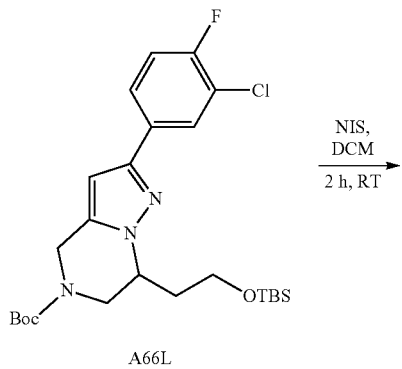

A66L

NIS, DCM
2 h, RT
→

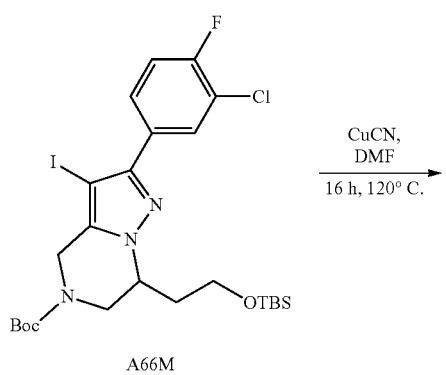

A66M

CuCN, DMF
16 h, 120° C.
→

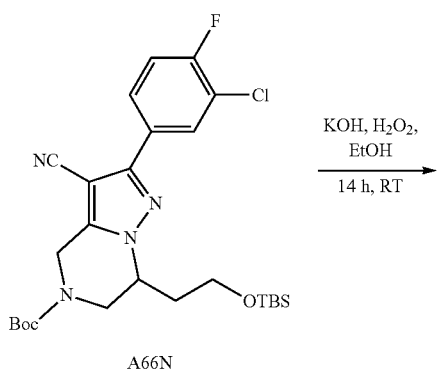

A66N

KOH, H$_2$O$_2$, EtOH
14 h, RT
→

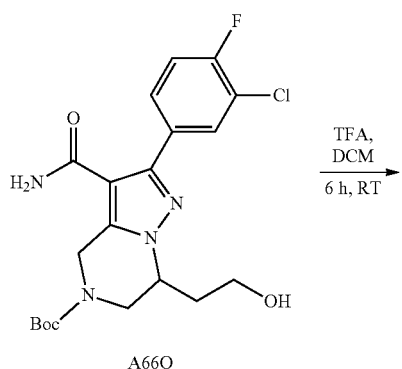

A66O

TFA, DCM
6 h, RT
→

514

-continued

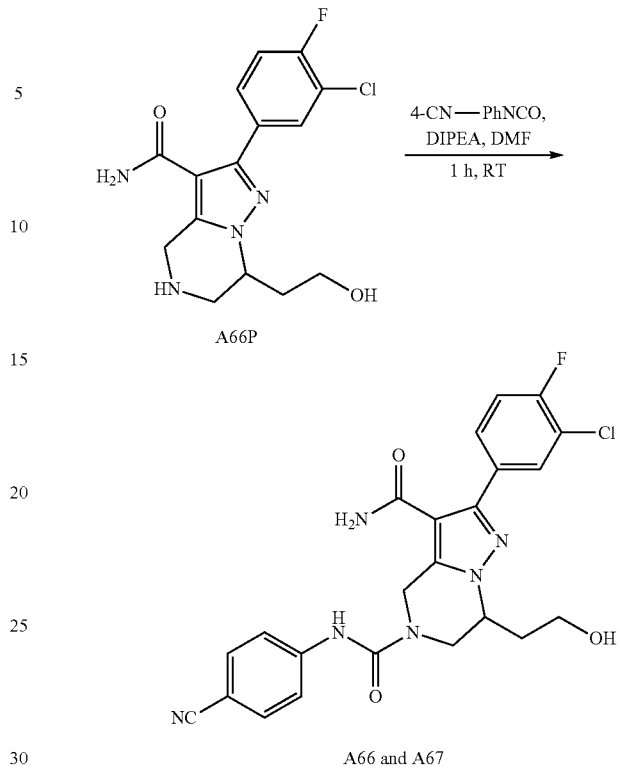

A66P

4-CN—PhNCO, DIPEA, DMF
1 h, RT
→

A66 and A67

Intermediate A66B: Methyl 4-((Tert-butoxycarbonyl)amino)-3-hydroxybutanoate

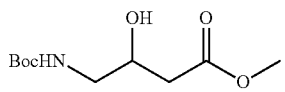

To a suspension of 4-amino-3-hydroxybutanoic acid (17.8 g, 149 mmol) in MeOH (150 mL) and DMF (2 mL) at 0° C. was added SOCl$_2$ (23.99 mL, 329 mmol) dropwise via a dropping funnel. The reaction mixture gradually became a clear solution. It was stirred at RT for 30 min. and then heated at 60° C. for 2 h. The reaction mixture was cooled to RT and concentrated. The residue was suspended in dioxane (150 mL) and added to a saturated aq. solution of sodium bicarbonate (74.7 mL, 149 mmol). BOC-anhydride (41.6 mL, 179 mmol) was added. The reaction mixture was stirred at RT overnight after which it was diluted with equal parts water and EtOAc. The organic layer was separated and the aqueous layer was extracted twice more with EtOAc. The combined organic layer was washed with brine, dried over Na$_2$SO$_4$, and filtered. The filtrate was concentrated. The crude product was purified by silica gel chromatography (330 g REDISEP® column, eluting with a gradient from 30-70% EtOAc in hexanes). Fractions containing the product were combined and evaporated to afford Intermediate A66B (25 g, 71.7% for two steps). $^1$H NMR (400 MHz, chloroform-d) δ ppm 4.22-4.04 (m, 1H), 3.74 (s, 3H), 3.51 (d, J=7.5 Hz, 1H), 3.20-3.08 (m, 1H), 2.57-2.48 (m, 2H), 1.52-1.40 (m, 9H).

Intermediate A66C:
tert-Butyl(2,4-dihydroxybutyl)carbamate

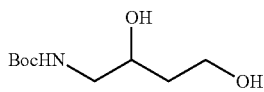

To a solution of Intermediate A66B (25 g, 107 mmol) in diethyl ether (200 mL) and MeOH (7.59 mL, 188 mmol) at 0° C. was added LiBH$_4$ (3.50 g, 161 mmol) in portions carefully. The reaction was stirred at RT for 1 h and heated at 60° C. for 1 h. The reaction was carefully quenched with MeOH and concentrated. The residue was diluted with equal parts of a saturated aq. NH$_4$Cl solution and EtOAc. The organic layer was separated and the aqueous layer was extracted twice more with EtOAc. The combined organic layer was washed with brine, dried over Na$_2$SO$_4$, and filtered. The filtrate was concentrated to afford Intermediate A66C (19 g, 86%) as an off-white solid. It was used as such without further purification. $^1$H NMR (400 MHz, chloroform-d) δ ppm 4.03-3.77 (m, 3H), 3.30 (ddd, J=14.1, 6.1, 3.1 Hz, 1H), 3.22-3.03 (m, 1H), 1.78-1.65 (m, 2H), 1.46 (s, 9H).

Intermediate A66D: tert-Butyl(4-((Tert-butyldimethylsilyl)oxy)-2-hydroxybutyl) carbamate

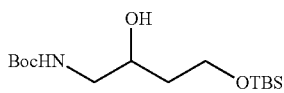 [SMILES: CC(C)(C)OC(=O)NCC(O)CCO[Si](C)(C)C(C)(C)C]

To a solution of Intermediate A66C (10 g, 48.7 mmol) and TEA (2.55 mL, 18.30 mmol) in DCM (80 mL) were added TBS-Cl (8.08 g, 53.6 mmol) and DMAP (0.060 g, 0.487 mmol). It was allowed to stir at RT for 4 h. The reaction mixture was diluted with equal parts water and EtOAc. The organic layer was separated and the aqueous layer was extracted twice more with EtOAc. The combined organic layer was washed with brine, dried over Na$_2$SO$_4$, and filtered. The filtrate was concentrated. The residue was purified by silica gel chromatography (240 g REDISEP® column, eluting with a gradient from 10-50% EtOAc in hexane). Fractions containing the product were combined and evaporated to afford Intermediate A66D (12 g, 77%). $^1$H NMR (400 MHz, chloroform-d) δ ppm 3.99-3.72 (m, 3H), 3.41-3.22 (m, 1H), 3.22-3.03 (m, 1H), 1.78-1.60 (m, 2H), 1.46 (s, 9H), 0.96-0.84 (m, 9H), 0.19-0.06 (m, 6H).

Intermediate A66E: Ethyl 4-(3-chloro-4-fluorophenyl)-2,4-dioxobutanoate

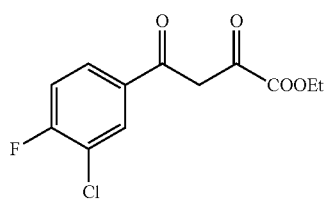 [SMILES: CCOC(=O)C(=O)CC(=O)c1ccc(F)c(Cl)c1]

Intermediate A66E was prepared analogous to Intermediate A1C by reacting 1-(3-chloro-4-fluorophenyl)ethanone with diethyl oxalate. MS(ES): m/z=273.1 [M+H]$^+$; $^1$H NMR (400 MHz, chloroform-d) δ ppm 8.10 (dd, J=6.9, 2.1 Hz, 1H), 7.93 (ddd, J=8.8, 4.5, 2.3 Hz, 1H), 7.36-7.20 (m, 1H), 7.13-6.95 (m, 1H), 4.44 (q, J=7.3 Hz, 2H), 1.45 (t, J=7.2 Hz, 3H).

Intermediate A66F: Ethyl 3-(3-chloro-4-fluorophenyl)-1H-pyrazole-5-carboxylate

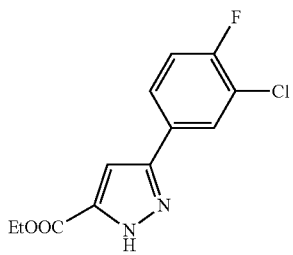 [SMILES: CCOC(=O)c1cc(-c2ccc(F)c(Cl)c2)n[nH]1]

Intermediate A66F was prepared analogous to Intermediate A1D by reacting Intermediate A66E with hydrazine hydrate. MS(ES): m/z=269.1 [M+H]$^+$; $^1$H NMR (400 MHz, chloroform-d) δ ppm 7.91 (dd, J=7.0, 2.0 Hz, 1H), 7.70 (ddd, J=8.5, 4.5, 2.3 Hz, 1H), 7.22 (t, J=8.7 Hz, 1H), 7.11 (s, 1H), 4.45 (q, J=7.2 Hz, 2H), 1.44 (t, J=7.2 Hz, 3H).

Intermediate A66G: Ethyl 3-(3-chloro-4-fluorophenyl)-1-(2,2,3,3,12,12-hexamethyl-10-oxo-4,11-dioxa-9-aza-3-silatridecan-7-yl)-1H-pyrazole-5-carboxylate

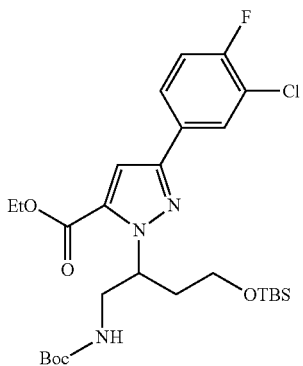 [SMILES: CCOC(=O)c1cc(-c2ccc(F)c(Cl)c2)nn1C(CCO[Si](C)(C)C(C)(C)C)CNC(=O)OC(C)(C)C]

To a solution of Intermediate A66F (10.7 g, 40 mmol) in THF (100 mL) at 0° C. were added Intermediate A66D (15.25 g, 48 mmol), TEA (5.6 mL, 40 mmol), triphenylphosphine (10.5 g, 40 mmol), and DTBAD (9.17 g, 40 mmol). The reaction mixture was stirred at RT for 2 h and concentrated. The residue was diluted with equal parts of water and EtOAc. The organic layer was separated and the aqueous layer was extracted twice more with EtOAc. The combined organic layer was washed with brine, dried over Na$_2$SO$_4$, and filtered. The filtrate was concentrated. The crude product was purified by silica gel chromatography (330 g REDISEP® column, eluting with a gradient from 10-40% EtOAc in hexane). Fractions containing the product were combined and evaporated to afford Intermediate A66G (16.5 g, 73%). MS(ES): m/z=592.3 [M+Na]+.

Intermediate A66H: Ethyl 1-(1-amino-4-hydroxybutan-2-yl)-3-(3-chloro-4-fluorophenyl)-1H-pyrazole-5-carboxylate bis HCl salt

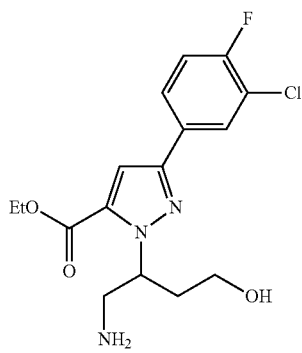 [SMILES: CCOC(=O)c1cc(-c2ccc(F)c(Cl)c2)nn1C(CN)CCO]

To a solution of Intermediate A66G (6.1 g, 10.70 mmol) in DMC (120 mL) was added 4 M HCl solution in dioxane (10.70 mL, 42.8 mmol). The reaction mixture was allowed to stir at RT overnight. The precipitated Intermediate A66H was collected by filtration. It was used as such without further purification. MS(ES): m/z=356.1 [M+H]+.

Intermediate A66I: 2-(3-Chloro-4-fluorophenyl)-7-(2-hydroxyethyl)-6,7-dihydropyrazolo[1,5-a]pyrazin-4(5H)-one

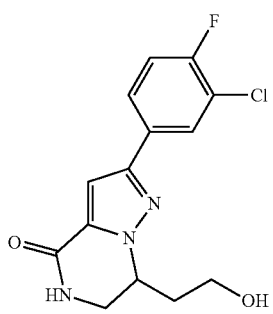 [SMILES: O=C1NCC(CCO)n2nc(-c3ccc(F)c(Cl)c3)cc21]

To a suspension of Intermediate A66H (4.20 g, 10.7 mmol) in ethanol (80 mL) was added 30% water solution of ammonia (80 mL, 3697 mmol). It was stirred at RT for 2 h and concentrated. The solid was collected by filtration, washed with water, and dried. The crude Intermediate A66I was used as such without further purification. MS(ES): m/z=310.0 [M+H]+; 1H NMR (400 MHz, DMSO-d6) δ ppm 8.27 (br. s., 1H), 8.07 (dd, J=7.3, 2.3 Hz, 1H), 7.89 (ddd, J=8.7, 4.8, 2.1 Hz, 1H), 7.48 (t, J=9.0 Hz, 1H), 7.34 (s, 1H), 4.74 (t, J=5.0 Hz, 1H), 4.67-4.47 (m, 1H), 3.79 (ddd, J=13.3, 4.4, 2.4 Hz, 1H), 3.66-3.55 (m, 2H), 3.50 (ddd, J=13.4, 5.6, 3.4 Hz, 1H), 2.17 (dd, J=13.8, 6.0 Hz, 1H), 2.03-1.81 (m, 1H).

Intermediate A66J: 7-(2-((Tert-Butyldimethylsilyl)oxy)ethyl)-2-(3-chloro-4-fluorophenyl)-6,7-dihydropyrazolo[1,5-a]pyrazin-4(5H)-one

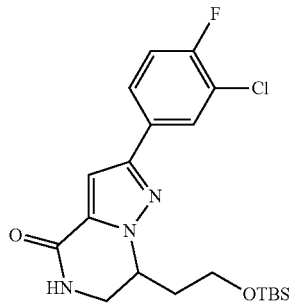 [SMILES: CC(C)(C)[Si](C)(C)OCCC1CNC(=O)c2cc(-c3ccc(F)c(Cl)c3)nn21]

To a suspension of Intermediate A66I in DCM (300 mL) and DMF (15 mL) were added TEA (10.80 mL, 77 mmol), TBS-Cl (9.34 g, 62.0 mmol), and DMAP (0.316 g, 2.58 mmol). The suspension was allowed to stir at RT overnight. The reaction mixture was diluted with equal parts water and DCM. The organic layer was separated and the aqueous layer was extracted twice more with DCM. The organic layer was washed with brine, dried over Na2SO4, and filtered. The filtrate was concentrated. The crude product was purified by silica gel chromatography (330 g REDISEP® column, eluting with a gradient from 0-40% EtOAc in DMC). Fractions containing the product were combined and evaporated to afford Intermediate A66J (17.8 g, 81%). MS(ES): m/z=446.2 [M+Na]+. 1H NMR (400 MHz, chloroform-d) δ ppm 7.91 (dd, J=7.2, 2.1 Hz, 1H), 7.66 (ddd, J=8.6, 4.6, 2.1 Hz, 1H), 7.27-7.10 (m, 2H), 6.25 (br. s., 1H), 4.78-4.51 (m, 1H), 4.02-3.79 (m, 3H), 3.72 (ddd, J=13.1, 5.5, 3.5 Hz, 1H), 2.47-2.23 (m, 1H), 2.23-1.96 (m, 1H), 1.00-0.88 (m, 9H), 0.18-0.05 (m, 6H).

Intermediate A66K: tert-Butyl 7-(2-((Tert-butyldimethylsilyl)oxy)ethyl)-2-(3-chloro-4-fluorophenyl)-4-oxo-6,7-dihydropyrazolo[1,5-a]pyrazine-5(4H)-carboxylate

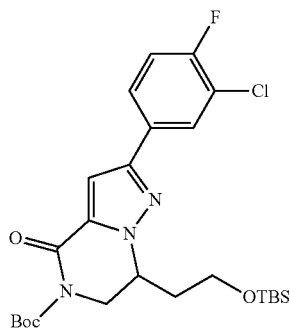 [SMILES: CC(C)(C)OC(=O)N1CC(CCO[Si](C)(C)C(C)(C)C)n2nc(-c3ccc(F)c(Cl)c3)cc2C1=O]

To a suspension of Intermediate A66J (13.64 g, 32.2 mmol) in toluene (120 mL) were added DMAP (5.90 g, 48.3 mmol) and BOC-anhydride (8.96 mL, 38.6 mmol). The reaction mixture was stirred at RT for 1 h and it became a clear solution after 5 min. The reaction mixture was concentrated and the residue was purified by silica gel chromatography (240 g REDISEP® column, eluting with a gradient from 0-40% EtOAc in DCM). Fractions containing the product were combined and evaporated to afford Intermediate A66K (17.8 g, 81%). MS(ES): m/z=524.4 [M+H]+; 1H NMR (400 MHz, chloroform-d) δ ppm 7.90 (dd, J=7.0, 2.0 Hz, 1H), 7.66 (ddd, J=8.5, 4.6, 2.1 Hz, 1H), 7.29 (s, 1H), 7.25-7.03 (m, 2H), 4.84-4.63 (m, 1H), 4.38-4.18 (m, 2H), 4.05-3.79 (m, 2H), 2.51-2.24 (m, 1H), 2.03 (dtd, J=14.4, 7.2, 2.3 Hz, 1H), 1.61 (s, 9H), 0.95 (s, 9H), 0.14 (s, 3H), 0.12 (s, 3H).

Intermediate A66L: tert-Butyl 7-(2-((Tert-butyldimethylsilyl)oxy)ethyl)-2-(3-chloro-4-fluorophenyl)-6,7-dihydropyrazolo[1,5-a]pyrazine-5(4H)-carboxylate

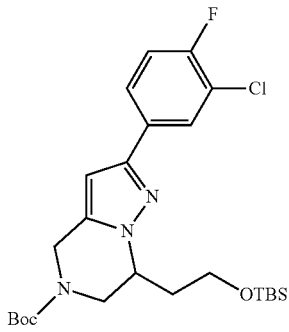 [SMILES: CC(C)(C)OC(=O)N1Cc2cc(-c3ccc(F)c(Cl)c3)nn2C(CCO[Si](C)(C)C(C)(C)C)C1]

To a solution of Intermediate A66K (1.5 g, 2.86 mmol) in THF (15 mL) was added a 2 M solution of BH$_3$.Me$_2$S in THF (4.29 mL, 8.59 mmol) dropwise at RT. The reaction mixture was heated to reflux for 4 h and cooled to 0° C. It was carefully quenched with MeOH. The reaction mixture was concentrated. The residue was diluted with equal parts of a saturated aq. NH$_4$Cl solution and EtOAc. The organic layer was separated and the aqueous layer was extracted twice more with EtOAc. The combined organic layer was washed with brine, dried over Na$_2$SO$_4$, and filtered. The filtrate was concentrated to afford Intermediate A66L (1.2 g, 82%), which was used as such without further purification. MS(ES): m/z=510.3 [M+H]+.

Intermediate A66M: tert-Butyl 7-(2-((Tert-butyldimethylsilyl)oxy)ethyl)-2-(3-chloro-4-fluorophenyl)-3-iodo-6,7-dihydropyrazolo[1,5-a]pyrazine-5(4H)-carboxylate

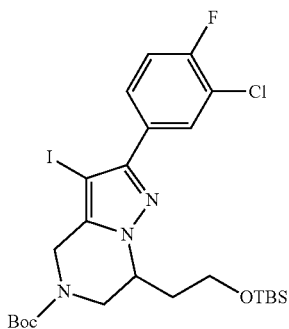 [SMILES: CC(C)(C)OC(=O)N1Cc2c(I)c(-c3ccc(F)c(Cl)c3)nn2C(CCO[Si](C)(C)C(C)(C)C)C1]

To a solution of Intermediate A66L (3.53 g, 6.92 mmol) in DMC (25 mL) and MeOH (10 mL) was added NIS (1.868 g, 8.30 mmol). The reaction mixture was stirred at RT for 2 h and concentrated. The residue was purified by silica gel chromatography (80 g REDISEP® column, eluting with a gradient from 0-25% EtOAc in hexane). Fractions containing the product were combined and evaporated to afford Intermediate A66M (3 g, 76%). MS(ES): m/z=636.2 [M+H]+.

Intermediate A66N: tert-Butyl 7-(2-((Tert-butyldimethylsilyl)oxy)ethyl)-2-(3-chloro-4-fluorophenyl)-3-cyano-6,7-dihydropyrazolo[1,5-a]pyrazine-5(4H)-carboxylate

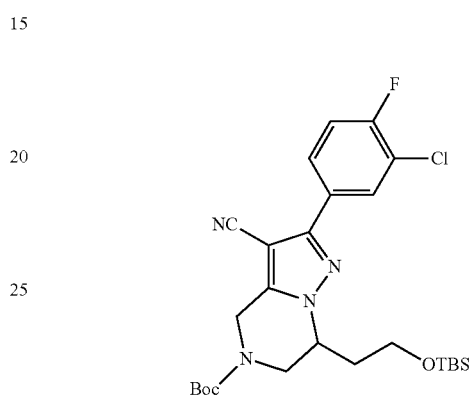

To a solution of Intermediate A66M (3 g, 4.72 mmol) in DMF (12 mL) was added copper(I) cyanide (1.056 g, 11.79 mmol). The reaction mixture was purged with nitrogen for 2 min. and heated at 120 OC overnight. It was cooled to RT, diluted with EtOAc, passed through a pad of CELITE®. The filter cake was washed with EtOAc. The filtrate was concentrated. The residue was purified by silica gel chromatography (80 g REDISEP® column, eluting with a gradient from 0-35% EtOAc in hexane). Fractions containing the product were combined and evaporated to afford Intermediate 66N (1.2 g, 48%). MS(ES): m/z=557.2 [M+Na]+.

Intermediate A66O: tert-Butyl 3-carbamoyl-2-(3-chloro-4-fluorophenyl)-7-(2-hydroxyethyl)-6,7-dihydropyrazolo[1,5-a]pyrazine-5(4H)-carboxylate

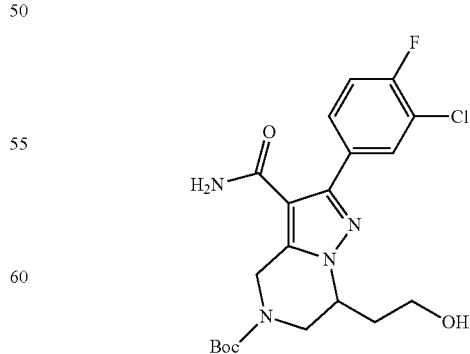

To a solution of Intermediate A66N (1.2 g, 2.242 mmol) in ethanol (10 mL) and THF (10 mL) were added a 5 M aq. solution of potassium hydroxide (2.242 mL, 11.21 mmol)

and H₂O₂(4.58 mL, 44.8 mmol). The reaction mixture was stirred at RT overnight and concentrated. The residue was diluted with equal parts water and EtOAc. The organic layer was separated and the aqueous layer was extracted twice more with EtOAc. The combined organic layer was washed with brine, dried over Na₂SO₄, filtered. The filtrate was concentrated to afford the crude Intermediate A66O (820 mg, 83%) as an off-white solid which was used as such without further purification. MS(ES): m/z=439.1 [M+H]⁺.

Intermediate A66P: 2-(3-Chloro-4-fluorophenyl)-7-(2-hydroxyethyl)-4,5,6,7-tetrahydropyrazolo[1,5-a]pyrazine-3-carboxamide, TFA salt

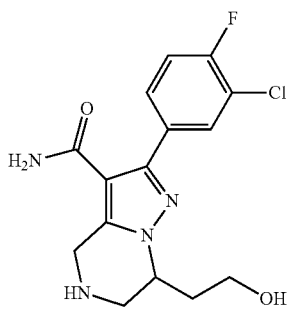 [SMILES: NC(=O)c1c(-c2ccc(F)c(Cl)c2)nn2c1CNCC2CCO]

To a solution of Intermediate A66O (95 mg, 0.216 mmol) in DCM (10 mL) was added TFA (1 mL). The reaction mixture was stirred at RT for 6 h and concentrated to afford the TFA salt of Intermediate A66P which was used as such without further purification. MS(ES): m/z=339.1 [M+H]⁺.

Compounds A66 and A67: 2-(3-Chloro-4-fluorophenyl)-N⁵-(4-cyanophenyl)-7-(2-hydroxyethyl)-6,7-dihydropyrazolo[1,5-a]pyrazine-3,5(4H)-dicarboxamide

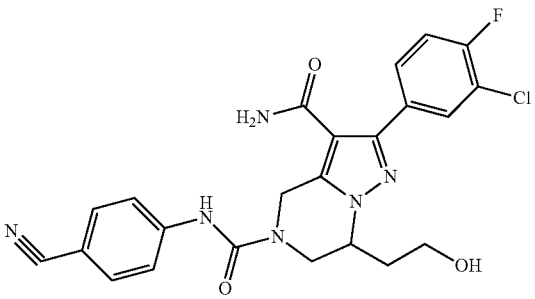 [SMILES: N#Cc1ccc(NC(=O)N2Cc3c(C(N)=O)c(-c4ccc(F)c(Cl)c4)nn3C(CCO)C2)cc1]

To a solution of Intermediate A66P (35 mg, 0.093 mmol) in DMF (1 mL) was added Hunig's base (0.033 mL, 0.187 mmol). The resulting mixture was allowed to stir for 5 min. prior to the addition of 4-isocyanatobenzonitrile (22.34 mg, 0.155 mmol). The reaction mixture was stirred at RT for 1 h after which it was filtered and purified by preparative HPLC to afford racemic mixture of Compounds A66 and A67. The racemate was subjected to chiral separation using preparative SFC to afford enantiomer A66 (Ret. Time 11.42 min, 11.9 mg, 23.9%) and enantiomer A67 (Ret. Time 13.16 min, 12.8 mg, 25.7%). Chiral HPLC Method: IA preparative Column 30×250 mm, 5 μm; Mobile Phase: 30% MeOH in CO₂, 130 bar; Flow rate: 70 mL/min for 16 min.; MS(ES): m/z=481.5 [M−H]⁺; HPLC Ret. Time 1.32 min. and MS(ES): m/z=483.5 [M+H]⁺ Ret. Time 2.22 min. (HPLC Methods H and I); ¹H NMR (500 MHz, DMSO-d₆) δ ppm 7.85 (d, J=6.6 Hz, 1H), 7.79-7.57 (m, 5H), 7.48 (t, J=9.0 Hz, 1H), 7.40 (br. s., 1H), 7.26 (br. s., 1H), 5.04 (m, 1H), 4.80 (d, J=17.2 Hz, 1H), 4.48 (d, J=3.7 Hz, 1H), 4.21-4.05 (m, 1H), 3.90 (d, J=10.3 Hz, 1H), 3.69 (d, J=4.8 Hz, 2H), 2.15-2.19 (m, 1H), 1.91-1.78 (m, 1H).

Scheme 55
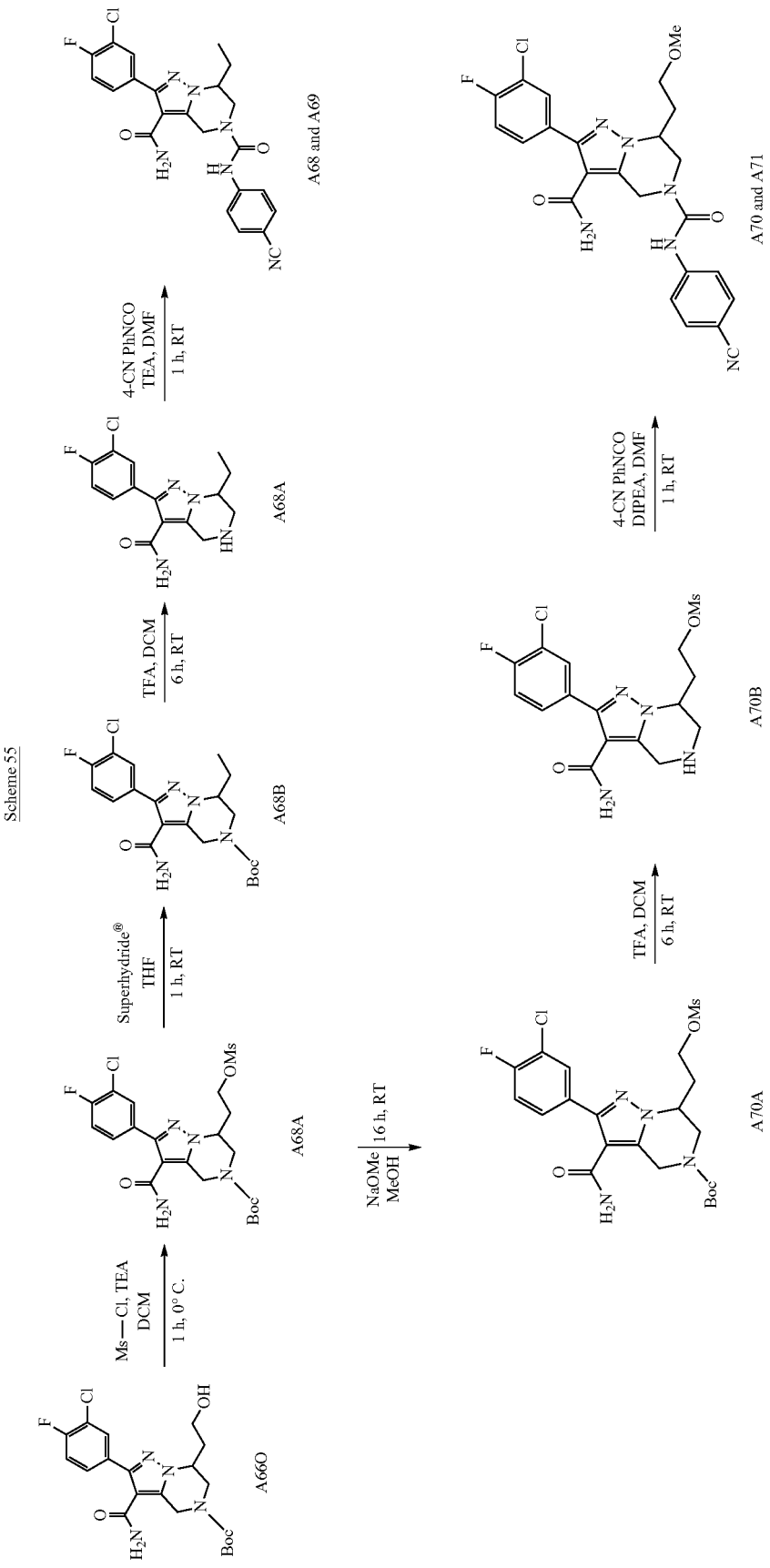

Intermediate A68A: tert-Butyl 3-carbamoyl-2-(3-chloro-4-fluorophenyl)-7-(2-((methylsulfonyl)oxy)ethyl)-6,7-dihydropyrazolo[1,5-a]pyrazine-5(4H)-carboxylate

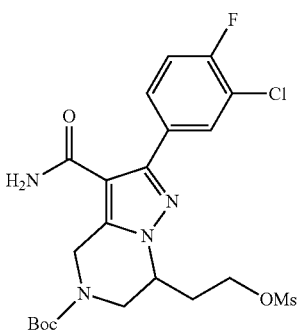 [SMILES: CC(C)(C)OC(=O)N1Cc2c(C(N)=O)c(-c3ccc(F)c(Cl)c3)nn2C(CCOS(C)(=O)=O)C1]

To a solution of Intermediate A68O (500 mg, 1.139 mmol) in DCM (12 mL) at 0° C. under nitrogen were added TEA (0.206 mL, 1.481 mmol) and MsCl (0.107 mL, 1.367 mmol). The reaction mixture was allowed to stir at 0° C. for 1 h before it was diluted with equal parts water and DCM. The organic layer was separated and the aqueous layer was extracted twice more with DCM. The combined organic layer was washed with brine, dried over $Na_2SO_4$, and filtered. The filtrate was concentrated. The crude product was purified by silica gel chromatography (40 g REDISEP® column, eluting with a gradient from 35-80% EtOAc in hexane). Fractions containing the product were combined and evaporated to afford Intermediate A68A (380 mg, 65%). MS(ES): m/z=517.1 [M+H]$^+$; $^1$H NMR (400 MHz, chloroform-d) δ ppm 7.68 (dd, J=7.0, 2.0 Hz, 1H), 7.49 (ddd, J=8.5, 4.5, 2.3 Hz, 1H), 7.32-7.19 (m, 1H), 5.19 (d, J=16.8 Hz, 1H), 4.73 (d, J=18.8 Hz, 1H), 4.52 (t, J=6.0 Hz, 3H), 4.31-4.16 (m, 1H), 3.76-3.59 (m, 1H), 3.09 (s, 3H), 2.50-2.32 (m, 1H), 2.32-2.14 (m, 1H), 1.56-1.47 (m, 9H).

Intermediate A68B: tert-Butyl 3-carbamoyl-2-(3-chloro-4-fluorophenyl)-7-ethyl-6,7-dihydropyrazolo[1,5-a]pyrazine-5(4H)-carboxylate

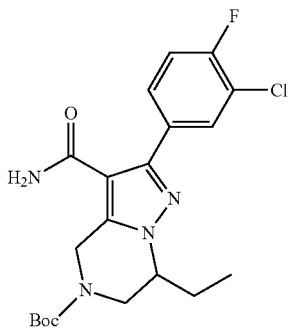 [SMILES: CCC1CN(C(=O)OC(C)(C)C)Cc2c(C(N)=O)c(-c3ccc(F)c(Cl)c3)nn21]

To a solution of Intermediate A68A (200 mg, 0.387 mmol) in THF (6 mL) at 0° C. under nitrogen was added a 1 M THF solution of SUPER-HYDRIDE® (1.934 mL, 1.934 mmol). The reaction mixture was allowed to stir at RT for 1 h before it was quenched with water. The resulting mixture was extracted with EtOAc. The combined organic layer was washed with brine, dried over $Na_2SO_4$, and filtered. The filtrate was concentrated. The crude product was purified by silica gel chromatography (40 g REDISEP® column, eluting with a gradient from 35-80% EtOAc in hexanes). Fractions containing the product were combined and evaporated to afford Intermediate A68B (128 m g, 78%). MS(ES): m/z=423.1 [M+H]$^+$.

Intermediate A68C: 2-(3-Chloro-4-fluorophenyl)-7-ethyl-4,5,6,7-tetrahydropyrazolo[1,5-a]pyrazine-3-carboxamide, TFA salt

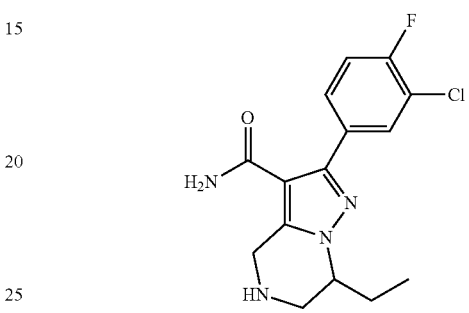

To a solution of Intermediate A68B (160 mg, 0.378 mmol) in DCM (20 mL) was added TFA (2 mL). The reaction mixture was stirred at RT for 6 h and concentrated to afford the TFA salt of Intermediate 68C which was used as such without further purification. MS(ES): m/z=323.1 [M+H]$^+$.

Compounds A68 and A69: 2-(3-Chloro-4-fluorophenyl)-N$^5$-(4-cyanophenyl)-7-ethyl-6,7-dihydropyrazolo[1,5-a]pyrazine-3,5(4H)-dicarboxamide

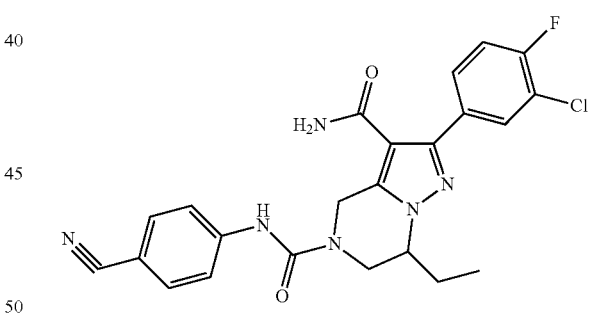

To a solution of Intermediate A68C (40 mg, 0.092 mmol) in DMF (1 mL) was added Hunig's base (0.064 mL, 0.366 mmol). The resulting mixture was allowed to stir for 5 min. prior to the addition 4-isocyanatobenzonitrile (13.20 mg, 0.092 mmol). The reaction mixture was stirred at RT for 1 h after which it was filtered and purified by preparative HPLC to afford racemic mixture of Compounds A68 and A69. The racemate was subjected to chiral separation using preparative SFC to afford enantiomer A68 (Ret. Time 18.9 min, 9.7 mg, 22.7%) and enantiomer A69 (Ret. Time 23.9 min, 10.1 mg, 23.6%). Chiral HPLC Method: Column: CHIRALPAK® OD 21×250 mm, 10 m; Mobile Phase A: 0.1% diethylamine/heptane; Mobile Phase B: ethanol; Gradient: hold at 20%-100% B over 38 minutes; Flow rate: 15 mL/min; MS(ES): m/z=465.5 [M−H]$^+$; HPLC Ret. Time 1.69 min. and MS(ES): m/z=467.5 [M+H]$^+$ Ret. Time 2.58 min. (HPLC Methods H and I); $^1$H NMR (500 MHz, DMSO-$d_6$) δ ppm 7.85 (d, J=7.0 Hz, 1H), 7.79-7.58 (m, 5H), 7.47 (t, J=9.2 Hz, 1H), 7.39 (br. s., 1H), 7.25 (br. s., 1H), 5.01 (d, J=16.9 Hz, 1H), 4.88 (d, J=16.9 Hz, 1H), 4.28 (br. s., 1H), 4.04 (dd, J=13.8, 5.0 Hz, 1H), 3.97-3.85 (m, 1H), 3.43-3.29 (m, 2H), 2.12-1.96 (m, 1H), 1.80-1.67 (m, 1H).

Intermediate A70A: tert-Butyl 3-carbamoyl-2-(3-chloro-4-fluorophenyl)-7-(2-methoxyethyl)-6,7-dihydropyrazolo[1,5-a]pyrazine-5(4H)-carboxylate

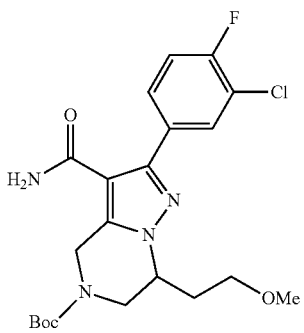

To a solution of Intermediate A68A (170 mg, 0.329 mmol) in MeOH (5 mL) was added 25% sodium methoxide solution in MeOH (426 mg, 1.973 mmol). The reaction mixture was stirred at RT overnight and concentrated. The residue was diluted with equal parts water and DCM. The organic layer was separated and the aqueous layer was extracted twice more with DCM. The combined organic layer was washed with brine, dried over Na$_2$SO$_4$, and filtered. The filtrate was concentrated. The crude product was purified by silica gel chromatography (40 g REDISEP® column, eluting with a gradient from 35-80% EtOAc in hexane). Fractions containing the product were combined and evaporated to afford Intermediate A70A (120 mg, 81%). MS(ES): m/z=453.1 [M+H]$^+$; $^1$H NMR (400 MHz, chloroform-d) δ ppm 7.77-7.64 (m, 1H), 7.55-7.44 (m, 1H), 7.34-7.16 (m, 1H), 5.44-5.27 (m, 1H), 4.79 (d, J=17.8 Hz, 1H), 4.56-4.39 (m, 1H), 4.14-4.04 (m, 1H), 3.74 (dd, J=13.8, 3.8 Hz, 1H), 3.62 (t, J=6.1 Hz, 2H), 3.39 (s, 3H), 2.45-2.25 (m, 1H), 1.98 (ddt, J=14.3, 8.5, 5.8 Hz, 1H), 1.59-1.48 (m, 9H).

Intermediate A70B: 2-(3-Chloro-4-fluorophenyl)-7-(2-methoxyethyl)-4,5,6,7-tetrahydropyrazolo[1,5-a]pyrazine-3-carboxamide, TFA salt

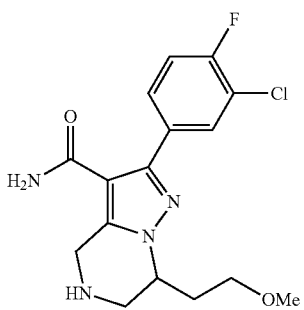 [SMILES: COCCC1CNCc2c(C(N)=O)c(-c3ccc(F)c(Cl)c3)nn21]

To a solution of Intermediate A70A (120 mg, 0.265 mmol) in DCM (15 mL) was added TFA (1 mL). The reaction mixture was stirred at RT for 6 h and concentrated to afford the TFA salt of Intermediate A70B which was used as such without further purification. MS(ES): m/z=353.0 [M+H]$^+$.

Compounds A70 and A71: 2-(3-Chloro-4-fluorophenyl)-N$^5$-(4-cyanophenyl)-7-(2-methoxyethyl)-6,7-dihydropyrazolo[1,5-a]pyrazine-3,5(4H)-dicarboxamide

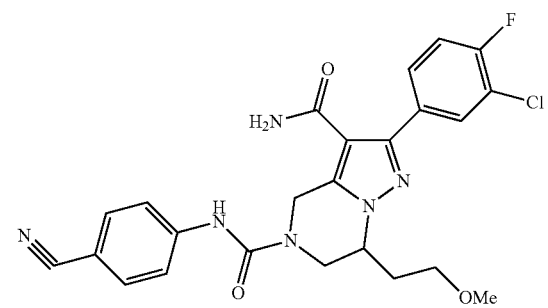 [SMILES: COCCC1CN(C(=O)Nc2ccc(C#N)cc2)Cc2c(C(N)=O)c(-c3ccc(F)c(Cl)c3)nn21]

To a solution of Intermediate A70B (35 mg, 0.075 mmol) in DMF (1 mL) was added Hunig's base (0.026 mL, 0.150 mmol). The resulting mixture was allowed to stir for 5 min. prior to the addition 4-isocyanatobenzonitrile (16.21 mg, 0.112 mmol). The reaction mixture was stirred at RT for 1 h after which it was filtered and purified by preparative HPLC to afford racemic mixture of Compounds A70 and A71. The racemate was subjected to chiral separation using preparative SFC to afford enantiomer A70 (Ret. Time 35.0 min, 7.2 mg, 19.3%) and enantiomer A71 (Ret. Time 39.5 min, 7.5 mg, 20.1%). Chiral HPLC Method: Column: CHIRALPAK® IC-H 30×250 mm, 5 μm; Mobile Phase: 20% MeOH in CO$_2$, 150 bar; Flow rate: 70 mL/min for 42 min.; MS(ES): m/z=495.5 [M-H]$^+$; HPLC Ret. Time 1.60 min. and MS(ES): m/z=497.5 [M+H]$^+$ Ret. Time 2.48 min. (HPLC Methods H and I); $^1$H NMR (500 MHz, DMSO-$d_6$)) δ ppm 7.85 (d, J=7.3 Hz, 1H), 7.86-7.66 (m, 5H), 7.48 (t, J=9.0 Hz, 1H), 7.40 (br. s., 1H), 7.26 (br. s., 1H), 5.02 (d, J=17.2 Hz, 1H), 4.85 (d, J=16.9 Hz, 1H), 4.44 (d, J=3.7 Hz, 1H), 4.06 (dd, J=14.1, 4.6 Hz, 1H), 3.91 (d, J=11.0 Hz, 1H), 3.56 (t, J=5.9 Hz, 2H), 3.28 (s, 3H), 2.23 (dd, J=13.8, 5.7 Hz, 1H), 2.00-1.82 (m, 1H).

Scheme 56
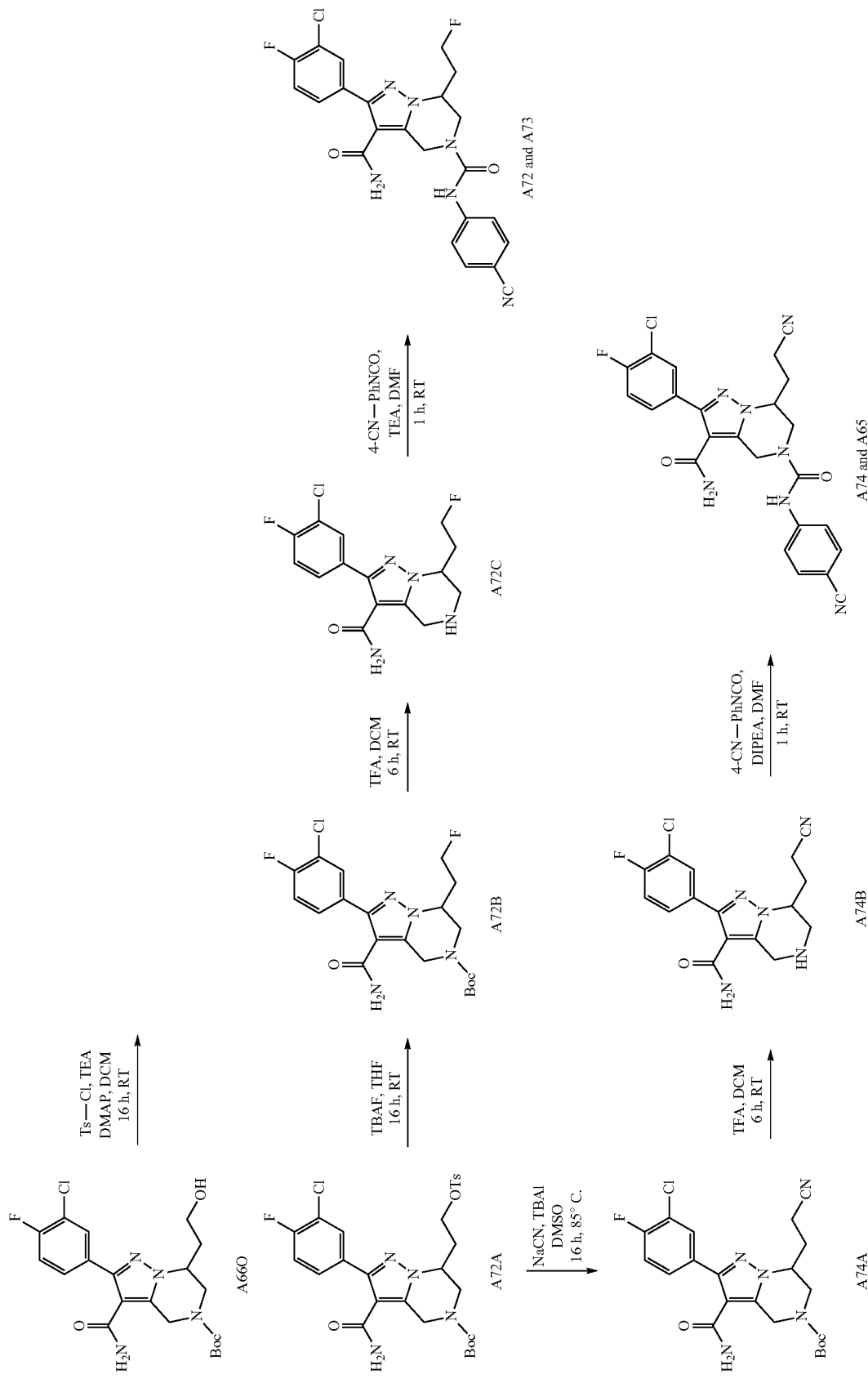

Intermediate A72A: tert-Butyl 3-carbamoyl-2-(3-chloro-4-fluorophenyl)-7-(2-(tosyloxy)ethyl)-6,7-dihydropyrazolo[1,5-a]pyrazine-5(4H)-carboxylate

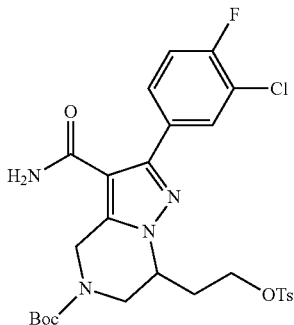 [SMILES: Cc1ccc(S(=O)(=O)OCCC2CN(C(=O)OC(C)(C)C)Cc3c(C(N)=O)c(-c4ccc(F)c(Cl)c4)nn32)cc1]

To a solution of Intermediate A66O (0.76 g, 1.732 mmol) in DCM (30 mL) were added TEA (0.483 mL, 3.46 mmol), TsCl (0.220 mL, 2.078 mmol), and DMAP (10.58 mg, 0.087 mmol). The reaction mixture was stirred at RT overnight and concentrated. The residue was purified by silica gel chromatography (40 g REDISEP® column, eluting with a gradient from 35-80% EtOAc in hexanes). Fractions containing the product were combined and evaporated to afford Intermediate A72A (0.76 g, 76%). MS(ES): m/z=593.1 [M+H]$^+$; $^1$H NMR (400 MHz, chloroform-d) δ ppm 7.85-7.78 (m, 2H), 7.64 (dd, J=7.0, 2.0 Hz, 1H), 7.46 (ddd, J=8.5, 4.5, 2.3 Hz, 1H), 7.39-7.18 (m, 3H), 5.12 (br. s., 1H), 4.73 (d, J=18.6 Hz, 1H), 4.43 (br. s., 1H), 4.32 (t, J=6.3 Hz, 2H), 4.06 (dd, J=14.1, 3.5 Hz, 1H), 3.67 (d, J=12.0 Hz, 1H), 2.45 (s, 3H), 2.41-2.29 (m, 1H), 2.19-2.08 (m, 1H), 1.59-1.44 (m, 9H).

Intermediate A72B: tert-Butyl 3-carbamoyl-2-(3-chloro-4-fluorophenyl)-7-(2-fluoroethyl)-6,7-dihydropyrazolo[1,5-a]pyrazine-5(4H)-carboxylate

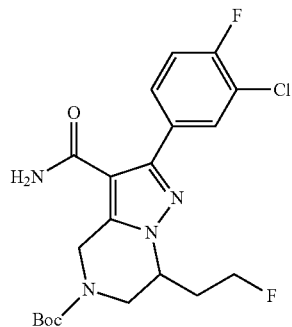 [SMILES: CC(C)(C)OC(=O)N1Cc2c(C(N)=O)c(-c3ccc(F)c(Cl)c3)nn2C(CCF)C1]

To a solution of Intermediate A72A (260 mg, 0.438 mmol) in THF (15 mL) at 0° C. under nitrogen was added a 1 M THF solution of tetrabutylammonium fluoride (0.526 mL, 0.526 mmol). The reaction mixture was stirred at RT overnight and concentrated. The residue was purified by silica gel chromatography (40 g REDISEP® column, eluting with a gradient from 35-80% EtOAc in hexanes). Fractions containing the product were combined and evaporated to afford Intermediate A72B (140 mg, 72%). MS(ES): m/z=441.1 [M+H]$^+$.

Intermediate A72C: 2-(3-Chloro-4-fluorophenyl)-7-(2-fluoroethyl)-4,5,6,7-tetrahydropyrazolo[1,5-a]pyrazine-3-carboxamide TFA salt

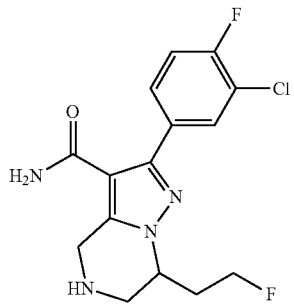 [SMILES: NC(=O)c1c(-c2ccc(F)c(Cl)c2)nn2c1CNCC2CCF]

To a solution of Intermediate A72B (140 mg, 0.318 mmol) in DCM (10 mL) was added TFA (1 mL). The reaction mixture was stirred at RT for 6 h and concentrated to afford the TFA salt of Intermediate A72C which was used as such without further purification. MS(ES): m/z=341.1 [M+H]$^+$.

Compounds A72 and A73: 2-(3-Chloro-4-fluorophenyl)-N$^5$-(4-cyanophenyl)-7-(2-fluoroethyl)-6,7-dihydropyrazolo[1,5-a]pyrazine-3,5(4H)-dicarboxamide

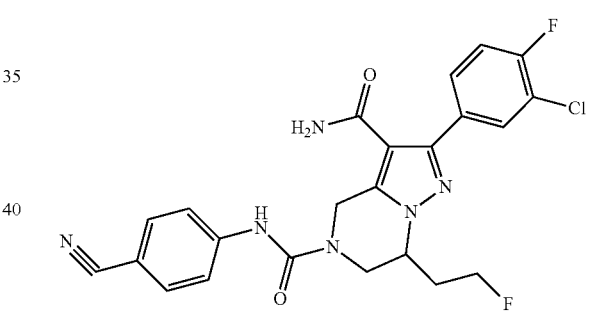

To a solution of Intermediate A72C (40 mg, 0.088 mmol) in DMF (1 mL) was added Hunig's base (0.030 mL, 0.173 mmol). The resulting mixture was allowed to stir for 5 min. prior to the addition of 4-isocyanatobenzonitrile (19.02 mg, 0.132 mmol). The reaction mixture was stirred at RT for 1 h after which it was filtered and purified by preparative HPLC to afford racemic mixture of Compounds A72 and A73. The racemate was subjected to chiral separation using preparative SFC to afford enantiomer A72 (Ret. Time 14.6 min, 12.3 mg, 28.8%) and enantiomer A73 (Ret. Time 18.4 min, 11.1 mg, 26%). Chiral HPLC Method: Column: CHIRALPAK® IC-H, 30×250 mm, 5 µm; Mobile Phase: 30% MeOH in CO$_2$, 150 bar; Flow rate: 70 mL/min for 22 min.; MS(ES): m/z=483.5 [M−H]$^+$; HPLC Ret. Time 1.61 min. and MS(ES): m/z=485.5 [M+H]$^+$ Ret. Time 2.46 min. (HPLC Methods H and I); $^1$H NMR (500 MHz, DMSO-d$_6$) δ ppm 7.85 (d, J=7.3 Hz, 1H), 7.79-7.58 (m, 5H), 7.48 (t, J=9.0 Hz, 1H), 7.41 (br. s., 1H), 7.26 (br. s., 1H), 5.00 (d, J=17.2 Hz, 1H), 4.91 (d, J=17.2 Hz, 1H), 4.78 (dd, J=12.5, 5.9 Hz, 1H), 4.67 (dd, J=12.5, 5.5 Hz, 1H), 4.52 (br. s., 1H), 4.07-3.93 (m, 2H), 2.45-2.28 (m, 1H), 2.14 (d, J=6.6 Hz, 1H).

Intermediate A74A: tert-Butyl 3-carbamoyl-2-(3-chloro-4-fluorophenyl)-7-(2-cyanoethyl)-6,7-dihydropyrazolo[1,5-a]pyrazine-5(4H)-carboxylate

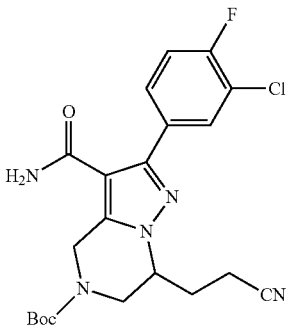 [SMILES: CC(C)(C)OC(=O)N1Cc2c(C(N)=O)c(-c3ccc(F)c(Cl)c3)nn2C(CCC#N)C1]

To a solution of Intermediate A72A (180 mg, 0.304 mmol) in DMSO (2 mL) were added tetrabutylammonium iodide (11.21 mg, 0.030 mmol) and sodium cyanide (74.4 mg, 1.518 mmol). The reaction mixture was heated at 85° C. for 16 h and cooled to RT. It was diluted with equal parts water and DCM. The organic layer was separated and the aqueous layer was extracted twice more with DCM. The combined organic layer was washed with brine, dried over $Na_2SO_4$, and filtered. The filtrate was concentrated. The crude product was purified by silica gel chromatography (40 g REDISEP® column, eluting with a gradient from 35-80% EtOAc in hexane). Fractions containing the product were combined and evaporated to afford Intermediate A74A (80 mg, 59%). MS(ES): m/z=448.1 [M+H]$^+$.

Intermediate A74B: 2-(3-Chloro-4-fluorophenyl)-7-(2-cyanoethyl)-4,5,6,7-tetrahydropyrazolo[1,5-a]pyrazine-3-carboxamide, TFA salt

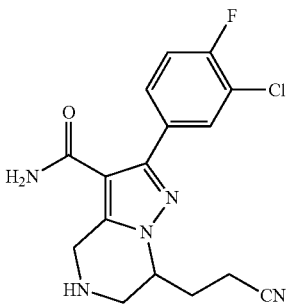 [SMILES: N#CCCC1CNCc2c(C(N)=O)c(-c3ccc(F)c(Cl)c3)nn21]

To a solution of Intermediate A74A (80 mg, 0.179 mmol) in DCM (10 mL) was added TFA (1 mL, 12.98 mmol). The reaction mixture was stirred at RT for 6 h and concentrated to afford the TFA salt of Intermediate A74B which was used as such without further purification. MS(ES): m/z=348.1 [M+H]$^+$.

Compounds A74 and A75: 2-(3-Chloro-4-fluorophenyl)-7-(2-cyanoethyl)-N-(4-cyanophenyl)-6,7-dihydropyrazolo[1,5-a]pyrazine-3,5(4H)-dicarboxamide

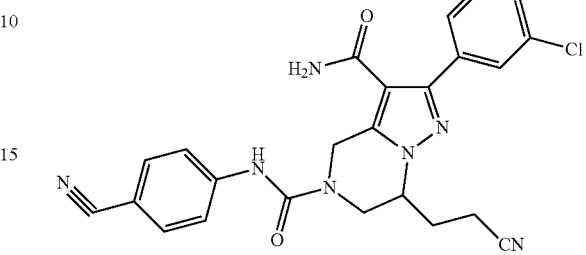

To a solution of Intermediate A74B (40 mg, 0.087 mmol) in DMF (1 mL) was added Hunig's base (0.030 mL, 0.173 mmol). The resulting mixture was allowed to stir for 5 min. prior to the addition of 4-isocyanatobenzonitrile (18.73 mg, 0.130 mmol). The reaction mixture was stirred at RT for 1 h after which it was filtered and purified by preparative HPLC to afford racemic mixture of Compounds A74 and A75. The racemate was subjected to chiral separation using preparative SFC to afford enantiomer A74 (Ret. Time 48.0 min, 5 mg, 11.7%) and enantiomer A75 (Ret. Time 50.9 min, 5.5 mg, 12.9%). Chiral HPLC Method: Column: CHIRALPAK® IC-H, 30×250 mm, 5 µm; Mobile Phase: 20% MeOH in $CO_2$, 150 bar; Flow rate: 70 mL/min for 60 min.; MS(ES): m/z=490.5 [M−H]$^+$; HPLC Ret. Time 1.47 min. and MS(ES): m/z=492.5 [M+H]$^+$ Ret. Time 2.27 min. (HPLC Methods H and I); $^1$H NMR (500 MHz, DMSO-d$_6$) δ ppm 7.87 (d, J=7.3 Hz, 1H), 7.80-7.58 (m, 5H), 7.48 (t, J=9.2 Hz, 1H), 7.42 (br. s., 1H), 7.24 (br. s., 1H), 5.03 (d, J=17.2 Hz, 1H), 4.87 (d, J=17.2 Hz, 1H), 4.44 (br. s., 1H), 4.07 (dd, J=13.4, 4.6 Hz, 1H), 3.91 (d, J=11.4 Hz, 1H), 2.79 (br. s., 2H), 2.22 (dd, J=13.8, 7.2 Hz, 1H), 2.11 (dd, J=13.8, 6.8 Hz, 1H).

Scheme 57

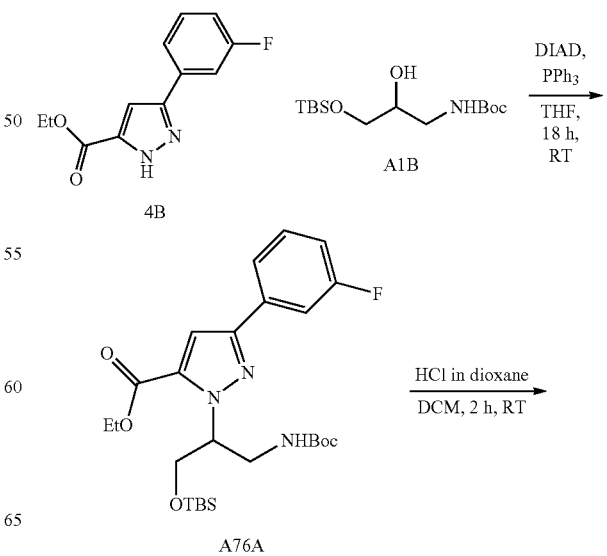

535
-continued
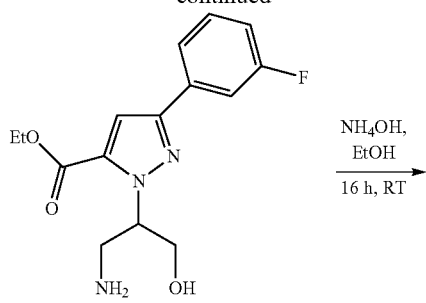
A76B
→ NH₄OH, EtOH
16 h, RT
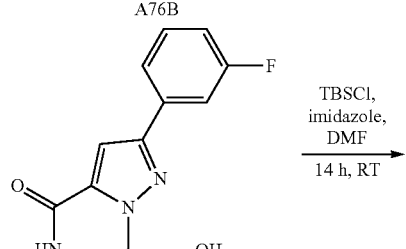
A76C
→ TBSCl, imidazole, DMF
14 h, RT
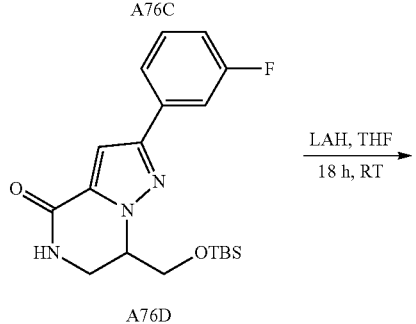
A76D
→ LAH, THF
18 h, RT
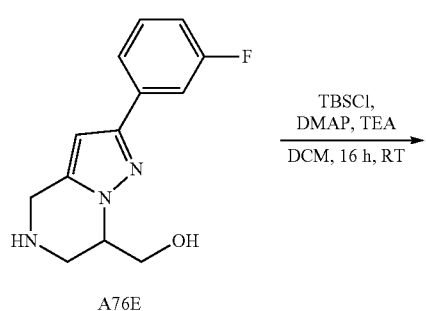
A76E
→ TBSCl, DMAP, TEA
DCM, 16 h, RT
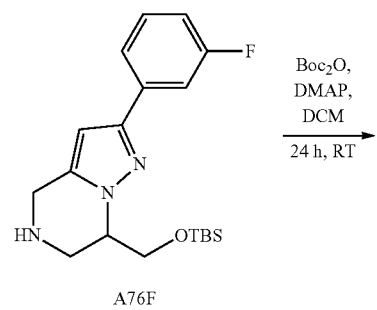
A76F
→ Boc₂O, DMAP, DCM
24 h, RT
536
-continued
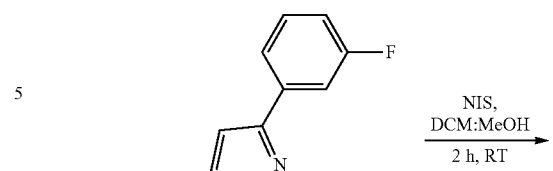
A76G
→ NIS, DCM:MeOH
2 h, RT
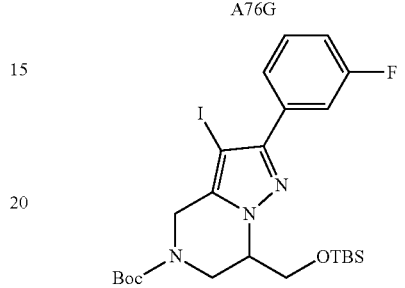
A76H
→ CuCN, DMF
16 h, 100° C.
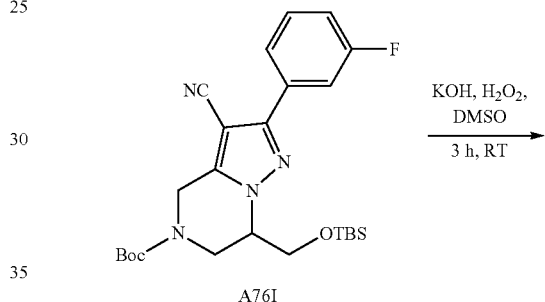
A76I
→ KOH, H₂O₂, DMSO
3 h, RT
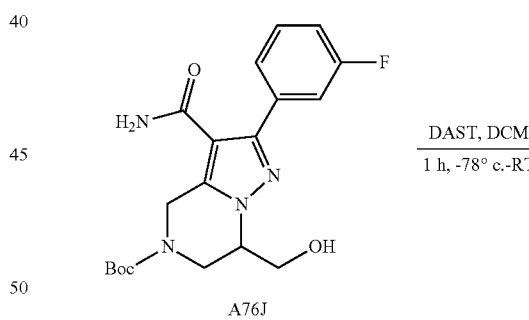
A76J
→ DAST, DCM
1 h, -78° c.-RT
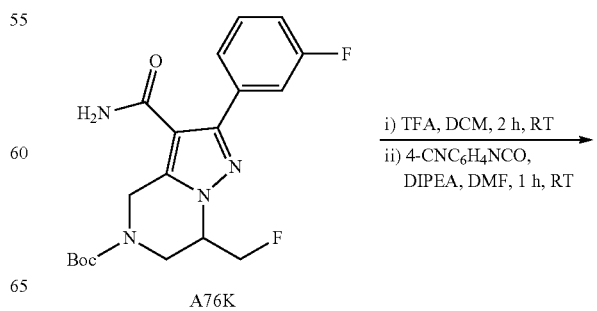
A76K
→ i) TFA, DCM, 2 h, RT
ii) 4-CNC₆H₄NCO, DIPEA, DMF, 1 h, RT -continued

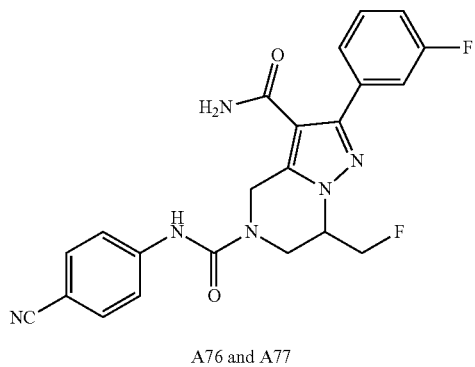

A76 and A77

Intermediate A76A: Ethyl 3-(3-fluorophenyl)-1-(2,2,3,3,11,11-hexamethyl-9-oxo-4,10-dioxa-8-aza-3-siladodecan-6-yl)-1H-pyrazole-5-carboxylate

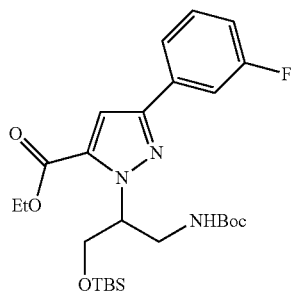 [SMILES: CCOC(=O)c1cc(-c2cccc(F)c2)nn1C(CNC(=O)OC(C)(C)C)CO[Si](C)(C)C(C)(C)C]

To a flask charged with triphenylphosphine (2.93 g, 11.16 mmol), sealed with a septum and purged with a dry atmosphere of nitrogen, was added THF (20 mL) via syringe and the reaction mixture was cooled to 0° C. Next, DIAD (2.170 mL, 11.16 mmol) was added via syringe resulting in a thick milky yellow solution. A solution of Intermediate A1B (3.28 g, 10.73 mmol) in THF (5.0 mL) was added to the ice-cold solution. After 15 minutes, pyrazole 4B (2.01 g, 8.58 mmol) was added as a solution in THF (5.0 mL). The reaction was then allowed to warm to RT. After 18 h, the reaction mixture was diluted with EtOAc (150 mL). The organic layer was washed with brine, dried over anhydrous $Na_2SO_4$, filtered and concentrated under reduced pressure to provide a crude oil. The crude reaction mixture was purified by silica gel chromatography (220 g REDISEP® column, eluting with 0 to 15% EtOAc in hexanes). Fractions containing the product were combined and evaporated to afford Intermediate A76A (4.5 g, 80%) as a thick syrup. MS(ES): m/z=522.09 [M+H]+; 1H NMR (400 MHz, chloroform-d) δ ppm 7.49-7.60 (2H, m), 7.32-7.41 (1H, m), 7.12 (1H, s), 6.99-7.07 (1H, m), 5.52-5.64 (1H, m), 4.92-5.07 (1H, m), 4.37 (2H, q, J=7.28 Hz), 3.97 (2H, d, J=6.53 Hz), 3.67-3.83 (2H, m), 1.37-1.50 (9H, m), 0.75-0.86 (9H, m), 0.04-0.11 (2H, m), −0.12-0.00 (6H, m).

Intermediate A76B: Ethyl 1-(1-amino-3-hydroxy-propan-2-yl)-3-(3-fluorophenyl)-1H-pyrazole-5-carboxylate

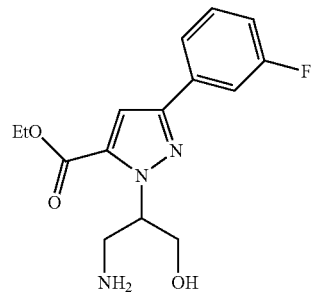 [SMILES: CCOC(=O)c1cc(-c2cccc(F)c2)nn1C(CN)CO]

To an ice-cooled solution of Intermediate A76A (4.35 g, 8.34 mmol) in DCM (50 mL) was added a 4M solution of HCl in 1,4-dioxane (12.5 mL, 50.0 mmol). The reaction mixture was allowed to stir at RT for 2 h. The white precipitate that was generated was filtered off and the filter cake was washed with diethyl ether. The solid was dried under vacuum for 16 h to afford Intermediate A76B as an HCl salt (2.56 g, >98%). MS(ES): m/z=308.0 [M+H]+. 1H NMR (400 MHz, DMSO-$d_6$) δ ppm 8.04 (1H, br. s.), 7.72-7.80 (1H, m), 7.44-7.54 (1H, m), 7.13-7.23 (1H, m), 5.46-5.58 (1H, m), 5.24 (1H, br. s.), 4.35 (2H, q, J=7.11 Hz), 3.58-3.80 (3H, m), 3.40 (1H, d, J=11.29 Hz), 1.31-1.40 (2H, m).

Intermediate A76C: 2-(3-Fluorophenyl)-7-(hydroxymethyl)-6,7-dihydropyrazolo[1,5-a]pyrazin-4(5H)-one

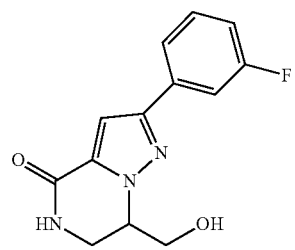 [SMILES: O=C1NCC(CO)n2nc(-c3cccc(F)c3)cc21]

To a suspension of Intermediate A76B (2.56 g, 8.34 mmol) in EtOH (50 mL) was added $NH_4OH$ (32.5 mL, 334 mmol, 40 wt %). After a few moments, the reaction mixture became homogeneous and the solution was allowed to stir at RT for 16 h. The crude reaction mixture was concentrated in vacuo and diluted with EtOAc. The aqueous solution was neutralized to pH=7 using a 1.0M aqueous solution of HCl. The organic layer was separated and the aqueous layer was extracted with EtOAc. The combined organic layers were then washed with brine, dried over sodium sulfate, and concentrated to afford Intermediate A76C (2.1 g, 96%) as a white solid. MS(ES): m/z=261.97 [M+H]+. 1H NMR (400 MHz, chloroform-d) δ ppm 7.49-7.61 (2H, m), 7.36-7.45 (1H, m), 7.16-7.21 (1H, s), 7.06 (1H, tdd, J=8.41, 8.41, 2.51, 1.00 Hz), 6.28 (1H, br. s.), 4.56-4.67 (1H, m), 4.07-4.23 (2H, m), 3.72-3.85 (2H, m), 3.14-3.37 (1H, m).

Intermediate A76D: 7-(((tert-Butyldimethylsilyl)oxy)methyl)-2-(3-fluorophenyl)-6,7-dihydropyrazolo[1,5-a]pyrazin-4(5H)-one

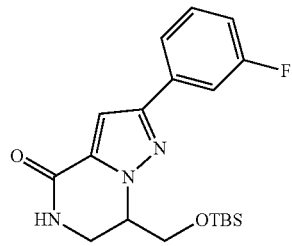 [SMILES: CC(C)(C)[Si](C)(C)OCC1CNC(=O)c2cc(-c3cccc(F)c3)nn21]

To a solution of Intermediate A76C (11.5 g, 44.1 mmol) in DMF (120 mL) were added imidazole (3.66 g, 53.8 mmol) and TBSCl (7.64 g, 50.7 mmol) and the reaction mixture was stirred at RT for 14 h. The solution was concentrated and the crude material was diluted with equal parts water and DCM (250 mL each). The organic layer was separated and washed several more times with water before being dried over sodium sulfate and concentrated to afford Intermediate A76D (13.57 g, 82%) as a white solid. MS(ES): m/z=375.95 [M+H]$^+$. $^1$H NMR (400 MHz, chloroform-d) δ ppm 7.52-7.63 (1H, m), 7.35-7.46 (1H, m), 7.13-7.20 (1H, m), 6.99-7.11 (1H, m), 6.01-6.25 (1H, m), 4.48-4.62 (1H, m), 4.10 (1H, dd, J=10.04, 4.27 Hz), 3.84-4.03 (3H, m), 0.90-0.93 (9H, m), 0.07-0.12 (6H, m).

Intermediate A76E: (2-(3-Fluorophenyl)-4,5,6,7-tetrahydropyrazolo[1,5-a]pyrazin-7-yl)methanol

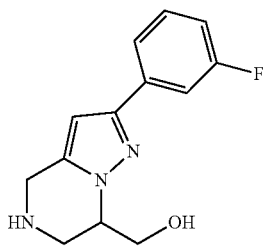 [SMILES: OCC1CNCc2cc(-c3cccc(F)c3)nn21]

To a solution of Intermediate A76D (5.162 g, 13.75 mmol) in THF (125 mL) cooled to −15° C., was introduced a 1M solution of LAH in THF (38.5 mL, 38.5 mmol) dropwise. The reaction mixture was allowed to gradually reach room temperature and stir for an additional 18 h. The reaction mixture was carefully quenched at −15 OC with sequential addition of H$_2$O (38.5 mL), NaOH (15% aq. solution, 38.5 mL) and H$_2$O (114 mL). The slurry was then allowed to stir at RT for 30 minutes, followed by the addition of anhydrous MgSO$_4$. The mixture was allowed to stir for 15 minutes and then the inorganics were filtered off. The filter cake was washed with DCM (150 mL). The biphasic filtrate was concentrated under reduced pressure to remove THF. The aqueous layer was then extracted with DCM (3×50 mL). The combined organic layers were washed with brine, dried over anhydrous Na$_2$SO$_4$, filtered and concentrated under reduced pressure to afford Intermediate A76E (3.41 g, >98%) as a white sticky solid. MS(ES): m/z=247.94 [M+H]$^+$. $^1$H NMR (400 MHz, chloroform-d) δ ppm 7.55 (1H, dt, J=7.84, 1.10 Hz), 7.48 (1H, ddd, J=10.16, 2.51, 1.63 Hz), 7.31-7.40 (1H, m), 6.96-7.04 (1H, m), 6.32 (1H, s), 4.26-4.35 (1H, m), 4.07-4.15 (2H, m), 4.01-4.07 (1H, m), 3.91-3.98 (1H, m), 3.41 (1H, dd, J=13.30, 4.77 Hz), 3.12 (1H, dd, J=13.18, 7.15 Hz).

Intermediate A76F: 7-(((tert-Butyldimethylsilyl)oxy)methyl)-2-(3-fluorophenyl)-4,5,6,7-tetrahydropyrazolo[1,5-a]pyrazine

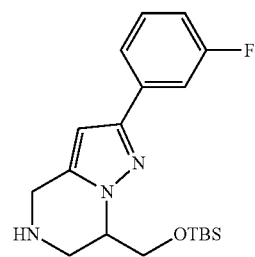 [SMILES: CC(C)(C)[Si](C)(C)OCC1CNCc2cc(-c3cccc(F)c3)nn21]

To a flask charged with Intermediate A76E (3.41 g, 13.79 mmol) was added DMAP (0.084 g, 0.690 mmol) and triethylamine (2.307 mL, 16.55 mmol). The reaction mixture was dissolved in DCM (125 mL) and finally TBSCl (2.286 g, 15.17 mmol) was added. The reaction mixture was then allowed to stir at 22° C. for 16 h after which the mixture was diluted with a saturated aq. solution of NaHCO$_3$ and the two layers were separated. The aqueous phase was extracted with DCM (2×50 mL). The combined organic layers were washed with water, brine, dried over anhydrous Na$_2$SO$_4$, filtered and concentrated under reduced pressure to afford a pale yellow oil. Crude Intermediate A76F (5.12 g, 92%) was found to be 90% pure and carried forward to amine protection with Boc-anhydride without further purification. MS(ES): m/z=361.94 [M+H]$^+$.

Intermediate A76G: tert-Butyl 7-(((tert-butyldimethylsilyl)oxy)methyl)-2-(3-fluorophenyl)-6,7-dihydropyrazolo[1,5-a]pyrazine-5(4H)-carboxylate

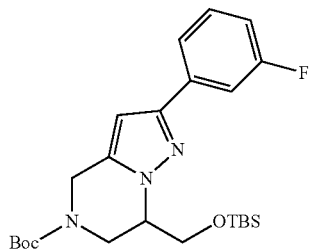 [SMILES: CC(C)(C)OC(=O)N1Cc2cc(-c3cccc(F)c3)nn2C(CO[Si](C)(C)C(C)(C)C)C1]

To a solution of Intermediate A76F (4.33 g, 11.98 mmol) in DCM (100 mL) was added triethylamine (6.68 mL, 47.9 mmol) and DMAP (0.073 g, 0.599 mmol). To the colorless solution was then added di-tert-butyl dicarbonate (3.92 g, 17.97 mmol) resulting in gas evolution. The reaction mixture was allowed to stir at 22° C. for 24 h prior to being quenched with a saturated aqueous solution of NaHCO$_3$. The layers were separated, and the aqueous layer was extracted twice more with DCM. The combined organic layers were washed with water, followed by brine, dried over sodium sulfate, and concentrated in vacuo. The crude product was purified by silica gel chromatography (120 g REDISEP® column, eluting with 20% EtOAc in hexanes). Fractions containing the product were combined and evaporated to afford Intermediate A76G (4.87 g, 88%) as a colorless oil. MS(ES): m/z=461.77 [M+H]⁺. ¹H NMR (400 MHz, chloroform-d) δ ppm 7.45-7.58 (1H, m), 7.35 (1H, td, J=8.03, 6.02 Hz), 6.95-7.05 (1H, m), 6.29-6.39 (1H, m), 4.55-4.79 (2H, m), 4.33 (1H, br. s.), 4.06-4.22 (2H, m), 3.74-4.03 (2H, m), 1.49-1.54 (9H, m), 0.83-0.95 (9H, m), −0.01-0.14 (6H, m).

Intermediate A76H: tert-Butyl 7-(((tert-butyldimethylsilyl)oxy)methyl)-2-(3-fluorophenyl)-3-iodo-6,7-dihydropyrazolo[1,5-a]pyrazine-5(4H)-carboxylate

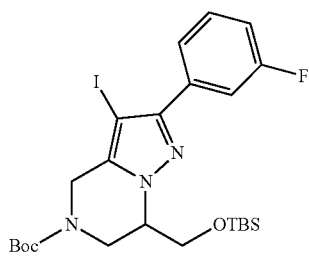 [SMILES: CC(C)(C)OC(=O)N1Cc2c(I)c(-c3cccc(F)c3)nn2C(CO[Si](C)(C)C(C)(C)C)C1]

To a solution of Intermediate A76G (4.87 g, 10.6 mmol) in DCM (56 mL) and MeOH (14 mL) was added NIS (7.12 g, 31.6 mmol) and the reaction mixture was allowed to stir at RT for 90 min. The solution was then concentrated under reduced pressure to provide a red oil. The crude reaction mixture was purified by silica gel chromatography (120 g REDISEP® column, eluting with a gradient of 0-30% EtOAc in hexanes). Fractions containing the product were combined and evaporated to afford Intermediate A76H (5.70 g, 92%) as a sticky solid. MS(ES): m/z=587.95 [M+H]⁺. ¹H NMR (400 MHz, chloroform-d) δ ppm 7.65 (1H, dq, J=7.78, 0.84 Hz), 7.54-7.60 (1H, m), 7.36-7.44 (1H, m), 7.08 (1H, tdd, J=8.44, 8.44, 2.57, 0.88 Hz), 4.50-4.71 (1H, m), 4.41-4.49 (1H, m), 4.02-4.40 (3H, m), 3.83-3.99 (1H, m), 3.75-3.82 (1H, m), 1.53 (8H, s), 0.84-0.93 (10H, m), −0.01-0.15 (6H, m).

Intermediate A76I: tert-Butyl 7-(((tert-butyldimethylsilyl)oxy)methyl)-2-(3-fluorophenyl)-3-cyano-6,7-dihydropyrazolo[1,5-a]pyrazine-5(4H)-carboxylate

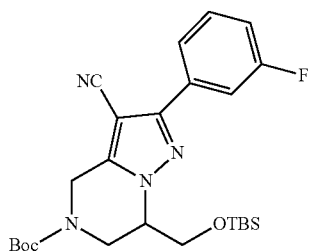 [SMILES: CC(C)(C)OC(=O)N1Cc2c(C#N)c(-c3cccc(F)c3)nn2C(CO[Si](C)(C)C(C)(C)C)C1]

To a flask equipped with a reflux condenser and charged with Intermediate A76H (3.84 g, 6.54 mmol) was added DMF (43.6 mL) and copper(I) cyanide (1.463 g, 16.34 mmol). The heterogeneous reaction mixture was heated to 100° C. for 18 h. The reaction mixture was cooled to RT and the solution was filtered through a pad of CELITE®. The filter cake was washed with EtOAc. The filtrate was concentrated under reduced pressure to afford the crude reaction mixture as a dark green oil. The product was purified by silica gel chromatography (80 g REDISEP® column, eluting with a gradient of 5-30% EtOAc in hexanes). Fractions containing the product were combined and evaporated to afford Intermediate A76I (1.441 g, 45%) as a white solid. MS(ES): m/z=431.0 [M+H₂O-OtBu]⁺; ¹H NMR (400 MHz, chloroform-d) δ ppm 7.62-7.83 (2H, m), 7.39-7.51 (1H, m), 7.08-7.19 (1H, m), 4.67-4.96 (2H, m), 4.34 (1H, br. s.), 3.84-4.19 (4H, m), 1.47-1.54 (9H, m), 0.79-0.91 (9H, m), −0.02-0.10 (6H, m).

Intermediate A76J: tert-Butyl 3-carbamoyl-2-(3-fluorophenyl)-7-(hydroxymethyl)-6,7-dihydropyrazolo[1,5-a]pyrazine-5(4H)-carboxylate

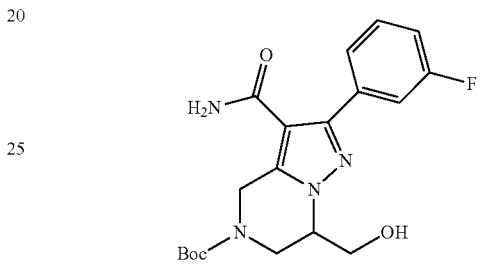

To an ice-cooled solution of Intermediate A76I (1.44 g, 2.96 mmol) in DMSO (20 mL) was added a 5 M aq. solution of KOH (2.96 mL, 14.8 mmol) and H₂O₂ (6.05 mL, 59.2 mmol, 30% w/v in H₂O) and the reaction mixture was stirred at 22° C. for 3 h. The reaction mixture was then partitioned between equal parts water and EtOAc and the layers were separated. The aqueous phase was extracted twice more with EtOAc. The combined organic layers were washed with water, brine, dried over anhydrous MgSO₄, filtered and concentrated under reduced pressure to afford a white solid. The crude reaction mixture was purified by silica gel chromatography (120 g REDISEP® column, eluting with a gradient of 75-100% EtOAc in hexanes). Fractions containing the product were combined and evaporated to afford Intermediate A76J (0.997 g, 52%) as a white solid contaminated with dimethyl sulfone. MS(ES): m/z=412.96 [M+Na]⁺.

Intermediate A76K: tert-Butyl 3-carbamoyl-7-(fluoromethyl)-2-(3-fluorophenyl)-6,7-dihydropyrazolo[1,5-a]pyrazine-5(4H)-carboxylate

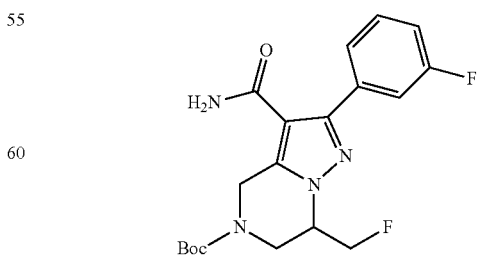

A suspension of Intermediate A76J (131.5 mg, 0.337 mmol) in DCM (5.5 mL) was allowed to cool to −78° C.

DAST (0.067 mL, 0.505 mmol) was added dropwise to the solution which was then allowed to warm to RT. After stirring at RT for 1 h, the reaction was quenched by the addition of a saturated aq. solution of NaHCO$_3$ at 0° C. The two layers were separated and the aqueous layer was extracted with DCM (3×10 mL). The combined organic layers were washed with brine, dried over anhydrous MgSO$_4$, filtered and concentrated under reduced pressure to afford an orange oil. The crude reaction mixture was purified by silica gel chromatography (24 g REDISEP® column, eluting with 75% EtOAc in hexanes). Fractions containing the product were combined and evaporated to afford Intermediate A76K (52.8 mg, 40%) as a white solid. MS(ES): m/z=393.0 [M+H]$^+$.

Compounds A76 and A77: N$^5$-(4-Cyanophenyl)-7-(fluoromethyl)-2-(3-fluorophenyl)-6,7-dihydropyrazolo[1,5-a]pyrazine-3,5(4H)-dicarboxamide

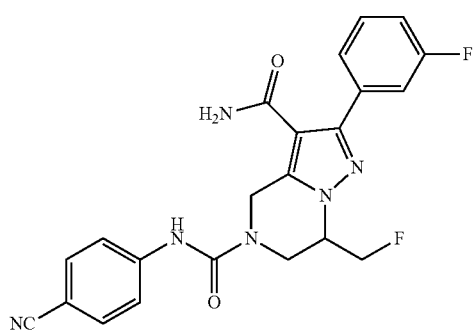 [SMILES: N#Cc1ccc(NC(=O)N2Cc3c(C(N)=O)c(-c4cccc(F)c4)nn3C(CF)C2)cc1]

To a solution of Intermediate A76K (0.053 g, 0.135 mmol) in DCM (3.0 mL) was added trifluoroacetic acid (0.103 mL, 1.346 mmol). The reaction mixture was then allowed to stir at RT for 3 h prior to the removal of the volatiles to afford the crude bis TFA salt.

The TFA salt was then dissolved in DMF (1.3 mL) and treated with DIPEA (0.117 mL, 0.673 mmol). The resulting mixture was allowed to stir for 5 min. prior to the addition of 4-isocyanatobenzonitrile (0.039 g, 0.269 mmol). The reaction was allowed to stir for 2 h after which it was filtered and purified via preparative HPLC. Fractions containing the desired product were combined and evaporated to afford the desired compound which was further purified through chiral separation using preparative SFC.: CHIRALPAK® IA-H, 30×250 mm, 5 μm eluted with 20% MeOH: 80% CO$_2$ at 150 bar and 35° C. at 70 mL/min. The first eluting enantiomer, r$_t$=23 min: Compound (S)-A76 (0.0166 g, 28%) and the second eluting enantiomer, r$_t$=35 min: Compound (R)-A77 (0.0207 g, 34%) were thus separated. MS(ES), m/z=437.4 [M+H]$^+$; HPLC Ret. Time 1.44 min. and 2.18 min. (Methods H and I respectively). $^1$H NMR (600 MHz, DMSO-d$_6$) δ ppm 7.62-7.74 (4H, m), 7.35-7.57 (4H, m), 7.17-7.33 (2H, m), 4.77-5.11 (4H, m), 4.59-4.72 (1H, m), 4.18 (1H, d, J=13.94 Hz), 4.04 (1H, dd, J=14.12, 6.42 Hz).

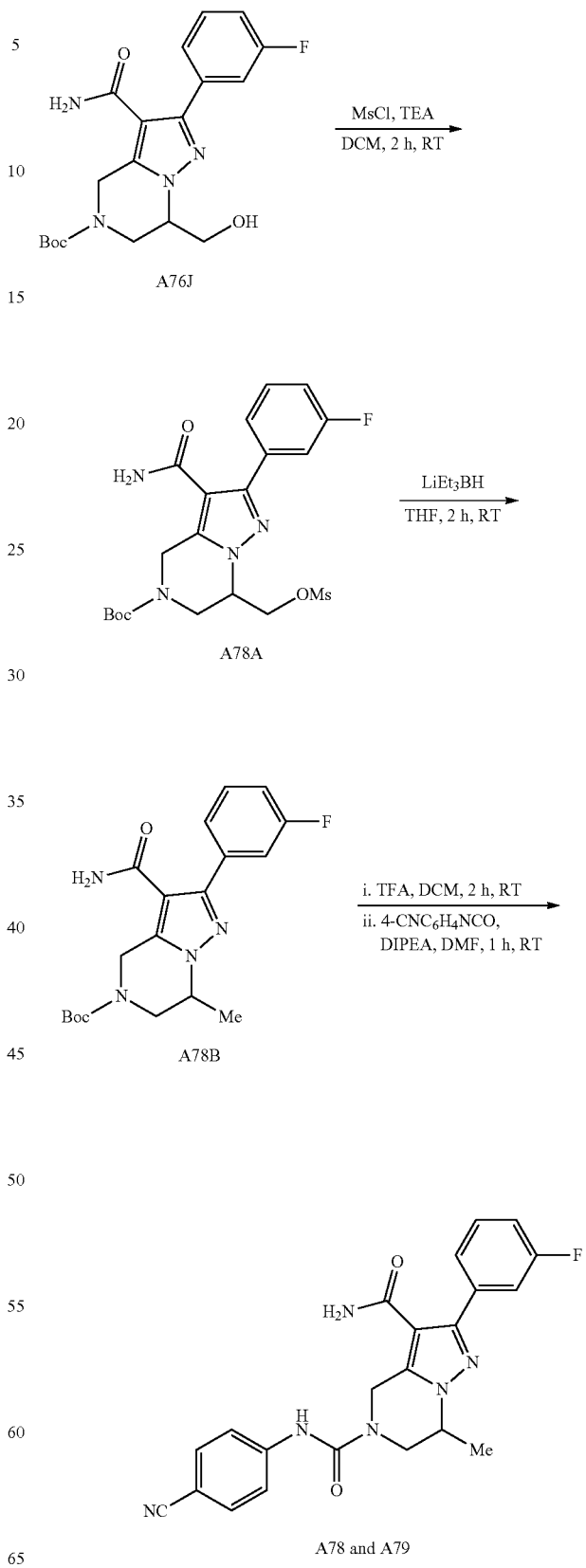

Scheme 58

Intermediate A78A: tert-Butyl 3-carbamoyl-2-(3-fluorophenyl)-7-(((methylsulfonyl)oxy)methyl)-6,7-dihydropyrazolo[1,5-a]pyrazine-5(4H)-carboxylate

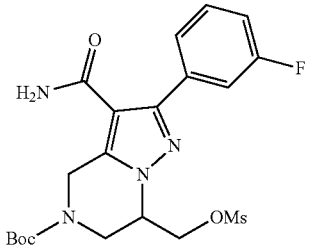 [SMILES: CC(C)(C)OC(=O)N1Cc2c(C(N)=O)c(-c3cccc(F)c3)nn2C(COS(C)(=O)=O)C1]

To an ice-cold suspension of Intermediate A76J (148.2 mg, 0.380 mmol) in DCM (3.8 mL) was added triethylamine (0.063 mL, 0.456 mmol) followed by the dropwise addition of methanesulfonyl chloride (0.032 mL, 0.418 mmol). The resultant homogeneous reaction mixture was allowed to warm to RT and continue to stir for an additional 2 h. The reaction was then quenched with a saturated aq. solution of NaHCO$_3$. The two layers were separated and the aqueous layer was extracted with DCM (2×10 mL). The combined organic layers were washed with brine, dried over anhydrous MgSO$_4$, filtered and the filtrate concentrated under reduced pressure to afford a colorless oil. The crude reaction mixture was purified by silica gel chromatography (24 g REDISEP® column, eluting with a gradient of 60-85% EtOAc in hexanes). Fractions containing the product were combined and evaporated to afford Intermediate A78A (0.0948 g, 33%) as a white solid. MS(ES): m/z=468.9 [M+H]$^+$.

Intermediate A78B: tert-Butyl 3-carbamoyl-2-(3-fluorophenyl)-7-methyl-6,7-dihydropyrazolo[1,5-a]pyrazine-5(4H)-carboxylate

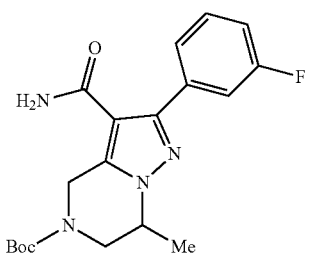 [SMILES: CC1CN(C(=O)OC(C)(C)C)Cc2c(C(N)=O)c(-c3cccc(F)c3)nn21]

To a solution of Intermediate A78A (0.0948 g, 0.202 mmol) in THF (2.0 mL) at RT was added dropwise a 1M solution of LiEt$_3$BH in THF (2.02 mL, 2.02 mmol), and the reaction mixture was stirred for 2 h. The reaction was then carefully quenched with a saturated aq. solution of NaHCO$_3$. The organic phase was separated and the aqueous layer was extracted twice more with DCM. The combined organic layers were washed with brine, dried over sodium sulfate, and concentrated to provide a pale yellow oil. The crude reaction mixture was purified by silica gel chromatography (24 g REDISEP® column, eluting with a gradient of 50-90% EtOAc in hexanes). Fractions containing the product were combined and evaporated to afford Intermediate A78B (0.029 g, 81%) as a white foam. MS(ES): m/z=375.08 [M+H]$^+$.

Compounds A78 and A79: N$^5$-(4-Cyanophenyl)-2-(3-fluorophenyl)-7-methyl-6,7-dihydropyrazolo[1,5-a]pyrazine-3,5(4H)-dicarboxamide

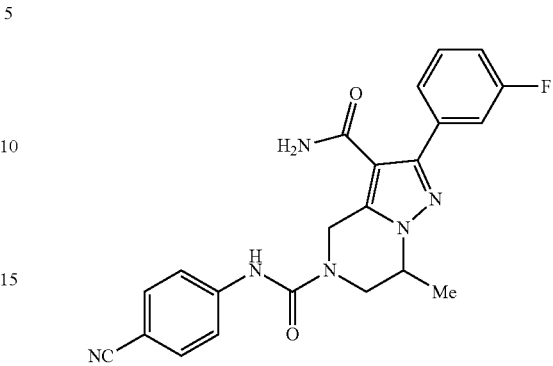

Compounds A78 and A79 were synthesized analogous to Compounds A76 and A77 by reacting deprotected A78B with 4-isocyanatobenzonitrile. The compound was purified by preparative HPLC and further purified through chiral separation using preparative HPLC: CHIRALCEL® OJ, 21×250 mm, 10 μm eluted with 65% 0.1% diethylamine in heptane: 35% EtOH at 15 mL/min. The first eluting enantiomer, r$_t$=12.3 min: Compound (S)-A78 (0.009 g, 32%) and the second eluting enantiomer, r$_t$=22.2 min: Compound (R)-A79 (0.009 g, 32%) were thus separated. MS(ES): m/z=419.1 [M+H]$^+$; HPLC Ret. Time 1.40 min and 2.26 min. (Methods H and I respectively); $^1$H NMR (500 MHz, DMSO-d$_6$) δ ppm 7.66-7.75 (4H, m), 7.34-7.55 (4H, m), 7.16-7.25 (2H, m), 4.82-5.02 (2H, m), 4.40-4.49 (1H, m), 4.09-4.17 (1H, m), 3.67-3.74 (1H, m), 1.49 (3H, d, J=6.60 Hz).

Scheme 59

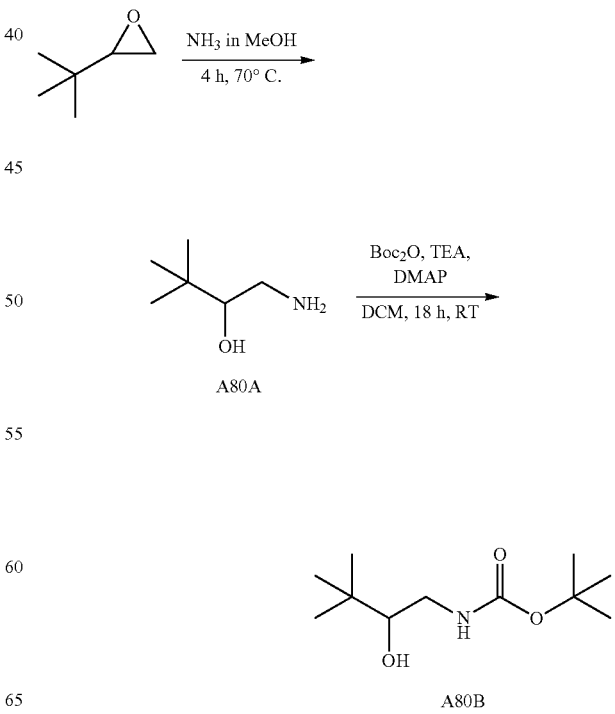

Intermediate A80A:
1-Amino-3,3-dimethylbutan-2-ol

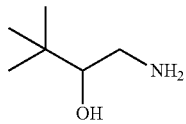

In a sealed pressure tube at RT was added 2-(tert-butyl) oxirane (1.0 g, 9.98 mmol) and ammonia in methanol (7N) (4.28 mL, 30.0 mmol). The reaction vessel was sealed and heated at 70° C. for 4 h. The reaction mixture was cooled to RT and concentrated and under reduced pressure. Crude Intermediate A80A (0.968, 83% yield) was used as such without further purification. $^1$H NMR (400 MHz, DMSO-$d_6$) δ 3.15-2.88 (m, 1H), 2.66-2.46 (m, 1H), 2.42-2.21 (m, 1H), 0.88-0.73 (m, 9H).

Intermediate A80B:
tert-Butyl(2-hydroxy-3,3-dimethylbutyl)carbamate

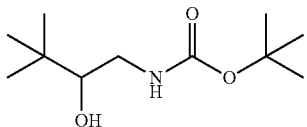

To a solution of Intermediate A80A (0.812 g, 6.93 mmol) in DCM (20 mL) were added TEA (2.414 mL, 17.32 mmol), DMAP (0.042 g, 0.346 mmol), and di-tert-butyl dicarbonate (2.268 g, 10.39 mmol). The reaction mixture was allowed to stir overnight at RT. The reaction mixture was diluted with EtOAc (500 mL) and washed with brine, dried (MgSO$_4$) and concentrated. The crude product was purified by silica gel chromatography (80 g REDISEP® column, eluting with a gradient from 0-30% EtOAc in hexanes). Fractions containing the product were combined and concentrated to afford Intermediate A80B (1.2 g, 80% yield). $^1$H NMR (400 MHz, DMSO-$d_6$) δ 4.07-3.93 (m, 1H), 3.92-3.80 (m, 1H), 3.62 (dd, J=10.3, 7.8 Hz, 1H), 1.46 (s, 9H), 0.87 (s, 9H).

Scheme 60

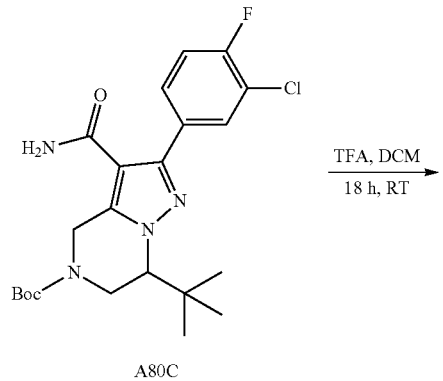

A80C

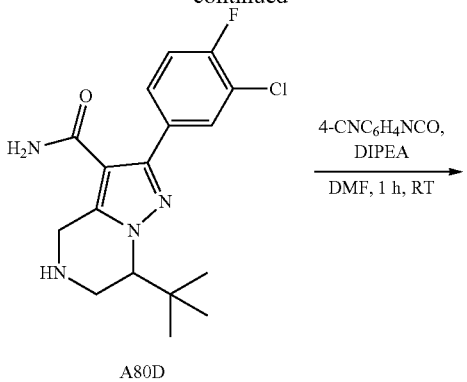

A80D

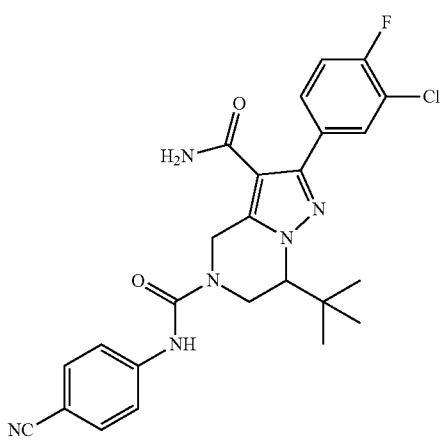

A80 and A81

Intermediate A80C: tert-Butyl 7-(tert-butyl)-3-carbamoyl-2-(3-chloro-4-fluorophenyl)-6,7-dihydropyrazolo[1,5-a]pyrazine-5(4H)-carboxylate

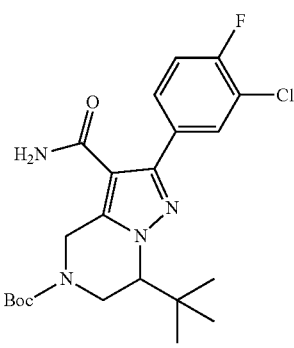 [SMILES: CC(C)(C)OC(=O)N1Cc2c(C(N)=O)c(-c3ccc(F)c(Cl)c3)nn2C(C(C)(C)C)C1]

Intermediate A80C was prepared using an analogous synthetic strategy to that employed for the preparation of Intermediate A1N (outlined in Scheme 41). Intermediate A80B was used in substitution for Intermediate A1B in the initial Mitsunobu coupling reaction. MS(ES) m/z=451 [M+H]$^+$.

Compounds A80 and A81: 7-(tert-Butyl)-2-(3-chloro-4-fluorophenyl)-N-(4-cyanophenyl)-6,7-dihydropyrazolo[1,5-a]pyrazine-3,5(4H)-dicarboxamide

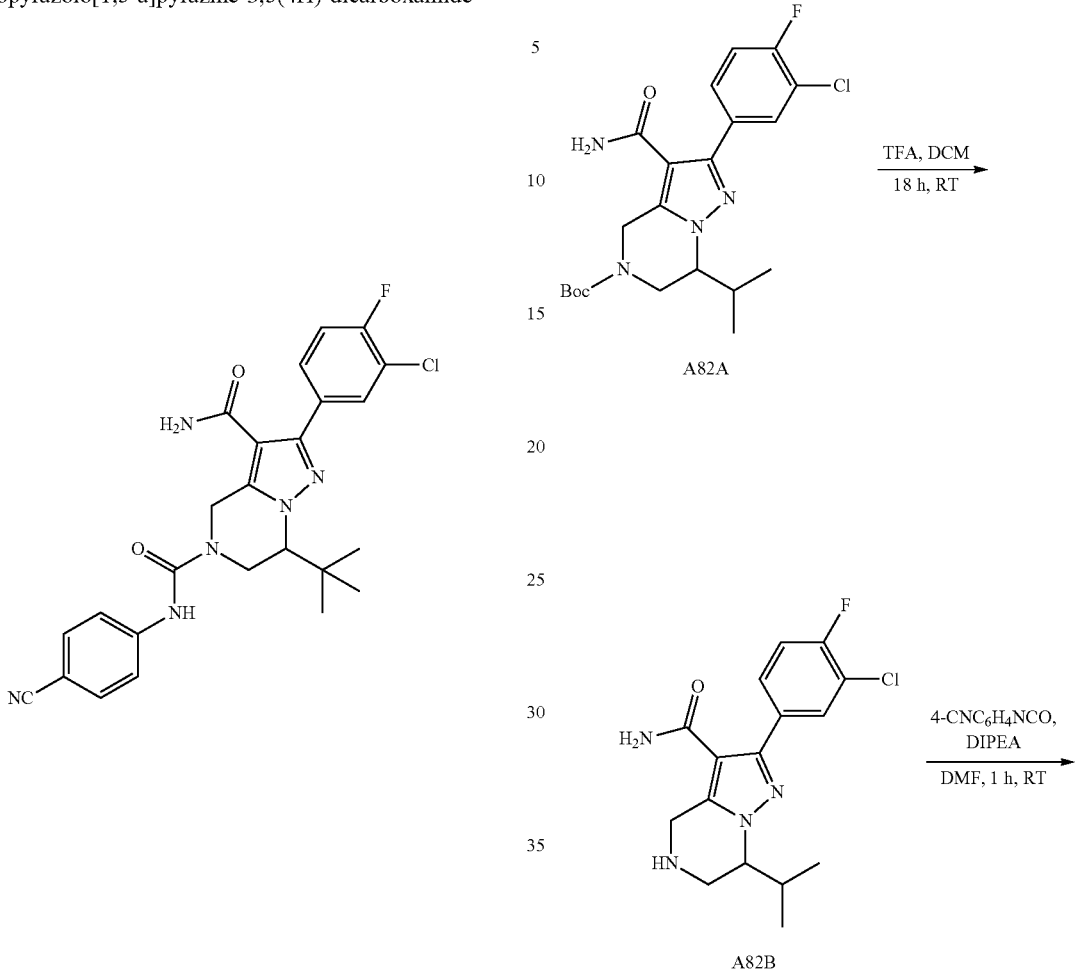

Scheme 61

To a solution of Intermediate A80C (0.305 g, 0.676 mmol) in DCM (20 mL) was added TFA (0.313 mL, 4.06 mmol) and the resulting solution was allowed to stir at RT for 18 h. The reaction was then concentrated under reduced pressure and the afforded crude bis TFA salt Intermediate A80D (0.314 g, >98% yield) used in the subsequent reaction with no purification. To a solution of Intermediate A80D (0.05 g, 0.143 mmol) in DMF (2 mL) at RT under nitrogen were added DIPEA (0.124 mL, 0.713 mmol) and 2,4-isocyanatobenzonitrile (0.041 g, 0.285 mmol). The reaction mixture was stirred for 1 h. The reaction mixture was filtered and concentrated. The crude material was purified via preparative HPLC. Fractions containing the desired product were combined and dried via centrifugal evaporation to obtain the racemic product. The compound was further purified through chiral separation using preparative HPLC: CHIRALPAK® AS, 21×250 mm, 10 μm column eluted with 80% heptanes with 0.1% diethylamine: 20% EtOH at 15 mL/min, and monitored by UV at 254 nm. The first eluting enantiomer, $r_t$=10.9 min: (S)-A80 and the second eluting enantiomer, $r_t$=17.1 min: (R)-A81 were thus separated. MS(ES) m/z=495 [M+H]$^+$; Ret. time=1.98 and 2.86 min. (Methods H and I respectively). $^1$H NMR (500 MHz, DMSO-d$_6$) δ 7.81-7.88 (1H, m), 7.61-7.77 (6H, m), 7.47 (1H, t, J=8.99 Hz), 7.20-7.45 (2H, m), 5.07-5.18 (1H, m), 4.71-4.84 (1H, m), 4.53-4.64 (1H, m), 4.17 (1H, br. s.), 0.94-1.07 (9H, m).

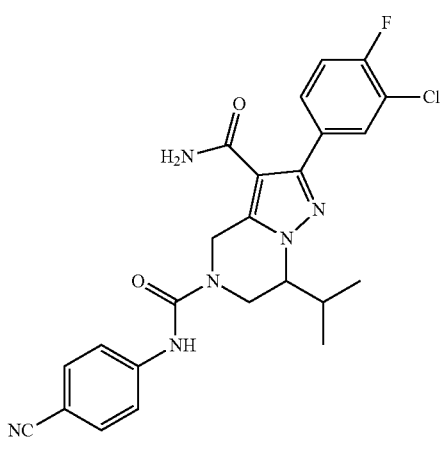

A82 and A83

Intermediate A82A: tert-Butyl 3-carbamoyl-2-(3-chloro-4-fluorophenyl)-7-isopropyl-6,7-dihydropyrazolo[1,5-a]pyrazine-5(4H)-carboxylate

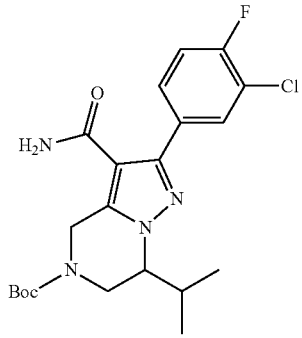 [SMILES: CC(C)C1CN(C(=O)OC(C)(C)C)Cc2c(C(N)=O)c(-c3ccc(F)c(Cl)c3)nn21]

Intermediate A82A was prepared using an analogous synthetic strategy to that employed for the preparation of Intermediate A80C. An analogous amino alcohol to Intermediate A80B was prepared commencing with 2-(iso-propyl)oxirane and used in substitution for Intermediate A1B in the initial Mitsunobu coupling reaction. MS(ES) m/z=437 [M+H]⁺.

Compounds A82 and A83: 2-(3-Chloro-4-fluorophenyl)-$N^5$-(4-cyanophenyl)-7-isopropyl-6,7-dihydropyrazolo[1,5-a]pyrazine-3,5(4H)-dicarboxamide

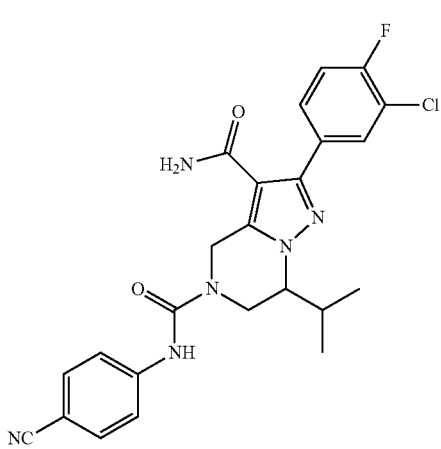 [SMILES: CC(C)C1CN(C(=O)Nc2ccc(C#N)cc2)Cc2c(C(N)=O)c(-c3ccc(F)c(Cl)c3)nn21]

Compounds A82 and A83 were prepared analogously to Compounds A80 and A81 using Intermediate A82B. The racemic compound obtained from preparative HPLC was further purified through chiral separation using preparative HPLC: CHIRALPAK® AD, 21×250 mm, 10 μm column eluted with 80% heptane with 0.1% diethylamine: 20% EtOH at 15 mL/min The first eluting enantiomer, r$_t$=18.4 min: (S)-A82 and the second eluting enantiomer, r$_t$=25.1 min: (R)-A83 were thus separated. MS(ES) m/z=481 [M+H]⁺; Ret. time=1.74 and 2.82 min. (Methods H and I respectively). ¹H NMR (500 MHz, DMSO-d₆) δ ppm 7.78-7.90 (1H, m), 7.61-7.76 (5H, m), 7.47 (1H, t, J=8.99 Hz), 7.14-7.43 (2H, m), 4.82-5.03 (2H, m), 4.16-4.24 (1H, m), 4.12 (1H, dd, J=14.12, 4.95 Hz), 3.72-3.84 (1H, m), 2.40 (1H, dq, J=13.11, 6.51 Hz), 1.01 (3H, d, J=6.97 Hz), 0.80-0.92 (3H, m).

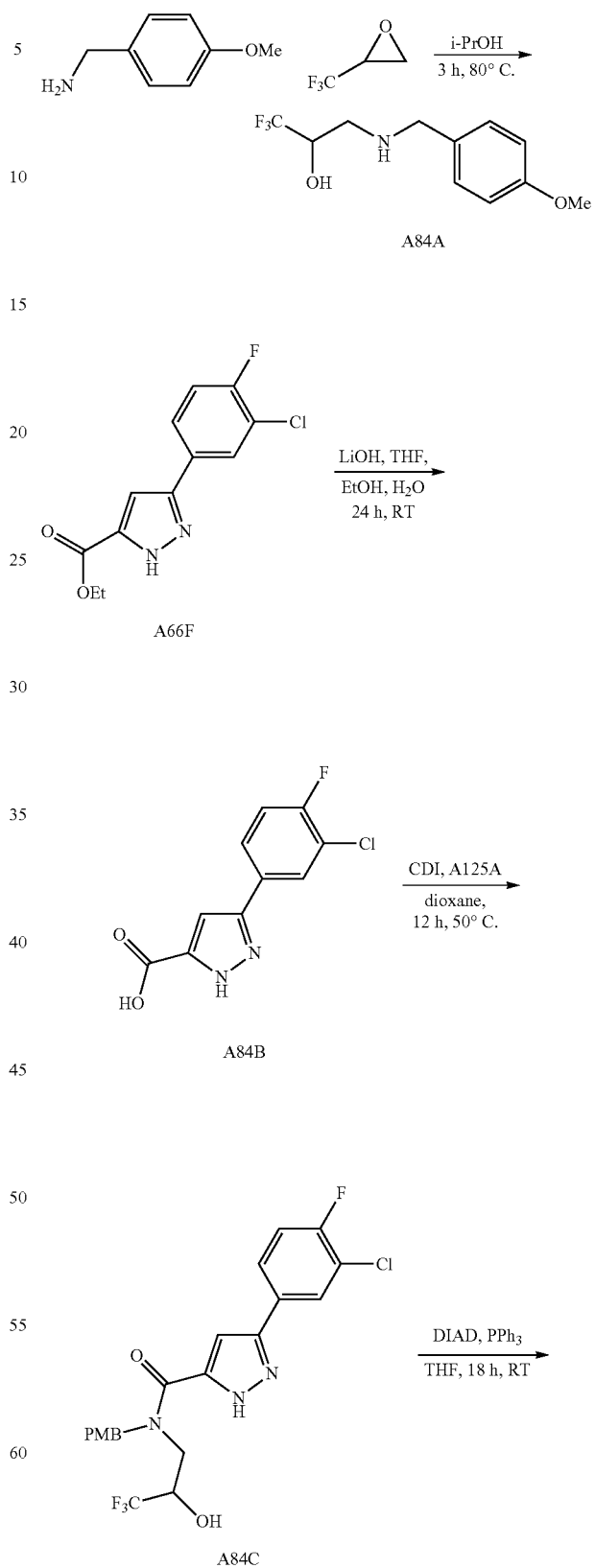

Scheme 62

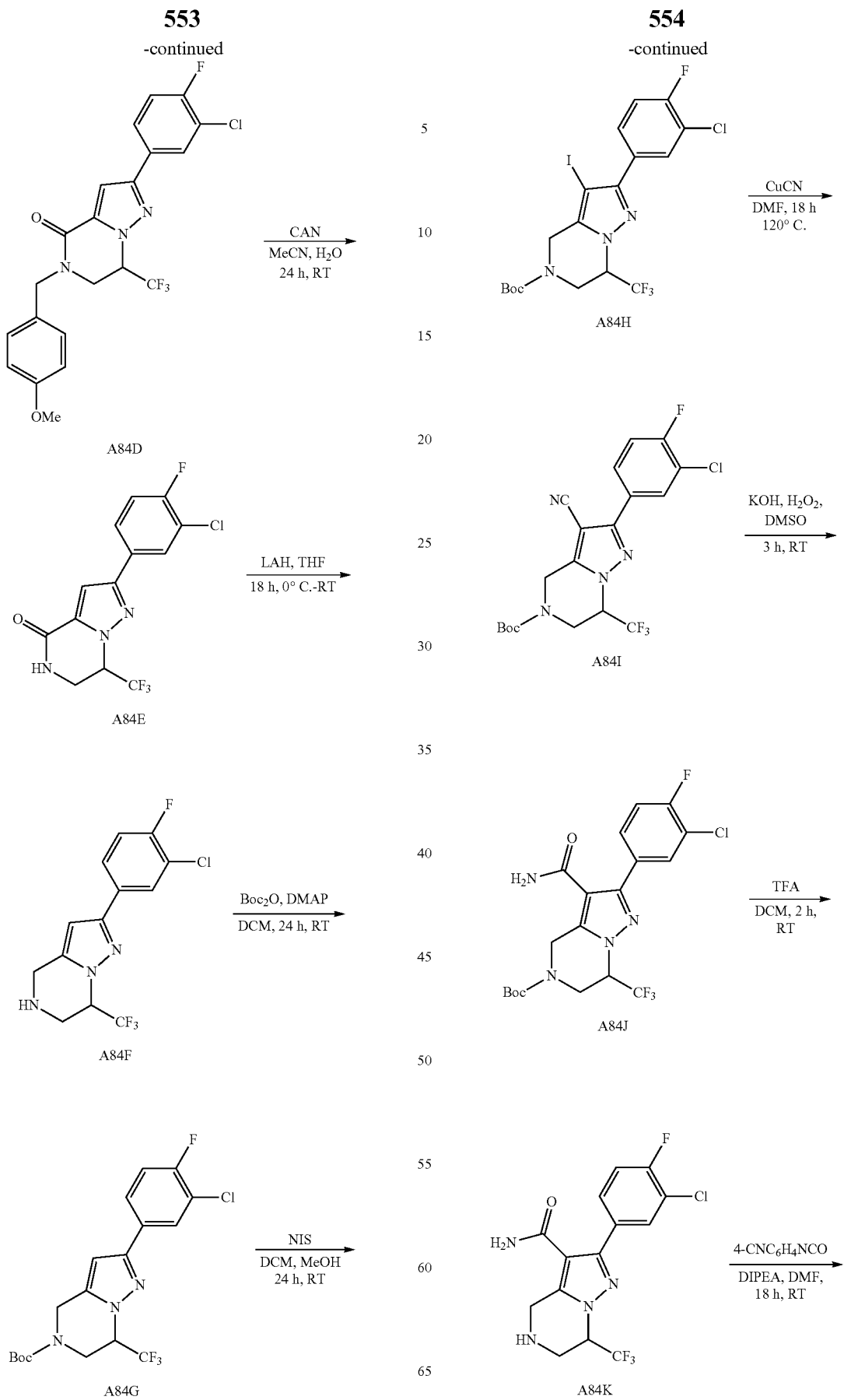

-continued

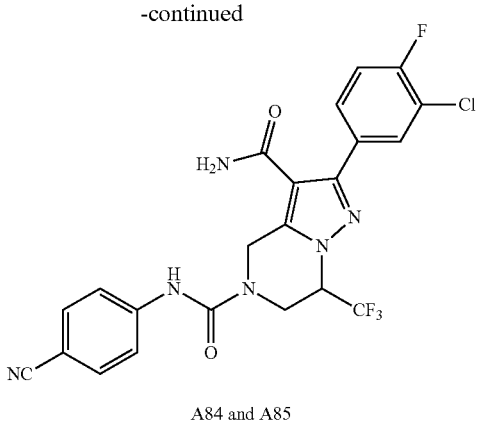

A84 and A85

Intermediate A84A: 1,1,1-Trifluoro-3-((4-methoxy-benzyl)amino)propan-2-ol

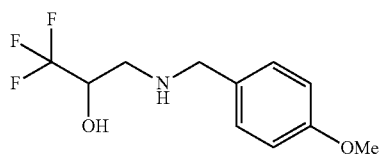 [SMILES: COc1ccc(CNCC(O)C(F)(F)F)cc1]

To a solution of 2-(trifluoromethyl)oxirane (2.00 g, 17.8 mmol) in isopropanol (20 mL) in a pressure tube was added (4-methoxyphenyl)methanamine (7.35 g, 53.5 mmol). The reaction vessel was capped and heated at 80° C. for 3 h. The reaction mixture was concentrated and purified by silica gel chromatography (80 g REDISEP® column, eluting with a gradient from 0-60% EtOAc in hexanes). The required fractions were concentrated to obtain Intermediate A84A (3.1 g, 71% yield) as a white solid. MS(ES) m/z=287 [M+H]$^+$. $^1$H NMR (400 MHz, DMSO-d$_6$) δ 7.29-7.17 (m, 2H), 6.87 (d, J=8.5 Hz, 2H), 6.25 (br. s., 1H), 4.04 (td, J=7.8, 3.3 Hz, 1H), 3.72 (s, 3H), 3.66 (d, J=1.8 Hz, 2H), 2.74-2.55 (m, 2H), 2.08 (br. s., 1H).

Intermediate A84B: 3-(3-Chloro-4-fluorophenyl)-1H-pyrazole-5-carboxylic acid

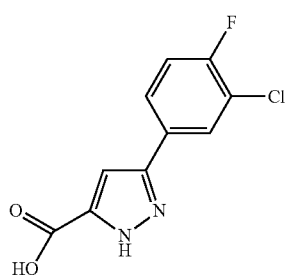 [SMILES: O=C(O)c1cc(-c2ccc(F)c(Cl)c2)n[nH]1]

To a solution of Intermediate A66F (5.0 g, 18.6 mmol) in EtOH (10 mL) and THF (20 mL) at RT was added a solution of LiOH (5.35 g, 223 mmol) in water (6.67 mL). The reaction mixture was stirred at RT overnight. The reaction mixture was concentrated and the resulting residue was dissolved in water (200 mL) and extracted with ether. The organic layer was separated and the aqueous layer was acidified to a pH of 2 using a conc. aq. solution of HCl. The aqueous layer was extracted with EtOAc (3×200 mL). The combined organic layers were washed with brine, dried (MgSO$_4$) and concentrated to obtain Intermediate A84B (3.02 g, 67.4% yield). The product was used as such without further purification. MS(ES) m/z=241 [M+H]$^+$.

Intermediate A84C: 3-(3-Chloro-4-fluorophenyl)-N-(4-methoxybenzyl)-N-(3,3,3-trifluoro-2-hydroxypropyl)-1H-pyrazole-5-carboxamide

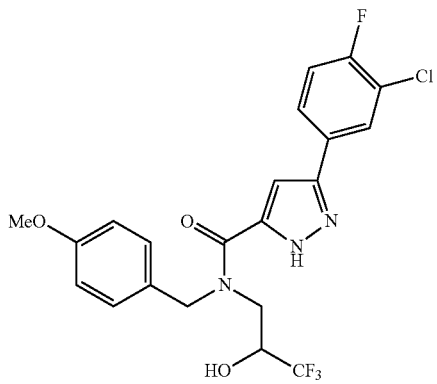 [SMILES: COc1ccc(CN(CC(O)C(F)(F)F)C(=O)c2cc(-c3ccc(F)c(Cl)c3)n[nH]2)cc1]

To a solution of Intermediate A84B (0.8 g, 3.32 mmol) in 1,4-dioxane heated at 50° C. was added CDI (0.593 g, 3.66 mmol). The reaction was heated for 30 min, and Intermediate A84A (0.911 g, 3.66 mmol) was added. The reaction mixture was allowed to stir for an additional 30 min. at 50° C. The reaction mixture was diluted with water, cooled to RT, and was extracted with EtOAc (3×100 mL). The combined organic layers were washed with brine, dried (MgSO$_4$), and concentrated. The residue was purified by silica gel chromatography (80 g REDISEP® column, eluting with a gradient from 0-30% EtOAc in hexanes). Fractions containing the product were combined and concentrated to afford Intermediate A84C (1.015 g, 64.7% yield). MS(ES) m/z=472 [M+H]$^+$.

Intermediate A84D: 2-(3-Chloro-4-fluorophenyl)-5-(4-methoxybenzyl)-7-(trifluoromethyl)-6,7-dihydropyrazolo[1,5-a]pyrazin-4(5H)-one

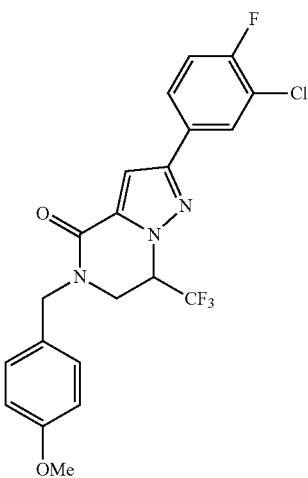 [SMILES: COc1ccc(CN2CC(C(F)(F)F)n3nc(-c4ccc(F)c(Cl)c4)cc3C2=O)cc1]

To an ice-cold stirred solution of triphenylphosphine (0.733 g, 2.80 mmol) in THF (30 mL) was added DIAD (0.544 mL, 2.80 mmol) resulting in a thick milky yellow solution. After 10 min. a solution of Intermediate A84C (1.015 g, 2.151 mmol) in THF (5.0 mL) was added. The reaction was then allowed to warm to RT and stir overnight. The reaction mixture was diluted with EtOAc (200 mL) and washed with brine, dried (MgSO$_4$) and concentrated in vacuo. The crude yellow oil was purified by BIOTAGE® chromatography (80 g REDISEP® column, eluting with a gradient from 0-40% EtOAc in hexanes). Fractions containing the product were combined and concentrated to afford Intermediate A84D (0.614 g, 62.8% yield). MS(ES) m/z=454 [M+H]$^+$. $^1$H NMR (400 MHz, chloroform-d) δ 7.88 (dd, J=7.0, 2.0 Hz, 1H), 7.66 (ddd, J=8.6, 4.6, 2.1 Hz, 1H), 7.31-7.14 (m, 4H), 6.94-6.85 (m, 2H), 5.01-4.89 (m, 1H), 4.72 (s, 2H), 4.06-3.96 (m, 1H), 3.85-3.74 (m, 4H).

Intermediate A84E: 2-(3-Chloro-4-fluorophenyl)-7-(trifluoromethyl)-6,7-dihydropyrazolo[1,5-a]pyrazin-4(5H)-one

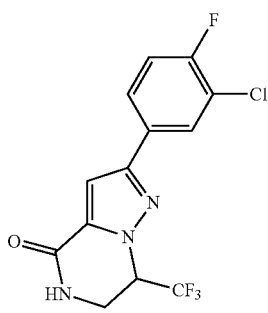 [SMILES: O=C1NCC(C(F)(F)F)n2nc(-c3ccc(F)c(Cl)c3)cc21]

To a solution of Intermediate A84D (0.405 g, 0.892 mmol) in acetonitrile (5 mL) and water (0.556 mL) at RT was added CAN (1.957 g, 3.57 mmol). The reaction mixture was allowed to stir at RT for 24 h. The reaction mixture was concentrated, the residue was dissolved in methanol and purified by reverse phase preparative HPLC using a 30×100 mm XTERRA® column eluted with 30-100% B, for 20 min. (Solvent A: 90% water, 10% methanol, 0.1% TFA: Solvent B: 10% water, 90% methanol, 0.1% TFA). The required fractions were combined and concentrated to obtain Intermediate A84E (0.1 g, 34% yield). MS(ES) m/z=334 [M+H]$^+$.

Intermediate A84F: 2-(3-Chloro-4-fluorophenyl)-7-(trifluoromethyl)-4,5,6,7-tetrahydropyrazolo[1,5-a]pyrazine

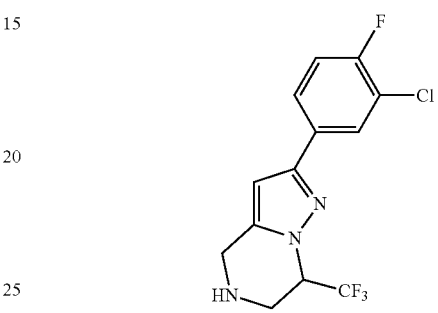

To a solution of Intermediate A84E (0.1 g, 0.300 mmol) in anhydrous THF (10 mL) at 0° C. under nitrogen was added a solution of LAH (0.180 mL, 0.360 mmol, 2M in THF). The reaction mixture was allowed to warm to RT and stirred for 4 h. The reaction mixture was cooled to 0° C. and an additional equivalent of LAH was added and the solution was warmed to RT and stirred for 5 h. The reaction mixture was again cooled to 0° C. and quenched by slow addition of a saturated aq. solution of Rochelle's salt. The solution was then extracted with EtOAc (3×) and the combined organic layers were washed with brine, dried (MgSO$_4$) and concentrated. The crude residue was purified by silica gel chromatography (24 g REDISEP® column, eluting with a gradient from 0-80% EtOAc in hexanes). Fractions containing the product were combined and concentrated to afford Intermediate A84F (0.06 g, 63% yield, contaminated with 15% of the des-chloro by-product). MS(ES) m/z=320 [M+H]$^+$.

Intermediate A84G: tert-Butyl 2-(3-chloro-4-fluorophenyl)-7-(trifluoromethyl)-6,7-dihydropyrazolo[1,5-a]pyrazine-5(4H)-carboxylate

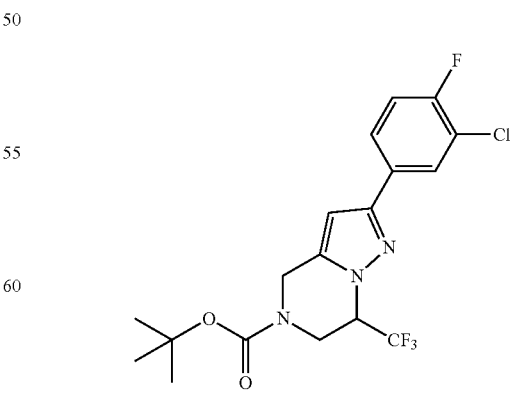

To a solution of Intermediate A84F (0.06 g, 0.188 mmol) in DCM (10 mL) were added TEA (0.065 mL, 0.469 mmol), DMAP (1.146 mg, 9.38 µmol), and Boc₂O (0.061 g, 0.282 mmol). The reaction mixture was stirred overnight at RT. The reaction mixture was diluted with EtOAc (300 mL) and washed with brine, dried (MgSO₄) and concentrated. The crude product was purified by silica gel chromatography using (24 g REDISEP® column, eluting with a gradient from 0-30% EtOAc in hexanes). Fractions containing the product were combined and concentrated to afford Intermediate A84G (0.055 g, 70% yield). MS(ES) m/z=420 [M+H]⁺.

Intermediate A84H: tert-Butyl 2-(3-chloro-4-fluorophenyl)-3-iodo-7-(trifluoromethyl)-6,7-dihydropyrazolo[1,5-a]pyrazine-5(4H)-carboxylate

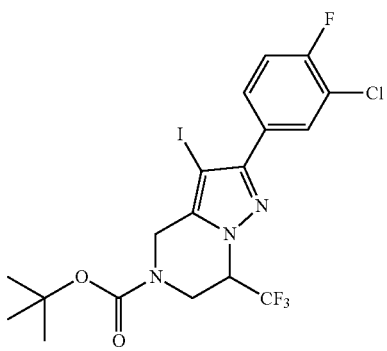 [SMILES: CC(C)(C)OC(=O)N1Cc2c(I)c(-c3ccc(F)c(Cl)c3)nn2C(C(F)(F)F)C1]

To a solution of Intermediate A84G (0.055 g, 0.131 mmol) in a 4:1 mixture of CH₂Cl₂ (10 mL) and MeOH (2.5 mL) was added NIS (0.088 g, 0.393 mmol). The reaction mixture was stirred at RT. After 90 min., another equivalent of NIS was added and the resulting solution was stirred overnight at RT. The reaction mixture was concentrated in vacuo affording the crude product as a red oil. The product was purified by silica gel chromatography using (24 g REDISEP® column, eluting with a gradient from 0-30% EtOAc in hexanes). Fractions containing the product were combined and concentrated to afford Intermediate A84H (0.059 g, 83% yield). MS(ES) m/z=546 [M+H]⁺.

Intermediate A84I: tert-Butyl 2-(3-chloro-4-fluorophenyl)-3-cyano-7-(trifluoromethyl)-6,7-dihydropyrazolo[1,5-a]pyrazine-5(4H)-carboxylate

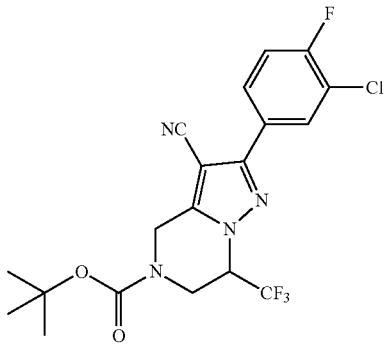 [SMILES: CC(C)(C)OC(=O)N1Cc2c(C#N)c(-c3ccc(F)c(Cl)c3)nn2C(C(F)(F)F)C1]

To a solution of Intermediate A84H (0.115 g, 0.245 mmol) in DMF (20 mL) was added CuCN (0.055 g, 0.613 mmol). The reaction mixture was heated in a sealed tube at 120° C. for 16 h. The reaction mixture was filtered through a pad of CELITE®, the filter cake washed with EtOAc and the filtrate was concentrated under reduced pressure. The crude reaction mixture was purified by silica gel chromatography (24 g REDISEP® column, eluting with a gradient from 0-40% EtOAc in hexanes). Fractions containing the product were combined and concentrated to afford Intermediate A84I (0.075 g, 83% yield). MS(ES) m/z=369 [M+H]⁺.

Intermediate A84J: tert-Butyl 3-carbamoyl-2-(3-chloro-4-fluorophenyl)-7-(trifluoromethyl)-6,7-dihydropyrazolo[1,5-a]pyrazine-5(4H)-carboxylate

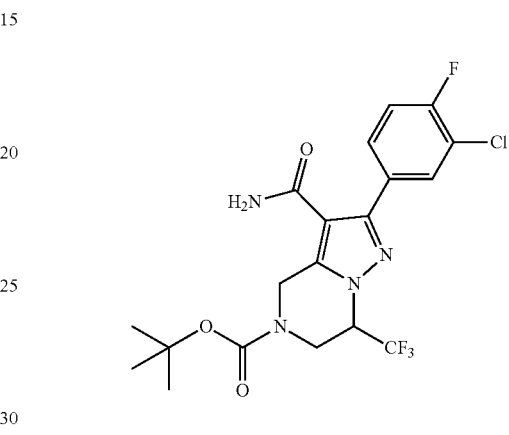

To a solution of Intermediate A84I (0.061 g, 0.137 mmol) in EtOH (10 mL) at RT was added a 5M aq. solution of KOH (0.137 mL, 0.686 mmol). The reaction mixture was cooled to 0° C. and hydrogen peroxide (0.280 mL, 2.74 mmol, 30% w/v in H₂O) was added dropwise. The reaction mixture was allowed to warm to RT and stir overnight. The reaction mixture was concentrated and the resulting residue was diluted with EtOAc. The solution was washed with water and brine, and then dried (MgSO₄) and concentrated. The crude product was purified by silica gel chromatography (24 g REDISEP® column, eluting with a gradient from 0-20% MeOH in DCM). The required fractions were concentrated to obtain Intermediate A84J (0.046 g, 72% yield) as a white solid. MS(ES) m/z=463 [M+H]⁺.

Intermediate A84K: 2-(3-Chloro-4-fluorophenyl)-7-(trifluoromethyl)-4,5,6,7-tetrahydropyrazolo[1,5-a]pyrazine-3-carboxamide, TFA

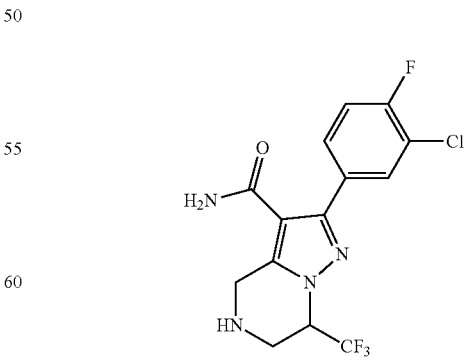

To a solution of Intermediate A84J (0.141 g, 0.305 mmol) in DCM (10 mL) was added TFA (0.141 mL, 1.828 mmol). The reaction mixture was stirred overnight at RT. The reaction mixture was concentrated to obtain crude Intermediate A84K (0.145 g, 0.304 mmol, 100% yield). The yield was assumed to be quantitative and the product was used as such without further purification. MS(ES) m/z=363 [M+H]$^+$.

Compounds A84 and A85: 2-(3-Chloro-4-fluorophenyl)-N$^5$-(4-cyanophenyl)-7-(trifluoromethyl)-6,7-dihydropyrazolo[1,5-a]pyrazine-3,5(4H)-dicarboxamide

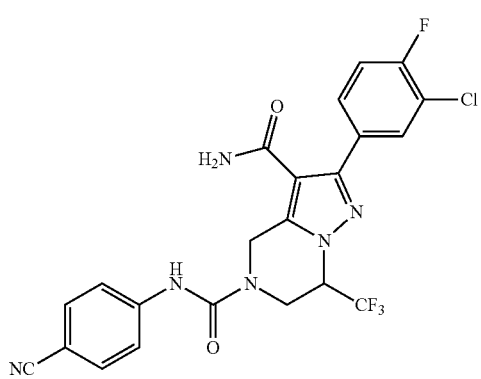 [SMILES: N#Cc1ccc(NC(=O)N2Cc3c(C(N)=O)c(-c4ccc(F)c(Cl)c4)nn3C(C(F)(F)F)C2)cc1]

To a solution of Intermediate A84K (0.036 g, 0.099 mmol) in DMF (2 mL) at RT under nitrogen were added DIPEA (0.087 mL, 0.496 mmol) and 2-isocyanato-2-methylpropane (0.029 g, 0.199 mmol). The reaction mixture was stirred for 1 h. The reaction mixture was filtered and concentrated. The crude material was purified via preparative HPLC. Fractions containing the desired product were combined and dried via centrifugal evaporation to obtain the racemic product. The compound was further purified through chiral separation using preparative HPLC: CHIRALCEL® OD 21×250 mm, 10 μm column eluted with 85% heptane with 0.1% diethylamine: 15% EtOH at 15 mL/min, monitored by UV at 254 nm. The first eluting enantiomer, r$_t$=29.3 min: (S)-A84 and the second eluting enantiomer, r$_t$=38.5 min: (R)-A85 were thus separated. MS(ES) m/z=507 [M+H]$^+$; Ret. time=1.74 and 2.98 min. (Methods H and I respectively). $^1$H NMR (500 MHz, DMSO-d$_6$) δ ppm 7.79-7.86 (1H, m), 7.70-7.75 (2H, m), 7.68 (1H, td, J=5.41, 2.38 Hz), 7.64 (2H, d, J=8.80 Hz), 7.36-7.57 (3H, m), 7.35-7.37 (1H, m), 5.50 (1H, br. s.), 5.39 (1H, d, J=17.2 Hz), 4.86 (1H, d, J=14.3 Hz), 4.63-4.75 (1H, m), 3.76 (1H, d, J=14.7 Hz).

Scheme 63

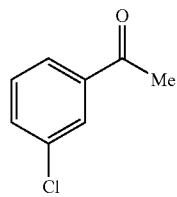

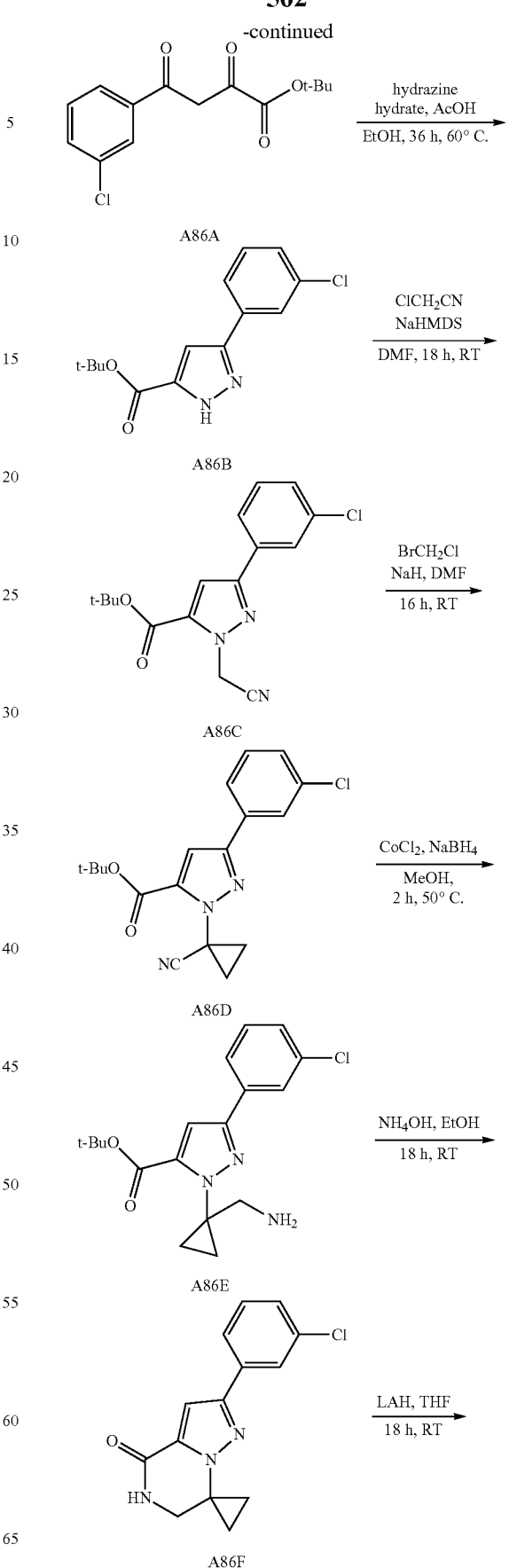

-continued

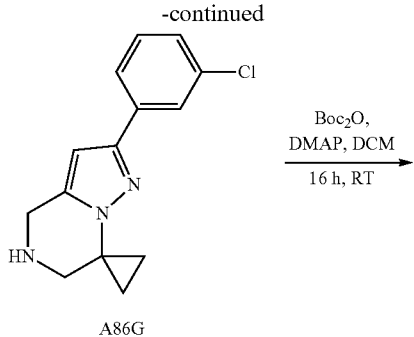

A86G

Boc₂O,
DMAP, DCM
⎯⎯⎯⎯⎯→
16 h, RT

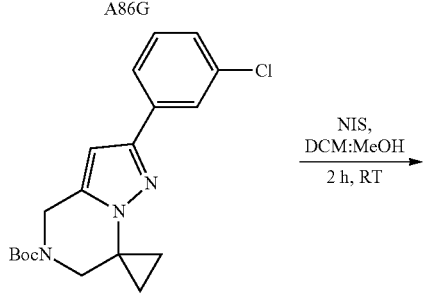

A86H

NIS,
DCM:MeOH
⎯⎯⎯⎯⎯→
2 h, RT

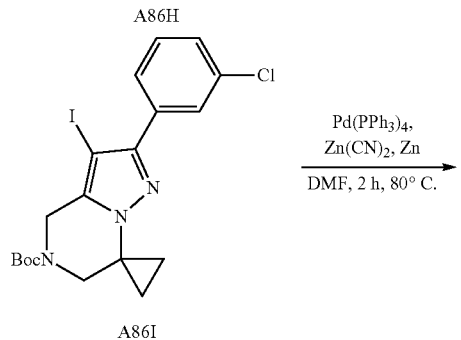

A86I

Pd(PPh₃)₄,
Zn(CN)₂, Zn
⎯⎯⎯⎯⎯→
DMF, 2 h, 80° C.

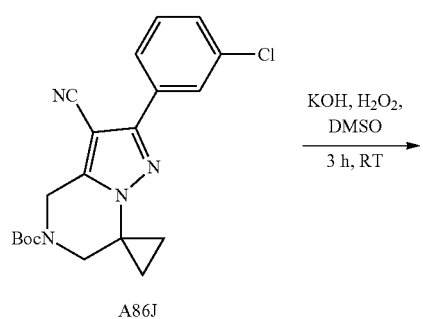

A86J

KOH, H₂O₂,
DMSO
⎯⎯⎯⎯⎯→
3 h, RT

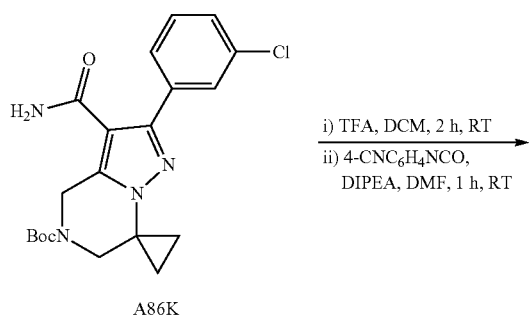

A86K i) TFA, DCM, 2 h, RT
ii) 4-CNC₆H₄NCO,
DIPEA, DMF, 1 h, RT
⎯⎯⎯⎯⎯→

-continued

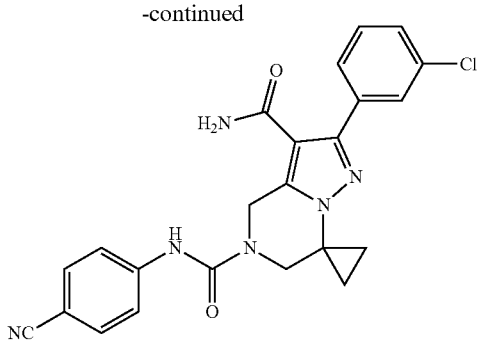

A86

Intermediate A86A: tert-Butyl 4-(3-chlorophenyl)-2,4-dioxobutanoate

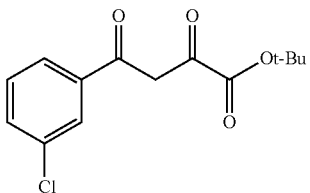 [SMILES: CC(C)(C)OC(=O)C(=O)CC(=O)c1cccc(Cl)c1]

Under an atmosphere of nitrogen, a solution of 3'-chloroacetophenone (1.015 mL, 7.82 mmol) in anhydrous diethyl ether (50 mL) was allowed to cool to −78° C. for 15 minutes prior to the slow addition of a 1.0 M solution of LHMDS (8.60 mL, 8.60 mmol) in THF. The enolate formation was allowed to stir for 45 minutes at −78° C., after which di-tert-butyl oxalate (1.898 g, 9.38 mmol) was added as a single portion. The pale yellow reaction mixture was allowed to warm to RT and stirred for 18 h. The dark-green solution was then quenched with 50 mL of a 1.0 M aq. solution of HCl. The two layers were separated and the aq. layer was extracted twice more with EtOAc. The combined organic layers were washed with brine, dried over anhydrous MgSO₄, filtered and the filtrate concentrated under reduced pressure to afford an orange oil which was purified by silica gel chromatography (40 g REDISEP® column, eluting with a gradient from 0-20% EtOAc in hexanes). Fractions containing the product were combined and evaporated to afford Intermediate A86A (2.17 g, 98%) as a pale yellow solid. ¹H NMR (400 MHz, chloroform-d) δ ppm 7.94-7.99 (1H, m), 7.86 (1H, dt, J=7.78, 1.38 Hz), 7.58 (1H, ddd, J=7.97, 2.20, 1.13 Hz), 7.43-7.49 (1H, m), 6.94-6.99 (1H, m), 1.58-1.63 (9H, m).

Intermediate A86B: tert-Butyl 3-(3-chlorophenyl)-1H-pyrazole-5-carboxylate

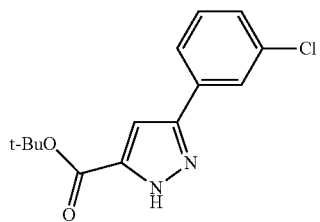 [SMILES: CC(C)(C)OC(=O)c1cc(-c2cccc(Cl)c2)n[nH]1]

To a solution of Intermediate A86A (2.17 g, 7.68 mmol) in ethanol (80 mL) was added hydrazine hydrate (0.471 mL, 7.68 mmol, 80% wt). The solution was allowed to stir for 18 h at RT. There was little conversion to the desired pyrazole so at this point acetic acid (5 mL) was added and the reaction mixture was heated to 60° C. for 24 h. The reaction mixture was diluted with EtOAc (100 mL) and quenched by the addition of a saturated aq. solution of NaHCO$_3$. The organic layer was separated and washed with brine (2×100 mL). The organic layer was dried over sodium sulfate and concentrated in vacuo. The crude reaction mixture was purified by silica gel chromatography (80 g REDISEP® column, eluting with a gradient of 0-60% EtOAc in hexanes). Fractions containing the product were combined and evaporated to afford Intermediate A86B (1.82 g, 83%) as a yellow crystalline solid. $^1$H NMR (400 MHz, DMSO-d$_6$) δ ppm 13.70-14.15 (1H, m), 7.93 (1H, t, J=1.76 Hz), 7.83 (1H, d, J=7.28 Hz), 7.22-7.53 (3H, m), 1.51-1.59 (9H, m).

Intermediate A86C: tert-Butyl 3-(3-chlorophenyl)-1-(cyanomethyl)-1H-pyrazole-5-carboxylate

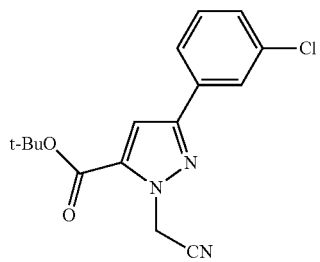 [SMILES: CC(C)(C)OC(=O)c1cc(-c2cccc(Cl)c2)nn1CC#N]

To a flask charged with an ice-cooled solution of Intermediate A86B (1.82 g, 6.53 mmol) in DMF (15 mL) is added a 2.0 M solution of NaHMDS in THF (3.43 mL, 6.86 mmol) dropwise. The reaction mixture is allowed to stir for 5 minutes and the ice bath is subsequently removed, chloroacetonitrile (0.456 mL, 7.19 mmol), which had been passed through a column of CELITE® and NaHCO$_3$, was added to the reaction mixture. The reaction was allowed to warm to RT and stirred for an additional 18 h. The reaction was quenched by the addition of 1 mL of a saturated aq. solution of NH$_4$Cl. The reaction was diluted with equal parts water and EtOAc and the resulting mixture was allowed to stir vigorously for 15 min. The organic layer was separated, dried over sodium sulfate, and concentrated in vacuo to afford an orange solid which was purified by silica gel chromatography (80 g REDISEP® column, eluting with a gradient of 0-50% EtOAc in hexanes). Fractions containing the product were combined and evaporated to afford Intermediate A86C (1.87 g, 90%) as a white solid. MS(ES): m/z=261.91 [M+H$_2$O-OtBu]$^+$. $^1$H NMR (400 MHz, chloroform-d) δ ppm 7.78-7.83 (1H, m), 7.66-7.73 (1H, m), 7.31-7.40 (2H, m), 7.08-7.15 (1H, m), 5.50-5.60 (2H, m), 1.59-1.69 (9H, m).

Intermediate A86D: tert-Butyl 3-(3-chlorophenyl)-1-(1-cyanocyclopropyl)-1H-pyrazole-5-carboxylate

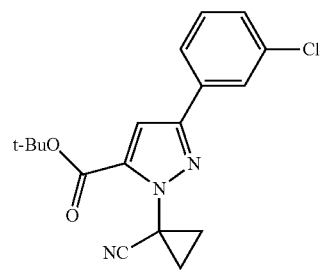 [SMILES: CC(C)(C)OC(=O)c1cc(-c2cccc(Cl)c2)nn1C1(C#N)CC1]

To an ice-cooled solution of Intermediate A86C (1.87 g, 5.88 mmol) and 1-bromo-2-chloroethane (0.844 mL, 7.36 mmol) in DMF (20 mL) was added NaH (0.588 g, 14.71 mmol) (60% dispersion in mineral oil) portionwise. The cloudy solution was allowed to slowly warm to RT and stirred for 16 h prior to quenching with the addition of 10 mL of a saturated aq. solution of NH$_4$Cl. The mixture was then partitioned in equal parts water and EtOAc (250 mL each) by vigorous stirring for 15 minutes. The organic layer was separated, washed with brine, dried over sodium sulfate, and concentrated in vacuo to afford an orange oil which was purified by silica gel chromatography (80 g REDISEP® column eluting with a gradient of 0-50% EtOAc in hexanes). Fractions containing the product were combined and evaporated to afford Intermediate A86D (1.02 g, 50%) as a white solid. MS(ES): m/z=287.96 [M+H$_2$O-OtBu]$^+$. $^1$H NMR (400 MHz, chloroform-d) δ ppm 7.78-7.82 (1H, m), 7.64-7.68 (1H, m), 7.33-7.37 (2H, m), 7.11 (1H, s), 1.67 (9H, s), 1.64 (2H, s), 1.54-1.58 (2H, m).

Intermediate A86E: tert-Butyl 1-(1-(aminomethyl)cyclopropyl)-3-(3-chlorophenyl)-1H-pyrazole-5-carboxylate

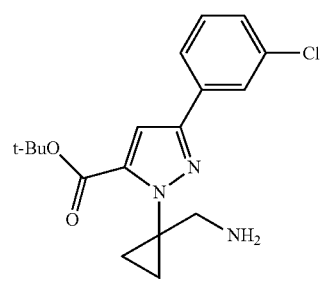 [SMILES: CC(C)(C)OC(=O)c1cc(-c2cccc(Cl)c2)nn1C1(CN)CC1]

To a solution of Intermediate A86D (0.211 g, 0.613 mmol) in MeOH (15 mL) was added cobalt(II) chloride (0.239 g, 1.838 mmol). The bright purple solution was allowed to cool to 0° C. prior to the slow and careful addition of sodium borohydride (0.232 g, 6.13 mmol). After stirring at 0° C. for 10 minutes, the reaction mixture was warmed to 50° C. After stirring for 2 h, the reaction was allowed to cool to RT and the heterogeneous mixture is plugged a short pad of CELITE®. The filtrate was diluted with EtOAc and 100 mL of a 1 M aq. solution of HCl. The acidic aqueous solution dissolved all of the cobalt salts (color change from dark brown to light pink). The pH of the aqueous layer was adjusted to pH=7 with a 1.0 M aq. solution of NaOH. The organic layer was then separated and the aqueous phase was extracted with EtOAc (3×). The combined organic phases were washed with brine, dried over sodium sulfate, and concentrated under vacuum to afford crude Intermediate A86E (0.213 g, 100%) as an oil. MS(ES): m/z=273.9 [M+H$_2$O-OtBu]$^+$. $^1$H NMR (400 MHz, chloroform-d) δ ppm 7.74-7.85 (1H, m), 7.59-7.69 (1H, m), 7.21-7.34 (1H, m), 6.98-7.06 (1H, m), 3.06 (2H, s), 1.54-1.63 (9H, m), 1.29-1.42 (4H, m), 1.08-1.16 (2H, m).

Intermediate A86F: 2'-(3-Chlorophenyl)-5',6'-dihydro-4'H-spiro[cyclopropane-1,7'-pyrazolo[1,5-a]pyrazin]-4'-one

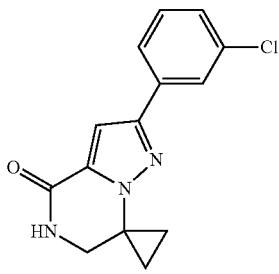 [SMILES: O=C1NCC2(CC2)n2nc(-c3cccc(Cl)c3)cc21]

To a solution of Intermediate A86E (0.213 g, 0.612 mmol) in EtOH (5.0 mL) was added ammonium hydroxide (0.954 mL, 24.5 mmol, 40 wt %). The solution was allowed to stir at RT for 18 h. The crude reaction mixture was concentrated under reduced pressure and diluted with EtOAc. The aqueous solution was neutralized to pH=7 using a 1M aq. solution of HCl. The organic layer was separated and the aqueous layer was extracted twice more with EtOAc. The combined organic layers were washed with brine, dried over sodium sulfate, and concentrated to afford Intermediate A86F (0.118 g, 69%) as a white solid. MS(ES): m/z=273.9 [M+H]$^+$. $^1$H NMR (400 MHz, chloroform-d) δ ppm 7.80-7.84 (1H, m), 7.65 (1H, dt, J=7.34, 1.47 Hz), 7.28-7.37 (2H, m), 7.15-7.19 (1H, m), 6.59 (1H, br. s.), 3.68-3.74 (2H, m), 1.71-1.77 (2H, m), 1.08-1.15 (2H, m).

Intermediate A86G: 2'-(3-Chlorophenyl)-5',6'-dihydro-4'H-spiro[cyclopropane-1,7'-pyrazolo[1,5-a]pyrazine]

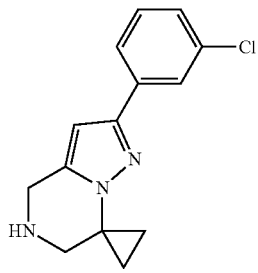 [SMILES: Clc1cccc(-c2cc3n(n2)C2(CC2)CNC3)c1]

A solution of Intermediate A86F (0.166 g, 0.606 mmol) in anhydrous THF (6.1 mL) placed under an atmosphere of N$_2$ was allowed to cool to −5° C. A 1.0 M solution of LAH (1.456 mL, 1.456 mmol) in THF was added dropwise. The ice bath was removed once the bubbling had subsided. The reaction was then allowed to warm to RT and stirred for an additional 18 h. The reaction mixture was cooled to 0° C. and carefully quenched with the sequential addition of 1.5 mL of H$_2$O, 1.5 mL of a 15% aq. solution of NaOH, and 4.5 mL of H$_2$O. The cooling bath was removed and the biphasic mixture was allowed to stir at RT for 30 min. Anhydrous MgSO$_4$ was added to the mixture and was stirred for 15 min. The reaction mixture was then filtered through pad of CELITE®. The filter cake was washed with DCM (2×20 mL). The organic layer of the filtrate was separated and the aqueous layer was extracted with 2×50 mL of DCM. The combined organic layers were washed with brine, dried over sodium sulfate, and concentrated in vacuo to provide a pale green oil. The crude reaction mixture was purified by silica gel chromatography (40 g REDISEP® column, eluting with a gradient from 50-100% EtOAc in hexanes). Fractions containing the product were combined and evaporated to afford Intermediate A86G (0.115 g, 73%) as a white solid. MS(ES): m/z=260.0 [M+H]$^+$.

Intermediate A86H: tert-Butyl 2'-(3-chlorophenyl)-4'H-spiro[cyclopropane-1,7'-pyrazolo[1,5-a]pyrazine]-5'(6'H)-carboxylate

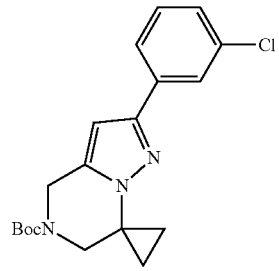 [SMILES: CC(C)(C)OC(=O)N1Cc2cc(-c3cccc(Cl)c3)nn2C2(CC2)C1]

To a vial charged with a solution of Intermediate A86G (0.175 g, 0.674 mmol) in DCM (4 mL) were added triethylamine (0.376 mL, 2.70 mmol) and DMAP (4.12 mg, 0.034 mmol). To the resulting solution was added di-tert-butyl dicarbonate (221 mg, 1.011 mmol). After stirring at RT for 16 h, the reaction was quenched by the addition of 20 mL of a saturated aq. solution of NaHCO$_3$. The layers were separated, and the aqueous layer was washed twice more with DCM. The combined organic layers were washed with water and brine, then dried over sodium sulfate, and concentrated in vacuo. The crude reaction mixture was purified by silica gel chromatography (40 g REDISEP® column, eluting with a gradient from 0 to 40% EtOAc in hexanes). Fractions containing the product were combined and evaporated to afford Intermediate A86H (0.240 g, 99%) as a colorless oil. MS(ES): m/z=360.08 [M+H]. $^1$H NMR (400 MHz, chloroform-d) δ ppm 7.75 (1H, t, J=1.76 Hz), 7.61 (1H, d, J=7.53 Hz), 7.21-7.34 (2H, m), 6.35 (1H, s), 4.80 (2H, br. s.), 3.81 (2H, s), 1.63-1.69 (2H, m), 1.50-1.54 (9H, m), 0.95-1.08 (2H, m).

Intermediate A86I: tert-Butyl 2'-(3-chlorophenyl)-3'-iodo-4'H-spiro[cyclopropane-1,7'-pyrazolo[1,5-a]pyrazine]-5'(6'H)-carboxylate

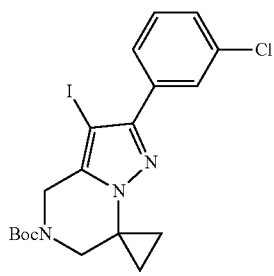 [SMILES: CC(C)(C)OC(=O)N1Cc2c(I)c(-c3cccc(Cl)c3)nn2C2(CC2)C1]

To a stirring solution of Intermediate A86H (241 mg, 0.670 mmol) in DCM (5.4 mL) and MeOH (1.4 mL) at RT was added NIS (452 mg, 2.009 mmol). After 1 h, the volatiles were removed under reduced pressured and the red oil was purified by silica gel chromatography (24 g REDISEP® column, eluting with a gradient from 0-25% EtOAc in hexanes). Fractions containing the product were combined and evaporated to afford Intermediate A86I (0.270 g, 83%) as a white foam. MS(ES): m/z=485.8 [M+H]$^+$. $^1$H NMR (400 MHz, chloroform-d) δ ppm 7.78-7.82 (1H, m), 7.73 (1H, dt, J=6.59, 1.98 Hz), 7.32-7.37 (2H, m), 4.59-4.76 (2H, m), 3.82 (2H, br. s.), 1.65 (2H, s), 1.52 (9H, s), 1.04 (2H, br. s.).

Intermediate A86J: tert-Butyl 7'-(3-chlorophenyl)-8'-cyano-1'H-spiro[cyclopropane-1,4'-pyrrolo[1,2-a]pyrazine]-2'(3'H)-carboxylate

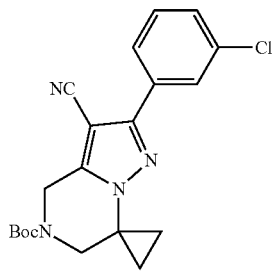 [SMILES: CC(C)(C)OC(=O)N1Cc2c(C#N)c(-c3cccc(Cl)c3)nn2C2(CC2)C1]

To a flask charged with Intermediate A86I (267.4 mg, 0.550 mmol), were added Pd(Ph$_3$P)$_4$ (63.6 mg, 0.055 mmol), dicyanozinc (71.1 mg, 0.606 mmol), and zinc (7.20 mg, 0.110 mmol). The flask was sealed with a septum and the contents were degassed with N$_2$ for 5 min. DMF (2.4 mL) was added and the yellow solution was degassed for an additional 5 min. The reaction mixture was then allowed to heat to 80° C. After 2 h, the reaction mixture was diluted with equal parts water and EtOAc. The organic layer was separated and the aqueous phase was extracted (3×50 mL) with EtOAc. The combined organic layers were washed with brine, dried over sodium sulfate, and concentrated in vacuo. The crude reaction mixture was purified by silica gel chromatography (40 g REDISEP® column, eluting with a gradient from 25-60% EtOAc in hexanes). Fractions containing the product were combined and evaporated to afford Intermediate A86J (0.186 g, 86%) as a white solid. MS(ES): m/z=385.0 [M+H]$^+$. $^1$H NMR (400 MHz, chloroform-d) δ ppm 7.89 (1H, d, J=1.00 Hz), 7.81-7.86 (1H, m), 7.29-7.40 (2H, m), 4.92 (2H, br. s.), 3.84 (2H, s), 1.66-1.71 (2H, m), 1.52 (9H, s), 1.10 (2H, d, J=2.51 Hz).

Intermediate A86K: tert-Butyl 8'-carbamoyl-7'-(3-chlorophenyl)-1'H-spiro[cyclopropane-1,4'-pyrrolo[1,2-a]pyrazine]-2'(3'H)-carboxylate

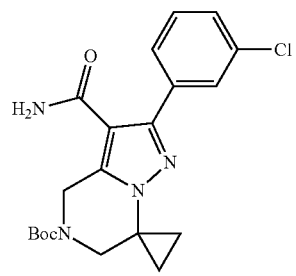 [SMILES: CC(C)(C)OC(=O)N1Cc2c(C(N)=O)c(-c3cccc(Cl)c3)nn2C2(CC2)C1]

To a solution of Intermediate A86J (0.145 g, 0.377 mmol) in DMSO (2 mL) at RT was added dropwise a 5 M aq. solution of KOH (0.38 mL, 1.884 mmol) followed by a 30 wt % solution of H$_2$O$_2$ (0.77 mL, 0.754 mmol). The reaction was allowed to stir at RT for 3 h after which the mixture was partitioned between equal parts EtOAc and water. The organic phase was separated and the aqueous layer was extracted twice more with EtOAc. The combined organic layers were washed with brine, dried over MgSO$_4$, filtered and the filtrate concentrated under reduced pressure to afford a white solid. The crude reaction mixture was purified by silica gel chromatography (40 g REDISEP® column, eluting with a gradient from 75-100% EtOAc in hexanes). Fractions containing the product were combined and evaporated to afford Intermediate A86K (0.117 g, 42%) as a white solid. MS(ES): m/z=403.08 [M+H]$^+$. $^1$H NMR (400 MHz, chloroform-d) δ ppm 8.67 (2H, br. s.), 7.35-7.58 (4H, m), 5.31-6.03 (2H, m), 4.96-5.15 (2H, m), 3.82 (2H, s), 1.59-1.69 (2H, m), 1.42-1.57 (9H, m), 0.94-1.17 (2H, m).

Compound A86: 2'-(3-Chlorophenyl)-N$^5$'-(4-cyanophenyl)-4'H-spiro[cyclopropane-1,7'-pyrazolo[1,5-a]pyrazine]-3',5'(6'H)-dicarboxamide

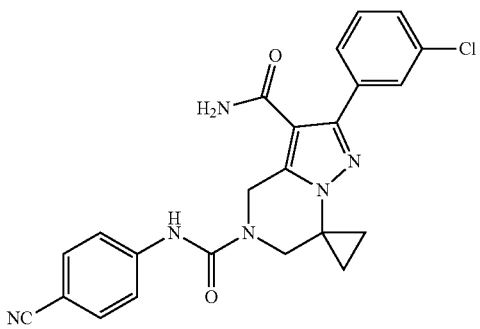 [SMILES: N#Cc1ccc(NC(=O)N2Cc3c(C(N)=O)c(-c4cccc(Cl)c4)nn3C3(CC3)C2)cc1]

Compound A86 was synthesized analogous to Compound A76 by reacting deprotected A86K with 4-isocyanatobenzonitrile. The product was purified by preparative HPLC (0.0224 g, 54%): MS(ES): m/z=447.2 [M+H]$^+$; HPLC Ret. Time 1.80 min and 2.60 min. (Methods H and I respectively); $^1$H NMR (500 MHz, DMSO-d$_6$) δ ppm 9.35 (1H, s), 7.56-7.77 (6H, m), 7.35-7.46 (2H, m), 7.23 (1H, br. s.), 5.03 (2H, s), 3.95-4.06 (2H, m), 1.42-1.53 (2H, m), 1.10-1.19 (2H, m).
Scheme 64
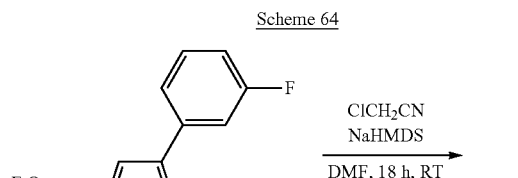
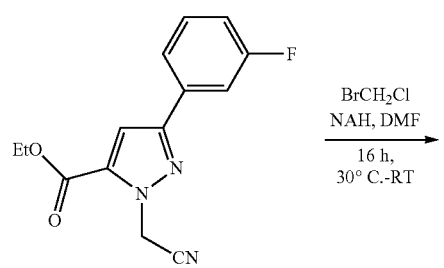
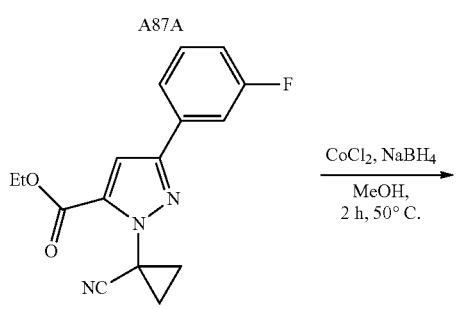
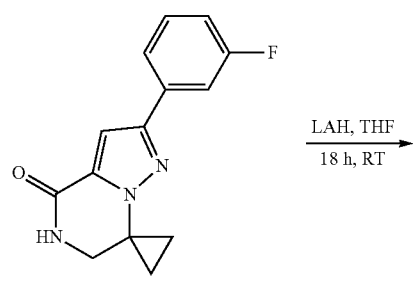
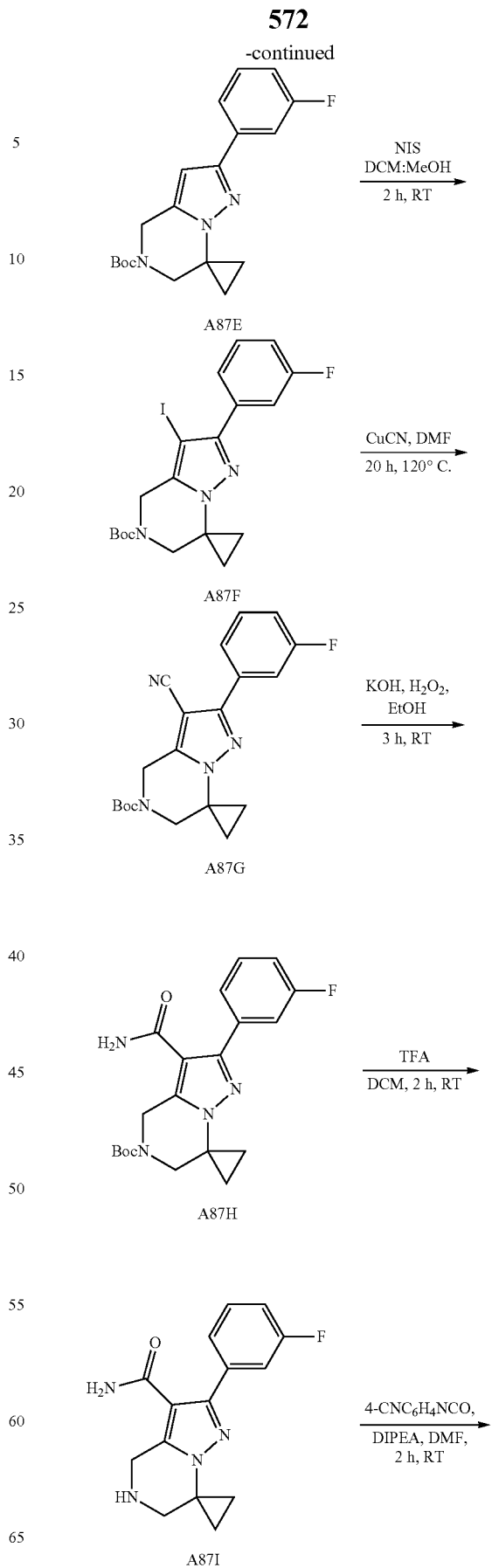

-continued

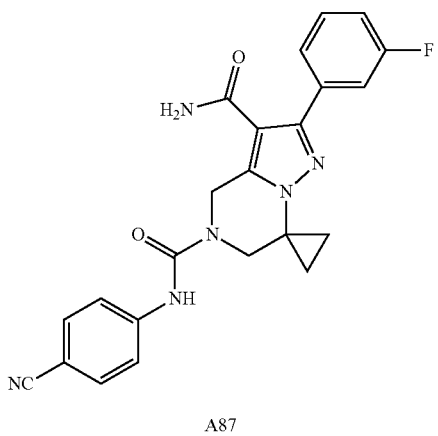 [SMILES: N#Cc1ccc(NC(=O)N2Cc3c(C(N)=O)c(-c4cccc(F)c4)nn3C3(CC3)C2)cc1 ; "A87"]

A87

Intermediate A87A: Ethyl 1-(cyanomethyl)-3-(3-fluorophenyl)-1H-pyrazole-5-carboxylate

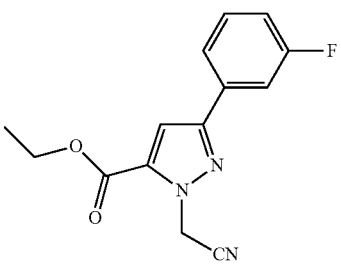 [SMILES: CCOC(=O)c1cc(-c2cccc(F)c2)nn1CC#N]

To an ice-cooled solution of Intermediate 4B (7.0 g, 29.9 mmol) in DMF (45 mL), was added dropwise a solution of LiHMDS (31.4 mL, 31.4 mmol, 1M in THF). The reaction mixture is allowed to stir for 5 min. and the ice bath is subsequently removed. 2-Chloroacetonitrile (2.482 g, 32.9 mmol) was added to the reaction mixture. The reaction was allowed to warm to RT and stirred for 18 h. The reaction was quenched by the addition of 1 mL of a satd. aq. solution of NH$_4$Cl. The reaction was diluted with equal parts water and EtOAc and the resulting mixture was allowed to stir vigorously for 15 min. The organic layer was separated, dried over sodium sulfate, and concentrated in vacuo. The crude reaction mixture was purified by silica gel chromatography (120 g REDISEP® column, eluting with a gradient from 0-40% EtOAc in hexanes). Fractions containing the product were combined and concentrated to afford Intermediate A87A (6.15 g, 75%) as a white solid. MS(ES) m/z=274 [M+H]$^+$.

Intermediate A87B: Ethyl 1-(1-cyanocyclopropyl)-3-(3-fluorophenyl)-1H-pyrazole-5-carboxylate

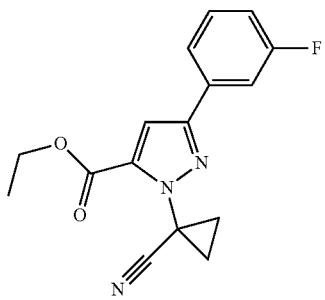 [SMILES: CCOC(=O)c1cc(-c2cccc(F)c2)nn1C1(C#N)CC1]

To an ice-cooled solution of Intermediate A87A (3.75 g, 13.72 mmol) and 1-bromo-2-chloroethane (2.362 g, 16.47 mmol) in DMF (40 mL) was added NaH (1.372 g, 34.3 mmol) (60% dispersion in mineral oil) portionwise. The cloudy solution was allowed to slowly warm to RT and stirred for 16 h. The reaction mixture was quenched by the addition of 10 mL of saturated aq. solution of NH$_4$Cl. The mixture was partitioned in a mixture of water and EtOAc. The organic layer was separated, washed with brine, dried over sodium sulfate, and concentrated in vacuo. The crude orange oil was purified by silica gel chromatography (80 g REDISEP® column, eluting with a gradient from 0-40% EtOAc in hexanes). Fractions containing the product were combined and concentrated to afford Intermediate A87B (0.51 g, 12%) as a yellow solid. MS(ES) m/z=300 [M+H]$^+$.

Intermediate A87C: 2'-(3-Fluorophenyl)-5',6'-dihydro-4'H-spiro[cyclopropane-1,7'-pyrazolo[1,5-a]pyrazin]-4'-one

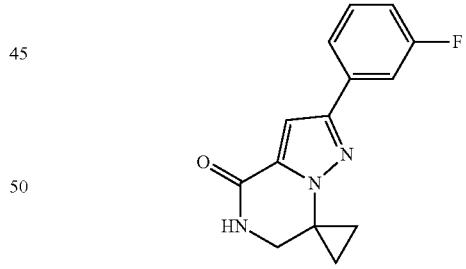

To an ice-cooled solution of Intermediate A87B (0.4 g, 1.336 mmol) and cobalt(II) chloride (0.521 g, 4.01 mmol) in MeOH (50 mL) was slowly added sodium borohydride (0.506 g, 13.36 mmol). The solution instantly turned black with vigorous gas evolution. The reaction was heated to 50° C. for 2 h. The reaction mixture was filtered through CELITE® and the filtrate was concentrated. The crude reaction mixture was purified by silica gel chromatography (24 g REDISEP® column, eluting with a gradient from 0-40% EtOAc in hexanes). Fractions containing the product were combined and evaporated to afford Intermediate A87C (0.16 g, 47%). MS(ES) m/z=258 [M+H]$^+$.

Intermediate A87D: 2'-(3-Fluorophenyl)-5',6'-dihydro-4'H-spiro[cyclopropane-1,7'-pyrazolo[1,5-a]pyrazine]

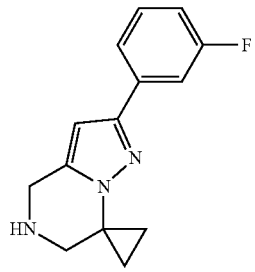 [SMILES: Fc1cccc(-c2cc3n(n2)C2(CC2)CNC3)c1]

To a stirred solution of Intermediate A87C (0.16 g, 0.622 mmol) in THF (10 mL) under an atmosphere of nitrogen at −10° C. was added dropwise a 1.0 M solution of LAH (1.87 mL, 1.87 mmol) in THF. The reaction was allowed to slowly reach RT and stir overnight, and was then heated at 50° C. for 4 h. The reaction was quenched by slow addition of a saturated aq. solution of Rochelle's salt at 0° C. The mixture was diluted with DCM, the organic layer was separated, and the aqueous layer was extracted with DCM (2×100 mL). The combined organic layers were washed with brine, dried (MgSO$_4$) and concentrated to obtain Intermediate A87D (0.14 g, 93% yield) as an off-white solid. The product was used as such without further purification. MS(ES) m/z=244 [M+H]$^+$.

Intermediate A87E: tert-Butyl 2'-(3-fluorophenyl)-4'H-spiro[cyclopropane-1,7'-pyrazolo[1,5-a]pyrazine]-5'(6'H)-carboxylate

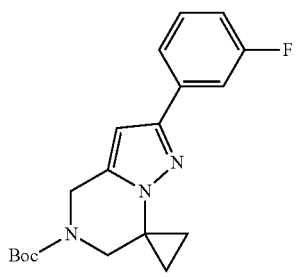

To a solution of Intermediate A87D (0.14 g, 0.575 mmol) in MeOH (5 mL) were added TEA (0.289 mL, 2.072 mmol) and di-tert-butyl dicarbonate (0.188 g, 0.863 mmol). The solution was allowed to stir overnight at RT. It was concentrated and purified by silica gel chromatography (24 g REDISEP® column, eluting with a gradient from 0-30% EtOAc in hexanes). Fractions containing the product were combined and concentrated to afford Intermediate A87E (0.156 g, 79% yield). MS(ES) m/z=344 [M+H]$^+$.

Intermediate A87F: tert-Butyl 2'-(3-fluorophenyl)-3'-iodo-4'H-spiro[cyclopropane-1,7'-pyrazolo[1,5-a]pyrazine]-5'(6'H)-carboxylate

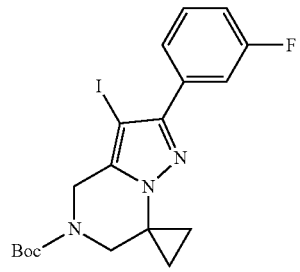 [SMILES: CC(C)(C)OC(=O)N1Cc2c(I)c(-c3cccc(F)c3)nn2C2(CC2)C1]

To a solution of Intermediate A87E (0.156 g, 0.454 mmol) in DCM (5 mL) and MeOH (1.25 mL) was added NIS (0.307 g, 1.363 mmol) and the reaction mixture was allowed to stir at RT. After stirring for 90 min., the solution was concentrated in vacuo affording a red oil which was purified by silica gel chromatography (24 g REDISEP® column, eluting with a gradient from 0-30% EtOAc in hexanes). Fractions containing the product were combined and concentrated to afford Intermediate A87F (0.14 g, 66% yield). MS(ES) m/z=470 [M+H]$^+$.

Intermediate A87G: tert-Butyl 3'-cyano-2'-(3-fluorophenyl)-4'H-spiro[cyclopropane-1,7'-pyrazolo[1,5-a]pyrazine]-5'(6'H)-carboxylate

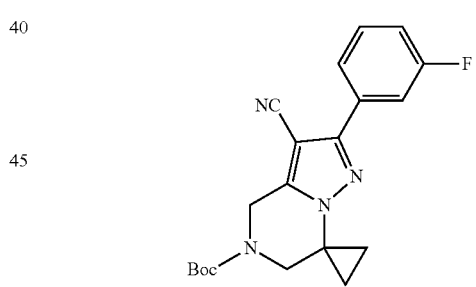

To a solution of Intermediate A87F (0.14 g, 0.298 mmol) in DMF (10 mL) was added copper(I) cyanide (0.067 g, 0.746 mmol). The reaction mixture was heated in a sealed tube at 120 OC for 16 h. The reaction mixture was cooled to RT and filtered. The filter cake was washed with EtOAc and the combined filtrate was concentrated. The residue was purified by silica gel chromatography (24 g REDISEP® column, eluting with a gradient from 0-40% EtOAc in hexanes). Fractions containing the product were combined and concentrated to afford Intermediate A87G (0.091 g, 83% yield). MS(ES) m/z=369 [M+H]$^+$.

Intermediate A87H: tert-Butyl 3'-carbamoyl-2'-(3-fluorophenyl)-4'H-spiro[cyclopropane-1,7'-pyrazolo[1,5-a]pyrazine]-5'(6'H)-carboxylate

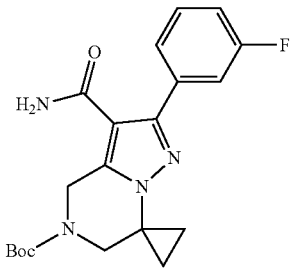 [SMILES: CC(C)(C)OC(=O)N1Cc2c(C(N)=O)c(-c3cccc(F)c3)nn2C2(CC2)C1]

To a solution of Intermediate A87G (0.091 g, 0.247 mmol) in EtOH (20 mL) at RT was added KOH (0.247 mL, 1.235 mmol). The reaction mixture was cooled to 0° C. prior to the dropwise addition of hydrogen peroxide (0.505 mL, 4.94 mmol, 30 wt %). The reaction mixture was allowed to warm to RT and stir overnight, then concentrated and the residue dissolved in EtOAc. The organic phase was washed with water and brine, and was then dried (MgSO$_4$) and concentrated. The residue was purified by silica gel chromatography (12 g REDISEP® column, eluting with a gradient from 0-20% MeOH in DCM). The required fractions were concentrated to obtain Intermediate A87H (0.075 g, 79% yield). MS(ES) m/z=387 [M+H]$^+$.

Intermediate A87I: 2'-(3-Fluorophenyl)-5',6'-dihydro-4'H-spiro[cyclopropane-1,7'-pyrazolo[1,5-a]pyrazine]-3'-carboxamide, TFA

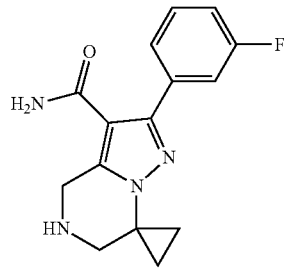 [SMILES: NC(=O)c1c(-c2cccc(F)c2)nn2c1CNCC21CC1]

To a solution of intermediate A87H (0.085 g, 0.220 mmol) in DCM (5 mL) at RT was added TFA (0.085 mL, 1.100 mmol) and the mixture was stirred overnight. The reaction mixture was concentrated to obtain the TFA salt of intermediate A87I (0.063 g, 0.220 mmol, >98% yield). The yield was assumed to be quantitative and the crude product was used as such without purification. MS(ES) m/z=287 [M+H]$^+$.

Compound A87: N$^{5'}$-(4-Cyanophenyl)-2'-(3-fluorophenyl)-4'H-spiro[cyclopropane-1,7'-pyrazolo[1,5-a]pyrazine]-3',5'(6'H)-dicarboxamide

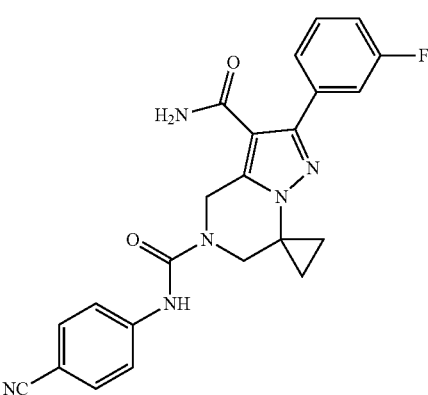 [SMILES: N#Cc1ccc(NC(=O)N2Cc3c(C(N)=O)c(-c4cccc(F)c4)nn3C3(CC3)C2)cc1]

To a solution of Intermediate A87I (0.055 g, 0.192 mmol) in DMF (2 mL) at RT under nitrogen were added DIPEA (0.168 mL, 0.961 mmol) and 2-isocyanato-2-methylpropane (0.055 g, 0.384 mmol). The reaction mixture was stirred for 1 h. The crude material was purified via preparative HPLC. Fractions containing the desired product were combined and evaporated to obtain Compound A87 (8.4 mg, 10% yield). MS(ES) m/z=431.2 [M+H]$^+$; Ret. time=1.70 and 2.51 min. (Methods H and I respectively); $^1$H NMR (500 MHz, DMSO-d$_6$) δ ppm 9.36 (s, 1H), 7.78-7.64 (m, 4H), 7.54-7.34 (m, 4H), 7.20 (t, J=7.0 Hz, 2H), 5.04 (s, 2H), 4.02 (s, 2H), 1.53-1.43 (m, 2H), 1.21-1.10 (m, 2H), 1.21-1.10 (m, 2H).

Scheme 65

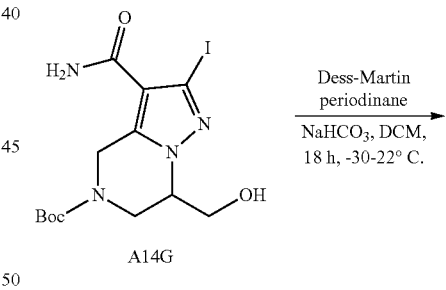

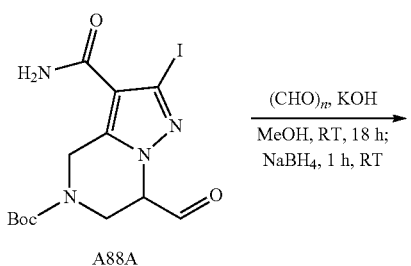

-continued

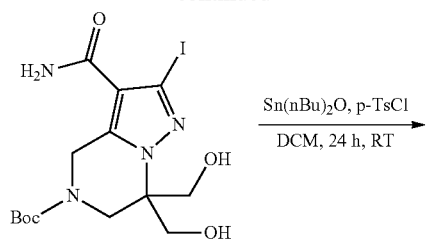

A88B

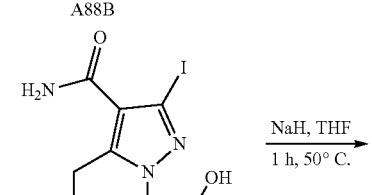

A88C

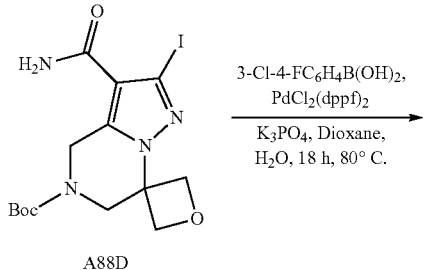

A88D

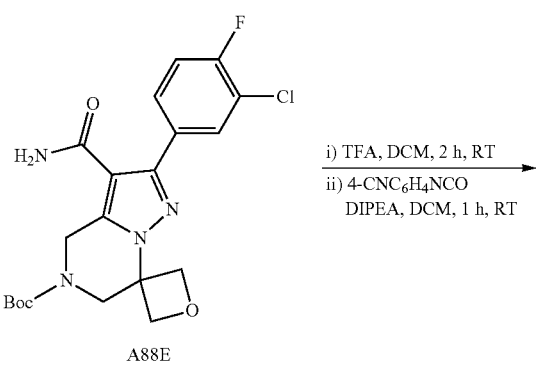

A88E

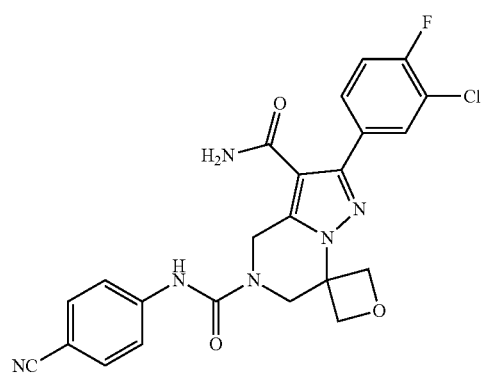

A88

Intermediate A88A: tert-Butyl 3-carbamoyl-7-formyl-2-iodo-6,7-dihydropyrazolo[1,5-a]pyrazine-5(4H)-carboxylate

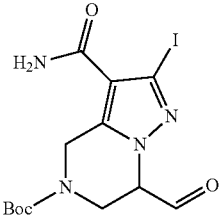

A suspension of Intermediate A14G (0.421 g, 0.997 mmol) and NaHCO$_3$ (84 mg, 0.997 mmol) in anhydrous DCM (5.0 mL) was allowed to cool to −30° C. for several minutes prior to the addition of Dess-Martin periodinane (0.508 g, 1.197 mmol). The reaction was maintained at −30° C. for 2 h after which the temperature was allowed to gradually reach 22° C. After having stirred for 18 h, the reaction was diluted with DCM and a saturated aq. solution of NaHCO$_3$. The organic layer was separated and the aqueous phase is extracted with DCM (3×10 mL). The combined organic layers were washed with brine, dried over anhydrous MgSO$_4$, filtered and the filtrate concentrated under reduced pressure. The crude reaction mixture was purified by silica gel chromatography (40 g REDISEP® column, eluting with a gradient from 50-100% EtOAc in hexanes). Fractions containing the product were combined and evaporated to afford Intermediate A88A (0.200 g, 47%) as a white foam. MS(ES): m/z=364.9 [M+H$_2$O-OtBu]$^+$. $^1$H NMR (400 MHz, chloroform-d) δ ppm 9.62-9.78 (1H, m), 5.81-6.83 (2H, m), 4.49-5.55 (4H, m), 3.58 (1H, d, J=11.80 Hz), 1.39-1.50 (9H, m).

Intermediate A88B: tert-Butyl 3-carbamoyl-7,7-bis(hydroxymethyl)-2-iodo-6,7-dihydropyrazolo[1,5-a]pyrazine-5(4H)-carboxylate

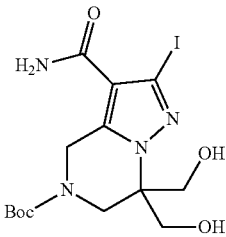 [SMILES: CC(C)(C)OC(=O)N1Cc2c(C(N)=O)c(I)nn2C(CO)(CO)C1]

To a solution of Intermediate A88A (0.200 g, 0.476 mmol) in MeOH (4.0 mL) was added dropwise at RT an 85% aq. solution of KOH (2.380 mL, 4.76 mmol) and a 37% w/w aq. solution of formaldehyde (0.886 mL, 11.90 mmol) in MeOH (1 mL). The reaction was allowed to stir at RT for 18 h after which the mixture was partitioned between equal parts EtOAc and water. The organic phase was separated and the aqueous layer was extracted twice more. The organic layers were combined, dried over sodium sulfate, and concentrated to provide the crude P3-hydroxy aldehyde intermediate. The crude material was dissolved in MeOH (2.0 mL) and treated with NaBH$_4$ (0.036 g, 0.952 mmol). After stirring at RT for 1 h, the reaction mixture was partitioned between equal parts water and EtOAc. The organic layer was separated and the aqueous phase was extracted twice more with EtOAc. The combined organic layers were dried over sodium sulfate, filtered, and concentrated to provide a crude colorless oil. The crude product was purified by silica gel chromatography (40 g REDISEP® column, eluting with a gradient from 50-100% EtOAc in hexanes). Fractions containing the product were combined and evaporated to afford Intermediate A88B (0.096 g, 45%) as a white solid. MS(ES): m/z=397.0 [M+H$_2$O-OtBu]$^+$. $^1$H NMR (400 MHz, chloroform-d) δ ppm 6.29-6.87 (1H, m), 5.84-6.34 (1H, m), 4.85-5.03 (2H, m), 3.72-3.97 (5H, m), 3.58 (2H, br. s.), 1.42-1.52 (9H, m).

Intermediate A88C: tert-Butyl 3-carbamoyl-7-(hydroxymethyl)-2-iodo-7-((Tosyloxy)methyl)-6,7-dihydropyrazolo[1,5-a]pyrazine-5(4H)-carboxylate

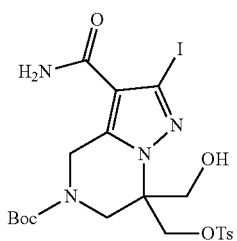 [SMILES: Cc1ccc(S(=O)(=O)OCC2(CO)CN(C(=O)OC(C)(C)C)Cc3c(C(N)=O)c(I)nn32)cc1]

To a stirring solution of Intermediate A88B (0.095 g, 0.210 mmol) and dibutyltin oxide (0.0261 g, 0.105 mmol) in DCM (1.0 mL) at RT was added triethylamine (0.029 mL, 0.210 mmol) followed by p-toluenesulfonyl chloride (0.040 g, 0.210 mmol). After 24 h, the reaction mass was filtered and concentrated. The crude reaction mixture was purified by silica gel chromatography (24 g REDISEP® column, eluting with a gradient from 50-100% EtOAc in hexanes). Fractions containing the product were combined and evaporated to afford Intermediate A88C (0.033 g, 26%) as a white foam. MS(ES): m/z=550.9 [M+H$_2$O-OtBu]$^+$.

Intermediate A88D: tert-Butyl 3'-carbamoyl-2'-iodo-4'H-spiro[oxetane-3,7'-pyrazolo[1,5-a]pyrazine-5'(6'H)-carboxylate

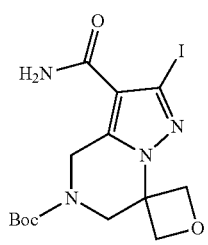

To an ice-cooled solution of Intermediate A88C (0.033 g, 0.054 mmol) in THF (1.0 mL) was added NaH (0.005 g, 0.136 mmol, 60% dispersion in mineral oil). The reaction was allowed to stir at 0° C. for 30 min. prior to heating the mixture to 50° C. for 1 h. The reaction was allowed to cool to RT, diluted with EtOAc, and quenched with a saturated aq. solution of NH$_4$Cl. The organic layer was separated and the aqueous phase was extracted twice with EtOAc. The combined organic phases were dried over sodium sulfate and concentrated under reduced pressure to afford an oil which was purified by silica gel chromatography (12 g REDISEP® column, eluting with a gradient from 50-100% EtOAc in hexanes). Fractions containing the product were combined and evaporated to afford Intermediate A88D (0.018 g, 76%) as a white solid. MS(ES): m/z=379.0 [M+H$_2$O-OtBu]$^+$. $^1$H NMR (400 MHz, chloroform-d) δ ppm 6.43-6.90 (1H, m), 5.38-5.70 (1H, m), 5.19-5.29 (2H, m), 4.87-4.99 (2H, m), 4.61 (2H, d, J=6.78 Hz), 4.07-4.23 (2H, m), 1.41-1.55 (9H, m).

Intermediate A88E: tert-Butyl 3'-carbamoyl-2'-(3-chloro-4-fluorophenyl)-4'H-spiro[oxetane-3,7'-pyrazolo[1,5-a]pyrazine-5'(6'H)-carboxylate

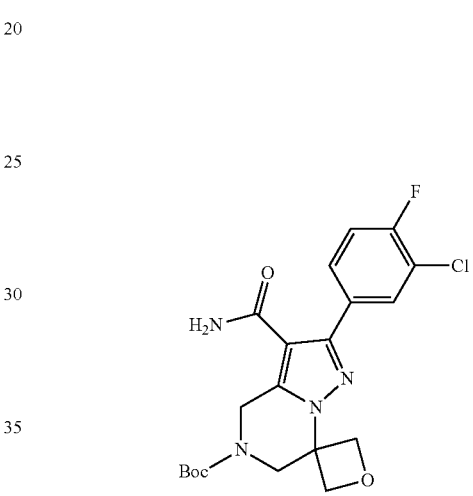

To a pressure vial equipped with a stir bar and charged with Intermediate A88D (0.018 g, 0.041 mmol) were added (3-chloro-4-fluorophenyl)boronic acid (10.8 mg, 0.062 mmol) and PdCl$_2$(dppf) (3.03 mg, 4.15 μmol). The reaction vial was capped and purged with dry N$_2$ for 5 minutes. Anhydrous 1,4-dioxane (1.0 mL) and a 2M aq. solution of K$_3$PO$_4$ (0.062 mL, 0.124 mmol) were added. The resulting red slurry was allowed to heat to 80° C. for 18 h under a N$_2$ atmosphere. The reaction was allowed to cool to RT and quenched by the addition of 50 mL of water followed by dilution with DCM. The organic phase was separated and the aqueous phase was extracted twice more with additional DCM. The combined organic layers were washed with a brine solution, dried over sodium sulfate, and concentrated in vacuo to provide a colorless oil which was purified by silica gel chromatography (12 g REDISEP® column, eluting with a gradient of 30-100% EtOAc in hexanes). Fractions containing the product were combined and evaporated to afford Intermediate A88E (0.017 g, 84%) as a white foam. MS(ES): m/z=437.0 [M+H]$^+$.

Compound A88: 2'-(3-Chloro-4-fluorophenyl)-N⁵'-(4-cyanophenyl)-4'H-spiro[oxetane-3,7'-pyrazolo[1,5-a]pyrazine]-3',5'(6'H)-dicarboxamide

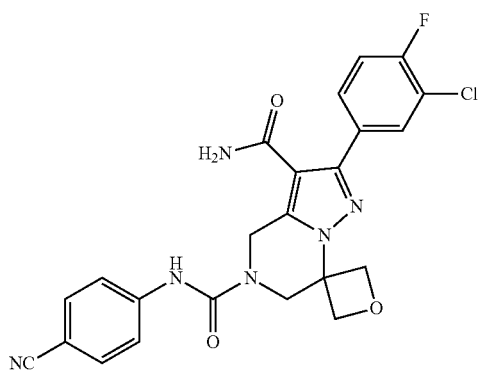 [SMILES: N#Cc1ccc(NC(=O)N2Cc3c(C(N)=O)c(-c4ccc(F)c(Cl)c4)nn3C3(COC3)C2)cc1]

Compound A88 was synthesized analogous to Compound A76 by reacting deprotected A88E with 4-isocyanatobenzonitrile. The product was purified by preparative HPLC. MS(ES): m/z=480.9 [M+H]⁺; HPLC Ret. Time 1.58 min and 2.82 min. (Methods H and I respectively); $^1$H NMR (500 MHz, DMSO-$d_6$) δ ppm 7.92 (1H, d, J=7.34 Hz), 7.63-7.79 (5H, m), 7.51 (1H, t, J=8.99 Hz), 7.23-7.47 (2H, m), 5.04-5.14 (2H, m), 4.86-4.99 (2H, m), 4.64-4.73 (2H, m), 4.26-4.44 (2H, m).

Scheme 66

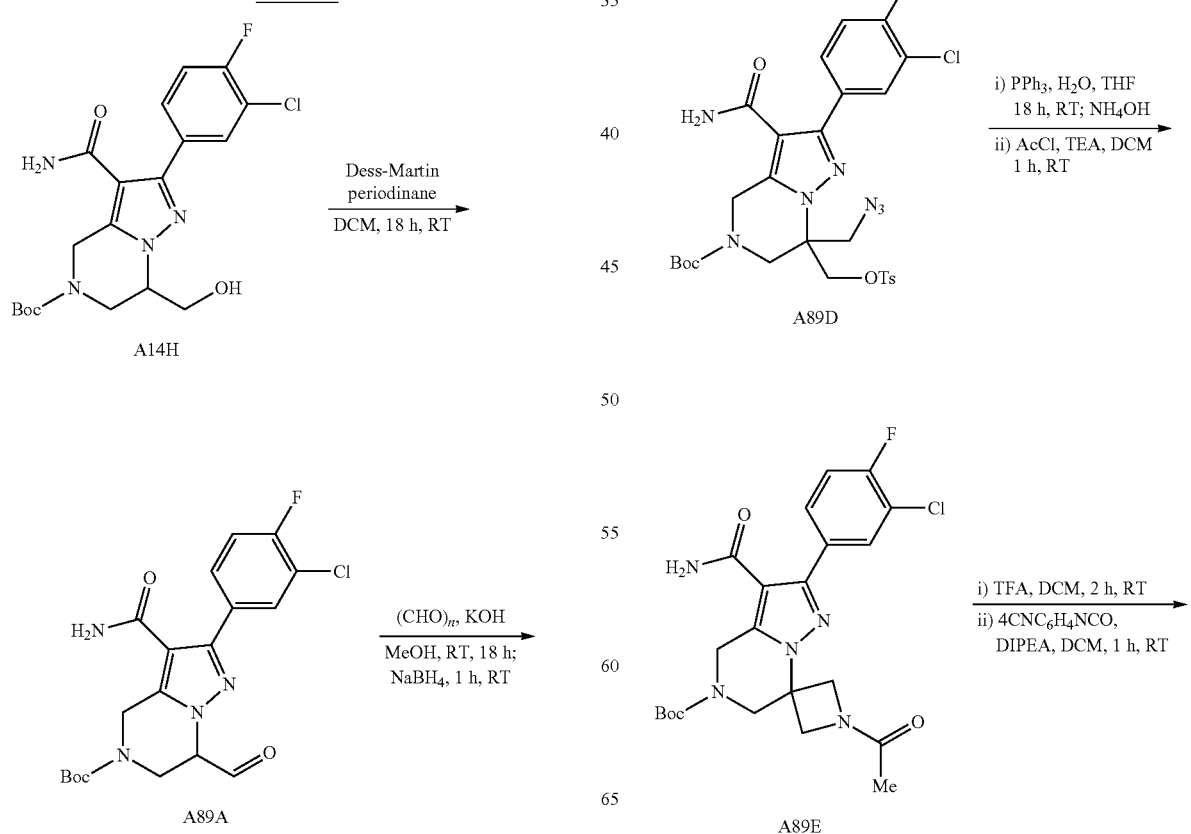

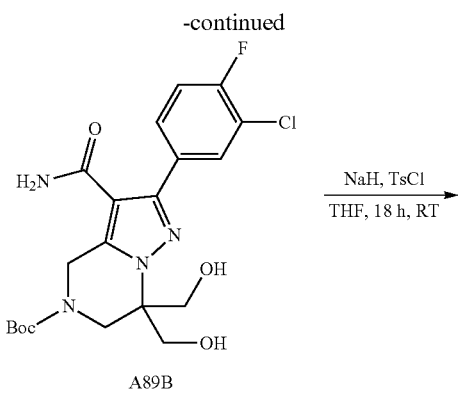

585
-continued

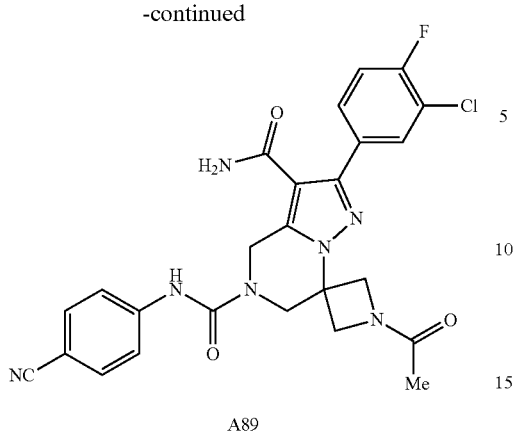

A89

Intermediate A89A: tert-Butyl 3-carbamoyl-2-(3-chloro-4-fluorophenyl)-7,7-bis(hydroxymethyl)-6,7-dihydropyrazolo[1,5-a]pyrazine-5(4H)-carboxylate

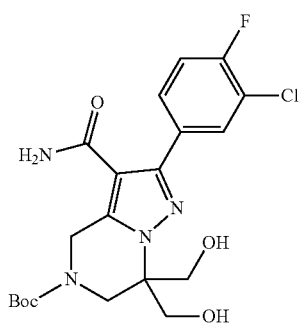 [SMILES: CC(C)(C)OC(=O)N1Cc2c(C(N)=O)c(-c3ccc(F)c(Cl)c3)nn2C(CO)(CO)C1]

To a solution of Intermediate A14H (0.425 g, 1.005 mmol) in MeOH (5.0 mL) at RT was added dropwise an 85% aq. solution of KOH (5.03 mL, 10.05 mmol) and a 37% w/w aq. solution of formaldehyde (1.871 mL, 25.1 mmol) in MeOH (1 mL). The reaction was allowed to stir at RT for 18 h after which the mixture was partitioned between equal parts EtOAc and water. The organic phase was separated and the aqueous layer was extracted twice more. The combined organic layers were dried over sodium sulfate, and concentrated to provide the crude P3-hydroxy aldehyde intermediate. The crude material was dissolved in MeOH (2.0 mL) and treated with NaBH$_4$ (0.076 g, 2.010 mmol). After stirring at RT for 1 h, the reaction mixture was partitioned in equal parts water and EtOAc. The organic layer was separated and the aqueous phase was extracted twice more with EtOAc. The combined organic layers were dried over sodium sulfate, filtered, and concentrated to provide a crude colorless oil. The crude product was purified by silica gel chromatography (40 g REDISEP® column, eluting with a gradient from 60-100% EtOAc in hexanes). Fractions containing the product were combined and evaporated to afford Intermediate A89A (0.210 g, 46%) as a white solid. MS(ES): m/z=399.0 [M+H$_2$O-OtBu]$^+$. $^1$H NMR (400 MHz, chloroform-d) δ ppm 7.64 (1H, ddd, J=7.84, 7.09, 2.13 Hz), 7.40-7.52 (1H, m), 7.23-7.32 (2H, m), 5.33-5.61 (1H, m), 4.97 (2H, s), 4.70-4.82 (1H, m), 3.70-4.06 (6H, m), 3.26-3.52 (2H, m), 1.50-1.56 (9H, m).

586

Intermediate A89B: tert-Butyl 3-carbamoyl-2-(3-chloro-4-fluorophenyl)-7,7-bis((tosyloxy)methyl)-6,7-dihydropyrazolo[1,5-a]pyrazine-5(4H)-carboxylate

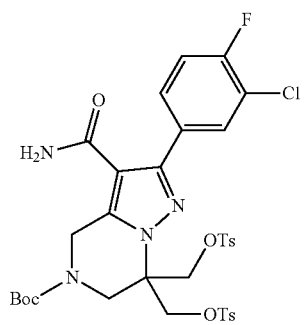 [SMILES: Cc1ccc(S(=O)(=O)OCC2(COS(=O)(=O)c3ccc(C)cc3)CN(C(=O)OC(C)(C)C)Cc3c(C(N)=O)c(-c4ccc(F)c(Cl)c4)nn32)cc1]

To an ice-cooled solution of Intermediate A89A (0.210 g, 0.462 mmol) in THF (5.0 mL) was added NaH (0.0739 g, 0.210 mmol, 60% dispersion in mineral oil) portionwise. After 10 minutes, a solution of p-toluenesulfonyl chloride (0.264 g, 1.385 mmol) in THF was added dropwise at 0° C. The reaction was then allowed to warm to 22° C. After 18 h, the reaction was quenched at 0° C. with a saturated aq. solution of NH$_4$Cl and diluted with EtOAc. The organic layer was separated and the aqueous phase was extracted twice more with EtOAc. The combined organic layers were dried over sodium sulfate, filtered, and concentrated to afford a colorless oil which was purified by silica gel chromatography (40 g REDISEP® column, eluting with a gradient from 40-100% EtOAc in hexanes). Fractions containing the product were combined and evaporated to afford Intermediate A89B (0.183 g, 52%) as a white solid. MS(ES): m/z=707.2 [M+H$_2$O-OtBu]$^+$.

Intermediate A89C: tert-Butyl 7-(azidomethyl)-3-carbamoyl-2-(3-chloro-4-fluorophenyl)-7-((Tosyloxy)methyl)-6,7-dihydropyrazolo[1,5-a]pyrazine-5(4H)-carboxylate

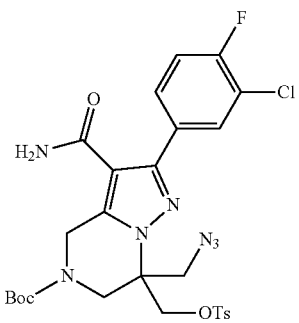 [SMILES: Cc1ccc(S(=O)(=O)OCC2(CN=[N+]=[N-])CN(C(=O)OC(C)(C)C)Cc3c(C(N)=O)c(-c4ccc(F)c(Cl)c4)nn32)cc1]

To a solution of Intermediate A89B (0.092 g, 0.121 mmol) in DMF (2.0 mL) was added sodium azide (9.40 mg, 0.145 mmol). The reaction was allowed to heat at 80° C. for 18 h followed by 20 h at 100° C. The mixture was allowed to cool to RT and partitioned between equal parts EtOAc and water. The aqueous layer was extracted twice more with EtOAc and the combined organic layers are washed with brine, dried over sodium sulfate, filtered, and concentrated to afford the crude material as a colorless oil which was purified by silica gel chromatography (40 g REDISEP® column, eluting with a gradient from 0-30% EtOAc in hexanes). Fractions containing the product were combined and evaporated to afford Intermediate A89C (0.029 g, 38%) as a white solid. MS(ES): m/z=578.1 [M+H$_2$O-OtBu]$^+$.

Intermediate A89D: tert-Butyl 1-acetyl-3'-carbamoyl-2'-(3-chloro-4-fluorophenyl)-4'H-spiro[azetidine-3,7'-pyrazolo[1,5-a]pyrazine-5'(6'H)-carboxylate

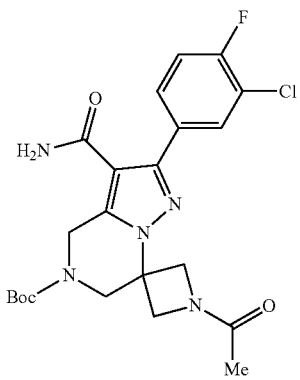 [SMILES: CC(=O)N1CC2(C1)CN(C(=O)OC(C)(C)C)Cc1c(C(N)=O)c(-c3ccc(F)c(Cl)c3)nn12]

To a solution of Intermediate A89C (29 mg, 0.046 mmol) in THF were added triphenylphosphine (13.20 mg, 0.050 mmol) and water (0.824 µL, 0.046 mmol). After stirring for 18 h at RT there was complete conversion to the iminophosphorane. The hydrolysis of the iminophosphorane is accomplished by treating the crude reaction mixture with NH$_4$OH (0.030 mL, 0.229 mmol, 40 wt %) at RT. After stirring for 2 h, the reaction mixture was allowed to heat to 40° C. for 2 h, after which the volatiles were removed under reduced pressure. The Intermediate crude azetidine was then acylated without purification. The crude oil was dissolved in DCM (0.50 mL) and treated with TEA (0.024 mL, 0.174 mmol) and a 1.0 M solution of acetyl chloride (0.065 mL, 0.065 mmol) in DCM. The reaction was allowed to stir at RT for 1 h after which the reaction mixture was diluted with equal parts EtOAc and water and the aqueous phase is extracted twice more with EtOAc. The combined organic layers were dried over sodium sulfate and concentrated under reduced pressure. The crude reaction mixture is purified by silica gel chromatography (24 g REDISEP® column, eluting with a gradient from 20-90% EtOAc in hexanes). Fractions containing the product were combined and evaporated to afford Intermediate A89D (0.0125 g, 48% over 3 steps) as a white solid. MS(ES): m/z=422.1 [M+H$_2$O-OtBu]$^+$.

Compound A89: 1-Acetyl-2'-(3-chloro-4-fluorophenyl)-N$^5$'-(4-cyanophenyl)-4'H-spiro[azetidine-3,7'-pyrazolo[1,5-a]pyrazine]-3',5'(6'H)-dicarboxamide

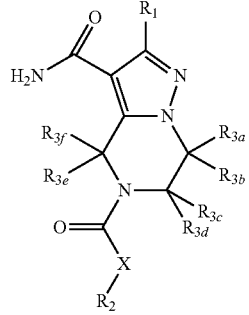

Compound A89 was synthesized analogous to Compound A76 by reacting deprotected A89D with 2-isocyanato-2-methylpropane. The product was purified by preparative HPLC. MS(ES): m/z=522.5 [M+H]$^+$; HPLC Ret. Time 1.31 min and 2.22 min. (Methods H and I respectively); $^1$H NMR (500 MHz, DMSO-d$_6$) δ ppm 7.85-7.93 (1H, m), 7.63-7.78 (5H, m), 7.39-7.56 (2H, m), 7.21-7.38 (1H, m), 4.89-5.03 (2H, m), 4.55-4.64 (1H, m), 4.39 (1H, d, J=8.80 Hz), 4.20-4.34 (3H, m), 4.09-4.18 (1H, m), 1.88 (3H, s).

What is claimed is:
1. A compound according to Formula (I):

$$\text{(I)}$$

or a pharmaceutically acceptable salt thereof, wherein:
X is independently O or NH;
R$_1$ is independently carbocyclyl substituted with 1-5 R$_5$, or heterocyclyl comprising carbon atoms and 1 to 3 heteroatoms selected from N, NR$_4$, O, S, and substituted with 1-5 R$_5$;
R$_2$ is independently aryl substituted with 1-8 R$_7$ or heteroaryl comprising carbon atoms and 1 to 4 heteroatoms selected from N, NR$_6$, O, S, and substituted with 1-8 R$_7$;
R$_{3a}$, R$_{3b}$, R$_{3c}$, R$_{3d}$, R$_{3e}$ and R$_{3f}$ are independently H, CN, C$_{1-4}$alkyl substituted with 1-3 R$_8$, —C(=O)OR$_b$, —C(=O)NR$_a$R$_a$, —C(=O)R$_b$, —NR$_a$C(=O)R$_b$, —NR$_a$C(=O)OR$_b$, —(CH$_2$)$_r$-carbocyclyl substituted with 1-3 R$_8$, or —(CH$_2$)$_r$-heterocyclyl substituted with 1-3 R$_8$;
alternatively, R$_{3a}$ and R$_{3b}$, or R$_{3c}$ and R$_{3d}$, or R$_{3e}$ and R$_{3f}$, together with the carbon atom to which they are both attached form a spiral carbocyclic or heterocyclic ring comprising carbon atoms and 1 to 4 heteroatoms selected from N, O, S, each substituted with 1-5 $R_8$;

alternatively, $R_{3a}$ and $R_{3c}$ or $R_{3b}$ and $R_{3d}$ together form a heterocyclic ring comprising carbon atoms and 1 to 4 heteroatoms selected from N, O, S, and substituted with 1-5 $R_8$;

$R_4$ is independently H, $C_{1-4}$ alkyl substituted with 0-3 $R_e$, —$(CH_2)_r$CN, —$(CH_2)_r$OR$_b$, $(CH_2)_r$S(O)$_p$R$_c$, —$(CH_2)_r$C(=O)R$_b$, —$(CH_2)_r$NR$_a$R$_a$, —$(CH_2)_r$C(=O)NR$_a$R$_a$, —$(CH_2)_r$NR$_a$C(=O)R$_b$, —$(CH_2)_r$NR$_a$C(=O)OR$_b$, —$(CH_2)_r$OC(=O)NR$_a$R$_a$, —$(CH_2)_r$NR$_a$C(=O)NR$_a$R$_a$, —$(CH_2)_r$C(=O)OR$_b$, —$(CH_2)_r$S(O)$_2$NR$_a$R$_a$, —$(CH_2)_r$NR$_a$S(O)$_2$NR$_a$R$_a$, —$(CH_2)_r$NR$_a$S(O)$_2$R$_c$, $(CH_2)_r$-carbocyclyl substituted with 0-3 $R_e$, or —$(CH_2)_r$-heterocyclyl substituted with 0-3 $R_e$;

$R_5$, at each occurrence, is independently H, $C_{1-4}$ alkyl substituted with 0-3 $R_e$, F, Cl, Br, =O, CN, NO$_2$, —OR$_b$, —$(CH_2)_r$CN, —$(CH_2)_r$OR$_b$, $(CH_2)_r$S(O)$_p$R$_c$, —$(CH_2)_r$C(=O)R$_b$, —$(CH_2)_r$NR$_a$R$_a$, —$(CH_2)_r$C(=O)NR$_a$R$_a$, —$(CH_2)_r$NR$_a$C(=O)R$_b$, —$(CH_2)_r$NR$_a$C(=O)OR$_b$, —$(CH_2)_r$OC(=O)NR$_a$R$_a$, —$(CH_2)_r$NR$_a$C(=O)NR$_a$R$_a$, —$(CH_2)_r$C(=O)OR$_b$, —$(CH_2)_r$S(O)$_2$NR$_a$R$_a$, —$(CH_2)_r$NR$_a$S(O)$_2$NR$_a$R$_a$, —$(CH_2)_r$NR$_a$S(O)$_2$R$_c$, $(CH_2)_r$-carbocyclyl substituted with 0-3 $R_e$, or —$(CH_2)_r$-heterocyclyl substituted with 0-3 $R_e$;

$R_6$ is independently H, —C(=O)R$_b$, —CO(=O)R$_b$, —S(O)$_p$R$_c$, $C_{1-6}$ alkyl substituted with 0-5 $R_e$, —$(CH_2)_r$—C$_{3-6}$carbocyclyl substituted with 0-5 $R_e$, or —$(CH_2)_r$-heterocyclyl substituted with 0-5 $R_e$;

$R_7$, at each occurrence, is independently H, F, Cl, Br, —$(CR_dR_d)_r$CN, NO$_2$, —$(CR_dR_d)_r$OR$_b$, —S(O)$_p$R$_c$, —C(=O)R$_b$, —$(CR_dR_d)_r$NR$_a$R$_a$, —$(CR_dR_d)_r$C(=O)NR$_a$R$_a$, —NR$_a$C(=O)R$_b$, —NR$_a$C(=O)OR$_b$, —OC(=O)NR$_a$R$_a$, —NR$_a$C(=O)NR$_a$R$_a$, —$(CR_dR_d)_r$C(=O)OR$_b$, —S(O)$_2$NR$_a$R$_a$, —NR$_a$S(O)$_2$NR$_a$R$_a$, —NR$_a$S(O)$_2$R$_e$, $C_{1-6}$ alkyl substituted with 0-5 $R_e$, —$(CR_dR_d)_r$—C$_{3-6}$carbocyclyl substituted with 0-5 $R_e$, or —$(CR_dR_d)_r$-heterocyclyl substituted with 0-5 $R_e$;

$R_8$, at each occurrence, is independently H, F, Cl, Br, CN, $C_{1-6}$ alkyl substituted with 0-5 $R_e$, $C_{2-6}$ alkenyl, $C_{2-6}$ alkynyl, —$(CH_2)_r$—C$_{3-6}$ cycloalkyl substituted with 0-5 $R_e$, —$(CH_2)_r$-aryl substituted with 0-5 $R_e$, —$(CH_2)_r$-heterocyclyl substituted with 0-5 $R_e$, CO$_2$H, —$(CH_2)_r$OR$_b$, or —$(CH_2)_r$NR$_a$R$_a$;

$R_a$, at each occurrence, is independently H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—C$_{3-10}$carbocyclyl substituted with 0-5 $R_e$, or —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—C$_{3-10}$carbocyclyl substituted with 0-5 $R_e$, or —$(CH_2)_r$-heterocyclyl substituted with 0-5 $R_e$;

$R_c$, at each occurrence, is independently $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, or heterocyclyl;

$R_d$, at each occurrence, is independently H or $C_{1-4}$alkyl substituted with 0-5 $R_e$;

$R_e$, at each occurrence, is independently F, Cl, Br, CN, NO$_2$, =O, $C_{1-6}$ alkyl substituted with 0-5 $R_f$, $C_{2-6}$ alkenyl, $C_{2-6}$ alkynyl, —$(CH_2)_r$—C$_{3-6}$ cycloalkyl, —$(CH_2)_r$-aryl, —$(CH_2)_r$-heterocyclyl, CO$_2$H, —$(CH_2)_r$ OR$_f$, SR$_f$, or —$(CH_2)_r$NR$_f$R$_f$;

$R_f$, at each occurrence, is independently H, $C_{1-5}$ alkyl optionally substituted with F, Cl, Br, $C_{3-6}$ cycloalkyl, or phenyl, or $R_f$ and $R_f$ together with the nitrogen atom to which they are both attached form a heterocyclic ring optionally substituted with $C_{1-4}$alkyl;

p, at each occurrence, is independently zero, 1, or 2; and
r, at each occurrence, is independently zero, 1, 2, 3, or 4.

2. The compound according to claim 1, having Formula (II):

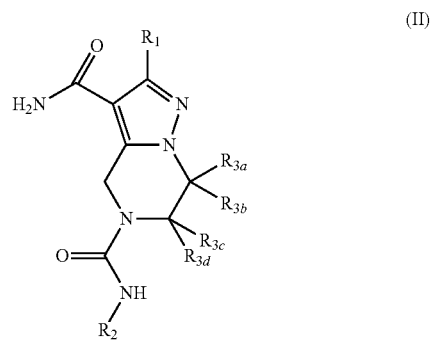

or a pharmaceutically acceptable salt thereof, wherein:

$R_1$ is independently aryl substituted with 1-4 $R_5$, or 5- to 12-membered heteroaryl comprising carbon atoms and 1 to 3 heteroatoms selected from N, NR$_4$, O, S, and substituted with 1-4 $R_5$;

$R_2$ is independently aryl substituted with 1-8 $R_7$ or heteroaryl comprising carbon atoms and 1 to 4 heteroatoms selected from N, NR$_6$, O, S, and substituted with 1-8 $R_7$;

$R_{3a}$, $R_{3b}$, $R_{6c}$, and $R_{3d}$ are independently H, CN, $C_{1-4}$alkyl substituted with 1-3 $R_8$, —C(=O)OR$_b$, —C(=O)NR$_a$R$_a$, —C(=O)R$_b$, —NR$_a$C(=O)R$_b$, —NR$_a$C(=O)OR$_b$, —$(CH_2)_r$-carbocyclyl substituted with 1-3 $R_8$, or —$(CH_2)_r$-heterocyclyl substituted with 1-3 $R_8$;

alternatively, $R_{3a}$ and $R_{3b}$, or $R_{3c}$ and $R_{3d}$, or $R_{3e}$ and $R_{3f}$ together with the carbon atom to which they are both attached form a spiral carbocyclic or heterocyclic ring comprising carbon atoms and 1 to 4 heteroatoms selected from N, O, S, each substituted with 0-5 $R_e$;

alternatively, $R_{3a}$ and $R_{3c}$ or $R_{3b}$ and $R_{3d}$ together form a heterocyclic ring comprising carbon atoms and 1 to 4 heteroatoms selected from N, O, S, and substituted with 0-5 $R_e$;

$R_4$ is independently H or $C_{1-4}$ alkyl substituted with 0-3 $R_e$;

$R_5$, at each occurrence, is independently H, $C_{1-4}$ alkyl substituted with 0-3 $R_e$, F, Cl, Br, =O, CN, NO$_2$, —OR$_b$, —$(CH_2)_r$CN, —$(CH_2)_r$OR$_b$, $(CH_2)_r$S(O)$_p$R$_c$, —$(CH_2)_r$C(=O)R$_b$, —$(CH_2)_r$NR$_a$R$_a$, —$(CH_2)_r$C(=O)NR$_a$R$_a$, —$(CH_2)_r$NR$_a$C(=O)R$_b$, —$(CH_2)_r$NR$_a$C(=O)OR$_b$, —$(CH_2)_r$OC(=O)NR$_a$R$_a$, —$(CH_2)_r$NR$_a$C(=O)NR$_a$R$_a$, —$(CH_2)_r$C(=O)OR$_b$, —$(CH_2)_r$S(O)$_2$NR$_a$R$_a$, —$(CH_2)_r$NR$_a$S(O)$_2$NR$_a$R$_a$, —$(CH_2)_r$NR$_a$S(O)$_2$R$_e$, $(CH_2)_r$-carbocyclyl substituted with 0-3 $R_e$, or —$(CH_2)_r$-heterocyclyl substituted with 0-3 $R_e$;

$R_6$ is independently H, —C(=O)R$_b$, —CO(=O)R$_b$, —S(O)$_p$R$_c$, $C_{1-6}$ alkyl substituted with 0-5 $R_e$, —$(CH_2)_r$—C$_{3-6}$carbocyclyl substituted with 0-5 $R_e$, or —$(CH_2)_r$-heterocyclyl substituted with 0-5 $R_e$;

R₇, at each occurrence, is independently H, F, Cl, Br, —(CR$_d$R$_d$)$_r$CN, NO₂, —(CR$_d$R$_d$)$_r$OR$_b$, —S(O)$_p$R$_c$, —C(=O)R$_b$, —(CR$_d$R$_d$)$_r$NR$_a$R$_a$, —(CR$_d$R$_d$)$_r$C(=O)NR$_a$R$_a$, —NR$_a$C(=O)R$_b$, —NR$_a$C(=O)NR$_b$, —OC(=O)NR$_a$R$_a$, —NR$_a$C(=O)NR$_a$R$_a$, —(CR$_d$R$_d$)$_r$C(=O)OR$_b$, —S(O)₂NR$_a$R$_a$, —NR$_a$S(O)₂NR$_a$R$_a$, —NR$_a$S(O)₂R$_c$, C₁₋₆ alkyl substituted with 0-5 R$_e$, —(CR$_d$R$_d$)$_r$—C₃₋₆carbocyclyl substituted with 0-5 R$_e$, or —(CR$_d$R$_d$)$_r$-heterocyclyl substituted with 0-5 R$_e$;

R₈, at each occurrence, is independently H, F, Cl, Br, CN, C₁₋₆ alkyl substituted with 0-5 R$_e$, C₂₋₆ alkenyl, C₂₋₆ alkynyl, —(CH₂)$_r$—C₃₋₆ cycloalkyl substituted with 0-5 R$_e$, —(CH₂)$_r$-aryl substituted with 0-5 R$_e$, —(CH₂)$_r$-heterocyclyl substituted with 0-5 R$_e$, CO₂H, —(CH₂)$_r$OR$_b$, or —(CH₂)$_r$NR$_a$R$_a$;

R$_a$, at each occurrence, is independently H, CN, C₁₋₆ alkyl substituted with 0-5 R$_e$, C₂₋₆ alkenyl substituted with 0-5 R$_e$, C₂₋₆ alkynyl substituted with 0-5 R$_e$, —(CH₂)$_r$—C₃₋₁₀carbocyclyl substituted with 0-5 R$_e$, or —(CH₂)$_r$-heterocyclyl substituted with 0-5 R$_e$; or R$_a$ and R$_a$ together with the nitrogen atom to which they are both attached form a heterocyclic ring substituted with 0-5 R$_e$;

R$_b$, at each occurrence, is independently H, C₁₋₆ alkyl substituted with 0-5 R$_e$, C₂₋₆ alkenyl substituted with 0-5 R$_e$, C₂₋₆ alkynyl substituted with 0-5 R$_e$, —(CH₂)$_r$—C₃₋₁₀carbocyclyl substituted with 0-5 R$_e$, or —(CH₂)$_r$-heterocyclyl substituted with 0-5 R$_e$;

R$_c$, at each occurrence, is independently C₁₋₆ alkyl substituted with 0-5 R$_e$, C₂₋₆ alkenyl substituted with 0-5 R$_e$, C₂₋₆alkynyl substituted with 0-5 R$_e$, C₃₋₆carbocyclyl, or heterocyclyl;

R$_d$, at each occurrence, is independently H or C₁₋₄alkyl substituted with 0-5 R$_e$;

R$_e$, at each occurrence, is independently F, Cl, Br, CN, NO₂, =O, C₁₋₆ alkyl substituted with 0-5 R$_f$, C₂₋₆ alkenyl, C₂₋₆ alkynyl, —(CH₂)$_r$—C₃₋₆ cycloalkyl, CO₂H, —(CH₂)$_r$OR$_f$, SR$_f$, or —(CH₂)$_r$NR$_f$R$_f$;

R$_f$, at each occurrence, is independently H, C₁₋₅ alkyl, C₃₋₆ cycloalkyl, or phenyl, or R$_f$ and R$_f$ together with the nitrogen atom to which they are both attached form a heterocyclic ring optionally substituted with C₁₋₄alkyl;

p, at each occurrence, is independently zero, 1, or 2; and
r, at each occurrence, is independently zero, 1, 2, 3, or 4.

3. The compound according to claim 2, wherein:
R₁ is independently aryl, pyridyl, pyrimidinyl, pyrazinyl, pyridazinyl, triazinyl, furyl, thienyl, imidazolyl, thiazolyl, indolyl, oxazolyl, isoxazolyl, pyrazolyl, triazolyl, tetrazolyl, indazolyl, 1,2,4-thiadiazolyl, isothiazolyl, quinolinyl, or isoquinolinyl, each substituted with 1-4 R₄ and R₅;

R₄, at each occurrence, is independently H or C₁₋₄ alkyl substituted with 0-3 R$_e$;

R₅, at each occurrence, is independently H, C₁₋₄ alkyl substituted with 0-3 R$_e$, F, Cl, Br, =O, CN, NO₂, —OR$_b$, —S(O)$_p$R$_c$, —CN, —OR$_b$, —(CH₂)$_r$C(=O)R$_b$, —(CH₂)$_r$NR$_a$R$_a$, —(CH₂)$_r$C(=O)NR$_a$R$_a$, —(CH₂)$_r$NHC(=O)R$_b$, —(CH₂)$_r$NHC(=O)OR$_b$, —(CH₂)$_r$OC(=O)NR$_a$R$_a$, —(CH₂)$_r$NHC(=O)NR$_a$R$_a$, —(CH₂)$_r$C(=O)OR$_b$, —(CH₂)$_r$S(O)₂NR$_a$R$_a$, —(CH₂)$_r$NHS(O)₂NR$_a$R$_a$, —(CH₂)$_r$NHS(O)₂R$_c$, (CH₂)$_r$-carbocyclyl substituted with 0-3 R$_e$, or —(CH₂)$_r$-heterocyclyl substituted with 0-3 R$_e$;

R$_a$, at each occurrence, is independently H, CN, C₁₋₆ alkyl substituted with 0-5 R$_e$, C₂₋₆ alkenyl substituted with 0-5 R$_e$, C₂₋₆ alkynyl substituted with 0-5 R$_e$, —(CH₂)$_r$—C₃₋₁₀carbocyclyl substituted with 0-5 R$_e$, or —(CH₂)$_r$-heterocyclyl substituted with 0-5 R$_e$; or R$_a$ and R$_a$ together with the nitrogen atom to which they are both attached form a heterocyclic ring substituted with 0-5 R$_e$;

R$_b$, at each occurrence, is independently H, C₁₋₆ alkyl substituted with 0-5 R$_e$, C₂₋₆ alkenyl substituted with 0-5 R$_e$, C₂₋₆ alkynyl substituted with 0-5 R$_e$, —(CH₂)$_r$—C₃₋₁₀carbocyclyl substituted with 0-5 R$_e$, or —(CH₂)$_r$-heterocyclyl substituted with 0-5 R$_e$;

R$_c$, at each occurrence, is independently C₁₋₆ alkyl substituted with 0-5 R$_e$, C₂₋₆ alkenyl substituted with 0-5 R$_e$, C₂₋₆alkynyl substituted with 0-5 R$_e$, C₃₋₆carbocyclyl, or heterocyclyl;

R$_e$, at each occurrence, is independently F, Cl, Br, CN, NO₂, =O, C₁₋₆ alkyl substituted with 0-5 R$_f$, C₂₋₆ alkenyl, C₂₋₆ alkynyl, —(CH₂)$_r$—C₃₋₆ cycloalkyl, CO₂H, —(CH₂)$_r$OR$_f$, SR$_f$, or —(CH₂)$_r$NR$_f$R$_f$;

R$_f$, at each occurrence, is independently H, C₁₋₅ alkyl, C₃₋₆ cycloalkyl, or phenyl, or R$_f$ and R$_f$ together with the nitrogen atom to which they are both attached form a heterocyclic ring optionally substituted with C₁₋₄alkyl;

p, at each occurrence, is independently zero, 1, or 2; and
r, at each occurrence, is independently zero, 1, 2, 3, or 4.

4. The compound according to claim 3, wherein:
R₁ is independently

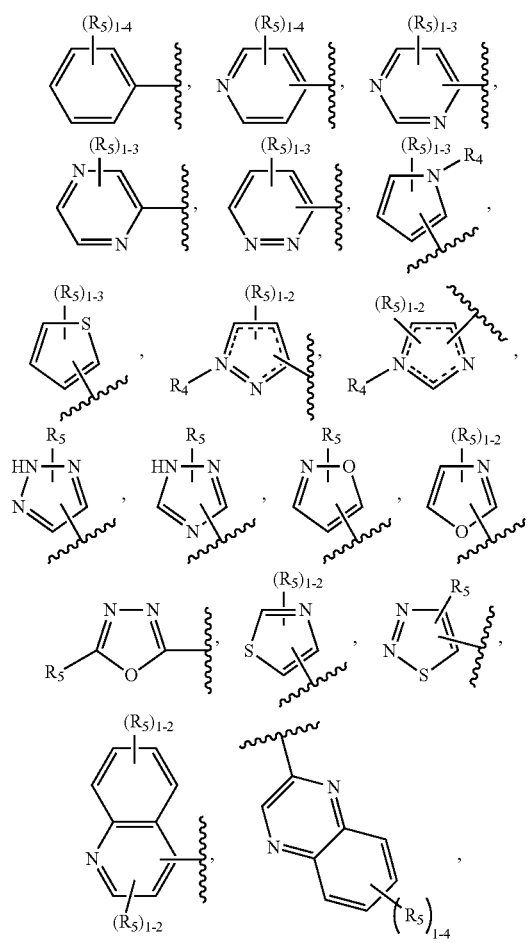

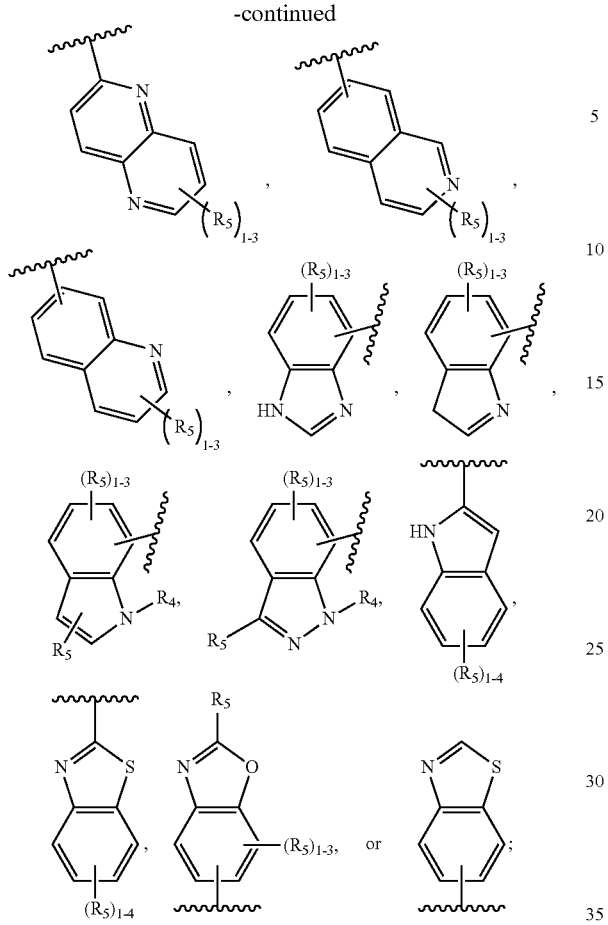

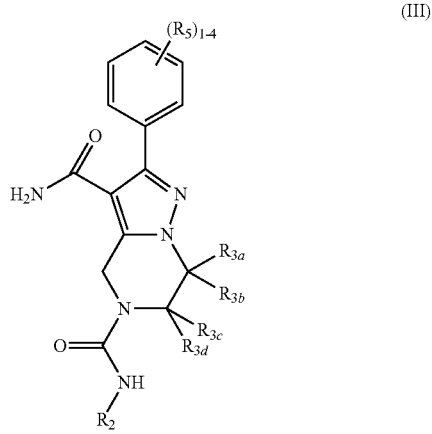

$R_4$, at each occurrence, is independently H or $C_{1-4}$ alkyl substituted with 0-3 $R_e$;

$R_5$, at each occurrence, is independently H, $C_{1-4}$ alkyl substituted with 0-3 $R_e$, F, Cl Br, =O, CN, $NO_2$, —$OR_b$, —$S(O)_pR_c$, —CN, —$OR_b$, —$(CH_2)_rC(=O)R_b$, —$(CH_2)_rNR_aR_a$, —$(CH_2)_rC(=O)NR_aR_a$, —$(CH_2)_rNHC(=O)R_b$, —$(CH_2)_rNHC(=O)OR_b$, —$(CH_2)_rOC(=O)NR_aR_a$, —$(CH_2)_rNHC(=O)NR_aR_a$, —$(CH_2)_rC(=O)OR_b$, —$(CH_2)_rS(O)_2NR_aR_a$, —$(CH_2)_rNHS(O)_2NR_aR_a$, —$(CH_2)_rNHS(O)_2R_c$, $(CH_2)_r$—$C_{3-6}$cycloalkyl, —$(CH_2)_r$-aryl substituted with 0-3 $R_e$, or —$(CH_2)_r$-heterocyclyl substituted with 0-3 $R_e$;

$R_a$, at each occurrence, is independently H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, or —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, or —$(CH_2)_r$-heterocyclyl substituted with 0-5 $R_e$;

$R_c$, at each occurrence, is independently $C_{1-6}$ alkyl substituted with 0-5 $R_e$, $C_{2-6}$ alkenyl substituted with 0-5 $R_e$, $C_{2-6}$alkynyl substituted with 0-5 $R_e$, $C_{3-6}$carbocyclyl, or heterocyclyl;

$R_e$, at each occurrence, is independently F, Cl, Br, CN, $NO_2$, =O, $C_{1-6}$ alkyl, $C_{2-6}$ alkenyl, $C_{2-6}$ alkynyl, —$(CH_2)_r$—$C_{3-6}$ cycloalkyl, or $CO_2H$;

p, at each occurrence, is independently zero, 1, or 2; and r, at each occurrence, is independently zero, 1, 2, 3, or 4.

5. The compound according to claim 4, having Formula (III),

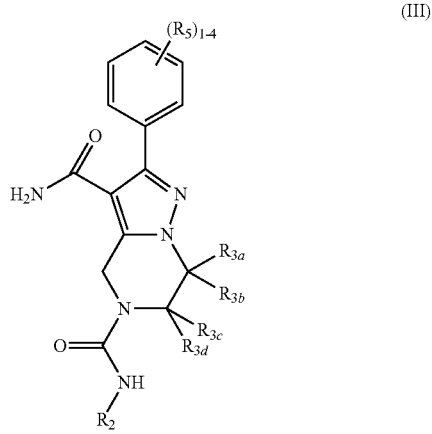

(III)

or a pharmaceutically acceptable salt thereof, wherein:

$R_2$ is independently aryl substituted with 1-8 $R_7$ or heteroaryl comprising carbon atoms and 1 to 4 heteroatoms selected from N, $NR_6$, O, S, and substituted with 1-8 $R_7$;

$R_{3a}$, $R_{3b}$, $R_{3c}$, and $R_{3d}$ are independently H, CN, $C_{1-4}$alkyl substituted with 1-3 $R_8$, —$C(=O)OR_b$, —$C(=O)NR_aR_a$, —$C(=O)R_b$, —$NR_aC(=O)R_b$, —$NR_aC(=O)OR_b$, —$(CH_2)_r$-carbocyclyl substituted with 1-3 $R_8$, or —$(CH_2)_r$-heterocyclyl substituted with 1-3 $R_8$;

alternatively, $R_{3a}$ and $R_{3b}$, or $R_{3c}$ and $R_{3d}$, together with the carbon atom to which they are both attached form a spiral carbocyclic or heterocyclic ring comprising carbon atoms and 1 to 4 heteroatoms selected from N, O, S, each substituted with 1-5 $R_8$;

alternatively, $R_{3a}$ and $R_{3c}$ or $R_{3b}$ and $R_{3d}$ together form a heterocyclic ring comprising carbon atoms and 1 to 4 heteroatoms selected from N, O, S, and substituted with 1-5 $R_8$;

$R_5$, at each occurrence, is independently H, $C_{1-4}$ alkyl substituted with 0-3 $R_e$, F, Cl, Br, —$S(O)_pR_c$, —CN, —$OR_b$, $NR_aR_a$, $C_{3-6}$cycloalkyl, aryl substituted with 0-3 $R_e$, or heterocyclyl substituted with 0-3 $R_e$;

$R_6$ is independently H, —$C(=O)R_b$, —$CO(=O)R_b$, —$S(O)_pR_c$, $C_{1-6}$ alkyl substituted with 0-5 $R_e$, —$(CH_2)_r$—$C_{3-6}$carbocyclyl substituted with 0-5 $R_e$, or —$(CH_2)_r$-heterocyclyl substituted with 0-5 $R_e$;

$R_7$, at each occurrence, is independently H, F, Cl, Br, —$(CR_dR_d)_rCN$, $NO_2$, —$(CR_dR_d)_rOR_b$, —$S(O)_pR_c$, —$C(=O)R_b$, —$(CR_dR_d)_rNR_aR_a$, —$(CR_dR_d)_rC(=O)NR_aR_a$, —$NR_aC(=O)R_b$, —$NR_aC(=O)OR_b$, —$OC(=O)NR_aR_a$, —$NR_aC(=O)NR_aR_a$, —$(CR_dR_d)_rC(=O)OR_b$, —$S(O)_2NR_aR_a$, —$NR_aS(O)_2NR_aR_a$, —$NR_aS(O)_2R_c$, $C_{1-6}$ alkyl substituted with 0-5 $R_e$, —$(CR_dR_d)_r$—$C_{3-6}$carbocyclyl substituted with 0-5 $R_e$, or —$(CR_dR_d)_r$-heterocyclyl substituted with 0-5 $R_e$;

$R_8$, at each occurrence, is independently H, F, Cl, Br, CN, $C_{1-6}$ alkyl substituted with 0-5 $R_e$, $C_{2-6}$ alkenyl, $C_{2-6}$ alkynyl, —$(CH_2)_r$—$C_{3-6}$ cycloalkyl substituted with 0-5 $R_e$, —$(CH_2)_r$-aryl substituted with 0-5 $R_e$, —$(CH_2)_r$-heterocyclyl substituted with 0-5 $R_e$, $CO_2H$, —$(CH_2)_rOR_b$, or —$(CH_2)_rNR_aR_a$;

$R_a$, at each occurrence, is independently H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, or —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, or —$(CH_2)_r$-heterocyclyl substituted with 0-5 $R_e$;

$R_c$, at each occurrence, is independently $C_{1-6}$ alkyl substituted with 0-5 $R_e$, $C_{2-6}$ alkenyl substituted with 0-5 $R_e$, $C_{2-6}$alkynyl substituted with 0-5 $R_e$, $C_{3-6}$carbocyclyl, or heterocyclyl;

$R_d$, at each occurrence, is independently H or $C_{1-4}$alkyl substituted with 0-5 $R_e$;

$R_e$, at each occurrence, is independently F, Cl, Br, CN, $NO_2$, =O, $CO_2H$, $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, —$(CH_2)_rOR_f$, $SR_f$, or —$(CH_2)_rNR_fR_f$;

$R_f$, at each occurrence, is independently H, $C_{1-5}$ alkyl, $C_{3-6}$ cycloalkyl, or phenyl, or $R_f$ and $R_f$ together with the nitrogen atom to which they are both attached form a heterocyclic ring optionally substituted with $C_{1-4}$alkyl;

p, at each occurrence, is independently zero, 1, or 2; and
r, at each occurrence, is independently zero, 1, 2, 3, or 4.

6. The compound according to claim 5, wherein:
$R_2$ is

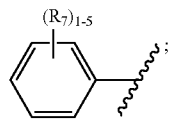

$R_{3a}$ and $R_{3b}$ are independently H, $CH_2CH_3$, $CH_3$, $CH_2OH$, $CH_2CH_2OH$, $CH_2CH_2OC_{1-4}$alkyl, $CH_2F$, $CHF_2$, $CH_2CH_2F$, $CF_3$, $CH_2OCHF_2$, $CH_2CN$, $CH_2CH_2CN$, $CH_2OC_{1-4}$alkyl, $C(CH_3)_3$, $CH(CH_3)_2$, $C(CH_3)_2OH$, $C(CH_3)_2F$, C(=O)NH—$C_{3-6}$cycloalkyl, C(=O)NH-heterocyclyl, or —$CH_2$-heterocyclyl, wherein the heterocyclyl is independently

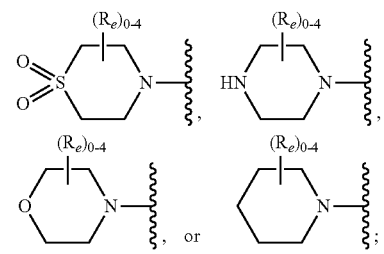

$R_{3c}$ and $R_{3d}$ are independently H, $CH_3$, $CH(CH_3)_2$, $CF_3$, or $C_{3-6}$ cycloalkyl;

$R_5$, at each occurrence, is independently H, $C_{1-4}$ alkyl substituted with 0-3 $R_e$, F, Cl, Br, —$S(O)_pR_c$, —CN, —$OR_b$, $NR_aR_a$, $C_{3-6}$cycloalkyl, or aryl substituted with 0-3 $R_e$;

$R_7$, at each occurrence, is independently H, F, Cl, Br, —$(CH_2)_rCN$, $NO_2$, —$(CH_2)_rOR_b$, —$S(O)_pR_c$, —C(=O)$R_b$, —$NR_aR_a$, —C(=O)$NR_aR_a$, —NHC(=O)$R_b$, —NHC(=O)$OR_b$, —OC(=O)$NR_aR_a$, —NHC(=O)$NR_aR_a$, —C(=O)$OR_b$, —$S(O)_2NR_aR_a$, —NHS(O)$_2NR_aR_a$, —NHS(O)$_2R_c$, $C_{1-6}$ alkyl substituted with 0-5 $R_e$, $C_{3-6}$cycloalkyl substituted with 0-5 $R_e$, aryl substituted with 0-5 $R_e$, or heterocyclyl substituted with 0-5 $R_e$;

$R_8$, at each occurrence, is independently H, F, Cl, Br, CN, $C_{1-6}$ alkyl substituted with 0-5 $R_e$, —$(CH_2)_r$—$C_{3-6}$cycloalkyl substituted with 0-5 $R_e$, —$(CH_2)_r$-aryl substituted with 0-5 $R_e$, —$(CH_2)_r$-heterocyclyl substituted with 0-5 $R_e$, $CO_2H$, —$(CH_2)_rOR_b$, or —$(CH_2)_rNR_aR_a$;

$R_a$, at each occurrence, is independently H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, or —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, aryl substituted with 0-5 $R_e$, or heterocyclyl substituted with 0-5 $R_e$;

$R_c$, at each occurrence, is independently $C_{1-6}$ alkyl substituted with 0-5 $R_e$, $C_{3-6}$carbocyclyl, or heterocyclyl;

$R_e$, at each occurrence, is independently F, Cl, Br, CN, $NO_2$, =O, $CO_2H$, $C_{1-6}$ alkyl, $C_{2-6}$ alkenyl, $C_{2-6}$ alkynyl, or —$(CH_2)_r$—$C_{3-6}$ cycloalkyl;

p, at each occurrence, is independently zero, 1, or 2; and
r, at each occurrence, is independently zero, 1, 2, 3, or 4.

7. The compound according to claim 5, wherein:
$R_2$ is

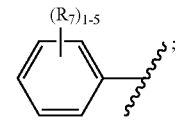

$R_7$, at each occurrence, is independently H, F, Cl, Br, CN, —$OC_{1-4}$alkyl substituted with 0-5 $R_e$, —$S(O)_2C_{1-4}$ alkyl, —C(=O)$R_b$, —$NR_aR_a$, —C(=O)$NR_aR_a$, $C_{1-4}$ alkyl substituted with 0-5 $R_e$, $C_{3-6}$ cycloalkyl substituted with 0-5 $R_e$, aryl substituted with 0-5 $R_e$, or heterocyclyl substituted with 0-5 $R_e$;

$R_a$, at each occurrence, is independently H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, or —$(CH_2)_r$-heterocyclyl substituted with 0-5 $R_e$; or $R_a$ and $R_a$ together with the nitrogen atom to which they are both attached form a heterocyclic ring substituted with 0-5 $R_e$; wherein the heterocyclic ring is independently and $R_e$, at each occurrence, is independently F, Cl, Br, CN, $NO_2$, =O, $CO_2H$, $C_{1-6}$ alkyl, $C_{2-6}$ alkenyl, $C_{2-6}$ alkynyl, or —$(CH_2)_r$—$C_{3-6}$ cycloalkyl.

8. The compound according to claim 5, wherein:

$R_2$ is independently

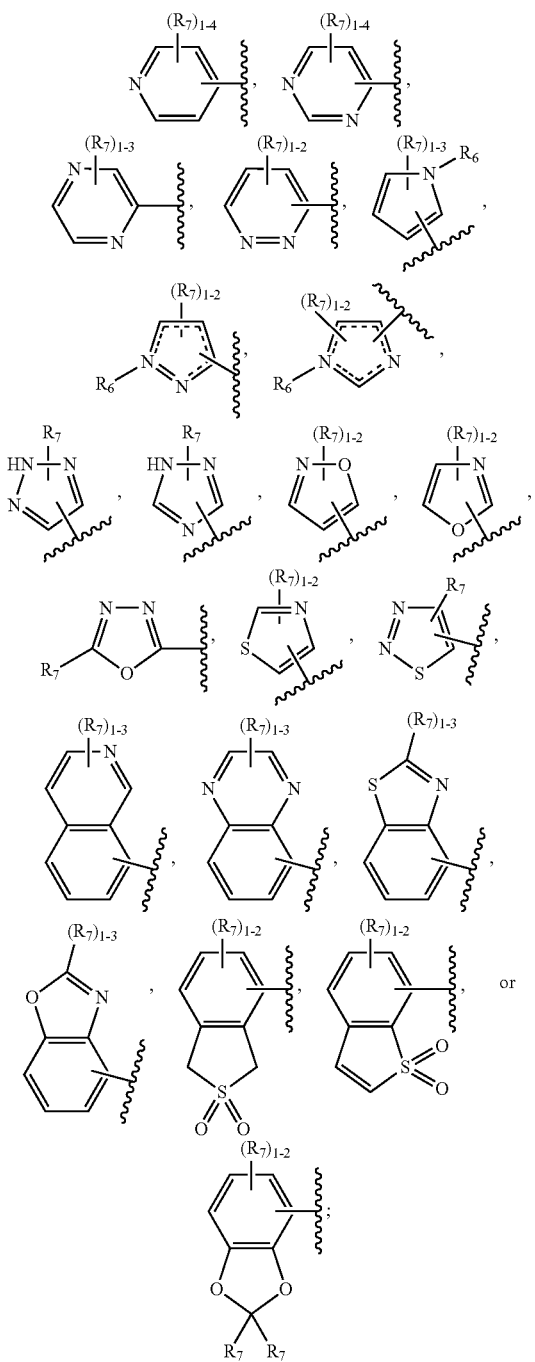

$R_{3a}$ and $R_{3b}$ are independently H, $CH_2CH_3$, $CH_3$, $CH_2OH$, $CH_2CH_2OH$, $CH_2CH_2OC_{1-4}$alkyl, $CH_2F$, $CHF_2$, $CH_2CH_2F$, $CF_3$, $CH_2OCHF_2$, $CH_2CN$, $CH_2CH_2CN$, $CH_2OC_{1-4}$alkyl, $C(CH_3)_3$, $CH(CH_3)_2$, $C(CH_3)_2OH$, $C(CH_3)_2F$, C(=O)NH—$C_{3-6}$cycloalkyl, C(=O)NH-heterocyclyl, or —$CH_2$-heterocyclyl, wherein the heterocyclyl is independently

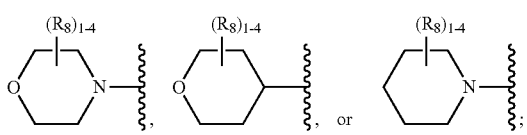

$R_{3c}$ and $R_{3d}$ are independently H, $CH_3$, $CH(CH_3)_2$, $CF_3$, or $C_{3-6}$ cycloalkyl;

$R_5$, at each occurrence, is independently H, $C_{1-4}$ alkyl substituted with 0-3 $R_e$, F, Cl, Br, —$S(O)_pR_c$, —CN, —$OR_b$, $NR_aR_a$, $C_{3-6}$cycloalkyl, or aryl substituted with 0-3 $R_e$;

$R_6$ is independently H or $C_{1-6}$ alkyl substituted with 0-5 $R_e$;

$R_7$, at each occurrence, is independently H, F, Cl, Br, —$(CH_2)_rCN$, $NO_2$, —$(CH_2)_rOR_b$, —$S(O)_pR_c$, —C(=O)$R_b$, —$NR_aR_a$, —C(=O)$NR_aR_a$, —NHC(=O)$R_b$, —NHC(=O)$OR_b$, —OC(=O)$NR_aR_a$, —NHC(=O)$NR_aR_a$, —C(=O)$OR_b$, —$S(O)_2NR_aR_a$, —$NHS(O)_2NR_aR_a$, —$NHS(O)_2R_c$, $C_{1-6}$ alkyl substituted with 0-5 $R_e$, $C_{3-6}$cycloalkyl substituted with 0-5 $R_e$, aryl substituted with 0-5 $R_e$, or heterocyclyl substituted with 0-5 $R_e$;

$R_8$, at each occurrence, is independently H, F, Cl, Br, CN, $C_{1-6}$ alkyl substituted with 0-5 $R_e$, —$(CH_2)_r$—$C_{3-6}$ cycloalkyl substituted with 0-5 $R_e$, —$(CH_2)_r$-aryl substituted with 0-5 $R_e$, —$(CH_2)_r$-heterocyclyl substituted with 0-5 $R_e$, $CO_2H$, —$(CH_2)_rOR_b$, or —$(CH_2)_rNR_aR_a$;

$R_a$, at each occurrence, is independently H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, or —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, aryl substituted with 0-5 $R_e$, or heterocyclyl substituted with 0-5 $R_e$;

$R_c$, at each occurrence, is independently $C_{1-6}$ alkyl substituted with 0-5 $R_e$, $C_{3-6}$carbocyclyl, or heterocyclyl;

$R_e$, at each occurrence, is independently F, Cl, Br, CN, $NO_2$, =O, $CO_2H$ $C_{1-6}$ alkyl, $C_{2-6}$ alkenyl, $C_{2-6}$ alkynyl, or —$(CH_2)_r$—$C_{3-6}$ cycloalkyl;

p, at each occurrence, is independently zero, 1, or 2; and r, at each occurrence, is independently zero, 1, 2, 3, or 4.

9. The compound according to claim 5, or a pharmaceutically acceptable salt thereof, wherein:

$R_{3a}$ and $R_{3b}$, together with the carbon atom to which they are both attached form a spiral carbocyclic or heterocyclic ring comprising carbon atoms and 1 to 4 heteroatoms selected from N, O, S, each substituted with 1-5 $R_8$; and alternatively, $R_{3c}$ and $R_{3d}$, together with the carbon atom to which they are both attached form a spiral carbocyclic ring comprising carbon atoms and 1 to 4 heteroatoms selected from N, O, S, each substituted with 1-5 $R_8$.

10. The compound according to claim 9, having Formula (IV):

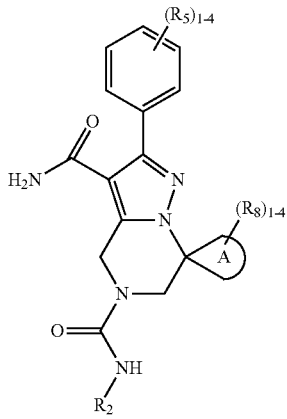

(IV)

or a pharmaceutically acceptable salt thereof, wherein:
Ring A is independently $C_{3-6}$ cycloalkyl or heterocyclyl;
$R_2$ is independently aryl substituted with 1-8 $R_7$ or heteroaryl comprising carbon atoms and 1 to 4 heteroatoms selected from N, O, S, and substituted with 1-8 $R_7$;
$R_5$, at each occurrence, is independently H, $C_{1-4}$ alkyl substituted with 0-3 $R_e$, F, Cl, Br, —S(O)$_p$R$_c$, —CN, —OR$_b$, NR$_a$R$_a$, $C_{3-6}$cycloalkyl, aryl substituted with 0-3 $R_e$, or heterocyclyl substituted with 0-3 $R_e$;
$R_7$, at each occurrence, is independently H, F, Cl, Br, CN, NO$_2$, —OR$_b$, —S(O)$_p$R$_c$, —C(=O)R$_b$, —NR$_a$R$_a$, —C(=O)NR$_a$R$_a$, —NHC(=O)R$_b$, —NHC(=O)OR$_b$, —OC(=O)NR$_a$R$_a$, —NHC(=O)NR$_a$R$_a$, —C(=O)OR$_b$, —S(O)$_2$NR$_a$R$_a$, $C_{1-6}$ alkyl substituted with 0-5 $R_e$, aryl substituted with 0-5 $R_e$, or heterocyclyl substituted with 0-5 $R_e$;
$R_8$, at each occurrence, is independently H, F, Cl, Br, CN, $C_{1-6}$ alkyl substituted with 0-5 $R_e$, $C_{2-6}$ alkenyl, $C_{2-6}$ alkynyl, —(CH$_2$)$_r$—$C_{3-6}$ cycloalkyl substituted with 0-5 $R_e$, —(CH$_2$)$_r$-aryl substituted with 0-5 $R_e$, —(CH$_2$)$_r$-heterocyclyl substituted with 0-5 $R_e$, CO$_2$H, —(CH$_2$)$_r$OR$_b$, or —(CH$_2$)$_r$NR$_a$R$_a$;
$R_a$, at each occurrence, is independently H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —(CH$_2$)$_r$—$C_{3-10}$carbocyclyl substituted with 0-5 $R_e$, or —(CH$_2$)$_r$-heterocyclyl substituted with 0-5 $R_e$; or $R_a$ and $R_a$ together with the nitrogen atom to which they are both attached form a heterocyclic ring substituted with 0-5 $R_e$;
$R_b$, at each occurrence, is independently H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, aryl substituted with 0-5 $R_e$, or heterocyclyl substituted with 0-5 $R_e$;
$R_c$, at each occurrence, is independently $C_{1-6}$ alkyl substituted with 0-5 $R_e$, $C_{3-6}$carbocyclyl, or heterocyclyl;
$R_e$, at each occurrence, is independently F, Cl, Br, CN, NO$_2$, =O, CO$_2$H, $C_{1-6}$ alkyl, $C_{2-6}$ alkenyl, $C_{2-6}$ alkynyl, or —(CH$_2$)$_r$—$C_{3-6}$ cycloalkyl;
p, at each occurrence, is independently zero, 1, or 2; and
r, at each occurrence, is independently zero, 1, 2, 3, or 4.
11. The compound according to claim 5, or a pharmaceutically acceptable salt thereof, wherein:

$R_{3a}$ and $R_{3c}$ together form a carbocyclic or heterocyclic ring comprising carbon atoms and 1 to 4 heteroatoms selected from N, O, S, wherein the carbocyclic or heterocyclic ring is substituted with 1-5 $R_8$; and
$R_{3b}$ and $R_{3d}$ are independently H or $C_{1-4}$alkyl.
12. The compound according to claim 11, having Formula (V):

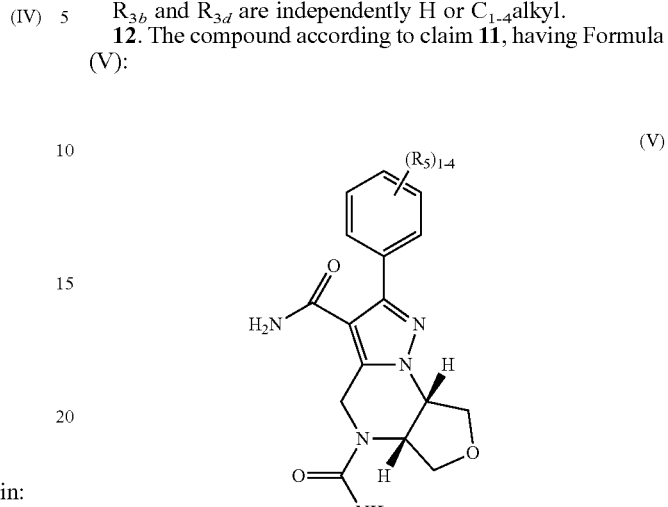

(V)

or a pharmaceutically acceptable salt thereof, wherein:
$R_2$ is independently aryl substituted with 1-8 $R_7$ or heteroaryl comprising carbon atoms and 1 to 4 heteroatoms selected from N, O, S, and substituted with 1-8 $R_7$;
$R_5$, at each occurrence, is independently H, $C_{1-4}$ alkyl substituted with 0-3 $R_e$, F, Cl, Br, —S(O)$_p$R$_c$, —CN, —OR$_b$, NR$_a$R$_a$, $C_{3-6}$cycloalkyl, aryl substituted with 0-3 $R_e$, or heterocyclyl substituted with 0-3 $R_e$;
$R_7$, at each occurrence, is independently H, F, Cl, Br, CN, NO$_2$, —OR$_b$, —S(O)$_p$R$_c$, —C(=O)R$_b$, —NR$_a$R$_a$, —C(=O)NR$_a$R$_a$, —NHC(=O)R$_b$, —NHC(=O)OR$_b$, —OC(=O)NR$_a$R$_a$, —NHC(=O)NR$_a$R$_a$, —C(=O)OR$_b$, —S(O)$_2$NR$_a$R$_a$, $C_{1-6}$ alkyl substituted with 0-5 $R_e$, aryl substituted with 0-5 $R_e$, or heterocyclyl substituted with 0-5 $R_e$;
$R_a$, at each occurrence, is independently H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —(CH$_2$)$_r$ $C_{3-10}$carbocyclyl substituted with 0-5 $R_e$, or —(CH$_2$)$_r$-heterocyclyl substituted with 0-5 $R_e$; or $R_a$ and $R_a$ together with the nitrogen atom to which they are both attached form a heterocyclic ring substituted with 0-5 $R_e$;
$R_b$, at each occurrence, is independently H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, aryl substituted with 0-5 $R_e$, or heterocyclyl substituted with 0-5 $R_e$;
$R_c$, at each occurrence, is independently $C_{1-6}$ alkyl substituted with 0-5 $R_e$, $C_{3-6}$carbocyclyl, or heterocyclyl;
$R_e$, at each occurrence, is independently F, Cl, Br, CN, NO$_2$, =O, CO$_2$H, $C_{1-6}$ alkyl, $C_{2-6}$ alkenyl, $C_{2-6}$ alkynyl, or —(CH$_2$)$_r$—$C_{3-6}$ cycloalkyl;
p, at each occurrence, is independently zero, 1, or 2; and
r, at each occurrence, is independently zero, 1, 2, 3, or 4.
13. A pharmaceutical composition comprising one or more compounds of claim 1 and a pharmaceutically acceptable carrier.

* * * * *